US012559474B2

(12) United States Patent
Tachibana et al.

(10) Patent No.: US 12,559,474 B2
(45) **Date of Patent: *Feb. 24, 2026**

(54) TRIAZINE DERIVATIVES HAVING VIRUS REPLICATION INHIBITORY ACTIVITY AND PHARMACEUTICAL COMPOSITION COMPRISING THE SAME

(71) Applicants: Shionogi & Co., Ltd., Osaka (JP); NATIONAL UNIVERSITY CORPORATION HOKKAIDO UNIVERSITY, Hokkaido (JP)

(72) Inventors: Yuki Tachibana, Osaka (JP); Shota Uehara, Osaka (JP); Yuto Unoh, Osaka (JP); Kenji Nakahara, Osaka (JP); Yoshiyuki Taoda, Osaka (JP); Koji Kasamatsu, Osaka (JP); Yukiko Yamatsu, Osaka (JP); Shigeru Ando, Osaka (JP); Takahiro Suto, Osaka (JP); Michihito Sasaki, Sapporo (JP)

(73) Assignees: SHIONOGI & CO., LTD., Osaka (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 758 days.

This patent is subject to a terminal disclaimer.

(21) Appl. No.: 17/790,358

(22) PCT Filed: Feb. 17, 2022

(86) PCT No.: PCT/JP2022/006495

§ 371 (c)(1),
(2) Date: Jun. 30, 2022

(87) PCT Pub. No.: WO2022/138987

PCT Pub. Date: Jun. 30, 2022

(65) Prior Publication Data

US 2023/0128162 A1 Apr. 27, 2023

(30) Foreign Application Priority Data

Apr. 14, 2021 (JP) ................................ 2021-068672
Jun. 25, 2021 (JP) ................................ 2021-105802
Sep. 22, 2021 (JP) ................................ 2021-153819

(51) Int. Cl.
*C07D 401/14* (2006.01)
*A61K 31/53* (2006.01)
(Continued)

(52) U.S. Cl.
CPC ............ *C07D 401/14* (2013.01); *A61K 31/53* (2013.01); *A61K 47/542* (2017.08); *A61P 31/14* (2018.01);
(Continued)

(58) Field of Classification Search
CPC .... A61K 31/53; A61K 47/542; A61K 9/0019; A61K 9/0053; A61P 31/14; A61P 43/00;
(Continued)

(56) References Cited

U.S. PATENT DOCUMENTS 4,950,670 A 8/1990 Frost et al.
5,162,326 A 11/1992 Naka et al.
(Continued)

FOREIGN PATENT DOCUMENTS

CN 102807568 12/2012
CN 104109147 10/2014
(Continued)

OTHER PUBLICATIONS

CAS Registry File 22933-24-0, Entered into STN Nov. 16, 1984, Obtained from the internet Apr. 8, 2025 (Year: 1984).*
Machine Translation of JP2019094314A (Year: 2019).*
CAS Registry File (108091-5; entered into STN May 29, 2015; obtained from the internet Aug. 1, 2025) (Year: 2015).*
Janet L. Ralbovsky et al., "Triazinediones as prokineticin 1 receptor antagonists. Part 1: SAR, synthesis and biological evaluation", Bioorganic & Medicinal Chemistry Letters, vol. 19, pp. 2661-2663, 2009.
Search Report issued Oct. 10, 2023 in corresponding Chinese Patent Application No. 202280000918.9, with English translation.
(Continued)

*Primary Examiner* — Jeffrey H Murray
*Assistant Examiner* — Daniel John Burkett
(74) *Attorney, Agent, or Firm* — Wenderoth, Lind & Ponack, L.L.P.

(57) ABSTRACT

A compound represented by Formula (I):

(I)

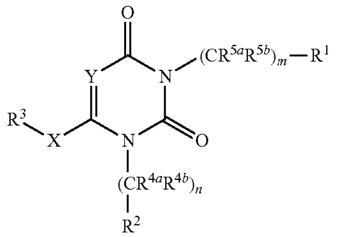

wherein Y is N or the like; $R^1$ is substituted or unsubstituted aromatic heterocyclyl or the like; $R^2$ is substituted or unsubstituted aromatic carbocyclyl or the like; $R^3$ is substituted or unsubstituted aromatic heterocyclyl or the like; —X— is —NH— or the like; m is 1 or the like; $R^{5a}$ is each independently a hydrogen atom or the like; $R^{5b}$ is each independently a hydrogen atom or the like; n is 1 or the like; $R^{4a}$ is each independently a hydrogen atom or the like; and $R^{4b}$ is each independently a hydrogen atom or the like, or a pharmaceutically acceptable salt thereof.

17 Claims, 15 Drawing Sheets

Specification includes a Sequence Listing.

(51) Int. Cl.

| | |
|---|---|
| ***A61K 47/54*** | (2017.01) |
| ***A61P 31/14*** | (2006.01) |
| ***C07D 401/04*** | (2006.01) |
| ***C07D 401/06*** | (2006.01) |
| ***C07D 403/06*** | (2006.01) |
| ***C07D 403/14*** | (2006.01) |
| ***C07D 405/14*** | (2006.01) |
| ***C07D 409/14*** | (2006.01) |
| ***C07D 413/14*** | (2006.01) |
| ***C07D 417/06*** | (2006.01) |
| ***C07D 417/14*** | (2006.01) |
| ***C07D 471/04*** | (2006.01) |
| ***C07D 487/04*** | (2006.01) |
| ***C07D 495/04*** | (2006.01) |
| ***C07D 498/04*** | (2006.01) |

(52) U.S. Cl.
CPC ......... *C07D 401/04* (2013.01); *C07D 401/06* (2013.01); *C07D 403/06* (2013.01); *C07D 403/14* (2013.01); *C07D 405/14* (2013.01); *C07D 409/14* (2013.01); *C07D 413/14* (2013.01); *C07D 417/06* (2013.01); *C07D 417/14* (2013.01); *C07D 471/04* (2013.01); *C07D 487/04* (2013.01); *C07D 495/04* (2013.01); *C07D 498/04* (2013.01); *C07B 2200/13* (2013.01)

(58) Field of Classification Search
CPC ............. C07B 2200/13; C07D 401/04; C07D 401/06; C07D 401/14; C07D 403/06; C07D 403/14; C07D 405/14; C07D 409/14; C07D 413/14; C07D 417/06; C07D 417/14; C07D 471/04; C07D 487/04; C07D 495/04; C07D 498/04
See application file for complete search history.

(56) References Cited

U.S. PATENT DOCUMENTS

| | | | | |
|---|---|---|---|---|
| 11,814,368 | B2 * | 11/2023 | Tachibana | A61K 9/0019 |
| 2011/0319400 | A1 | 12/2011 | Flores et al. | |
| 2011/0319414 | A1 | 12/2011 | Kai et al. | |
| 2011/0319418 | A1 * | 12/2011 | Flores | A61P 25/00 544/212 |
| 2013/0172317 | A1 | 7/2013 | Kai et al. | |
| 2013/0225596 | A1 | 8/2013 | Kai et al. | |
| 2016/0024072 | A1 | 1/2016 | Kai et al. | |
| 2016/0052892 | A1 | 2/2016 | Kai et al. | |
| 2016/0115151 | A1 | 4/2016 | Kai | |
| 2016/0185736 | A1 | 6/2016 | Kai et al. | |
| 2016/0244410 | A1 | 8/2016 | Tu et al. | |
| 2017/0158704 | A1 | 6/2017 | Nagano et al. | |
| 2017/0298058 | A1 | 10/2017 | Kai et al. | |
| 2017/0362199 | A1 | 12/2017 | Kai | |
| 2023/0212154 | A1 | 7/2023 | Tachibana et al. | |
| 2025/0127788 | A1 * | 4/2025 | Tachibana | A61P 31/12 |

FOREIGN PATENT DOCUMENTS

| | | |
|---|---|---|
| CN | 113620888 | 11/2021 |
| CN | 113666914 | 11/2021 |
| CN | 113735838 | 12/2021 |
| CN | 113773300 | 12/2021 |
| CN | 113801097 | 12/2021 |
| JP | 2-138266 | 5/1990 |
| JP | 4-330072 | 11/1992 |
| JP | 2007-509947 | 4/2007 |
| JP | 2008-534500 | 8/2008 |
| JP | 2011-502154 | 1/2011 |
| JP | 2013-530231 | 7/2013 |
| JP | 2019-94314 | 6/2019 |
| JP | 2019094314 A * | 6/2019 |
| WO | 01/55119 | 8/2001 |
| WO | 2005/042534 | 5/2005 |
| WO | 2005/095381 | 10/2005 |
| WO | 2006/ 104715 | 10/2006 |
| WO | 2007/007161 | 1/2007 |
| WO | 2007/035629 | 3/2007 |
| WO | 2007/112368 | 10/2007 |
| WO | 2009/058653 | 5/2009 |
| WO | 2010/092966 | 8/2010 |
| WO | 2012/006004 | 1/2012 |
| WO | 2012/009258 | 1/2012 |
| WO | 2012/020742 | 2/2012 |
| WO | 2012/020749 | 2/2012 |
| WO | 2013/089212 | 6/2013 |
| WO | 2013/118855 | 8/2013 |
| WO | 2014/200078 | 12/2014 |
| WO | 2021/205298 | 10/2021 |
| WO | 2021/250648 | 12/2021 |
| WO | 2023/027198 | 3/2023 |
| WO | 2023/054292 | 4/2023 |
| WO | 2023/054732 | 4/2023 |

OTHER PUBLICATIONS

Extended European Search Report issued Nov. 27, 2024 in European Patent Application No. 24168486.9.
International Search Report mailed Apr. 26, 2022 in corresponding international (PCT) Patent Application No. PCT/JP2022/006495, with English language translation, pp. 1-13.
Written Opinion of the International Searching Authority mailed Apr. 26, 2022 in corresponding International (PCT) Patent Application No. PCT/JP2022/006495, with English language translation, pp. 1-18.
International Search Report mailed Apr. 26, 2022 in counterpart International (PCT) Patent Application No. PCT/JP2022/006496, with English language translation, pp. 1-7.
Written Opinion of the International Searching Authority mailed Apr. 26, 2022 in counterpart International (PCT) Patent Application No. PCT/JP2022/006496, with English language translation, pp. 1-6.
Patent Search Report issued in corresponding Chinese Patent Application No. 2022107421862, with English language translation (Feb. 28, 2023), pp. 1-7.
STN Registry, Li Answer 1 of 1, pp. 1-3, RN 2647530-73-0, PX1_STN_RN 2647530 (Jun. 16, 2021).
Michihito Sasaki et al., "Oral administration of S-217622, a SARS-CoV-2 main protease inhibitor, decreases viral load and accelerates recovery from clinical aspects of Covid-19", pp. 1-51 (Feb. 15, 2022).
"Covid-19 Dashboard by the Center for Systems Science and Engineering at Johns Hopkins University", [online], Johns Hopkins University [searched on Jan. 28, 2022], <URL:https://coronavirus.jhu.edu/map.html>.
"Aerosol and Surface Stability of SARS-CoV-2 as Compared with SARS-CoV-1", The New England Journal of Medicine, vol. 382, No. 16, pp. 1564-1567, Apr. 6, 2020.
Kanchan Anand et al., "Coronavirus Main Proteinase ($3CL^{pro}$) Structure: Basis for Design of Anti-SARS Drugs", Science, vol. 300, 1763-1767, Jun. 13, 2003.
Maren de Vries et al., "A Comparative Analysis of SARS-CoV-2 Antivirals Characterizes $3CL^{pro}$ Inhibitor PF-00835231 as a Potential New Treatment for Covid-19", Journal of Virology, vol. 95, issue 10, e01819-20, pp. 1-22, May 2021.
Chunlong Ma et al., "Boceprevir, GC-376, and calpain inhibitors II, XII inhibit SARS-CoV-2 viral replication by targeting the viral main protease", Cell Research, vol. 30, 678-692, Jun. 15, 2020.
Linlin Zhang et al., "Crystal structure of SARS-CoV-2 main protease provides a basis for design of improved α-ketoamide inhibitors", Science, vol. 368, 409-412, Apr. 24, 2020.
Chun-Hui Zhang et al., "Potent Noncovalent Inhibitors of the Main Protease of SARS-CoV-2 from Molecular Sculpting of the Drug Perampanel Guided by Free Perturbation Calculations", ACS Central Science, vol. 7, No. 3, 467-475, 2021.

(56) References Cited

OTHER PUBLICATIONS

G Atassi et al., "Preclinical evaluation of the anti tumour activity of new epoxyde derivatives", Cancer Treatment Reviews (Mar. 1984), vol. 11, Supplement 1, pp. 99-110, Abstract.
Atassi, G et al., "Preclinical evaluation of antitumor activity of new epoxide derivatives", Contributions to Oncology (1984), vol. 18, pp. 221-234.
Fischer, H. et al., "Investigation of the antitumor activity of new epoxide derivatives. Part II: N-Glycidylated oxo-nitrogen heterocycles", Arzneimittel-Forschung (1984) vol. 34, issue 6, pp. 663-668.
Dafydd Owen, "Oral inhibitors of the SARS-CoV-2 main protease for the treatment of Covid-19", 261$^{st}$ American Chemical Society (ACS) Spring Meeting, 2021, Abstract 243.
Dafydd R. Owen et al., "An oral SARS-CoV-2 M$^{pro}$ inhibitor clinical candidate for the treatment of Covid-19", Science, vol. 374, pp. 1586-1593, Dec. 24, 2021.
"Pfizer's Novel Covid-19 Oral Antiviral Treatment Candidate Reduced Risk of Hospitalization or Death by 89% in Interim Analysis of Phase 2/3 EPIC-HR Study", Nov. 5, 2021, published only at https://www.pfizer.com/news/press-release/press-release-detail/pfizers-novel-covid-19-oral-antiviral-treatment-candidate.
Olujide O. Olubiyi et al., "High Throughput Virtual Screening to Discover Inhibitors of the Main Protease of the Coronavirus SARS-CoV-2", Molecules, 2020, vol. 25, 3193, pp. 1-20.
Kenichi Akaji et al., "Design and Evaluation of Anti-SARS-Coronavirus Agents Based on Molecular Interactions with the Viral Protease", Molecules, 2020, vol. 25, 3920, pp. 1-19.
Yuzhi Liu et al., "The development of Coronavirus 3C-Like protease (3CL$^{pro}$) inhibitors from 2010 to 2020", European Journal of Medicinal Chemistry, 2020, vol. 206, 112711, pp. 1-18.
Andreas Luttens et al., "Ultralarge Virtual Screening Identifies SARS-CoV-2 Main Protease Inhibitors with Broad-Spectrum Activity against Coronaviruses", J. Am. Chem. Soc., 2022, 144, 2905-2920.
Zeng-Wei Lai et al., "Discovery of highly potent DPP-4 inhibitors by hybrid compound design based on linagliptin and alogliptin", European Journal of Medicinal Chemistry, 2014, vol. 83, pp. 547-560.
CAS Registry No. 1347270-26-1 (2022).
CAS Registry No. 1349375-80-9 (2022).
Yuto Unoh et al., "Discovery of S-217622, a Non-Covalent Oral SARS-CoV-2 3CL Protease Inhibitor Clinical Candidate for Treating Covid-19", bioRxiv posted Jan. 26, 2022, pp. 1-52.
Yuto Unoh et al., "Discovery of S-217622, a Noncovalent Oral SARS-CoV-2 3CL Protease Inhibitor Clinical Candidate for Treating Covid-19", J. Med. Chem. 2022, 65, 6499-6512.
"Report of the WHO-China Joint Mission on Coronavirus Disease 2019 (Covid-19)", Feb. 16-24, 2020, pp. 1-40, available at https://www.who.int/docs/default-source/coronaviruse/who-china-joint-mission-on-covid-19-final-report.pdf.
Extended European Search Report issued Jul. 31, 2023 in corresponding European Patent Application No. 22733282.2.

* cited by examiner

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial sequence
<220> FEATURE:
<223> OTHER INFORMATION: Substrate Peptide

<400> SEQUENCE: 1

Glu Met Lys Arg Phe Gly Ser Gln Leu Val Ala Ser Thr Lys
1               5                   10


<210> SEQ ID NO 2
<211> LENGTH: 7
<212> TYPE: PRT
<213> ORGANISM: Artificial sequence
<220> FEATURE:
<223> OTHER INFORMATION: Internal Standard Peptide

<400> SEQUENCE: 2

Gln Leu Val Ala Ser Thr Lys
1               5
```

TRIAZINE DERIVATIVES HAVING VIRUS REPLICATION INHIBITORY ACTIVITY AND PHARMACEUTICAL COMPOSITION COMPRISING THE SAME

TECHNICAL FIELD

The present invention relates to a compound exhibiting coronavirus 3CL protease inhibitory activity and a pharmaceutical composition comprising a compound exhibiting coronavirus 3CL protease inhibitory activity. Furthermore, the present invention relates to a crystal and a cocrystal of a compound or a pharmaceutically acceptable salt thereof, exhibiting 3CL protease inhibitory activity or a pharmaceutical composition comprising the same.

BACKGROUND ART

Coronaviruses, which belong to the order Nidovirales, family Coronaviridae, and the subfamily Coronavirinae, are positive-sense single-stranded RNA viruses that have a genome size of about 30 kilobases and are the largest among the known RNA viruses. Coronaviruses are classified into four genera, namely, the genus Alphacoronavirus, the genus Betacoronavirus, Gammacoronavirus, and Deltacoronavirus, and a total of seven types of coronaviruses, including two kinds in the genus Alphacoronavirus (HCoV-229E and HCoV-NL63) and five kinds in the genus Betacoronavirus (HCoV-HKU1, HCoV-OC43, SARS-CoV, MERS-CoV, and SARS-CoV-2), are known as coronaviruses that infect humans. Among these, four kinds (HCoV-229E, HCoV-NL63, HCoV-HKU1, and HCoV-OC43) are pathogens of common cold, while the other three kinds are severe acute respiratory syndrome (SARS) coronavirus (SARS-CoV), Middle East respiratory syndrome (MERS) coronavirus (MERS-CoV), and a novel coronavirus (SARS-CoV-2), all of which cause severe pneumonia.

Novel coronavirus infections (COVID-19) that occurred in Wuhan, China, in December 2019, rapidly spread to the international community, and the pandemic was announced by the WHO on Mar. 11, 2020. The number of infected people confirmed as of Jan. 28, 2022, was more than 360 million, and the number of deaths reached more than 5.63 million (Non-patent Document 1). Droplet infection, contact infection, and aerosol infection have been reported as main routes of infection of SARS-CoV-2, and it has been confirmed that SARS-CoV-2 continues to drift in air together with aerosols and maintains infectivity for about 3 hours (Non-patent Document 2). The incubation period is about 2 to 14 days, and cold-like symptoms such as fever (87.9%), dry cough (67.7%), malaise (38.1%), and phlegm (33.4%) are typical (Non-patent Document 3). In severe cases, respiratory failure due to acute respiratory distress syndrome, acute lung injury, interstitial pneumonia, and the like occurs. Furthermore, multiple organ failure such as renal failure and hepatic failure has also been reported.

In Japan, as a result of drug repositioning of existing drugs, remdesivir, which is an antiviral drug, dexamethasone, which is an anti-inflammatory drug, and baricitinib, which is an antirheumatic drug, have been approved as therapeutic agents against COVID-19, and in January 2022, tocilizumab, which is an anti-IL-6 receptor antibody, have been received additional approval. Furthermore, in July 2021, ronapreve(casirivimab/imdevimab), which is an antibody cocktail therapy, was approved as special case approval, in September 2021, sotrovimab was approved as special case approval, and in December 2021, molnupiravir was approved as special case approval. Sufficient evidence has not been obtained on the efficacy and safety of these drugs. Accordingly, it is imperative to create therapeutic agents against COVID-19.

Upon infection of cells, coronaviruses synthesize two polyproteins. In these two polyproteins, structural proteins for producing new viral particles, replication complexes producing viral genomes, and two proteases are included. Proteases play an indispensable role for cleaving the polyproteins synthesized by viruses and causing each of the proteins to function. Between these two proteases, 3CL protease (main protease) bears most of the cleavage of the polyproteins (Non-patent Document 4).

Regarding COVID-19 therapeutic agents targeting 3CL proteases, it was published in ClinicalTrials.gov that Phase 1b trials for Lufotrelvir (PF-07304814), which is a prodrug of PF-00835231, have completed by Pfizer Inc (NCT04535167). Furthermore, in March 2021, Pfizer Inc. announced that Phase 1 trials for PF-07321332, a therapeutic agent against novel coronavirus infections, will be initiated. The structural formulae of PF-00835231, Lufotrelvir and PF-07321332 are as shown below, and these agents are different from the compound of the present invention in chemical structure (Non-patent Documents 5, 12 and 13 and Patent Documents 6 and 7)

[Chemical Formula 1]

PF-00835231

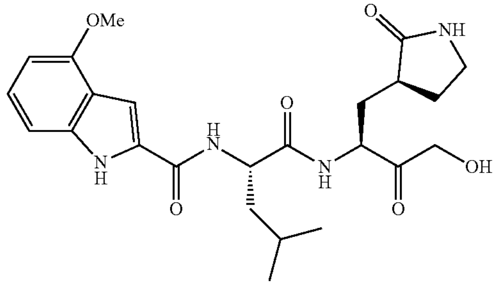

[Chemical Formula 2]

(PF-07304814)

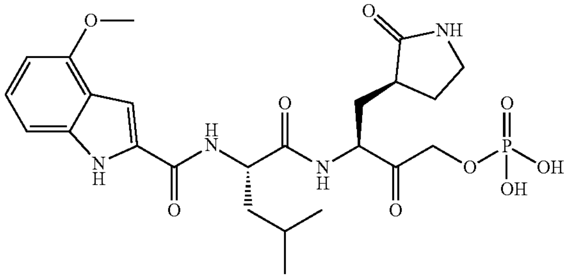

Lufotrelvir

-continued

[Chemical Formula 3]

PF-07321332

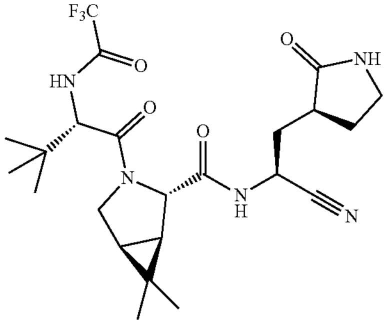

Furthermore, in July 2021, it was published in ClinicalTrials.gov that Phase 2/3 trials for a combination of PF-07321332 and ritonavir targeting COVID-19 patients with high-risk factors will be initiated (NCT04960202). Moreover, in November 2021, it was reported on the Pfizer website, PAXLOVID™ (PF-07321332; ritonavir) reduced the risk of hospitalization or death by 89% in high-risk adult patients compared to placebo (Non-Patent Document 14). Furthermore, in December 2021, PAXLOVID™ was approved for emergency use in the United States, and on Feb. 10, 2022, the Paxlovid® PACK was approved as special case approval in Japan.

Compounds having 3CL protease inhibitory activity are disclosed in Non-patent Documents 5 to 8; however, the compounds related to the present invention are neither described nor suggested in any of the documents.

Triazine derivatives and uracil derivatives having $P2X_3$ and/or $P2X_{2/3}$ receptor antagonistic activity have been disclosed in Patent Documents 1 to 4 and 8 to 12; however, the 3CL protease inhibitory activity and the antiviral effect are neither described nor suggested in any of the documents.

Triazine derivatives having antitumor effects have been disclosed in Non-patent Documents 9 to 11; however, the coronavirus 3CL protease inhibitory activity and the antiviral effects are described in none of the documents, and the compounds related to the present invention are neither described nor suggested in any of the documents.

Triazine derivatives having galanin receptor-regulating effects have been disclosed in Patent Document 5; however, the coronavirus 3CL protease inhibitory activity and the antiviral effects are not described in the document, and the compounds related to the present invention are neither described nor suggested in the documents.

PRIOR ART REFERENCES

Patent Document

[Patent Document 1] International Publication WO 2012/020749A
[Patent Document 2] International Publication WO 2013/089212A
[Patent Document 3] International Publication WO 2010/092966A
[Patent Document 4] International Publication WO 2014/200078A
[Patent Document 5] International Publication WO 2012/009258A
[Patent Document 6] International Publication WO 2021/205298A
[Patent Document 7] International Publication WO 2021/250648A
[Patent Document 8] China Patent Application Publication CN 113620888A
[Patent Document 9] China Patent Application Publication CN 113666914A
[Patent Document 10] China Patent Application Publication CN 113735838A
[Patent Document 11] Chinese Patent Application Publication CN 113773300A
[Patent Document 12] Chinese Patent Application Publication CN 113801097A

Non-Patent Document

[Non-patent Document 1] "COVID-19 Dashboard by the Center for Systems Science and Engineering at Johns Hopkins University", [online], Johns Hopkins University, [retrieved on Jan. 28, 2022], Internet <URL: https://coronavirus.jhu.edu/map.html>,
[Non-patent Document 2] The NEW ENGLAND JOURNAL of MEDICINE (2020), Vol. 382, pp. 1564-1567.
[Non-patent Document 3] "Report of the WHO-China Joint Mission on Coronavirus Disease 2019 (COVID-19)", [online], Feb. 28, 2020, WHO, [retrieved on Feb. 8, 2021], Internet <URL: https://www.who.int/docs/default-source/coronaviruse/who-china-joint-mission-on-covid-19-final-report.pdf>.
[Non-patent Document 4] Science (2003), Vol. 300, pp. 1763-1767.
[Non-patent Document 5] "A comparative analysis of SARS-CoV-2 antivirals characterizes 3CLpro inhibitor PF-00835231 as a potential new treatment for COVID-19", Journal of Virology, Apr. 26, 2021, [retrieved on Feb. 15, 2022], Internet <URL: https://journals.asm.org/doi/10.1128/JVI.01819-20><doi: 10.1128/JVI.01819-20>
[Non-patent Document 6] Cell Research (2020), Vol. 30, pp. 678-692. [Non-patent Document 7] Science (2020), Vol. 368, pp. 409-412. [Non-patent Document 8] ACS Central Science (2021), Vol. 7, No. 3, pp. 467-475.
[Non-patent Document 9] Cancer Treatment Reviews (1984), Vol. 11, Supplement 1, pp. 99-110.
[Non-patent Document 10] Contributions to Oncology (1984), Vol. 18, pp. 221-234.
[Non-patent Document 11] Arzneimittel-Forschung (1984), Vol. 11, No. 6, pp. 663-668.
[Non-patent Document 12] 261st Am Chem Soc (ACS) Natl Meet 2021 Apr. 5/2021 Apr. 16 Virtual, N/A Abst 243
[Non-patent Document 13] Science (2021), Vol. 374, pp. 1586-1593.
[Non-patent Document 14] "Pfizer's Novel COVID-19 Oral Antiviral Treatment Candidate Reduced Risk Of Hospitalization Or Death By 89% In Interim Analysis Of Phase 2/3 EPIC-HR Study", [online], Nov. 5, 2021, Pfizer Press Release, [retrieved on Feb. 15, 2022], Internet <URL: https://www.pfizer.com/news/press-release/press-release-detail/pfizers-novel-covid-19-oral-antiviral-treatment-candidate>

SUMMARY OF THE INVENTION

Problems to be Solved by the Invention

An object of the present invention is to provide a compound having coronavirus 3CL protease inhibitory activity. Preferably, the present invention provides a compound having an antiviral activity, particularly a coronavirus replication inhibitory activity, and a medicament comprising the compound. Furthermore, another object of the present invention is to provide a crystalline form and a cocrystal of a compound or a pharmaceutically acceptable salt thereof, exhibiting 3CL protease inhibitory activity and a medicament containing the same.

Means for Solving the Problem

The present invention relates to the following.

(1''') A compound represented by Formula (I):

[Chemical Formula 4]

(I)

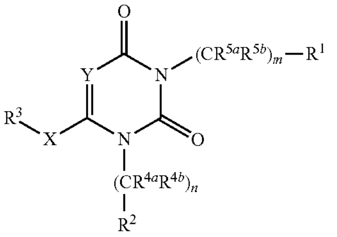

wherein

Y is N, or $CR^7$;

$R^7$ is a hydrogen atom, or substituted or unsubstituted alkyl;

$R^1$ is substituted or unsubstituted aromatic heterocyclyl, substituted or unsubstituted non-aromatic heterocyclyl, substituted or unsubstituted carbamoyl, or substituted or unsubstituted amino;

$R^2$ is substituted or unsubstituted aromatic carbocyclyl (provided that para-monofluorophenyl, para-monochlorophenyl, and para-monomethylphenyl are excluded), substituted or unsubstituted non-aromatic carbocyclyl, substituted or unsubstituted aromatic heterocyclyl, or substituted or unsubstituted non-aromatic heterocyclyl;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

—X— is $—NR^6—$, $—CR^6R^{6'}—$, —O—, —S—, or a single bond;

$R^6$ and $R^{6'}$ are each independently a hydrogen atom, or substituted or unsubstituted alkyl;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

n is 0, 1, or 2;

$R^{4a}$ is each independently a hydrogen atom, or substituted or unsubstituted alkyl;

$R^{4b}$ is each independently a hydrogen atom, or substituted or unsubstituted alkyl;

$R^{4a}$ and $R^{4b}$ may be taken together to form a substituted or unsubstituted non-aromatic carbocycle or a substituted or unsubstituted non-aromatic heterocycle;

provided that the following compounds are excluded:

[Chemical Formula 5]

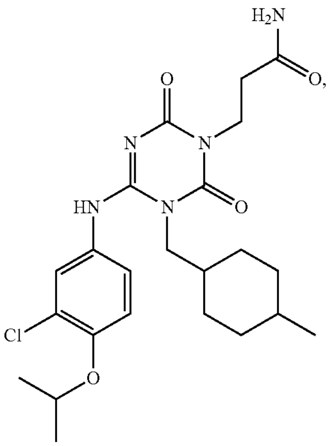

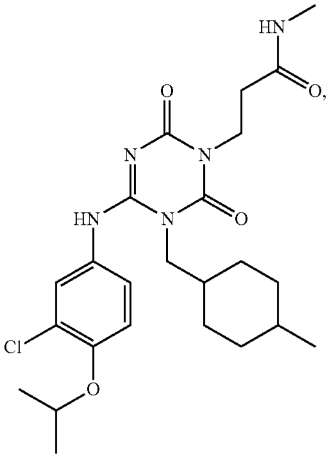

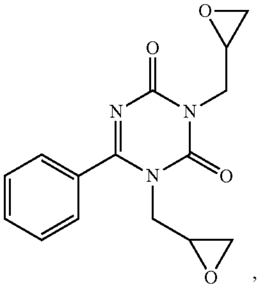

,

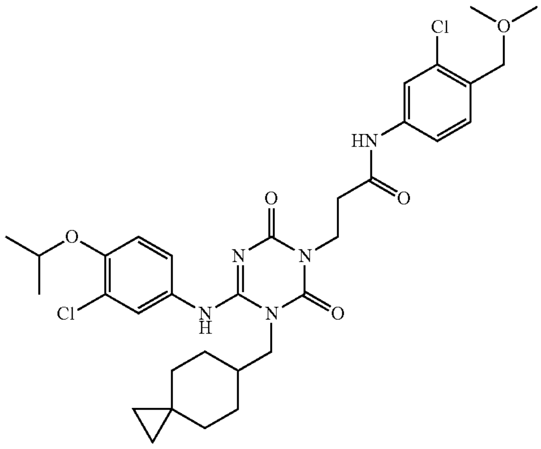

and

-continued

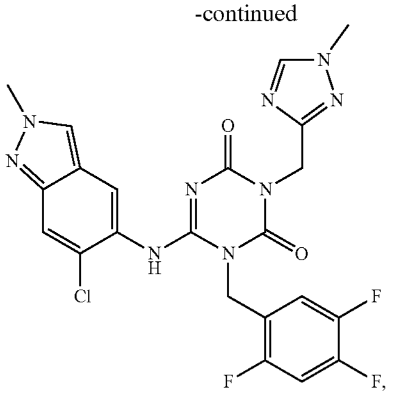

or a pharmaceutically acceptable salt thereof.

(1") A compound represented by Formula

[Chemical Formula 6]

(I)

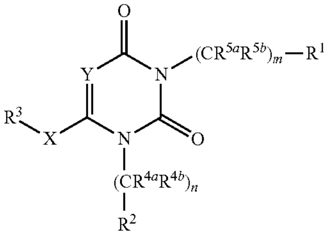

wherein

Y is N, or $CR^7$;

$R^7$ is a hydrogen atom, or substituted or unsubstituted alkyl;

$R^1$ is substituted or unsubstituted aromatic heterocyclyl, substituted or unsubstituted non-aromatic heterocyclyl, substituted or unsubstituted carbamoyl, or substituted or unsubstituted amino;

$R^2$ is substituted or unsubstituted aromatic carbocyclyl (provided that para-monofluorophenyl, para-monochlorophenyl, and para-monomethylphenyl are excluded), substituted or unsubstituted non-aromatic carbocyclyl, substituted or unsubstituted aromatic heterocyclyl, or substituted or unsubstituted non-aromatic heterocyclyl;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

$R^6$ and $R^{6'}$ are each independently a hydrogen atom, or substituted or unsubstituted alkyl;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

n is 0, 1, or 2;

$R^{4a}$ is each independently a hydrogen atom, or substituted or unsubstituted alkyl;

$R^{4b}$ is each independently a hydrogen atom, or substituted or unsubstituted alkyl;

provided that the following compounds are excluded:

[Chemical Formula 5]

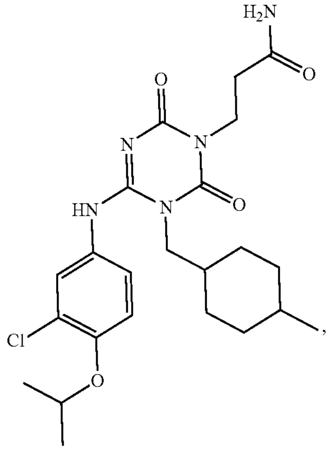

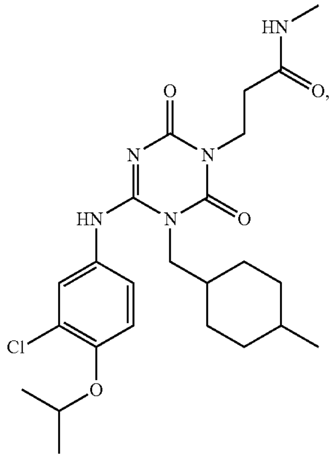

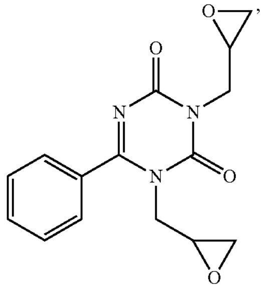

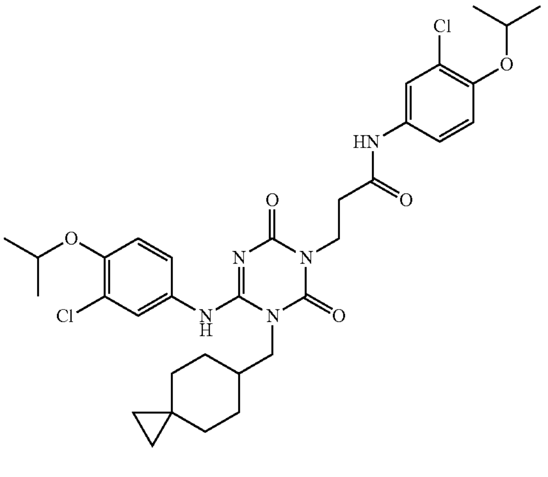

and

-continued

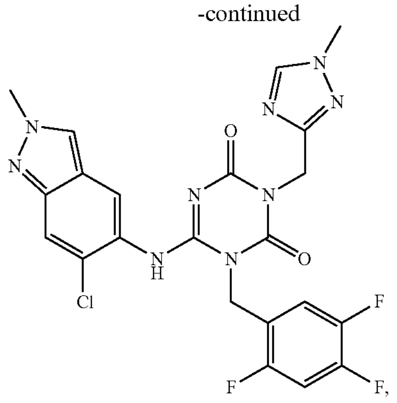

or a pharmaceutically acceptable salt thereof.

(2") The compound according to the above items (1") or (1'"), wherein

Y is N, or a pharmaceutically acceptable salt thereof.

(3") The compound according to any one of the above items (1"), (2") and (1'"), wherein —X— is —NH—, or a pharmaceutically acceptable salt thereof.

(4") The compound according to any one of the above items (1") to (3") and (1'"), wherein $R^2$ is substituted or unsubstituted 6 to 14 membered aromatic carbocyclyl, substituted or unsubstituted 5- to 10-membered non-aromatic carbocyclyl, substituted or unsubstituted 5- to 10-membered aromatic heterocyclyl, or substituted or unsubstituted 5- to 10-membered non-aromatic heterocyclyl, or a pharmaceutically acceptable salt thereof.

(5") The compound according to any one of the above items (1") to (4") and (1'"), wherein $R^2$ is 6-membered aromatic carbocyclyl substituted with one halogen or one cyano, and further substituted with 1, 2, 3 or 4 substituent(s) selected from substituent group G, or 6-membered aromatic heterocyclyl substituted with one halogen or one cyano, and further substituted with 1 or 2 substituent(s) selected from substituent group G; wherein the substituent group G is the group consisting of halogen, cyano, alkyl, alkenyl, alkynyl, haloalkyl, alkyloxy, alkenyloxy, alkynyloxy and haloalkyloxy, or a pharmaceutically acceptable salt thereof.

(6") The compound according to any one of the above items (1") to (5") and (1'"), wherein m is 0 or 1, or a pharmaceutically acceptable salt thereof.

(7") The compound according to any one of the above items (1") to (6") and (1'"), wherein n is 0 or 1, or a pharmaceutically acceptable salt thereof.

(8") The compound according to any one of the above items (1") to (7") and (1'"), wherein $R^{4a}$ is each independently a hydrogen atom or unsubstituted alkyl, and $R^{4b}$ is each independently a hydrogen atom, or a pharmaceutically acceptable salt thereof.

(9") The compound according to any one of the above items (1") to (8") and (1'"), wherein $R^{4a}$ is each independently a hydrogen atom, and $R^{4b}$ is each independently a hydrogen atom, or a pharmaceutically acceptable salt thereof.

(10") The compound according to any one of the above items (1") to (9") and (1'"), wherein $R^1$ is substituted or unsubstituted aromatic heterocyclyl, or a pharmaceutically acceptable salt thereof.

(11") The compound according to any one of the above items (1") to (9") and (1'"), wherein $R^1$ is substituted or unsubstituted aromatic heterocyclyl, m is 1, $R^{5a}$ is a hydrogen atom, and $R^{5b}$ is a hydrogen atom, or pharmaceutically acceptable salt thereof.

(12") The compound according to any one of the above items (1") to (9") and (1'"), wherein $R^1$ is substituted or unsubstituted aromatic heterocyclyl, and m is 0, or a pharmaceutically acceptable salt thereof.

(13") The compound according to any one of the above items (1") to (12") and (1'"), wherein $R^3$ is substituted or unsubstituted 6-membered aromatic carbocyclyl, substituted or unsubstituted 3- to 10-membered non-aromatic carbocyclyl, substituted or unsubstituted 5- to 6-membered aromatic heterocyclyl, substituted or unsubstituted 9- to 10-membered aromatic heterocyclyl, substituted or unsubstituted 13- to 15-membered aromatic heterocyclyl, or substituted or unsubstituted 3- to 20-membered non-aromatic heterocyclyl, or a pharmaceutically acceptable salt thereof.

(14") The compound according to any one of the above items (1") to (12") and (1'"), wherein $R^3$ is substituted or unsubstituted 6-membered aromatic carbocyclyl, substituted or unsubstituted 9- to 10-membered aromatic heterocyclyl, or substituted or unsubstituted 9- to 13-membered non-aromatic heterocyclyl, or a pharmaceutically acceptable salt thereof.

(15") The compound according to the above items (1") or (1'"), wherein

Formula (I) is Formula (I'):

[Chemical Formula 8]

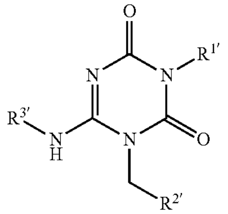

(I')

wherein $R^{1'}$ is a group represented by Formula:

[Chemical Formula 9]

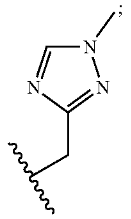

$R^{2'}$ is a group represented by Formula:

[Chemical Formula 10]

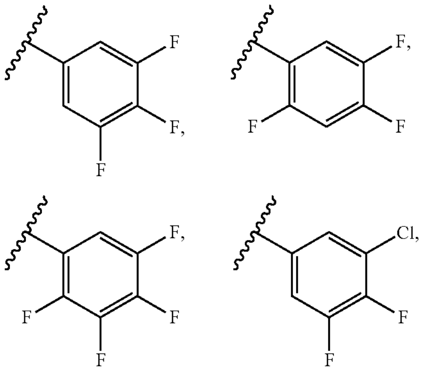

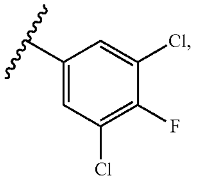

or

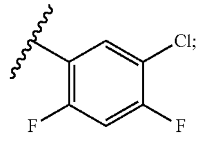

$R^{3'}$ is a group represented by Formula:

[Chemical Formula 11]

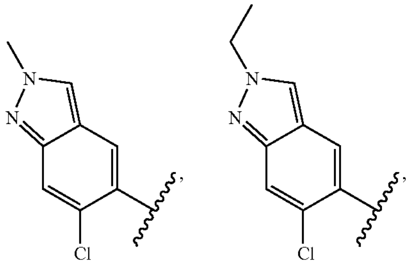

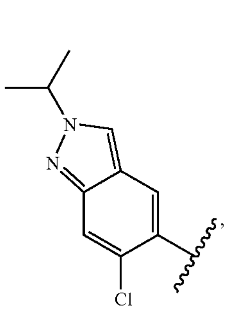

or

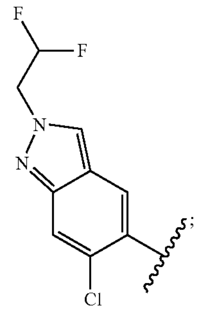

or a pharmaceutically acceptable salt thereof.

(16") The compound according to the above items (1") or (1'''), wherein Formula (I) is Formula (I')

[Chemical Formula 12]

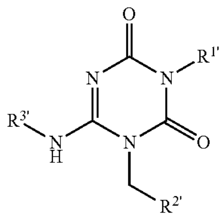

(I')

wherein $R^{1'}$ is a group represented by Formula:

[Chemical Formula 13]

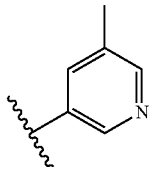

or

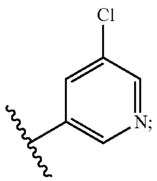

$R^{2'}$ is a group represented by Formula:

[Chemical Formula 14]

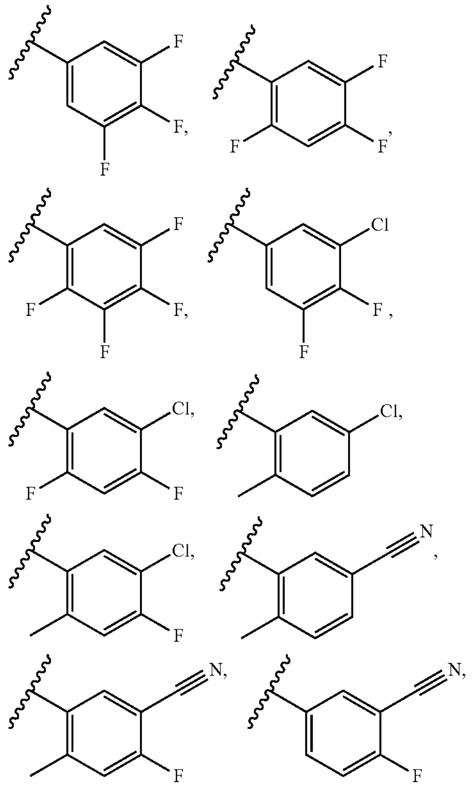

-continued
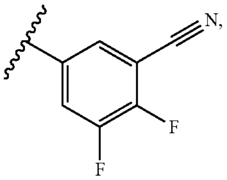
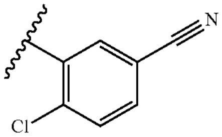
or
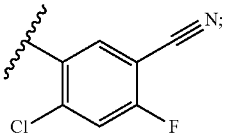
R$^{3'}$ is a group represented by Formula:
[Chemical Formula 15]
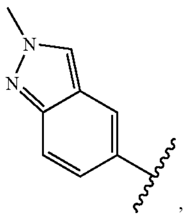
,
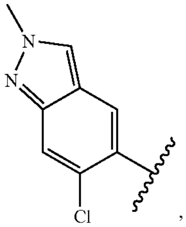
,
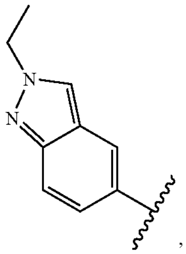
,
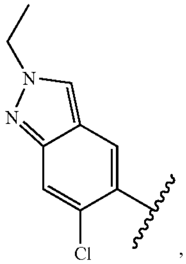
,
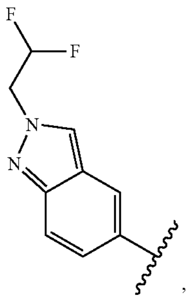
,
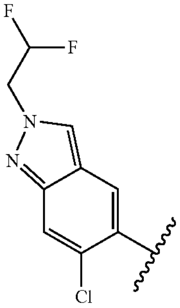
or
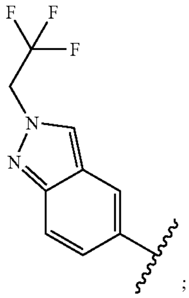
;
or a pharmaceutically acceptable salt thereof.
(17") The compound according to the above items (1") or (1'"), wherein
the compound is selected from the group consisting of:
[Chemical Formula 16]
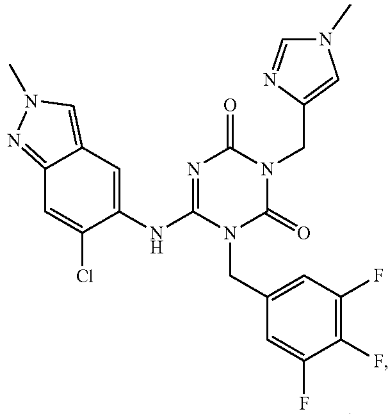
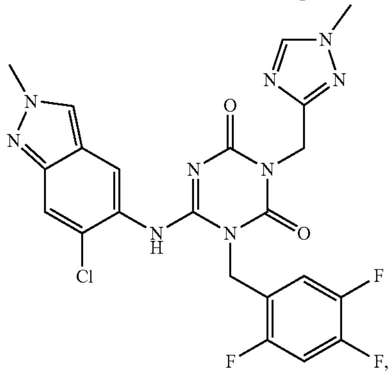
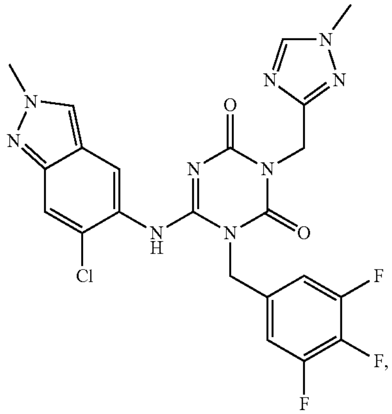
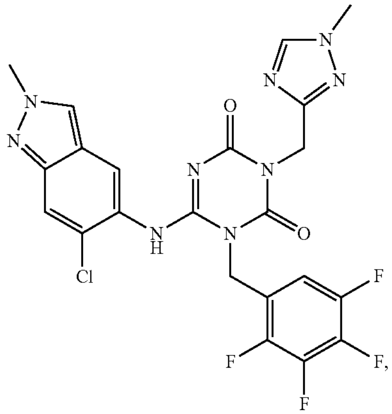

-continued
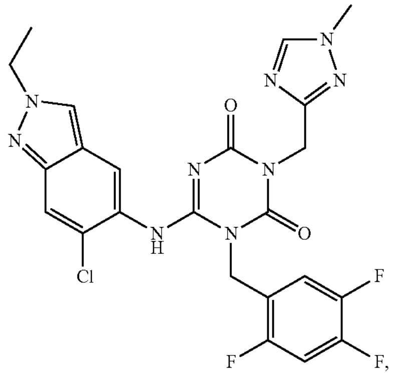 [SMILES: Cn1cnc(Cn2c(=O)nc(Nc3cc4cn(C)nc4cc3Cl)n(Cc3cc(F)c(F)cc3F)c2=O)n1]
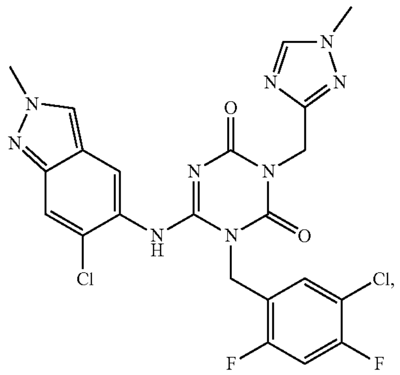
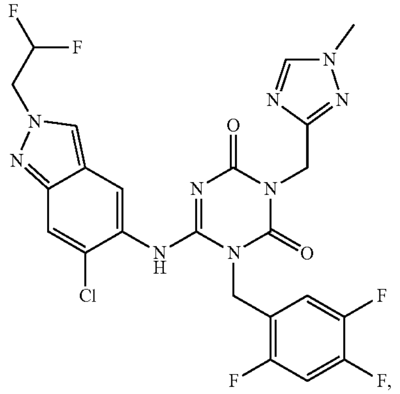
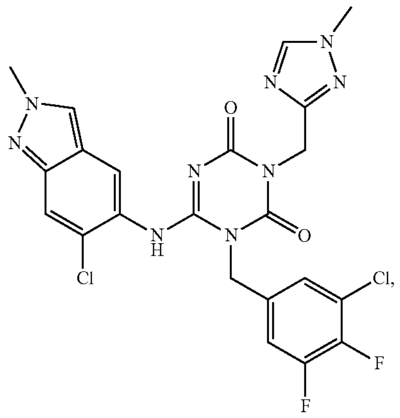
-continued
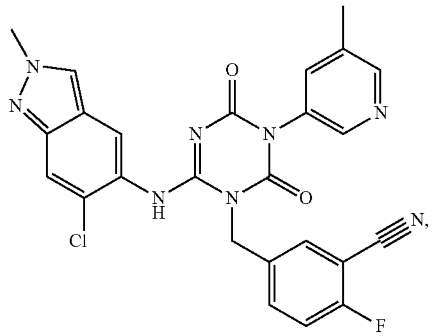
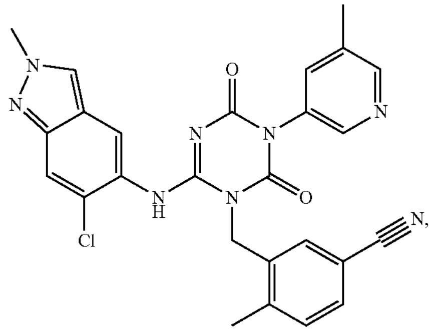
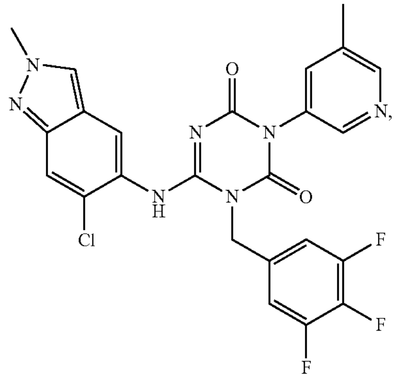
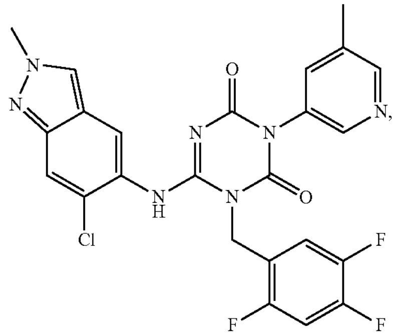
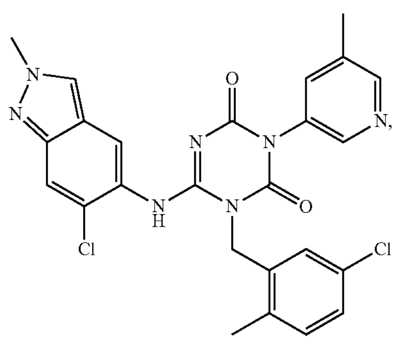

-continued

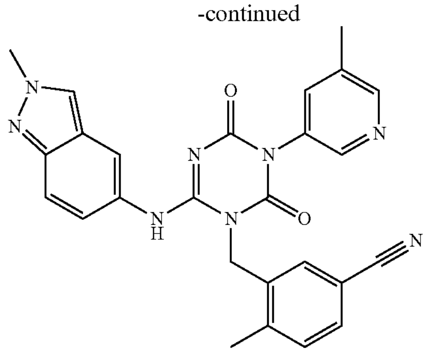

and

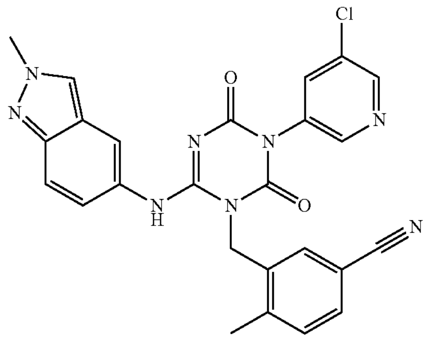

or a pharmaceutically acceptable salt thereof.

(18") A pharmaceutical composition comprising the compound according to any one of the above items (1") to (17") and (1'''), or a pharmaceutically acceptable salt thereof.

(19") A coronavirus 3CL protease inhibitor comprising the compound according to any one of the above items (1") to (17") and (1'''), or a pharmaceutically acceptable salt thereof.

(20") A coronavirus replication inhibitor comprising the compound according to any one of the above items (1") to (17") and (1'''), or a pharmaceutically acceptable salt thereof.

(21") The coronavirus replication inhibitor according to the above item (20"), wherein the coronavirus is an alpha coronavirus and/or beta coronavirus.

(22") The coronavirus replication inhibitor according to the above item (20"), wherein the coronavirus is SARS-CoV-2.

(23") A method for treating and/or preventing a disease associated with coronavirus 3CL proteases, characterized by administering the compound according to any one of the above items (1") to (17") and (1"), or a pharmaceutically acceptable salt thereof.

(24") The compound according to any one of the above items (1") to (17") and (1'''), or a pharmaceutically acceptable salt thereof for use in treating and/or preventing a disease associated with coronavirus 3CL proteases.

(1') A compound represented by Formula (I):

[Chemical Formula 17]

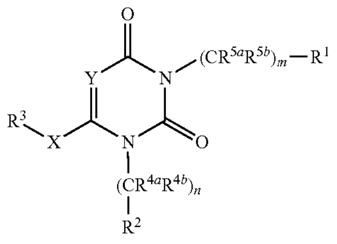

(I)

wherein

Y is N, or $CR^7$;

$R^7$ is a hydrogen atom, or substituted or unsubstituted alkyl;

$R^1$ is substituted or unsubstituted aromatic heterocyclyl, substituted or unsubstituted non-aromatic heterocyclyl, substituted or unsubstituted carbamoyl, or substituted or unsubstituted amino;

$R^2$ is substituted or unsubstituted aromatic carbocyclyl (provided that para-monofluorophenyl, para-monochlorophenyl, and para-monomethylphenyl are excluded), substituted or unsubstituted non-aromatic carbocyclyl, substituted or unsubstituted aromatic heterocyclyl, or substituted or unsubstituted non-aromatic heterocyclyl;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

—X— is $—NR^6—$, $—CR^6R^{6'}—$, —O—, —S—, or a single bond;

$R^6$ and $R^{6'}$ are each independently a hydrogen atom, or substituted or unsubstituted alkyl;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

n is 0, 1, or 2;

$R^{4a}$ is each independently a hydrogen atom, or substituted or unsubstituted alkyl;

$R^{4b}$ is each independently a hydrogen atom, or substituted or unsubstituted alkyl;

provided that the following compounds are excluded:

[Chemical Formula 18]

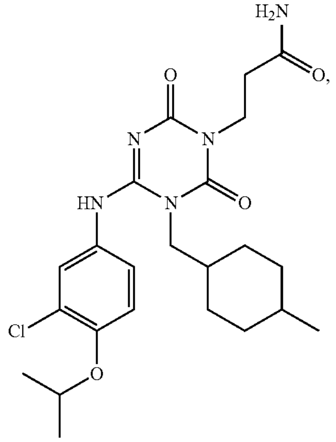

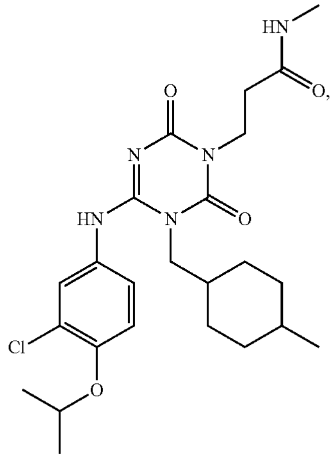

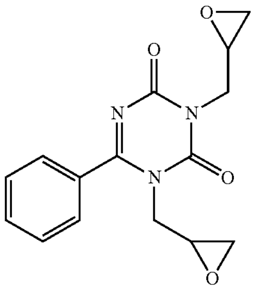

and

-continued

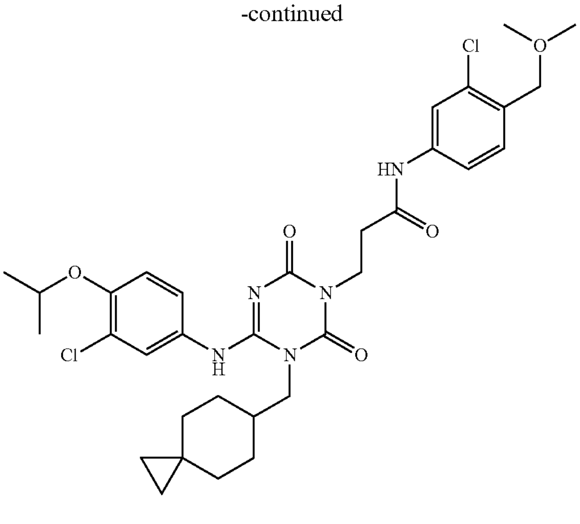

or a pharmaceutically acceptable salt thereof.

(1) A compound represented by Formula (I):

[Chemical Formula 19]

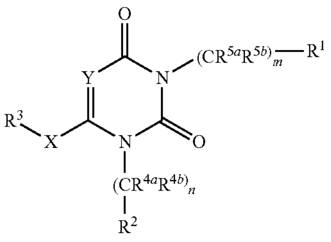

(I)

wherein

Y is N, or $CR^7$;

$R^7$ is a hydrogen atom, or substituted or unsubstituted alkyl;

$R^1$ is substituted or unsubstituted aromatic heterocyclyl, substituted or unsubstituted non-aromatic heterocyclyl, substituted or unsubstituted carbamoyl, or substituted or unsubstituted amino;

$R^2$ is substituted or unsubstituted aromatic carbocyclyl (provided that para-fluorophenyl, para-chlorophenyl, and para-methylphenyl are excluded), substituted or unsubstituted non-aromatic carbocyclyl, substituted or unsubstituted aromatic heterocyclyl, substituted or unsubstituted non-aromatic heterocyclyl, or substituted or unsubstituted alkyl;

$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

—X— is —$NR^6$—, —$CR^6R^{6'}$—, —O—, —S—, or a single bond;

$R^6$ and $R^{6'}$ are each independently a hydrogen atom, or substituted or unsubstituted alkyl;

m is 0, 1, or 2;

$R^{5a}$ is each independently a hydrogen atom, or substituted or unsubstituted $R^{5b}$ is each independently a hydrogen atom, or substituted or unsubstituted alkyl;

n is 0, 1, or 2;

$R^{4a}$ is each independently a hydrogen atom, or substituted or unsubstituted alkyl;

$R^{4b}$ is each independently a hydrogen atom, or substituted or unsubstituted alkyl;

provided that the following compounds are excluded:

[Chemical Formula 20]

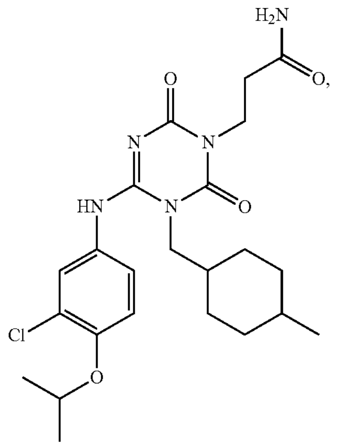

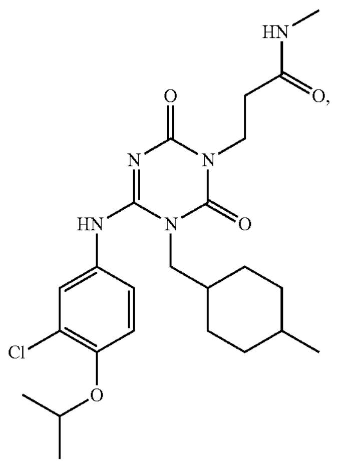

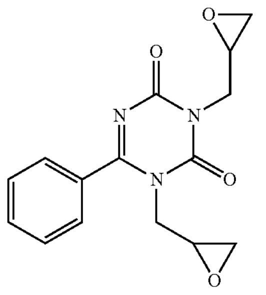

and

-continued

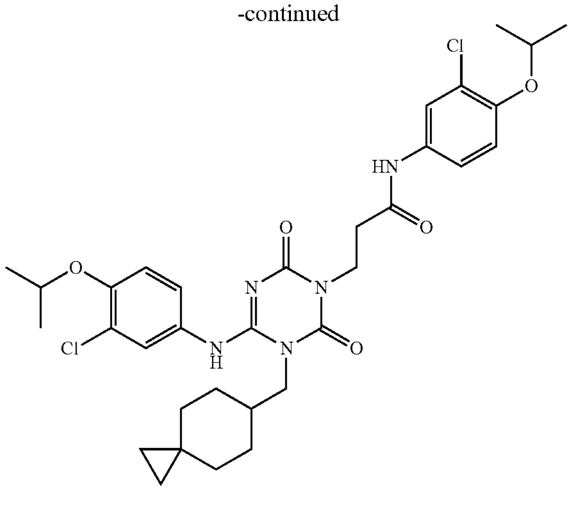

or a pharmaceutically acceptable salt thereof.

(2) The compound according to the above item (1) or (1'), wherein

Y is N, or a pharmaceutically acceptable salt thereof.

(3) The compound according to the above item (1), (2), or (1'), wherein

—X— is —NH—, or a pharmaceutically acceptable salt thereof.

(4') The compound according to any one of the above items (1) to (3) and (1'), wherein $R^2$ is substituted or unsubstituted 6-, 10-, or 14-membered aromatic carbocyclyl, substituted or unsubstituted 5-, 6-, 9-, or 10-membered non-aromatic carbocyclyl, substituted or unsubstituted 5-, 6-, 9-, or 10-membered aromatic heterocyclyl, or substituted or unsubstituted 5-, 6-, 9-, or 10-membered non-aromatic heterocyclyl, or a pharmaceutically acceptable salt thereof.

(4) The compound according to any one of the above items (1) to (3) and (1'), wherein $R^2$ is substituted or unsubstituted 6-membered aromatic carbocyclyl, substituted or unsubstituted 9- or 10-membered non-aromatic carbocyclyl, substituted or unsubstituted 5- or 6-membered aromatic heterocyclyl, or substituted or unsubstituted 9- or 10-membered non-aromatic heterocyclyl, or a pharmaceutically acceptable salt thereof.

(5') The compound according to any one of the above items (1) to (4), (1'), and (4'), wherein $R^2$ is 6-membered aromatic carbocyclyl substituted with one halogen or one cyano and further substituted with 1, 2, 3 or 4 substituent(s) selected from substituent group G, or 6-membered aromatic heterocyclyl substituted with one halogen or one cyano and further substituted with 1 or 2 substituent(s) selected from substituent group G; wherein the substituent group G is the group consisting of halogen, cyano, alkyl, alkenyl, alkynyl, haloalkyl, alkyloxy, alkenyloxy, alkynyloxy, and haloalkyloxy, or a pharmaceutically acceptable salt thereof.

Here, the 1, 2, 3, or 4 substituent(s) selected from substituent group G may be each identical or different.

(5) The compound according to any one of the above items (1) to (4), (1') and (4'), wherein $R^2$ is 6-membered aromatic carbocyclyl substituted with one halogen and further substituted with 1, 2, 3 or 4 substituent(s) selected from substituent group G, or 6-membered aromatic heterocyclyl substituted with one halogen and further substituted with 1 or 2 substituent(s) selected from substituent group G; wherein the substituent group G is the group consisting of halogen, cyano, alkyl, alkenyl, alkynyl, haloalkyl, alkyloxy, alkenyloxy, alkynyloxy, and haloalkyloxy, or a pharmaceutically acceptable salt thereof.

(6) The compound according to any one of the above items (1) to (5), (1'), (4'), and (5'), wherein m is 0 or 1, or a pharmaceutically acceptable salt thereof.

(7) The compound according to any one of the above items (1) to (6), (1'), (4'), and (5'), wherein n is 0 or 1, or a pharmaceutically acceptable salt thereof.

(8) The compound according to any one of the above items (1) to (7), (1'), (4'), and (5'), wherein $R^{4a}$ is each independently a hydrogen atom or unsubstituted alkyl, and $R^{4b}$ is each independently a hydrogen atom, or a pharmaceutically acceptable salt thereof.

(9) The compound according to any one of the above items (1) to (8), (1'), (4'), and (5'), wherein $R^{5a}$ is each independently a hydrogen atom, and $R^{5b}$ is each independently a hydrogen atom, or a pharmaceutically acceptable salt thereof.

(10) The compound according to any one of the above items (1) to (9), (1'), (4'), and (5'), wherein $R^1$ is substituted or unsubstituted non-aromatic heterocyclyl or substituted or unsubstituted aromatic heterocyclyl, or a pharmaceutically acceptable salt thereof.

(10') The compound according to any one of the above items (1) to (9), (1'), (4'), and (5'), wherein $R^1$ is substituted or unsubstituted aromatic heterocyclyl, or a pharmaceutically acceptable salt thereof.

(11) The compound according to any one of the above items (1) to (9), (1'), (4'), and (5'), wherein $R^1$ is substituted or unsubstituted non-aromatic heterocyclyl or substituted or unsubstituted aromatic heterocyclyl, m is 1, $R^{5a}$ is a hydrogen atom, and $R^{5b}$ is a hydrogen atom, or a pharmaceutically acceptable salt thereof.

(11') The compound according to any one of the above items (1) to (9), (1'), (4') and (5'), wherein $R^1$ is substituted or unsubstituted aromatic heterocyclyl, m is 1, $R^{5a}$ is a hydrogen atom, and $R^{5b}$ is a hydrogen atom, or pharmaceutically acceptable salt thereof.

(12) The compound according to any one of the above items (1) to (9), (1'), (4') and (5'), wherein $R^1$ is substituted or unsubstituted aromatic heterocyclyl, and m is 0, or a pharmaceutically acceptable salt thereof.

(13) The compound according to any one of the above items (1) to (12), (1'), (4'), (5'), (10'), and (11'), wherein $R^3$ is substituted or unsubstituted 6-membered aromatic carbocyclyl, substituted or unsubstituted 3- to 10-membered non-aromatic carbocyclyl, substituted or unsubstituted 5- or 6-membered aromatic heterocyclyl, substituted or unsubstituted 9- or 10-membered aromatic heterocyclyl, substituted or unsubstituted 13- to 15-membered aromatic heterocyclyl, or substituted or unsubstituted 3- to 20-membered non-aromatic heterocyclyl, or a pharmaceutically acceptable salt thereof.

(14) The compound according to any one of the above items (1) to (13), (1'), (4'), (5'), (10'), and (11'), wherein $R^3$ is substituted or unsubstituted 6-membered aromatic carbocyclyl, substituted or unsubstituted 9- or 10-membered aromatic heterocyclyl, or substituted or unsubstituted 9- to 13-membered non-aromatic heterocyclyl, or a pharmaceutically acceptable salt thereof.

(15-1) The compound according to the above item (1) or (1'), wherein

Formula (I) is Formula (I'):

[Chemical Formula 21]

(I')

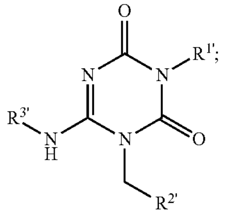

wherein $R^{1'}$ is a group represented by Formula:

[Chemical Formula 22]

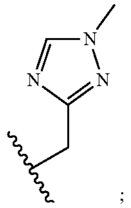

;

$R^{2'}$ is a group represented by Formula:

[Chemical Formula 23]

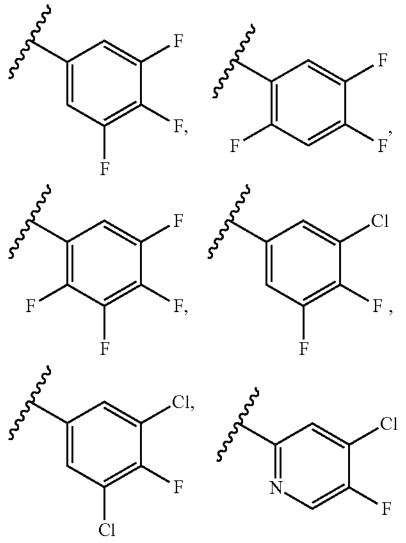

-continued
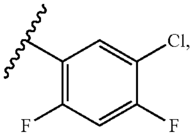
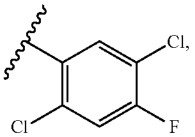
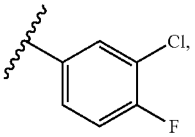
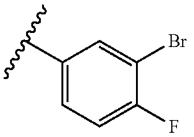
or
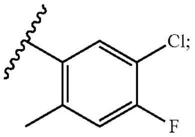
and
$R^{3'}$ is a group represented by Formula:
[Chemical Formula 24]
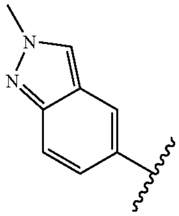
,
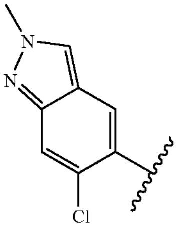
,
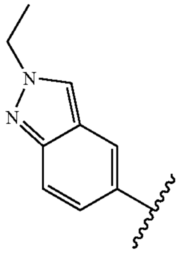
,
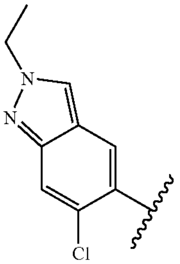
,
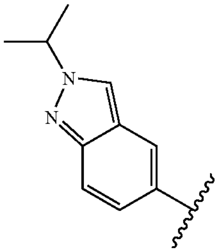
,
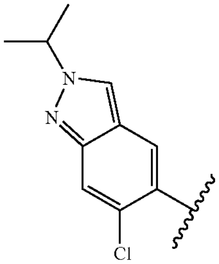
,
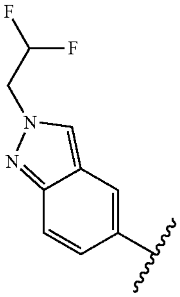
,
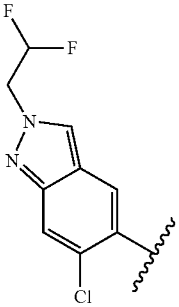
,
-continued
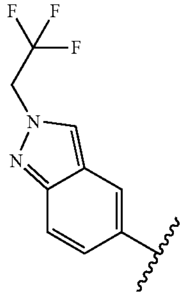
,
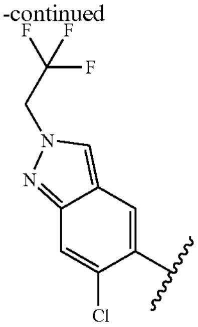
,
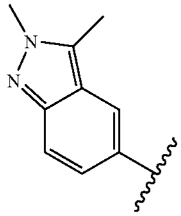
or,
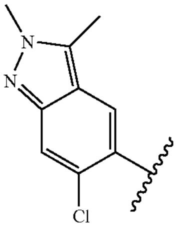
;
or a pharmaceutically acceptable salt thereof.
(16-1) The compound according to the above item (1) or (1'), wherein
Formula (I) is Formula (I'):
[Chemical Formula 25]
(I')
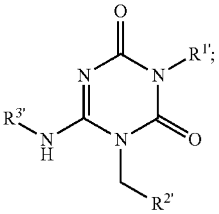
wherein
$R^{1'}$ is a group represented by Formula:
[Chemical Formula 26]
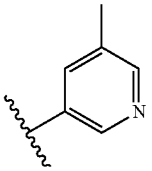
or
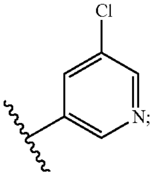
$R^{2'}$ is a group represented by Formula:
[Chemical Formula 27]
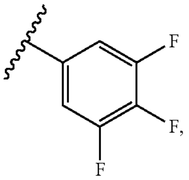
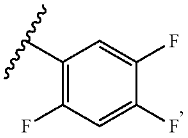

-continued
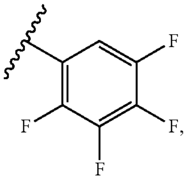
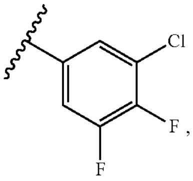
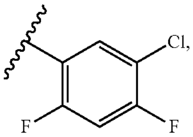
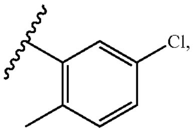
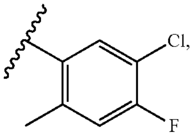
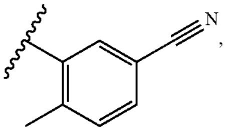
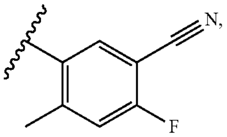
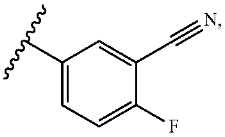
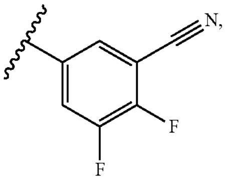
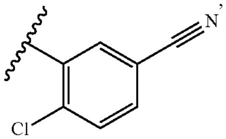
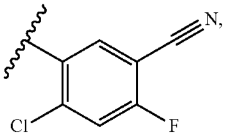
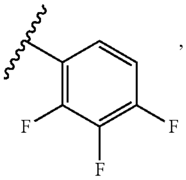
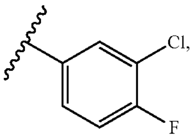
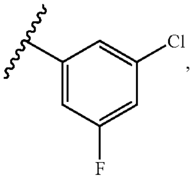
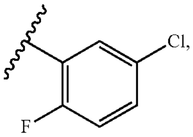
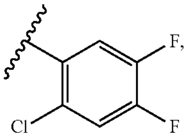
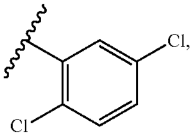
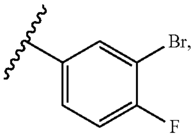
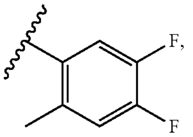
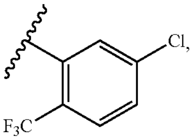
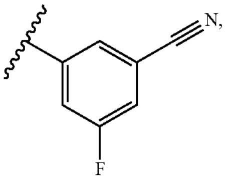
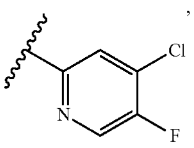
-continued
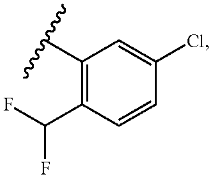
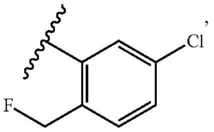
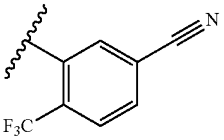
or
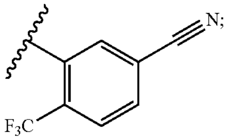
and
$R^{3'}$ is a group represented by Formula:
[Chemical Formula 28]
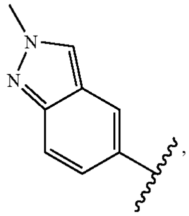
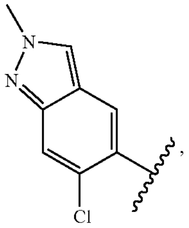
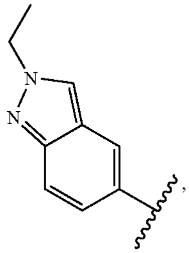
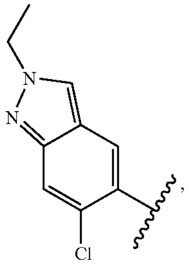
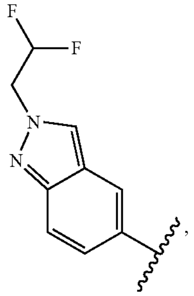
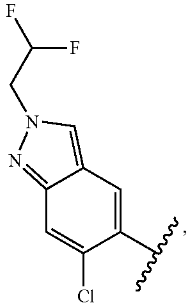
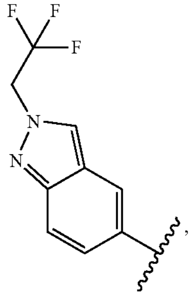
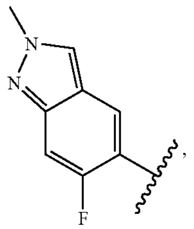

-continued
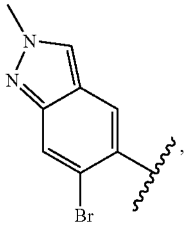,
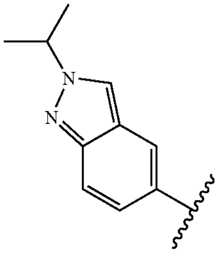,
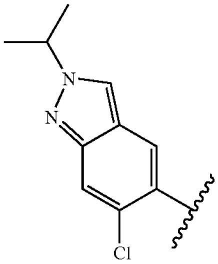,
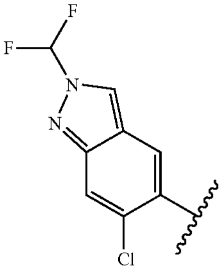,
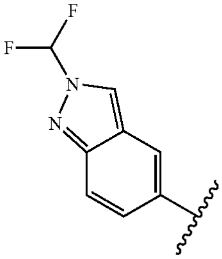,
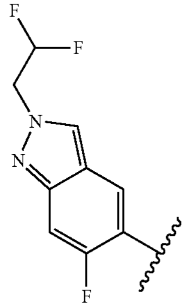,
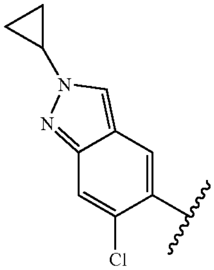,
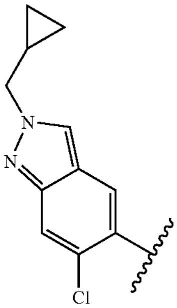,
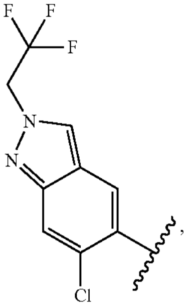,
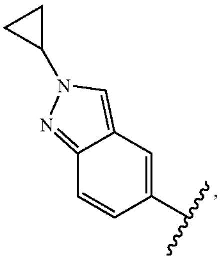,
-continued
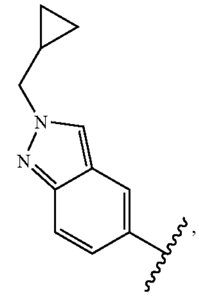,
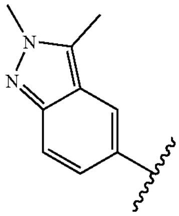 or
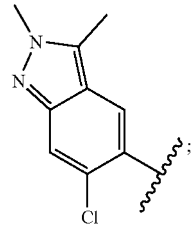;
or a pharmaceutically acceptable salt thereof.
(15') The compound according to the above item (1) or (1'), wherein
Formula (I) is Formula (P):
[Cheical Formula 29]
(I')
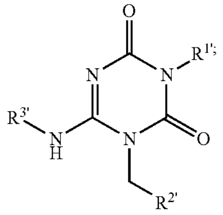
wherein
$R^{1'}$ is a group represented by Formula:
[Chemical Formula 30]
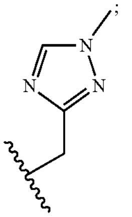
$R^{2'}$ is a group represented by Formula:
[Chemical Formula 31]
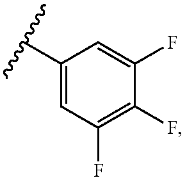,
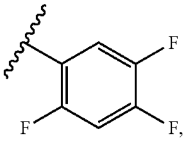, -continued
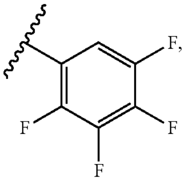
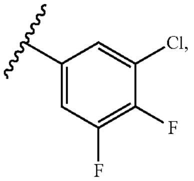
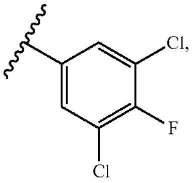 or 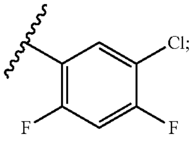
and
$R^{3'}$ is a group represented by Formula:
[Chemical Formula 32]
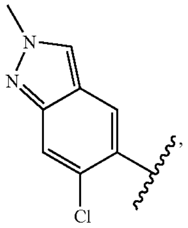
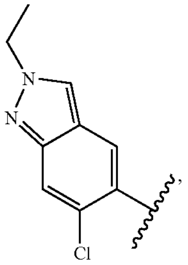
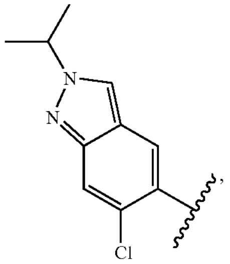 or 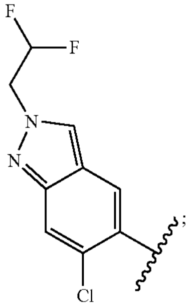
or a pharmaceutically acceptable salt thereof.
(16') The compound according to the above item (1) or (1'), wherein
Formula (I) is Formula (I'):
[Chemical Formula 33]
(I')
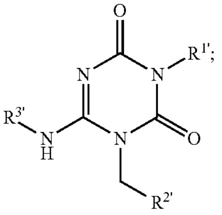
wherein
$R^{1'}$ is a group represented by Formula:
[Chemical Formula 34]
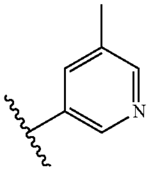 or 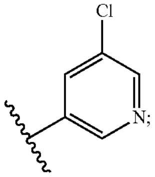
$R^{2'}$ is a group represented by Formula:
[Chemical Formula 35]
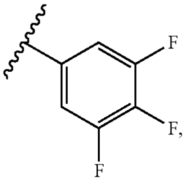
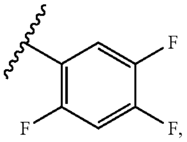
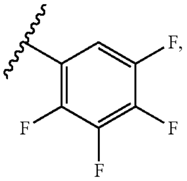
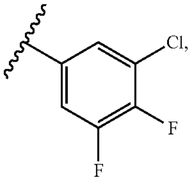
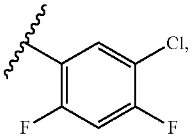
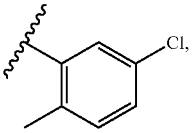
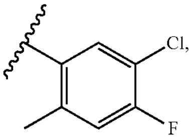
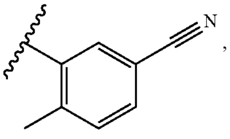
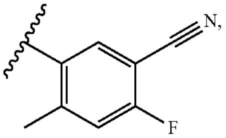
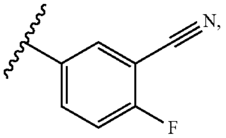
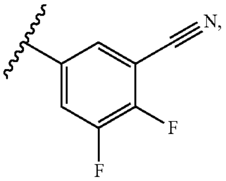
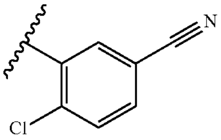 or
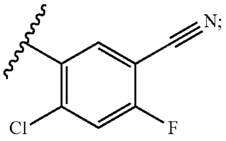

and
$R^{3'}$ is a group represented by Formula:
[Chemical Formula 36]
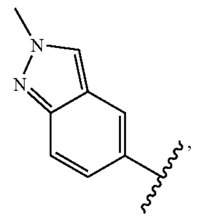
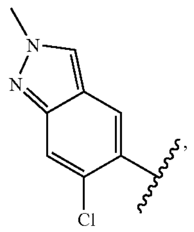
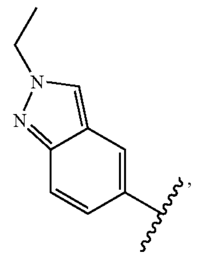
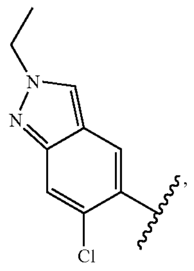
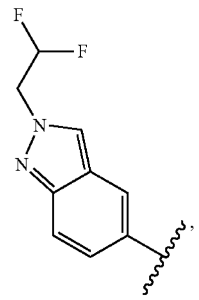
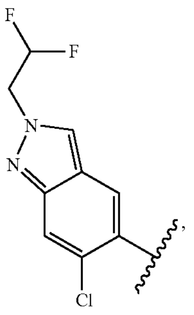
or
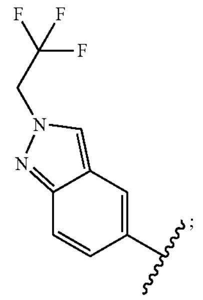
or a pharmaceutically acceptable salt thereof.
(17') The compound according to the above item (1) or (1'), wherein
the compound is selected from the group consisting of:
[Chemical Formula 37]
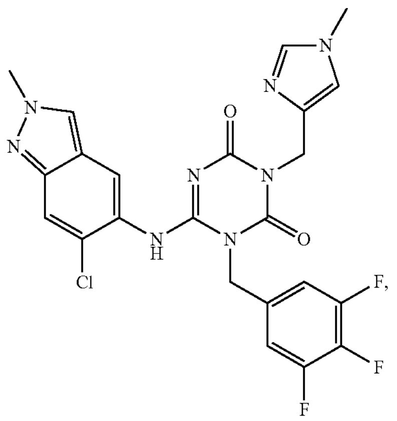
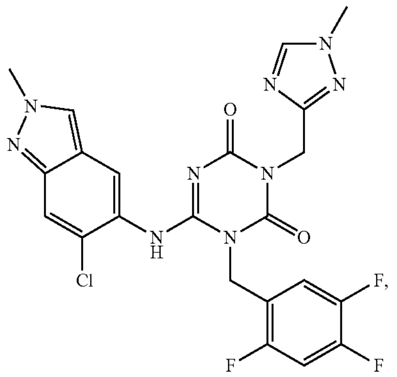
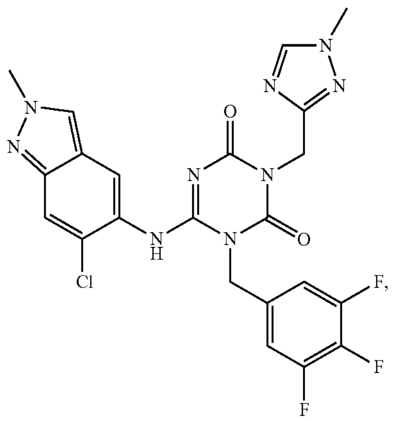

-continued
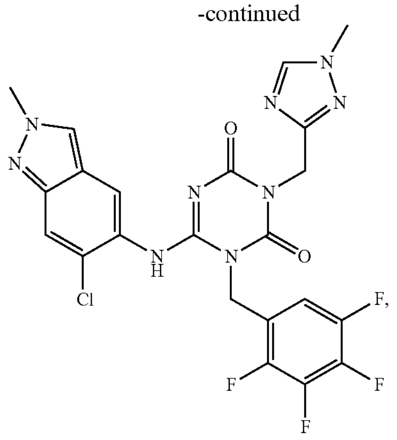
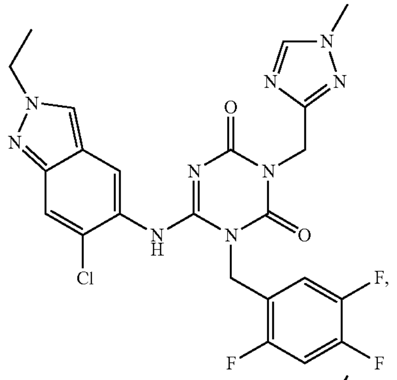
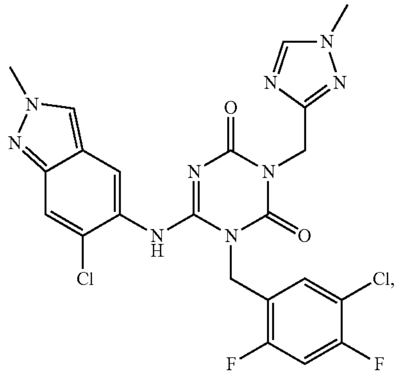
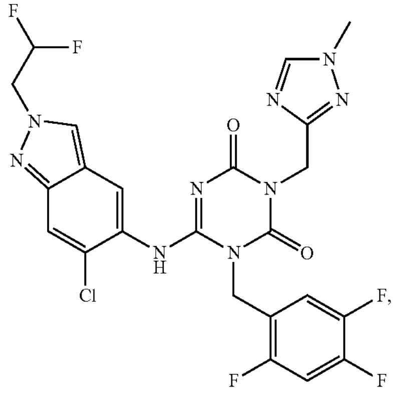
-continued
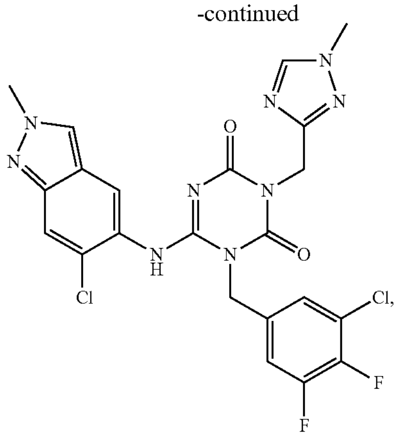
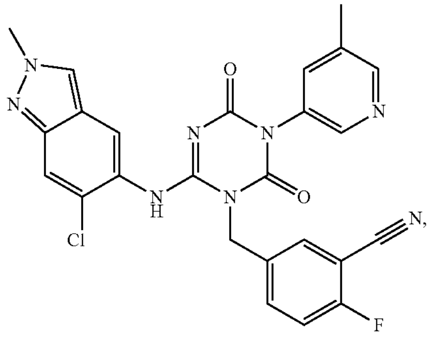
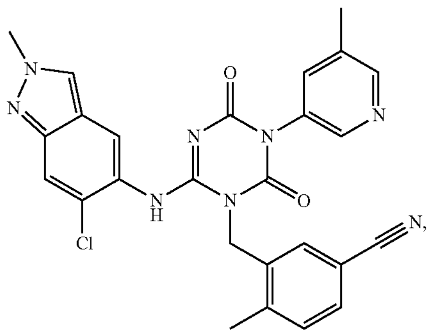
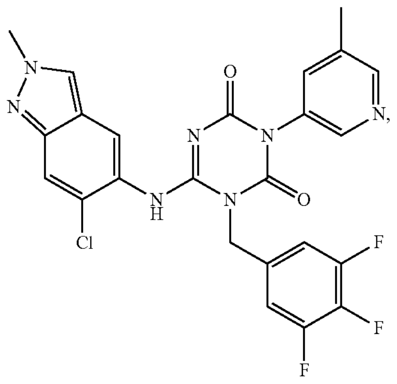

-continued

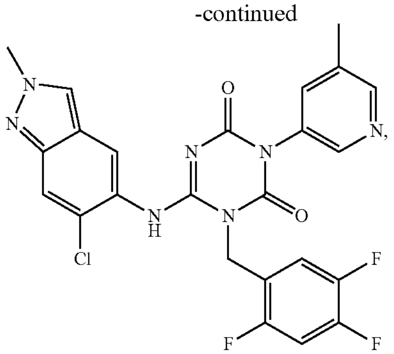

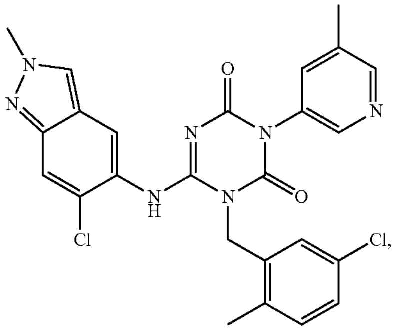

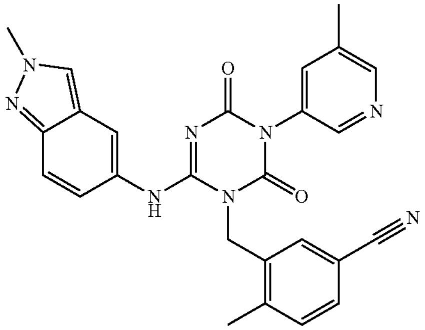

and

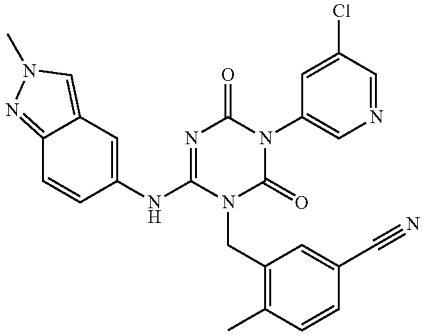

or a pharmaceutically acceptable salt thereof.

(15) A pharmaceutical composition comprising the compound according to any one of the above items (1) to (14), (1'), (4'), (5'), (10'), (11'), and (15') to (17'), (15-1) and (16-1), or a pharmaceutically acceptable salt thereof.

(16) A coronavirus 3CL protease inhibitor comprising the compound according to any one of the above items (1) to (14), (1'), (4'), (5'), (10'), (11'), and (15') to (17'), (15-1) and (16-1), or a pharmaceutically acceptable salt thereof.

(17) A coronavirus replication inhibitor comprising the compound according to any one of the above items (1) to (14), (1'), (4'), (5'), (10'), (11% and (15') to (17'), (15-1) and (16-1), or a pharmaceutically acceptable salt thereof.

(18) The coronavirus replication inhibitor according to the above item (17), wherein the coronavirus is an alphacoronavirus and/or betacoronavirus.

(19) The coronavirus replication inhibitor according to the above item (17), wherein the coronavirus is SARS-CoV-2.

(20) A pharmaceutical composition for preventing and/or treating coronavirus infections, the pharmaceutical composition comprising the compound according to any one of the above items (1) to (14), (1'), (4'), (5'), (10'), (11'), (15') to (17'), (15-1), (16-1), (1") and (1'"), or a pharmaceutically acceptable salt thereof.

(21) The pharmaceutical composition according to the above item (20), for preventing and/or treating novel coronavirus infections (COVID-19).

(22) The pharmaceutical composition according to the above item (20), for preventing and/or treating infections caused by SARS-CoV-2.

(23) A method for inhibiting replication of coronavirus, the method including administering the compound according to any one of the above items (1) to (14), (1'), (4'), (5'), (10'), (11'), (15') to (17'), (15-1), (16-1), (1") and (1"), or a pharmaceutically acceptable salt thereof.

(23-1) The method for inhibiting replication according to the above item (23), wherein the coronavirus is an alphacoronavirus and/or betacoronavirus.

(24) The method for inhibiting replication according to the above item (23), wherein the coronavirus is SARS-CoV-2.

(25) A method for treating and/or preventing a disease associated with coronavirus 3CL proteases, the method including administering the compound according to any one of the above items (1) to (14), (1'), (4'), (5'), (10'), (11'), (15') to (17'), (15-1), (16-1) (1") and (1'"), or a pharmaceutically acceptable salt thereof.

(26) A method for treating and/or preventing coronavirus infections, the method including administering the compound according to any one of the above items (1) to (14), (1'), (4'), (5'), (10'), (11'), (15') to (17'), (15-1), (16-1), (1") and (1'"), or a pharmaceutically acceptable salt thereof.

(27) The method for preventing and/or treating according to the above item (26), wherein the coronavirus infections are novel coronavirus infections (COVID-19).

(28) The method for preventing and/or treating according to the above item (26), wherein the coronavirus infections are infections caused by SARS-CoV-2.

(29) Use of the compound according to any one of the above items (1) to (14), (1'), (4'), (5'), (10'), (10, (15') to (17'), (15-1), (16-1), (1") and (1'"), or a pharmaceutically acceptable salt thereof, for producing a therapeutic and/or prophylactic agent for a disease associated with coronavirus 3CL proteases.

(30) Use of the compound according to any one of the above items (1) to (14), (1'), (4'), (5'), (10'), (11'), (15') to (17'), (15-1), (16-1), (1") and (1'"), or a pharmaceutically acceptable salt thereof, for producing a replication inhibitor for coronavirus.

(31) The use according to the above item (30), wherein the coronavirus is an alphacoronavirus and/or betacoronavirus.

(32) The use according to the above item (30), wherein the coronavirus is SARS-CoV-2.

(33) Use of the compound according to any one of the above items (1) to (14), (1'), (4'), (5'), (10'), (11'), (15') to (17'), (15-1), (16-1), (1") and (1'''), or a pharmaceutically acceptable salt thereof, for producing a therapeutic and/or prophylactic agent for coronavirus infections.

(34) The use according to the above item (33), wherein the coronavirus infections are novel coronavirus infections (COVID-19).

(35) The use according to the above item (33), wherein the coronavirus infections are infections caused by SARS-CoV-2.

(36) The compound according to any one of the above items (1) to (14), (1'), (4'), (51, (10'), (11'), (15') to (17'), (15-1), (16-1), (1") and (1'''), or a pharmaceutically acceptable salt thereof, for use in the treatment and/or prevention of a disease associated with coronavirus 3CL proteases.

(37) The compound according to any one of the above items (1) to (14), (1'), (4'), (5'), (10'), (11'), (15') to (17'), (15-1), (16-1), (1") and (1'''), or a pharmaceutically acceptable salt thereof, for use in the inhibition of replication of coronavirus.

(37-1) The compound according to the above item (37), or a pharmaceutically acceptable salt thereof, wherein the coronavirus is an alphacoronavirus and/or betacoronavirus.

(37-2) The compound according to the above item (37), or a pharmaceutically acceptable salt thereof, wherein the coronavirus is SARS-CoV-2.

(38) The compound according to any one of the above items (1) to (14), (1'), (4'), (5), (10'), (11'), (15') to (17'), (15-1), (16-1), (1") and (1'''), or a pharmaceutically acceptable salt thereof, for use in treating and/or preventing coronavirus infections.

(39) The compound according to the above item (38), or a pharmaceutically acceptable salt thereof, wherein the coronavirus infections are novel coronavirus infections (COVID-19).

(40) The compound according to the above item (38), or a pharmaceutically acceptable salt thereof, wherein the coronavirus infections are infections caused by SARS-CoV-2.

(41) A compound represented by Formula (I);

[Chemical Formula 38]

(I)

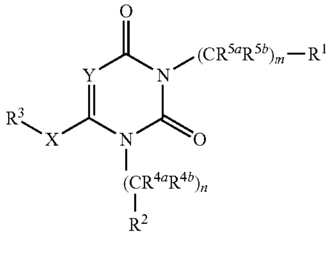

wherein

Y is N, or $CR^7$;

$R^7$ is a hydrogen atom, or substituted or unsubstituted alkyl;

$R^1$ is substituted or unsubstituted non-aromatic heterocyclyl, substituted or unsubstituted aromatic heterocyclyl, substituted or unsubstituted carbamoyl, or substituted or unsubstituted amino;

$R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

$R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

—X— is —$NR^6$—, —$CR^6R^{6'}$—, —O—, —S—, or a single bond;

$R^6$ and $R^{6'}$ are each independently a hydrogen atom, or substituted or unsubstituted alkyl;

m is 0, 1, or 2;

$R^{5a}$ is each independently a hydrogen atom, or substituted or unsubstituted alkyl;

$R^{5b}$ is each independently a hydrogen atom, or substituted or unsubstituted.

n is 0, 1, or 2;

$R^{4a}$ is each independently a hydrogen atom, or substituted or unsubstituted $R^{4b}$ is each independently a hydrogen atom, or substituted or unsubstituted alkyl, or a pharmaceutically acceptable salt thereof.

(42) The compound according to the above item (41), wherein

Y is N, or a pharmaceutically acceptable salt thereof.

(43) The compound according to the above item (41) or (42), wherein $R^1$ is substituted or unsubstituted aromatic heterocyclyl, or a pharmaceutically acceptable salt thereof.

(44) The compound according to any one of the above items (41) to (43), wherein $R^2$ is substituted or unsubstituted 6-membered aromatic carbocyclyl, or a pharmaceutically acceptable salt thereof.

(45) The compound according to any one of the above items (41) to (44), wherein $R^3$ is substituted or unsubstituted aromatic heterocyclyl, or a pharmaceutically acceptable salt thereof.

(46) The compound according to any one of the above items (41) to (45), wherein

—X— is —NH—, or a pharmaceutically acceptable salt thereof.

(47) The compound according to any one of the above items (41) to (46), wherein m is 0 or 1, or a pharmaceutically acceptable salt thereof.

(48) The compound according to any one of the above items (41) to (47), wherein $R^{5a}$ is a hydrogen atom, or a pharmaceutically acceptable salt thereof.

(49) The compound according to any one of the above items (41) to (48), wherein $R^{5b}$ is a hydrogen atom, or a pharmaceutically acceptable salt thereof.

(50) The compound according to any one of the above items (41) to (49), wherein n is 1, or a pharmaceutically acceptable salt thereof.

(51) The compound according to any one of the above items (41) to (50, wherein $R^{4a}$ is a hydrogen atom, or a pharmaceutically acceptable salt thereof.

(52) The compound according to any one of the above items (41) to (51), wherein $R^{4b}$ is a hydrogen atom, or a pharmaceutically acceptable salt thereof.

(53) The compound according to any one of the above items (41) to (52), wherein $R^1$ is substituted or unsubstituted 5- or 6-membered aromatic heterocyclyl, or a pharmaceutically acceptable salt thereof.

(54) The compound according to any one of the above items (41) to (53), wherein $R^2$ is 6-membered aromatic carbocyclyl substituted with 1, 2, or 3 substituents selected from substituent group G; wherein the substituent group G is a group consisting of halogen, cyano, and alkyl, or a pharmaceutically acceptable salt thereof.

(55) The compound according to any one of the above items (41) to (54), wherein $R^3$ is substituted or unsubstituted 9- or 10-membered aromatic heterocyclyl, or a pharmaceutically acceptable salt thereof.

(AA1) A compound represented by Formula:

[Chemical Formula 39]

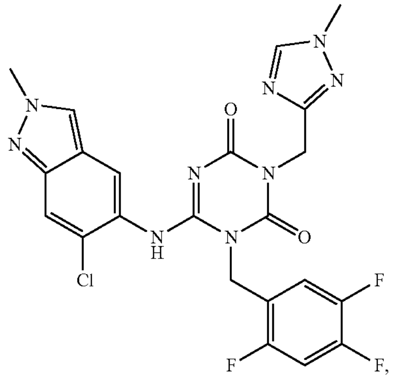 [SMILES: Cn1cnc(Cn2c(=O)nc(Nc3cc4cn(C)nc4cc3Cl)n(Cc3cc(F)c(F)cc3F)c2=O)n1]

or a pharmaceutically acceptable salt thereof.

(AA1') A compound represented by Formula:

[Chemical Formula 40]

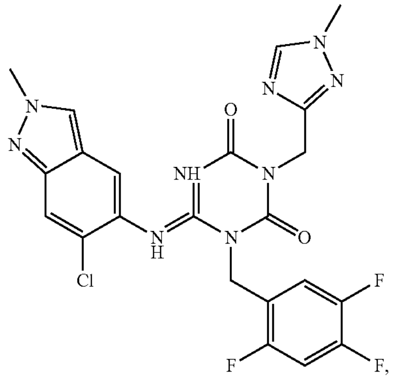

or a pharmaceutically acceptable salt thereof.

(AA2) A pharmaceutical composition comprising the compound according to the above items (AA1) or (AA1'), or a pharmaceutically acceptable salt thereof.

(AA3) A coronavirus 3CL protease inhibitor comprising the compound according to the above items (AA1) or (AA1'), or a pharmaceutically acceptable salt thereof.

(AA4) A coronavirus replication inhibitor comprising the compound according to the above items (AA1) or (AA1'), or a pharmaceutically acceptable salt thereof.

(AA5) The coronavirus replication inhibitor according to the above item (AA4), wherein the coronavirus is an alpha coronavirus and/or beta coronavirus.

(AA6) The coronavirus replication inhibitor according to the above item (AA4), wherein the coronavirus is SARS-CoV-2.

(AA7) A method for treating and/or preventing a disease associated with coronavirus 3CL proteases, characterized by administering the compound according to the above items (AA1) or (AA1'), or a pharmaceutically acceptable salt thereof.

(AA8) The compound according to the above items (AA1) or (AA1'), or a pharmaceutically acceptable salt thereof for use in treating and/or preventing a disease associated with coronavirus 3CL proteases.

Furthermore, the present invention relates to the following.

(1A) A p-toluenesulfonate salt of a compound represented by Formula (I-A):

[Chemical Formula 41]

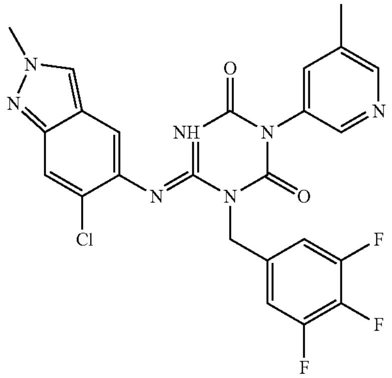

or solvate thereof.

(2A) A crystalline form of p-toluenesulfonate salt of a compound represented by Formula (I-A):

[Chemical Formula 42]

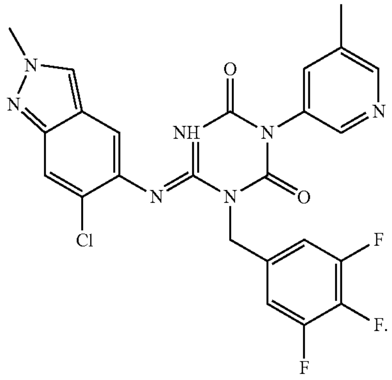

(3A) The crystalline form of p-toluenesulfonate Form I according to the above item (2A), which exhibits a powder X-ray diffraction pattern having peaks at diffraction angles (2θ): 9.1±0.2°, 15.2±0.2°, 18.8±0.2°, 23.6±0.2° and 24.9±0.2°.

(4A) The crystalline form of p-toluenesulfonate Form I according to the above item (2A), which exhibits a powder X-ray diffraction pattern having peaks at diffraction angles (2θ): 9.1±0.2°, 11.5±0.2°, 14.6±0.2°, 15.2±0.2°, 18.8±0.2°, 20.2±0.2°, 23.6±0.2°, 24.2±0.2°, 24.9±0.2° and 26.9±0.2°.

(5A) A pharmaceutical composition comprising the crystalline form according to any one of the above items (2A) to (4A).

(6A) The crystalline form of p-toluenesulfonate Form I according to the above item (2A), whose crystallographic data when measured at 298 K is characterized by the following crystallographic data:

Space group: P-1
a=8.8 Å±0.5 Å
b=10.3 Å±0.5 Å
c=18.0 Å±0.5 Å
α=103.7°±0.5°
β=97.4°±0.5°
γ=100.4°±0.5°

(7A) The crystalline form of p-toluenesulfonate Form I according to the above item (2A), whose crystallographic data when measured at 298 K is substantially in accordance with the following crystallographic data:

Space group: P-1
a=8.7844 Å
b=10.2991 Å
c=18.0182 Å
α=103.727°
β=97.411°
γ=100.358°

(8A) The crystalline form of p-toluenesulfonate Form I according to the above item (2A), characterized by a powder X-ray diffraction pattern substantially identical to that shown in FIG. 1.

(9A) A pharmaceutical composition comprising the crystalline form according to any one of the above items (6A) to (8A).

(1B) A complex comprising a compound represented by Formula (I-B):

[Chemical Formula 43]

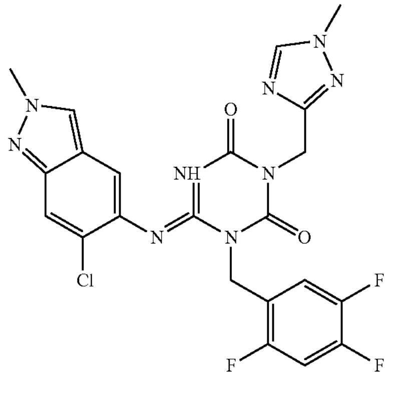

and fumaric acid.

(2B) The complex according to the above item (1B), wherein the compound represented by Formula (I-B):

[Chemical Formula 44]

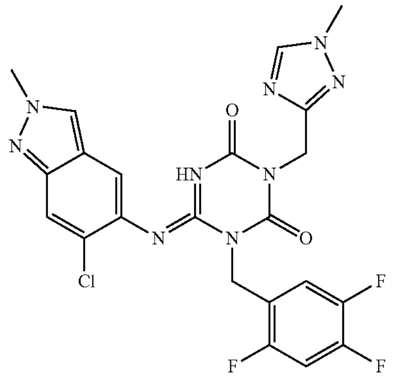

and fumaric acid are present in a molar ratio of 1:1.

(3B) A fumaric acid cocrystal according to the above item (1B) or (2B).

(4B) The fumaric acid cocrystal Form I according to the above item (3B), which exhibits a powder X-ray diffraction pattern having peaks at diffraction angles (2θ): 9.5±0.2°, 10.9±0.2°, 18.6±0.2°, 23.5±0.2°, and 24.6±0.2°.

(5B) The fumaric acid cocrystal Form I according to the above item (3B), which exhibits a powder X-ray diffraction pattern having peaks at diffraction angles (2θ): 7.8±0.2°, 9.5±0.2°, 10.1±0.2°, 10.9±0.2°, 13.8±0.2°, 14.7±0.2°, 18.6±0.2°, 22.6±0.2°, 23.5±0.2°, and 24.6±0.2°.

(6B') The fumaric acid cocrystal Form I according to the above item (3B), which exhibits a Raman spectrum having Raman spectral peaks at 676.3 $cm^{-1}$±2 $cm^{-1}$, 748.0 $cm^{-1}$±2 $cm^{-1}$, 1029.3 $cm^{-1}$±2 $cm^{-1}$, 1374.4 $cm^{-1}$±2 $cm^{-1}$, 1515.5 $cm^{-1}$±2 $cm^{-1}$, 1665.7 $cm^{-1}$±2 $cm^{-1}$, 1715.7 $cm^{-1}$±2 $cm^{-1}$, and 1739.1 $cm^{-1}$±2 $cm^{-1}$.

(6B) A pharmaceutical composition comprising the cocrystal according to any one of the above items (3B) to (5B) and (6B').

(7B) The fumaric acid cocrystal Form I according to the above item (3B), whose crystallographic data when measured at 298 K is characterized by the following crystallographic data:

Space group: P-1
a=8.4 Å±0.5 Å
b=11.7 Å±0.5 Å
c=15.2 Å±0.5 Å
α=83.8°±0.5°
β=78.9°±0.5°
γ=77.1°±0.5°

(8B) The fumaric acid cocrystal Form I according to the above item (3B), whose crystallographic data when measured at 298 K is substantially in accordance with the following crystallographic data:

Space group: P-1
a=8.4374 Å
b=11.6780 Å
c=15.1612 Å
α=83.827°
β=78.868°
γ=77.147°

(9B) The fumaric acid cocrystal Form I according to the above item (3B), characterized by spectrum(spectra) and/or a curve selected from the following (a) to (c)

(a) a X ray powder diffraction spectrum substantially corresponding to FIG. 3;

(b) a Raman spectrum substantially corresponding to FIG. 5;

(c) a differential scanning calorimetry curve substantially corresponding to FIG. 6.

(10B) A pharmaceutical composition comprising the cocrystal according to any one of the above items (7B) to (9B).

Effect of the Invention

The compound of the present invention has inhibitory activity against coronavirus 3CL proteases and is useful as a therapeutic(treating) agent and/or prophylactic(preventing) agent for coronavirus infections.

Furthermore, among the compounds according to the present invention, Compound (I-0113) or Compound (I-0115) are useful as active pharmaceutical ingredients.

In addition, a pharmaceutical composition comprising a crystalline form of p-toluenesulfonate of Compound (I-0113) or a fumaric acid cocrystal of Compound (I-0115) is highly useful as a therapeutic agent for novel coronavirus infections (COVID-19).

MODE FOR CARRYING OUT THE INVENTION

Figure 1:
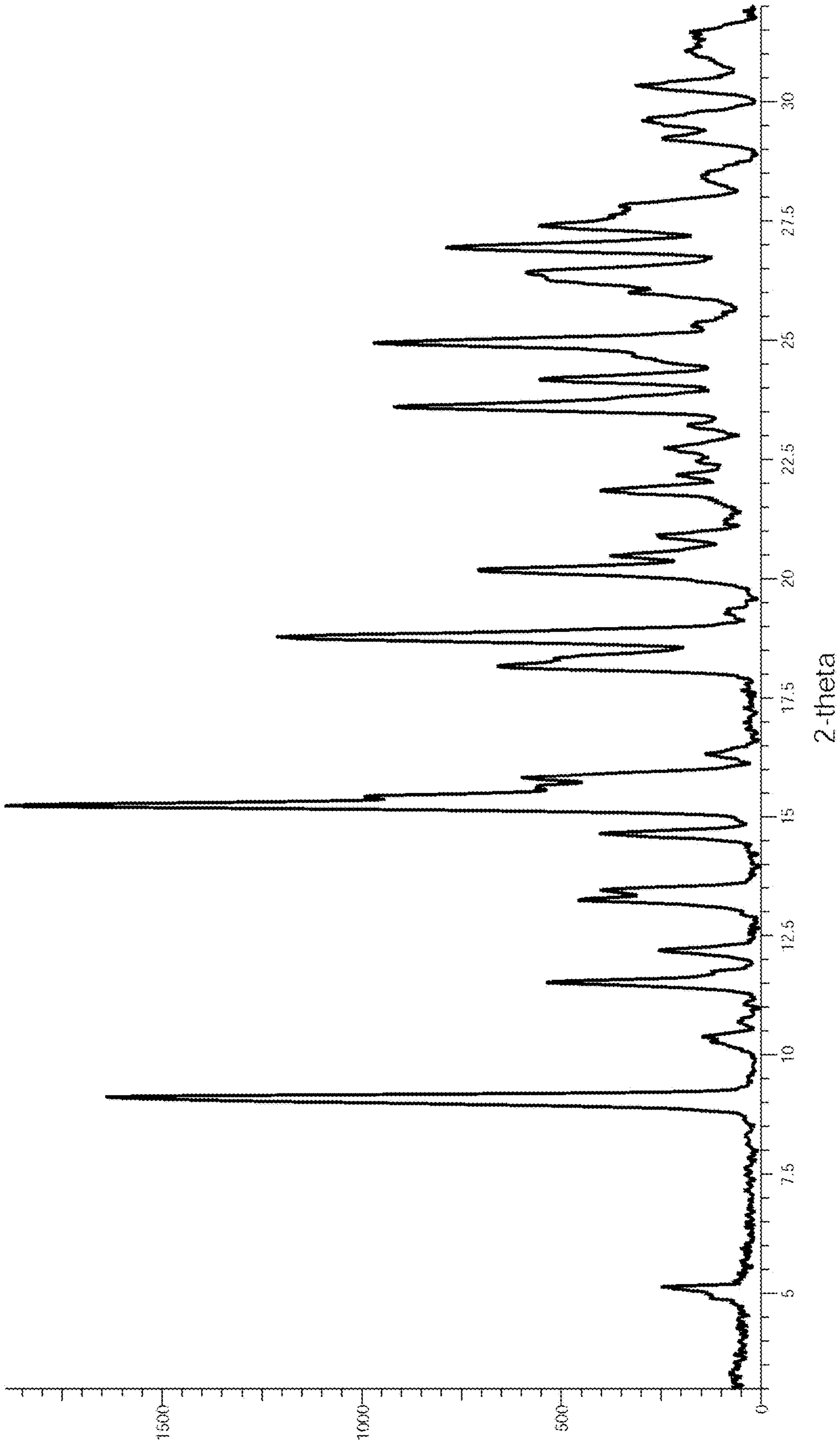
FIG. 1 shows a powder X-ray diffraction pattern of a crystalline form of p-toluenesulfonate Form I (Form I) of a compound represented by Formula (1-A). The axis of abscissa represents 2θ(°), and the axis of ordinate represents the intensity (Count).

Hereinafter, the meaning of each term used in the present specification will be described. Unless particularly stated otherwise, each term is used in the same sense, either alone or in combination with other terms.

The term "consist of" means having only the constituent elements.

The term "comprise" means that elements are not limited to the constituent elements, and elements that are not described are not excluded.

Hereinafter, the present invention will be described while showing exemplary embodiments. Throughout the present specification, it should be understood that, unless particularly stated otherwise, an expression of a singular form also includes the concept of a plural form thereof. Therefore, it should be understood that, unless particularly stated otherwise, an article for a singular form (for example, in the case of English, "a", "an", "the", or the like) also includes the concept of a plural form thereof.

Furthermore, it should be understood that, unless particularly stated otherwise, the terms used in the present specification are used in the meanings normally used in the above-described art. Accordingly, unless otherwise defined, all terminologies and scientific and technical terms used in the present specification have the same meanings as commonly understood by those having ordinary skill in the art to which the present invention belongs. In a case of contradiction, priority is given to the present specification (including definitions).

"Halogen" includes a fluorine atom, a chlorine atom, a bromine atom, and an iodine atom. Particularly, a fluorine atom and a chlorine atom are preferred.

"Alkyl" includes linear or branched hydrocarbon groups each having 1 to 15 carbon atoms, preferably 1 to 10 carbon atoms, more preferably 1 to 6 carbon atoms, and even more preferably 1 to 4 carbon atoms. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Preferred embodiments of "alkyl" include methyl, ethyl, n-propyl, isopropyl, n-butyl, isobutyl, sec-butyl, tert-butyl, and n-pentyl. More preferred embodiments include methyl, ethyl, n-propyl, isopropyl, and tert-butyl.

"Alkenyl" includes linear or branched hydrocarbon groups each having one or more double bonds at any position and having 2 to 15 carbon atoms, preferably 2 to 10 carbon atoms, more preferably 2 to 6 carbon atoms, and even more preferably 2 to 4 carbon atoms. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

Preferred embodiments of "alkenyl" include vinyl, allyl, propenyl, isopropenyl, and butenyl. More preferred embodiments include ethenyl and n-propenyl.

"Alkynyl" includes linear or branched hydrocarbon groups each having one or more triple bonds at any position and having 2 to 10 carbon atoms, preferably 2 to 8 carbon atoms, more preferably 2 to 6 carbon atoms, and even more preferably 2 to 4 carbon atoms. Alkynyl may further have a double bond at any position. Examples include ethynyl, propynyl, butynyl, pentynyl, hexynyl, heptynyl, octynyl, nonynyl, and decynyl.

Preferred embodiments of "alkynyl" include ethynyl, propynyl, butynyl, and pentynyl. More preferred embodiments include ethynyl and propynyl.

"Aromatic carbocyclyl" means a cyclic aromatic hydrocarbon group having a single ring or two or more rings. Examples include phenyl, naphthyl, anthryl, and phenanthryl. Examples of 6-membered aromatic carbocyclyl include phenyl. Examples of 10-membered aromatic carbocyclyl include naphthyl. Examples of 14-membered aromatic carbocyclyl include anthryl and phenanthryl.

Preferred embodiments of the "aromatic carbocyclyl" include phenyl.

"Aromatic carbocycle" means a ring derived from the above-described "aromatic carbocyclyl".

Examples of "substituted or unsubstituted aromatic carbocycle formed by $R^{1b}$ and $R^{1c}$ together with the carbon atom to which $R^{1b}$ and $R^{1c}$ are bonded" include the following ring.

[Chemical Formula 45]

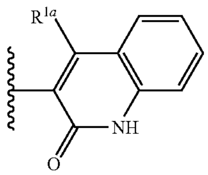

"Non-aromatic carbocyclyl" means a cyclic saturated hydrocarbon group or a cyclic non-aromatic unsaturated hydrocarbon group, both having a single ring or two or more rings. The "non-aromatic carbocyclyl" having two or more rings also includes a non-aromatic carbocyclyl having a single ring or two or more rings, to which the ring in the "aromatic carbocyclyl" is fused.

Furthermore, the "non-aromatic carbocyclyl" also includes a bridged group or a group forming a Spiro ring, such as follows.

[Chemicl Formula 46]

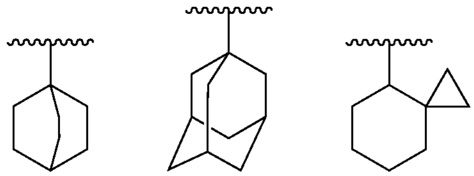

A non-aromatic carbocyclyl having a single ring preferably has 3 to 16 carbon atoms, more preferably 3 to 12 carbon atoms, and even more preferably 4 to 8 carbon atoms. Examples include cyclopropyl, cyclobutyl, cyclopentyl, cyclohexyl, cyclobeptyl, cyclooctyl, cyclononyl, cyclodecyl, cyclopropenyl, cyclobutenyl, cyclopentenyl, cyclohexenyl, cycloheptenyl, and cyclohexadienyl. Examples of 5-membered non-aromatic carbocyclyl include cyclopentyl and cyclopentenyl. Examples of 6-membered non-aromatic carbocyclyl include cyclohexyl, cyclohexenyl, and cyclohexadienyl.

A non-aromatic carbocyclyl having two or more rings preferably has 4 to 20 carbon atoms, and more preferably 8 to 16 carbon atoms. Examples include indanyl, indenyl, acenaphthyl, tetrahydronaphthyl, and fluorenyl. Examples of 4-membered non-aromatic carbocyclyl include bicyclo [1.1.1]pentyl. Examples of 9-membered non-aromatic carbocyclyl include indanyl and indenyl. Examples of 10-membered non-aromatic carbocyclyl include dihydronaphthyl and tetrahydronaphthyl.

"Non-aromatic carbocycle" means a ring derived from the above-described "non-aromatic carbocyclyl".

Examples of "substituted or unsubstituted non-aromatic carbocycle formed by $R^{4a}$ and $R^{4b}$ together" include the following ring.

[Chemical Formula 47]

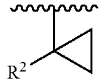

"Aromatic heterocyclyl" means an aromatic cyclyl having a single ring or two or more rings, which has one or more identical or different heteroatoms optionally selected from O, S, and N in the ring(s).

An aromatic heterocyclyl having two or more rings also includes an aromatic heterocyclyl having a single ring or two or more rings, to which a ring in the "aromatic carbocyclyl" is fused, and the linking bond may be carried by any of the rings.

The aromatic heterocyclyl having a single ring is preferably a 5- to 8-membered ring, and more preferably a 5-membered or 6-membered ring. Examples of 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl. Examples of 6-membered aromatic heterocyclyl include pyridyl, pyridazinyl, pyrimidinyl, pyrazinyl, and triazinyl.

The aromatic heterocyclyl having two rings is preferably an 8- to 10-membered ring, and more preferably a 9-membered or 10-membered ring. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl. Examples of 9-membered aromatic heterocyclyl include indolyl, isoindolyl, indazolyl, indolizinyl, purinyl, benzimidazolyl, benzisoxazolyl, benzoxazolyl, benzoxadiazolyl, benzisothiazolyl, benzothiazolyl, benzothiadiazolyl, benzotriazolyl, benzofuranyl, imidazopyridyl, triazolopyridyl, oxazolopyridyl, and thiazolopyridyl. Examples of 10-membered aromatic heterocyclyl include quinolinyl, isoquinolinyl, cinnolinyl, phthalazinyl, quinazolinyl, naphthyridinyl, quinoxalinyl, pteridinyl, and pyrazinopyridazinyl.

An aromatic heterocyclyl having three or more rings is preferably a 13- to 15-membered group. Examples include carbazolyl, acridinyl, xanthenyl, phenothiazinyl, phenoxathiinyl, phenoxazinyl, and dibenzofuryl.

"Aromatic heterocycle" means a ring derived from the above-described "aromatic heterocyclyl".

Examples of "substituted or unsubstituted aromatic heterocycle formed by Rib and $R^{1c}$ together with the carbon atom to which $R^{1b}$ and Rig are bonded" include the following rings.

[Chemical Formula 48]

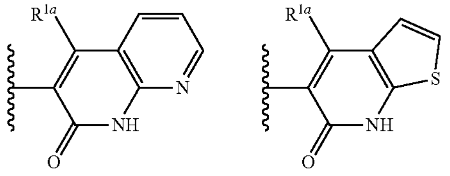

"Non-aromatic heterocyclyl" means a non-aromatic cyclyl having a single ring or two or more rings, which has one or more identical or different heteroatoms optionally selected from O, S, and N in the ring(s). A non-aromatic heterocyclyl having two or more rings also includes a non-aromatic heterocyclyl having a single ring or two or more rings, to which a ring in each of the "aromatic carbocyclyl", "non-aromatic carbocyclyl", and/or "aromatic heterocyclyl" is fused, as well as a non-aromatic carbocyclyl having a single ring or two or more rings, to which a ring in the "aromatic heterocyclyl" is fused, and the linking bond may be carried by any of the rings.

Furthermore, the "non-aromatic heterocyclyl" also includes a bridged group or a group forming a Spiro ring, such as follows.

[Chemical Formula 49]

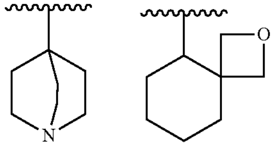

The non-aromatic heterocyclyl having a single ring is preferably a 3- to 8-membered ring, and more preferably a 5-membered or 6-membered ring.

Examples of 3-membered non-aromatic heterocyclyl include thiiranyl, oxiranyl, and aziridinyl. Examples of 4-membered non-aromatic heterocyclyl include oxetanyl and azetidinyl. Examples of 5-membered non-aromatic heterocyclyl include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl, and thiolanyl. Examples of 6-membered non-aromatic heterocyclyl include dioxanyl, thianyl, piperidyl, piperazinyl, morpholinyl, morpholino, thiomorpholinyl, thiomorpholino, dihydropyridyl, tetrahydropyridyl, tetrahydropyranyl, dihydroxazinyl, tetrahydropyridazinyl, hexahydropyrimidinyl, dioxazinyl, thiinyl, and thiazinyl. Examples of 7-membered non-aromatic heterocyclyl include hexahydroazepinyl, tetrahydrodiazepinyl, and oxepanyl.

The non-aromatic heterocyclyl having two or more rings is preferably an 8- to 20-membered ring, more preferably an 8- to 13-membered ring, and even more preferably an 8- to 10-membered ring. Examples include indolinyl, isoindolinyl, chromanyl, and isochromanyl. Examples of 9-membered non-aromatic heterocyclyl include indolinyl and isoindolinyl. Examples of 10-membered non-aromatic heterocyclyl include chromanyl and isochromanyl.

"Non-aromatic heterocycle" means a ring derived from the above-described "non-aromatic heterocyclyl".

Examples of "substituted or unsubstituted non-aromatic heterocycle formed by $R^{4a}$ and $R^{4b}$ together" include the following ring.

[Chemical Formula 50]

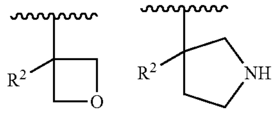

"Trialkylsilyl" means a group in which three moieties of the above-described "alkyl" are bonded to a silicon atom. The three alkyl groups may be identical or different. Examples include trimethylsilyl, triethylsilyl, and tert-butyldimethylsilyl.

"Cyclylsulfoxyiminyl" means a group in which two carbon atoms which bind to sulfur atom of sulfoxyiminyl group, together with the sulfur atom to which two carbon atoms are bonded, form non-aromatic heterocycle. Examples include the following group.

[Chemical Formula 51]

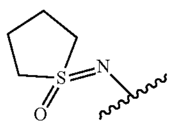

In the present specification, the phrase "may be substituted with substituent group α" means that "may be substituted with one or more group(s) selected from substituent group α". The same also applies to substituent groups β, γ, and γ'.

Substituents for "substituted alkyl", "substituted alkenyl", "substituted alkynyl", "substituted alkyloxy", "substituted alkenyloxy", "substituted alkynyloxy", "substituted alkylcarbonyloxy", "substituted alkenylcarbonyloxy", "substituted alkynylcarbonyloxy", "substituted alkylcarbonyl", "substituted alkenylcarbonyl", "substituted alkynylcarbonyl", "substituted alkyloxycarbonyl", "substituted alkenyloxycarbonyl", "substituted alkynyloxycarbonyl", "substituted alkylsulfanyl", "substituted alkenylsulfanyl", "substituted alkynylsulfanyl", "substituted alkylsulfinyl", "substituted alkenylsulfinyl", "substituted alkynylsulfinyl", "substituted alkylsulfonyl", "substituted alkenylsulfonyl", "substituted alkynylsulfonyl", "substituted dialkylsulfoxyimino", and the like include the following substituent group A. A carbon atom at any position may be bonded to one or more group(s) selected from the following substituent group A.

Substituent group A: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azido, hydrazino, ureido, amidino, guanidino, pentafluorothio, trialkylsilyl, alkyloxy which may be substituted with substituent group α, alkenyloxy which may be substituted with substituent group α, alkynyloxy which may be substituted with substituent group α, alkylcarbonyloxy which may be substituted with substituent group α, alkenylcarbonyloxy which may be substituted with substituent group α, alkynylcarbonyloxy which may be substituted with substituent group α, alkylcarbonyl which may be substituted with substituent group α, alkenylcarbonyl which may be substituted with substituent group α, alkynylcarbonyl which may be substituted with substituent group α, alkyloxycarbonyl which may be substituted with substituent group α, alkynyloxycarbonyl which may be substituted with substituent group α, alkynyloxycarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group β, imino which may be substituted with substituent group β, carbamoyl which may be substituted with substituent group β, sulfamoyl which may be substituted with substituent group β, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclyloxy which may be substituted with substituent group γ, non-aromatic carbocyclyloxy which may be substituted with substituent group γ', aromatic heterocyclyloxy which may be substituted with substituent group γ, non-aromatic heterocyclyloxy which may be substituted with substituent group γ', aromatic carbocyclylcarbonyloxy which may be substituted with substituent group γ, non-aromatic carbocyclylcarbonyloxy which may be substituted with substituent group γ', aromatic heterocyclylcarbonyloxy which may be substituted with substituent group γ, non-aromatic heterocyclylcarbonyloxy which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylalkyloxy which may be substituted with substituent group γ, non-aromatic carbocyclylalkyloxy which may be substituted with substituent group γ', aromatic heterocyclylalkyloxy which may be substituted with substituent group γ, non-aromatic heterocyclylalkyloxy which may be substituted with substituent group γ', aromatic carbocyclylalkyloxycarbonyl which may be substituted with substituent group γ, non-aromatic carbocyclylalkyloxycarbonyl which may be substituted with substituent group γ', aromatic heterocyclylalkyloxycarbonyl which may be substituted with substituent group γ, non-aromatic heterocyclylalkyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Substituent group α: halogen, hydroxy, carboxy, alkyloxy, haloalkyloxy, alkenyloxy, alkynyloxy, sulfanyl, and cyano.

Substituent group β: halogen, hydroxy, carboxy, cyano, alkyl which may be substituted with substituent group α, alkenyl which may be substituted with substituent group α, alkynyl which may be substituted with substituent group α, alkylcarbonyl which may be substituted with substituent group α, alkenylcarbonyl which may be substituted with substituent group α, alkynylcarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Substituent group γ: substituent group α, alkyl, haloalkyl, hydroxyalkyl, alkenyl, alkynyl, alkylcarbonyl, haloalkylcarbonyl, alkenylcarbonyl, and alkynylcarbonyl.

Substituent group γ': substituent group γ and oxo.

The substituents on the rings of "aromatic carbocycle" and "aromatic heterocycle", such as "substituted aromatic carbocyclyl", "substituted aromatic heterocyclyl", "substituted aromatic carbocyclyloxy", "substituted aromatic heterocyclyloxy", "substituted aromatic carbocyclylcarbonyloxy", "substituted aromatic heterocyclylcarbonyloxy", "substituted aromatic carbocyclylcarbonyl", "substituted aromatic heterocyclylcarbonyl", "substituted aromatic carbocyclyloxycarbonyl", "substituted aromatic heterocyclyloxycarbonyl", "substituted aromatic carbocyclylsulfonyl", "substituted aromatic heterocyclylsulfonyl", "substituted aromatic carbocyclylsulfinyl", "substituted aromatic heterocyclylsulfinyl", "substituted aromatic carbocyclylsulfonyl", and "substituted aromatic heterocyclylsulfonyl" include the following substituent group B. An atom at any position on the ring may be bonded to one or more group(s) selected from the following substituent group B.

Substituent group B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azido, hydrazino, ureido, amidino, guanidino, pentafluorothio, trialkylsilyl, alkyl which may be substituted with substituent group α, alkenyl which may be substituted with substituent group α, alkynyl which may be substituted with substituent group α, alkyloxy which may be substituted with substituent group α, alkenyloxy which may be substituted with substituent group α, alkynyloxy which may be substituted with substituent group α, alkylcarbonyloxy which may be substituted with substituent group α, alkynylcarbonyloxy which may be substituted with substituent group α, alkynylcarbonyloxy which may be substituted with substituent group α, alkylcarbonyl which may be substituted with substituent group α, alkenylcarbonyl which may be substituted with substituent group α, alkynylcarbonyl which may be substituted with substituent group α, alkyloxycarbonyl which may be substituted with substituent group α, alkenyloxycarbonyl which may be substituted with substituent group α, alkynyloxycarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group β, imino which may be substituted with substituent group β, carbamoyl which may be substituted with substituent group β, sulfamoyl which may be substituted with substituent group β, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclyloxy which may be substituted with substituent group γ, non-aromatic carbocyclyloxy which may be substituted with substituent group γ', aromatic heterocyclyloxy which may be substituted with substituent group γ, non-aromatic heterocyclyloxy which may be substituted with substituent group γ', aromatic carbocyclylcarbonyloxy which may be substituted with substituent group γ, non-aromatic carbocyclylcarbonyloxy which may be substituted with substituent group γ', aromatic heterocyclylcarbonyloxy which may be substituted with substituent group γ, and non-aromatic heterocyclylcarbonyloxy which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylalkyloxy which may be substituted with substituent group γ, non-aromatic carbocyclylalkyloxy which may be substituted with substituent group γ', aromatic heterocyclylalkyloxy which may be substituted with substituent group γ, non-aromatic heterocyclylalkyloxy which may be substituted with substituent group γ', aromatic carbocyclylalkyloxycarbonyl which may be substituted with substituent group γ, non-aromatic carbocyclylalkyloxycarbonyl which may be substituted with substituent group γ', aromatic heterocyclylalkyloxycarbonyl which may be substituted with substituent group γ, non-aromatic heterocyclylalkyloxycarbonyl which may be substituted with substituent group γ', aromatic carbocyclylalkyloxyalkyl which may be substituted with substituent group γ, non-aromatic carbocyclylalkyloxyalkyl which may be substituted with substituent group γ', aromatic heterocyclylalkyloxyalkyl which may be substituted with substituent group γ, non-aromatic heterocyclylalkyloxyalkyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

The substituents on the ring of "non-aromatic carbocycle" and "non-aromatic heterocycle" of "substituted non-aromatic carbocyclyl", "substituted non-aromatic heterocyclyl", "substituted non-aromatic carbocyclyloxy", "substituted non-aromatic heterocyclyloxy", "substituted non-aromatic carbocyclylcarbonyloxy", "substituted non-aromatic heterocyclylcarbonyloxy", "substituted non-aromatic carbocyclylcarbonyl", "substituted non-aromatic heterocyclylcarbonyl", "substituted non-aromatic carbocyclyloxycarbonyl", "substituted non-aromatic heterocyclyloxycarbonyl", "substituted non-aromatic carbocyclylsulfanyl", "substituted non-aromatic heterocyclylsulfanyl", "substituted non-aromatic carbocyclylsulfinyl", "substituted non-aromatic heterocyclylsulfinyl", "substituted non-aromatic carbocyclylsulfonyl", "substituted non-aromatic heterocyclylsulfonyl", "substituted or unsubstituted non-aromatic carbocycle formed by $R^{4a}$ and $R^{4b}$ together", and "substituted or unsubstituted non-aromatic heterocycle formed by $R^{4a}$ and $R^{4b}$ together" include the following substituent group C. An atom at any position on the ring may be bonded to one or more group(s) selected from the following substituent group C.

Substituent group C: substituent group B and oxo.

When the "non-aromatic carbocycle" and the "non-aromatic heterocycle" are substituted with "oxo", this means a ring in which two hydrogen atoms on a carbon atom are substituted as follows.

[Chemical Formula 52]

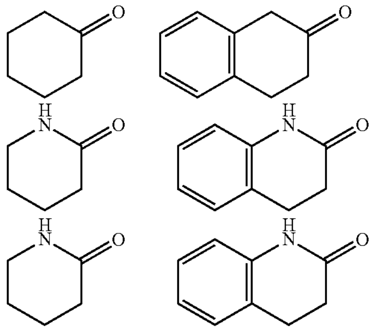

The substituents for "substituted amino", "substituted imino", "substituted carbamoyl", and "substituted sulfamoyl" include the following substituent group D. These moieties may be substituted with one or two group(s) selected from substituent group D.

Substituent group D: halogen, hydroxy, carboxy, cyano, alkyl which may be substituted with substituent group α, alkenyl which may be substituted with substituent group α, alkynyl which may be substituted with substituent group α, alkylcarbonyl which may be substituted with substituent group α, alkenylcarbonyl which may be substituted with substituent group α, alkynylcarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group β, imino which may be substituted with substituent group β, carbamoyl which may be substituted with substituent group β, sulfamoyl which may be substituted with substituent group β, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Examples of the substituents of the "substituent or unsubstituted non-aromatic heterocyclyl" in $R^1$ include;

oxo; thioxo; halogen; cyano; nitro; carboxy;
substituted or unsubstituted carbamoyl;
substituted or unsubstituted alkyl;
substituted or unsubstituted alkyloxy;
substituted or unsubstituted alkylcarbonyl;
substituted or unsubstituted alkyloxycarbonyl;
substituted or unsubstituted alkylsulfanyl;
substituted or unsubstituted amino;
substituted or unsubstituted aromatic carbocyclyl;
substituted or unsubstituted aromatic heterocyclyl;
substituted or unsubstituted non-aromatic carbocyclyl;
substituted or unsubstituted non-aromatic heterocyclyl;
substituted or unsubstituted non-aromatic heterocyclylcarbonyl. It may be substituted with one or more group(s) selected from these.

Examples of the substituents of the "substituent or unsubstituted non-aromatic heterocyclyl" in $R^1$ include:

oxo; tioxo; halogen; cyano; nitro; carboxy;
substituted carbamoyl (Examples of the substituents include alkyl, alkylaminoalkyl, non-aromatic carbocyclyl); unsubstituted carbamoyl;
substituted alkyl (Examples of the substituents include halogen, hydroxy); unsubstituted alkyl;
unsubstituted alkyloxy;
unsubstituted alkylcarbonyl;
unsubstituted alkyloxycarbonyl;
unsubstituted alkylsulfanyl;
substituted amino (Examples of the substituents include alkyl, alkylcarbonyl, hydroxyalkyl);
substituent aromatic carbocyclyl (Examples of the substituents include halogen); unsubstituted aromatic carbocyclyl;
substituent aromatic heterocyclyl (Examples of the substituents include alkyl); unsubstituted aromatic heterocyclyl;
unsubstituted non-aromatic carbocyclyl;
unsubstituted non-aromatic heterocyclyl;
unsubstituted non-aromatic heterocyclylcarbonyl. It may be substituted with one or more group(s) selected from these.

Examples of the substituents of the "substituted or unsubstituted aromatic heterocyclyl" in $R^1$ include:

halogen; cyano; hydroxy;
substituted or unsubstituted alkyl;
substituted or unsubstituted alkyloxy;
substituted or unsubstituted alkyloxycarbonyl;
substituted or unsubstituted aromatic carbocyclyl. It may be substituted with one or more group(s) selected from these.

Examples of the substituents of the "substituted or unsubstituted aromatic heterocyclyl" in $R^1$ include:

halogen; cyano; hydroxy;
substituted alkyl (Examples of the substituents include halogen, hydroxy, carbamoyl, aromatic carbocyclyl, non-aromatic carbocyclyl); unsubstituted alkyl;
unsubstituted alkyloxy;
unsubstituted alkyloxycarbonyl;
unsubstituted aromatic carbocyclyl. It may be substituted with one or more group(s) selected from these.

Examples of the substituents of "substituted or unsubstituted carbamoyl" in $R^1$ include:

substituted or unsubstituted alkyl; substituted or unsubstituted amino. It may be substituted with one or more group(s) selected from these.

Examples of the substituents of "substituted or unsubstituted carbamoyl" in $R^1$ include:

substituted alkyl (Examples of the substituents include aromatic carbocyclyl); unsubstituted alkyl; unsubstituted amino. It may be substituted with one or more group(s) selected from these.

Examples of the substituents of the "substituted or unsubstituted aromatic carbocyclyl" in $R^2$ include:

halogen; cyano;
substituted or unsubstituted alkyl; substituted or unsubstituted alkyloxy. It may be substituted with one or more group(s) selected from these.

Examples of the substituents of the "substituted or unsubstituted aromatic carbocyclyl" in $R^2$ include:

halogen; cyano;
substituted alkyl (Examples of the substituents include halogen); unsubstituted alkyl;
substituted alkyloxy (Examples of the substituents include halogen, aromatic carbocyclyl); unsubstituted alkyloxy. It may be substituted with one or more group(s) selected from these.

Examples of the substituents of the "substituted or unsubstituted non-aromatic carbocyclyl" in $R^2$ include:

halogen. It may be substituted with one or more group(s) selected from these.

Examples of the substituents of the "substituted or unsubstituted aromatic heterocyclyl" in $R^2$ include:

halogen; substituted or unsubstituted alkyl. It may be substituted with one or more group(s) selected from these.

Examples of the substituents of the "substituted or unsubstituted aromatic heterocyclyl" in $R^2$ include:

halogen; unsubstituted alkyl. It may be substituted with one or more group(s) selected from these.

Examples of the substituents of the "substituted or unsubstituted aromatic carbocyclyl" in $R^3$ include:

halogen; cyano; hydroxy; carboxy;
substituted or unsubstituted alkyl;
substituted or unsubstituted alkynyl;
substituted or unsubstituted alkyloxy;
substituted or unsubstituted alkylcarbonyl;
substituted or unsubstituted alkyloxycarbonyl;
substituted or unsubstituted alkylsulfanyl;
substituted or unsubstituted alkylsulfinyl;
substituted or unsubstituted alkylsulfonyl;
substituted or unsubstituted amino;
substituted or unsubstituted carbamoyl;
substituted or unsubstituted non-aromatic carbocyclyl;
substituted or unsubstituted aromatic heterocyclyl;
substituted or unsubstituted non-aromatic heterocyclyl;
substituted or unsubstituted non-aromatic carbocyclyloxy. It may be substituted with one or more group(s) selected from these.

Examples of the substituents of the "substituted or unsubstituted aromatic carbocyclyl" in $R^3$ include:

halogen; cyano; hydroxy; carboxy;
substituted alkyl (Examples of the substituents include halogen); unsubstituted alkyl;
unsubstituted alkynyl;
substituted alkyloxy (Examples of the substituents include halogen, hydroxy, carboxy, alkyloxy, alkyloxycarbonyl, carbamoyl, alkylcarbamoyl, alkylamino, aromatic carbocyclyl); unsubstituted alkyloxy;
substituted alkylcarbonyl (Examples of the substituents include amino); unsubstituted alkyloxycarbonyl;
unsubstituted alkylsulfanyl;
unsubstituted alkylsulfinyl;
unsubstituted alkylsulfonyl;
substituted amino (Examples of the substituents include alkylcarbonyl, alkylcarbamoyl, alkylsulfonyl);
substituted carbamoyl (Examples of the substituents include alkyl); unsubstituted carbamoyl;
unsubstituted non-aromatic carbocyclyl;
substituted aromatic heterocyclyl (Examples of the substituents include alkyl);
unsubstituted aromatic heterocyclyl;
substituted non-aromatic heterocyclyl (Examples of the substituents include oxo); unsubstituted non-aromatic carbocyclyloxy. It may be substituted with one or more group(s) selected from these.

Examples of the substituents of the "substituted or unsubstituted non-aromatic carbocyclyl" in $R^3$ include:

hydroxy; substituted or unsubstituted alkyloxy. It may be substituted with one or more group(s) selected from these.

Examples of the substituents of the "substituted or unsubstituted non-aromatic carbocyclyl" in $R^3$ include:

hydroxy; unsubstituted alkyloxy. It may be substituted with one or more group(s) selected from these.

Examples of the substituents of the "substituted or unsubstituted aromatic heterocyclyl" in $R^3$ include:

halogen; hydroxy;
substituted or unsubstituted alkyl;
substituted or unsubstituted alkyloxy;
substituted or unsubstituted amino;
substituted or unsubstituted non-aromatic carbocyclyl;
substituted or unsubstituted non-aromatic heterocyclyl. It may be substituted with one or more group(s) selected from these.

Examples of the substituents of the "substituted or unsubstituted aromatic heterocyclyl" in $R^3$ include:

halogen; hydroxy;
substituted alkyl (Examples of the substituents include halogen, hydroxy, alkyloxy, haloalkyloxy, alkylamino, alkylcarbonylamino, alkylcarbamoyl, alkylsulfonyl, non-aromatic carbocyclyl, non-aromatic heterocyclyl); unsubstituted alkyl;
unsubstituted alkyloxy;
substituted amino (Examples of the substituents include alkyl, alkylcarbonyl, alkyloxycarbonyl); unsubstituted amino;
substituted non-aromatic carbocyclyl (Examples of the substituents include halogen, hydroxy); unsubstituted non-aromatic carbocyclyl;
substituted non-aromatic heterocyclyl (Examples of the substituents include alkylcarbonyl); unsubstituted non-aromatic heterocyclyl. It may be substituted with one or more group(s) selected from these.

Examples of the substituents of the "substituent or unsubstituted non-aromatic heterocyclyl" in $R^3$ include:

halogen; oxo;
substituted or unsubstituted alkyl;
substituted or unsubstituted alkyloxy;
substituted or unsubstituted amino. It may be substituted with one or more group(s) selected from these.

Examples of the substituents of the "substituent or unsubstituted non-aromatic heterocyclyl" in $R^3$ include:

halogen; oxo;
substituted alkyl (Examples of the substituents include carbamoyl); unsubstituted alkyl;
unsubstituted alkyloxy;
substituted amino (Examples of the substituents include alkylcarbonyl). It may be substituted with one or more group(s) selected from these.

Examples of the substituents of the "substituted or unsubstituted aromatic heterocyclyl" in $R^1$ include:

halogen;
cyano;
hydroxy;
substituted or unsubstituted alkyl;
substituted or unsubstituted alkynyl;
substituted or unsubstituted alkyloxy;
substituted or unsubstituted amino;
substituted or unsubstituted alkyloxycarbonyl;
substituted or unsubstituted aromatic carbocyclyl;
substituted or unsubstituted non-aromatic carbocyclyl;
substituted or unsubstituted aromatic heterocyclyl. It may be substituted with one or more group(s) selected from these.

Examples of the substituents of the "substituted or unsubstituted aromatic heterocyclyl" in $R^1$ include:

cyano;
hydroxy;
substituted alkyl (Examples of the substituents include halogen, hydroxy, alkyloxy, alkyloxycarbonyl, carbamoyl; optionally substituted with one or more group(s) selected from these); unsubstituted alkyl;
unsubstituted alkynyl;
unsubstituted alkyloxy;
substituted amino (Examples of the substituents include alkyl); unsubstituted amino; unsubstituted alkyloxycarbonyl;

unsubstituted aromatic carbocyclyl;

unsubstituted non-aromatic carbocyclyl;

substituent aromatic heterocyclyl (Examples of the substituents include alkyl); It may be substituted with one or more group(s) selected from these.

In one embodiment, examples of the substituents of the "substituted or unsubstituted aromatic heterocyclyl" in $R^1$ include:

halogen;

substituted alkyl (Examples of the substituents include halogen, hydroxy, alkyloxy, alkyloxycarbonyl, carbamoyl; optionally substituted with one or more group(s) selected from these); unsubstituted alkyl. It may be substituted with one or more group(s) selected from these.

In one embodiment, examples of the substituents of the "substituted or unsubstituted aromatic heterocyclyl" in $R^1$ include:

halogen, unsubstituted alkyl, unsubstituted alkenyl, unsubstituted alkynyl, haloalkyl and unsubstituted alkyloxy. It may be substituted with one or more group(s) selected from these.

Examples of the substituents of the "substituent or unsubstituted non-aromatic heterocyclyl" in R' include:

oxo;

thioxo;

halogen;

cyano;

carboxy;

substituted or unsubstituted carbamoyl;

substituted or unsubstituted alkyl;

substituted or unsubstituted alkyloxy;

substituted or unsubstituted aromatic carbocyclyl;

substituted or unsubstituted aromatic heterocyclyl;

substituted or unsubstituted non-aromatic heterocyclyl; It may be substituted with one or more group(s) selected from these.

Examples of the substituents of the "substituent or unsubstituted non-aromatic heterocyclyl" in $R^1$ include:

oxo;

thioxo;

halogen;

carboxy;

substituted carbamoyl (Examples of the substituents include alkyl, alkylaminoalkyl, non-aromatic carbocyclyl, alkyl-aromatic heterocyclyl-alkyl; optionally substituted with one or more group(s) selected from these); non-substituted carbamoyl;

substituted alkyl (Examples of the substituents include halogen), unsubstituted alkyl;

unsubstituted alkyloxy;

unsubstituted aromatic carbocyclyl;

substituted aromatic heterocyclyl (Examples of the substituents include alkyl);

unsubstituted aromatic heterocyclyl;

unsubstituted non-aromatic heterocyclyl. It may be substituted with one or more group(s) selected from these.

Examples of the substituents of "substituted or unsubstituted carbamoyl" in $R^1$ include:

substituted or unsubstituted alkyl;

substituted or unsubstituted non-aromatic carbocyclyl. It may be substituted with one or more group(s) selected from these.

Examples of the substituents of "substituted or unsubstituted carbamoyl" in $R^1$ include:

unsubstituted alkyl; unsubstituted non-aromatic carbocyclyl. It may be substituted with one or more group(s) selected from these.

Examples of the substituents of "substituted or unsubstituted amino" in $R^1$ include:

unsubstituted alkyl; unsubstituted alkylcarbonyl; unsubstituted alkyloxycarbonyl; unsubstituted alkylaminocarbonyl; unsubstituted alkylsulfonyl. It may be substituted with one or more group(s) selected from these.

In one embodiment, examples of the substituents of "substituted or unsubstituted amino" in $R^1$ include: unsubstituted alkyl. It may be substituted with one or more group(s) selected from these.

Examples of the substituents of the "substituted or unsubstituted aromatic carbocyclyl" in $R^2$ include:

halogen;

cyano;

nitro;

hydroxy;

substituted or unsubstituted alkyl;

substituted or unsubstituted alkenyl;

substituted or unsubstituted alkynyl;

substituted or unsubstituted alkyloxy;

substituted or unsubstituted alkyloxycarbonyl;

substituted or unsubstituted amino;

substituted or unsubstituted non-aromatic carbocyclyl. It may be substituted with one or more group(s) selected from these.

Examples of the substituents of the "substituted or unsubstituted aromatic carbocyclyl" in $R^2$ include:

halogen;

cyano;

nitro;

hydroxy;

substituted alkyl (Examples of the substituents include halogen, hydroxy, aromatic carbocyclyl, halogenated-aromatic carbocyclyl, hydroxyalkyl-aromatic carbocyclyl, alkyl-aromatic heterocyclyl, optionally substituted with one or more group(s) selected from these); unsubstituted alkyl;

unsubstituted alkenyl;

unsubstituted alkynyl;

substituted alkyloxy (Examples of the substituents include halogen, hydroxy, halogenated-aromatic carbocyclyl, non-aromatic carbocyclyl; optionally substituted with one or more group(s) selected from these); unsubstituted alkyloxy; unsubstituted alkyloxycarbonyl;

substituted amino (Examples of the substituents include alkylcarbonyl);

unsubstituted amino;

unsubstituted non-aromatic carbocyclyl; It may be substituted with one or more group(s) selected from these.

In one embodiment, examples of the substituents of the "substituted or unsubstituted aromatic carbocyclyl" in $R^2$ include:

halogen;

cyano;

substituted alkyl (Examples of the substituents include halogen, hydroxy, aromatic carbocyclyl, halogenated-aromatic carbocyclyl, hydroxyalkyl-aromatic carbocyclyl, alkyl-aromatic heterocyclyl; optionally substituted with one or more group(s) selected from these); unsubstituted alkyl. It may be substituted with one or more group(s) selected from these.

In one embodiment, examples of the substituents of the "substituted or unsubstituted aromatic carbocyclyl" in $R^2$ include:

halogen;

cyano;

substituted alkyl (Examples of the substituents include halogen); unsubstituted alkyl. It may be substituted with one or more group(s) selected from these.

Examples of the substituent of the "substituted or unsubstituted non-aromatic carbocyclyl" in $R^2$ include halogen. It may be substituted with one or more group(s) selected from these.

Examples of the substituents of the "substituted or unsubstituted aromatic heterocyclyl" in $R^2$ include:

halogen; cyano; substituted or unsubstituted alkyl. It may be substituted with one or more group(s) selected from these.

Examples of the substituents of the "substituted or unsubstituted aromatic heterocyclyl" in $R^2$ include:

halogen; cyano; unsubstituted alkyl. It may be substituted with one or more group(s) selected from these.

Examples of the substituents of the "substituted or unsubstituted non-aromatic heterocyclyl" in $R^2$ include:

halogen; substituted or unsubstituted alkylcarbonyl. It may be substituted with one or more group(s) selected from these.

Examples of the substituents of the "substituted or unsubstituted non-aromatic heterocyclyl" in $R^2$ include:

halogen; substituted alkylcarbonyl (Examples of the substituents include haloalkylcarbonylamino). It may be substituted with one or more group(s) selected from these.

Examples of the substituents of the "substituted or unsubstituted aromatic carbocyclyl" in $R^3$ include:

halogen;

hydroxy;

carboxy;

substituted or unsubstituted alkyl;

substituted or unsubstituted alkyloxy;

substituted or unsubstituted alkylsulfonyl;

substituted or unsubstituted dialkyl-sulfoxyiminyl;

substituted or unsubstituted cyclic sulfoxyiminyl;

substituted or unsubstituted amino;

substituted or unsubstituted carbamoyl;

substituted or unsubstituted aromatic heterocyclyl;

substituted or unsubstituted non-aromatic heterocyclyl;

substituted or unsubstituted non-aromatic carbocyclyloxy;

substituted or unsubstituted aromatic heterocyclyloxy. It may be substituted with one or more group(s) selected from these.

Examples of the substituents of the "substituted or unsubstituted aromatic carbocyclyl" in $R^3$ include:

halogen;

hydroxy;

carboxy;

substituted alkyl (Examples of the substituents include halogen); unsubstituted alkyl;

substituted alkyloxy (Examples of the substituents include halogen, hydroxy, carboxy, alkyloxy, alkyloxycarbonyl, alkylcarbamoyl; optionally substituted with one or more group(s) selected from these); unsubstituted alkyloxy;

unsubstituted alkylsulfonyl;

unsubstituted dialkyl-sulfoxyiminyl;

unsubstituted cyclic sulfoxyiminyl;

substituted amino (Examples of the substituents include alkylsulfonyl);

substituted carbamoyl (Examples of the substituents include alkyl);

unsubstituted aromatic heterocyclyl;

unsubstituted non-aromatic heterocyclyl unsubstituted non-aromatic carbocyclyloxy;

substituted aromatic heterocyclyloxy (Examples of the substituents include alkyl). It may be substituted with one or more group(s) selected from these.

In one embodiment, examples of the substituents of the "substituted or unsubstituted aromatic carbocyclyl" in $R^3$ include:

halogen;

hydroxy;

unsubstituted alkyloxy;

unsubstituted dialkyl-sulfoxyiminyl;

unsubstituted cyclic sulfoxyiminyl. It may be substituted with one or more group(s) selected from these.

In one embodiment, examples of the substituents of the "substituted or unsubstituted aromatic carbocyclyl" in $R^3$ include:

halogen;

unsubstituted alkyloxy. It may be substituted with one or more group(s) selected from these.

Examples of the substituents of the "substituted or unsubstituted non-aromatic carbocyclyl" in $R^3$ include:

halogen;

substituted or unsubstituted alkyloxy;

substituted or unsubstituted amino;

substituted or unsubstituted aromatic carbocyclyl;

substituted or unsubstituted aromatic heterocyclyl. It may be substituted with one or more group(s) selected from these.

Examples of the substituents of the "substituted or unsubstituted non-aromatic carbocyclyl" in $R^3$ include:

halogen;

unsubstituted alkyloxy;

substituent amino (Examples of the substituents include alkyloxycarbonyl, aromatic heterocyclyl, halogenated-aromatic heterocyclyl, dihalogenated-aromatic heterocyclyl, alkyl-aromatic heterocyclyl, dialkyl-aromatic heterocyclyl, haloalkyl-aromatic heterocyclyl, alkyloxy-aromatic heterocyclyl, dialkyloxy-aromatic heterocyclyl, non-aromatic carbocyclyl-aromatic heterocyclyl; optionally substituted with one or more group (s) selected from these);

substituted aromatic carbocyclyl (Examples of the substituents include alkylcarbamoyl);

substituted aromatic heterocyclyl (Examples of the substituents include alkyl). It may be substituted with one or more group(s) selected from these.

Examples of the substituents of the "substituted or unsubstituted aromatic heterocyclyl" in $R^3$ include:

halogen;

cyano;

substituted or unsubstituted alkyl;

substituted or unsubstituted alkyloxy;

substituted or unsubstituted amino;

substituted or unsubstituted non-aromatic carbocyclyl;

substituted or unsubstituted aromatic heterocyclyl;

substituted or unsubstituted non-aromatic heterocyclyl. It may be substituted with one or more group(s) selected from these.

Examples of the substituents of the "substituted or unsubstituted aromatic heterocyclyl" in $R^3$ include:

halogen;

cyano;

substituted alkyl (Examples of the substituents include halogen, hydroxy, cyano, carboxy, alkyloxy, haloalkyloxy, alkyloxycarbonyl, amino, alkylamino, alkylcarbamoyl, substituted carbamoyl (substituents: alkyloxyalkyl and alkyl), substituted carbamoyl (substituents: non-aromatic carbocyclyl and alkyl), alkylsulfonyl, non-aromatic carbocyclyl, cyano-non-aromatic carbocyclyl, hydroxy-non-aromatic carbocyclyl, amino-non-aromatic carbocyclyl, alkyloxycarbamoyl-non-aromatic carbocyclyl, alkyl-aromatic heterocyclyl, aromatic heterocyclyl, non-aromatic heterocyclyl, alkyl-non-aromatic heterocyclyl, hydroxyalkyl-non-aromatic heterocyclyl, non-aromatic carbocyclylcarbamoyl, non-aromatic heterocyclylcarbonyl, halogenated non-aromatic heterocyclylcarbonyl; optionally substituted with one or more group(s) selected from these); unsubstituted alkyl;

substituted alkyloxy (Examples of the substituents include halogen); unsubstituted alkyloxy;

substituent amino (Examples of the substituents include alkyl, haloalkyl, non-aromatic carbocyclylalkyl, alkylcarbonyl, alkyloxycarbonyl, alkylsulfonyl, non-aromatic carbocyclyl; optionally substituted with one or more group(s) selected from these); unsubstituted amino;

substitutable non-aromatic carbocyclyl (Examples of the substituents include halogen, hydroxy, amino; optionally substituted with one or more group(s) selected from these); unsubstituted non-aromatic carbocyclyl;

unsubstituted aromatic heterocyclyl;

substituted non-aromatic heterocyclyl (Examples of the substituents include oxo, alkyl, alkylcarbonyl; optionally substituted with one or more group(s) selected from these); unsubstituted non-aromatic heterocyclyl. It may be substituted with one or more group(s) selected from these.

In one embodiment, examples of the substituents of the "substituted or unsubstituted aromatic heterocyclyl" in $R^3$ include:

halogen;

substituted alkyl (Examples of the substituents include halogen, hydroxy, cyano, carboxy, alkyloxy, haloalkyloxy, alkyloxycarbonyl, amino, alkylamino, alkylcarbamoyl, substituted carbamoyl (substituents: alkyloxyalkyl and alkyl), substituted carbamoyl (substituents: non-aromatic carbocyclyl and alkyl), alkylsulfonyl, non-aromatic carbocyclyl, hydroxy-non-aromatic carbocyclyl, alkyl-non-aromatic heterocyclyl, non-aromatic carbocyclylcarbamoyl; optionally substituted with one or more group(s) selected from these); unsubstituted alkyl;

substituted amino (Examples of the substituents include alkyl, haloalkyl, non-aromatic carbocyclylalkyl, alkylcarbonyl, alkyloxycarbonyl, alkylsulfonyl, non-aromatic carbocyclyl; optionally substituted with one or more group(s) selected from these); unsubstituted amino;

substituted non-aromatic carbocyclyl (Examples of the substituents include halogen, hydroxy, amino; optionally substituted with one or more group(s) selected from these); unsubstituted non-aromatic carbocyclyl;

unsubstituted aromatic heterocyclyl;

substituted non-aromatic heterocyclyl (Examples of the substituents include oxo, alkyl, alkylcarbonyl; optionally substituted with one or more group(s) selected from these); unsubstituted non-aromatic heterocyclyl. It may be substituted with one or more group(s) selected from these.

In one embodiment, examples of the substituents of the "substituted or unsubstituted aromatic heterocyclyl" in $R^3$ include:

halogen;

substituted alkyl (Examples of the substituents include halogen, non-aromatic carbocyclyl; optionally substituted with one or more group(s) selected from these); unsubstituted alkyl;

substituted amino (Examples of the substituents include alkyl); unsubstituted amino. It may be substituted with one or more group(s) selected from these.

Examples of the substituents of the "substituted or unsubstituted non-aromatic heterocyclyl" in $R^3$ include:

halogen;

oxo;

substituted or unsubstituted alkyl;

substituted or unsubstituted alkyloxycarbonyl;

substituted or unsubstituted aromatic carbocyclyl;

substituted or unsubstituted aromatic heterocyclyl. It may be substituted with one or more group(s) selected from these.

Examples of the substituents of the "substituted or unsubstituted non-aromatic heterocyclyl" in $R^3$ include:

halogen;

oxo;

unsubstituted alkyl;

unsubstituted alkyloxycarbonyl;

substituted aromatic carbocyclyl (Examples of the substituents include halogen); unsubstituted aromatic heterocyclyl. It may be substituted with one or more group(s) selected from these.

Examples of the substituents of "substituted or unsubstituted alkyl" in $R^3$ include:

halogen;

substituted or unsubstituted aromatic carbocyclyl;

substituted or unsubstituted non-aromatic carbocyclyl. It may be substituted with one or more group(s) selected from these.

Examples of the substituents of "substituted or unsubstituted alkyl" in $R^3$ include:

halogen;

substituted aromatic carbocyclyl (Examples of the substituents include halogen, hydroxy; optionally substituted with one or more group(s) selected from these);

unsubstituted aromatic carbocyclyl;

unsubstituted non-aromatic carbocyclyl. It may be substituted with one or more group(s) selected from these.

Examples of the substituents of "substituted or unsubstituted alkyl" in $R^7$ include:

halogen;

hydroxy;

unsubstituted alkyloxy. It may be substituted with one or more group(s) selected from these.

Examples of the substituents of the "substituted or unsubstituted alkyl" in $R^6$ include:

halogen;

hydroxy;

unsubstituted alkyloxy; It may be substituted with one or more group(s) selected from these.

Examples of the substituents of the "substituted or unsubstituted alkyl" in $R^{6'}$ include:

halogen;

hydroxy;

unsubstituted alkyloxy. It may be substituted with one or more group(s) selected from these.

Examples of the substituents of the "substituted or unsubstituted alkyl" in $R^{5a}$ include:

halogen;

hydroxy. It may be substituted with one or more group(s) selected from these.

Examples of the substituents of the "substituted or unsubstituted alkyl" in $R^{5b}$ include:

halogen;

hydroxy. It may be substituted with one or more group(s) selected from these.

Examples of the substituents of the "substituted or unsubstituted alkyl" in $R^{4a}$ include:

halogen;

hydroxy;

unsubstituted alkyloxy. It may be substituted with one or more group(s) selected from these.

Examples of the substituents of the "substituted or unsubstituted alkyl" in $R^{4b}$ include:

halogen;

hydroxy;

unsubstituted alkyloxy. It may be substituted with one or more group(s) selected from these.

With regard to a compound represented by Formula (I):

[Chemical Formula 53]

(I)

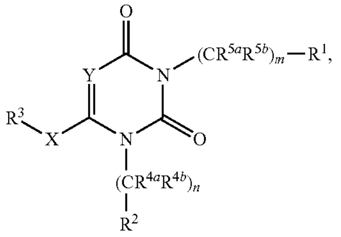

preferred embodiments of Y, $R^7$, $R^1$, $R^2$, $R^3$, —X—, $R^6$, $R^{6'}$, m, $R^{5a}$, $R^{5b}$, n, $R^{4a}$, $R^{4b}$, Z, $R^{1a}$, $R^{1b}$, and $R^{1c}$ will be shown below. Regarding the compound represented by Formula (I), embodiments of all the combinations of specific examples shown below are mentioned as examples.

In the present specification, the phrase "may be substituted with substituent group ω" means that "may be substituted with one or more group(s) selected from substituent group ω". The same also applies to substituent groups ω1, ω2, ω3, ω4, ω5 and ω'.

Y may be N or $CR^7$ (hereinafter, referred to as AA-1).

Y may be N (hereinafter, referred to as AA-2).

Y may be CH (hereinafter, referred to as AA-3).

$R^7$ may be a hydrogen atom or substituted or unsubstituted alkyl (hereinafter, referred to as AA-4).

$R^7$ may be a hydrogen atom (hereinafter, also referred to as AA-5).

$R^1$ may be substituted or unsubstituted non-aromatic heterocyclyl, substituted or unsubstituted aromatic heterocyclyl, substituted or unsubstituted carbamoyl, or substituted or unsubstituted amino (hereinafter, may be referred to as A-1).

$R^1$ may be substituted or unsubstituted non-aromatic heterocyclyl, substituted or unsubstituted aromatic heterocyclyl, or substituted or unsubstituted carbamoyl (hereinafter, referred to as A-2).

$R^1$ may be substituted or unsubstituted non-aromatic heterocyclyl, or substituted or unsubstituted aromatic heterocyclyl (hereinafter, referred to as A-3).

$R^1$ may be substituted or unsubstituted non-aromatic heterocyclyl (hereinafter, referred to as A-4).

$R^1$ may be substituted or unsubstituted aromatic heterocyclyl (hereinafter, referred to as A-5).

$R^1$ may be substituted or unsubstituted 5-membered non-aromatic heterocyclyl, substituted or unsubstituted 6-membered non-aromatic heterocyclyl, substituted or unsubstituted 10-membered non-aromatic heterocyclyl, substituted or unsubstituted 5-membered aromatic heterocyclyl, substituted or unsubstituted. 6-membered aromatic heterocyclyl, substituted or unsubstituted 9-membered aromatic heterocyclyl, or substituted or unsubstituted 10-membered aromatic heterocyclyl (hereinafter, referred to as A-6).

$R^1$ may be 5-membered non-aromatic heterocyclyl which is substituted with oxo and may be further substituted with one or more group(s), 6-membered non-aromatic heterocyclyl which is substituted with oxo and may be further substituted with one or more group(s), 10-membered non-aromatic heterocyclyl which is substituted with oxo and may be further substituted with one or more groups, substituted or unsubstituted 5-membered aromatic heterocyclyl, substituted or unsubstituted 6-membered aromatic heterocyclyl, substituted or unsubstituted 9-membered aromatic heterocyclyl, or substituted or unsubstituted 10-membered aromatic heterocyclyl (hereinafter, referred to as A-7).

$R^1$ may be 5-membered non-aromatic heterocyclyl which may be substituted with substituent group C, 6-membered non-aromatic heterocyclyl which may be substituted with substituent group C, 10-membered non-aromatic heterocyclyl which may be substituted with substituent group C, 5-membered aromatic heterocyclyl which may be substituted with substituent group B, 6-membered aromatic heterocyclyl which may be substituted with substituent group B, 9-membered aromatic heterocyclyl which may be substituted with substituent group B, or 10-membered aromatic heterocyclyl which may be substituted with substituent group B (hereinafter, referred to as A-8).

$R^1$ may be 5-membered non-aromatic heterocyclyl which is substituted with oxo and may be substituted with substituent group C, 6-membered non-aromatic heterocyclyl which is substituted with oxo and may be substituted with substituent group C, 10-membered non-aromatic heterocyclyl which is substituted with oxo and may be substituted with substituent group C, 5-membered aromatic heterocyclyl which may be substituted with substituent group B, 6-membered aromatic heterocyclyl which may be substituted with substituent group B, 9-membered aromatic heterocyclyl which may be substituted with substituent group B, or 10-membered aromatic heterocyclyl which may be substituted with substituent group B (hereinafter, referred to as A-9).

$R^1$ may be 5-membered non-aromatic heterocyclyl which is substituted with oxo and may be substituted with substituent group ω2, 6-membered non-aromatic heterocyclyl which is substituted with oxo and may be substituted with substituent group ω2, 10-membered non-aromatic heterocyclyl which is substituted with oxo and may be substituted with substituent group ω2, 5-membered aromatic heterocyclyl which may be substituted with substituent group ω1, 6-membered aromatic heterocyclyl which may be substituted with substituent group ω1, 9-membered aromatic heterocyclyl which may be substituted with substituent group ω1, or 10-membered aromatic heterocyclyl which may be substituted with substituent group ω1 (hereinafter, referred to as A-10).

Substituent group ω1: halogen, cyano, nitro, hydroxy, carboxy, carbamoyl which may be substituted with substituent group ω', alkyl which may be substituted with substituent group ω, alkenyl which may be substituted with substituent group ω', alkynyl which may be substituted with substituent group ω', alkyloxy which may be substituted with substituent group ω', alkynyloxy which may be substituted with substituent group ω', alkynyloxy which may be substituted with substituent group ω', alkylcarbonyl which may be substituted with substituent group ω', alkenylcarbonyl which may be substituted with substituent group ω', alkynylcarbonyl which may be substituted with substituent group ω', alkyloxycarbonyl which may be substituted with substituent group ω', alkenyloxycarbonyl which may be substituted with substituent group ω', alkynyloxycarbonyl which may be substituted with substituent group ω', alkylsulfanyl which may be substituted with substituent group ω', alkenylsulfanyl which may be substituted with substituent group ω', alkynylsulfanyl which may be substituted with substituent group ω', amino which may be substituted with substituent group ω', aromatic carbocyclyl which may be substituted with substituent group α, aromatic heterocyclyl which may be substituted with substituent group ω', non-aromatic carbocyclyl which may be substituted with substituent group ω', non-aromatic heterocyclyl which may be substituted with substituent group ω', and non-aromatic heterocyclylcarbonyl which may be substituted with substituent group ω';

substituent group ω2: substituent group ω1, oxo, and thioxo;

substituent group ω': halogen, hydroxy, alkyl, hydroxyalkyl, alkylaminoalkyl, alkylcarbonyl, carbamoyl, aromatic carbocyclyl, and non-aromatic carbocyclyl.

$R^1$ may be 5-membered non-aromatic heterocyclyl which is substituted with oxo and may be further substituted with substituent group C, 6-membered non-aromatic heterocyclyl which is substituted with oxo and may be further substituted with substituent group C, or 10-membered non-aromatic heterocyclyl which is substituted with oxo and may be further substituted with substituent group C (hereinafter, referred to as A-11).

$R^1$ may be 5-membered non-aromatic heterocyclyl which is substituted with oxo and may be further substituted with substituent group ω2, 6-membered non-aromatic heterocyclyl which is substituted with oxo and may be further substituted with substituent group ω2, or 10-membered non-aromatic heterocyclyl which is substituted with oxo and may be further substituted with substituent group ω2 (hereinafter, referred to as A-12).

$R^1$ may be 5-membered aromatic heterocyclyl which may be substituted with substituent group B, 6-membered aromatic heterocyclyl which may be substituted with substituent group B, 9-membered aromatic heterocyclyl which may be substituted with substituent group B, or 10-membered aromatic heterocyclyl which may be substituted with substituent group B (hereinafter, referred to as A-13).

$R^1$ may be 5-membered aromatic heterocyclyl which may be substituted with substituent group ω1, 6-membered aromatic heterocyclyl which may be substituted with substituent group ω1, 9-membered aromatic heterocyclyl which may be substituted with substituent group ω1, or 10-membered aromatic heterocyclyl which may be substituted with substituent group ω1 (hereinafter, referred to as A-14).

$R^1$ may be substituted or unsubstituted dihydropyridinyl, substituted or unsubstituted dihydropyrimidinyl, substituted or unsubstituted dihydropyridazinyl, substituted or unsubstituted dihydropyrazinyl, substituted or unsubstituted dihydroquinolinyl, substituted or unsubstituted dihydronaphthyridinyl, substituted or unsubstituted dihydrothienopyridinyl, substituted or unsubstituted tetrahydropyrimidinyl, substituted or unsubstituted benzopyranyl, substituted or unsubstituted pyrrolidinyl, substituted or unsubstituted dihydropyrazolyl, substituted or unsubstituted pyrazolyl, substituted or unsubstituted imidazolyl, substituted or unsubstituted triazolyl, substituted or unsubstituted oxazolyl, substituted or unsubstituted isoxazolyl, substituted or unsubstituted thiazolyl, substituted or unsubstituted oxadiazolyl, substituted or unsubstituted pyridinyl, substituted or unsubstituted imidazopyridinyl, substituted or unsubstituted indazolyl, substituted or unsubstituted benzisoxadiazolyl, substituted or unsubstituted pyrazolopyridinyl, substituted or unsubstituted naphthyridinyl, or substituted or unsubstituted isoquinolinyl (hereinafter, referred to as A-15).

$R^1$ may be substituted or unsubstituted oxodihydropyridinyl, substituted or unsubstituted oxodihydropyrimidinyl, substituted or unsubstituted oxodihydropyrazinyl, substituted or unsubstituted oxodihydroquinolinyl, substituted or unsubstituted oxodihydronaphthyridinyl, substituted or unsubstituted oxodihydrothienopyridinyl, substituted or unsubstituted dioxotetrahydropyrimidinyl, substituted or unsubstituted oxothioxotetrahydropyrimidinyl, substituted or unsubstituted dioxodihydropyridazinyl, substituted or unsubstituted oxobenzopyranyl, substituted or unsubstituted oxopyrrolidinyl, substituted or unsubstituted oxodihydropyrazolyl, substituted or unsubstituted pyrazolyl, substituted or unsubstituted imidazolyl, substituted or unsubstituted triazolyl, substituted or unsubstituted oxazolyl, substituted or unsubstituted isoxazolyl, substituted or unsubstituted thiazolyl, substituted or unsubstituted oxadiazolyl, substituted or unsubstituted pyridinyl, substituted or unsubstituted imidazopyridinyl, substituted or unsubstituted indazolyl, substituted or unsubstituted benzisoxadiazolyl, substituted or unsubstituted pyrazolopyridinyl, substituted or unsubstituted naphthyridinyl, or substituted or unsubstituted isoquinolinyl (hereinafter, referred to as A-16).

$R^1$ may be substituted or unsubstituted dihydropyridinyl (hereinafter, referred to as A-17).

$R^1$ may be dihydropyridinyl which may be substituted with substituent group ω2 (hereinafter, referred to as A-18).

$R^1$ may be substituted or unsubstituted dihydronaphthyridinyl (hereinafter, referred to as A-19).

$R^1$ may be dihydronaphthyridinyl which may be substituted with substituent group ω2 (hereinafter, referred to as A-20).

$R^1$ may be substituted or unsubstituted triazolyl (hereinafter, referred to as A-21).

$R^1$ may be triazolyl substituted with one or more substituent(s) selected from substituent group ω1 (hereinafter, referred to as A-22).

$R^1$ may be triazolyl substituted with alkyl (hereinafter, referred to as A-23).

$R^1$ may be unsubstituted triazolyl (hereinafter, referred to as A-24).

$R^1$ may be substituted or unsubstituted pyridinyl (hereinafter, referred to as A-25).

$R^1$ may be pyridinyl substituted with one or more substituent(s) selected from substituent group ω1 (hereinafter, referred to as A-26).

$R^1$ may be pyridinyl substituted with one or more substituent(s) selected from substituent group ω4 (hereinafter, referred to as A-27).

Substituent group ω4: halogen, alkyl, alkenyl, alkynyl, haloalkyl, and alkyloxy.

$R^1$ may be unsubstituted pyridinyl (hereinafter, referred to as A-28).

$R^1$ may be substituted or unsubstituted isoquinolinyl (hereinafter, referred to as A-29).

$R^1$ may be isoquinolinyl substituted with one or more substituent(s) selected from substituent group col (hereinafter, referred to as A-30).

$R^1$ may be unsubstituted isoquinolinyl (hereinafter, referred to as A-31).

$R^1$ may be a group represented by Formula:

[Chemical Formula 54]

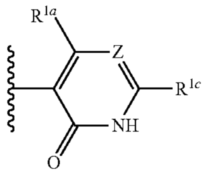

wherein

Z is $CR^{1b}$ or N;

$R^{1a}$ is a hydrogen atom, halogen, or substituted or unsubstituted alkyl;

$R^{1b}$ is a hydrogen atom, halogen, carboxy, cyano, nitro, substituted or unsubstituted carbamoyl, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted amino, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, or substituted or unsubstituted non-aromatic heterocyclylcarbonyl; and $R^{1c}$ is a hydrogen atom, halogen, carboxy, cyano, nitro, substituted or unsubstituted carbamoyl, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted amino, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, or substituted or unsubstituted non-aromatic heterocyclylcarbonyl (hereinafter, referred to as A-32).

$R^1$ may be a group represented by Formula:

[Chemical Formula 55]

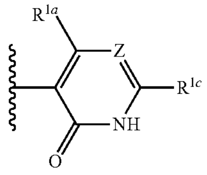

wherein $R^{1a}$, $R^{1b}$, and $R^{1c}$ have the same meanings as the above-described A-32;

Z is $CR^{1b}$; and $R^{1b}$ and $R^{1c}$ may be joined together with the carbon atom to which $R^{1b}$ and $R^{1c}$ are bonded, and may form a substituted or unsubstituted aromatic carbocyclyl, or substituted or unsubstituted aromatic heterocyclyl (hereinafter, referred to as A-33).

$R^1$ may be a group represented by Formula:

[Chemical Formula 56]

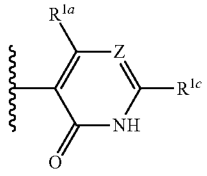

wherein $R^{1a}$ is a hydrogen atom; Z is $CR^{1b}$;

$R^{1b}$ is a hydrogen atom, halogen, alkyl, haloalkyl, hydroxyalkyl, carbamoyl, or alkylcarbamoyl; and $R^{1c}$ is a hydrogen atom (hereinafter, referred to as A-34).

$R^1$ may be a group represented by Formula:

[Chemical Formula 57]

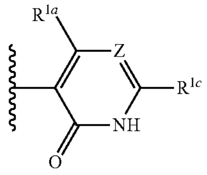

wherein $R^{1a}$ is a hydrogen atom; Z is CH; and $R^{1c}$ is a hydrogen atom (hereinafter, referred to as A-35).

$R^1$ may be a group represented by Formula:

[Chemical Formula 58]

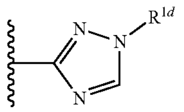

wherein $R^{1d}$ is substituted or unsubstituted alkyl (hereinafter, referred to as A-36).

$R^1$ may be a group represented by Formula:

[Chemical Formula 59]

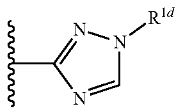

wherein $R^{1d}$ is unsubstituted alkyl (hereinafter, referred to as A-37).

$R^1$ may be a group represented by Formula:

[Chemical Formula 60]

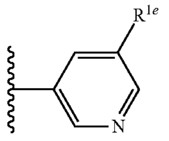

wherein $R^{1e}$ is halogen, cyano, alkyl, alkenyl, alkynyl, haloalkyl, alkyloxy, amino, or alkylamino (hereinafter, referred to as A-38).

$R^1$ may be a group represented by Formula:

[Chemical Formula 61]

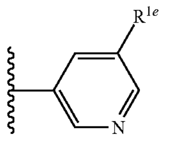

wherein $R^{1e}$ is halogen or unsubstituted alkyl (hereinafter, referred to as A-39).

$R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl (hereinafter, referred to as B-1).

$R^2$ is substituted or unsubstituted aromatic carbocyclyl (provided that para-monofluorophenyl, para-monochlorophenyl, and para-monomethylphenyl are excluded), substituted or unsubstituted non-aromatic carbocyclyl, substituted or unsubstituted aromatic heterocyclyl, or substituted or unsubstituted non-aromatic heterocyclyl (hereinafter, referred to as B-2).

$R^2$ is substituted or unsubstituted 6-, 10-, or 14-membered aromatic carbocyclyl (provided that para-monofluorophenyl, para-monochlorophenyl, and para-monomethylphenyl are excluded), substituted or unsubstituted 5-, 6-, 9-, or 10-membered non-aromatic carbocyclyl, substituted or unsubstituted 5-, 6-, 9-, or 10-membered aromatic heterocyclyl, or substituted or unsubstituted 5-, 6-, 9-, or 10-membered non-aromatic heterocyclyl (hereinafter, referred to as B-3-1).

$R^2$ is substituted or unsubstituted 6-membered aromatic carbocyclyl (provided that para-monofluorophenyl, para-monochlorophenyl, and para-monomethylphenyl are excluded), substituted or unsubstituted 6-membered non-aromatic carbocyclyl, substituted or unsubstituted 9- or 10-membered non-aromatic carbocyclyl, substituted or unsubstituted 5- or 6-membered aromatic heterocyclyl, or substituted or unsubstituted 9- or 10-membered non-aromatic heterocyclyl (hereinafter, referred to as B-3).

$R^2$ is substituted or unsubstituted 6-membered aromatic carbocyclyl (provided that para-monofluorophenyl, para-monochlorophenyl, and para-monomethylphenyl are excluded), substituted or unsubstituted 9- or 10-membered non-aromatic carbocyclyl, substituted or unsubstituted 5- or 6-membered aromatic heterocyclyl, or substituted or unsubstituted 9- or 10-membered non-aromatic heterocyclyl (hereinafter, referred to as B-4).

$R^2$ may be 6-membered aromatic carbocyclyl which is substituted with one halogen or one cyano and is further substituted with 1, 2, 3, or 4 substituents selected from substituent group G, or 6-membered aromatic heterocyclyl which is substituted with one halogen or one cyano and is further substituted with 1 or 2 substituents selected from substituent group G (hereinafter, referred to as B-5).

Substituent group G: halogen, cyano, alkyl, alkenyl, alkynyl, haloalkyl, alkyloxy, alkenyloxy, alkynyloxy, and haloalkyloxy.

$R^2$ may be meta-monochlorophenyl; meta-monocyanophenyl; 6-membered aromatic carbocyclyl which is substituted with one halogen or one cyano and is further substituted with 1, 2, 3, or 4 substituents selected from substituent group G; or 6-membered aromatic heterocyclyl which is substituted with one halogen or one cyano and is further substituted with 1 or 2 substituents selected from substituent group G (hereinafter, referred to as B-15).

$R^2$ may be 6-membered aromatic carbocyclyl which is substituted with one halogen or one cyano and is further substituted with 1, 2, 3, or 4 substituents selected from substituent group G (hereinafter, referred to as B-6).

$R^2$ may be 6-membered aromatic carbocyclyl which is substituted with one halogen or one cyano and is further substituted with 1, 2, 3, or 4 substituents selected from substituent group G' (hereinafter, referred to as B-7).

Substituent group G': halogen and cyano.

$R^2$ may be 6-membered aromatic carbocyclyl which is substituted with one halogen or one cyano and is further substituted 1 or 2 substituents selected from substituent group G (hereinafter, referred to as B-8).

$R^2$ may be 6-membered aromatic carbocyclyl which is substituted with one halogen or one cyano and is further substituted 1 or 2 substituents selected from substituent group G' (hereinafter, referred to as B-9).

$R^2$ may be phenyl which is substituted with one halogen or one cyano and is further substituted with 1, 2, 3, or 4 substituents selected from substituent group G (hereinafter, referred to as B-10).

$R^2$ may be phenyl which is substituted with one halogen or one cyano and is further substituted with 1, 2, 3, or 4 substituents selected from substituent group G' (hereinafter, referred to as B-11).

$R^2$ may be phenyl which is substituted with one halogen or one cyano and is further substituted with 1 or 2 substituents selected from substituent group G (hereinafter, referred to as B-12).

$R^2$ may be phenyl which is substituted with one halogen or one cyano and is further substituted with 1 or 2 substituents selected from substituent group G' (hereinafter, referred to as B-13).

$R^2$ may be phenyl substituted with 3 halogens (hereinafter, referred to as B-14).

$R^3$ may be substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl (hereinafter, referred to as C-1).

$R^3$ may be substituted or unsubstituted 6-membered aromatic carbocyclyl, substituted or unsubstituted 3- to 10-membered non-aromatic carbocyclyl, substituted or unsubstituted 5- or 6-membered aromatic heterocyclyl, substituted or unsubstituted 9- or 10-membered aromatic heterocyclyl, substituted or unsubstituted 13- to 15-membered aromatic heterocyclyl, or substituted or unsubstituted 3- to 20-membered non-aromatic heterocyclyl (hereinafter, referred to as C-2).

$R^3$ may be substituted or unsubstituted alkyl (hereinafter, referred to as C-33).

$R^3$ may be substituted or unsubstituted 6-membered aromatic carbocyclyl, substituted or unsubstituted 3- to 10-membered non-aromatic carbocyclyl, substituted or unsubstituted 5- or 6-membered aromatic heterocyclyl, substituted or unsubstituted 9- or 10-membered aromatic heterocyclyl, or substituted or unsubstituted 3- to 10-membered non-aromatic heterocyclyl (hereinafter, referred to as C-3).

$R^3$ may be substituted or unsubstituted 6-membered aromatic carbocyclyl, substituted or unsubstituted 9- or 10-membered aromatic heterocyclyl, or substituted or unsubstituted 9- or 10-membered non-aromatic heterocyclyl (hereinafter, referred to as C-4).

$R^3$ may be substituted or unsubstituted 6-membered aromatic carbocyclyl (hereinafter, referred to as C-5).

$R^3$ may be substituted or unsubstituted 9- or 10-membered aromatic heterocyclyl, or substituted or unsubstituted 9- or 10-membered non-aromatic heterocyclyl (hereinafter, referred to as C-6).

$R^3$ may be 6-membered aromatic carbocyclyl which may be substituted with substituent group β, 9- or 10-membered aromatic heterocyclyl which may be substituted with substituent group β, or 9- or 10-membered non-aromatic heterocyclyl which may be substituted with substituent group C (hereinafter, referred to as C-7).

$R^3$ may be 6-membered aromatic carbocyclyl which may be substituted with substituent group B (hereinafter, referred to as C-8).

$R^3$ may be 9- or 10-membered aromatic heterocyclyl which may be substituted with substituent group B, or 9- or 10-membered non-aromatic heterocyclyl which may be substituted with substituent group C (hereinafter, referred to as C-9).

$R^3$ may be 6-membered aromatic carbocyclyl substituted with substituent group ω3 (hereinafter, referred to as C-10).

Substituent group ω3: halogen, cyano, hydroxy, carboxy, substituted alkyl (as the substituent, halogen), unsubstituted alkyl, substituted alkyloxy (as the substituent, halogen, hydroxy, carboxy, alkyloxy, alkyloxycarbonyl, carbamoyl, alkylcarbamoyl, alkylamino, and aromatic carbocyclyl), unsubstituted alkyloxy, substituted alkylcarbonyl (as the substituent, amino), unsubstituted alkyloxycarbonyl, unsubstituted alkylsulfanyl, unsubstituted alkylsulfinyl, unsubstituted alkylsulfonyl, substituted amino (as the substituent, alkylcarbonyl, alkylcarbamoyl, and alkylsulfonyl), substituted carbamoyl (as the substituent, unsubstituted carbamoyl, unsubstituted dialkylsulfoxyimino, unsubstituted non-aromatic carbocyclyl, substituted aromatic heterocyclyl (as the substituent, alkyl), unsubstituted aromatic heterocyclyl, substituted non-aromatic heterocyclyl (as the substituent, oxo), and unsubstituted non-aromatic carbocyclyloxy.

$R^3$ may be 6-membered aromatic carbocyclyl substituted with halogen and alkyloxy, dihydrobenzofuranyl which may be substituted with substituent group B, dihydrobenzofuranyl substituted with halogen, unsubstituted dihydrobenzofuranyl, indazolyl which may be substituted with substituent group C, indazolyl substituted with halogen and alkyl, unsubstituted indazolyl, benzoxazolyl which may be substituted with substituent group B, benzothiazolyl which may be substituted with substituent group B, or benzimidazolyl which may be substituted with substituent group B (hereinafter, referred to as C-11).

$R^3$ may be 6-membered aromatic carbocyclyl substituted with halogen and alkyloxy (hereinafter, referred to as C-12).

$R^3$ may be dihydrobenzofuranyl which may be substituted with substituent group B (hereinafter, referred to as C-13).

$R^3$ may be dihydrobenzofuranyl substituted with halogen (hereinafter, referred to as C-14).

$R^3$ may be unsubstituted dihydrobenzofuranyl (hereinafter, referred to as C-15)

$R^3$ may be indazolyl which may be substituted with substituent group C (hereinafter, referred to as C-16).

$R^3$ may be indazolyl substituted with halogen and alkyl (hereinafter, referred to as C-17).

$R^3$ may be unsubstituted indazolyl (hereinafter, referred to as C-18).

$R^3$ may be benzoxazolyl which may be substituted with substituent group B (hereinafter, referred to as C-1).

$R^3$ may be benzothiazolyl which may be substituted with substituent group B (hereinafter, referred to as C'-2).

$R^3$ may be benzimidazolyl which may be substituted with substituent group B (hereinafter, referred to as C'-3).

$R^3$ may be benzoxazolyl substituted with one or more group(s) selected from substituent group ω5 (hereinafter, referred to as C'-4).

Substituent group ω5: halogen, alkyl, haloalkyl, cycloalkyl, hydroxyalkyl, alkylcarbonylalkyl, alkylamino, and alkyloxycarbonylamino.

$R^3$ may be unsubstituted benzoxazolyl (hereinafter, referred to as C'-5).

$R^3$ may be benzothiazolyl substituted with one or more group(s) selected from substituent group ω5 (hereinafter, referred to as C'-6).

$R^3$ may be unsubstituted benzothiazolyl (hereinafter, referred to as C'-7).

$R^3$ may be benzimidazolyl substituted with one or more group(s) selected from substituent group ω5 (hereinafter, referred to as C'-8).

$R^3$ may be unsubstituted benzimidazolyl (hereinafter, referred to as C'-9). $R^3$ may be substituted or unsubstituted aromatic heterocyclyl, substituted or unsubstituted non-aromatic heterocyclyl, substituted or unsubstituted aromatic carbocyclyl, or substituted or unsubstituted non-aromatic carbocyclyl (hereinafter, referred to as C-19).

$R^3$ may be substituted or unsubstituted aromatic heterocyclyl, or substituted or unsubstituted non-aromatic heterocyclyl (hereinafter, referred to as C-20).

$R^3$ may be aromatic heterocyclyl substituted with one or more substituent(s) selected from substituent group d (substituent group d: substituted or unsubstituted alkyl; substituted or unsubstituted amino; and halogen), or unsubstituted aromatic heterocyclyl (hereinafter, referred to as C-21).

$R^3$ may be aromatic heterocyclyl substituted with one or more substituent(s) selected from substituent group d' (substituent group d': substituted alkyl (substituent: halogen, non-aromatic carbocyclyl) or unsubstituted alkyl; substituted amino (substituent: alkyl) or unsubstituted amino; and halogen), or unsubstituted aromatic heterocyclyl (hereinafter referred to as C-22).

$R^3$ may be aromatic heterocyclyl substituted with alkyl and halogen, or unsubstituted aromatic heterocyclyl (hereinafter, referred to as C-23).

$R^3$ may be aromatic heterocyclyl substituted with alkyl and halogen (hereinafter, referred to as C-24).

$R^3$ may be aromatic heterocyclyl substituted with unsubstituted alkyl and halogen, or unsubstituted aromatic heterocyclyl (hereinafter, referred to as C-25).

$R^3$ may be aromatic heterocyclyl substituted with unsubstituted alkyl and halogen (hereinafter, referred to as C-26).

$R^3$ may be 9-membered aromatic heterocyclyl substituted with unsubstituted alkyl and halogen, or unsubstituted 9-membered aromatic heterocyclyl (hereinafter, referred to as C-27).

$R^3$ may be 9-membered aromatic heterocyclyl substituted with unsubstituted alkyl and halogen (hereinafter, referred to as C-28).

$R^3$ may be indazolyl substituted with unsubstituted alkyl and halogen (hereinafter, referred to as C-29).

$R^3$ may be a group represented by Formula:

[Chemical Formula 62]

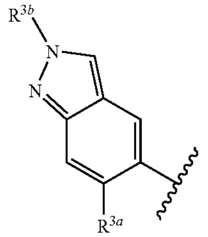

wherein $R^{3a}$ is a hydrogen atom or halogen; and $R^{3b}$ is substituted or unsubstituted alkyl (hereinafter, referred to as C-30).

$R^3$ may be a group represented by Formula:

[Chemical Formula 63]

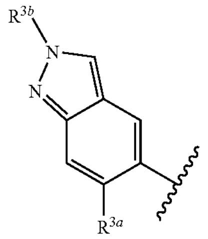

wherein $R^{3a}$ is halogen; and $R^{3b}$ is substituted alkyl (substituent: halogen or non-aromatic carbocyclyl), or unsubstituted alkyl (hereinafter, referred to as C-31).

$R^3$ may be a group represented by Formula:

[Chemical Formula 64]

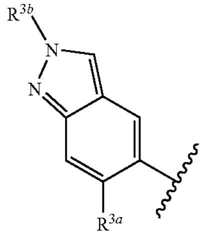

wherein $R^{3a}$ is halogen; and $R^{3b}$ is alkyl substituted with halogen, or unsubstituted alkyl (hereinafter, referred to as C-32).

—X— may be —$NR^6$—, —$CR^6R^{6'}$—, —O—, —S—, or a single bond (hereinafter, referred to as D-1).

—X— may be —$NR^6$—, —O—, or a single bond (hereinafter, referred to as D-2).

—X— may be —NH— or a single bond (hereinafter, referred to as D-4).

—X— may be —NH— (hereinafter, referred to as D-3).

$R^6$ and $R^{6'}$ may be each independently a hydrogen atom, or substituted or unsubstituted alkyl (hereinafter, referred to as E-1).

$R^6$ and $R^{6'}$ may be each independently a hydrogen atom (hereinafter, referred to as E-2).

m may be 0, 1, or 2 (hereinafter, referred to as F-1).

m may be 0 or 1 (hereinafter, referred to as F-2).

m may be 0 (hereinafter, referred to as F-3).

m may be 1 (hereinafter, referred to as F-4).

$R^{5a}$ may be each independently a hydrogen atom or substituted or unsubstituted alkyl (hereinafter, referred to as G-1).

$R^{5a}$ may be each independently a hydrogen atom (hereinafter, referred to as G-2).

$R^{5b}$ may be each independently a hydrogen atom or substituted or unsubstituted alkyl (hereinafter, referred to as G'-1).

$R^{5b}$ may be each independently a hydrogen atom (hereinafter, referred to as G'-2).

n may be 0, 1, or 2 (hereinafter, referred to as H-1).

n may be 0 or 1 (hereinafter, referred to as H-2).

n may be 0 (hereinafter, referred to as H-3).

n may be 1 (hereinafter, referred to as H-4).

$R^{4a}$ may be each independently a hydrogen atom or substituted or unsubstituted alkyl (hereinafter, referred to as J-1).

$R^{4a}$ may be each independently a hydrogen atom or unsubstituted alkyl (hereinafter, referred to as J-2).

$R^{4a}$ may be each independently a hydrogen atom (hereinafter, referred to as J-3).

$R^{4b}$ may be each independently a hydrogen atom or substituted or unsubstituted alkyl (hereinafter, referred to as X-1).

$R^{4b}$ may be each independently a hydrogen atom (hereinafter, referred to as J'-2)

$R^{4a}$ and $R^{4b}$ take together to form a substituted or unsubstituted non-aromatic carbocycle (hereinafter, referred to as K-1).

Examples of the compound represented by Formula (I);

[Chemical Formula 65]

(I)

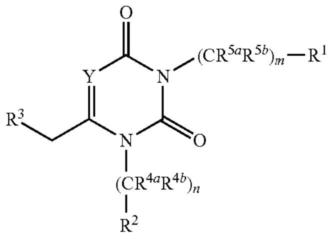

include the following embodiments. Regarding the compound represented by Formula (I), embodiments of all the combinations of specific examples shown below are mentioned as examples.

Y is preferably AA-2.

$R^1$ is preferably A-5, A-6, A-7, A-9, A-10, A-13, A-14, A-15, A-16, A-21, A-22, A-23, A-25, A-26, A-27, A-28, A-36, A-37, A-38, or A-39.

$R^2$ is preferably B-4, B-5, B-6, B-7, B-8, B-9, B-10, B-11, B-12, B-13, or B-14.

$R^3$ is preferably C-6, C-9, C-16, C-17, C-19, C-20, C-21, C-22, C-23, C-24, C-25, C-26, C-27, C-28, C-29, C-30, C-31, or C-32.

X is preferably D-3.

m is preferably F-2, F-3, or F-4.

$R^{5a}$ is preferably G-2.

$R^{5b}$ is preferably G'-2.

n is preferably H-4.

$R^{4a}$ is preferably J-3.

$R^{4b}$ is preferably J'-2.

Exemplary embodiments of a compound represented by Formula (I");

[Chemical Formula 66]

(I")

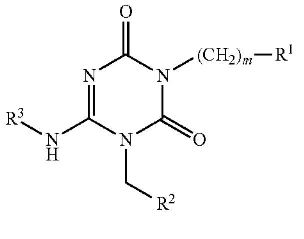

wherein

Y is AA-2; X is D-3; $R^{5a}$ is G-2; $R^{5b}$ is G'-2; n is H-4; $R^{4a}$ is J-3; and $R^{4b}$ is J'-2, include the following combinations.

(a1)

$R^1$ is A-36, A-37, A-38, or A-39;

$R^2$ is B-12, B-13, or B-14;

$R^3$ is C-30, C-31, or C-32; and m is F-2, F-3, or F-4.

(a2)

$R^1$ is A-37;

$R^2$ is B-14;

$R^3$ is C-32; and m is F-4.

(a3)

$R^1$ is A-39;

$R^2$ is B-12;

$R^3$ is C-30 or C-32; and m is F-3.

The compounds represented by Formulas (I), Formula (I') and Formula (I") are not limited to specific isomers, but include all possible isomers (eg, keto-enol isomer, imine-enamin isomers, diastereoisomers, optical isomers, rotational isomers, etc.), racemates or mixtures thereof. For example, the compound in Formula (I) wherein Y is N and X is NH includes the following tautomers.

[Chemical Formula 67]

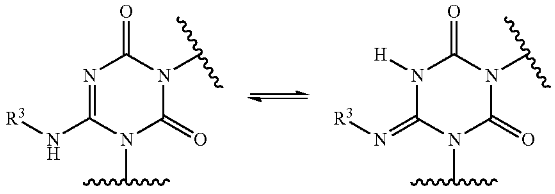

For example, the compound in Formula (I) wherein Y is C and X is NH includes the following tautomers.

[Chemical Formula 68]

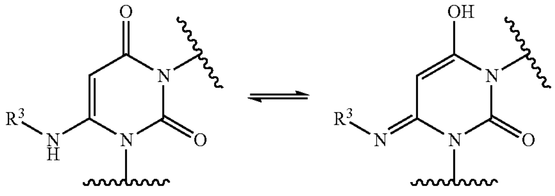

For example, Compound (I-0113) includes the following tautomers.

[Chemical Formula 69]

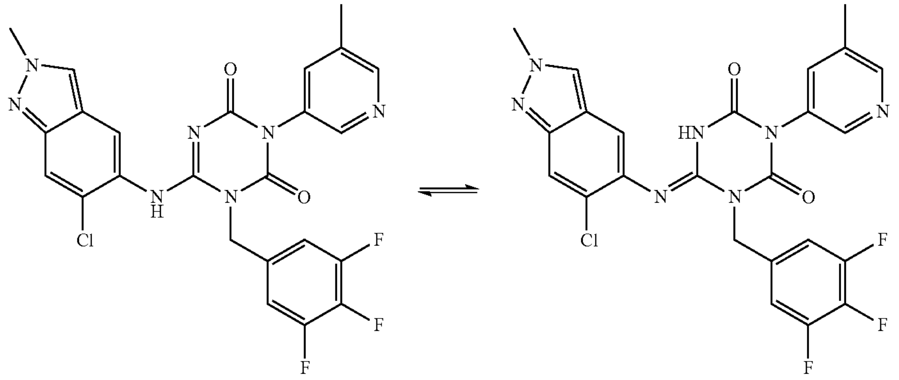

For example, Compound (I-0115) includes the following tautomers.

[Chemical Formula 70]

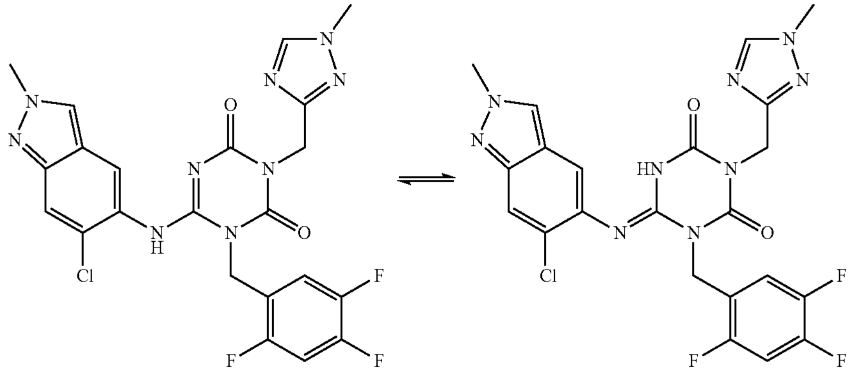

One or more hydrogen, carbon, and/or other atom(s) of the compounds represented by Formula (I), Formula (I'), and Formula (I") may be substituted by isotope(s) of hydrogen, carbon, and/or other atom(s), respectively. Examples of such isotopes include hydrogen, carbon, nitrogen, oxygen, phosphorus, sulfur, fluorine, iodine, and chlorine, as in the cases of $^{2}H$, $^{3}H$, $^{11}C$, $^{13}O$, $^{14}C$, $^{15}N$, $^{18}O$, $^{17}O$, $^{31}P$, $^{32}P$, $^{35}S$, $^{18}F$, $^{123}I$, and $^{36}Cl$, respectively. The compounds represented by Formula (I), Formula (I'), and Formula (I") also include compounds substituted with such isotopes. The compounds substituted with the isotopes are also useful as pharmaceutical products and include all radiolabeled forms of the compounds represented by Formula (I), Formula (I'), and Formula (I"). Furthermore, a "radiolabeling method" for producing the "radiolabeled forms" is also included in the present invention, and the "radiolabeled forms" are useful as tools for metabolic pharmacokinetics studies, studies on binding assay, and/or diagnostics.

Furthermore, the crystalline form of the present invention may also be a deuterated form. The crystalline form of the present invention may also be labeled with radioisotopes (for example, $^{3}H$, $^{14}C$, $^{36}S$, and $^{125}I$).

Radiolabeled forms of the compounds represented by Formula (I), Formula (I'), and Formula (I") can be prepared by methods well known in the pertinent art. For example, a tritium-labeled compound represented by Formula (I), Formula (I'), and Formula (I") can be prepared by introducing tritium into a specific compound represented by Formula (I), Formula (I'), and Formula (I"), by a catalytic dehalogenation reaction using tritium. This method includes causing precursors obtained by appropriately substituting compounds represented by Formula (I), Formula (I'), and Formula (I") with halogen, to react with tritium gas in the presence of an appropriate catalyst, for example, Pd/C and in the presence or absence of a base. Regarding other appropriate methods for preparing tritium-labeled compounds, "Isotopes in the Physical and Biomedical Sciences, Vol. 1, Labeled Compounds (Part A), Chapter 6 (1987)" can be referred to. A $^{14}C$-labeled compound can be prepared by using a raw material having $^{14}C$ carbon.

Examples of pharmaceutically acceptable salts of the compounds represented by Formula (I), Formula (I'), and Formula (I") include salts of compounds represented by Formula (I), Formula (I'), and Formula (I") with alkali metals (for example, lithium, sodium, and potassium), alkaline earth metals (for example, calcium and barium), magnesium, transition metals (for example, zinc and iron), ammonia, organic bases (for example, trimethylamine, triethylamine, dicyclohexylamine, ethanolamine, diethanolamine, triethanolamine, meglumine, ethylenediamine, pyridine, picoline, and quinoline), and amino acids, or salts with inorganic acids (for example, hydrochloric acid, sulfuric acid, nitric acid, carbonic acid, hydrobromic acid, phosphoric acid, and hydroiodic acid) and organic acids (for example, formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, and trifluoroacetic acid). These salts can be formed according to methods that are conventionally carried out.

A pharmaceutically acceptable salt of a compound represented by Formula (I-A) is composed of, for example, a compound represented by Formula (I-A) and a counter molecule or a counterion and may include any number of counter molecules or counterions. A pharmaceutically acceptable salt of a compound represented by Formula (I-A) implies involving ionic bonding by transferring protons between the compound and a counter molecule or a counter atom.

The compounds represented by Formula (I), Formula (I'), and Formula (I") of the present invention or pharmaceutically acceptable salts thereof may form solvates (for example, hydrates), cocrystals, and/or crystalline polymorphs, and the present invention also includes such various solvates, cocrystals, and crystalline polymorphs. The "solvates" may have the compounds represented by Formula (I), Formula (I'), and Formula (I") coordinated with any number of solvent molecules (for example, water molecules). Furthermore, crystalline polymorphs may be formed by recrystallizing the compounds represented by Formula (I), Formula (I'), and Formula (I") or pharmaceutically acceptable salts thereof.

"Crystal" as used in the present specification means a solid in which constituent atoms, ions, molecules, and the like are three-dimensionally arranged with regularity, and is distinguished from an amorphous solid that does not have such a regular internal structure. The crystal of the present invention may be a single crystal, a twin crystal, a polycrystal, or the like.

Furthermore, the "crystal" may include "crystalline polymorphs" that have the same composition but different arrangements in the crystal, and crystals including those crystalline polymorphs are referred to as "crystalline forms".

In addition, the compounds represented by Formula (I), Formula (I'), and Formula (I") may be converted to pharmaceutically acceptable salts thereof or pharmaceutically acceptable solvates of these compounds and salts. The crystal of the present invention may be any of these salts, hydrates, solvates, and crystalline polymorphs, and even mixtures of two or more are intended to be included in the scope of the invention.

The crystalline form and the crystallinity can be measured by numerous technologies including, for example, powder X-ray diffraction measurement, Raman spectroscopy, infrared absorption spectrometry, water absorption and desorption measurement, differential scanning calorimetry, and dissolution characteristics.

"Cocrystal" as used in the present specification means that, for example, a compound represented by Formula (I-B) and a counter molecule are regularly arranged in the same crystal lattice, and may include any number of counter molecules. Furthermore, cocrystal implies that an intermolecular interaction between a compound and a counter molecule involves non-covalent and non-ionic chemical interaction such as hydrogen bonding and van der Waals force. A cocrystal is distinguished from a salt from the viewpoint that the compound is essentially uncharged or neutral. The cocrystal is distinguished from hydrate or solvate from the viewpoint that the counter molecule is neither water nor a solvent.

A complex comprising the compound represented by Formula (I-B) of the present invention includes, in a broad sense, a salt, a co-crystal and a clathrate compound, or a solvate thereof.

The "solvate" as used in the present specification means that, for example, with regard to the compounds represented by Formula (I), Formula (I'), Formula (I"), Formula (I-A), and Formula (I-B), the compounds and any number of solvent molecules are arranged with regularity.

Examples of the solvent molecules include acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methyl butyl ketone, methylcyclohexane, N-methylpyrrolidone, nitromethane, pyridine, sulfolane, tetralin, toluene, 1,1,2-trichloroethene, xylene, acetic acid, anisole, 1-butanol, 2-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate, tetrahydrofuran, water (that is, hydrate), ethanol, acetone, 1,1-diethoxypropane, 1,1-dimethoxymethane, 2,2-dimethoxypropane, isooctane, isopropyl ether, methyl isopropyl ketone, methyltetrahydrofuran, petroleum ether, trichloroacetic acid, and trifluoroacetic acid; preferably acetic acid, anisole, 1-butanol, 2-butanol, n-butyl acetate, t-butyl methyl ether, cumene, dimethyl sulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate, tetrahydrofuran, water (that is, hydrate), ethanol, acetone, 1,1-diethoxypropane, 1,1-dimethoxymethane, 2,2-dimethoxypropane, isooctane, isopropyl ether, methyl isopropyl ketone, methyltetrahydrofuran, petroleum ether, trichloroacetic acid, and trifluoroacetic acid; and more preferably water (that is, hydrate), ethanol, acetone, 1,1-diethoxypropane, 1,1-dimethoxymethane, 2,2-dimethoxypropane, isooctane, isopropyl ether, methyl isopropyl ketone, methyltetrahydrofuran, petroleum ether, trichloroacetic acid, and trifluoroacetic acid.

Furthermore, the compounds represented by Formula (I), Formula (I'), and Formula (I"), or pharmaceutically acceptable salts, cocrystals, and complexes of the compounds absorb moisture by being left to stand in atmosphere and may have water of adsorption attached thereto or may form hydrates.

The compounds represented by Formula (I), Formula (I'), and Formula (I") of the present invention or pharmaceutically acceptable salts thereof may form prodrugs, and the present invention also includes such various prodrugs. A prodrug is a derivative of a compound of the present invention having a group that can be chemically or metabolically degraded, and is a compound which becomes a pharmaceutically active compound of the present invention in vivo as a result of solvolysis or under physiological conditions. Prodrugs include compounds that are subjected to enzymatic oxidation, reduction, hydrolysis, and the like under physiological conditions in the living body and are converted to the compounds represented by Formula (I), Formula (I'), and Formula (I"); compounds that are hydrolyzed by gastric acid or the like and are converted to the compounds represented by Formula (I), Formula (I'), and Formula (I"); and the like. Methods for selecting and producing an appropriate prodrug derivative are described in, for example, "Design of Prodrugs, Elsevier, Amsterdam, 1985". A prodrug may have activity per se.

When the compounds represented by Formula (I), Formula (I'), and Formula (I") or pharmaceutically acceptable salts thereof have a hydroxyl group, for example, prodrugs such as an acyloxy derivative and a sulfonyloxy derivative produced by reacting a compound having a hydroxyl group with an appropriate acyl halide, an appropriate acid anhydride, an appropriate sulfonyl chloride, an appropriate sulfonyl anhydride, and mixed anhydrides, or reacting the compounds using a condensing agent, may be mentioned. Examples include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CH_3CHNH_2)COO$—, $CH_2N(CH_3)_2COO$—, $CH_3SO_3$—, $CH_3CH_2SO_3$—, $CF_3SO_3$—, $CH_2FSO_3$—, $CF_3CH_2SO_3$—, p- $CH_3O$—$PhSO_3$—, $PhSO_3$—, and p-$CH_3PhSO_3$—.

(Powder X-Ray Diffraction (XRPD))

Powder X-ray diffraction (XRPD) is one of the most highly sensitive analysis methods for measuring the crystalline form and crystallinity of a solid. When X-rays are irradiated on a crystal, the rays are reflected at crystal lattice planes, interfere with each other, and show well-ordered diffraction lines corresponding to the period of the structure. On the other hand, in an amorphous solid, a diffraction phenomenon does not occur because an amorphous solid usually does not have a well-ordered repetitive period in the structure, and an uncharacterized broad XRPD pattern (also called halo pattern) is exhibited.

The crystalline forms of compounds represented by Formula (I-A) and Formula (I-B) are discernable by powder X-ray diffraction patterns and characteristic diffraction peaks. The crystalline forms of the compounds represented by Formula (I-A) and Formula (I-B) can be distinguished from other crystalline forms by the presence of characteristic diffraction peaks.

Characteristic diffraction peaks used in the present specification are peaks selected from an observed diffraction pattern. Characteristic diffraction peaks are preferably selected from about 10 peaks, more preferably about 5 peaks, and even more preferably about 3 peaks, in a diffraction pattern.

When distinguishing a plurality of crystals, a peak that is identified in the relevant crystal and is not identified in other crystals becomes a characteristic peak preferable for characterizing the crystal, rather than the intensity of a peak. With such characteristic peaks, even one or two peaks can characterize the crystal. When the charts obtained by measurement are compared and these characteristic peaks are found to coincide, it can be said that the powder X-ray diffraction patterns substantially coincide.

Generally, since the diffraction angle (2θ) in powder X-ray diffraction may cause an error within the range of ±0.2°, it should be understood that a value of the diffraction angle of powder X-ray diffraction also includes numerical values within the range of about ±0.2°. Therefore, not only crystals in which the diffraction angles of peaks in powder X-ray diffraction perfectly coincide, but also crystals in which the diffraction angles of peaks coincide with an error of about 0.2°, are included in the present invention.

It is known that generally, the intensity of a peak indicated in the following tables and drawings may fluctuate due to many factors, for example, the effect of selective orientation of crystals with respect to an X-ray beam, the influence of coarse particles, the purity of the substance to be analyzed, or the crystallinity of a sample. Furthermore, the peak position can also be shifted based on the fluctuation of the sample height. In addition, when the peak position is measured using different wavelengths, different shifts can be obtained according to Bragg equation ($n\lambda=2d \sin \theta$); however, other XRPD patterns obtainable by using such other wavelengths are also included in the scope of the present invention.

(Single Crystal Structure Analysis)

In one of the methods for characterizing a crystal, crystallographic parameters for the relevant crystal, as well as the atomic coordinates (values indicating the spatial positional relationship of each atom) and a three-dimensional structural model can be obtained. See "Guidance on X-ray Structural Analysis", written by Toshio Sakurai, published by Shokabo Co., Ltd. (1983); X-Ray Structure Determination: A Practical Guide, written by Stout & Jensen, Macmillan Co, New York (1968); and the like. When the crystal structures of a complex, a salt, an optical isomer, a tautomer, and a geometrical isomer such as the present invention are identified, single crystal structure analysis is useful.

(Raman Spectroscopy)

Raman spectroscopy shows the characteristics of the oscillation of a molecular or composite system. Its origin lies in the inelastic collision between molecules and photons, which are particles of light including light rays. Collision between molecules and photons results in the exchange of energy, which results in a change in energy, and thereby the wavelength of the photons changes. That is, since the Raman spectrum is a spectral line of very narrow wavelengths, which is emitted when photons are incident on a molecule of interest, lasers and the like are used as light sources. The wavelength of each Raman line is indicated by the wavenumber shift from incident light, and this is the difference between the Raman line and the reciprocal of the wavelength of incident light. Raman spectroscopy is to measure the state of oscillation of molecules, and this is determined by the molecular structure thereof.

Generally, since Raman spectral peaks ($cm^{-1}$) can cause errors within the range of ±2 $cm^{-1}$, it should be understood that the values of the above-described Raman spectral peaks also include numerical values within the range of about ±2 $cm^{-1}$. Therefore, not only the crystals whose Raman spectral peaks in the Raman spectra perfectly coincide, but also the crystals whose Raman spectral peaks coincide with errors of about ±2 $cm^{-1}$, are included in the present invention.

(Differential Scanning Calorimetry (DSC))

DSC is one of important measurement methods for thermal analysis and is a method of measuring the thermal properties of a substance as an aggregate of atoms and molecules.

A differential scanning calorimetric curve is obtained by measuring the temperature-related or time-related change in the calorific value of a pharmaceutically active ingredient by DSC and plotting the obtained data with respect to temperature or time. From the differential scanning calorimetric curve, information on the onset temperature at the time of melting of the pharmaceutically active ingredient, the maximum value of the endothermic peak curve associated with melting, and the enthalpy can be obtained.

With regard to DSC, it is known that the temperature to be observed may depend on the rate of temperature change as well as the sample preparation technique and the particular apparatus used. Therefore, the "melting point" in DSC refers to the onset temperature that is not likely to be affected by the sample preparation technique. The error range for the onset temperature obtainable from the differential scanning calorimetry curve is approximately ±2° C. For the recognition of identity of crystals, not only the melting point but also the overall pattern are important, and there may be some variation depending on the measurement conditions and the measuring equipment.

(Simultaneous Differential Thermal Analysis and Thermogravimetric Analysis (TG/DTA))

TG/DTA is one of important measurement methods for thermal analysis and is a method of measuring the weight and thermal properties of a substance as an aggregate of atoms and molecules.

TG/DTA is a method of measuring the temperature-related or time-related changes in weight and calorific value of a pharmaceutically active ingredient, and a TG (thermogravimetric) and DTA (differential thermal) curve is obtained by plotting obtained data with respect to temperature or time. From the TG/DTA curve, information on the changes in weight and calorific value in relation to degradation, dehydration, oxidation, reduction, sublimation, and evaporation of a pharmaceutically active ingredient can be obtained.

With regard to TG/DTA, it is known that the temperature to be observed and the weight change may depend on the rate of temperature change as well as the sample preparation technique and the particular apparatus used. Therefore, the "melting point" in TG/DTA refers to the onset temperature that is not likely to be affected by the sample preparation technique. For the recognition of identity of crystals, not only the melting point but also the overall pattern are important, and there may be some variation depending on the measurement conditions and the measuring equipment.

Since the compound according to the present invention has coronavirus 3CL protease inhibitory activity, the compound is useful as a therapeutic and/or prophylactic agent for a disease associated with coronavirus 3CL proteases. When the term "therapeutic agent and/or prophylactic agent" is used in the present invention, this also includes a symptom ameliorating agent. The disease associated with coronavirus 3CL proteases may be viral infections, and preferably coronavirus infections.

According to an aspect, the coronavirus may be a coronavirus that infects human beings. The coronavirus that infects human beings may be HCoV-229E, HCoV-NL63, HCoV-HKU1, HCoV-OC43, SARS-CoV, MERS-CoV, and/or SARS-CoV-2.

According to an aspect, the coronavirus may be alphacoronavirus and/or betacoronavirus, and more preferably betacoronavirus.

According to an aspect, the alphacoronavirus may be HCoV-229E and HCoV-NL63. The alphacoronavirus may be particularly preferably HCoV-229E.

According to an aspect, the betacoronavirus may be HCoV-HKU1, HCoV-OC43, SARS-CoV, MERS-CoV, and/or SARS-CoV-2. The betacoronavirus may be HCoV-OC43 or SARS-CoV-2, and particularly preferably SARS-CoV-2.

According to an aspect, the betacoronavirus may be betacoronavirus lineage A (β-coronavirus lineage A), betacoronavirus lineage B (β-coronavirus lineage B), and betacoronavirus lineage C (β-coronavirus lineage C). The betacoronavirus may be more preferably betacoronavirus lineage A (β-coronavirus lineage A) and betacoronavirus lineage B (β-coronavirus lineage B) and particularly preferably betacoronavirus lineage B (β-coronavirus lineage B).

According to an aspect, the betacoronavirus may be a betacoronavirus of the subgenus Sarbecovirus.

Examples of the betacoronavirus lineage A (β-coronavirus lineage A) include HCoV-HKU1 and HCoV-OC43, and preferably HCoV-OC43. Examples of the betacoronavirus lineage B (β-coronavirus lineage B) include SARS-CoV and SARS-CoV-2, and preferably SARS-CoV-2. The betacoronavirus lineage C (β-coronavirus lineage C) may be MERS-CoV.

According to an aspect, the coronavirus may be HCoV-229E, HCoV-OC43, and/or SARS-CoV-2, and particularly preferably SARS-CoV-2.

The coronavirus infections may be infections caused by HCoV-229E, HCoV-NL63, HCoV-OC43, HCoV-HKU1, SARS-CoV, MERS-CoV, and/or SARS-CoV-2. Preferably, the coronavirus infections may be infections caused by HCoV-229E, HCoV-OC43, and/or SARS-CoV-2, and particularly preferably infection caused by SARS-CoV-2.

The coronavirus infections may be particularly preferably novel coronavirus infections (COVID-19).

(Method for Producing Compound of Present Invention)

The compounds represented by Formula (I), Formula (I'), and Formula (I") according to the present invention can be produced by, for example, the general synthesis method described below. Regarding extraction, purification, and the like, the treatments carried out in ordinary experiments of organic chemistry may be carried out.

The compounds of the present invention can be produced with reference to techniques known in the art. For example, the compounds can be produced with reference to WO2010092966, WO2012020749, WO2013089212, WO2014200078, WO2012020742, and WO2013118855.

(Method A) when Y is N, and X is $NR^6$ or O

[Chemical Formula 71]

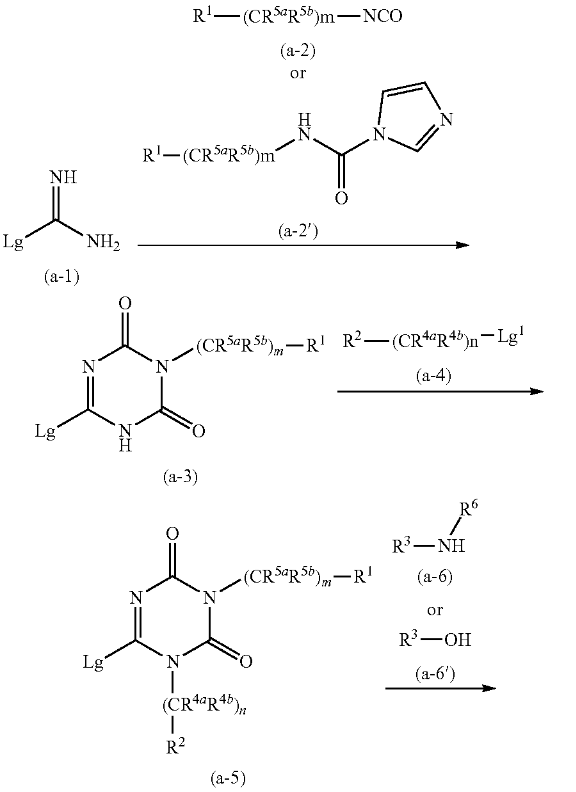

-continued

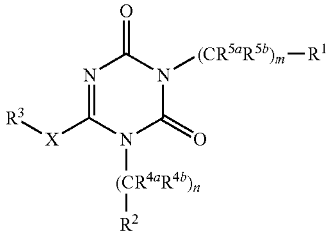

(I-a)

Lg = 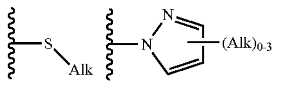

(wherein Alk is C1-C3 alkyl; $Lg^1$ is a leaving group; and reference symbols other than those have the same meanings as described above).

(First Step)

Compound (a-1), or hydrochloride or bromate thereof is reacted with isocyanate (a-2) or 1-carbamoylimidazole (a-2') in a solvent such as N,N-dimethylformamide, N, N-dimethylacetamide, N,N'-dimethylimidazolidinone, dimethyl sulfoxide, or THF, in the presence of a base such as DBU, triethylamine, N,N-diisopropylethylamine, or pyridine (preferably, DBU), at −20° C. to 50° C., and preferably −10° C. to a condition under ice cooling. Subsequently, Compound (a-3) can be produced by reacting the reaction mixture with a carbonylating agent such as 1,1'-carbonyldiimidazole, phosgene, or triphosgene, and a base such as DBU, triethylamine, N,N-diisopropylethylamine, or pyridine (preferably, DBU), at −20° C. to 50° C., and preferably −10° C. to a condition under ice cooling.

(Second Step)

Compound (a-5) can be produced by reacting Compound (a-3) with Compound (a-4) in a solvent such as acetonitrile, acetone, DMF, or DMSO, in the presence of a base such as potassium carbonate, sodium carbonate, or N,N-diisopropylethylamine, at 50° C. to a condition of heating under reflux, and preferably under a condition of heating under reflux.

Examples of the leaving group include halogen and $—OSO_2(C_tF_{2t+1})$ (wherein t is an integer of 1 to 4). The halogen is preferably chlorine, iodine, and bromine, and the $OSO_2(C_tF_{2t+1})$ group is preferably an —OTf group (trifluoromethanesulfonic acid ester).

(Third Step)

A compound represented by Compound (I-a) can be produced by reacting Compound (a-5) with Compound (a-6) or Compound (a-6') in a solvent such as NMP, DMF, DMA, DMSO, tert-butanol, or 2-methyl-2-butanol, in the presence or absence of an acid such as acetic acid, at 60° C. to 150° C., and preferably 80° C. to 120° C.

A compound represented by optically active Compound (I-a) can be produced by using optically active isocyanate (a-2).

(Method B) when Y is N, and X is —S— or $—CR^6R^{6'}—$

[Chemical Formula 72]

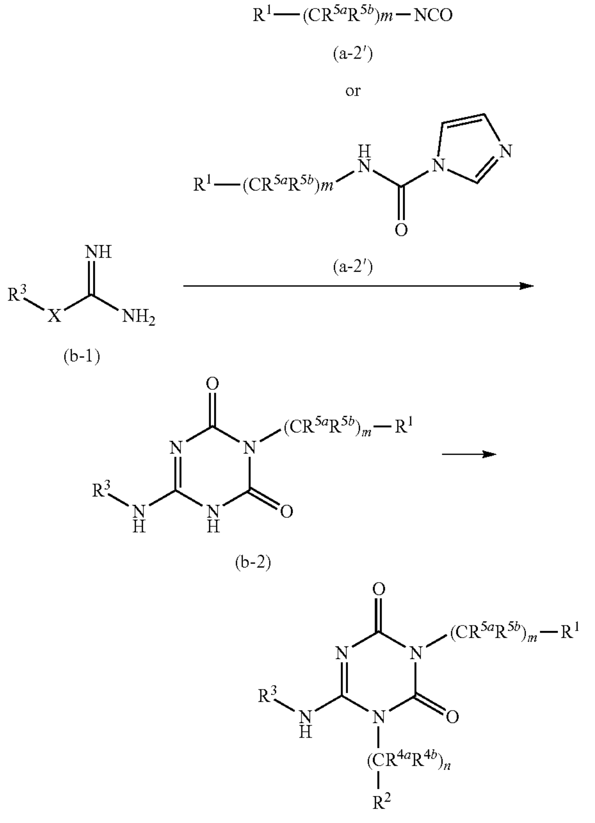

(a-2')
or
(a-2')
(b-1)
(b-2)
(I-b)

(wherein the reference symbols have the same meanings as described above).

(First Step)

Compound (b-2) can be produced by reacting Compound (b-1) with Compound (a-2) or (a-2') in the same manner as in the first step of the above-described method A.

(Second Step)

A compound represented by Compound (I-b) can be produced in the same manner as in the second step of the above-described method A.

(Method C) when Y is N, and X is a Single Bond

[Chemical Formula 73]

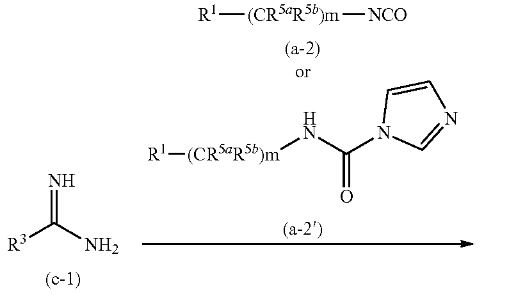

(a-2)
or
(a-2')
(c-1)

-continued

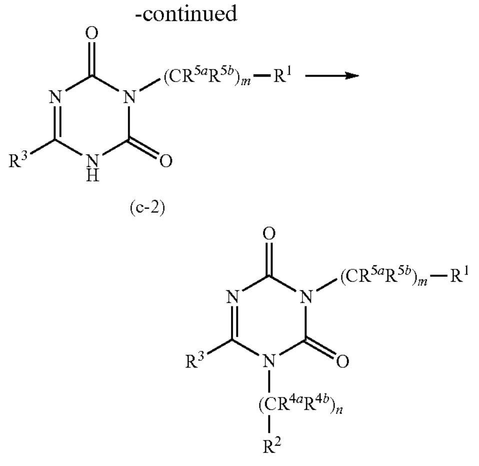

(c-2)

(I-C)

(wherein the reference symbols have the same meanings as described above).

(First Step)

Compound (c-2) can be produced by reacting Compound (c-1) with Compound (a-2) or (a-2') in the same manner as in the first step of the above-described method A.

(Second Step)

A compound represented by Compound (I-C) can be produced in the same manner as in the second step of the above-described method A.

(Method D) when Y is N, and m is 1

[Chemical Formula 74]

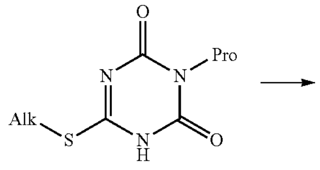

(d-1)

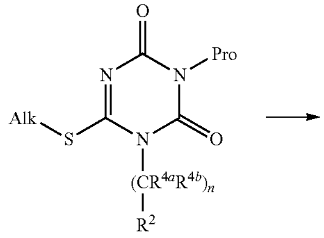

(d-2)

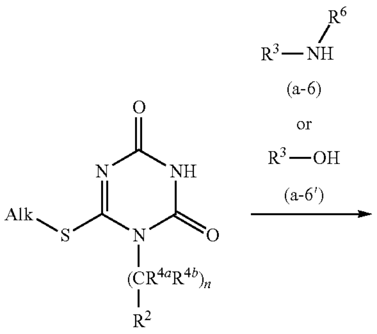

(d-3)

-continued

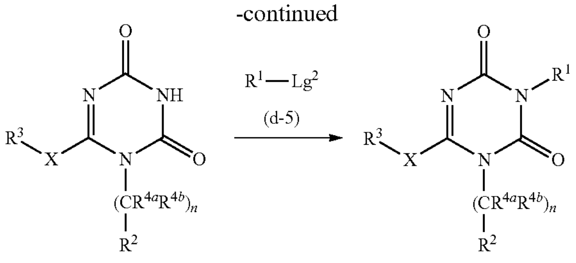

(d-4)

(I-D)

(wherein Pro is C1-C4 alkyl or tert-butoxycarbonyl; $Lg^2$ is a leaving group; and other reference symbols have the same meanings as described above).

(First Step)

Compound (d-2) can be produced from Compound (d-1) in the same manner as in the second step of the above-described method A.

(Second Step)

Compound (d-3) can be produced by treating Compound (d-2) with a strong acid such as TFA, in the presence or absence of an organic solvent, at −20° C. to room temperature, and preferably room temperature.

(Third Step)

Compound (d-4) can be produced from Compound (d-3) in the same manner as in the third step of the above-described method A.

(Fourth Step)

Compound (I-D) can be produced by a Goldberg amination reaction using Compound (d-4) and Compound (d-5). The leaving group may be the leaving group described in Step 1 of the above-described method A.

Regarding the catalyst, for example, commercially available copper catalysts such as copper iodide, copper cyanide, and copper bromide, can be used.

Regarding the ligand, 1,2-dimethylethylenediamine, trans-N,N'-dimethylcyclohexane-1,2-diamine, and the like can be used.

Regarding the base, potassium carbonate, potassium phosphate, and the like can be used.

Regarding the solvent, NMP, dioxane, DMSO, and the like can be used.

Regarding the reaction temperature, the reaction may be carried out at from room temperature to a temperature at which the solvent refluxes, and preferably, the reaction may be carried out by heating under reflux.

(Method E) when Y is N, and m is 1 or 2

[Chemical Formula 75]

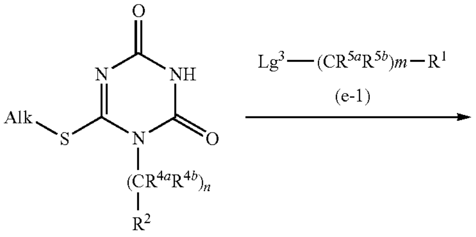

(d-3)

-continued

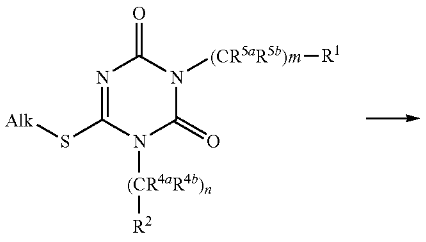

(e-2)

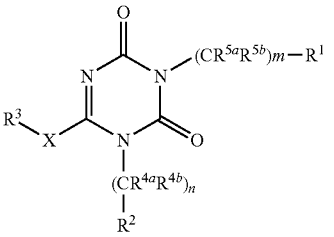

(I-E)

(wherein Alk is C1 to C3 alkyl; $Lg^3$ is a leaving group; and other reference symbols have the same meanings as described above).

(First Step)

Compound (e-2) can be produced in the same manner as in the second step of the above-described method A.

The leaving group may be the leaving group described in Step 1 of the above-described method A.

(Second Step)

A compound represented by Compound (I-E) can be produced in the same manner as in the third step of the above-described method A.

(Method F) when Y is C

[Chemical Formula 76]

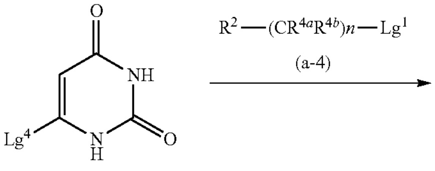

(f-1)

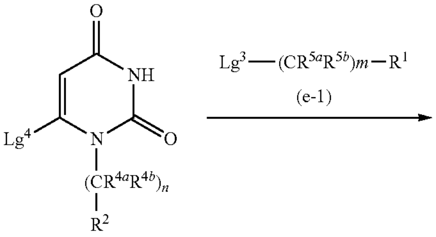

(f-2)

-continued

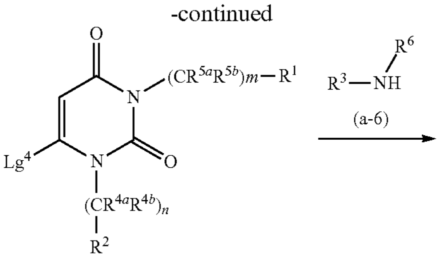

(f-3)

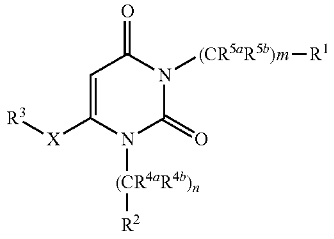

(I-F)

(wherein $Lg^4$ is a leaving group; and other reference symbols have the same meanings as described above).

(First Step)

Compound (f-2) can be produced by reacting Compound (f-1) with Compound (a-4) in the presence of a base and an organolithium reagent.

The leaving group may be the leaving group described in Step 1 of the above-described method A.

As the base, sodium hydride and the like can be used.

As the organolithium reagent, lithium bromide, lithium iodide, and the like can be used.

As the solvent, DMF, DMA, and the like can be used.

Regarding the reaction temperature, the reaction may be carried out at from −20° C. to room temperature, and preferably, the reaction may be carried out at from 0° C. to room temperature.

(Second Step)

Compound (f-3) can be produced in the same manner as in the first step of the above-described method E.

(Third Step)

Compound (I-F) can be produced by reacting Compound (f-3) with Compound (a-6) in the presence of a palladium catalyst, a phosphine ligand, and a base.

As the palladium catalyst, $Pd_2(dba)_3$, $PdCl_2dppf$, $PdCl_2(PPh_3)_2$, $Pd(OAc)_2$, $Pd(PPh_3)_4$, Pd/C, $PdCl_2$, Pd-PEPPSI™-IPr, Bis[cinnamyl palladium Cl], $PdCl_2$ (Xantphos), or $Pd(OH)_2$ can be used.

As the phosphine ligand, Xantphos, $P(2\text{-furyl})_3$, $PPh_3$, $P(o\text{-tol})_3$, $P(OPh)_3$, $P(OMe)_3$, dppp, dppb, dppf, BINAP, X-Phos, $P(t\text{-Bu})_3$, $P(Oi\text{-Pr})_3$, $P(p\text{-MeOPh})_3$, DPEPhos, or the like can be used.

The base may be cesium carbonate, potassium carbonate, sodium carbonate, potassium phosphate, or the like.

As the solvent, 1,4-dioxane, THF, and the like can be used.

Regarding the reaction temperature, the reaction may be carried out at from room temperature to a temperature at which the solvent refluxes, and preferably, the reaction may be carried out by heating under reflux.

Since the compound of the present invention has coronavirus 3CL protease inhibitory activity, the compound is useful as a therapeutic and/or prophylactic agent for coronavirus infections.

Furthermore, the compound of the present invention has utility as a medicine, and preferably, the compound of the present invention has any one or a plurality of the following excellent features.

a) Inhibitory activity against CYP enzymes (for example, CYP1A2, CYP2C9, CYP2C19, CYP2D6, and CYP3A4) is weak.

b) Satisfactory pharmacokinetics such as high bioavailability and adequate clearance are exhibited.

c) Metabolic stability is high.

d) Irreversible inhibitory activity is not exhibited against CYP enzymes (for example, CYP3A4) within the concentration range of the measurement conditions described in the present specification.

e) Mutagenicity is not exhibited.

f) The cardiovascular risk is low.

g) High solubility is exhibited.

h) The protein unbinding rate (fu value) is high.

i) High coronavirus 3CL protease selectivity is exhibited.

j) High coronavirus replication inhibitory activity is exhibited. For example, high coronavirus replication inhibitory activity is exhibited when human blood serum (HS) or human serum albumin (HSA) is added.

Regarding the coronavirus replication inhibitor, for example, an aspect in which in the CPE effect (SARS-CoV-2) that will be described below, for example, $EC_{50}$ is 10 μM or less, preferably 1 μM or less, and more preferably 100 nM or less, may be mentioned.

Furthermore, a salt, a crystalline form, a composite, and a cocrystal of the compound according to the present invention have utility as medicines, and preferably, they have any one or a plurality of the following excellent features.

bb) Satisfactory pharmacokinetics such as high bioavailability, adequate clearance, high AUC, and high maximum blood concentration are exhibited.

gg) High solubility, high chemical stability, and low hygroscopic properties are exhibited.

The pharmaceutical composition of the present invention can be administered by either an oral method or a parenteral method. Examples of a parenteral administration method include percutaneous, subcutaneous, intravenous, intra-arterial, intramuscular, intraperitoneal, transmucosal, inhalation, transnasal, ocular instillation, ear instillation, and intravaginal administration.

In the case of oral administration, the pharmaceutical composition may be prepared into any dosage form that is commonly used, such as a solid preparation for internal use (for example, a tablet, a powder preparation, a granular preparation, a capsule, a pill, or a film preparation), or a liquid preparation for internal use (for example, a suspension, an emulsion, an elixir, a syrup, a limonade, a spirit preparation, an aromatic water preparation, an extraction, a decoction, or a tincture) and administered. The tablet may be a dragee, a film-coated tablet, an enteric-coated tablet, a sustained release tablet, a troche, a sublingual tablet, a buccal tablet, a chewable tablet, or an orally disintegrating tablet; the powder preparation and granular preparation may be dry syrups; and the capsule may be a soft capsule, a microcapsule, or a sustained release capsule.

In the case of parenteral administration, the pharmaceutical composition can be suitably administered in any dosage form that is commonly used, such as an injectable preparation, an infusion, or a preparation for external use (for example, an eye drop, a nasal drop, an ear drop, an aerosol, an inhalant, a lotion, an impregnating agent, a liniment, a gargling agent, an enema, an ointment, a plaster, a jelly, a cream, a patch, a poultice, a powder preparation for external use, or a suppository). The injectable preparation may be an O/W, W/O, O/W/O, or W/O/W type emulsion, or the like.

A pharmaceutical composition can be obtained by mixing an effective amount of the compound of the present invention with various pharmaceutical additives appropriate for the dosage form, such as an excipient, a binder, a disintegrating agent, and a lubricating agent, as necessary. Furthermore, the pharmaceutical composition can be prepared into a pharmaceutical composition for use for a child, an elderly, a patient with a serious case, or a surgical operation, by appropriately changing the effective amount of the compound of the present invention, the dosage form, and/or various pharmaceutical additives. For example, a pharmaceutical composition for use for a child may be administered to a neonate (less than 4 weeks after birth), an infant (from 4 weeks after birth to less than 1 year), a preschool child (from 1 year to less than 7 years), a child (from 7 years to less than 15 years), or a patient 15 year to 18 years of age. For example, a pharmaceutical composition for an elderly may be administered to a patient 65 years of age or older.

It is desirable to set the amount of administration of the pharmaceutical composition of the present invention (for example, a pharmaceutical composition comprising a crystalline form of p-toluenesulfonate Form I of a compound represented by Formula (I-A), or a pharmaceutical composition comprising a fumaric acid cocrystal Form I of a compound represented by Formula (I-B)), after considering the age and body weight of the patient, the type and degree of the disease, the route of administration, and the like; however, in the case of oral administration, the amount of administration is usually 0.05 to 200 mg/kg/day and is preferably in the range of 0.1 to 100 mg/kg/day. In the case of parenteral administration, the amount of administration may vary greatly depending on the route of administration; however, the amount of administration is usually 0.005 to 200 mg/kg/day and is preferably in the range of 0.01 to 100 mg/kg/day. This may be administered once a day or several times a day.

The compound of the present invention may be used in combination with, for example, another therapeutic agent for novel coronavirus infections (COVID-19) (the therapeutic agent includes an approved drug and a drug that is under development or to be developed in the future) (hereinafter, referred to as concomitant drug), for the purpose of enhancing the action of the compound, reducing the amount of administration of the compound, or the like. At this time, the timing of administration for the compound of the present invention and the concomitant drug is not limited, and these may be administered simultaneously to the target of administration or may be administered with a time difference. Furthermore, the compound of the present invention and the concomitant drug may be administered as two or more kinds of preparations each including active ingredients, or may be administered as a single preparation including those active ingredients.

The amount of administration of the concomitant drug can be appropriately selected based on the clinically used dosage. Furthermore, the blending ratio of the compound of the present invention and the concomitant drug can be appropriately selected according to the target of administration, the route of administration, the target disease, symptoms, combination, and the like. For example, when the target of administration is a human being, 0.01 to 100 parts by weight of the concomitant drug may be used with respect to 1 part by weight of the compound of the present invention.

EXAMPLES

Hereinafter, the present invention will be described in more detail by way of Examples, Reference Examples, and Test Examples; however, the present invention is not intended to be limited by these.

Furthermore, abbreviations used in the present specification denote the following meanings.

Boc: tert-butoxycarbonyl
CDI: Carbonyldiimidazole
DBU: 1,8-Diazabicyclo[5.4.0]-7-undecene
DIEA: N,N-diisopropylethylamine
DMA: N,N-dimethylacetamide
DMF: N,N-dimethylformamide
DMSO: Dimethyl sulfoxide
DTT: Dithiothreitol
EDC: 1-Ethyl-3-(3-dimethylaminopropyl)carbodiimide
EDT: 1,2-Ethanedithiol
EDTA: Ethylenediaminetetraacetic acid
FBS; Fetal bovine serum
HOBT: 1-Hydroxybenzotriazole
LHMDS: Lithium bis(trimethylsilyl)amide
MEM: Eagle's Minimum Essential Medium
NMP: N-methylpyrrolidone
$Pd(OAc)_2$: Palladium acetate
TFA: Trifluoroacetic acid
THF: Tetrahydrofuran
TMSCl: Chlorotrimethylsilane
Xantphos: 4,5'-Bis(diphenylphosphine)-9,9'-dimethylxanthene
mM: mmol/L
μM: μmol/L
nM: nmol/L (Method for Identifying Compound)

The NMR analysis obtained in each Example was performed at 400 MHz, and measurement was made using DMSO-$d_6$, $CDCl_3$ and MeOH-$d_4$. Furthermore, when NMR data are shown, there are occasions in which all the measured peaks are not described.

The term RT in the specification indicates retention time in an LC/MS: liquid chromatography/mass analysis, and the retention time was measured under the following conditions.

(Measurement Conditions 1)

Column: ACQUITY UPLC (registered trademark) BEH C18 (1.7 μm i.d. 2.1×50 mm) (Waters)
Flow rate: 0.8 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 5% to 100% solvent [B] was carried out for 3.5 minutes, and then 100% solvent [B] was maintained for 0.5 minutes.

(Measurement Conditions 2)

Column: ACQUITY UPLC (registered trademark) BEH C18 (1.7 μm i.d. 2.1×50 mm) (Waters)
Flow rate: 0.55 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 5% to 100% solvent [B] was carried out for 3 minutes, and then 100% solvent [B] was maintained for 0.5 minutes.

(Measurement Conditions 3)

Column: Shim-pack XR-ODS (2.2 μm, i.d. 3.0×50 mm) (Shimadzu)
Flow rate: 1.6 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 10% to 100% solvent [B] was carried out for 3 minutes, and then 100% solvent [B] was maintained for 0.5 minutes.

(Measurement Conditions 4)

Column: ACQUITY UPLC (registered trademark) BEH C18 (1.7 μm i.d. 2.1×50 mm) (Waters)
Flow rate: 0.8 mL/min
UV detection wavelength: 254 nm
Mobile phase: [A] was 10 mmol/L ammonium carbonate-containing aqueous solution, and [B] was acetonitrile.
Gradient: A linear gradient of 5% to 100% solvent [B] was carried out for 3.5 minutes, and then 100% solvent [B] was maintained for 0.5 minutes.

(Measurement Conditions 5)

Column: Shim-pack XR-ODS (2.2 μm, i.d. 3.0×50 mm) (Shimadzu)
Flow rate: 1.6 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 10% to 100% solvent [B] was carried out for 8 minutes, and then 100% solvent [B] was maintained for 0.5 minutes.

Incidentally, in the specification, the description of MS (m/z) indicates a value observed by mass analysis.

(Measurement of Powder X-Ray Diffraction Pattern)

Powder X-ray diffraction measurement of crystals obtained in each Example was performed according to the powder X-ray diffraction measurement method described in the General Testing Methods of the Japanese Pharmacopoeia. Measurement conditions are shown below.

(Apparatus)

SmartLab manufactured by Rigaku Corporation (Operation Method)

Measurement method: Reflection method
Wavelength used: CuKα radiation
Tube current: 200 mA
Tube voltage: 45 kV
Sample plate: Aluminum
Incident angle of X-rays: 2.5°
Sampling width: 0.02°
Detector: HyPix-3000 (two-dimensional detection mode)

(Measurement and Analysis Method for Single Crystal Structure Analysis)

The measurement conditions and analysis method for single crystal structure analysis will be described below.

(Apparatus)

XtaLAB P200 MM007 manufactured by Rigaku Corporation (Measurement Conditions)

Measurement temperature: 25° C.
Wavelength used: CuKα radiation (λ=1.5418 Å)
Software: CrysAlisPro 1.171.39.46e (Rigaku Oxford Diffraction, 2018)

(Data Processing)

Software: CrysAlisPro 1.171.39.46e (Rigaku Oxford Diffraction, 2018)

The data were subjected to Lorentz and polarization correction and absorption correction.

(Crystal Structure Analysis)

Phase determination was performed using a direct method program, ShelXT (Sheldrick, G. M., 2015), and regarding refinement, a full-matrix least squares method was carried out using ShelXL (Sheldrick, G. M., 2015). The temperature factors of non-hydrogen atoms were all subjected to refinement with anisotropy. Hydrogen atoms were computationally introduced using the default parameters of ShelXL and were treated as riding atoms. All the hydrogen atoms were subjected to refinement with isotropic parameters.

Figure 2:
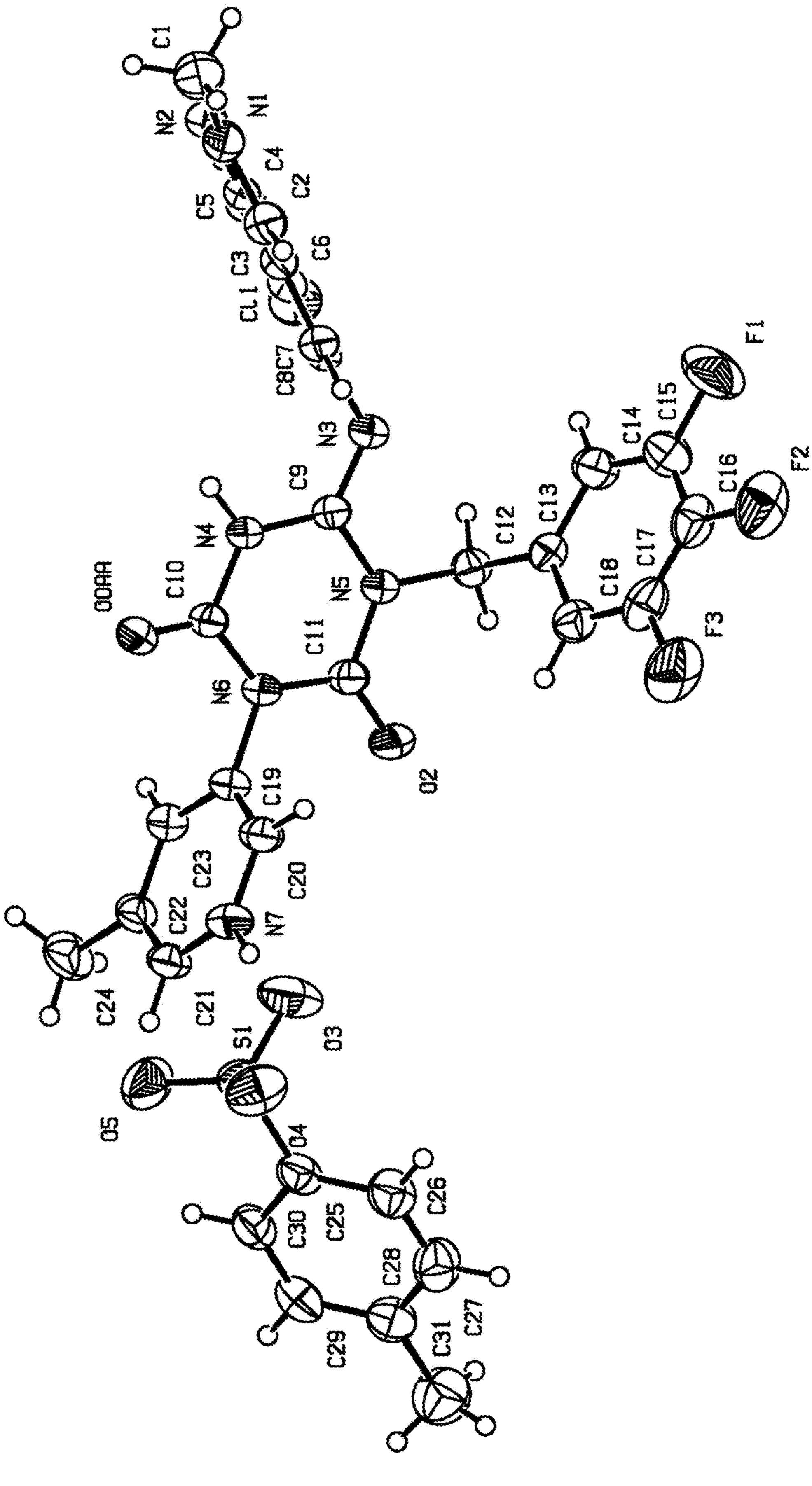
FIG. 2 shows a molecular structure in an asymmetric unit of the crystalline form of p-toluenesulfonate Form I of the compound represented by Formula (I-A).
Figure 3:
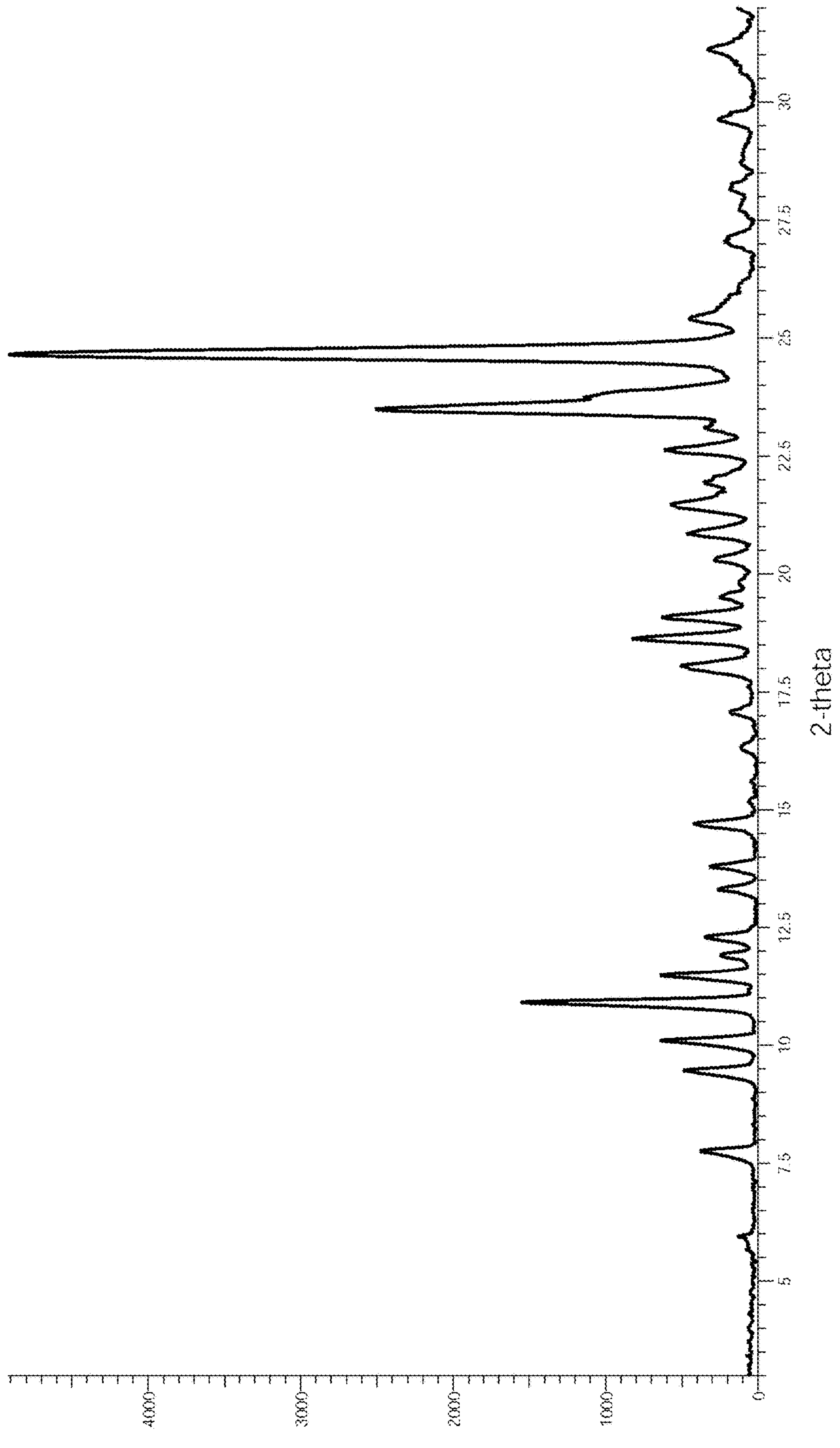
FIG. 3 shows a powder X-ray diffraction pattern of a fumaric acid cocrystal Form I (Form I) of the compound represented by Formula (I-B). The axis of abscissa represents 2θ(°), and the axis of ordinate represents the intensity (Count).
Figure 4:
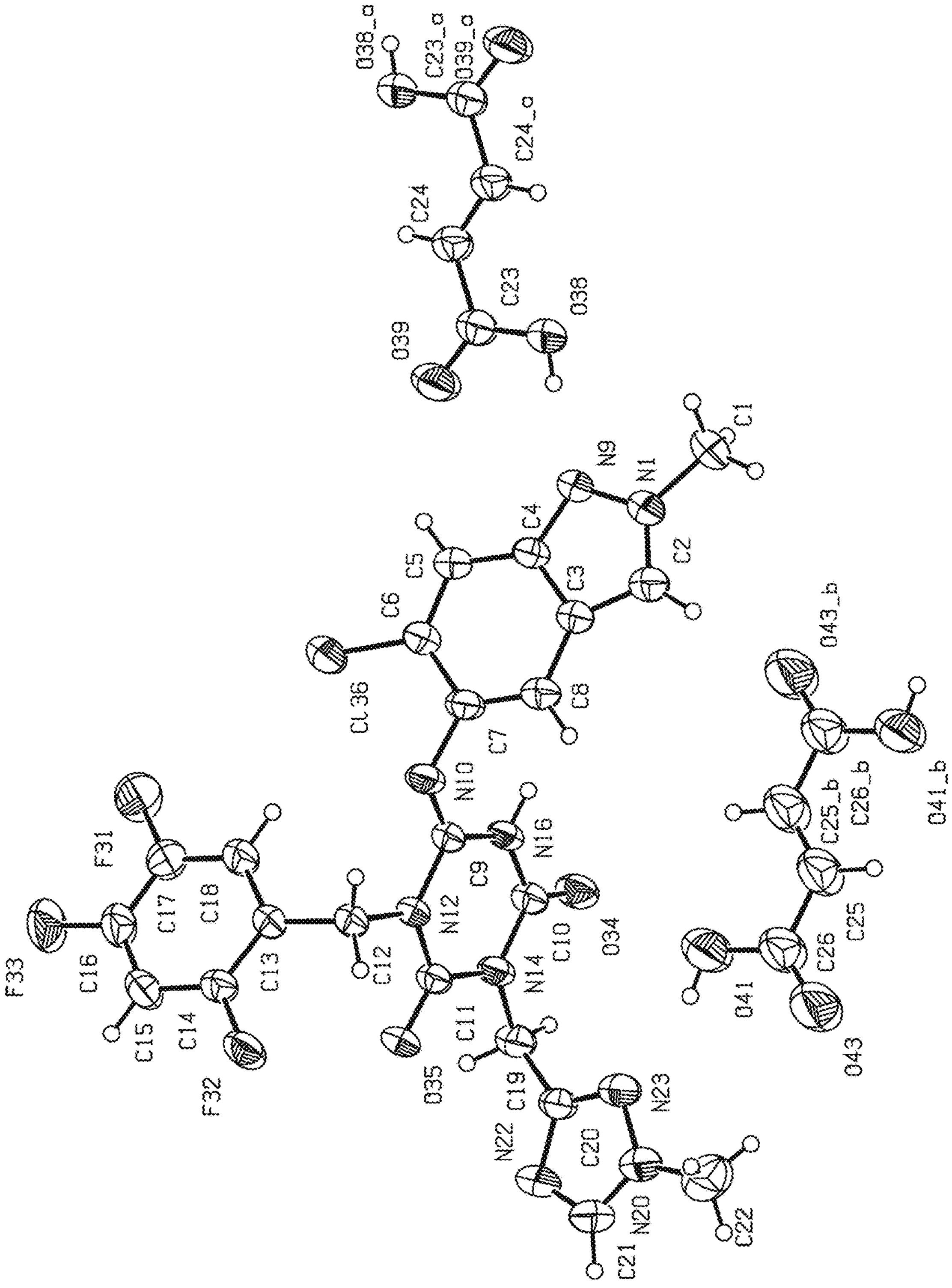
FIG. 4 shows a molecular structure in an asymmetric unit of the fumaric acid cocrystal Form I (Form I) of the compound represented by Formula (I-B).

For the construction of FIG. 2 and FIG. 4, PLUTON (Spek, 1991)/ORTEP (Johnson, 1976) was used.

(Measurement of Raman Spectrum)

Measurement of the Raman spectrum of crystals obtained in each Example was performed. Measurement conditions are shown below.

Measuring instrument: RAMANTouch Vis2-NIR-SNU (manufactured by Nanophoton Corporation)

Measurement method: Microscopic laser Raman spectrometry

Laser wavelength: 671 nm

Diffraction grating: 600 grooves/mm

Detector: CCD detector

Object lens: 50× (NA 0.80)

Cumulative number: 3 to 10 times

Exposure time: 1 to 10 seconds (Measurement of Differential Scanning Calorimetry (DSC))

About 3 mg of a sample obtained in each Example was weighed into an aluminum crimped pan, and DSC measurement was performed. Measurement conditions are shown below. Incidentally, in the measurement made by differential scanning calorimetry (DSC), an error can occur in the range of 2° C.

Apparatus: TA Instrument Q1000/TA Instrument

Measurement temperature range: 0° C. to 295° C.

Rate of temperature increase: 10° C./min

Atmosphere: Na 50 mL/min (Measurement of TG/DTA Data)

About 3 mg of the crystals obtained in each Example were weighed and packed into an aluminum pan, and measurement was performed in an open system. Measurement conditions are as follows.

(Measurement Conditions 1)

Apparatus: Hitachi High-Technologies TG/DTA STA7200RV

Measurement temperature range: Room temperature to 400° C.

Rate of temperature increase: 10° C./min

Example 1

Synthesis of Compound (I-0001)

[Chemical Formula 77]

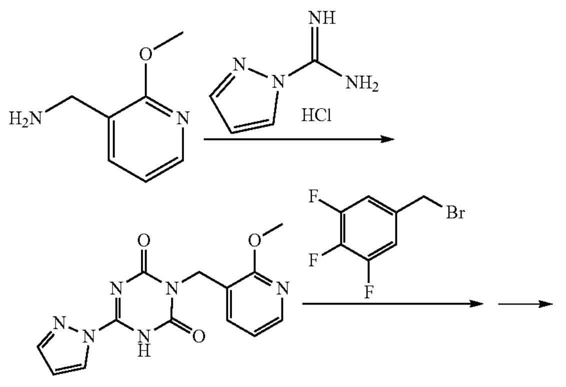

1

-continued

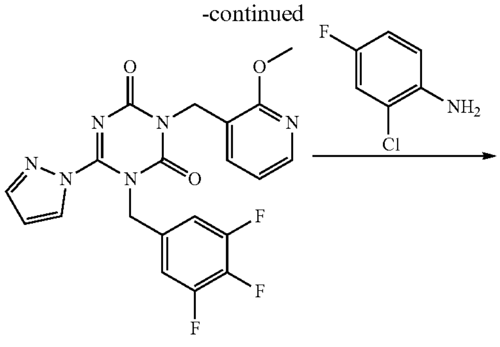

2

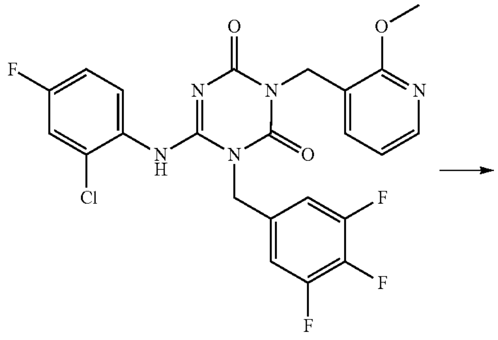

3

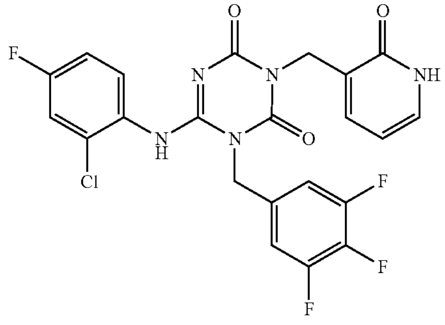 [SMILES: O=c1[nH]cccc1Cn1c(=O)nc(Nc2ccc(F)cc2Cl)n(Cc2cc(F)c(F)c(F)c2)c1=O]

I-0001

Step 1 Synthesis of Compound 1

Under a nitrogen atmosphere, DMA (50 mL) was added to [(2-methoxypyridin-3-yl)methyl]amine (10.0 g, 72.4 mmol), and the mixture was ice-cooled. CDI (12.9 g, 80.0 mmol) was slowly added to the reaction solution, and the mixture was stirred for 50 minutes at room temperature. The reaction solution was ice-cooled, 1-amidinopyrazole hydrochloride (10.6 g, 72.4 mmol) and DBU (11.5 mL, 76.0 mmol) were added thereto, and the mixture was stirred for 17 hours at room temperature. The reaction solution was ice-cooled, CDT (17.6 g, 109 mmol) and DBU (16.4 mL, 109 mmol) were added thereto, and the mixture was stirred for 2 hours at room temperature. The reaction solution was ice-cooled, CDT (11.7 g, 72.4 mmol) and DBU (10.9 mL, 72.4 mmol) were added thereto, and the mixture was stirred for 2 hours at room temperature.

The reaction solution was poured into a 2 mol/L aqueous solution of hydrochloric acid (362 mL, 724 mmol), and the mixture was stirred for 1 hour at 0° C. The precipitated solid was collected by filtration and washed with water. The solids thus obtained were dried under reduced pressure, and Compound 1 (17.5 g, 58.3 mmol, yield 81%) was obtained.

LC/MS (ESI): m/z=301[M+H]$^+$, RT=1.27 min, LC/MS measurement conditions 1

Step 2 Synthesis of Compound 2

Compound 1 (5.0 g, 16.7 mmol) was dissolved in DMA (50 mL), DIEA (3.78 mL, 21.7 mmol) and 3,4,5-trifluorobenzyl bromide (2.33 mL, 17.5 mmol) were added thereto, and the mixture was stirred for 3 hours at 60° C. The reaction solution was cooled to room temperature, and ice water (200 mL) was added thereto. A precipitate thus produced was separated by filtration and dissolved in ethyl acetate. The obtained solution was dried over sodium sulfate and filtered. The solvent was distilled off under reduced pressure, the residue was washed with a diisopropyl ether/hexane mixed solution, and Compound 2 (5.46 g, 12.3 mmol, yield 74%) was obtained. The filtrate of the diisopropyl ether/hexane mixed solution was concentrated, the residue thus obtained was washed with a diisopropyl ether/hexane mixed solution, and Compound 2 (1.19 g, 2.68 mmol, yield 22%) was obtained.

LC/MS (ESI): m/z=445 $[M+H]^+$, RT=2.27 min, LC/MS measurement conditions 1

Step 3 Synthesis of Compound 3

Under a nitrogen atmosphere, 2-chloro-4-fluoroaniline (16.0 μL, 0.135 mmol) and Compound 2 were dissolved in NMP (0.5 mL). Methanesulfonic acid (7.31 μL, 0.113 mmol) was added to the reaction solution, and the mixture was stirred for 1 hour and 35 minutes at 80° C. Ethyl acetate (5 mL) and water (5 mL) were added to the reaction solution, the mixture was extracted with ethyl acetate, the organic layer was washed with water and brine, and the organic layer was dried over sodium sulfate and filtered. The solvent was distilled off under reduced pressure, the residue thus obtained was purified by silica gel column chromatography (hexane:ethyl acetate=2:1), the solvent was distilled off under reduced pressure, and Compound 3 (33.6 mg, 0.064 mmol, yield 57.2%) was obtained.

LC/MS (ESI): m/z=522 $[M+H]^+$, RT=2.51 min, LC/MS measurement conditions 3

Step 4 Synthesis of Compound (I-0001)

Under a nitrogen atmosphere, Compound 3 (32.7 mg, 0.063 mmol) and sodium iodide (18.8 mg, 0.125 mmol) were dissolved in acetonitrile (0.7 mL) at room temperature. TMSCl (0.016 mL, 0.125 mmol) was added to the reaction solution, and the mixture was stirred for 50 minutes at 65° C. Ethyl acetate (5 mL) and a 10% aqueous solution of sodium thiosulfate (5 mL) were added to the reaction solution, and the mixture was extracted with ethyl acetate. The organic layer was washed with water and brine, dried over sodium sulfate, and filtered. The solvent was distilled off under reduced pressure, the solids thus obtained were washed with a hexane/ethyl acetate mixed solution (hexane: ethyl acetate=5:1), and Compound (I-0001) (28.8 mg, 0.057 mmol, yield 91%) was obtained.

$^1H$-NMR ($CDCl_3$) δ: 4.63 (s, 2H), 5.13 (s, 2H), 6.15 (t, 1H, J=6.7 Hz), 6.96 (brs, 1H), 7.13 (brs, 1H), 7.30 (d, 1H, J=6.0 Hz), 7.31-7.40 (m, 2H), 7.40-7.47 (m, 2H), 11.01 (brs, 1H), 11.69 (s, 1H)

LC/MS (ESI): m/z=507 $[M+H]^+$, RT=2.05 min, LC/MS measurement conditions 3

Example 2

Synthesis of Compound (I-0135)

[Chemical Formula 78]

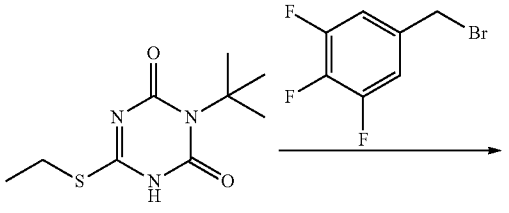

4

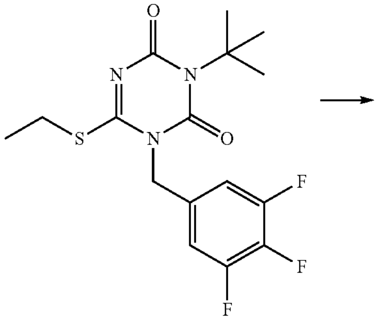

5

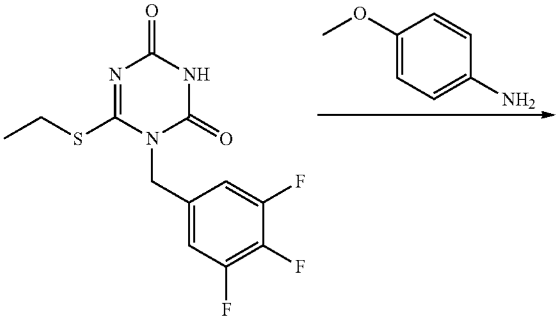

6

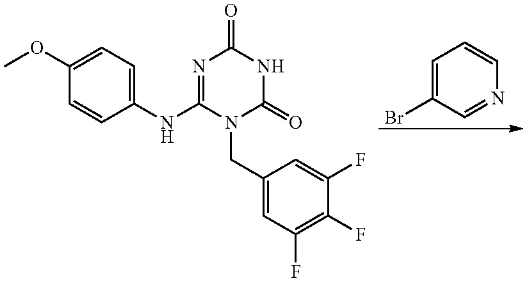

7

-continued

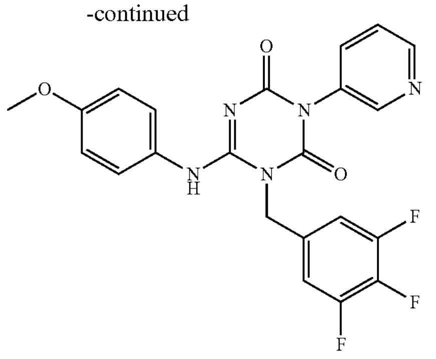

I-0135

Step 1 Synthesis of Compound 5

Under a nitrogen atmosphere, Compound 4 (20.0 g, 87.0 mmol) (for the synthesis method, see WO2012020749, WO2013089212, and WO2014200078), acetonitrile (160 mL), potassium carbonate (15.7 g, 113 mmol), and 3,4,5-trifluorobenzyl bromide (21.6 g, 96.0 mmol) were mixed, and the solution thus obtained was stirred at 80° C. for 1 hour and 25 minutes. The solution was cooled to room temperature and then diluted with ethyl acetate (50 mL). A precipitate thus produced was separated by filtration and washed with ethyl acetate. The solution was concentrated, a mixed solution (30 mL) of ethyl acetate:hexane=1:10 was added thereto, and a precipitate thus produced was collected by filtration and washed with a mixed solution of ethyl acetate:hexane=1:10. The residue thus obtained was dried under reduced pressure, and Compound 5 (31.0 g, 83.0 mmol, yield 95%) was obtained.

LC/MS (ESI): m/z=374, RT=2.65 min, LC/MS measurement conditions 1

Step 2 Synthesis of Compound 6

Under a nitrogen atmosphere, trifluoroacetic acid (45.0 mL) was added to Compound 5 (15.0 g, 40.2 mmol), and the mixture was stirred at room temperature for 2 hours and 20 minutes. The reaction solution was concentrated, the resultant was azeotropically boiled with toluene (20 mL), and trifluoroacetic acid was removed. Diisopropyl ether (15 mL) was added to the residue, and a precipitate thus produced was collected by filtration and washed with diisopropyl ether. The residue thus obtained was dried under reduced pressure, and Compound 6 (12.2 g, 38.5 mmol, yield 96%) was obtained.

LC/MS (ESI): m/z=318, RT=1.88 min, LC/MS measurement conditions 1

Step 3 Synthesis of Compound 7

Compound 6 (515 mg, 1.62 mmol), p-anisidine (300 mg, 2.44 mmol), tert-butanol (5.2 mL), and acetic acid (1.39 mL, 24.4 mmol) were mixed, and the solution thus obtained was stirred at 100° C. for 2 hours and 15 minutes. The reaction solution was cooled in an ice bath, and the precipitate thus obtained was collected by filtration and washed with tert-butanol. The residue thus obtained was dried under reduced pressure, and Compound 7 (473 mg, 1.25 mmol, yield 77%) was obtained. The filtrate was concentrated, the residue thus obtained was purified by silica gel column chromatography (hexane:ethyl acetate=8:2 to 4:6), the solvent was distilled off under reduced pressure, and Compound 7 (129 mg, 0.341 mmol, yield 21%) was obtained.

LC/MS (ESI): m/z=379, RT=1.85 min, LC/MS measurement conditions 1

Step 4 Synthesis of Compound (I-0135)

Under a nitrogen atmosphere, Compound 7 (10.0 mg, 0.026 mmol), 3-bromopyridine (5.01 mg, 0.032 mmol), copper iodide (1.51 mg, 7.93 μmol), trans-N,N'-dimethylcyclohexane-1,2-diamine (racemate, 2.26 mg, 0.016 mmol), and DMA (400 μL) were mixed, and the solution thus obtained was stirred at 100° C. for 17 hours. A saturated aqueous solution of ammonium chloride (10 mL) was added to the reaction solution, and the mixture was extracted with ethyl acetate. The organic layer was washed with water, dried over sodium sulfate, and filtered. The filtrate was concentrated, and Compound (1-0135) (8.0 mg, 0.018 mmol, yield 67%) was obtained.

$^1$H-NMR (DMSO-d6) δ: 3.75 (s, 3H), 5.25 (s, 2H), 6.88-7.00 (m, 2H), 7.19-7.32 (m, 2H), 7.42-7.54 (m, 2H), 7.80 (d, J=6.1 Hz, 1H), 8.48-8.69 (m, 2H), 9.31 (s, 1H)

LC/MS (ESI): m/z=456, RT=1.85 min, LC/MS measurement conditions 1

Example 31

Synthesis of Compound (I-0335)

[Chemical Formula 79]

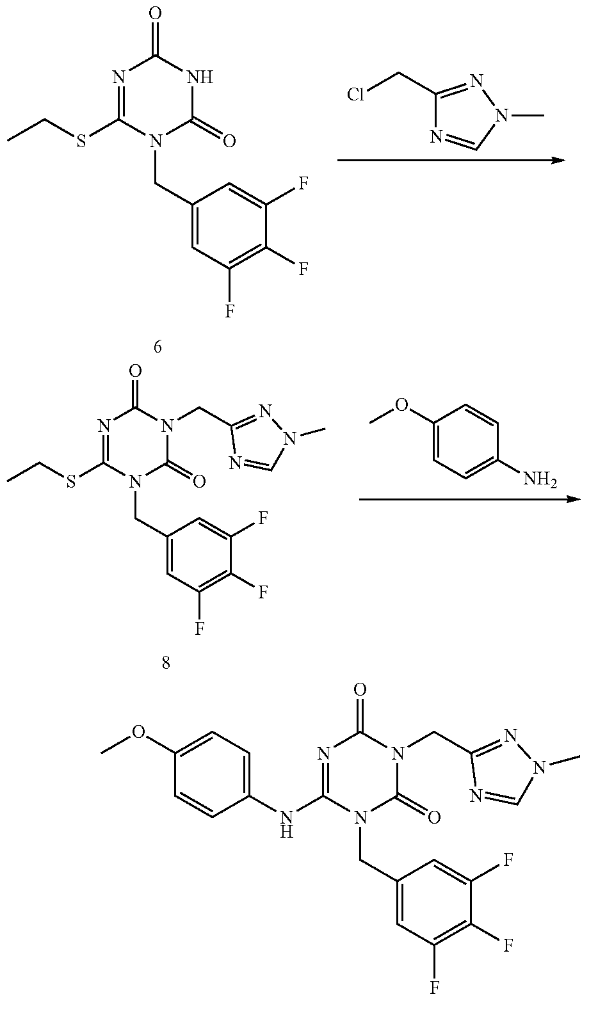

6

8

I-0335

Step 1 Synthesis of Compound 8

Compound 6 (100 mg, 0.315 mmol), potassium carbonate (56.6 mg, 0.410 mmol), 3-(chloromethyl)-1-methyl-1H-1,2,4-triazole (45.6 mg, 0.347 mmol), and DMF (1.0 mL) were mixed, and the solution thus obtained was stirred for 2 hours at 60° C. A saturated aqueous solution of ammonium chloride (5 mL) was added to the reaction solution, and the mixture was extracted with ethyl acetate. The organic layer was washed with water, dried over sodium sulfate, and filtered. The filtrate was concentrated, and Compound 8 (109 mg, 0.264 mmol, yield 84%) was obtained. The obtained Compound 8 was used in the next step without further purification.

LC/MS (ESI): m/z=413, RT=1.82 min, LC/MS measurement conditions 1

Step 2 Synthesis of Compound (1-0335)

Compound (1-0335) (26.5 mg, 0.056 mmol, yield 46%) was obtained in the same manner as in Step 3 of Example 2.

$^1$H-NMR (DMSO-d6) δ: 3.75 (s, 3H), 3.79 (s, 3H), 4.94 (s, 2H), 5.27 (s, 2H), 6.93 (d, J=7.8 Hz, 2H), 7.22 (d, 7.8 Hz, 2H), 7.33 (dd, J=6.5, 9.0 Hz, 2H), 8.35 (s, 1H), 9.28 (s, 1H)

LC/MS (ESI): m/z=474.15, RT=1.78 min, LC/MS measurement conditions 1

Example 4

Synthesis of Compound (I-0329)

[Chemical Formula 80]

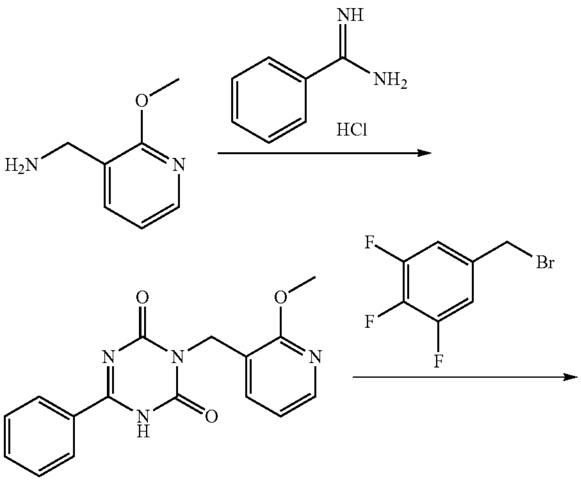

9

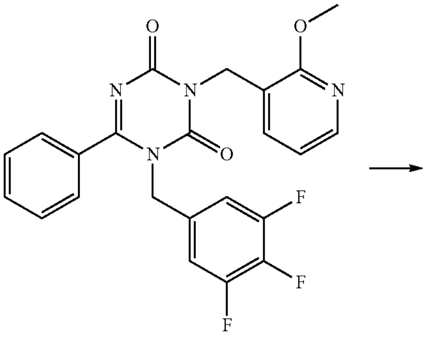

10

-continued

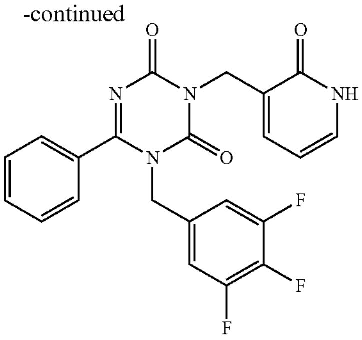

I-0329

Step 1 Synthesis of Compound 9

[(2-Methoxypyridin-3-yl)methyl]amine (200 mg, 1.45 mmol) and DMA (2.0 mL) were mixed, and the solution thus obtained was cooled to 0° C. CDT (258 mg, 1.60 mmol) was added to the solution, and the mixture was stirred for 10 minutes at room temperature. Benzamidine hydrochloride (227 mg, 1.45 mmol) and DBU (240 µL, 1.59 mmol) were added to the reaction solution at room temperature, and the mixture was stirred for 30 minutes. CDT (352 mg, 2.17 mmol) and DBU (327 µL, 2.17 mmol) were added thereto, and the mixture was stirred for 10 minutes at room temperature and was left to stand for 3 days. Ice water was added to the reaction solution, the pH was adjusted to 3 to 4 with a 2 mol/L aqueous solution of hydrochloric acid, and a precipitate thus produced was collected by filtration and was washed with water and diisopropyl ether. The residue was dried under reduced pressure at 40° C., and Compound 9 (324 mg, 1.04 mmol, yield 72%) was obtained.

LC/MS (ESI): m/z=311, RT=1.41 min, LC/MS measurement conditions 1

Step 2 Synthesis of Compound 10

A crude product of Compound 10 was obtained in the same manner as in Step 2 of Example 1.

LC/MS (EST): m/z=455, RT=2.32 min, LC/MS measurement conditions 1

The obtained Compound 10 was used in the next step without further purification.

Step 3 Synthesis of Compound (I-0329)

Compound (1-0329) was obtained in the same manner as in Step 4 of Example 1.

$^1$H-NMR (DMSO-d6) δ: 4.76 (s, 2H), 4.87 (s, 2H), 6.16 (t, J=6.4 Hz, 1H), 7.25 (dd, J=6.8, 9.2 Hz, 2H), 7.31-7.35 (m, 2H), 7.44-7.56 (m, 5H), 11.71, (brs, 1H).

LC/MS (ESI): m/z=441, RT=1.89 min, LC/MS measurement conditions 1

Example 5

Synthesis of Compound (I-0326)

[Chemical Formula 81]

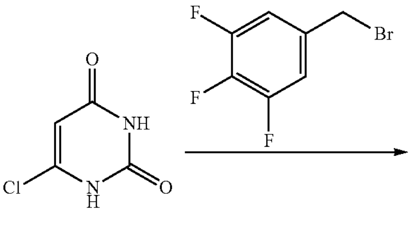

-continued

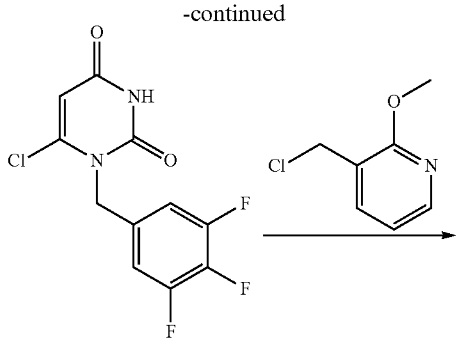

11

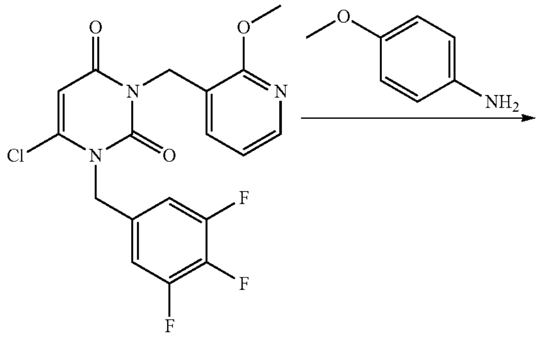

12

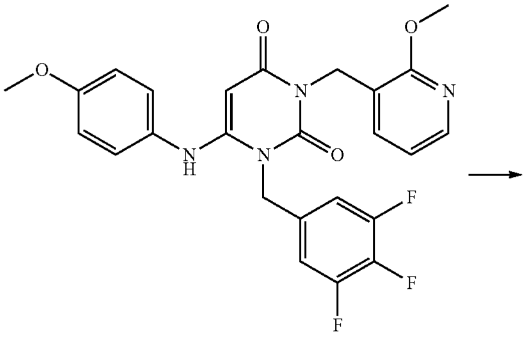

13

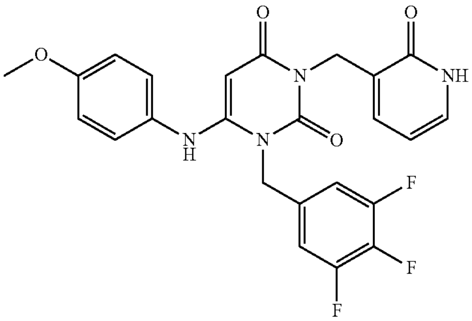

I-0326

Step 1 Synthesis of Compound 11

6-Chlorouracil (600 mg, 4.09 mmol) was dissolved in DMF (6000 μL), and the solution was cooled to 0° C. Sodium hydride (197 mg, 4.91 mmol) was added thereto, and the mixture was stirred for 5 minutes at 0° C. Lithium bromide (356 mg, 4.09 mmol) was added thereto, and the mixture was stirred for 30 minutes at 0° C. Furthermore, 5-(bromomethyl)-1,2,3-trifluorobenzene (1013 mg, 4.50 mmol) was added thereto, and the mixture was stirred overnight at room temperature. A saturated aqueous solution of ammonium chloride and water were added to the obtained reaction solution, and the mixture was extracted with ethyl acetate. The organic layer was washed with water and brine, dried over sodium sulfate, and filtered. The filtrate was concentrated, and the residue was suspended in an ethyl acetate/diisopropyl ether mixed solution and filtered. The residue was washed with an ethyl acetate/diisopropyl ether mixed solution, and Compound 11 (202 mg, 0.695 mmol, yield 17%) was obtained.

LC/MS (ESI): m/z=296, RT=1.76 min, LC/MS measurement conditions 1

Step 2 Synthesis of Compound 12

Compound 11 (100 mg, 0.344 mmol), 3-(chloromethyl)-2-methoxypyridine (65.1 mg, 0.413 mmol), potassium carbonate (71.3 mg, 0.516 mmol), and sodium iodide (77 mg, 0.516 mg) were mixed in DMF (1000 μL). The reaction solution thus obtained was stirred for 4 hours at 60° C. and was extracted with ethyl acetate. The organic layer was washed with water and brine, dried over sodium sulfate, and filtered. The filtrate was concentrated, the residue was purified by column chromatography (hexane/ethyl acetate), and Compound 12 (119.4 mg, 0.29 mmol, yield 84%) was obtained.

LC/MS (ESI): m/z=412, RT=2.33 min, LC/MS measurement conditions 1

Step 3 Synthesis of Compound 13

Compound 12 (94 mg, 0.228 mmol), p-anisidine (30.9 mg, 0.251 mmol), $Pd(OAc)_2$ (5.13 mg, 0.023 mmol), Xantphos (19.81 mg, 0.034 mmol), and cesium carbonate (112 mg, 0.342 mmol) were mixed in 1,4-dioxane (1880 μL). The reaction solution thus obtained was stirred for 4 hours at 120° C. and was extracted with ethyl acetate. The organic layer was washed with water and brine, dried over sodium sulfate, and filtered. The filtrate was concentrated, and the residue thus obtained was triturated with ethyl acetate and filtered. The residue was washed with diisopropyl ether and hexane, and Compound 13 (62.1 mg, 0.125 mmol, yield 55%) was obtained.

LC/MS(ESI): m/z=499, RT=2.27 min, LC/MS measurement conditions 1

Step 4 Synthesis of Compound (I-0326)

Compound (1-0326) was obtained in the same manner as in Step 4 of Example 1.

$^1$H-NMR (DMSO-d6) δ: 3.77 (s, 3H), 4.49 (s, 1H), 4.68 (s, 2H), 5.26 (s, 2H), 6.05-6.11 (m, 1H), 6.87-6.89 (m, 1H), 6.97-7.02 (m, 2H), 7.12-7.18 (m, 2H), 7.22-7.31 (m, 3H), 8.51 (s, 1H), 11.6 (brs, 1H)

LC/MS (ESI): m/z=485, RT=1.83 min, LC/MS measurement conditions 1

Example 61

Synthesis of Compound (I-0113)

[Chemical Formula 82]

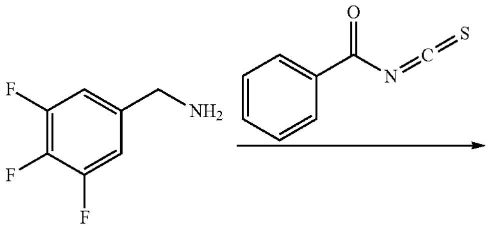

-continued

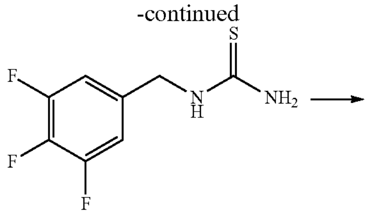

14

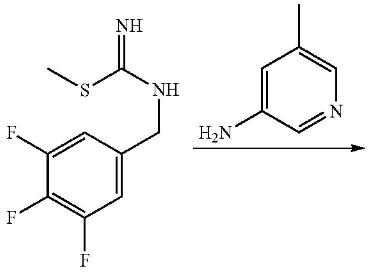

15

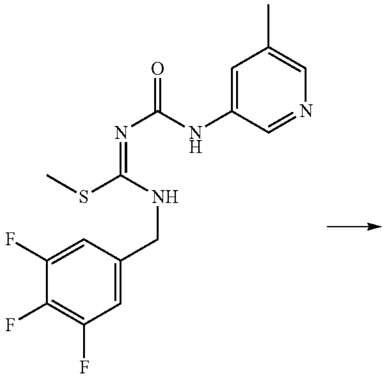

16

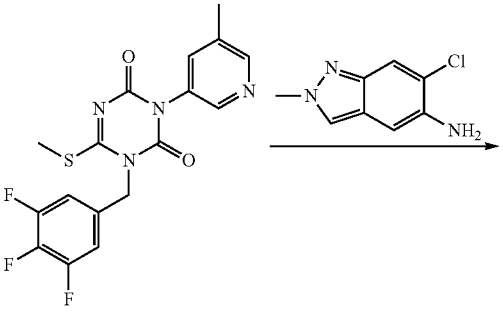

17

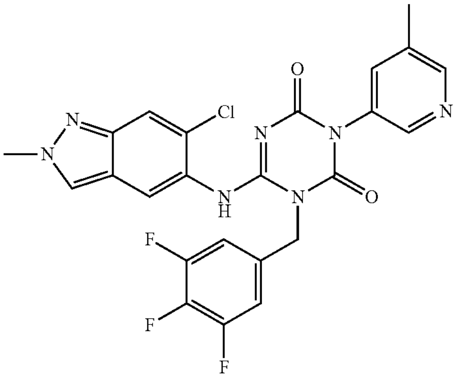

I-0113

Step 1 Synthesis of Compound 14

3,4,5-Trifluorobenzylamine (3.34 g, 20.7 mmol) was dissolved in dichloromethane (33.4 mL), and the solution was cooled in a water bath. Benzoyl isothiocyanate (2.93 mL, 21.8 mmol) was added to the reaction solution, and the mixture was stirred for 30 minutes at room temperature.

The solvent was distilled off, the residue was diluted with methanol, and a 1 mol/L aqueous solution of sodium hydroxide (7.45 mL, 7.45 mmol) was added thereto. The reaction solution was stirred for 30 minutes at room temperature, and a 2 mol/L aqueous solution of hydrochloric acid was added thereto. The aqueous layer was extracted with ethyl acetate, and the organic layer was washed with a saturated aqueous solution of sodium hydrogen carbonate and brine. The organic layer was dried over sodium sulfate, the solvent was distilled off under reduced pressure, and then a crude product of Compound 14 (8.3 g) was obtained. This crude product was used in the next step as a yield of 100% without further purification.

LC/MS (EST): m/z=221, RT=1.45 min, LC/MS measurement conditions 3

Step 2 Synthesis of Compound 15

A crude product of Compound 14 (8.3 g), DMF (85 mL), and methyl iodide (4.84 mL, 77 mmol) were mixed, and the reaction solution was stirred for 40 minutes at 50° C. Water was added to the reaction solution, and the mixture was extracted with ethyl acetate and washed with water. A 2 mol/L aqueous solution of sodium hydroxide was added to the aqueous layer, and the aqueous layer was extracted with ethyl acetate. The organic layer was washed with water and brine and was dried over sodium sulfate. The solvent was distilled off under reduced pressure, and a crude product of Compound 15 (3.86 g, 16.5 mmol, yield 80%) was obtained.

LC/MS (ESI): m/z=235, RT=0.84 min, LC/MS measurement conditions 3

Step 3 Synthesis of Compound 16

Triphosgene (0.507 g, 1.71 mmol) and THF (6 mL) were mixed, and the reaction solution was cooled in an ice bath. 3-Amino-5-methylpyridine (0.462 g, 4.27 mmol) and triethylamine (1.48 mL, 10.7 mmol) were mixed in THF (6 mL), and the solution thus obtained was added dropwise to the reaction solution. The reaction solution was stirred for 40 minutes at room temperature and then was cooled in an ice bath. Compound 15 (1 g, 4.27 mmol) was added to the reaction solution, and the mixture was stirred for 55 minutes at room temperature. Water was added thereto, the aqueous layer was extracted with ethyl acetate, and the organic layer was washed with water. The organic layer was dried over magnesium sulfate, the solvent was distilled off under reduced pressure, and a crude product of Compound 16 (1.57 g, 4.26 mmol, yield: quantitative) was obtained.

LC/MS (ESI): m/z=369, RT=1.52 min, LC/MS measurement conditions 1

Step 4 Synthesis of Compound 17

CDI (2.78 g, 17.2 mmol), Compound 16 (1.58 g, 4.29 mmol), and DMF (12.6 mL) were mixed. Diisopropylethylamine (3.00 mL, 17.2 mmol) was added to the reaction solution, and the mixture was irradiated with microwaves for 30 minutes while being stirred at 110° C. The reaction solution was poured into ice, and a precipitate thus produced was separated by filtration and washed with water. The residue thus obtained was dried under reduced pressure, and a crude product of Compound 17 (649 mg, 1.51 mmol, yield 35%) was obtained.

LC/MS (ESI): m/z=395, RT=1.74 min, LC/MS measurement conditions 1

Step 5 Synthesis of Compound (I-0113)

6-Chloro-2-methyl-2H-indazole-5-amine (55.3 mg, 0.304 mmol), Compound 17 (100 mg, 0.254 mmol), and THF (1 mL) were mixed. The reaction solution was cooled in an ice bath, and LHMDS (0.761 mL, 0.761 mmol) was added thereto. The reaction solution was stirred in an ice bath for 40 minutes, and a saturated aqueous solution of ammonium chloride was added thereto. The organic layer was extracted with ethyl acetate and was concentrated under reduced pressure. The residue was purified by silica gel column chromatography (chloroform/methanol), and Compound (I-0113) (80 mg, 0.145 mmol, yield 57.4%) was obtained.

$^1$H-NMR (Methanol-d4) δ: 8.43 (d, J=1.0 Hz, 1H), 8.36 (d, J=2.0 Hz, 1H), 8.18 (s, 1H), 7.74 (s, 1H), 7.72 (br s, 1H), 7.48-7.35 (m, 3H), 5.32 (s, 2H), 4.20 (s, 3H), 2.42 (s, 3H).

LC/MS (ESI): m/z=528, RT=1.93 min, LC/MS measurement conditions 1

Example 7

Synthesis of Compound (I-0115)

[Chemical Formula 83]

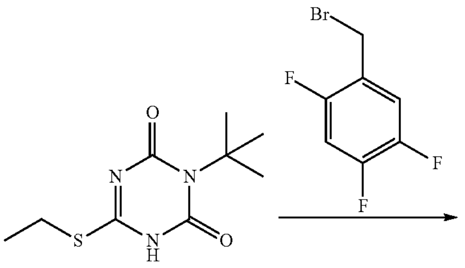

4

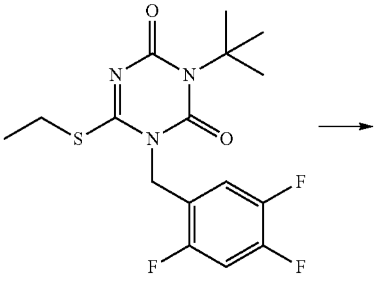

18

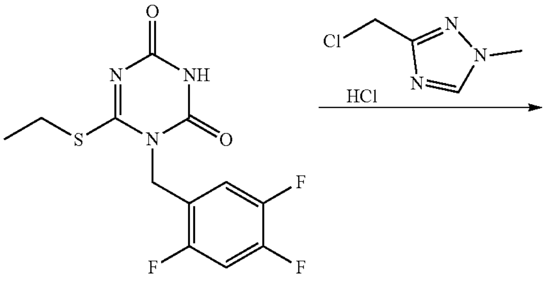

19

-continued

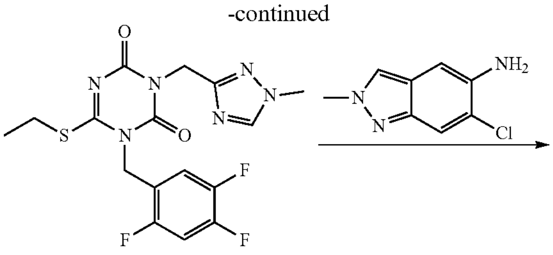

20

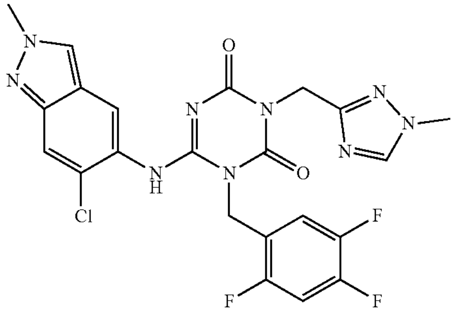

I-0115

Step 1 Synthesis of Compound 18

Compound 4 (926 mg, 4.04 mmol), acetonitrile (7.41 mL), potassium carbonate (726 mg, 5.25 mmol) and 2,4,5-trifluorobenzyl bromide (1000 mg, 4.44 mmol) were mixed. The reaction solution was stirred at 80° C. for 40 minutes, allowed to cool, and then diluted with ethyl acetate. After filtration of the insoluble material, the filtrate was concentrated to give the crude product of Compound 18 (1.51 g, 4.04 mmol, yield: quant.)

LC/MS (ESI): m/z=374, RT=2.54 min, LC/MS measured condition 1

Step 2 Synthesis of Compound 19

Compound 18 (1.51 g, 4.04 mmol) and TFA (3.02 mL) were mixed. The reaction solution was stirred at room temperature for 4 hours and allowed to stand overnight. TFA was distilled off under reduced pressure, and then toluene was added to the residue and azeotroped. Isopropyl Ether was added to the residue, suspended, and collected by filtration to give Compound 19 (1.22 g, 3.84 mmol, yield: 95%)

LC/MS (ESI): m/z=318, RT=1.68 min, LC/MS measured condition 1

Step 3 Synthesis of Compound 20

Compound 19 (200 mg, 0.63 mmol), DMF (1.8 mL), Potassium Carbonate (261 mg, 1.89 mmol) and 3-(chloromethyl)-1-methyl-1H-1,2,4-triazole hydrochloride (159 mg, 0.946 mmol) were mixed. The reaction solution was stirred for 2 hours at 60° C., and a saturated aqueous ammonium chloride solution was added. The aqueous layer was extracted with ethyl acetate and the organic layer was washed with brine. The organic layer was dried over magnesium sulfate, filtered and concentrated. The residue was suspended in a mixed solvent of isopropyl ether, hexane, ethyl acetate and chloroform and collected by filtration. The residue, DMF (1.8 mL), potassium carbonate (261 mg, 1.89 mmol) and 3-(chloromethyl)-1-methyl-1H-1,2,4-triazole hydrochloride (159 mg, 0.946 mmol) were mixed. The reaction solution was stirred at 60° C. for 6 hours, and a saturated aqueous ammonium chloride solution was added. The aqueous layer was extracted with ethyl acetate and the organic layer was washed with brine. The organic layer was dried over magnesium sulfate, filtered and concentrated. The residue was suspended in a mixed solvent of isopropyl ether, hexane, ethyl acetate and chloroform and collected by filtration to give Compound 20 (116 mg, 0.281 mmol, 45% yield)

LC/MS (ESI): m/z=413, RT=1.84 min, LC/MS measured condition: 1

Step 4 Synthesis of Compound (I-0115)

Compound 20 (115 mg, 0.279 mmol), THF (2.30 mL) and 6-chloro-2-methyl-2H-indazole-5-amine (60.8 mg, 0.335 mmol) were mixed. The reaction mixture was added drop-wise LHMDS (558 μM, 0.558 mmol) at 0° C. The reaction mixture was stirred at 0° C. for 2.5 hours and stirred at room temperature for 40 minutes, then saturated ammonium chloride solution was added to the reaction mixture. The reaction mixture was extracted with chloroform and the organic layer was concentrated. The residue was purified by silicagel column chromatography (chloroform/methanol) to give Compound (I-0115) (61.8 mg, 0.116 mmol, Yield 42%).

$^1$H-NMR ($CDCl_3$) δ: 7.96 (s, 1H), 7.82 (d, J=2.5 Hz, 2H), 7.48 (br s, 1H), 7.45-7.37 (m, 1H), 7.08 (s, 1H), 6.97-6.88 (m, 1H), 5.35 (s, 2H), 5.17 (s, 2H), 4.21 (s, 3H), 3.89 (s, 3H).

LC/MS(ESI): m/z=532, RT=1.70 min, LC/MS measurement method 1

The following compounds were synthesized according to the above general synthesis method and the method described in Examples. The structure and physical properties (LC/MS and NMR data) are shown in the table below.

The compound described by the amino structure:

[Chemical Formula 84]

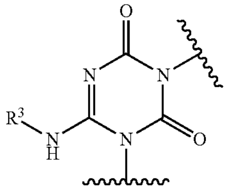

in the table, in which Y is N and X is NH in Formula (I), may have an imino structure

[Chemical Formula 85]

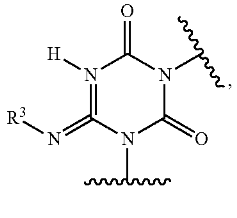

and the compound represented by the imino structure also may have the amino structure That is, even with the same compound, there are cases where it has an imino structure or an amino structure, depending on crystallization conditions and the like. Even with forming its salt or complex, the salt or the complex may have an amino structure or an imino structure. Even with the same counter molecule of the salt or the complex, they may have an amino structure or an imino structure depending on crystallization conditions and the like. It may also be the mixture of a compound having an imino structure, its salt or a complex thereof, and a compound having an amino structure, its salt or a complex thereof.

Incidentally, in the structural formula, "wedge form" and "broken line" indicate the configuration. Particularly, with regard to compounds whose configurations are described, a compound described as "a" in the item of "Configuration" indicates that configuration is determined as shown in the chemical structure.

Furthermore, with regard to compounds in which a bond forming an asymmetric carbon is described as a solid line, a compound described as "b" in the item of "Configuration" is a racemic compound.

TABLE 1

| Compound No. | Structure | LC/MS Measured condition | Retention time (min) | m/z | Con-figration |
|---|---|---|---|---|---|
| I-0001 | 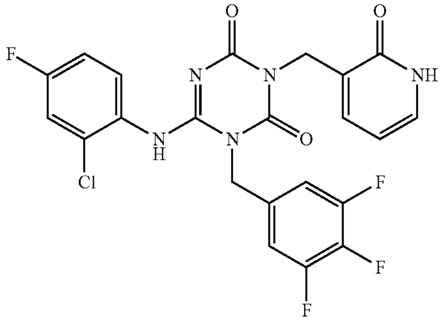 | 3 | 2.05 | 508 | |

TABLE 1-continued
| Compound No. | Structure | LC/MS Measured condition | Retention time (min) | m/z | Con-figration |
|---|---|---|---|---|---|
| I-0005 | 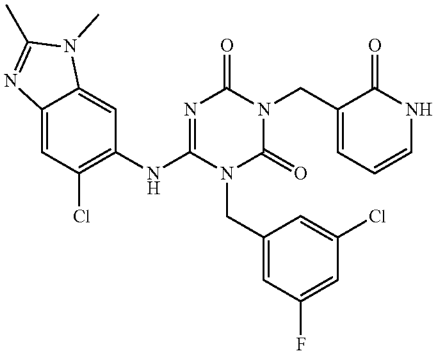 [SMILES: Cc1nc2cc(Cl)c(Nc3nc(=O)n(Cc4ccc[nH]c4=O)c(=O)n3Cc3cc(F)cc(Cl)c3)cc2n1C] | 1 | 1.57 | 556 | |
| I-0006 | 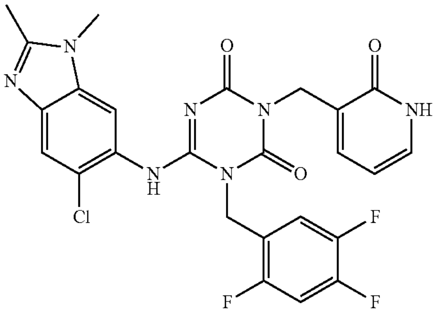 [SMILES: Cc1nc2cc(Cl)c(Nc3nc(=O)n(Cc4ccc[nH]c4=O)c(=O)n3Cc3cc(F)c(F)cc3F)cc2n1C] | 1 | 1.50 | 558 | |
| I-0007 | 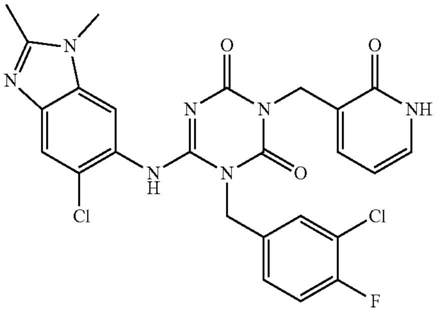 [SMILES: Cc1nc2cc(Cl)c(Nc3nc(=O)n(Cc4ccc[nH]c4=O)c(=O)n3Cc3ccc(F)c(Cl)c3)cc2n1C] | 1 | 1.57 | 556 | |
| I-0008 | 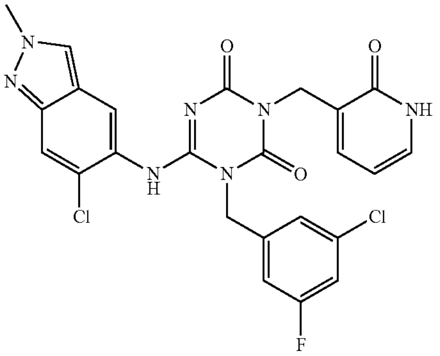 [SMILES: Cn1cc2cc(Nc3nc(=O)n(Cc4ccc[nH]c4=O)c(=O)n3Cc3cc(F)cc(Cl)c3)c(Cl)cc2n1] | 1 | 1.90 | 542 | |

TABLE 2
| Compound No. | Structure | LC/MS Measured condition | Retention time (min) | m/z | Con-figuration |
|---|---|---|---|---|---|
| I-0009 | 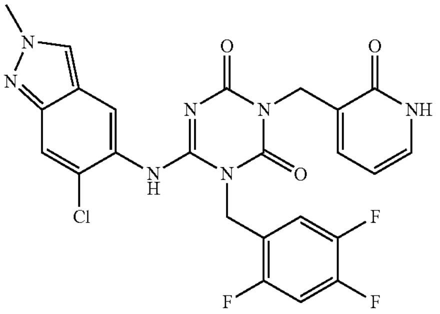 [SMILES: Cn1cc2cc(Nc3nc(=O)n(Cc4ccc[nH]c4=O)c(=O)n3Cc3cc(F)c(F)cc3F)c(Cl)cc2n1] | 1 | 1.81 | 544 | |
| I-0010 | 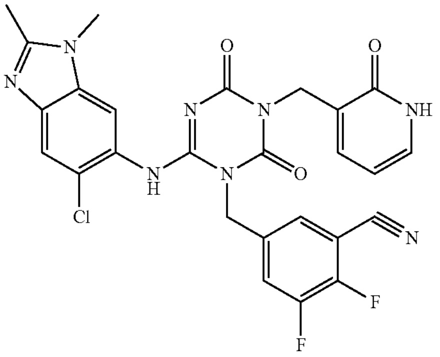 [SMILES: Cc1nc2cc(Cl)c(Nc3nc(=O)n(Cc4ccc[nH]c4=O)c(=O)n3Cc3cc(F)c(F)c(C#N)c3)cc2n1C] | 1 | 1.53 | 565 | |
| I-0011 | 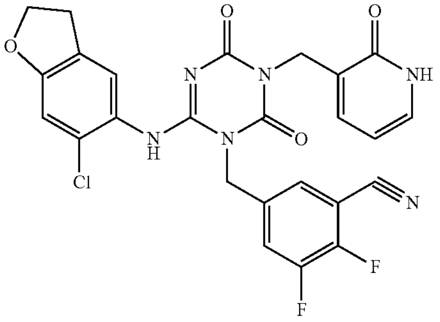 [SMILES: N#Cc1cc(Cn2c(Nc3cc4c(cc3Cl)OCC4)nc(=O)n(Cc3ccc[nH]c3=O)c2=O)cc(F)c1F] | 1 | 2.03 | 539 | |
| I-0012 | 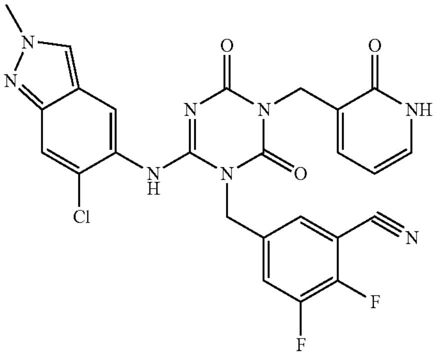 [SMILES: Cn1cc2cc(Nc3nc(=O)n(Cc4ccc[nH]c4=O)c(=O)n3Cc3cc(F)c(F)c(C#N)c3)c(Cl)cc2n1] | 1 | 1.81 | 551 | |

TABLE 2-continued
| Compound No. | Structure | LC/MS Measured condition | Retention time (min) | m/z | Con-figration |
|---|---|---|---|---|---|
| I-0013 | 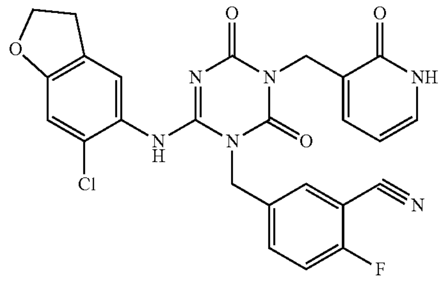 [SMILES: N#Cc1cc(Cn2c(Nc3cc4c(cc3Cl)OCC4)nc(=O)n(Cc3ccc[nH]c3=O)c2=O)ccc1F] | 1 | 1.92 | 521 | |
TABLE 3
| Compound No. | Structure | LC/MS Measured condition | Retention time (min) | m/z | Con-figration |
|---|---|---|---|---|---|
| I-0016 | 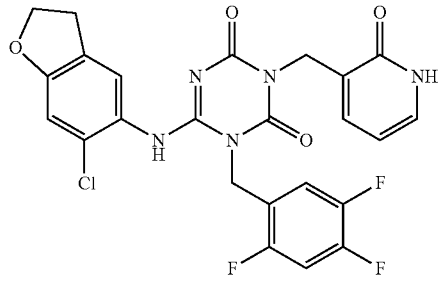 [SMILES: O=c1[nH]cccc1Cn1c(=O)nc(Nc2cc3c(cc2Cl)OCC3)n(Cc2cc(F)c(F)cc2F)c1=O] | 1 | 2.03 | 532 | |
| I-0019 | 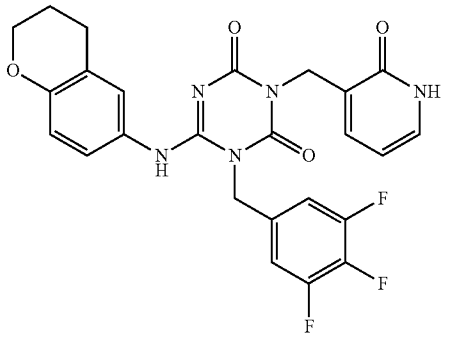 [SMILES: O=c1[nH]cccc1Cn1c(=O)nc(Nc2ccc3c(c2)CCCO3)n(Cc2cc(F)c(F)c(F)c2)c1=O] | 1 | 1.99 | 512.2 | |
| I-0020 | 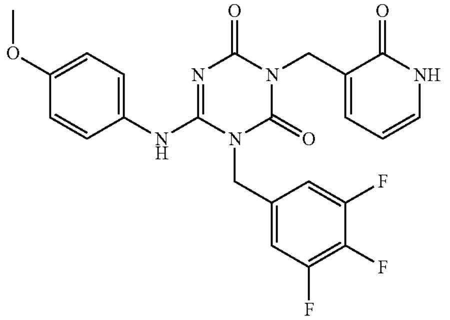 [SMILES: COc1ccc(Nc2nc(=O)n(Cc3ccc[nH]c3=O)c(=O)n2Cc2cc(F)c(F)c(F)c2)cc1] | 1 | 1.91 | 486.1 | |

TABLE 3-continued
| Compound No. | Structure | LC/MS Measured condition | Retention time (min) | m/z | Con-figration |
|---|---|---|---|---|---|
| I-0025 | 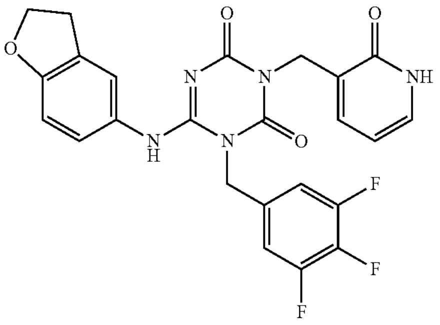 [SMILES: O=c1[nH]cccc1Cn1c(=O)nc(Nc2ccc3c(c2)CCO3)n(Cc2cc(F)c(F)c(F)c2)c1=O] | 1 | 1.89 | 498.1 | |
| I-0026 | 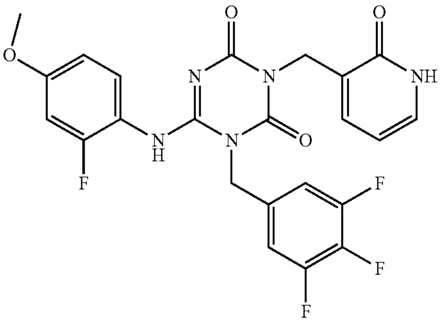 [SMILES: COc1ccc(Nc2nc(=O)n(Cc3ccc[nH]c3=O)c(=O)n2Cc2cc(F)c(F)c(F)c2)c(F)c1] | 1 | 2.05 | 504.1 | |
TABLE 4
| Compound No. | Structure | LC/MS Measured condition | Retention time (min) | m/z | Con-figration |
|---|---|---|---|---|---|
| I-0027 | 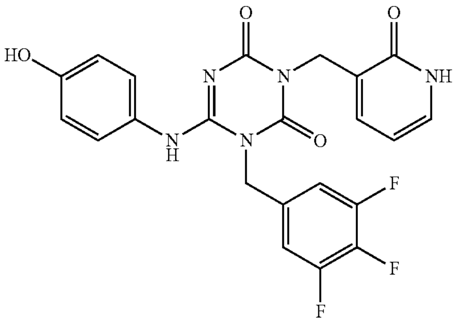 [SMILES: O=c1[nH]cccc1Cn1c(=O)nc(Nc2ccc(O)cc2)n(Cc2cc(F)c(F)c(F)c2)c1=O] | 1 | 1.67 | 472.1 | |
| I-0029 | 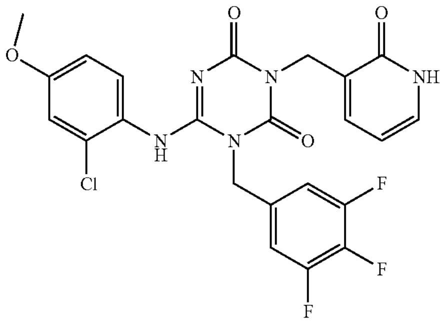 | 1 | 2.05 | 504.1 | |

TABLE 4-continued
| Compound No. | Structure | LC/MS Measured condition | Retention time (min) | m/z | Con-figration |
|---|---|---|---|---|---|
| I-0031 | 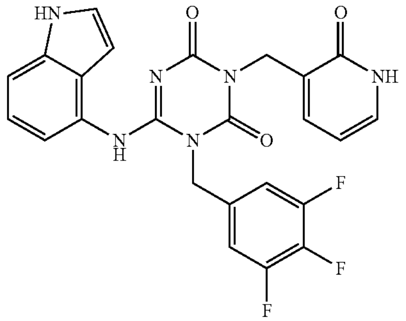 [SMILES: O=c1[nH]cccc1Cn1c(=O)nc(Nc2cccc3[nH]ccc23)n(Cc2cc(F)c(F)c(F)c2)c1=O] | 3 | 1.91 | 495.1 | |
| I-0033 | 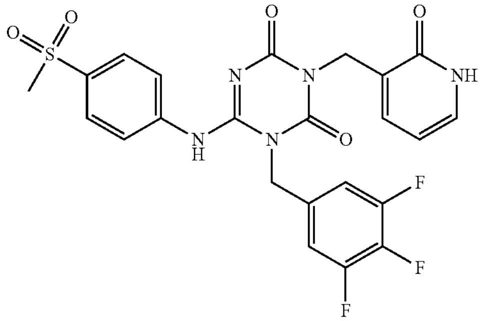 [SMILES: CS(=O)(=O)c1ccc(Nc2nc(=O)n(Cc3ccc[nH]c3=O)c(=O)n2Cc2cc(F)c(F)c(F)c2)cc1] | 1 | 1.95 | 534.1 | |
| I-0035 | 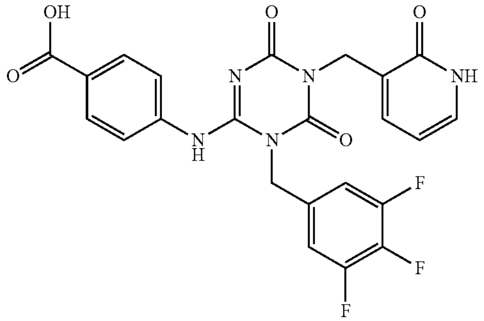 [SMILES: O=C(O)c1ccc(Nc2nc(=O)n(Cc3ccc[nH]c3=O)c(=O)n2Cc2cc(F)c(F)c(F)c2)cc1] | 1 | 1.82 | 500.1 | |
TABLE 5
| Compound No. | Structure | LC/MS Measured condition | Retention time (min) | m/z | Con-figration |
|---|---|---|---|---|---|
| I-0038 | 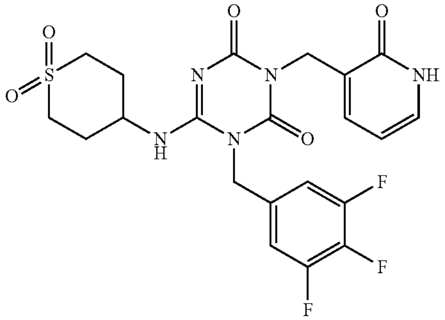 [SMILES: O=c1[nH]cccc1Cn1c(=O)nc(NC2CCS(=O)(=O)CC2)n(Cc2cc(F)c(F)c(F)c2)c1=O] | 1 | 1.55 | 512.1 | |

TABLE 5-continued
| Compound No. | Structure | LC/MS Measured condition | Retention time (min) | m/z | Con-figration |
|---|---|---|---|---|---|
| I-0042 | 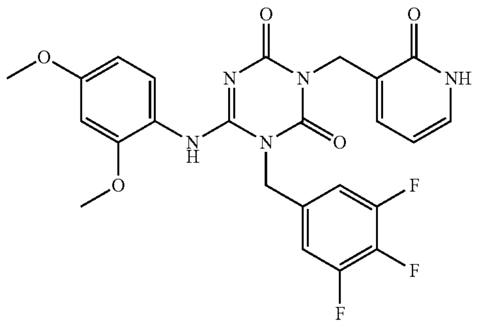 [SMILES: COc1ccc(Nc2nc(=O)n(Cc3ccc[nH]c3=O)c(=O)n2Cc2cc(F)c(F)c(F)c2)c(OC)c1] | 1 | 1.89 | 516.1 | |
| I-0048 | 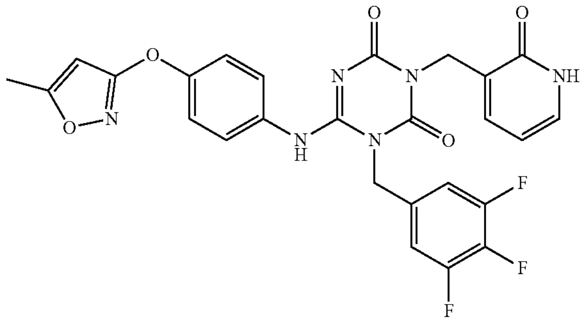 [SMILES: Cc1cc(Oc2ccc(Nc3nc(=O)n(Cc4ccc[nH]c4=O)c(=O)n3Cc3cc(F)c(F)c(F)c3)cc2)no1] | 1 | 2.12 | 553.1 | |
| I-0056 | 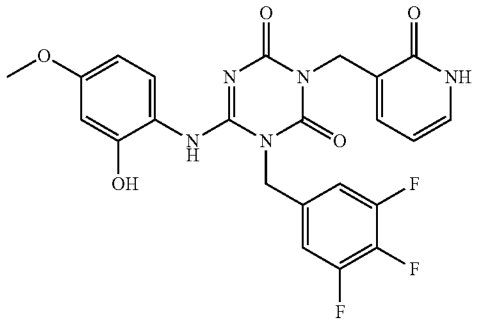 [SMILES: COc1ccc(Nc2nc(=O)n(Cc3ccc[nH]c3=O)c(=O)n2Cc2cc(F)c(F)c(F)c2)c(O)c1] | 1 | 1.73 | 502.1 | |
| I-0063 | 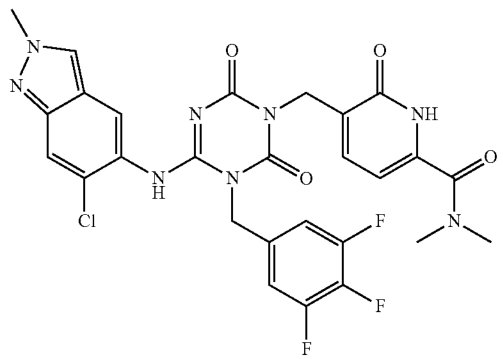 [SMILES: CN(C)C(=O)c1ccc(Cn2c(=O)nc(Nc3cc4cn(C)nc4cc3Cl)n(Cc3cc(F)c(F)c(F)c3)c2=O)c(=O)[nH]1] | 1 | 1.87 | 615.1 | |

TABLE 6
| Compound No. | Structure | LC/MS Measured condition | Retention time (min) | m/z | Con-figration |
|---|---|---|---|---|---|
| I-0064 | 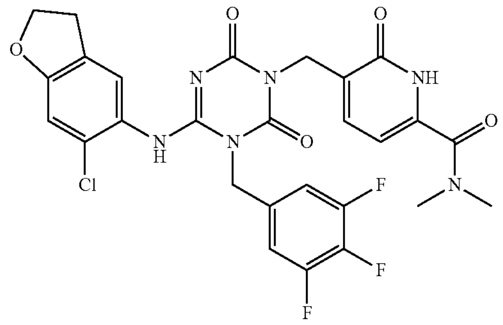 [SMILES: CN(C)C(=O)c1ccc(Cn2c(=O)nc(Nc3cc4c(cc3Cl)OCC4)n(Cc3cc(F)c(F)c(F)c3)c2=O)c(=O)[nH]1] | 1 | 2.08 | 603.1 | |
| I-0066 | 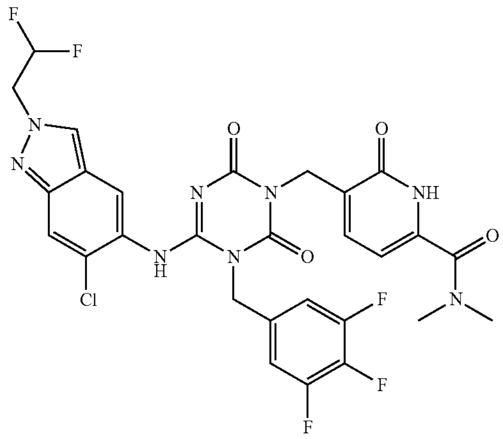 [SMILES: CN(C)C(=O)c1ccc(Cn2c(=O)nc(Nc3cc4cn(CC(F)F)nc4cc3Cl)n(Cc3cc(F)c(F)c(F)c3)c2=O)c(=O)[nH]1] | 1 | 2.04 | 665.1 | |
| I-0069 | 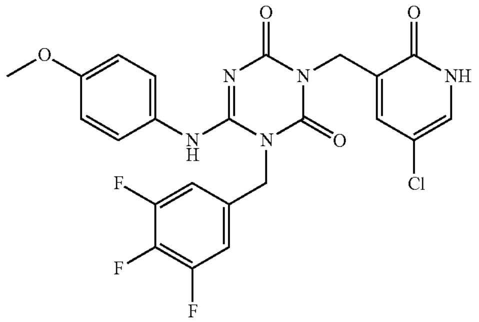 [SMILES: COc1ccc(Nc2nc(=O)n(Cc3cc(Cl)c[nH]c3=O)c(=O)n2Cc2cc(F)c(F)c(F)c2)cc1] | 1 | 1.95 | 520 | |
| I-0072 | 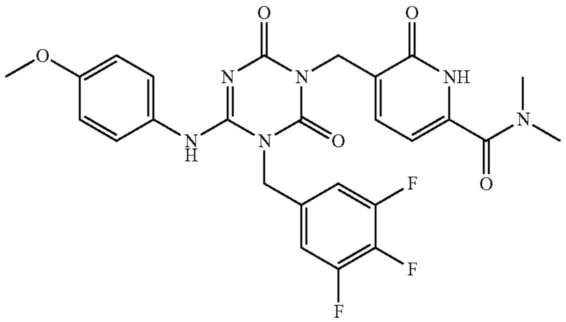 | 1 | 1.78 | 557 | |

TABLE 6-continued
| Compound No. | Structure | LC/MS Measured condition | Retention time (min) | m/z | Con-figration |
|---|---|---|---|---|---|
| I-0074 | 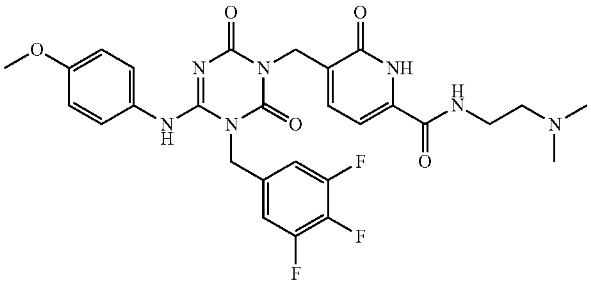 | 1 | 1.49 | 600 | |
TABLE 7
| Compound No. | Structure | LC/MS Measured condition | Retention time (min) | m/z | Con-figration |
|---|---|---|---|---|---|
| I-0077 | 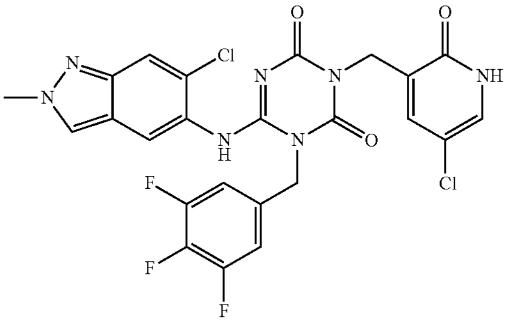 [SMILES: Cn1cc2cc(Nc3nc(=O)n(Cc4cc(Cl)c[nH]c4=O)c(=O)n3Cc3cc(F)c(F)c(F)c3)c(Cl)cc2n1] | 1 | 1.96 | 578 | |
| I-0078 | 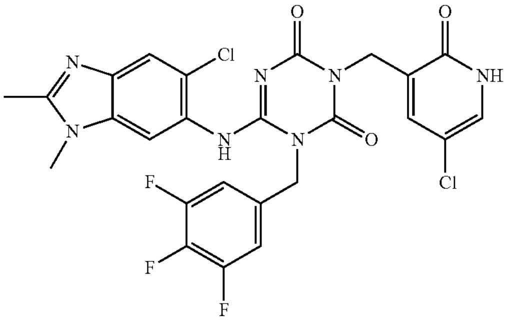 [SMILES: Cc1nc2cc(Cl)c(Nc3nc(=O)n(Cc4cc(Cl)c[nH]c4=O)c(=O)n3Cc3cc(F)c(F)c(F)c3)cc2n1C] | 1 | 1.64 | 592 | |
| I-0079 | 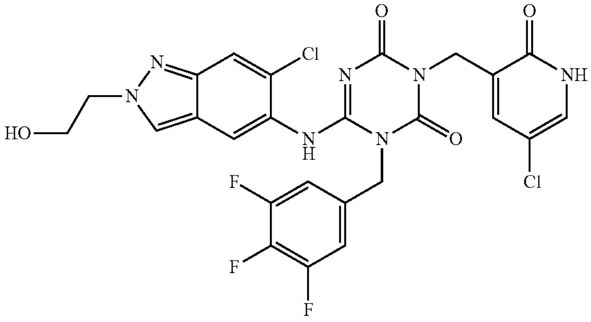 [SMILES: O=c1[nH]cc(Cl)cc1Cn1c(=O)nc(Nc2cc3cn(CCO)nc3cc2Cl)n(Cc2cc(F)c(F)c(F)c2)c1=O] | 1 | 1.84 | 608 | |

TABLE 7-continued
| Compound No. | Structure | LC/MS Measured condition | Retention time (min) | m/z | Con-figration |
|---|---|---|---|---|---|
| I-0080 | 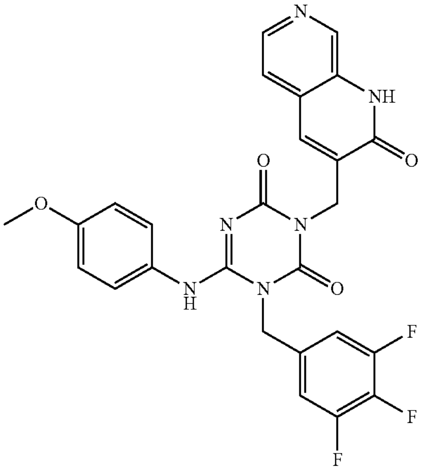 [SMILES: COc1ccc(Nc2nc(=O)n(Cc3cc4ccncc4[nH]c3=O)c(=O)n2Cc2cc(F)c(F)c(F)c2)cc1] | 2 | 1.78 | 537.2 | |
| I-0081 | 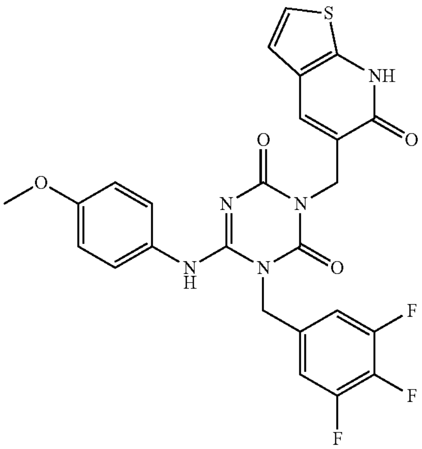 [SMILES: COc1ccc(Nc2nc(=O)n(Cc3cc4ccsc4[nH]c3=O)c(=O)n2Cc2cc(F)c(F)c(F)c2)cc1] | 2 | 2.00 | 542.2 | |
TABLE 8
| Compound No. | Structure | LC/MS Measured condition | Retention time (min) | m/z | Con-figration |
|---|---|---|---|---|---|
| I-0083 | 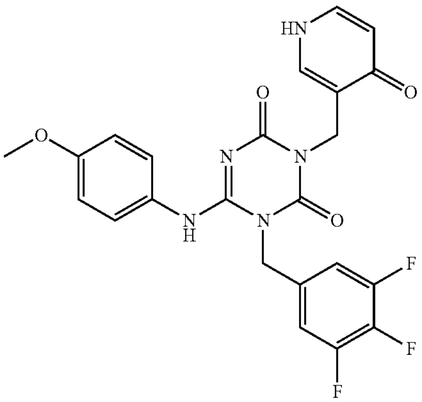 [SMILES: COc1ccc(Nc2nc(=O)n(Cc3c[nH]ccc3=O)c(=O)n2Cc2cc(F)c(F)c(F)c2)cc1] | 2 | 1.58 | 486.2 | |

TABLE 8-continued
| Compound No. | Structure | LC/MS Measured condition | Retention time (min) | m/z | Con-figration |
|---|---|---|---|---|---|
| I-0084 | 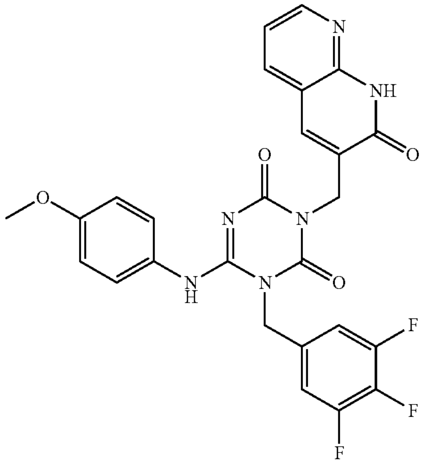 [SMILES: COc1ccc(Nc2nc(=O)n(Cc3cc4cccnc4[nH]c3=O)c(=O)n2Cc2cc(F)c(F)c(F)c2)cc1] | 2 | 1.94 | 537.2 | |
| I-0087 | 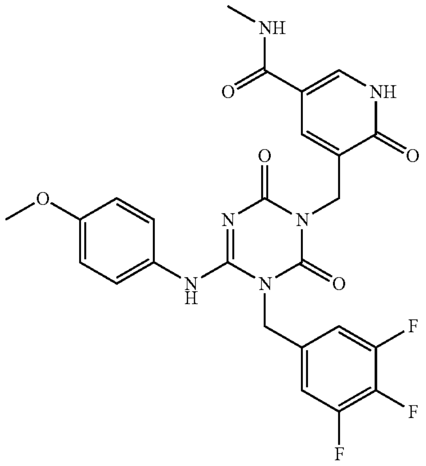 [SMILES: CNC(=O)c1c[nH]c(=O)c(Cn2c(=O)nc(Nc3ccc(OC)cc3)n(Cc3cc(F)c(F)c(F)c3)c2=O)c1] | 2 | 1.77 | 543.3 | |
| I-0088 | 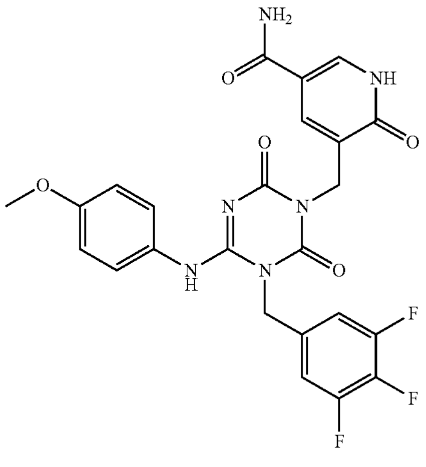 [SMILES: COc1ccc(Nc2nc(=O)n(Cc3cc(C(N)=O)c[nH]c3=O)c(=O)n2Cc2cc(F)c(F)c(F)c2)cc1] | 2 | 1.71 | 529.2 | |

TABLE 8-continued
| Compound No. | Structure | LC/MS Measured condition | Retention time (min) | m/z | Con-figration |
|---|---|---|---|---|---|
| I-0089 | 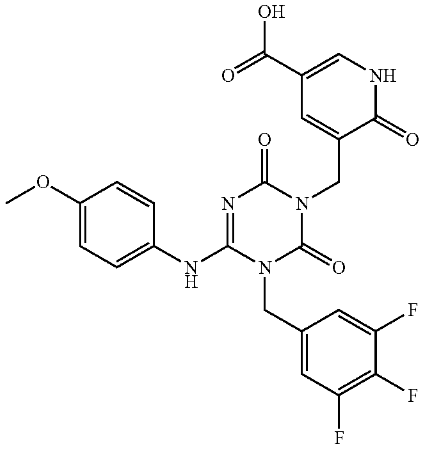 | 2 | 1.76 | 530.2 | |
TABLE 9
| Compound No. | Structure | LC/MS Measured condition | Retention time (min) | m/z | Configration |
|---|---|---|---|---|---|
| I-0092 | 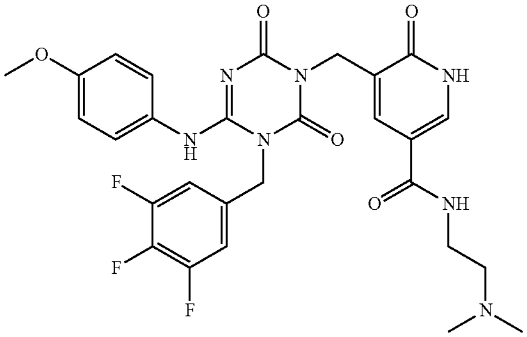 | 2 | 1.37 | 600.3 | |
| I-0094 | 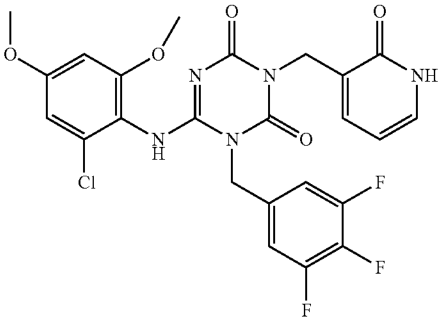 [SMILES: COc1cc(Cl)c(Nc2nc(=O)n(Cc3ccc[nH]c3=O)c(=O)n2Cc2cc(F)c(F)c(F)c2)c(OC)c1] | 1 | 1.97 | 550.3 | |

TABLE 9-continued
| Compound No. | Structure | LC/MS Measured condition | Retention time (min) | m/z | Configration |
|---|---|---|---|---|---|
| I-0095 | 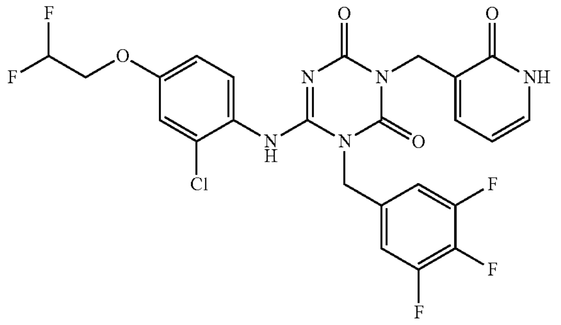 [SMILES: O=c1[nH]cccc1Cn1c(=O)nc(Nc2ccc(OCC(F)F)cc2Cl)n(Cc2cc(F)c(F)c(F)c2)c1=O] | 1 | 2.10 | 570.2 | |
| I-0096 | 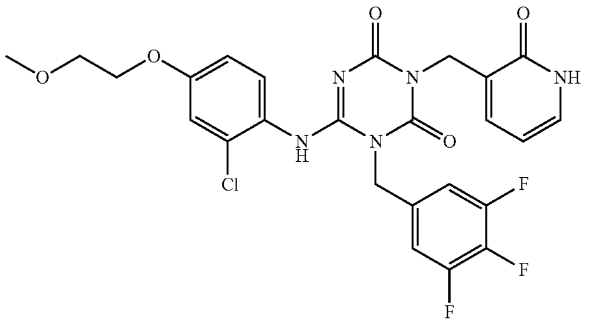 [SMILES: COCCOc1ccc(Nc2nc(=O)n(Cc3ccc[nH]c3=O)c(=O)n2Cc2cc(F)c(F)c(F)c2)c(Cl)c1] | 1 | 1.94 | 564.3 | |
| I-0097 | 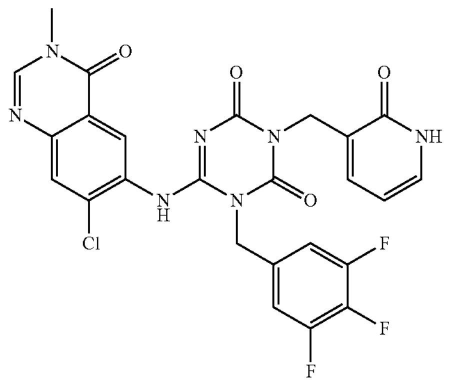 [SMILES: Cn1cnc2cc(Cl)c(Nc3nc(=O)n(Cc4ccc[nH]c4=O)c(=O)n3Cc3cc(F)c(F)c(F)c3)cc2c1=O] | 1 | 1.78 | 572.2 | |

TABLE 10
| Compound No. | Structure | LC/MS Measured condition | Retention time (min) | m/z | Configration |
| --- | --- | --- | --- | --- | --- |
| I-0098 | 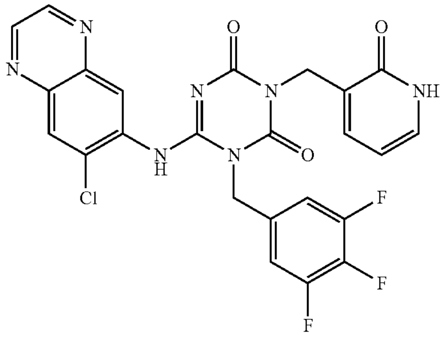 | 1 | 1.90 | 542.2 | |
| I-0099 | 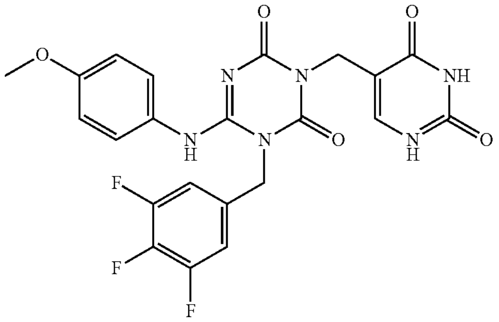 | 1 | 1.57 | 503 | |
| I-0100 | 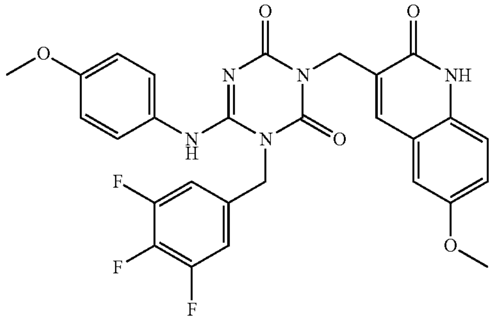 | 1 | 1.98 | 566 | |
| I-0102 | 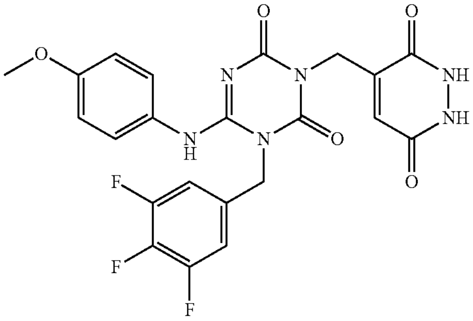 [SMILES: COc1ccc(Nc2nc(=O)n(Cc3cc(=O)[nH][nH]c3=O)c(=O)n2Cc2cc(F)c(F)c(F)c2)cc1] | 1 | 1.62 | 503 | |

TABLE 10-continued
| Compound No. | Structure | LC/MS Measured condition | Retention time (min) | m/z | Configration |
|---|---|---|---|---|---|
| I-0103 | 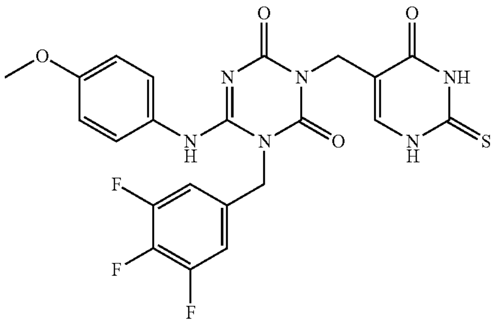 [SMILES: COc1ccc(Nc2nc(=O)n(Cc3c[nH]c(=S)[nH]c3=O)c(=O)n2Cc2cc(F)c(F)c(F)c2)cc1] | 1 | 1.69 | 519 | |
TABLE 11
| Compound No. | Structure | LC/MS Measured condition | Retention time (min) | m/z | Configration |
|---|---|---|---|---|---|
| I-0105 | 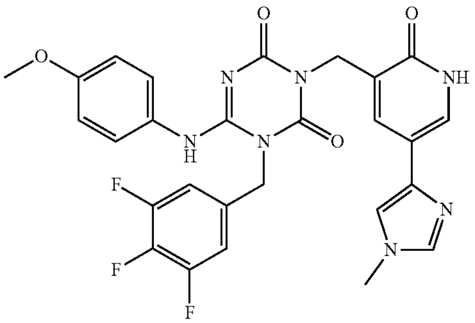 [SMILES: COc1ccc(Nc2nc(=O)n(Cc3cc(-c4cn(C)cn4)c[nH]c3=O)c(=O)n2Cc2cc(F)c(F)c(F)c2)cc1] | 1 | 1.45 | 566 | |
| I-0106 | 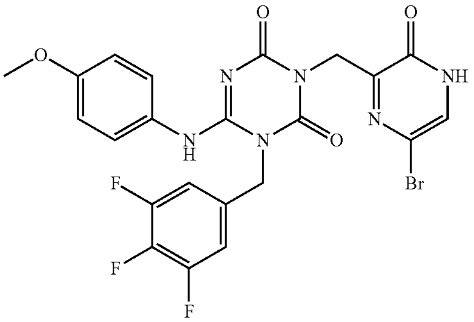 [SMILES: COc1ccc(Nc2nc(=O)n(Cc3nc(Br)c[nH]c3=O)c(=O)n2Cc2cc(F)c(F)c(F)c2)cc1] | 1 | 1.86 | 565 | |
| I-0110 | 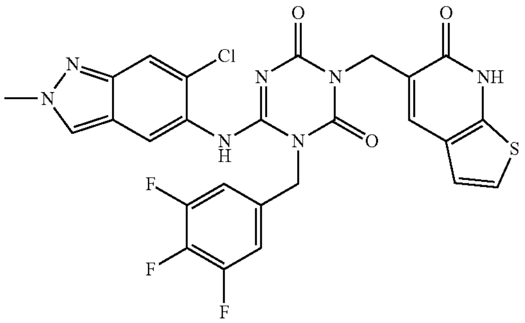 [SMILES: Cn1cc2cc(Nc3nc(=O)n(Cc4cc5ccsc5[nH]c4=O)c(=O)n3Cc3cc(F)c(F)c(F)c3)c(Cl)cc2n1] | 1 | 1.94 | 600 | |

TABLE 11-continued
| Compound No. | Structure | LC/MS Measured condition | Retention time (min) | m/z | Configration |
|---|---|---|---|---|---|
| I-0111 | 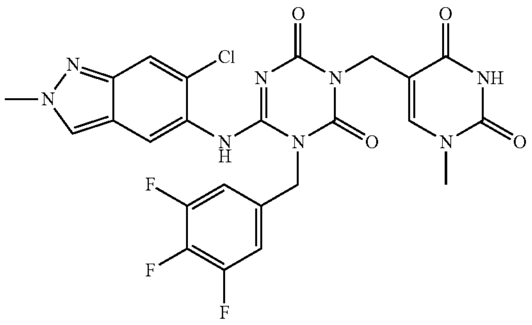 [SMILES: Cn1cc2cc(Nc3nc(=O)n(Cc4cn(C)c(=O)[nH]c4=O)c(=O)n3Cc3cc(F)c(F)c(F)c3)c(Cl)cc2n1] | 1 | 1.70 | 575 | |
| I-0112 | 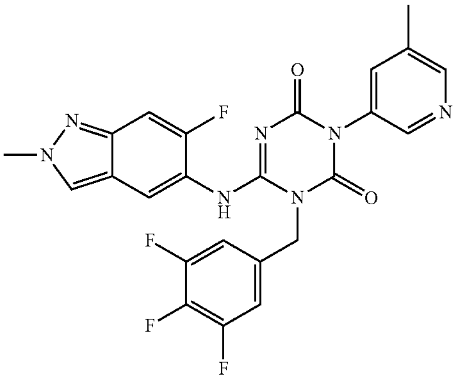 [SMILES: Cc1cncc(-n2c(=O)nc(Nc3cc4cn(C)nc4cc3F)n(Cc3cc(F)c(F)c(F)c3)c2=O)c1] | 1 | 1.80 | 512 | |
TABLE 12
| Compound No. | Structure | LC/MS Measured condition | Retention time (min) | m/z | Configration |
|---|---|---|---|---|---|
| I-0113 | 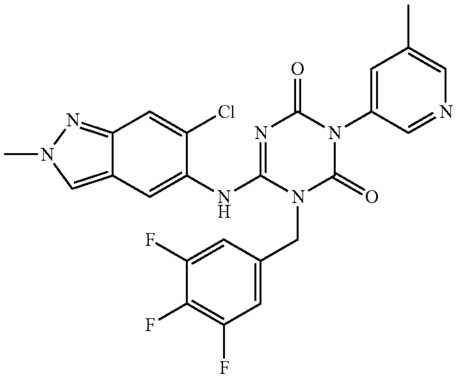 [SMILES: Cc1cncc(-n2c(=O)nc(Nc3cc4cn(C)nc4cc3Cl)n(Cc3cc(F)c(F)c(F)c3)c2=O)c1] | 1 | 1.93 | 528 | |

TABLE 12-continued
| Compound No. | Structure | LC/MS Measured condition | Retention time (min) | m/z | Configration |
|---|---|---|---|---|---|
| I-0114 | 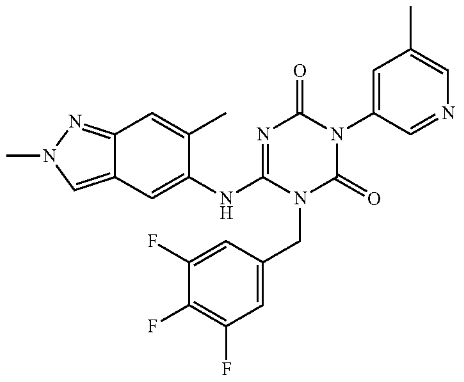 [SMILES: Cc1cncc(-n2c(=O)nc(Nc3cc4cn(C)nc4cc3C)n(Cc3cc(F)c(F)c(F)c3)c2=O)c1] | 1 | 1.68 | 508 | |
| I-0115 | 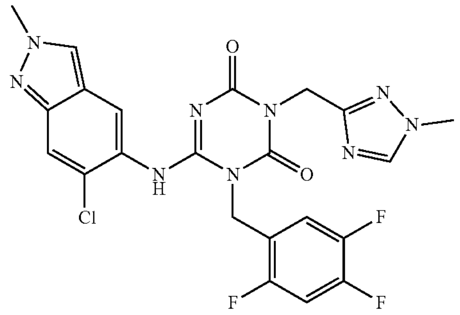 | 1 | 1.70 | 532 | |
| I-0116 | 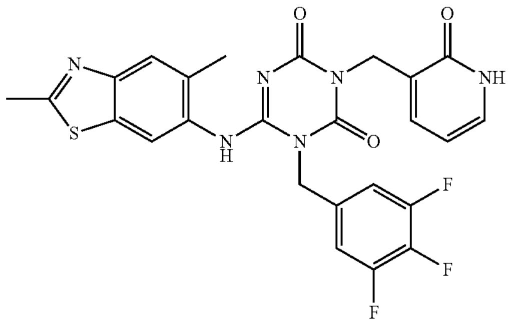 [SMILES: Cc1nc2cc(C)c(Nc3nc(=O)n(Cc4ccc[nH]c4=O)c(=O)n3Cc3cc(F)c(F)c(F)c3)cc2s1] | 1 | 1.96 | 541 | |
| I-0128 | 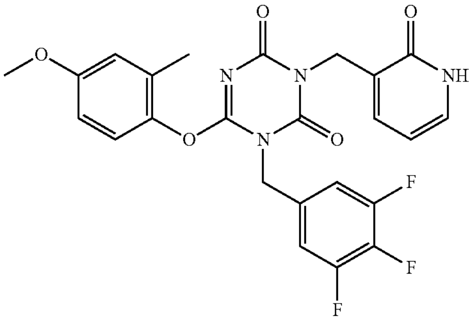 [SMILES: COc1ccc(Oc2nc(=O)n(Cc3ccc[nH]c3=O)c(=O)n2Cc2cc(F)c(F)c(F)c2)c(C)c1] | 1 | 2.12 | 501 | |

TABLE 13
| Compound No. | Structure | LC/MS Measured condition | Retention time (min) | m/z | Configration |
|---|---|---|---|---|---|
| I-0129 | 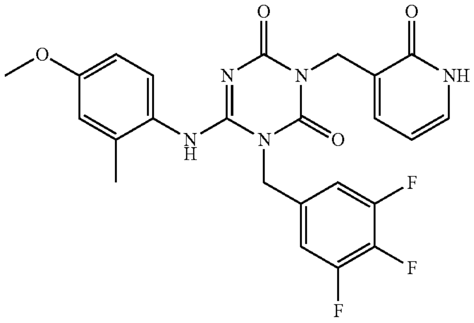 [SMILES: COc1ccc(Nc2nc(=O)n(Cc3ccc[nH]c3=O)c(=O)n2Cc2cc(F)c(F)c(F)c2)c(C)c1] | 1 | 1.88 | 500 | |
| I-0132 | 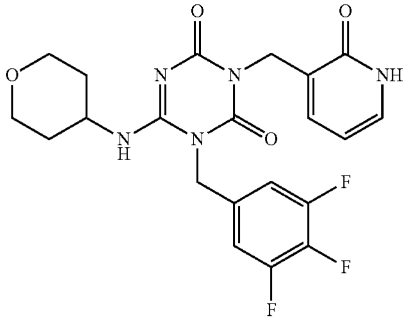 [SMILES: O=c1[nH]cccc1Cn1c(=O)nc(NC2CCOCC2)n(Cc2cc(F)c(F)c(F)c2)c1=O] | 1 | 1.44 | 464 | |
| I-0133 | 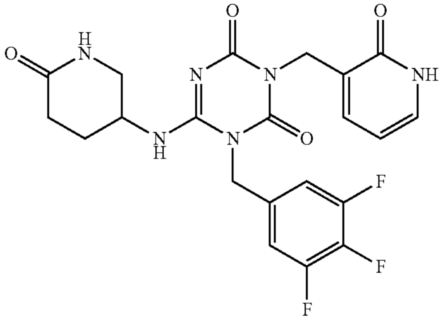 [SMILES: O=C1CCC(Nc2nc(=O)n(Cc3ccc[nH]c3=O)c(=O)n2Cc2cc(F)c(F)c(F)c2)CN1] | 1 | 1.26 | 477 | b |
| I-0134 | 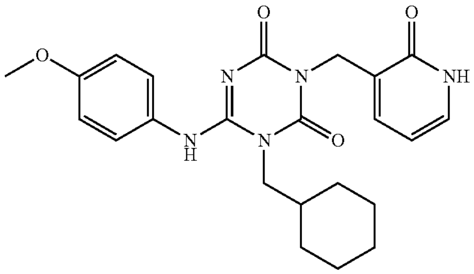 [SMILES: COc1ccc(Nc2nc(=O)n(Cc3ccc[nH]c3=O)c(=O)n2CC2CCCCC2)cc1] | 1 | 1.77 | 438 | |

TABLE 13-continued
| Compound No. | Structure | LC/MS Measured condition | Retention time (min) | m/z | Configration |
|---|---|---|---|---|---|
| I-0135 | 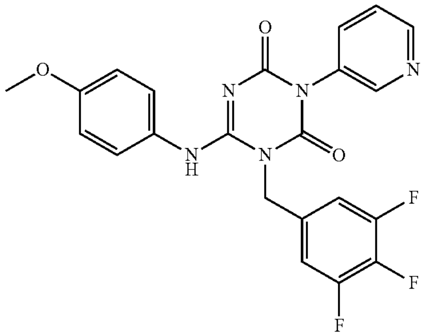 [SMILES: COc1ccc(Nc2nc(=O)n(-c3cccnc3)c(=O)n2Cc2cc(F)c(F)c(F)c2)cc1] | 1 | 1.87 | 456 | |
TABLE 14
| Compound No. | Structure | LC/MS Measured condition | Retention time (min) | m/z | Configration |
|---|---|---|---|---|---|
| I-0136 | 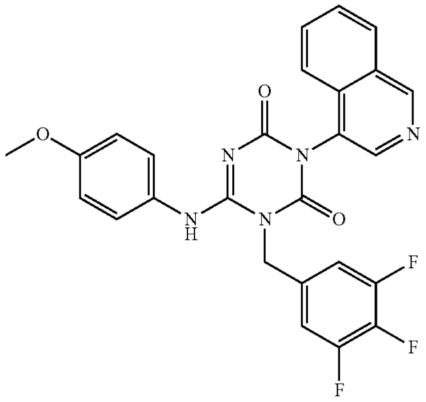 [SMILES: COc1ccc(Nc2nc(=O)n(-c3cncc4ccccc34)c(=O)n2Cc2cc(F)c(F)c(F)c2)cc1] | 1 | 2.03 | 506 | |
| I-0143 | 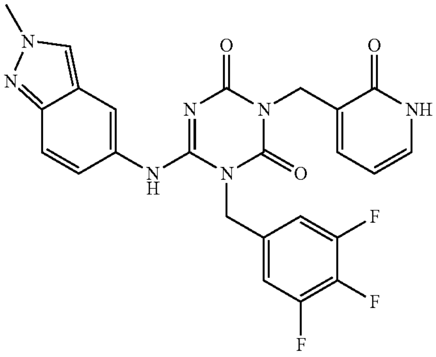 [SMILES: Cn1cc2cc(Nc3nc(=O)n(Cc4ccc[nH]c4=O)c(=O)n3Cc3cc(F)c(F)c(F)c3)ccc2n1] | 1 | 1.70 | 510 | |

TABLE 14-continued
| Compound No. | Structure | LC/MS Measured condition | Retention time (min) | m/z | Configration |
|---|---|---|---|---|---|
| I-0144 | 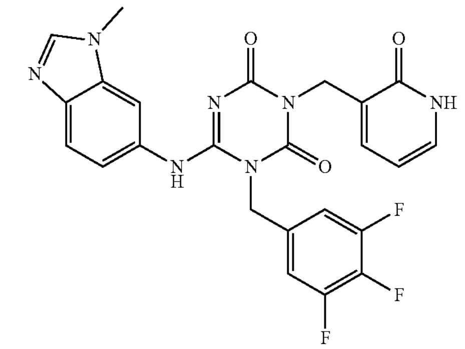 [SMILES: Cn1cnc2ccc(Nc3nc(=O)n(Cc4ccc[nH]c4=O)c(=O)n3Cc3cc(F)c(F)c(F)c3)cc21] | 1 | 1.64 | 510 | |
| I-0149 | 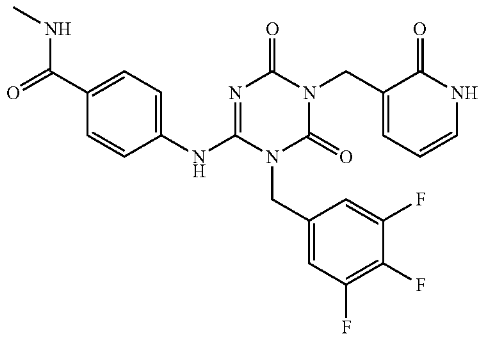 [SMILES: CNC(=O)c1ccc(Nc2nc(=O)n(Cc3ccc[nH]c3=O)c(=O)n2Cc2cc(F)c(F)c(F)c2)cc1] | 1 | 1.59 | 513 | |
| I-0151 | 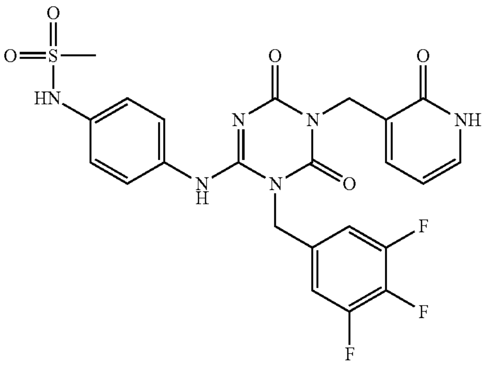 [SMILES: CS(=O)(=O)Nc1ccc(Nc2nc(=O)n(Cc3ccc[nH]c3=O)c(=O)n2Cc2cc(F)c(F)c(F)c2)cc1] | 1 | 1.69 | 549 | |

TABLE 15
| Compound No. | Structure | LC/MS Measured condition | Retention time (min) | m/z | Configration |
|---|---|---|---|---|---|
| I-0152 | 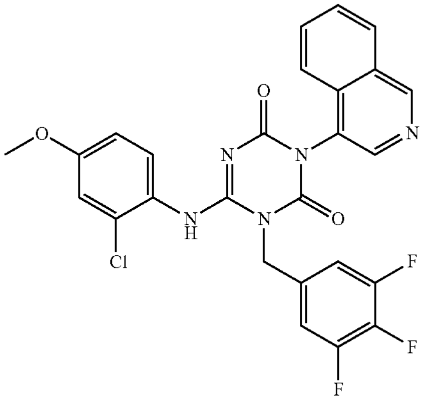 [SMILES: COc1ccc(Nc2nc(=O)n(-c3cncc4ccccc34)c(=O)n2Cc2cc(F)c(F)c(F)c2)c(Cl)c1] | 1 | 2.35 | 540 | |
| I-0154 | 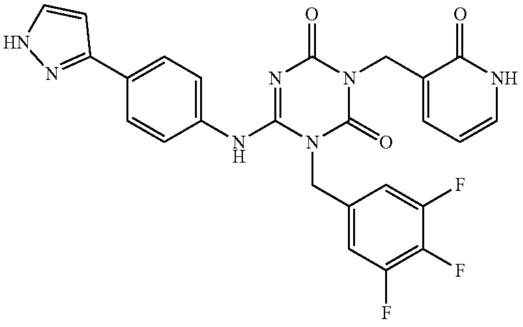 [SMILES: O=c1[nH]cccc1Cn1c(=O)nc(Nc2ccc(-c3cc[nH]n3)cc2)n(Cc2cc(F)c(F)c(F)c2)c1=O] | 1 | 1.81 | 522 | |
| I-0165 | 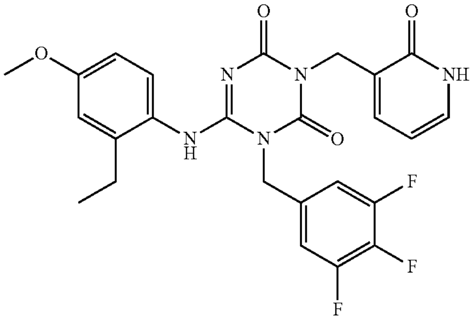 [SMILES: CCc1cc(OC)ccc1Nc1nc(=O)n(Cc2ccc[nH]c2=O)c(=O)n1Cc1cc(F)c(F)c(F)c1] | 1 | 2.07 | 514 | |
| I-0166 | 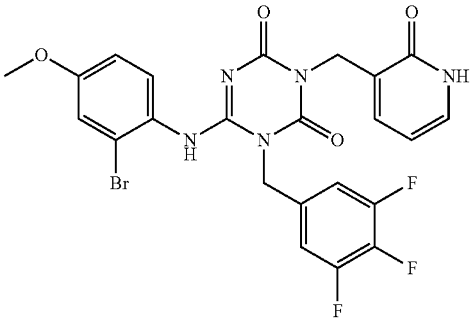 [SMILES: COc1ccc(Nc2nc(=O)n(Cc3ccc[nH]c3=O)c(=O)n2Cc2cc(F)c(F)c(F)c2)c(Br)c1] | 1 | 2.03 | 564 | |

TABLE 15-continued
| Compound No. | Structure | LC/MS Measured condition | Retention time (min) | m/z | Configration |
|---|---|---|---|---|---|
| I-0180 | 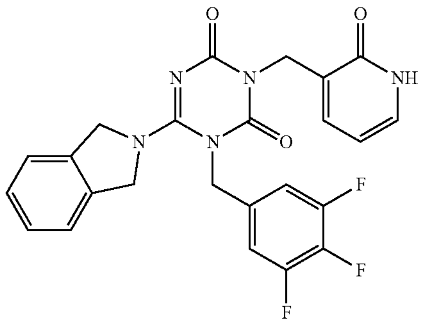 [SMILES: O=c1[nH]cccc1Cn1c(=O)nc(N2Cc3ccccc3C2)n(Cc2cc(F)c(F)c(F)c2)c1=O] | 1 | 1.88 | 482 | |
TABLE 16
| Compound No. | Structure | LC/MS Measured condition | Retention time (min) | m/z | Configration |
|---|---|---|---|---|---|
| I-0194 | 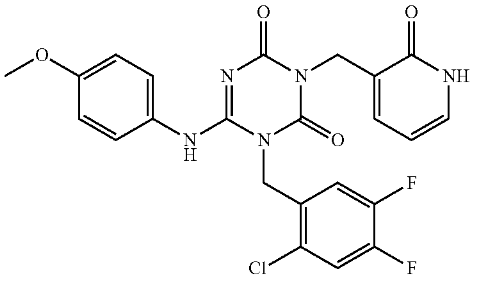 | 1 | 1.92 | 502 | |
| I-0196 | 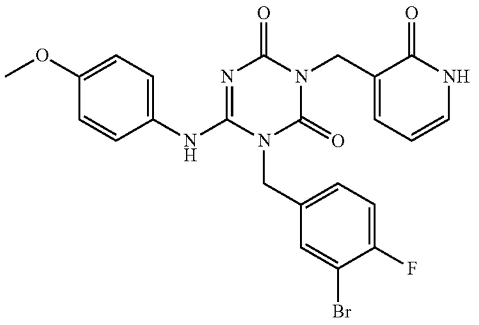 [SMILES: COc1ccc(Nc2nc(=O)n(Cc3ccc[nH]c3=O)c(=O)n2Cc2ccc(F)c(Br)c2)cc1] | 1 | 1.91 | 528 | |
| I-0204 | 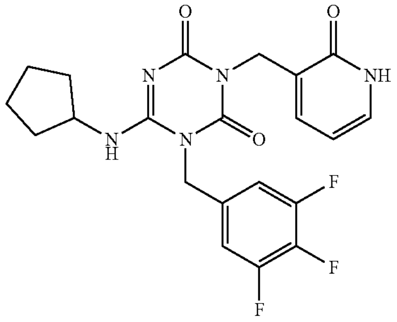 [SMILES: O=c1[nH]cccc1Cn1c(=O)nc(NC2CCCC2)n(Cc2cc(F)c(F)c(F)c2)c1=O] | 1 | 1.84 | 448 | |

TABLE 16-continued
| Compound No. | Structure | LC/MS Measured condition | Retention time (min) | m/z | Configration |
| --- | --- | --- | --- | --- | --- |
| I-0207 | 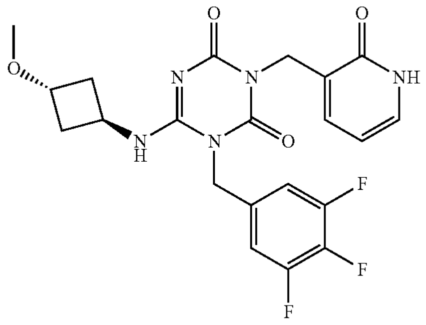 [SMILES: CO[C@H]1C[C@H](Nc2nc(=O)n(Cc3ccc[nH]c3=O)c(=O)n2Cc2cc(F)c(F)c(F)c2)C1] | 1 | 1.61 | 464 | a |
| I-0208 | 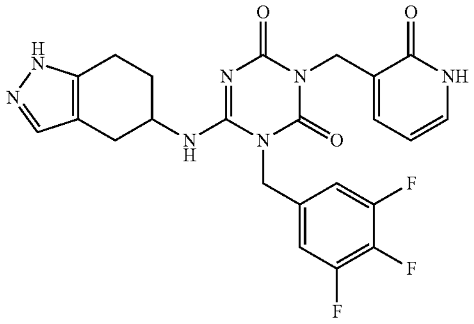 [SMILES: O=c1[nH]cccc1Cn1c(=O)nc(NC2CCc3[nH]ncc3C2)n(Cc2cc(F)c(F)c(F)c2)c1=O] | 1 | 1.23 | 500 | b |
TABLE 17
| Compound No. | Structure | LC/MS Measured condition | Retention time (min) | m/z | Configration |
| --- | --- | --- | --- | --- | --- |
| I-0213 | 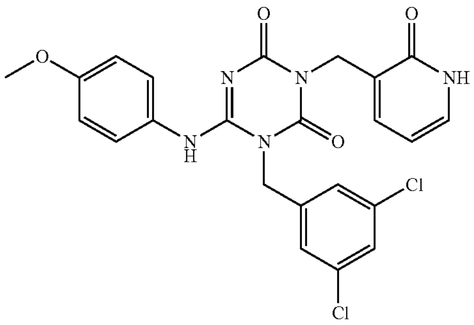 | 1 | 2.04 | 500 | |
| I-0214 | 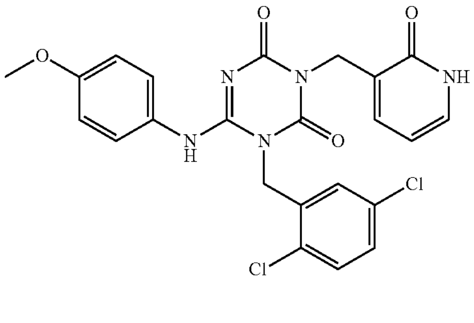 [SMILES: COc1ccc(Nc2nc(=O)n(Cc3ccc[nH]c3=O)c(=O)n2Cc2cc(Cl)ccc2Cl)cc1] | 1 | 1.93 | 500 | |

TABLE 17-continued
| Compound No. | Structure | LC/MS Measured condition | Retention time (min) | m/z | Configration |
|---|---|---|---|---|---|
| I-0223 | 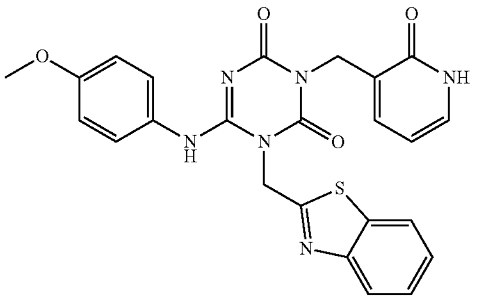 [SMILES: COc1ccc(Nc2nc(=O)n(Cc3ccc[nH]c3=O)c(=O)n2Cc2nc3ccccc3s2)cc1] | 1 | 1.80 | 489 | |
| I-0226 | 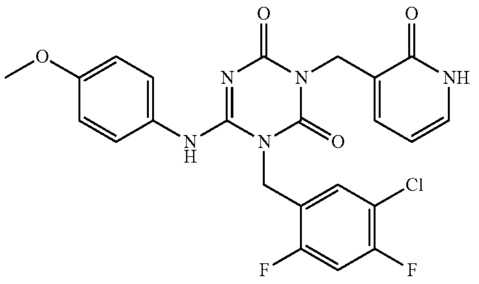 [SMILES: COc1ccc(Nc2nc(=O)n(Cc3ccc[nH]c3=O)c(=O)n2Cc2cc(Cl)c(F)cc2F)cc1] | 1 | 1.91 | 502 | |
| I-0227 | 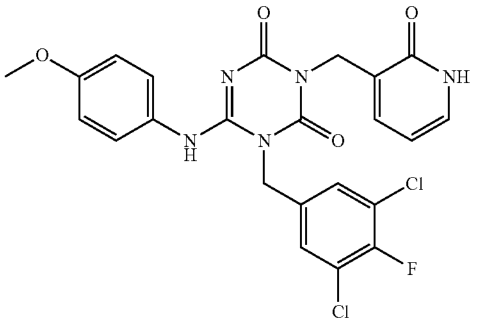 [SMILES: COc1ccc(Nc2nc(=O)n(Cc3ccc[nH]c3=O)c(=O)n2Cc2cc(Cl)c(F)c(Cl)c2)cc1] | 1 | 2.08 | 518 | |
TABLE 18
| Compound No. | Structure | LC/MS Measured condition | Retention time (min) | m/z | Configration |
|---|---|---|---|---|---|
| I-0231 | 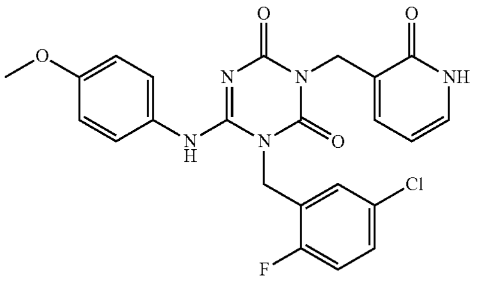 [SMILES: COc1ccc(Nc2nc(=O)n(Cc3ccc[nH]c3=O)c(=O)n2Cc2cc(Cl)ccc2F)cc1] | 1 | 1.84 | 484 | |

TABLE 18-continued
| Compound No. | Structure | LC/MS Measured condition | Retention time (min) | m/z | Configration |
|---|---|---|---|---|---|
| I-0234 | 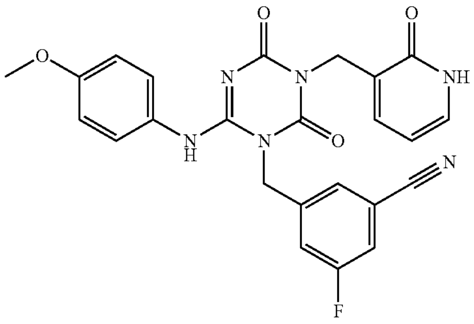 [SMILES: COc1ccc(Nc2nc(=O)n(Cc3ccc[nH]c3=O)c(=O)n2Cc2cc(F)cc(C#N)c2)cc1] | 1 | 1.72 | 475 | |
| I-0236 | 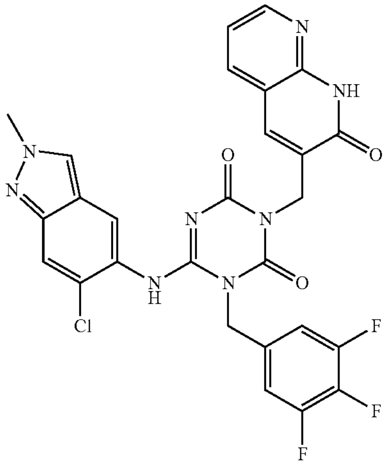 [SMILES: Cn1cc2cc(Nc3nc(=O)n(Cc4cc5cccnc5[nH]c4=O)c(=O)n3Cc3cc(F)c(F)c(F)c3)c(Cl)cc2n1] | 1 | 2.00 | 595 | |
| I-0237 | 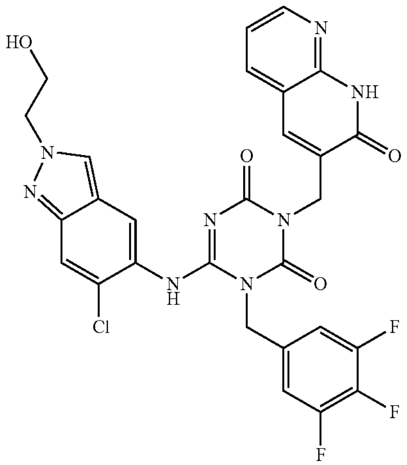 [SMILES: O=c1[nH]c2ncccc2cc1Cn1c(=O)nc(Nc2cc3cn(CCO)nc3cc2Cl)n(Cc2cc(F)c(F)c(F)c2)c1=O] | 1 | 1.87 | 625 | |

TABLE 18-continued
| Compound No. | Structure | LC/MS Measured condition | Retention time (min) | m/z | Configration |
|---|---|---|---|---|---|
| I-0239 | 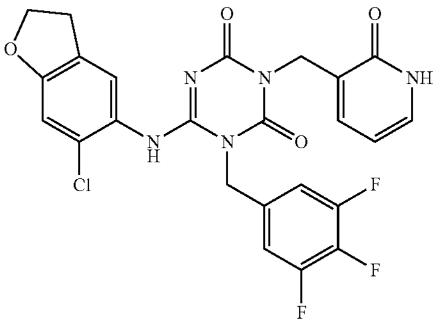 [SMILES: O=c1[nH]cccc1Cn1c(=O)nc(Nc2cc3c(cc2Cl)OCC3)n(Cc2cc(F)c(F)c(F)c2)c1=O] | 1 | 1.95 | 532.2 | |
TABLE 19
| Compound No. | Structure | LC/MS Measured condition | Retention time (min) | m/z | Configration |
|---|---|---|---|---|---|
| I-0242 | 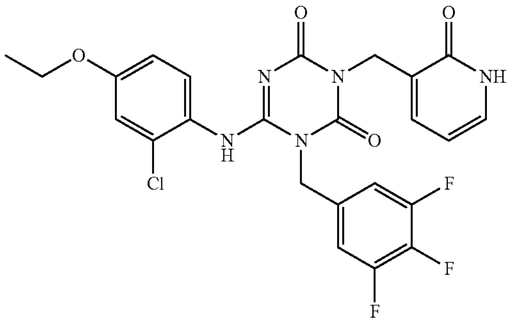 [SMILES: CCOc1ccc(Nc2nc(=O)n(Cc3ccc[nH]c3=O)c(=O)n2Cc2cc(F)c(F)c(F)c2)c(Cl)c1] | 1 | 2.12 | 534.3 | |
| I-0244 | 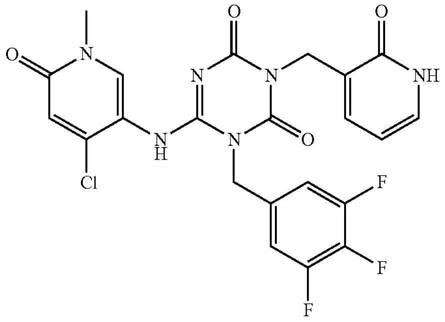 [SMILES: Cn1cc(Nc2nc(=O)n(Cc3ccc[nH]c3=O)c(=O)n2Cc2cc(F)c(F)c(F)c2)c(Cl)cc1=O] | 1 | 1.50 | 521.3 | |
| I-0245 | 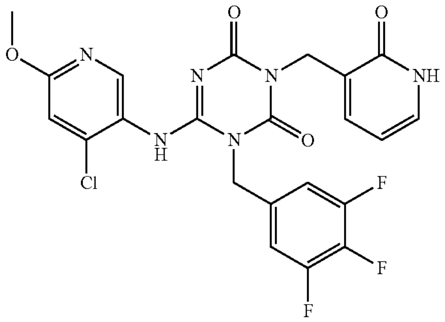 | 1 | 1.50 | 521.3 | |

TABLE 19-continued
| Compound No. | Structure | LC/MS Measured condition | Retention time (min) | m/z | Configration |
|---|---|---|---|---|---|
| I-0246 | 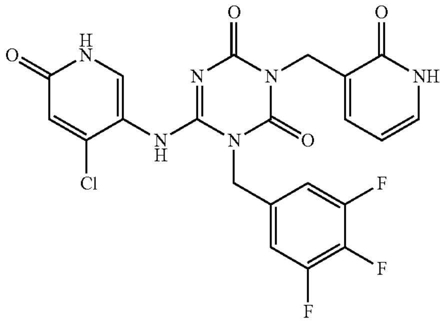 [SMILES: O=c1cc(Cl)c(Nc2nc(=O)n(Cc3ccc[nH]c3=O)c(=O)n2Cc2cc(F)c(F)c(F)c2)c[nH]1] | 1 | 1.43 | 507.2 | |
| I-0247 | 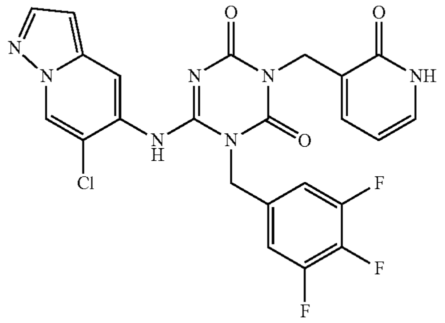 [SMILES: O=c1[nH]cccc1Cn1c(=O)nc(Nc2cc3ccnn3cc2Cl)n(Cc2cc(F)c(F)c(F)c2)c1=O] | 1 | 1.91 | 530.2 | |
TABLE 20
| Compound No. | Structure | LC/MS Measured condition | Retention time (min) | m/z | Configration |
|---|---|---|---|---|---|
| I-0248 | 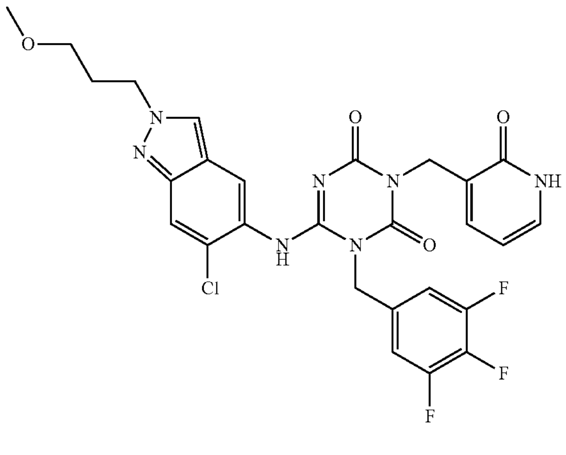 [SMILES: COCCCn1cc2cc(Nc3nc(=O)n(Cc4ccc[nH]c4=O)c(=O)n3Cc3cc(F)c(F)c(F)c3)c(Cl)cc2n1] | 1 | 1.86 | 602.3 | |

TABLE 20-continued
| Compound No. | Structure | LC/MS Measured condition | Retention time (min) | m/z | Configration |
|---|---|---|---|---|---|
| I-0249 | 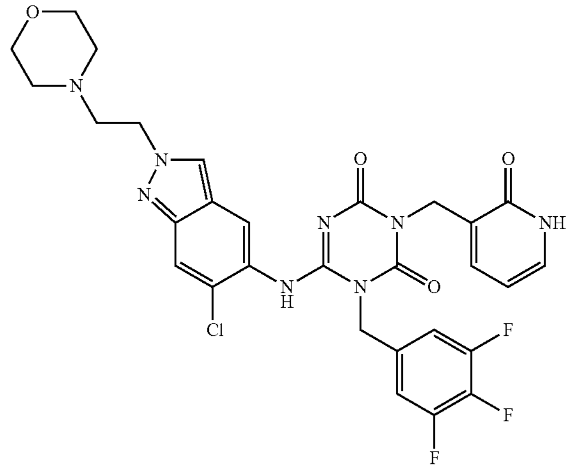 [SMILES: O=c1[nH]cccc1Cn1c(=O)nc(Nc2cc3cn(CCN4CCOCC4)nc3cc2Cl)n(Cc2cc(F)c(F)c(F)c2)c1=O] | 1 | 1.51 | 643.3 | |
| I-0250 | 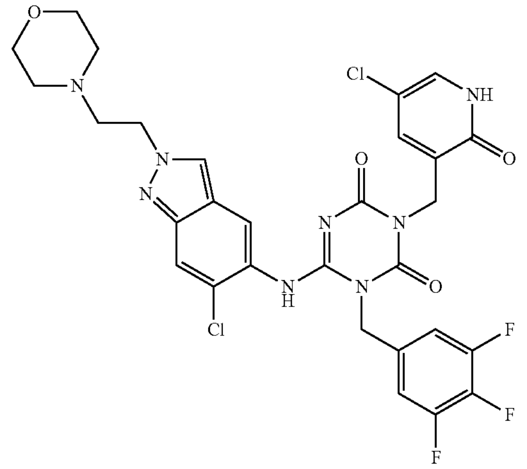 [SMILES: O=c1[nH]cc(Cl)cc1Cn1c(=O)nc(Nc2cc3cn(CCN4CCOCC4)nc3cc2Cl)n(Cc2cc(F)c(F)c(F)c2)c1=O] | 1 | 1.67 | 677.3 | |
| I-0251 | 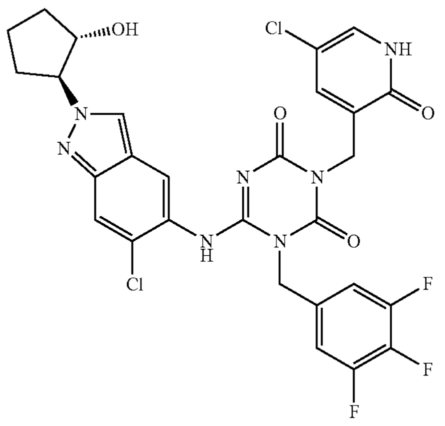 [SMILES: O=c1[nH]cc(Cl)cc1Cn1c(=O)nc(Nc2cc3cn([C@H]4CCC[C@@H]4O)nc3cc2Cl)n(Cc2cc(F)c(F)c(F)c2)c1=O] | 1 | 1.97 | 648.2 | a |

TABLE 20-continued
| Compound No. | Structure | LC/MS Measured condition | Retention time (min) | m/z | Configration |
|---|---|---|---|---|---|
| I-0252 | 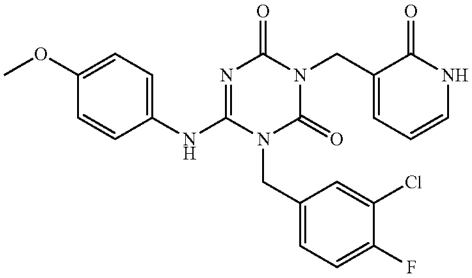 [SMILES: COc1ccc(Nc2nc(=O)n(Cc3ccc[nH]c3=O)c(=O)n2Cc2ccc(F)c(Cl)c2)cc1] | 1 | 1.81 | 484 | |
TABLE 21
| Compound No. | Structure | LC/MS Measured condition | Retention time (min) | m/z | Con-figration |
|---|---|---|---|---|---|
| I-0253 | 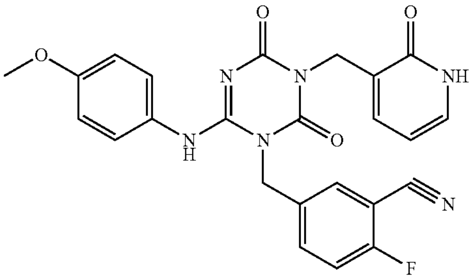 [SMILES: COc1ccc(Nc2nc(=O)n(Cc3ccc[nH]c3=O)c(=O)n2Cc2ccc(F)c(C#N)c2)cc1] | 1 | 1.65 | 475 | |
| I-0254 | 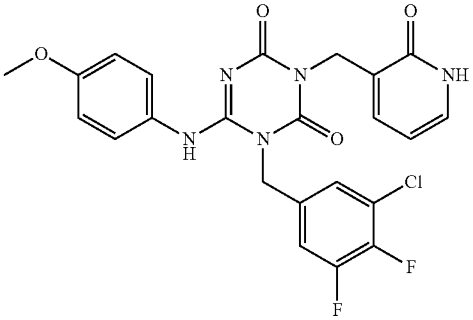 | 1 | 1.92 | 502 | |
| I-0255 | 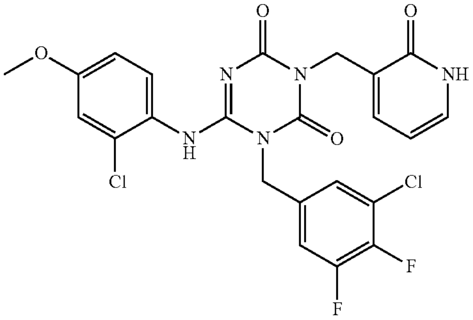 | 1 | 2.21 | 536 | |

TABLE 21-continued
| Compound No. | Structure | LC/MS Measured condition | Retention time (min) | m/z | Con-figration |
|---|---|---|---|---|---|
| I-0256 | 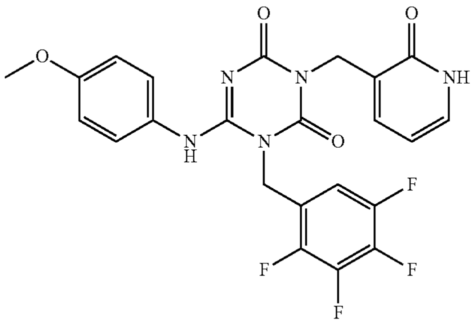 [SMILES: COc1ccc(Nc2nc(=O)n(Cc3ccc[nH]c3=O)c(=O)n2Cc2cc(F)c(F)c(F)c2F)cc1] | 1 | 1.88 | 504 | |
| I-0257 | 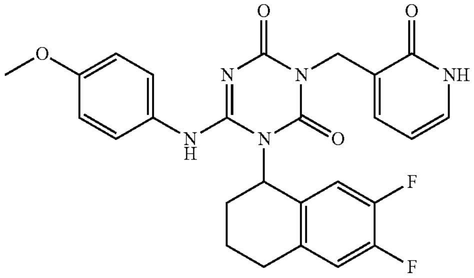 [SMILES: COc1ccc(Nc2nc(=O)n(Cc3ccc[nH]c3=O)c(=O)n2C2CCCc3cc(F)c(F)cc32)cc1] | 1 | 1.98 | 508.1 | b |
TABLE 22
| Compound No. | Structure | LC/MS Measured condition | Retention time (min) | m/z | Con-figration |
|---|---|---|---|---|---|
| I-0258 | 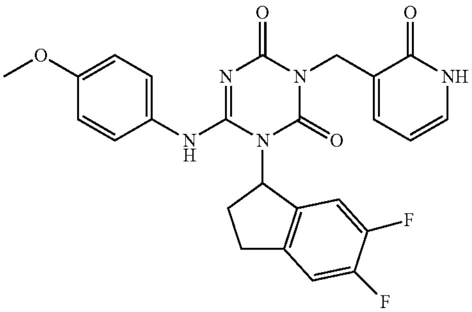 [SMILES: COc1ccc(Nc2nc(=O)n(Cc3ccc[nH]c3=O)c(=O)n2C2CCc3cc(F)c(F)cc32)cc1] | 2 | 1.89 | 494.1 | b |
| I-0259 | 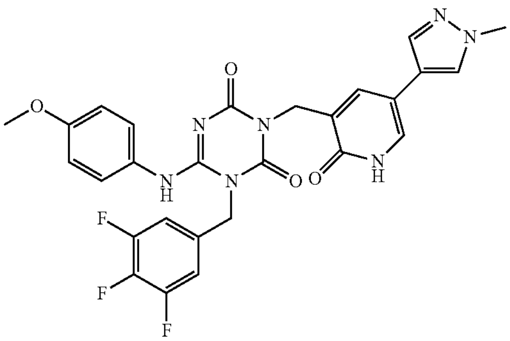 | 2 | 1.78 | 566.1 | |

TABLE 22-continued
| Compound No. | Structure | LC/MS Measured condition | Retention time (min) | m/z | Con-figration |
|---|---|---|---|---|---|
| I-0260 | 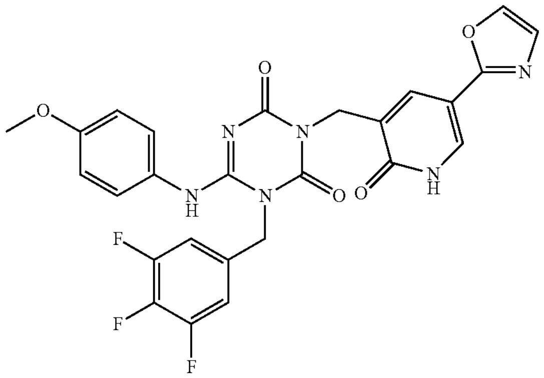 [SMILES: COc1ccc(Nc2nc(=O)n(Cc3cc(-c4ncco4)c[nH]c3=O)c(=O)n2Cc2cc(F)c(F)c(F)c2)cc1] | 2 | 1.88 | 553 | |
| I-0264 | 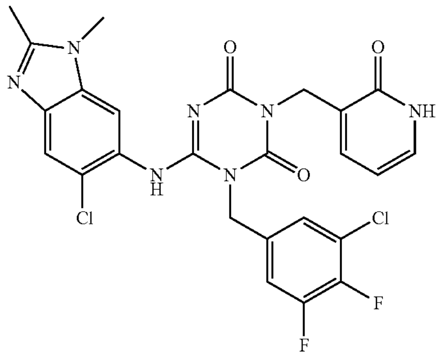 [SMILES: Cc1nc2cc(Cl)c(Nc3nc(=O)n(Cc4ccc[nH]c4=O)c(=O)n3Cc3cc(F)c(F)c(Cl)c3)cc2n1C] | 2 | 1.64 | 574 | |
| I-0265 | 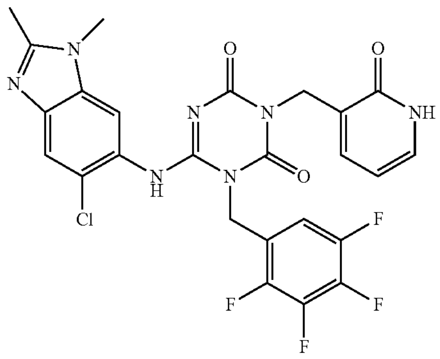 [SMILES: Cc1nc2cc(Cl)c(Nc3nc(=O)n(Cc4ccc[nH]c4=O)c(=O)n3Cc3cc(F)c(F)c(F)c3F)cc2n1C] | 2 | 1.62 | 576 | |

TABLE 23
| Compound No. | Structure | LC/MS Measured condition | Retention time (min) | m/z | Con-figration |
|---|---|---|---|---|---|
| I-0266 | 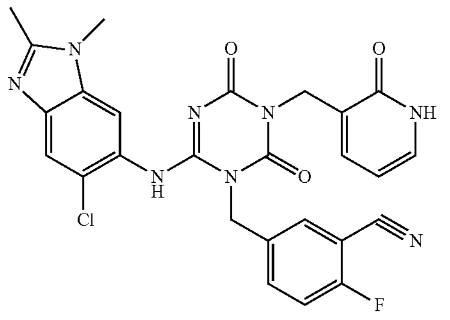 [SMILES: Cc1nc2cc(Cl)c(Nc3nc(=O)n(Cc4ccc[nH]c4=O)c(=O)n3Cc3ccc(F)c(C#N)c3)cc2n1C] | 2 | 1.43 | 547 | |
| I-0267 | 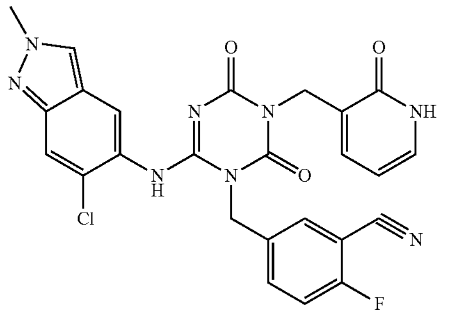 [SMILES: Cn1cc2cc(Nc3nc(=O)n(Cc4ccc[nH]c4=O)c(=O)n3Cc3ccc(F)c(C#N)c3)c(Cl)cc2n1] | 3 | 1.71 | 533 | |
| I-0268 | 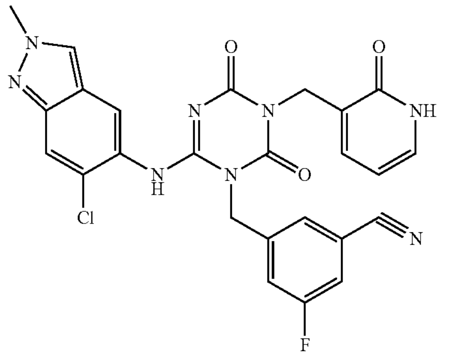 [SMILES: Cn1cc2cc(Nc3nc(=O)n(Cc4ccc[nH]c4=O)c(=O)n3Cc3cc(F)cc(C#N)c3)c(Cl)cc2n1] | 1 | 1.60 | 533.2 | |
| I-0269 | 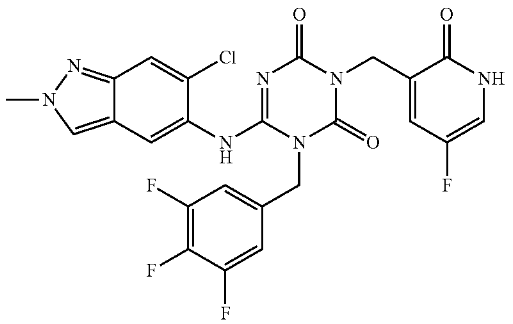 [SMILES: Cn1cc2cc(Nc3nc(=O)n(Cc4cc(F)c[nH]c4=O)c(=O)n3Cc3cc(F)c(F)c(F)c3)c(Cl)cc2n1] | 1 | 1.94 | 591.7 | |

TABLE 23-continued
| Compound No. | Structure | LC/MS Measured condition | Retention time (min) | m/z | Con-figuration |
|---|---|---|---|---|---|
| I-0270 | 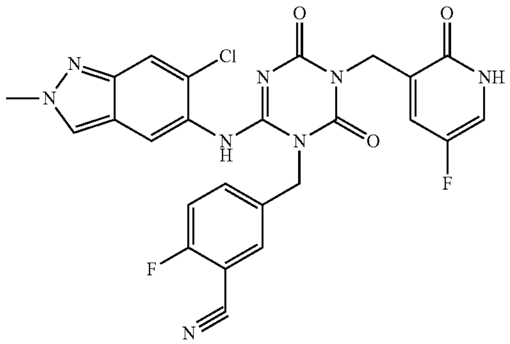 [SMILES: Cn1cc2cc(Nc3nc(=O)n(Cc4cc(F)c[nH]c4=O)c(=O)n3Cc3ccc(F)c(C#N)c3)c(Cl)cc2n1] | 1 | 1.78 | 551 | |
TABLE 24
| Compound No. | Structure | LC/MS Measured condition | Retention time (min) | m/z | Con-figuration |
|---|---|---|---|---|---|
| I-0271 | 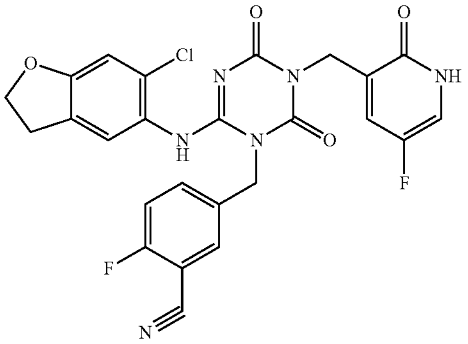 [SMILES: N#Cc1cc(Cn2c(Nc3cc4c(cc3Cl)OCC4)nc(=O)n(Cc3cc(F)c[nH]c3=O)c2=O)ccc1F] | 1 | 1.98 | 539 | |
| I-0272 | 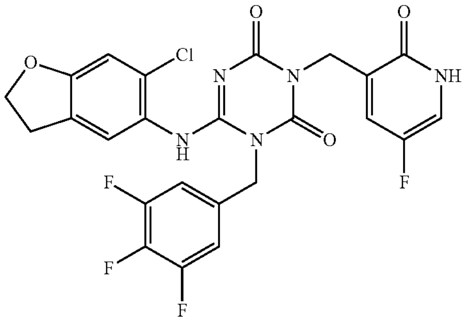 [SMILES: O=c1[nH]cc(F)cc1Cn1c(=O)nc(Nc2cc3c(cc2Cl)OCC3)n(Cc2cc(F)c(F)c(F)c2)c1=O] | 1 | 2.17 | 550 | |
| I-0279 | 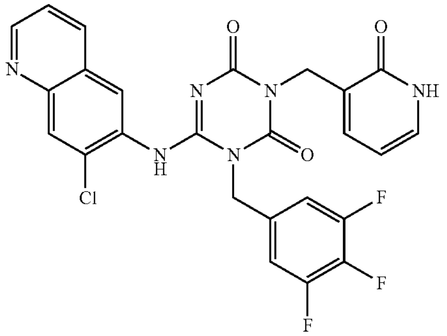 [SMILES: O=c1[nH]cccc1Cn1c(=O)nc(Nc2cc3cccnc3cc2Cl)n(Cc2cc(F)c(F)c(F)c2)c1=O] | 1 | 1.79 | 541.1 | |

TABLE 24-continued
| Compound No. | Structure | LC/MS Measured condition | Retention time (min) | m/z | Con-figuration |
|---|---|---|---|---|---|
| I-0281 | 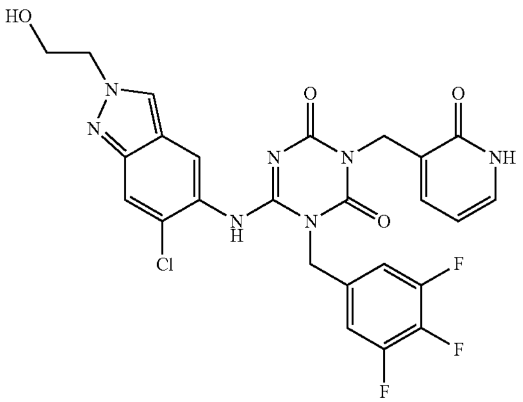 [SMILES: O=c1[nH]cccc1Cn1c(=O)nc(Nc2cc3cn(CCO)nc3cc2Cl)n(Cc2cc(F)c(F)c(F)c2)c1=O] | 3 | 1.58 | 574 | |
| I-0284 | 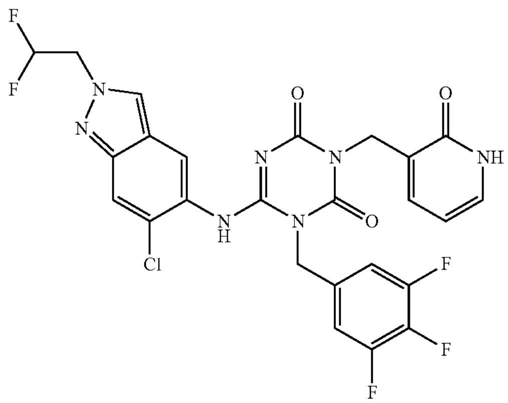 [SMILES: O=c1[nH]cccc1Cn1c(=O)nc(Nc2cc3cn(CC(F)F)nc3cc2Cl)n(Cc2cc(F)c(F)c(F)c2)c1=O] | 3 | 1.87 | 594 | |
TABLE 25
| Compound No. | Structure | LC/MS Measured condition | Retention time (min) | m/z | Con-figuration |
|---|---|---|---|---|---|
| I-0285 | 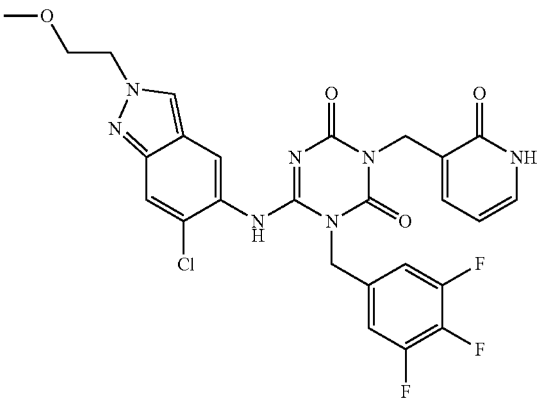 [SMILES: COCCn1cc2cc(Nc3nc(=O)n(Cc4ccc[nH]c4=O)c(=O)n3Cc3cc(F)c(F)c(F)c3)c(Cl)cc2n1] | 1 | 1.86 | 588.2 | |

TABLE 25-continued
| Compound No. | Structure | LC/MS Measured condition | Retention time (min) | m/z | Con-figration |
|---|---|---|---|---|---|
| I-0286 | 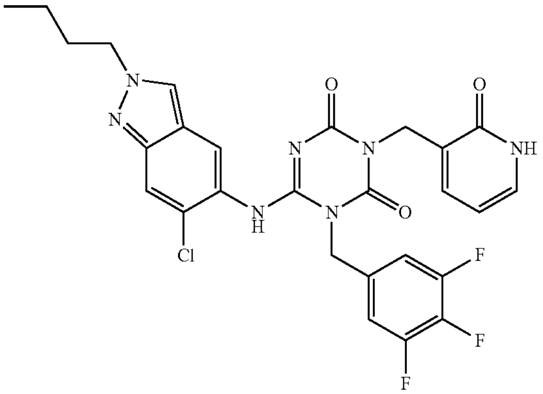 [SMILES: CCCCn1cc2cc(Nc3nc(=O)n(Cc4ccc[nH]c4=O)c(=O)n3Cc3cc(F)c(F)c(F)c3)c(Cl)cc2n1] | 1 | 2.15 | 586.2 | |
| I-0287 | 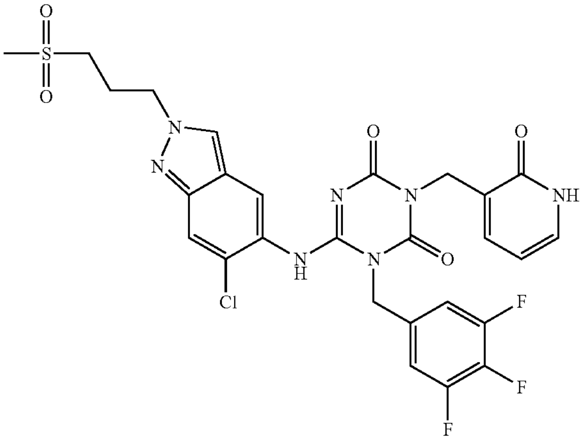 [SMILES: CS(=O)(=O)CCCn1cc2cc(Nc3nc(=O)n(Cc4ccc[nH]c4=O)c(=O)n3Cc3cc(F)c(F)c(F)c3)c(Cl)cc2n1] | 3 | 1.65 | 650.2 | |
| I-0288 | 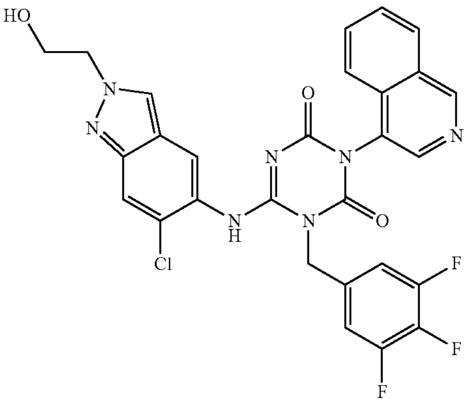 [SMILES: O=c1nc(Nc2cc3cn(CCO)nc3cc2Cl)n(Cc2cc(F)c(F)c(F)c2)c(=O)n1-c1cncc2ccccc12] | 3 | 1.82 | 594 | |

TABLE 25-continued
| Compound No. | Structure | LC/MS Measured condition | Retention time (min) | m/z | Con-figuration |
|---|---|---|---|---|---|
| I-0289 | 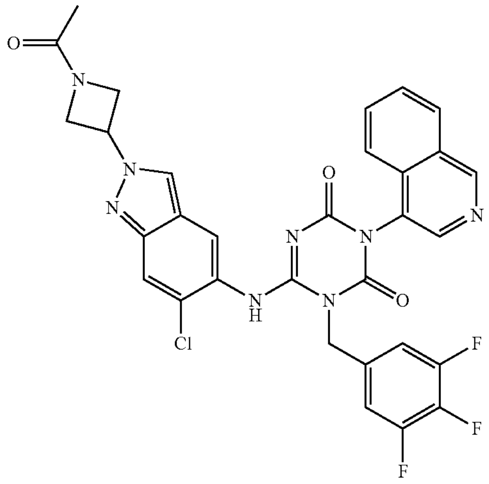 [SMILES: CC(=O)N1CC(n2cc3cc(Nc4nc(=O)n(-c5cncc6ccccc56)c(=O)n4Cc4cc(F)c(F)c(F)c4)c(Cl)cc3n2)C1] | 1 | 1.93 | 647.2 | |
25
TABLE 26
| Compound No. | Structure | LC/MS Measured condition | Retention time (min) | m/z | Con-figuration |
|---|---|---|---|---|---|
| I-0290 | 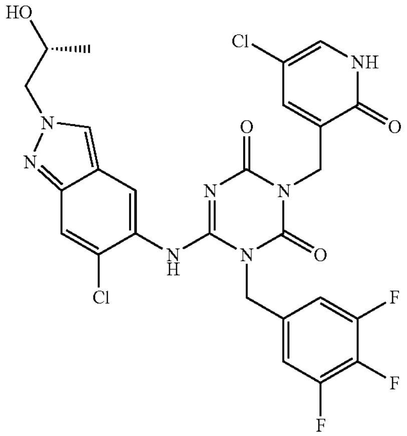 [SMILES: C[C@@H](O)Cn1cc2cc(Nc3nc(=O)n(Cc4cc(Cl)c[nH]c4=O)c(=O)n3Cc3cc(F)c(F)c(F)c3)c(Cl)cc2n1] | 1 | 1.90 | 622.2 | a |
| I-0301 | 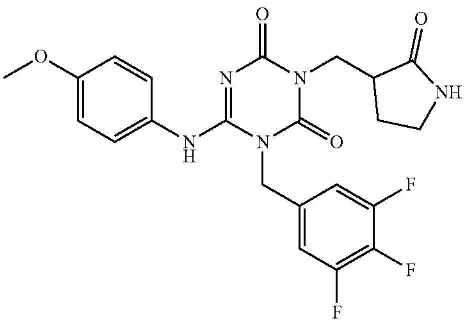 [SMILES: COc1ccc(Nc2nc(=O)n(CC3CCNC3=O)c(=O)n2Cc2cc(F)c(F)c(F)c2)cc1] | 1 | 1.93 | 476.1 | b |

TABLE 26-continued
| Compound No. | Structure | LC/MS Measured condition | Retention time (min) | m/z | Con-figration |
|---|---|---|---|---|---|
| I-0306 | 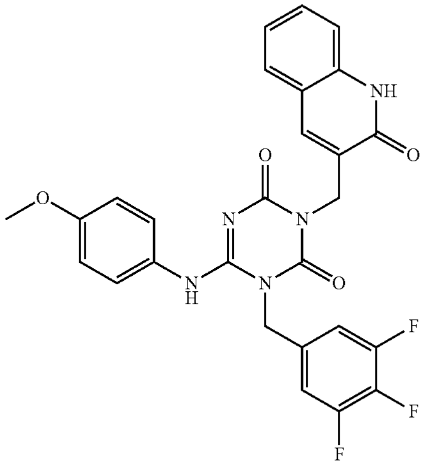 | 1 | 2.22 | 536.1 | |
| I-0307 | 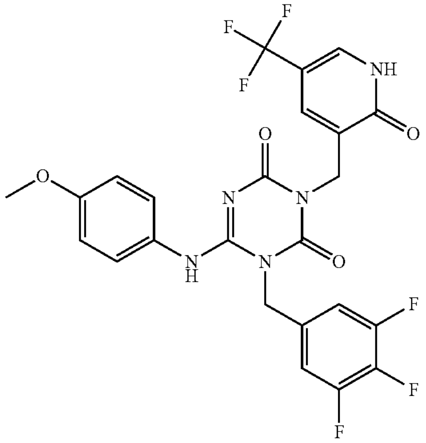 [SMILES: COc1ccc(Nc2nc(=O)n(Cc3cc(C(F)(F)F)c[nH]c3=O)c(=O)n2Cc2cc(F)c(F)c(F)c2)cc1] | 1 | 2.15 | 554.1 | |
| I-0310 | 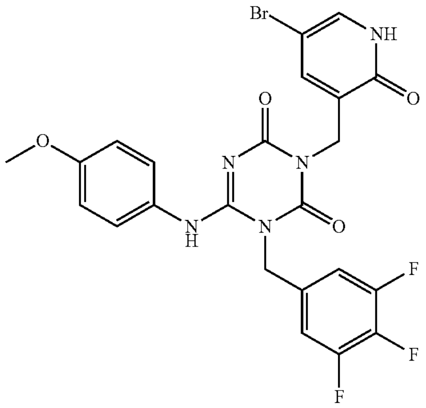 [SMILES: COc1ccc(Nc2nc(=O)n(Cc3cc(Br)c[nH]c3=O)c(=O)n2Cc2cc(F)c(F)c(F)c2)cc1] | 1 | 2.05 | 564.1 | |

TABLE 27
| Compound No. | Structure | LC/MS Measured condition | Retention time (min) | m/z | Con-figration |
|---|---|---|---|---|---|
| I-0316 | 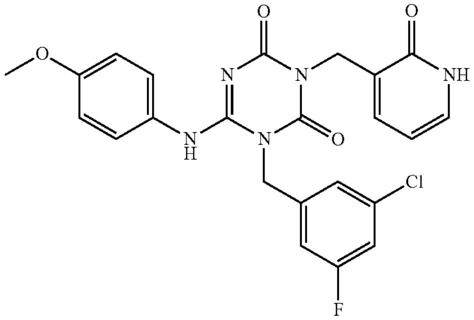 [SMILES: COc1ccc(Nc2nc(=O)n(Cc3ccc[nH]c3=O)c(=O)n2Cc2cc(F)cc(Cl)c2)cc1] | 1 | 1.91 | 484.1 | |
| I-0318 | 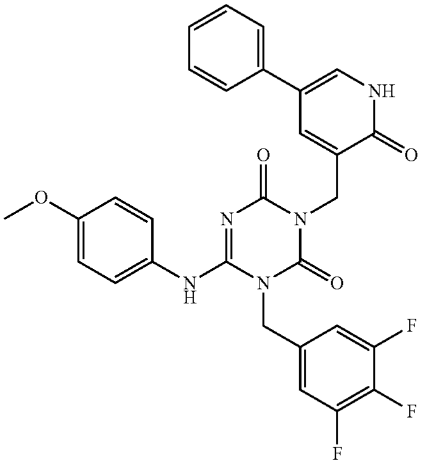 [SMILES: COc1ccc(Nc2nc(=O)n(Cc3cc(-c4ccccc4)c[nH]c3=O)c(=O)n2Cc2cc(F)c(F)c(F)c2)cc1] | 1 | 2.19 | 562.1 | |
| I-0320 | 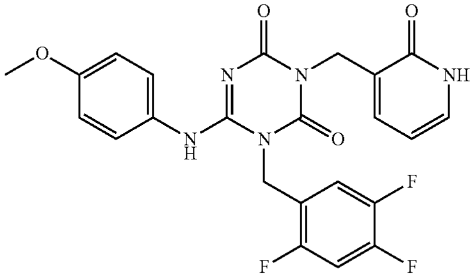 [SMILES: COc1ccc(Nc2nc(=O)n(Cc3ccc[nH]c3=O)c(=O)n2Cc2cc(F)c(F)cc2F)cc1] | 1 | 1.79 | 486.1 | |
| I-0321 | 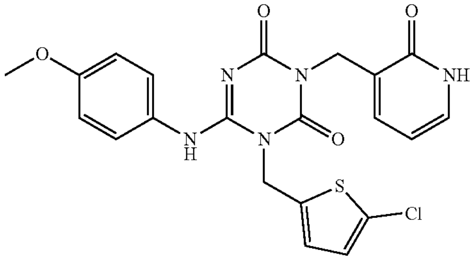 [SMILES: COc1ccc(Nc2nc(=O)n(Cc3ccc[nH]c3=O)c(=O)n2Cc2ccc(Cl)s2)cc1] | 1 | 1.89 | 472 | |

TABLE 27-continued
| Compound No. | Structure | LC/MS Measured condition | Retention time (min) | m/z | Con-figration |
|---|---|---|---|---|---|
| I-0326 | 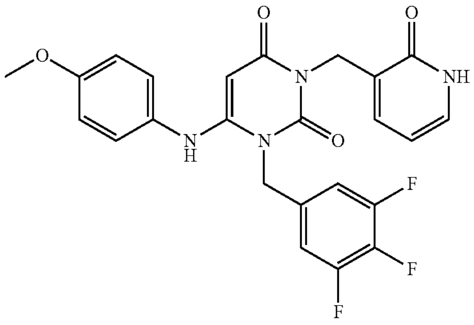 [SMILES: COc1ccc(Nc2cc(=O)n(Cc3ccc[nH]c3=O)c(=O)n2Cc2cc(F)c(F)c(F)c2)cc1] | 1 | 1.83 | 485.1 | |
TABLE 28
| Compound No. | Structure | LC/MS Measured condition | Retention time (min) | m/z | Con-figration |
|---|---|---|---|---|---|
| I-0329 | 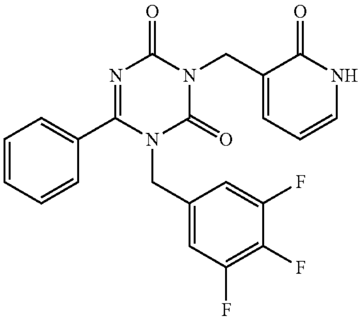 [SMILES: O=c1[nH]cccc1Cn1c(=O)nc(-c2ccccc2)n(Cc2cc(F)c(F)c(F)c2)c1=O] | 1 | 1.89 | 441 | |
| I-0330 | 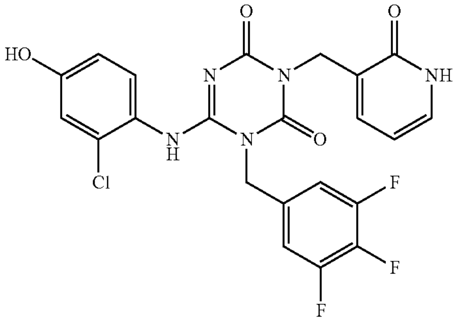 [SMILES: O=c1[nH]cccc1Cn1c(=O)nc(Nc2ccc(O)cc2Cl)n(Cc2cc(F)c(F)c(F)c2)c1=O] | 1 | 1.84 | 506 | |
| I-0331 | 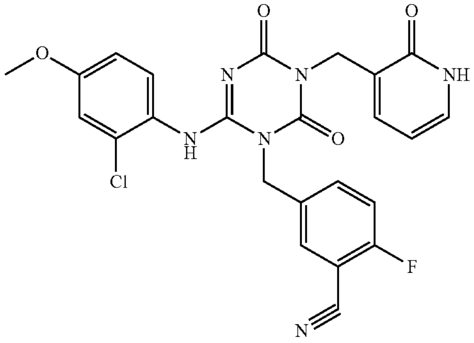 [SMILES: COc1ccc(Nc2nc(=O)n(Cc3ccc[nH]c3=O)c(=O)n2Cc2ccc(F)c(C#N)c2)c(Cl)c1] | 1 | 1.94 | 509.1 | |

TABLE 28-continued
| Compound No. | Structure | LC/MS Measured condition | Retention time (min) | m/z | Con-figration |
|---|---|---|---|---|---|
| I-0332 | 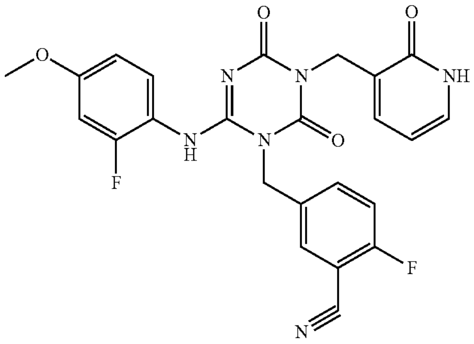 [SMILES: COc1ccc(Nc2nc(=O)n(Cc3ccc[nH]c3=O)c(=O)n2Cc2ccc(F)c(C#N)c2)c(F)c1] | 1 | 1.83 | 493 | |
| I-0333 | 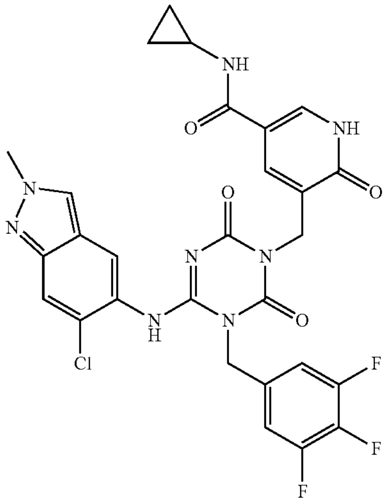 [SMILES: Cn1cc2cc(Nc3nc(=O)n(Cc4cc(C(=O)NC5CC5)c[nH]c4=O)c(=O)n3Cc3cc(F)c(F)c(F)c3)c(Cl)cc2n1] | 1 | 1.89 | 627.1 | |
TABLE 29
| Compound No. | Structure | LC/MS Measured condition | Retention time (min) | m/z | Con-figration |
|---|---|---|---|---|---|
| I-0334 | 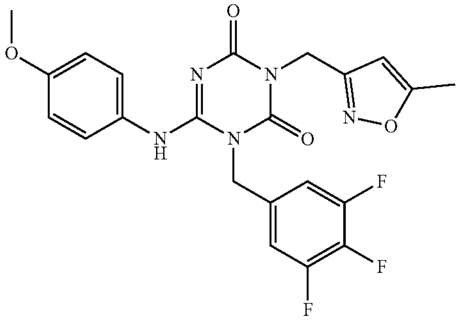 [SMILES: COc1ccc(Nc2nc(=O)n(Cc3cc(C)on3)c(=O)n2Cc2cc(F)c(F)c(F)c2)cc1] | 1 | 2.14 | 474.2 | |

TABLE 29-continued
| Compound No. | Structure | LC/MS Measured condition | Retention time (min) | m/z | Con-figration |
|---|---|---|---|---|---|
| I-0335 | 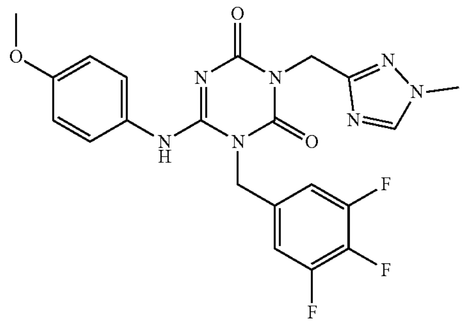 [SMILES: COc1ccc(Nc2nc(=O)n(Cc3ncn(C)n3)c(=O)n2Cc2cc(F)c(F)c(F)c2)cc1] | 1 | 1.78 | 474.2 | |
| I-0339 | 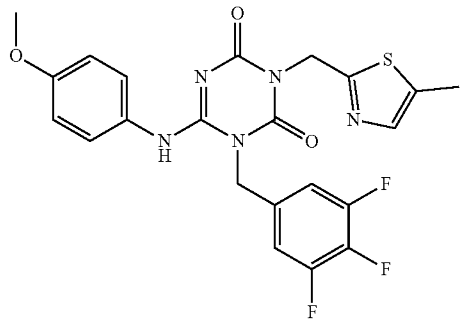 [SMILES: COc1ccc(Nc2nc(=O)n(Cc3ncc(C)s3)c(=O)n2Cc2cc(F)c(F)c(F)c2)cc1] | 1 | 2.15 | 490.2 | |
| I-0340 | 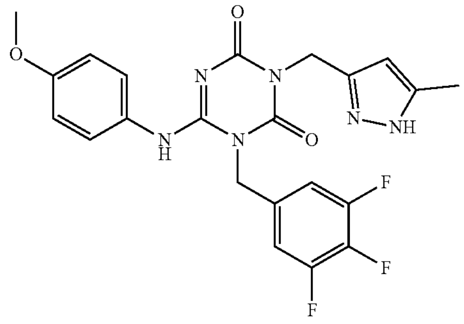 [SMILES: COc1ccc(Nc2nc(=O)n(Cc3cc(C)[nH]n3)c(=O)n2Cc2cc(F)c(F)c(F)c2)cc1] | 1 | 1.92 | 473 | |
| I-0344 | 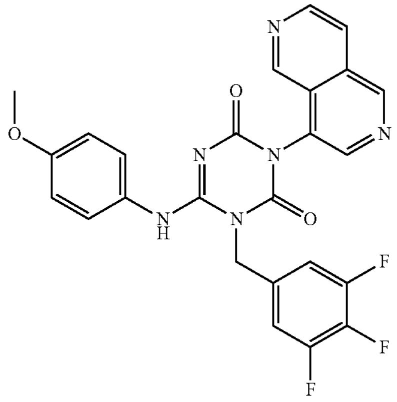 [SMILES: COc1ccc(Nc2nc(=O)n(-c3cncc4ccncc34)c(=O)n2Cc2cc(F)c(F)c(F)c2)cc1] | 1 | 1.88 | 507.2 | |

TABLE 30
| Compound No. | Structure | LC/MS Measured condition | Retention time (min) | m/z | Con-figuration |
|---|---|---|---|---|---|
| I-0346 | 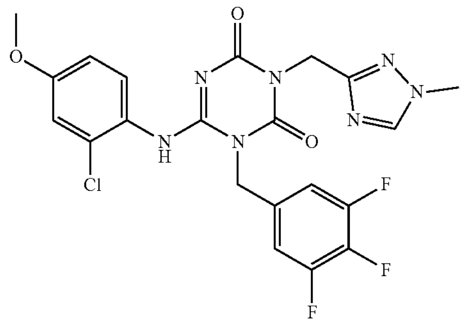 [SMILES: COc1ccc(Nc2nc(=O)n(Cc3ncn(C)n3)c(=O)n2Cc2cc(F)c(F)c(F)c2)c(Cl)c1] | 1 | 2.03 | 508.2 | |
| I-0348 | 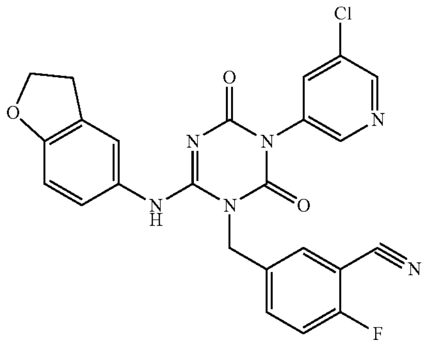 [SMILES: N#Cc1cc(Cn2c(Nc3ccc4c(c3)CCO4)nc(=O)n(-c3cncc(Cl)c3)c2=O)ccc1F] | 1 | 1.95 | 491.1 | |
| I-0349 | 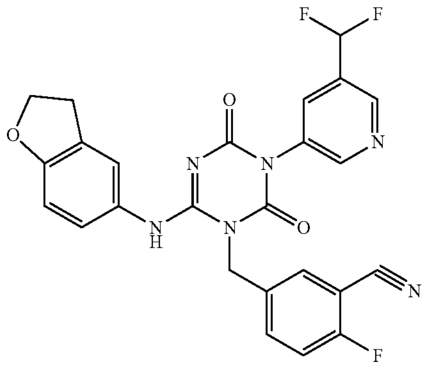 [SMILES: N#Cc1cc(Cn2c(Nc3ccc4c(c3)CCO4)nc(=O)n(-c3cncc(C(F)F)c3)c2=O)ccc1F] | 1 | 1.93 | 507.2 | |
| I-0350 | 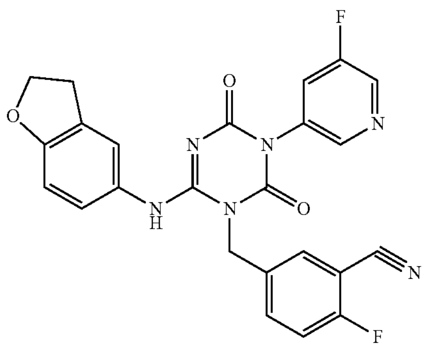 [SMILES: N#Cc1cc(Cn2c(Nc3ccc4c(c3)CCO4)nc(=O)n(-c3cncc(F)c3)c2=O)ccc1F] | 1 | 1.84 | 475.2 | |

TABLE 30-continued
| Compound No. | Structure | LC/MS Measured condition | Retention time (min) | m/z | Con-figration |
|---|---|---|---|---|---|
| I-0351 | 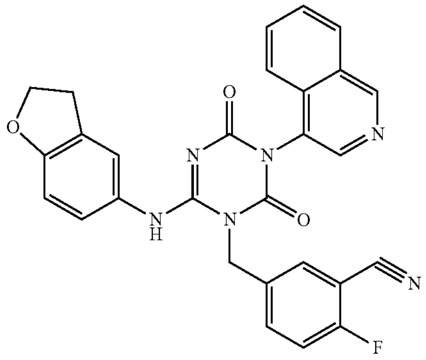 [SMILES: N#Cc1cc(Cn2c(Nc3ccc4c(c3)CCO4)nc(=O)n(-c3cncc4ccccc34)c2=O)ccc1F] | 1 | 1.81 | 507.2 | |
TABLE 31
| Compound No. | Structure | LC/MS Measured condition | Retention time (min) | m/z | Con-figration |
|---|---|---|---|---|---|
| I-0352 | 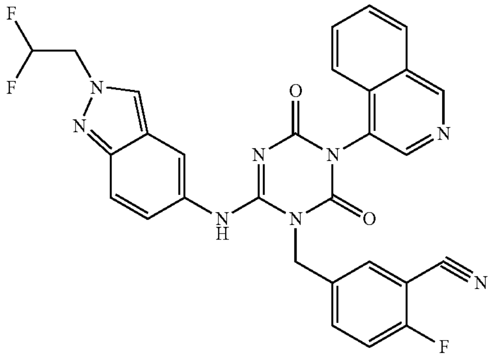 [SMILES: N#Cc1cc(Cn2c(Nc3ccc4nn(CC(F)F)cc4c3)nc(=O)n(-c3cncc4ccccc34)c2=O)ccc1F] | 1 | 1.83 | 569.2 | |
| I-0353 | 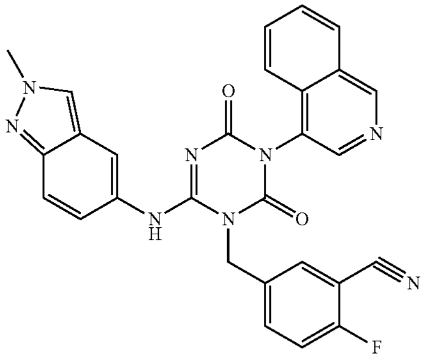 [SMILES: Cn1cc2cc(Nc3nc(=O)n(-c4cncc5ccccc45)c(=O)n3Cc3ccc(F)c(C#N)c3)ccc2n1] | 1 | 1.68 | 519.2 | |

TABLE 31-continued
| Compound No. | Structure | LC/MS Measured condition | Retention time (min) | m/z | Con-figration |
|---|---|---|---|---|---|
| I-0354 | 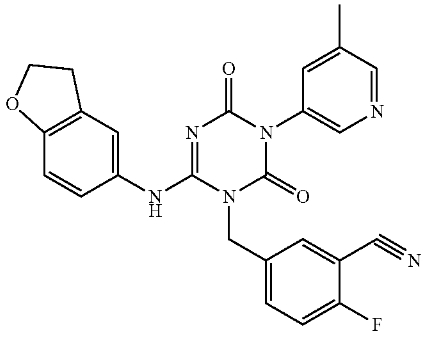 [SMILES: Cc1cncc(-n2c(=O)nc(Nc3ccc4c(c3)CCO4)n(Cc3ccc(F)c(C#N)c3)c2=O)c1] | 1 | 1.72 | 471.2 | |
| I-0355 | 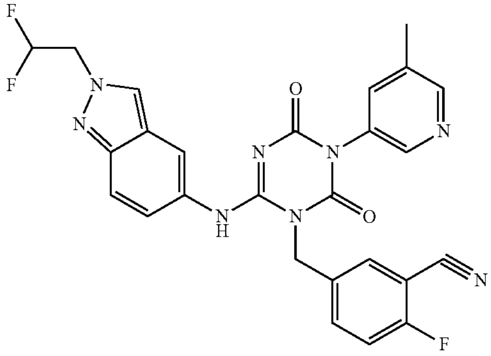 [SMILES: Cc1cncc(-n2c(=O)nc(Nc3ccc4nn(CC(F)F)cc4c3)n(Cc3ccc(F)c(C#N)c3)c2=O)c1] | 1 | 1.68 | 533 | |
| I-0356 | 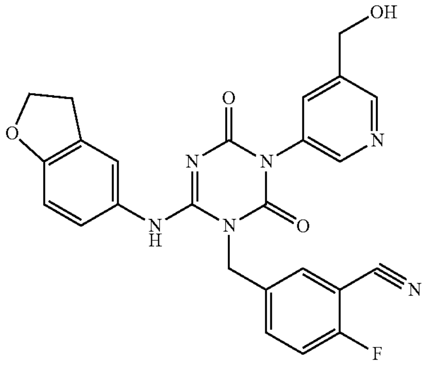 [SMILES: N#Cc1cc(Cn2c(Nc3ccc4c(c3)CCO4)nc(=O)n(-c3cncc(CO)c3)c2=O)ccc1F] | 1 | 1.54 | 487 | |

TABLE 32
| Compound No. | Structure | LC/MS Measured condition | Retention time (min) | m/z | Con-figration |
|---|---|---|---|---|---|
| I-0357 | 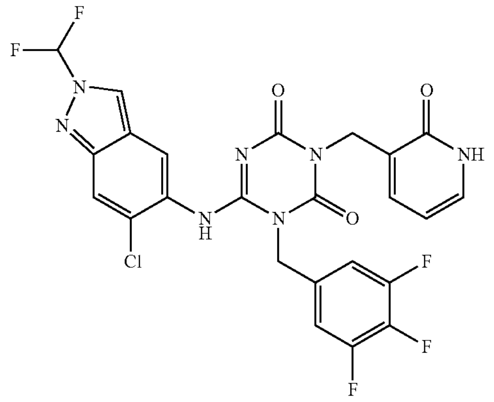 [SMILES: O=c1[nH]cccc1Cn1c(=O)nc(Nc2cc3cn(C(F)F)nc3cc2Cl)n(Cc2cc(F)c(F)c(F)c2)c1=O] | 1 | 2.09 | 580 | |
| I-0358 | 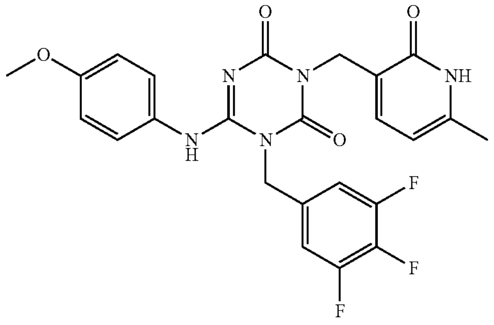 | 1 | 2.06 | 500 | |
| I-0359 | 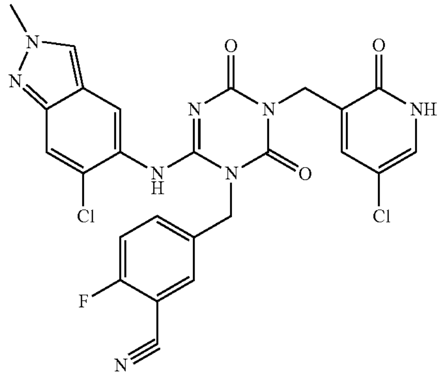 [SMILES: Cn1cc2cc(Nc3nc(=O)n(Cc4cc(Cl)c[nH]c4=O)c(=O)n3Cc3ccc(F)c(C#N)c3)c(Cl)cc2n1] | 1 | 1.79 | 567 | |
| I-0361 | 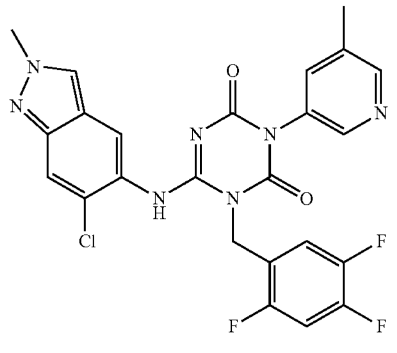 [SMILES: Cc1cncc(-n2c(=O)nc(Nc3cc4cn(C)nc4cc3Cl)n(Cc3cc(F)c(F)cc3F)c2=O)c1] | 1 | 1.85 | 528 | |

TABLE 32-continued
| Compound No. | Structure | LC/MS Measured condition | Retention time (min) | m/z | Con-figuration |
|---|---|---|---|---|---|
| I-0364 | 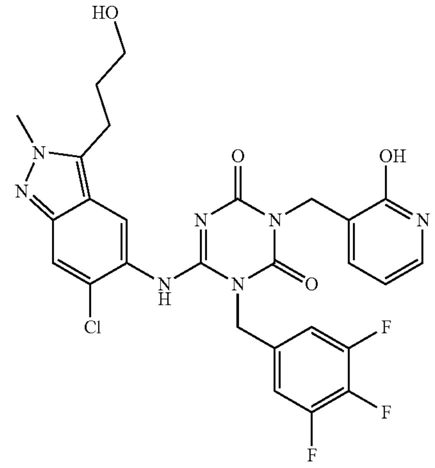 [SMILES: Cn1nc2cc(Cl)c(Nc3nc(=O)n(Cc4cccnc4O)c(=O)n3Cc3cc(F)c(F)c(F)c3)cc2c1CCCO] | 1 | 1.66 | 602 | |
TABLE 33
| Compound No. | Structure | LC/MS Measured condition | Retention time (min) | m/z | Con-figuration |
|---|---|---|---|---|---|
| I-0365 | 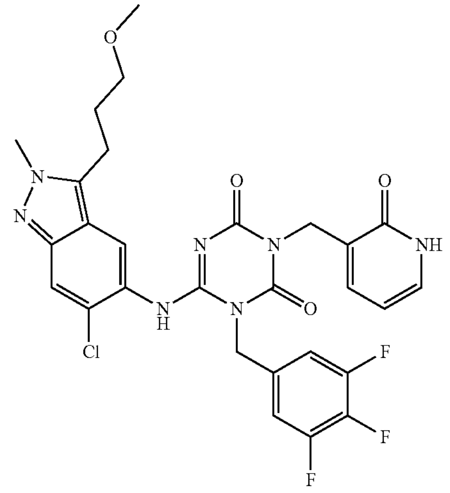 [SMILES: COCCCc1c2cc(Nc3nc(=O)n(Cc4ccc[nH]c4=O)c(=O)n3Cc3cc(F)c(F)c(F)c3)c(Cl)cc2nn1C] | 1 | 1.86 | 616 | |
| I-0366 | 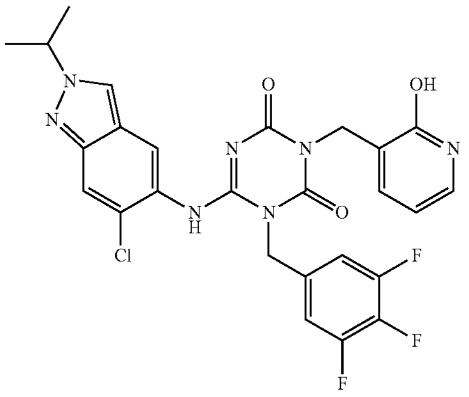 [SMILES: CC(C)n1cc2cc(Nc3nc(=O)n(Cc4cccnc4O)c(=O)n3Cc3cc(F)c(F)c(F)c3)c(Cl)cc2n1] | 1 | 1.95 | 571.9 | |

TABLE 33-continued
| Compound No. | Structure | LC/MS Measured condition | Retention time (min) | m/z | Con-figration |
|---|---|---|---|---|---|
| I-0367 | 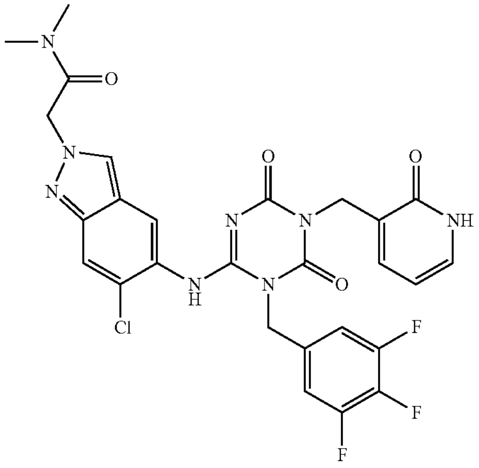 [SMILES: CN(C)C(=O)Cn1cc2cc(Nc3nc(=O)n(Cc4ccc[nH]c4=O)c(=O)n3Cc3cc(F)c(F)c(F)c3)c(Cl)cc2n1] | 1 | 1.66 | 615 | |
| I-0368 | 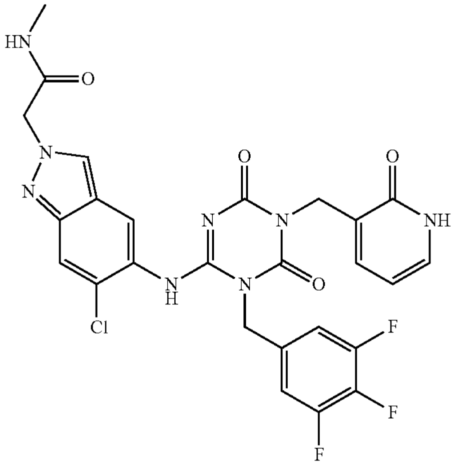 [SMILES: CNC(=O)Cn1cc2cc(Nc3nc(=O)n(Cc4ccc[nH]c4=O)c(=O)n3Cc3cc(F)c(F)c(F)c3)c(Cl)cc2n1] | 1 | 1.62 | 601 | |
| I-0369 | 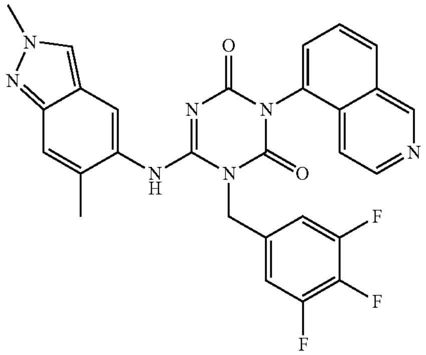 [SMILES: Cc1cc2nn(C)cc2cc1Nc1nc(=O)n(-c2cccc3cnccc23)c(=O)n1Cc1cc(F)c(F)c(F)c1] | 1 | 1.81 | 544 | |

TABLE 34
| Compound No. | Structure | LC/MS Measured condition | Retention time (min) | m/z | Con-figration |
|---|---|---|---|---|---|
| I-0370 | 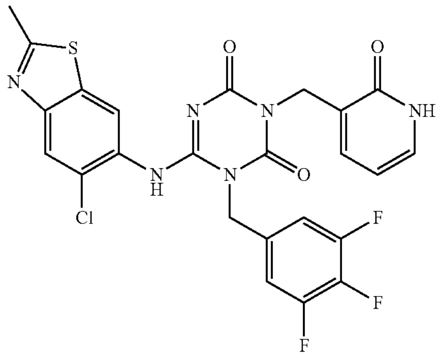 | 3 | 2.01 | 561 | |
| I-0371 | 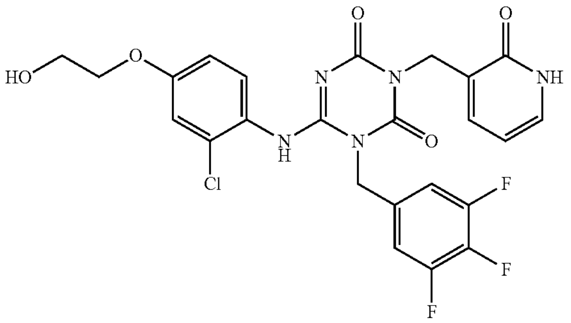 [SMILES: O=c1[nH]cccc1Cn1c(=O)nc(Nc2ccc(OCCO)cc2Cl)n(Cc2cc(F)c(F)c(F)c2)c1=O] | 3 | 1.65 | 550 | |
| I-0372 | 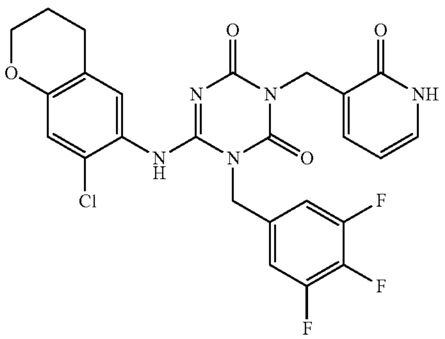 | 3 | 2.04 | 546 | |
| I-0374 | 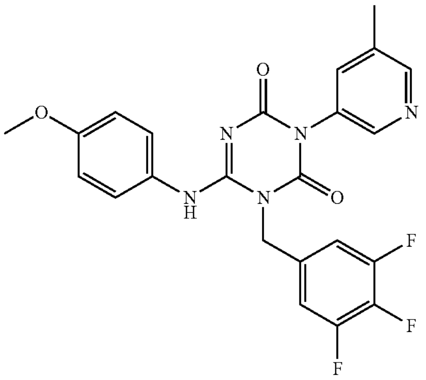 | 1 | 1.88 | 470 | |

TABLE 34-continued
| Compound No. | Structure | LC/MS Measured condition | Retention time (min) | m/z | Con-figration |
|---|---|---|---|---|---|
| I-0377 | 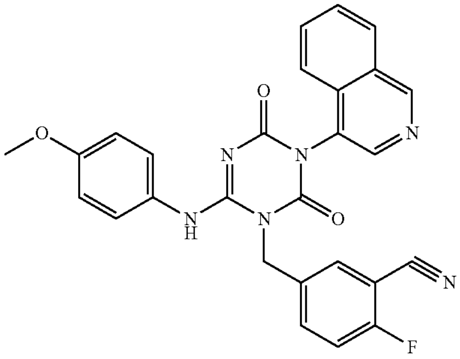 [SMILES: COc1ccc(Nc2nc(=O)n(-c3cncc4ccccc34)c(=O)n2Cc2ccc(F)c(C#N)c2)cc1] | 3 | 1.70 | 495 | |
TABLE 35
| Compound No. | Structure | LC/MS Measured condition | Retention time (min) | m/z | Con-figration |
|---|---|---|---|---|---|
| I-0378 | 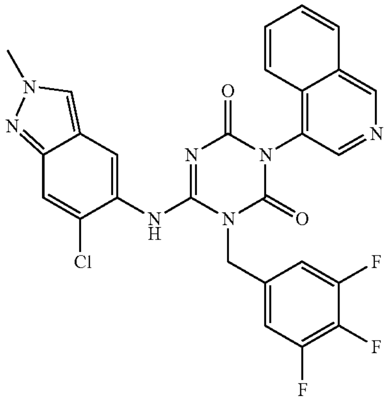 [SMILES: Cn1cc2cc(Nc3nc(=O)n(-c4cncc5ccccc45)c(=O)n3Cc3cc(F)c(F)c(F)c3)c(Cl)cc2n1] | 3 | 1.96 | 564 | |
| I-0379 | 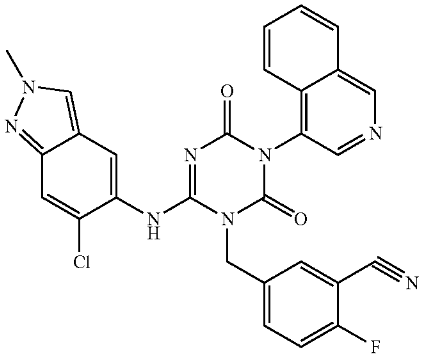 [SMILES: Cn1cc2cc(Nc3nc(=O)n(-c4cncc5ccccc45)c(=O)n3Cc3ccc(F)c(C#N)c3)c(Cl)cc2n1] | 3 | 1.76 | 553 | |

TABLE 35-continued
| Compound No. | Structure | LC/MS Measured condition | Retention time (min) | m/z | Con-figration |
|---|---|---|---|---|---|
| I-0380 | 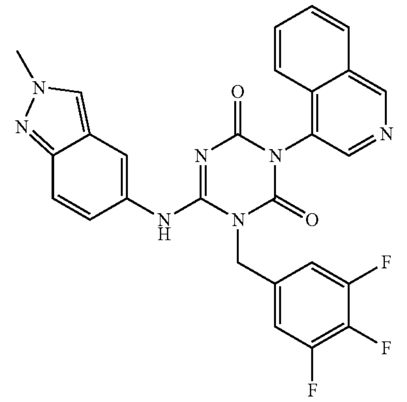 [SMILES: Cn1cc2cc(Nc3nc(=O)n(-c4cncc5ccccc45)c(=O)n3Cc3cc(F)c(F)c(F)c3)ccc2n1] | 3 | 1.70 | 530 | |
| I-0381 | 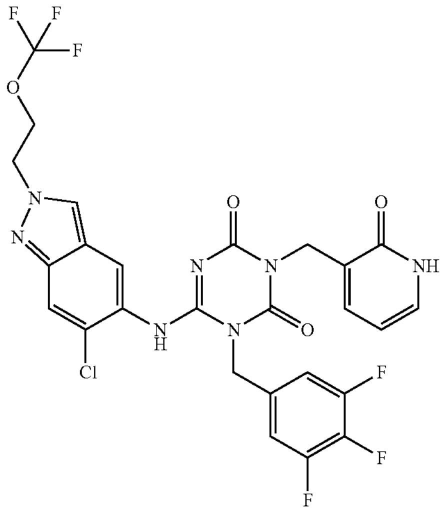 [SMILES: O=c1[nH]cccc1Cn1c(=O)nc(Nc2cc3cn(CCOC(F)(F)F)nc3cc2Cl)n(Cc2cc(F)c(F)c(F)c2)c1=O] | 3 | 2.04 | 642 | |
| I-0382 | 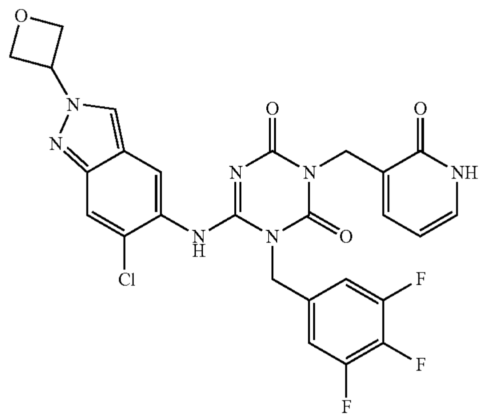 [SMILES: O=c1[nH]cccc1Cn1c(=O)nc(Nc2cc3cn(C4COC4)nc3cc2Cl)n(Cc2cc(F)c(F)c(F)c2)c1=O] | 3 | 1.72 | 586 | |

TABLE 36
| Compound No. | Structure | LC/MS Measured condition | Retention time (min) | m/z | Con-figration |
|---|---|---|---|---|---|
| I-0383 | 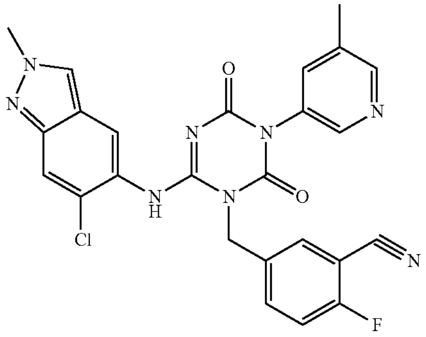 [SMILES: Cc1cncc(-n2c(=O)nc(Nc3cc4cn(C)nc4cc3Cl)n(Cc3ccc(F)c(C#N)c3)c2=O)c1] | 3 | 1.64 | 517 | |
| I-0384 | 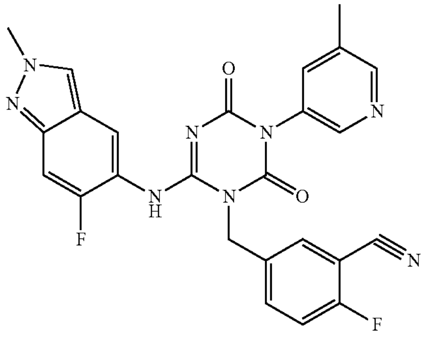 [SMILES: Cc1cncc(-n2c(=O)nc(Nc3cc4cn(C)nc4cc3F)n(Cc3ccc(F)c(C#N)c3)c2=O)c1] | 3 | 1.54 | 501 | |
| I-0385 | 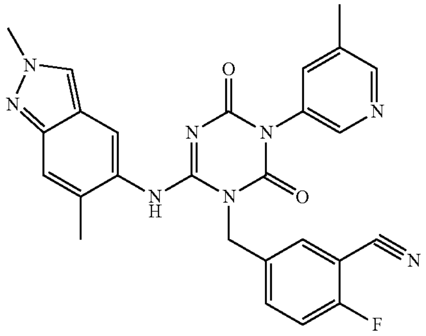 [SMILES: Cc1cncc(-n2c(=O)nc(Nc3cc4cn(C)nc4cc3C)n(Cc3ccc(F)c(C#N)c3)c2=O)c1] | 3 | 1.49 | 497 | |
| I-0386 | 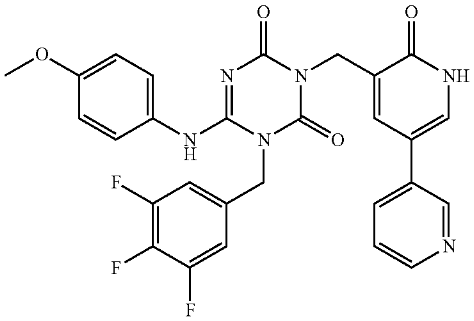 [SMILES: COc1ccc(Nc2nc(=O)n(Cc3cc(-c4cccnc4)c[nH]c3=O)c(=O)n2Cc2cc(F)c(F)c(F)c2)cc1] | 1 | 1.57 | 563.2 | |

TABLE 36-continued
| Compound No. | Structure | LC/MS Measured condition | Retention time (min) | m/z | Con-figuration |
|---|---|---|---|---|---|
| I-0390 | 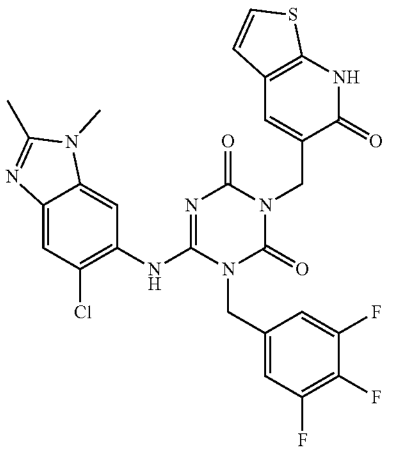 [SMILES: Cc1nc2cc(Cl)c(Nc3nc(=O)n(Cc4cc5ccsc5[nH]c4=O)c(=O)n3Cc3cc(F)c(F)c(F)c3)cc2n1C] | 1 | 1.66 | 614.2 | |
TABLE 37
| Compound No. | Structure | LC/MS Measured condition | Retention time (min) | m/z | Con-figuration |
|---|---|---|---|---|---|
| I-0391 | 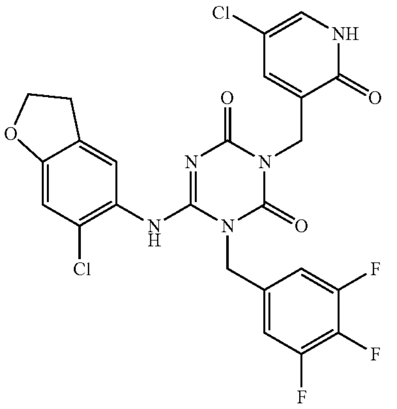 [SMILES: O=c1[nH]cc(Cl)cc1Cn1c(=O)nc(Nc2cc3c(cc2Cl)OCC3)n(Cc2cc(F)c(F)c(F)c2)c1=O] | 1 | 2.08 | 565.9 | |
| I-0392 | 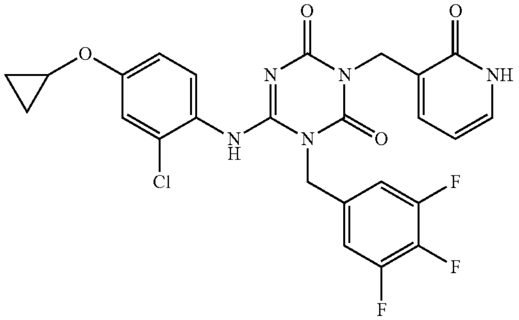 [SMILES: O=c1[nH]cccc1Cn1c(=O)nc(Nc2ccc(OC3CC3)cc2Cl)n(Cc2cc(F)c(F)c(F)c2)c1=O] | 1 | 2.23 | 546.2 | |

TABLE 37-continued
| Compound No. | Structure | LC/MS Measured condition | Retention time (min) | m/z | Con-figration |
|---|---|---|---|---|---|
| I-0396 | 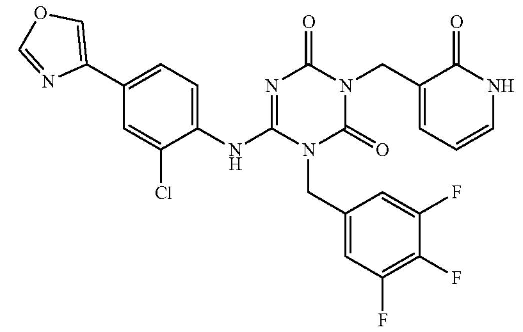 [SMILES: O=c1[nH]cccc1Cn1c(=O)nc(Nc2ccc(-c3cocn3)cc2Cl)n(Cc2cc(F)c(F)c(F)c2)c1=O] | 1 | 2.05 | 557.2 | |
| I-0397 | 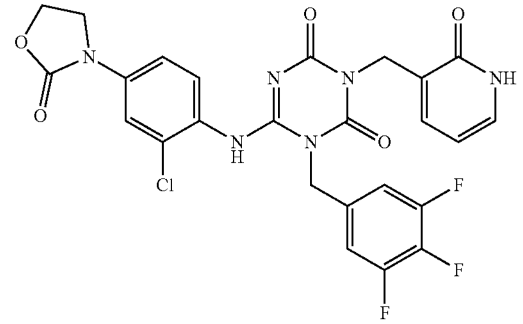 [SMILES: O=C1OCCN1c1ccc(Nc2nc(=O)n(Cc3ccc[nH]c3=O)c(=O)n2Cc2cc(F)c(F)c(F)c2)c(Cl)c1] | 1 | 1.91 | 575.2 | |
| I-0399 | 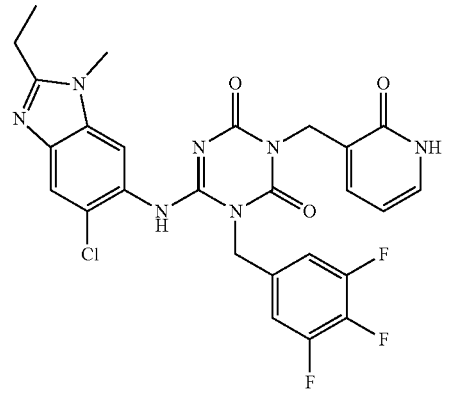 [SMILES: CCc1nc2cc(Cl)c(Nc3nc(=O)n(Cc4ccc[nH]c4=O)c(=O)n3Cc3cc(F)c(F)c(F)c3)cc2n1C] | 1 | 1.54 | 572.2 | |
TABLE 38
| Compound No. | Structure | LC/MS Measured condition | Retention time (min) | m/z | Con-figration |
|---|---|---|---|---|---|
| I-0400 | 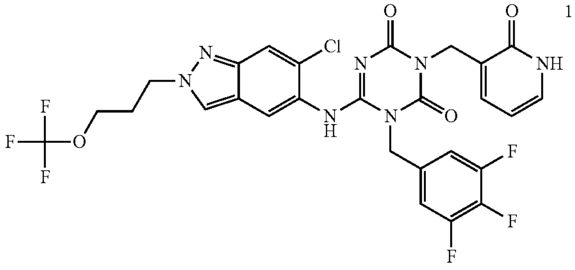 | 1 | 2.24 | 656.2 | |

TABLE 38-continued
| Compound No. | Structure | LC/MS Measured condition | Retention time (min) | m/z | Con-figration |
|---|---|---|---|---|---|
| I-0401 | 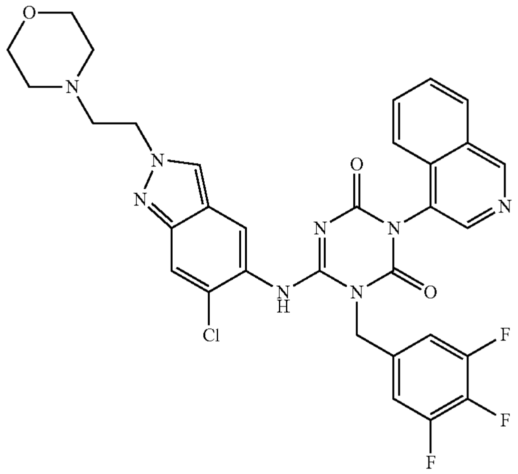 [SMILES: O=c1nc(Nc2cc3cn(CCN4CCOCC4)nc3cc2Cl)n(Cc2cc(F)c(F)c(F)c2)c(=O)n1-c1cncc2ccccc12] | 1 | 1.68 | 663.3 | |
| I-0402 | 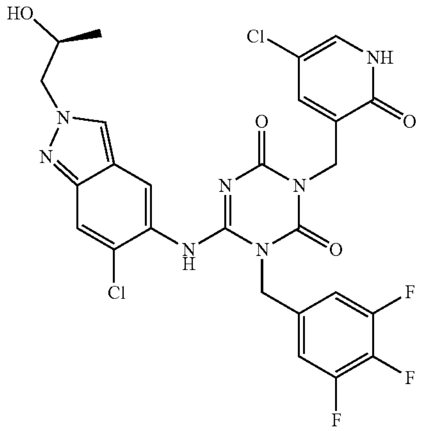 [SMILES: C[C@H](O)Cn1cc2cc(Nc3nc(=O)n(Cc4cc(Cl)c[nH]c4=O)c(=O)n3Cc3cc(F)c(F)c(F)c3)c(Cl)cc2n1] | 1 | 1.90 | 622.2 | a |
| I-0403 | 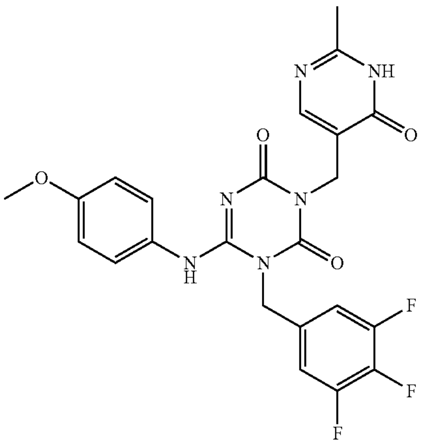 [SMILES: COc1ccc(Nc2nc(=O)n(Cc3cnc(C)[nH]c3=O)c(=O)n2Cc2cc(F)c(F)c(F)c2)cc1] | 1 | 1.69 | 501.2 | |

TABLE 38-continued
| Compound No. | Structure | LC/MS Measured condition | Retention time (min) | m/z | Con-figration |
|---|---|---|---|---|---|
| I-0404 | 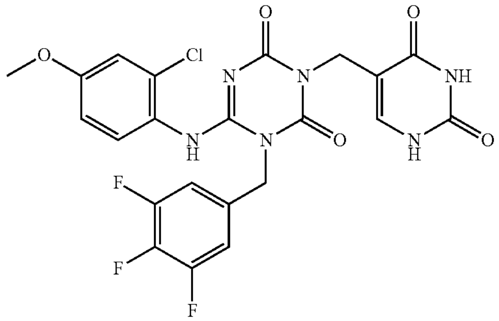 [SMILES: COc1ccc(Nc2nc(=O)n(Cc3c[nH]c(=O)[nH]c3=O)c(=O)n2Cc2cc(F)c(F)c(F)c2)c(Cl)c1] | 1 | 1.93 | 537.1 | |
TABLE 39
| Compound No. | Structure | LC/MS Measured condition | Retention time (min) | m/z | Con-figration |
|---|---|---|---|---|---|
| I-0405 | 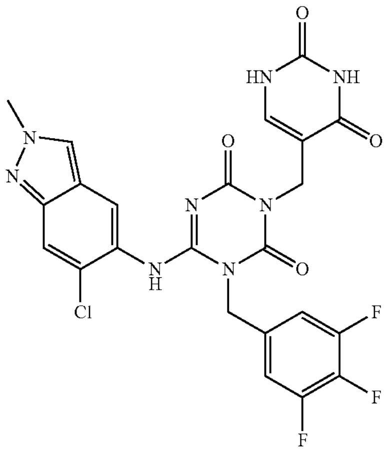 [SMILES: Cn1cc2cc(Nc3nc(=O)n(Cc4c[nH]c(=O)[nH]c4=O)c(=O)n3Cc3cc(F)c(F)c(F)c3)c(Cl)cc2n1] | 1 | 1.73 | 561.2 | |
| I-0406 | 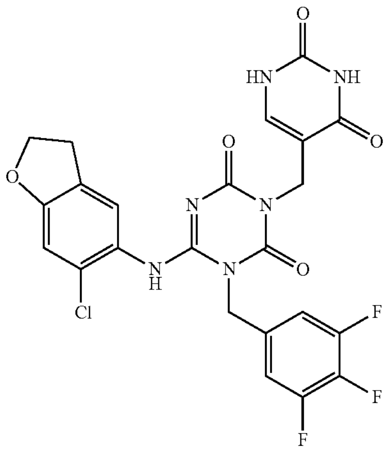 [SMILES: O=c1[nH]cc(Cn2c(=O)nc(Nc3cc4c(cc3Cl)OCC4)n(Cc3cc(F)c(F)c(F)c3)c2=O)c(=O)[nH]1] | 1 | 1.92 | 549.2 | |

TABLE 39-continued
| Compound No. | Structure | LC/MS Measured condition | Retention time (min) | m/z | Con-figration |
|---|---|---|---|---|---|
| I-0407 | 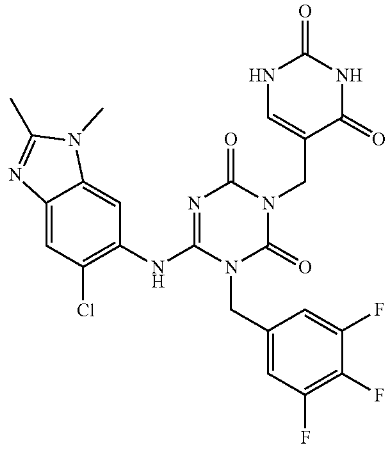 [SMILES: Cc1nc2cc(Cl)c(Nc3nc(=O)n(Cc4c[nH]c(=O)[nH]c4=O)c(=O)n3Cc3cc(F)c(F)c(F)c3)cc2n1C] | 1 | 1.41 | 575.2 | |
| I-0408 | 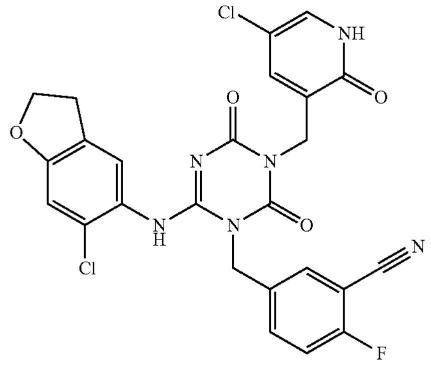 [SMILES: N#Cc1cc(Cn2c(Nc3cc4c(cc3Cl)OCC4)nc(=O)n(Cc3cc(Cl)c[nH]c3=O)c2=O)ccc1F] | 1 | 2.00 | 555.1 | |
| I-0412 | 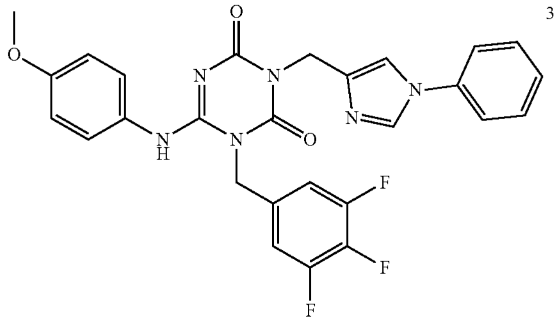 | 3 | 1.65 | 535 | |

TABLE 40
| Compound No. | Structure | LC/MS Measured condition | Retention time (min) | m/z | Con-figration |
|---|---|---|---|---|---|
| I-0414 | 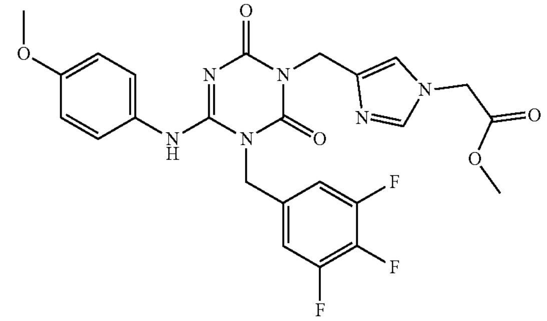 [SMILES: COC(=O)Cn1cnc(Cn2c(=O)nc(Nc3ccc(OC)cc3)n(Cc3cc(F)c(F)c(F)c3)c2=O)c1] | 1 | 1.57 | 531 | |
| I-0415 | 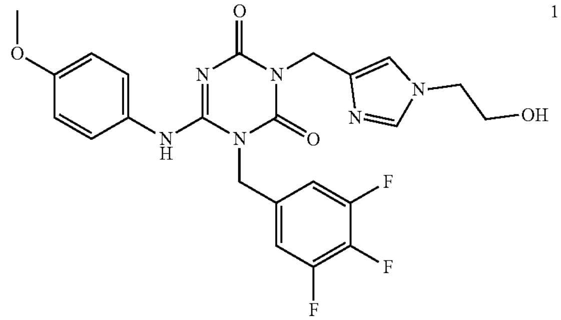 [SMILES: COc1ccc(Nc2nc(=O)n(Cc3cn(CC(N)=O)cn3)c(=O)n2Cc2cc(F)c(F)c(F)c2)cc1] | 1 | 1.48 | 503 | |
| I-0416 | 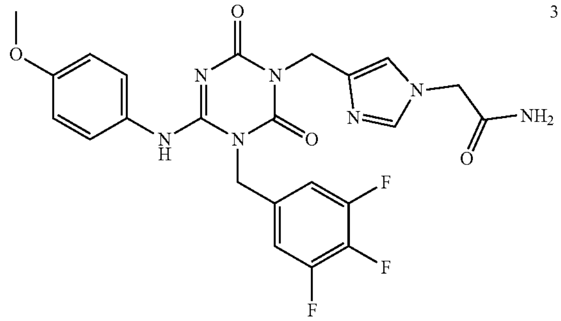 | 3 | 1.25 | 516 | |
| I-0421 | 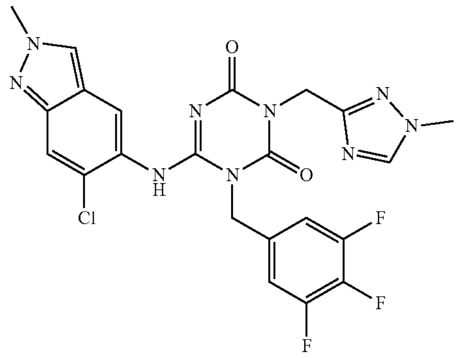 | 3 | 1.80 | 532 | |

TABLE 40-continued
| Compound No. | Structure | LC/MS Measured condition | Retention time (min) | m/z | Con-figration |
|---|---|---|---|---|---|
| I-0422 | 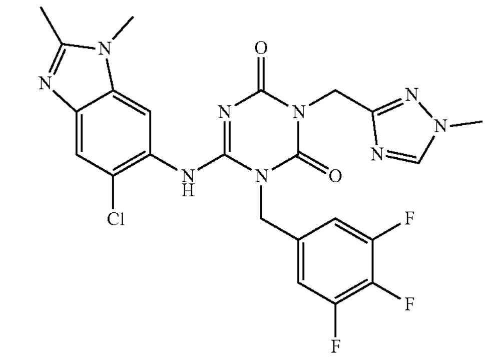 | 3 | 1.49 | 546 | |
TABLE 41
| Compound No. | Structure | LC/MS Measured condition | Retention time (min) | m/z | Con-figration |
|---|---|---|---|---|---|
| I-0423 | 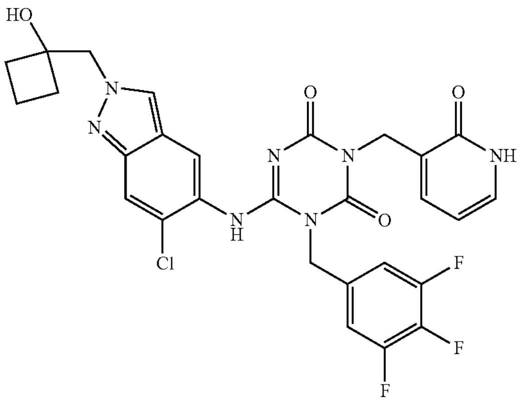 [SMILES: O=c1[nH]cccc1Cn1c(=O)nc(Nc2cc3cn(CC4(O)CCC4)nc3cc2Cl)n(Cc2cc(F)c(F)c(F)c2)c1=O] | 3 | 1.90 | 614 | |
| I-0424 | 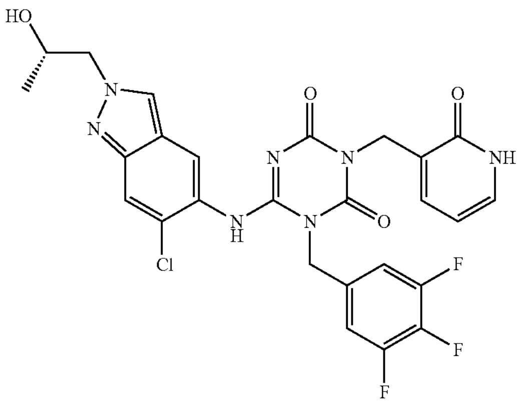 [SMILES: C[C@H](O)Cn1cc2cc(Nc3nc(=O)n(Cc4ccc[nH]c4=O)c(=O)n3Cc3cc(F)c(F)c(F)c3)c(Cl)cc2n1] | 3 | 1.66 | 588 | a |

TABLE 41-continued
| Compound No. | Structure | LC/MS Measured condition | Retention time (min) | m/z | Con-figration |
|---|---|---|---|---|---|
| I-0425 | 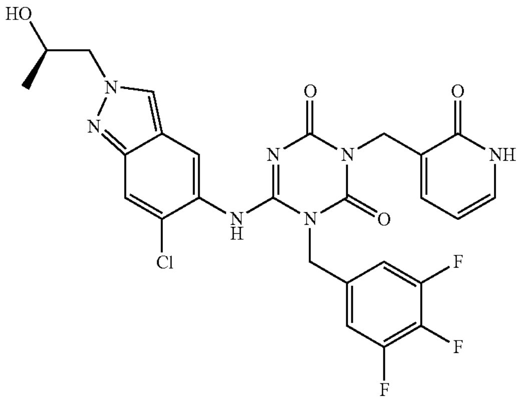 [SMILES: C[C@@H](O)Cn1cc2cc(Nc3nc(=O)n(Cc4ccc[nH]c4=O)c(=O)n3Cc3cc(F)c(F)c(F)c3)c(Cl)cc2n1] | 3 | 1.66 | 588 | a |
| I-0426 | 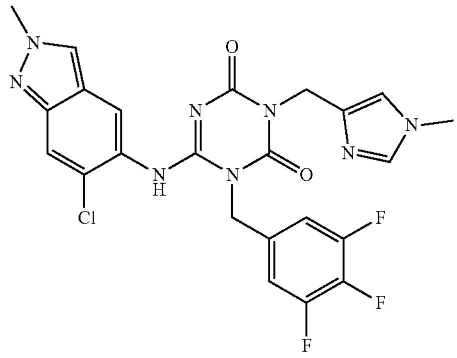 | 3 | 1.31 | 531 | |
| I-0427 | 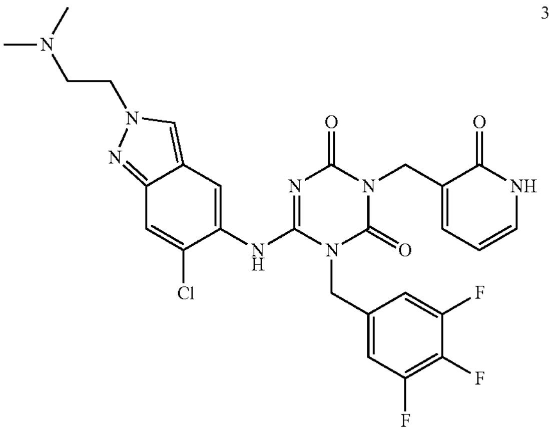 | 3 | 1.30 | 601 | |

TABLE 42
| Compound No. | Structure | LC/MS Measured condition | Retention time (min) | m/z | Con-figration |
|---|---|---|---|---|---|
| I-0428 | 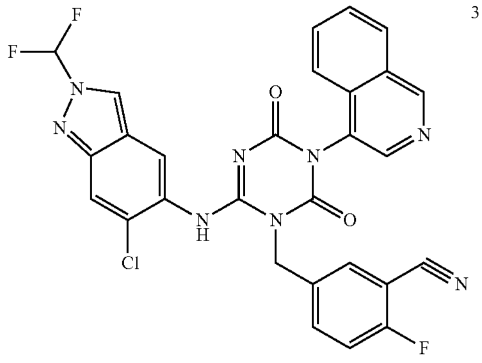 | 3 | 2.04 | 589 | |
| I-0429 | 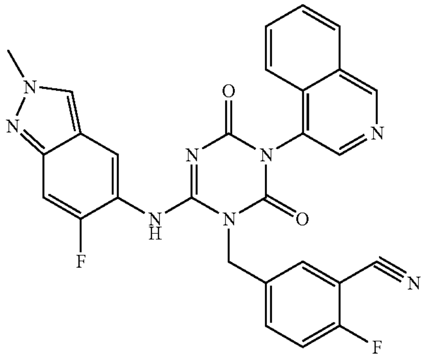 [SMILES: Cn1cc2cc(Nc3nc(=O)n(-c4cncc5ccccc45)c(=O)n3Cc3ccc(F)c(C#N)c3)c(F)cc2n1] | 3 | 1.76 | 537 | |
| I-0430 | 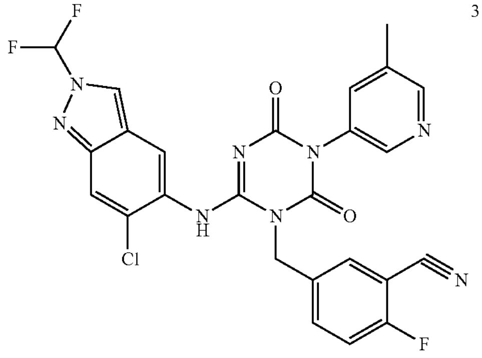 | 3 | 2.05 | 553 | |
| I-0431 | 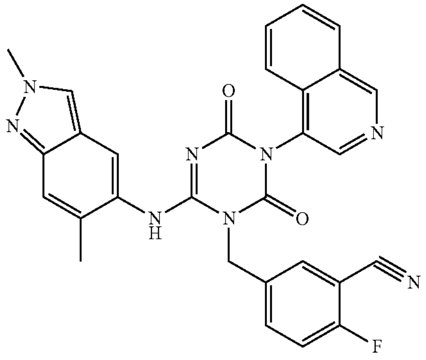 [SMILES: Cc1cc2nn(C)cc2cc1Nc1nc(=O)n(-c2cncc3ccccc23)c(=O)n1Cc1ccc(F)c(C#N)c1] | 3 | 1.61 | 533 | |

TABLE 42-continued
| Compound No. | Structure | LC/MS Measured condition | Retention time (min) | m/z | Con-figration |
|---|---|---|---|---|---|
| I-0432 | 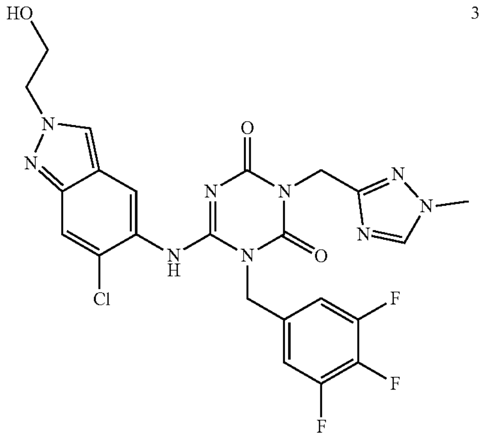 | 3 | 1.69 | 562 | |
TABLE 43
| Compound No. | Structure | LC/MS Measured condition | Retention time (min) | m/z | Con-figration |
|---|---|---|---|---|---|
| I-0433 | 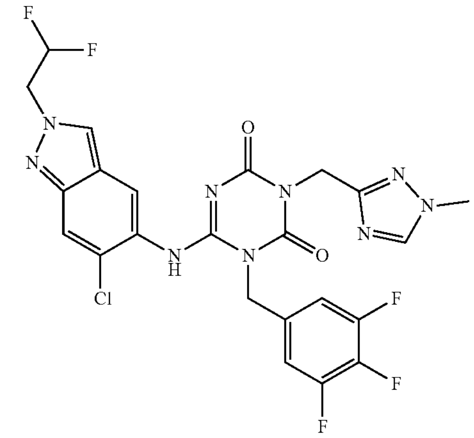 [SMILES: Cn1cnc(Cn2c(=O)nc(Nc3cc4cn(CC(F)F)nc4cc3Cl)n(Cc3cc(F)c(F)c(F)c3)c2=O)n1] | 3 | 1.98 | 582 | |
| I-0434 | 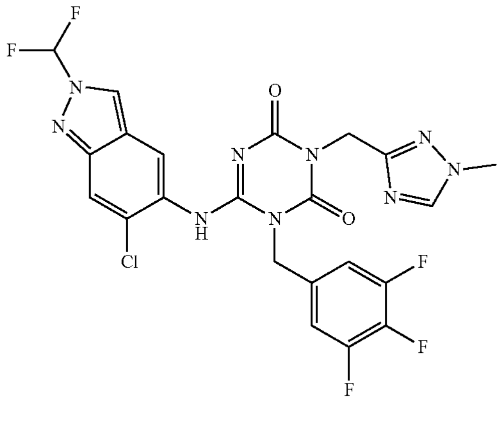 [SMILES: Cn1cnc(Cn2c(=O)nc(Nc3cc4cn(C(F)F)nc4cc3Cl)n(Cc3cc(F)c(F)c(F)c3)c2=O)n1] | 3 | 2.00 | 568 | |

TABLE 43-continued
| Compound No. | Structure | LC/MS Measured condition | Retention time (min) | m/z | Con-figration |
|---|---|---|---|---|---|
| I-0435 | 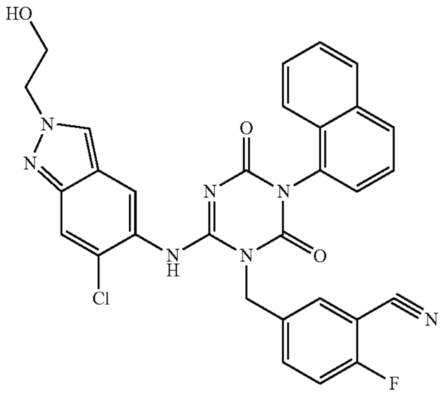 [SMILES: N#Cc1cc(Cn2c(Nc3cc4cn(CCO)nc4cc3Cl)nc(=O)n(-c3cccc4ccccc34)c2=O)ccc1F] | 3 | 1.74 | 583 | |
| I-0436 | 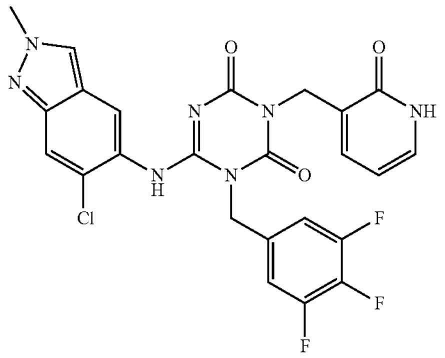 [SMILES: Cn1cc2cc(Nc3nc(=O)n(Cc4ccc[nH]c4=O)c(=O)n3Cc3cc(F)c(F)c(F)c3)c(Cl)cc2n1] | 1 | 1.76 | 544 | |
| I-0437 | 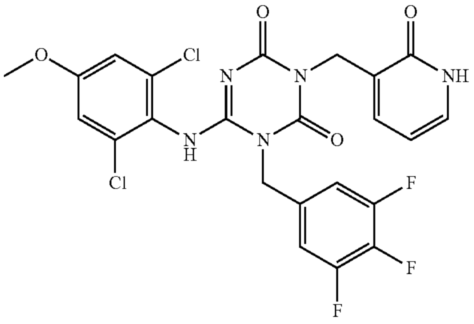 [SMILES: COc1cc(Cl)c(Nc2nc(=O)n(Cc3ccc[nH]c3=O)c(=O)n2Cc2cc(F)c(F)c(F)c2)c(Cl)c1] | 1 | 2.26 | 554.1 | |

TABLE 44
| Compound No. | Structure | LC/MS Measured condition | Retention time (min) | m/z | Con-figration |
|---|---|---|---|---|---|
| I-0438 | 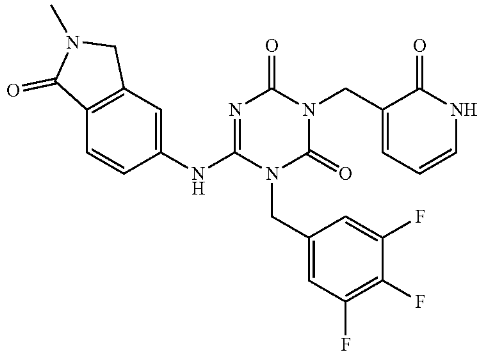 [SMILES: CN1Cc2cc(Nc3nc(=O)n(Cc4ccc[nH]c4=O)c(=O)n3Cc3cc(F)c(F)c(F)c3)ccc2C1=O] | 1 | 1.65 | 525.2 | |
| I-0439 | 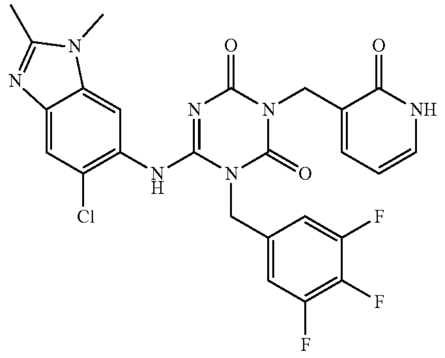 | 1 | 1.55 | 558.2 | |
| I-0440 | 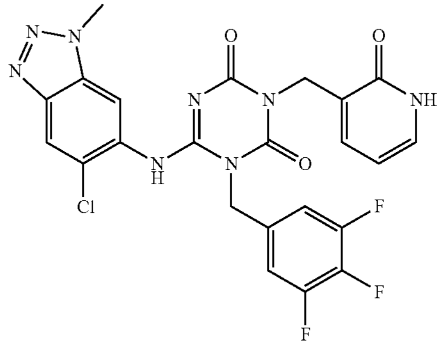 [SMILES: Cn1nnc2cc(Cl)c(Nc3nc(=O)n(Cc4ccc[nH]c4=O)c(=O)n3Cc3cc(F)c(F)c(F)c3)cc21] | 1 | 1.93 | 545.2 | |
| I-0441 | 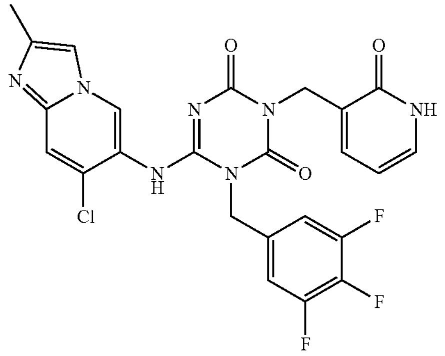 [SMILES: Cc1cn2cc(Nc3nc(=O)n(Cc4ccc[nH]c4=O)c(=O)n3Cc3cc(F)c(F)c(F)c3)c(Cl)cc2n1] | 1 | 1.49 | 544.1 | |

TABLE 44-continued
| Compound No. | Structure | LC/MS Measured condition | Retention time (min) | m/z | Con-figration |
|---|---|---|---|---|---|
| I-0442 | 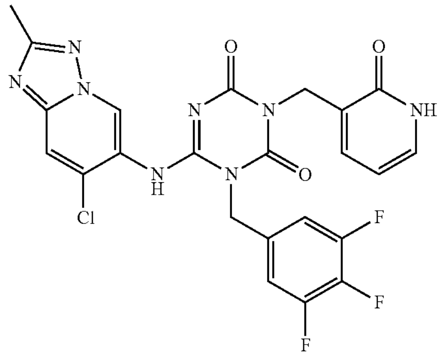 [SMILES: Cc1nc2cc(Cl)c(Nc3nc(=O)n(Cc4ccc[nH]c4=O)c(=O)n3Cc3cc(F)c(F)c(F)c3)cn2n1] | 1 | 1.80 | 545.2 | |
TABLE 45
| Compound No. | Structure | LC/MS Measured condition | Retention time (min) | m/z | Con-figration |
|---|---|---|---|---|---|
| I-0443 | 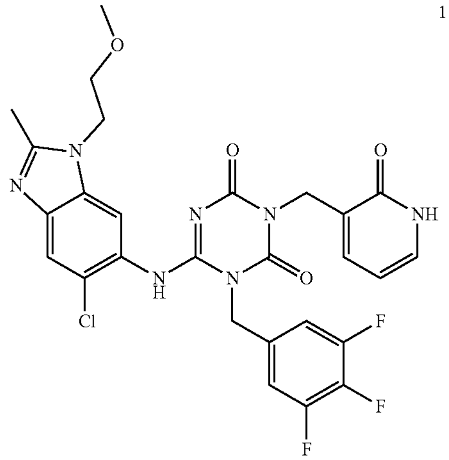 | 1 | 1.57 | 602.2 | |
| I-0444 | 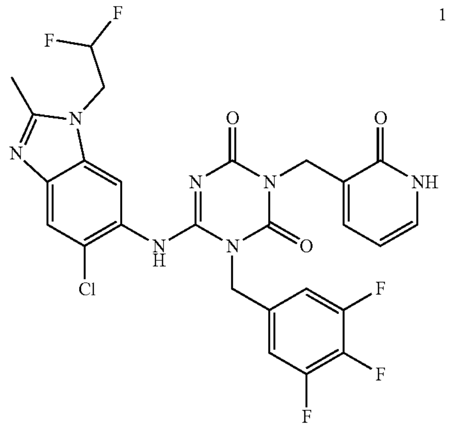 | 1 | 1.66 | 608 | |

TABLE 45-continued
| Compound No. | Structure | LC/MS Measured condition | Retention time (min) | m/z | Con-figuration |
|---|---|---|---|---|---|
| I-0445 | 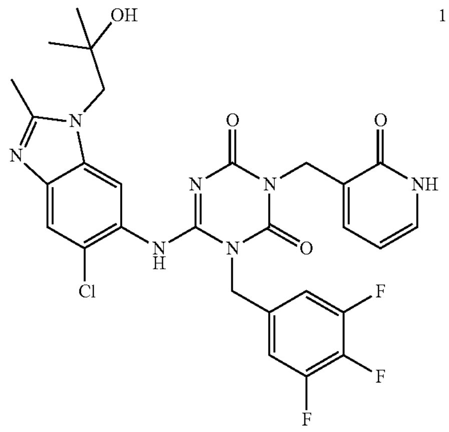 | 1 | 1.51 | 616.2 | |
| I-0446 | 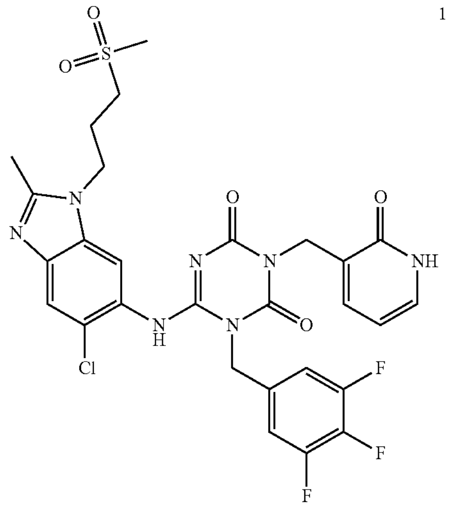 | 1 | 1.52 | 664.2 | |
| I-0447 | 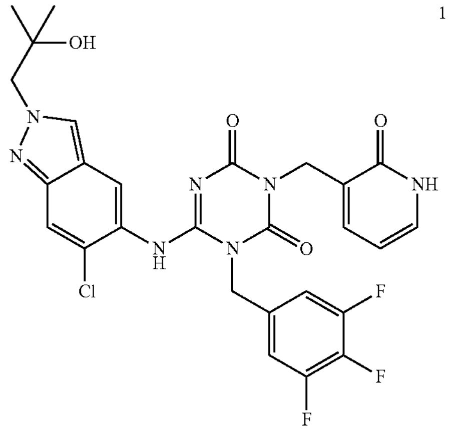 | 1 | 1.83 | 602.2 | |

TABLE 46
| Compound No. | Structure | LC/MS Measured condition | Retention time (min) | m/z | Con-figration |
|---|---|---|---|---|---|
| I-0448 | 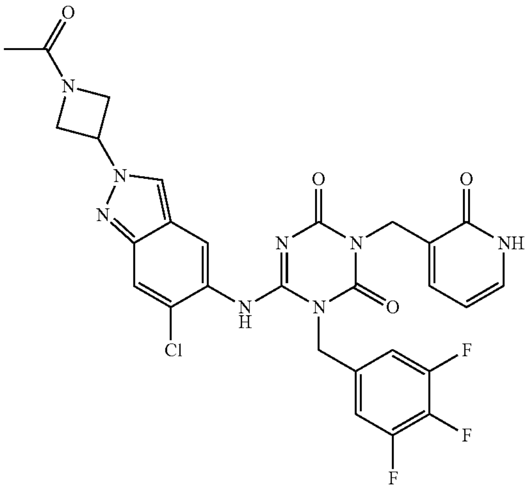 [SMILES: CC(=O)N1CC(n2cc3cc(Nc4nc(=O)n(Cc5ccc[nH]c5=O)c(=O)n4Cc4cc(F)c(F)c(F)c4)c(Cl)cc3n2)C1] | 1 | 1.72 | 627.2 | |
| I-0449 | 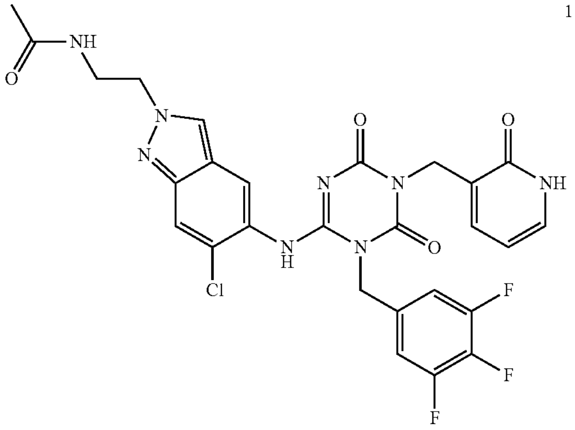 | 1 | 1.61 | 615 | |
| I-0450 | 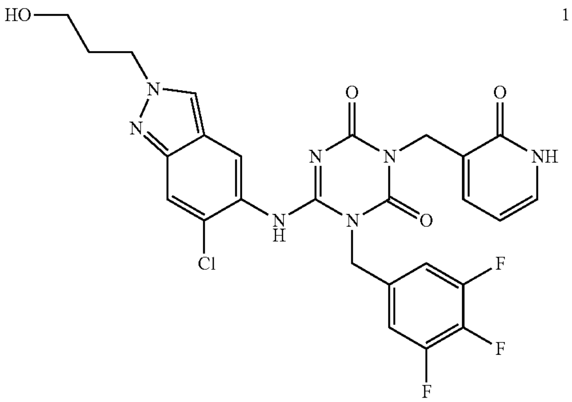 | 1 | 1.72 | 588.2 | |

TABLE 46-continued
| Compound No. | Structure | LC/MS Measured condition | Retention time (min) | m/z | Con-figuration |
|---|---|---|---|---|---|
| I-0451 | 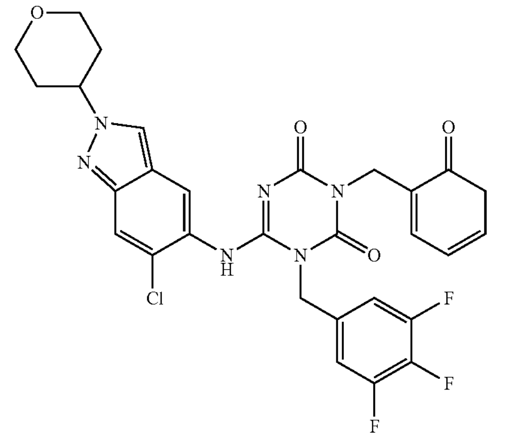 [SMILES: O=C1CC=CC=C1Cn1c(=O)nc(Nc2cc3cn(C4CCOCC4)nc3cc2Cl)n(Cc2cc(F)c(F)c(F)c2)c1=O] | 1 | 1.87 | 614 | |
| I-0452 | 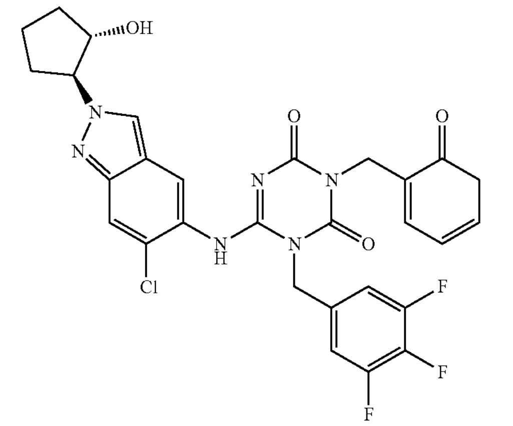 [SMILES: O=C1CC=CC=C1Cn1c(=O)nc(Nc2cc3cn([C@H]4CCC[C@@H]4O)nc3cc2Cl)n(Cc2cc(F)c(F)c(F)c2)c1=O] | 1 | 1.85 | 614 | a |
TABLE 47
| Compound No. | Structure | LC/MS Measured condition | Retention time (min) | m/z | Con-figuration |
|---|---|---|---|---|---|
| I-0453 | 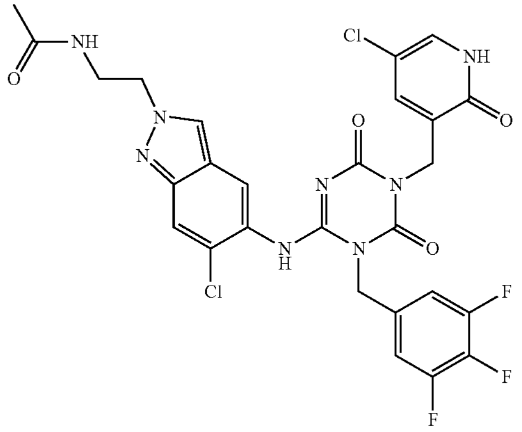 [SMILES: CC(=O)NCCn1cc2cc(Nc3nc(=O)n(Cc4cc(Cl)c[nH]c4=O)c(=O)n3Cc3cc(F)c(F)c(F)c3)c(Cl)cc2n1] | 1 | 1.78 | 649 | |

TABLE 47-continued
| Compound No. | Structure | LC/MS Measured condition | Retention time (min) | m/z | Con-figration |
|---|---|---|---|---|---|
| I-0454 | 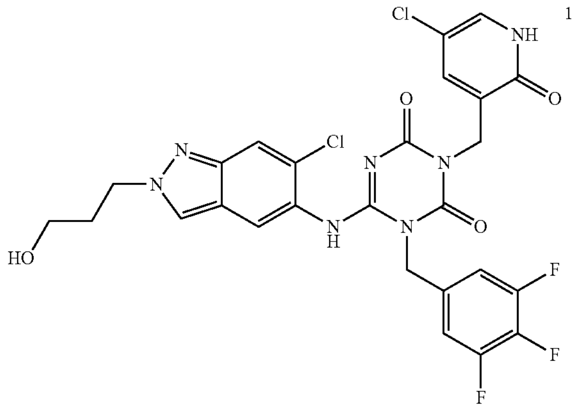 | 1 | 1.82 | 622 | |
| I-0455 | 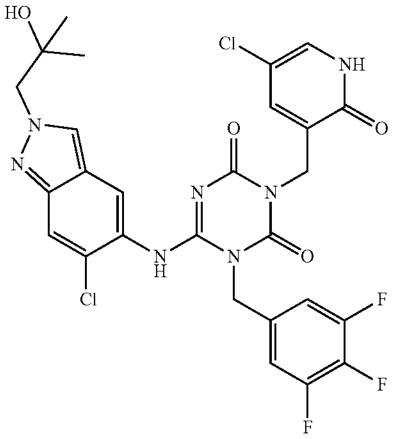 [SMILES: CC(C)(O)Cn1cc2cc(Nc3nc(=O)n(Cc4cc(Cl)c[nH]c4=O)c(=O)n3Cc3cc(F)c(F)c(F)c3)c(Cl)cc2n1] | 1 | 1.92 | 636 | |
| I-0456 | 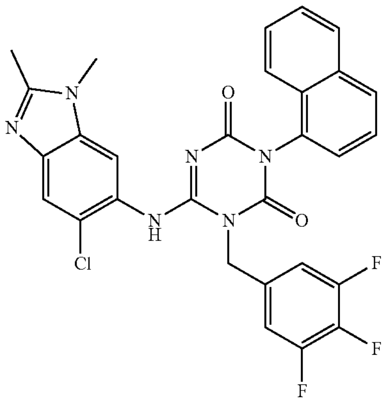 [SMILES: Cc1nc2cc(Cl)c(Nc3nc(=O)n(-c4cccc5ccccc45)c(=O)n3Cc3cc(F)c(F)c(F)c3)cc2n1C] | 1 | 1.71 | 578.2 | |

TABLE 47-continued
| Compound No. | Structure | LC/MS Measured condition | Retention time (min) | m/z | Con-figration |
|---|---|---|---|---|---|
| I-0457 | 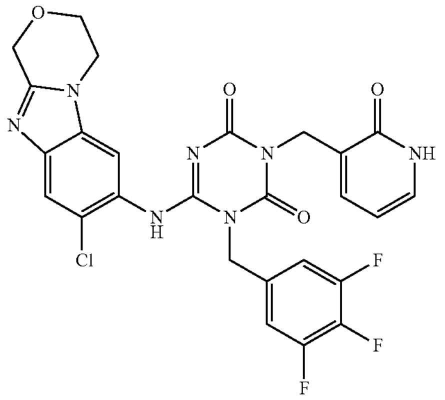 [SMILES: O=c1[nH]cccc1Cn1c(=O)nc(Nc2cc3c(cc2Cl)nc2n3CCOC2)n(Cc2cc(F)c(F)c(F)c2)c1=O] | 1 | 1.61 | 586 | |
TABLE 48
| Compound No. | Structure | LC/MS Measured condition | Retention time (min) | m/z | Con-figration |
|---|---|---|---|---|---|
| I-0458 | 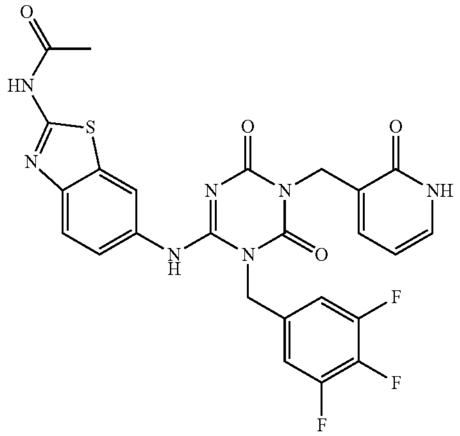 [SMILES: CC(=O)Nc1nc2ccc(Nc3nc(=O)n(Cc4ccc[nH]c4=O)c(=O)n3Cc3cc(F)c(F)c(F)c3)cc2s1] | 3 | 1.60 | 570.2 | |
| I-0459 | 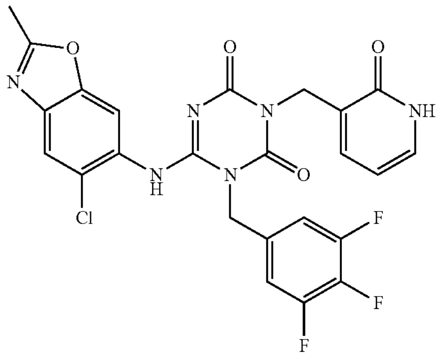 [SMILES: Cc1nc2cc(Cl)c(Nc3nc(=O)n(Cc4ccc[nH]c4=O)c(=O)n3Cc3cc(F)c(F)c(F)c3)cc2o1] | 1 | 1.99 | 545.2 | |

TABLE 48-continued
| Compound No. | Structure | LC/MS Measured condition | Retention time (min) | m/z | Con-figuration |
|---|---|---|---|---|---|
| I-0460 | 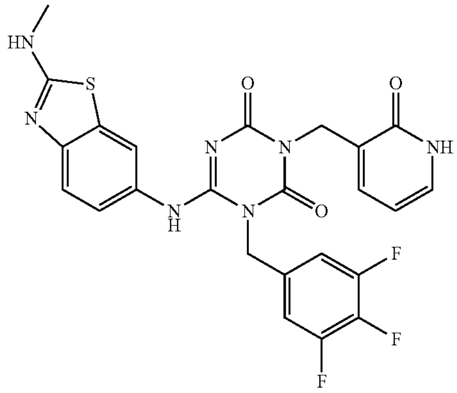 [SMILES: CNc1nc2ccc(Nc3nc(=O)n(Cc4ccc[nH]c4=O)c(=O)n3Cc3cc(F)c(F)c(F)c3)cc2s1] | 3 | 1.36 | 542 | |
| I-0461 | 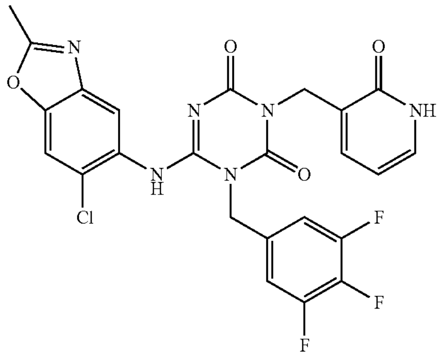 [SMILES: Cc1nc2cc(Nc3nc(=O)n(Cc4ccc[nH]c4=O)c(=O)n3Cc3cc(F)c(F)c(F)c3)c(Cl)cc2o1] | 1 | 2.01 | 545 | |
| I-0462 | 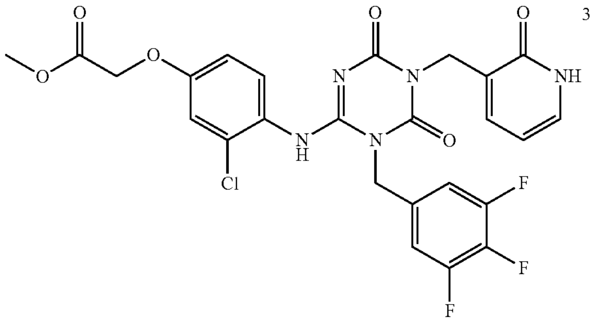 | 3 | 1.89 | 577.9 | |
TABLE 49
| Compound No. | Structure | LC/MS Measured condition | Retention time (min) | m/z | Con-figuration |
|---|---|---|---|---|---|
| I-0463 | 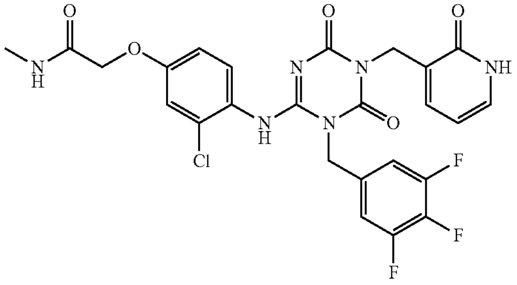 [SMILES: CNC(=O)COc1ccc(Nc2nc(=O)n(Cc3ccc[nH]c3=O)c(=O)n2Cc2cc(F)c(F)c(F)c2)c(Cl)c1] | 1 | 1.77 | 577.2 | |

TABLE 49-continued
| Compound No. | Structure | LC/MS Measured condition | Retention time (min) | m/z | Con-figration |
|---|---|---|---|---|---|
| I-0464 | 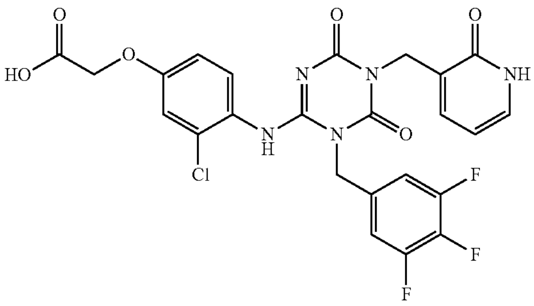 [SMILES: O=C(O)COc1ccc(Nc2nc(=O)n(Cc3ccc[nH]c3=O)c(=O)n2Cc2cc(F)c(F)c(F)c2)c(Cl)c1] | 1 | 1.83 | 564.2 | |
| I-0465 | 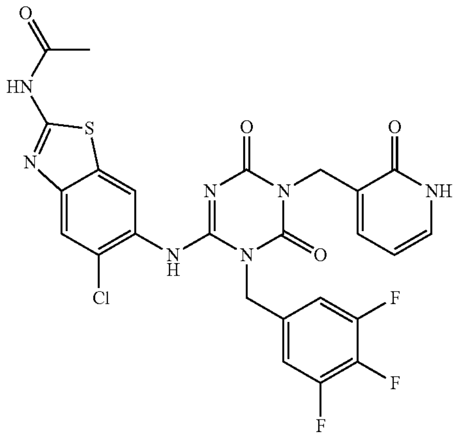 [SMILES: CC(=O)Nc1nc2cc(Cl)c(Nc3nc(=O)n(Cc4ccc[nH]c4=O)c(=O)n3Cc3cc(F)c(F)c(F)c3)cc2s1] | 1 | 1.99 | 604 | |
| I-0466 | 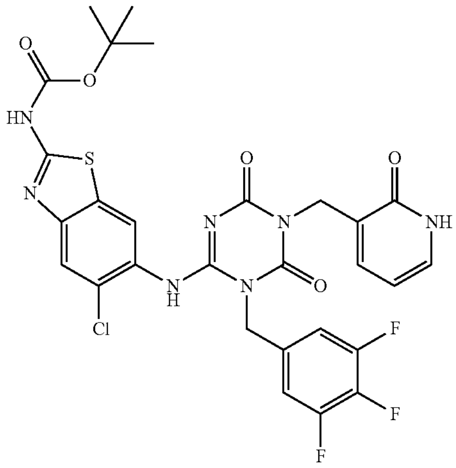 [SMILES: CC(C)(C)OC(=O)Nc1nc2cc(Cl)c(Nc3nc(=O)n(Cc4ccc[nH]c4=O)c(=O)n3Cc3cc(F)c(F)c(F)c3)cc2s1] | 3 | 2.24 | 662 | |

TABLE 49-continued
| Compound No. | Structure | LC/MS Measured condition | Retention time (min) | m/z | Con-figration |
|---|---|---|---|---|---|
| I-0467 | 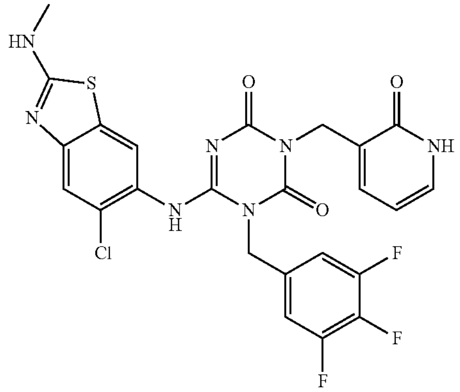 [SMILES: CNc1nc2cc(Cl)c(Nc3nc(=O)n(Cc4ccc[nH]c4=O)c(=O)n3Cc3cc(F)c(F)c(F)c3)cc2s1] | 1 | 1.79 | 576.1 | |
TABLE 50
| Compound No. | Structure | LC/MS Measured condition | Retention time (min) | m/z | Con-figration |
|---|---|---|---|---|---|
| I-0468 | 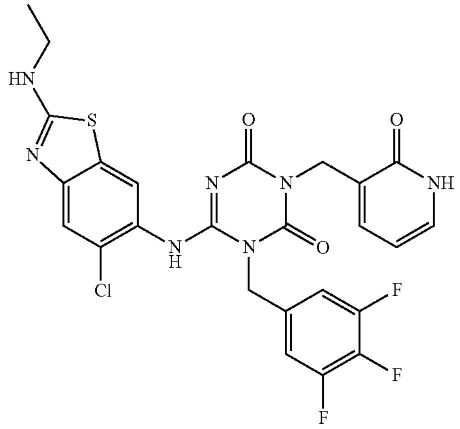 [SMILES: CCNc1nc2cc(Cl)c(Nc3nc(=O)n(Cc4ccc[nH]c4=O)c(=O)n3Cc3cc(F)c(F)c(F)c3)cc2s1] | 1 | 1.89 | 590.1 | |
| I-0469 | 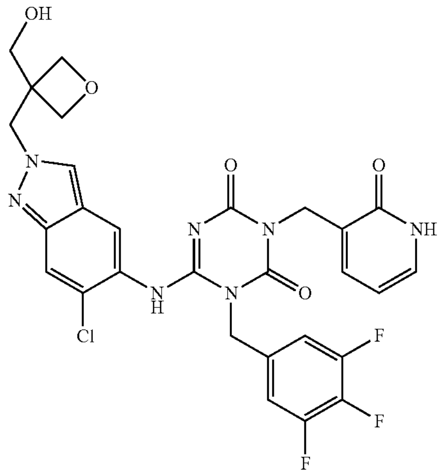 [SMILES: O=c1[nH]cccc1Cn1c(=O)nc(Nc2cc3cn(CC4(CO)COC4)nc3cc2Cl)n(Cc2cc(F)c(F)c(F)c2)c1=O] | 1 | 1.73 | 630 | |

TABLE 50-continued
| Compound No. | Structure | LC/MS Measured condition | Retention time (min) | m/z | Con-figration |
|---|---|---|---|---|---|
| I-0470 | 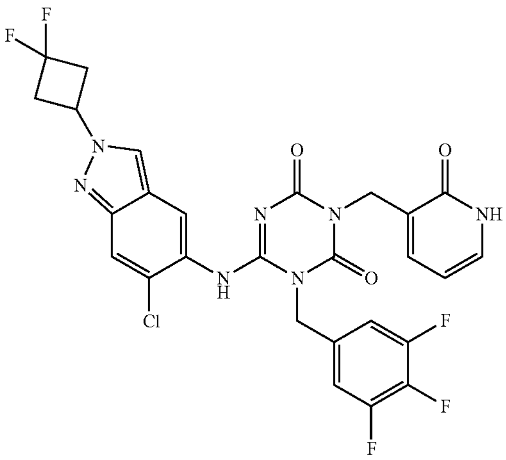 [SMILES: O=c1[nH]cccc1Cn1c(=O)nc(Nc2cc3cn(C4CC(F)(F)C4)nc3cc2Cl)n(Cc2cc(F)c(F)c(F)c2)c1=O] | 1 | 2.17 | 620 | |
| I-0471 | 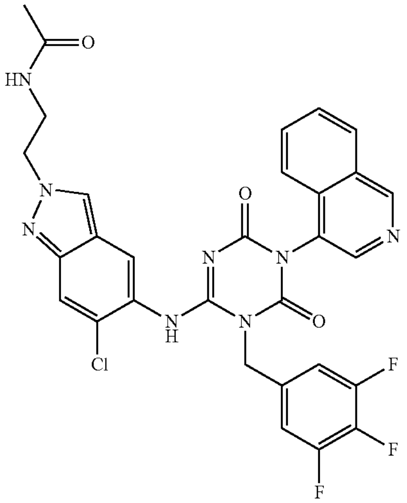 [SMILES: CC(=O)NCCn1cc2cc(Nc3nc(=O)n(-c4cncc5ccccc45)c(=O)n3Cc3cc(F)c(F)c(F)c3)c(Cl)cc2n1] | 1 | 1.94 | 635 | |
| I-0472 | 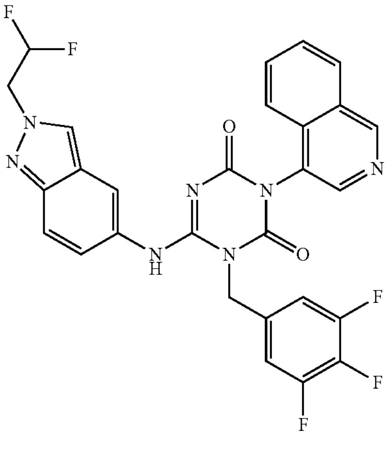 [SMILES: O=c1nc(Nc2ccc3nn(CC(F)F)cc3c2)n(Cc2cc(F)c(F)c(F)c2)c(=O)n1-c1cncc2ccccc12] | 3 | 1.87 | 580 | |

TABLE 51
| Compound No. | Structure | LC/MS Measured condition | Retention time (min) | m/z | Con-figration |
|---|---|---|---|---|---|
| I-0477 | 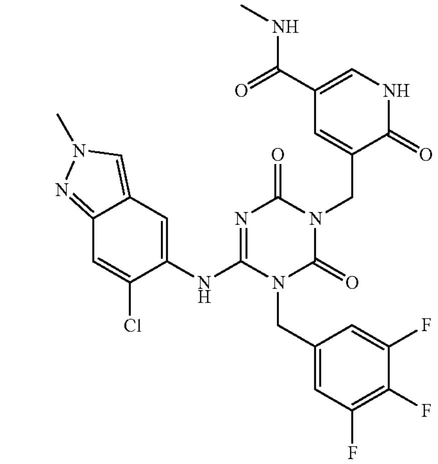 [SMILES: CNC(=O)c1c[nH]c(=O)c(Cn2c(=O)nc(Nc3cc4cn(C)nc4cc3Cl)n(Cc3cc(F)c(F)c(F)c3)c2=O)c1] | 1 | 1.80 | 601 | |
| I-0478 | 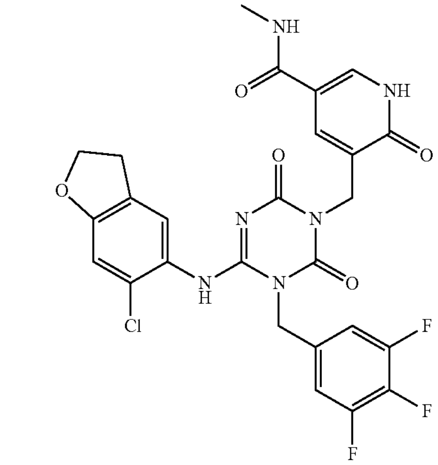 [SMILES: CNC(=O)c1c[nH]c(=O)c(Cn2c(=O)nc(Nc3cc4c(cc3Cl)OCC4)n(Cc3cc(F)c(F)c(F)c3)c2=O)c1] | 1 | 1.99 | 589 | |
| I-0479 | 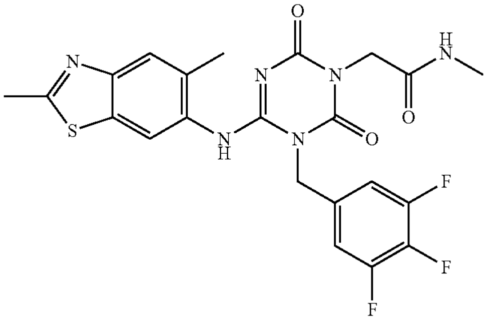 | 1 | 2.00 | 505.1 | |

TABLE 51-continued
| Compound No. | Structure | LC/MS Measured condition | Retention time (min) | m/z | Con-figuration |
|---|---|---|---|---|---|
| I-480 | 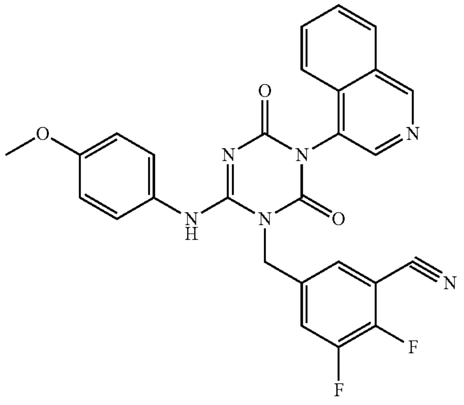 [SMILES: COc1ccc(Nc2nc(=O)n(-c3cncc4ccccc34)c(=O)n2Cc2cc(F)c(F)c(C#N)c2)cc1] | 1 | 2.03 | 513 | |
| I-0481 | 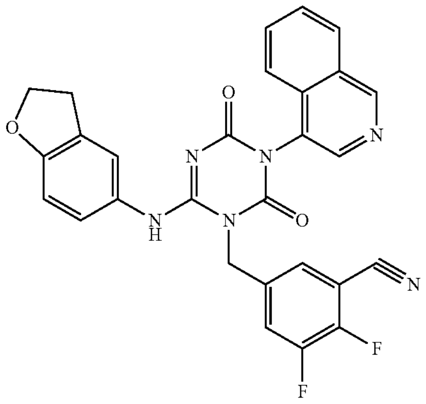 [SMILES: N#Cc1cc(Cn2c(Nc3ccc4c(c3)CCO4)nc(=O)n(-c3cncc4ccccc34)c2=O)cc(F)c1F] | 1 | 2.00 | 525 | |
TABLE 52
| Compound No. | Structure | LC/MS Measured condition | Retention time (min) | m/z | Con-figuration |
|---|---|---|---|---|---|
| I-0482 | 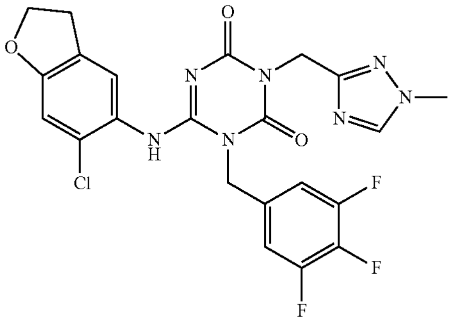 [SMILES: Cn1cnc(Cn2c(=O)nc(Nc3cc4c(cc3Cl)OCC4)n(Cc3cc(F)c(F)c(F)c3)c2=O)n1] | 2 | 2.12 | 520 | |

TABLE 52-continued
| Compound No. | Structure | LC/MS Measured condition | Retention time (min) | m/z | Con-figration |
|---|---|---|---|---|---|
| I-0483 | 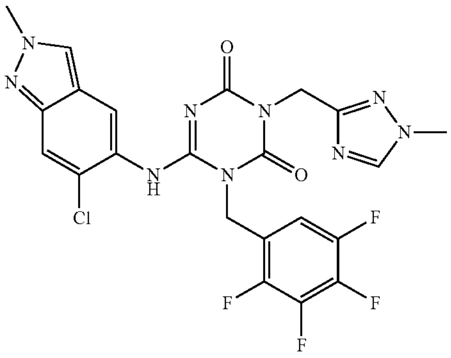 | 1 | 1.93 | 550 | |
| II-0001 | 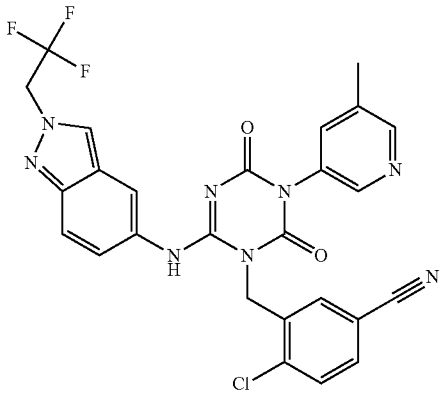 [SMILES: Cc1cncc(-n2c(=O)nc(Nc3ccc4nn(CC(F)(F)F)cc4c3)n(Cc3cc(C#N)ccc3Cl)c2=O)c1] | 1 | 1.83 | 567.2 | |
| II-0002 | 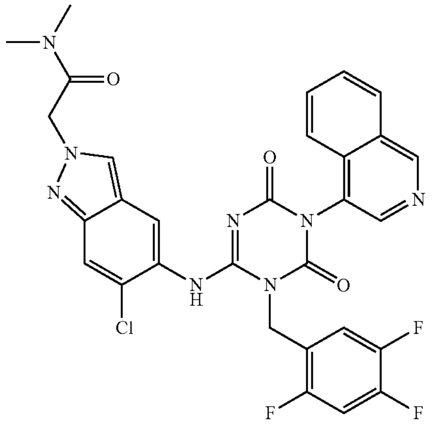 [SMILES: CN(C)C(=O)Cn1cc2cc(Nc3nc(=O)n(-c4cncc5ccccc45)c(=O)n3Cc3cc(F)c(F)cc3F)c(Cl)cc2n1] | 1 | 1.91 | 635.3 | |

TABLE 52-continued
| Compound No. | Structure | LC/MS Measured condition | Retention time (min) | m/z | Con-figuration |
|---|---|---|---|---|---|
| II-0003 | 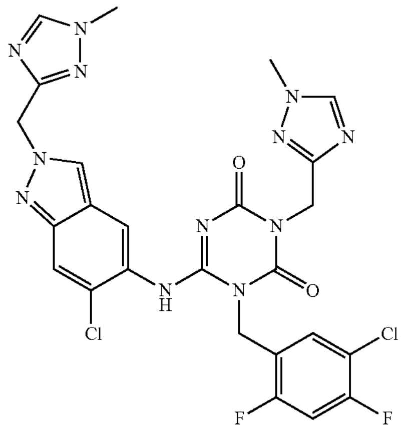 [SMILES: Cn1cnc(Cn2cc3cc(Nc4nc(=O)n(Cc5ncn(C)n5)c(=O)n4Cc4cc(Cl)c(F)cc4F)c(Cl)cc3n2)n1] | 1 | 1.75 | 629.2 | |
TABLE 53
| Compound No. | Structure | LC/MS Measured condition | Retention time (min) | m/z | Con-figuration |
|---|---|---|---|---|---|
| II-0004 | 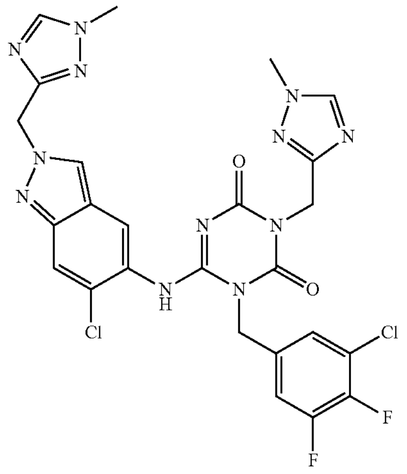 [SMILES: Cn1cnc(Cn2cc3cc(Nc4nc(=O)n(Cc5ncn(C)n5)c(=O)n4Cc4cc(F)c(F)c(Cl)c4)c(Cl)cc3n2)n1] | 1 | 1.80 | 629.2 | |
| II-0005 | 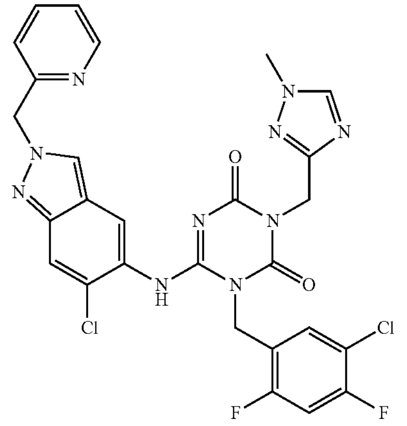 [SMILES: Cn1cnc(Cn2c(=O)nc(Nc3cc4cn(Cc5ccccn5)nc4cc3Cl)n(Cc3cc(Cl)c(F)cc3F)c2=O)n1] | 1 | 1.85 | 625.1 | |

TABLE 53-continued
| Compound No. | Structure | LC/MS Measured condition | Retention time (min) | m/z | Con-figration |
|---|---|---|---|---|---|
| II-0006 | 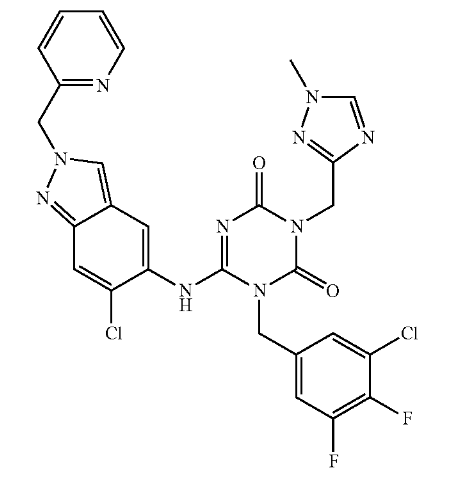 [SMILES: Cn1cnc(Cn2c(=O)nc(Nc3cc4cn(Cc5ccccn5)nc4cc3Cl)n(Cc3cc(F)c(F)c(Cl)c3)c2=O)n1] | 1 | 1.91 | 625.1 | |
| II-0007 | 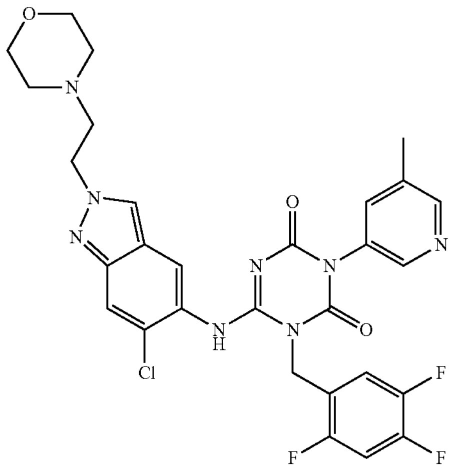 [SMILES: Cc1cncc(-n2c(=O)nc(Nc3cc4cn(CCN5CCOCC5)nc4cc3Cl)n(Cc3cc(F)c(F)cc3F)c2=O)c1] | 1 | 1.36 | 627.3 | |
| II-0008 | 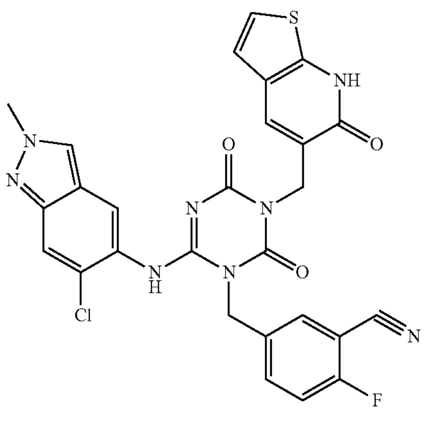 [SMILES: Cn1cc2cc(Nc3nc(=O)n(Cc4cc5ccsc5[nH]c4=O)c(=O)n3Cc3ccc(F)c(C#N)c3)c(Cl)cc2n1] | 1 | 1.72 | 590 | |

TABLE 54
| Compound No. | Structure | LC/MS Measured condition | Retention time (min) | m/z | Con-figration |
|---|---|---|---|---|---|
| II-0009 | 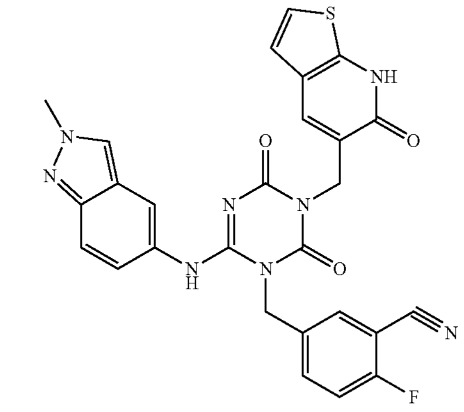 [SMILES: Cn1cc2cc(Nc3nc(=O)n(Cc4cc5ccsc5[nH]c4=O)c(=O)n3Cc3ccc(F)c(C#N)c3)ccc2n1] | 1 | 1.65 | 555 | |
| II-0010 | 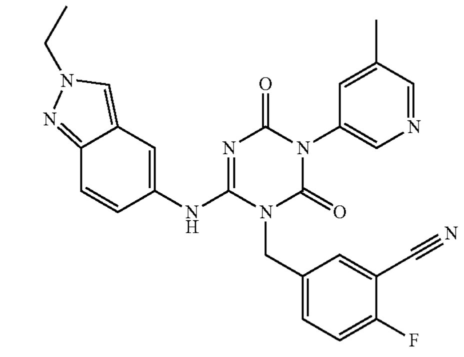 [SMILES: CCn1cc2cc(Nc3nc(=O)n(-c4cncc(C)c4)c(=O)n3Cc3ccc(F)c(C#N)c3)ccc2n1] | 1 | 1.62 | 497.2 | |
| II-0011 | 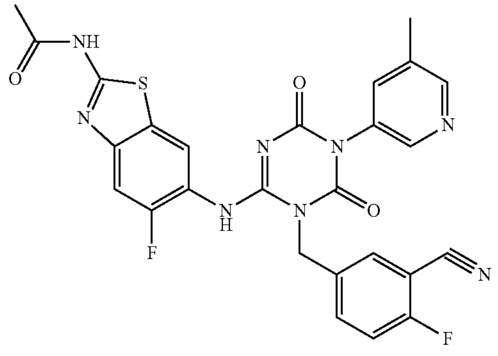 [SMILES: CC(=O)Nc1nc2cc(F)c(Nc3nc(=O)n(-c4cncc(C)c4)c(=O)n3Cc3ccc(F)c(C#N)c3)cc2s1] | 1 | 1.78 | 561.2 | |
| II-0012 | 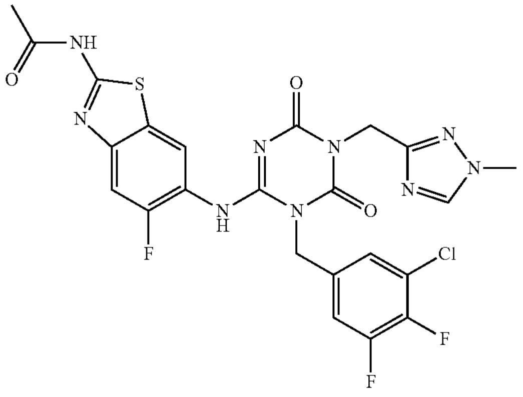 [SMILES: CC(=O)Nc1nc2cc(F)c(Nc3nc(=O)n(Cc4ncn(C)n4)c(=O)n3Cc3cc(F)c(F)c(Cl)c3)cc2s1] | 1 | 1.91 | 592.1 | |

TABLE 54-continued
| Compound No. | Structure | LC/MS Measured condition | Retention time (min) | m/z | Con-figration |
|---|---|---|---|---|---|
| II-0013 | 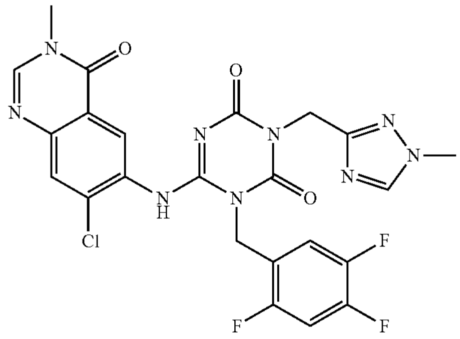 [SMILES: Cn1cnc(Cn2c(=O)nc(Nc3cc4c(=O)n(C)cnc4cc3Cl)n(Cc3cc(F)c(F)cc3F)c2=O)n1] | 1 | 1.79 | 560.1 | |
TABLE 55
| Compound No. | Structure | LC/MS Measured condition | Retention time (min) | m/z | Con-figration |
|---|---|---|---|---|---|
| II-0014 | 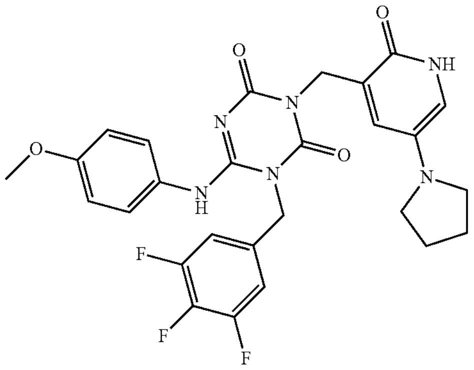 [SMILES: COc1ccc(Nc2nc(=O)n(Cc3cc(N4CCCC4)c[nH]c3=O)c(=O)n2Cc2cc(F)c(F)c(F)c2)cc1] | 2 | 1.89 | 555.3 | |
| II-0015 | 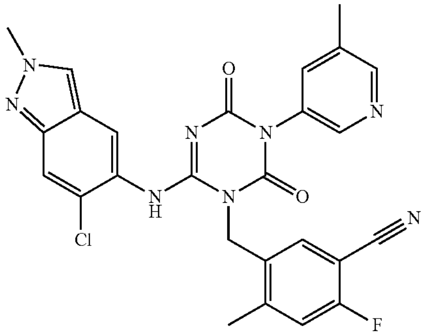 | 1 | 1.82 | 531 | |

TABLE 55-continued
| Compound No. | Structure | LC/MS Measured condition | Retention time (min) | m/z | Con-figration |
|---|---|---|---|---|---|
| II-0017 | 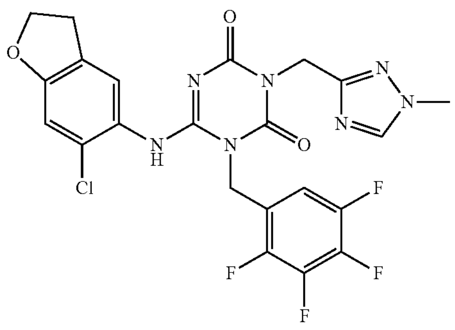 [SMILES: Cn1cnc(Cn2c(=O)nc(Nc3cc4c(cc3Cl)OCC4)n(Cc3cc(F)c(F)c(F)c3F)c2=O)n1] | 1 | 2.07 | 538 | |
| II-0018 | 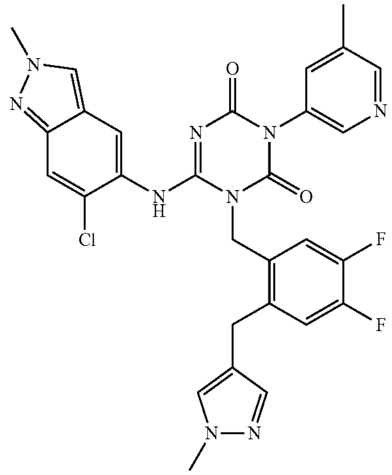 [SMILES: Cc1cncc(-n2c(=O)nc(Nc3cc4cn(C)nc4cc3Cl)n(Cc3cc(F)c(F)cc3Cc3cnn(C)c3)c2=O)c1] | 1 | 1.87 | 604 | |
| II-0019 | 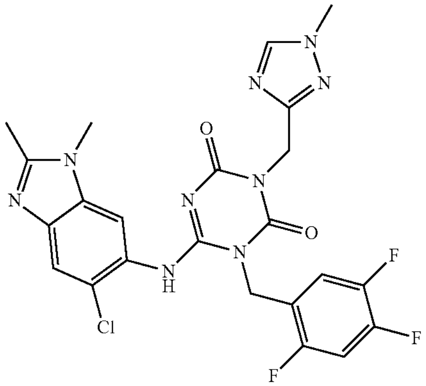 [SMILES: Cc1nc2cc(Cl)c(Nc3nc(=O)n(Cc4ncn(C)n4)c(=O)n3Cc3cc(F)c(F)cc3F)cc2n1C] | 1 | 1.63 | 546 | |

TABLE 56
| Compound No. | Structure | LC/MS Measured condition | Retention time (min) | m/z | Con-figration |
|---|---|---|---|---|---|
| II-0020 | 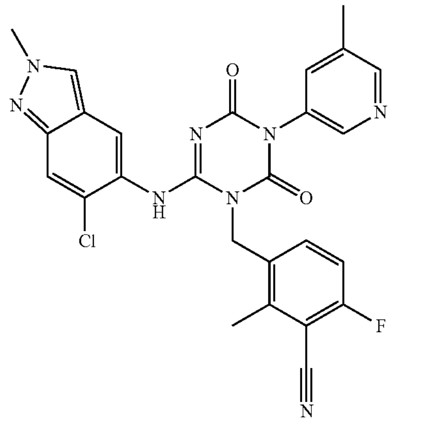 [SMILES: Cc1cncc(-n2c(=O)nc(Nc3cc4cn(C)nc4cc3Cl)n(Cc3ccc(F)c(C#N)c3C)c2=O)c1] | 1 | 1.83 | 531 | |
| II-0021 | 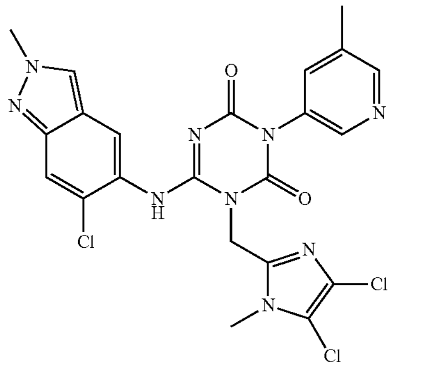 [SMILES: Cc1cncc(-n2c(=O)nc(Nc3cc4cn(C)nc4cc3Cl)n(Cc3nc(Cl)c(Cl)n3C)c2=O)c1] | 1 | 1.83 | 546 | |
| II-0022 | 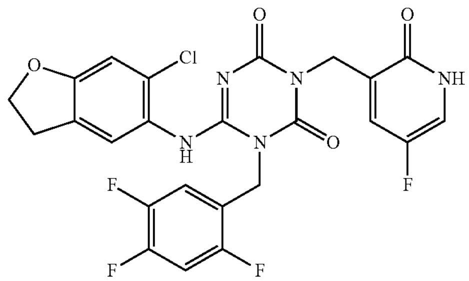 [SMILES: O=c1[nH]cc(F)cc1Cn1c(=O)nc(Nc2cc3c(cc2Cl)OCC3)n(Cc2cc(F)c(F)cc2F)c1=O] | 2 | 2.14 | 550 | |
| II-0023 | 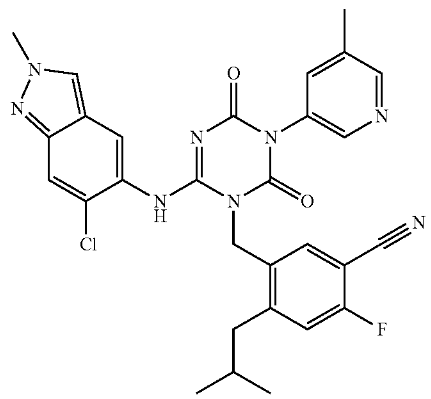 [SMILES: Cc1cncc(-n2c(=O)nc(Nc3cc4cn(C)nc4cc3Cl)n(Cc3cc(C#N)c(F)cc3CC(C)C)c2=O)c1] | 1 | 2.34 | 573.2 | |

TABLE 56-continued
| Compound No. | Structure | LC/MS Measured condition | Retention time (min) | m/z | Con-figration |
|---|---|---|---|---|---|
| II-0024 | 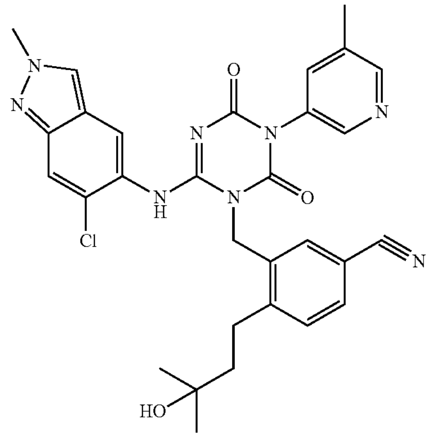 [SMILES: Cc1cncc(-n2c(=O)nc(Nc3cc4cn(C)nc4cc3Cl)n(Cc3cc(C#N)ccc3CCC(C)(C)O)c2=O)c1] | 1 | 1.76 | 585.2 | |
TABLE 57
| Compound No. | Structure | LC/MS Measured condition | Retention time (min) | m/z | Con-figration |
|---|---|---|---|---|---|
| II-0025 | 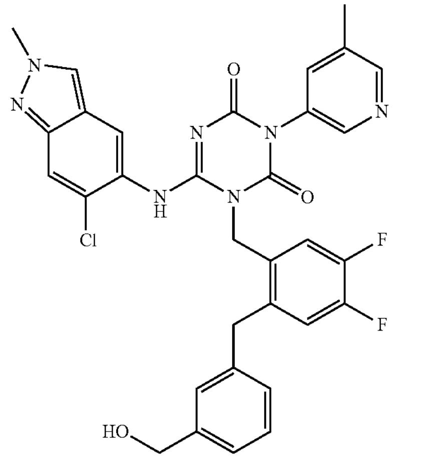 [SMILES: Cc1cncc(-n2c(=O)nc(Nc3cc4cn(C)nc4cc3Cl)n(Cc3cc(F)c(F)cc3Cc3cccc(CO)c3)c2=O)c1] | 1 | 2.02 | 630.1 | |

TABLE 57-continued
| Compound No. | Structure | LC/MS Measured condition | Retention time (min) | m/z | Con-figration |
|---|---|---|---|---|---|
| II-0027 | 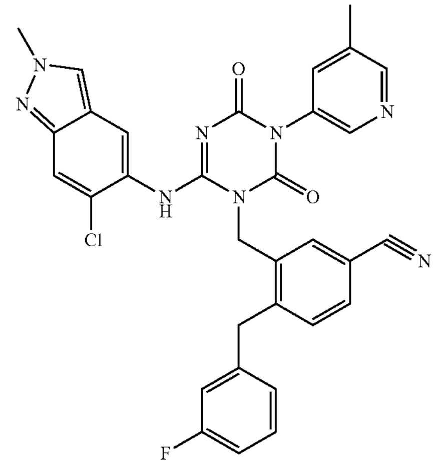 [SMILES: Cc1cncc(-n2c(=O)nc(Nc3cc4cn(C)nc4cc3Cl)n(Cc3cc(C#N)ccc3Cc3cccc(F)c3)c2=O)c1] | 1 | 2.22 | 607.1 | |
| II-0028 | 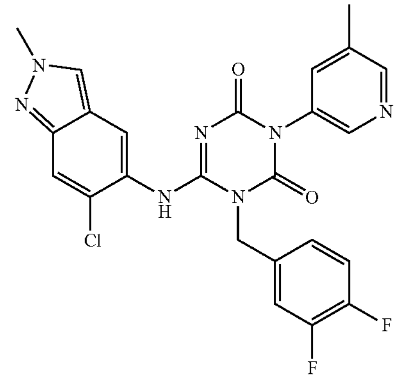 [SMILES: Cc1cncc(-n2c(=O)nc(Nc3cc4cn(C)nc4cc3Cl)n(Cc3ccc(F)c(F)c3)c2=O)c1] | 1 | 1.92 | 510 | |
| II-0029 | 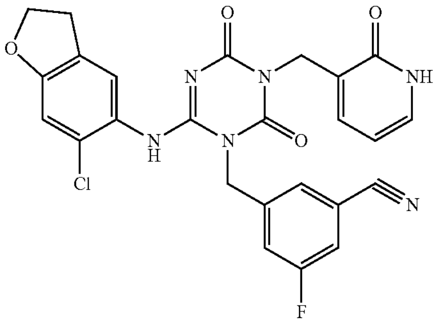 [SMILES: N#Cc1cc(F)cc(Cn2c(Nc3cc4c(cc3Cl)OCC4)nc(=O)n(Cc3ccc[nH]c3=O)c2=O)c1] | 1 | 1.95 | 521 | |
| II-0030 | 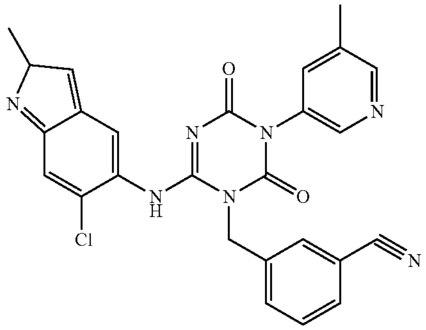 [SMILES: Cc1cncc(-n2c(=O)nc(Nc3cc4c(cc3Cl)=NC(C)C=4)n(Cc3cccc(C#N)c3)c2=O)c1] | 1 | 1.77 | 499.1 | |

TABLE 58
| Compound No. | Structure | LC/MS Measured condition | Retention time (min) | m/z | Con-figration |
|---|---|---|---|---|---|
| II-0031 | 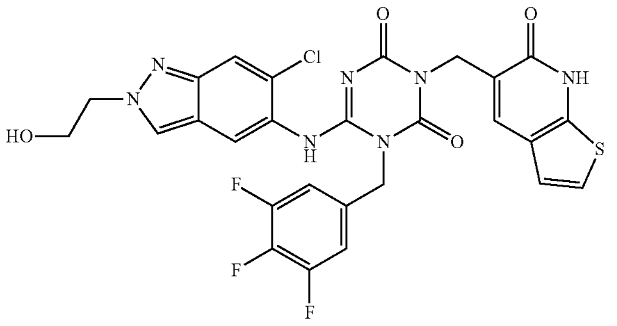 [SMILES: O=c1[nH]c2sccc2cc1Cn1c(=O)nc(Nc2cc3cn(CCO)nc3cc2Cl)n(Cc2cc(F)c(F)c(F)c2)c1=O] | 1 | 1.87 | 630 | |
| II-0032 | 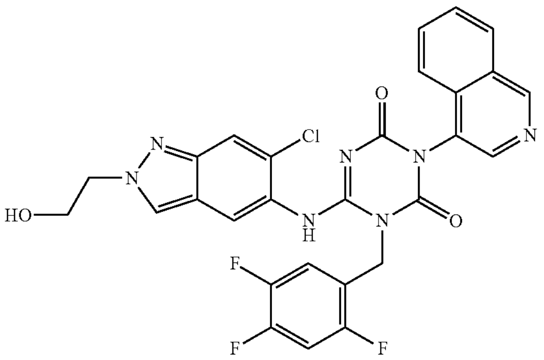 [SMILES: O=c1nc(Nc2cc3cn(CCO)nc3cc2Cl)n(Cc2cc(F)c(F)cc2F)c(=O)n1-c1cncc2ccccc12] | 1 | 1.86 | 594 | |
| II-0033 | 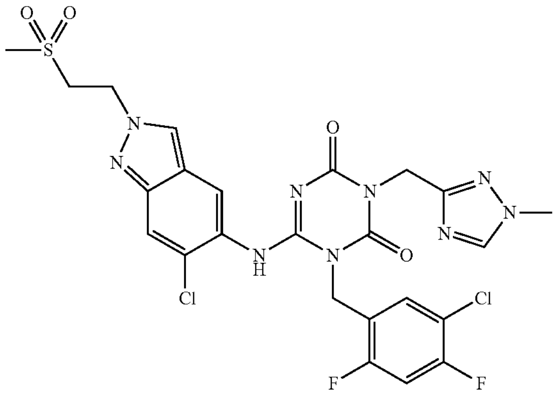 | 1 | 1.81 | 640 | |
| II-0034 | 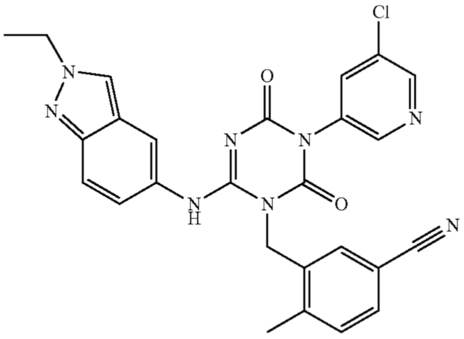 [SMILES: CCn1cc2cc(Nc3nc(=O)n(-c4cncc(Cl)c4)c(=O)n3Cc3cc(C#N)ccc3C)ccc2n1] | 1 | 1.82 | 513 | |

TABLE 58-continued
| Compound No. | Structure | LC/MS Measured condition | Retention time (min) | m/z | Con-figuration |
|---|---|---|---|---|---|
| II-0035 | 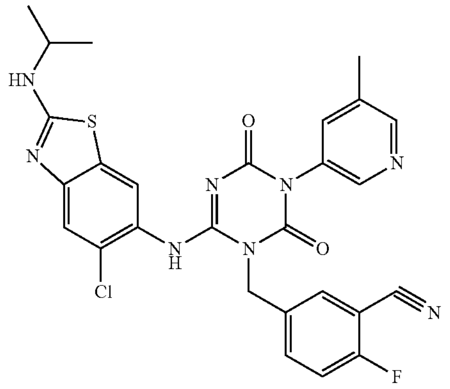 [SMILES: Cc1cncc(-n2c(=O)nc(Nc3cc4sc(NC(C)C)nc4cc3Cl)n(Cc3ccc(F)c(C#N)c3)c2=O)c1] | 1 | 1.95 | 577 | |
TABLE 59
| Compound No. | Structure | LC/MS Measured condition | Retention time (min) | m/z | Con-figuration |
|---|---|---|---|---|---|
| II-0036 | 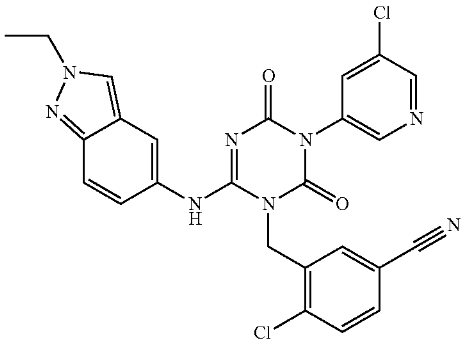 [SMILES: CCn1cc2cc(Nc3nc(=O)n(-c4cncc(Cl)c4)c(=O)n3Cc3cc(C#N)ccc3Cl)ccc2n1] | 1 | 1.90 | 533 | |
| II-0037 | 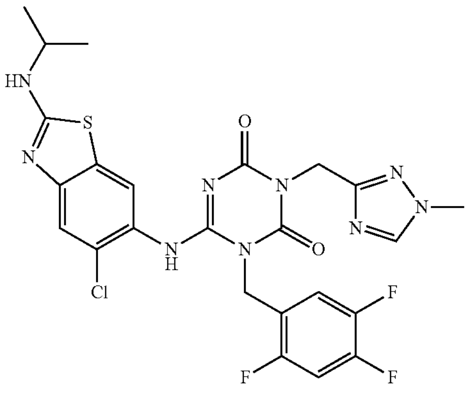 [SMILES: CC(C)Nc1nc2cc(Cl)c(Nc3nc(=O)n(Cc4ncn(C)n4)c(=O)n3Cc3cc(F)c(F)cc3F)cc2s1] | 1 | 1.92 | 592 | |

TABLE 59-continued
| Compound No. | Structure | LC/MS Measured condition | Retention time (min) | m/z | Con-figration |
|---|---|---|---|---|---|
| II-0038 | 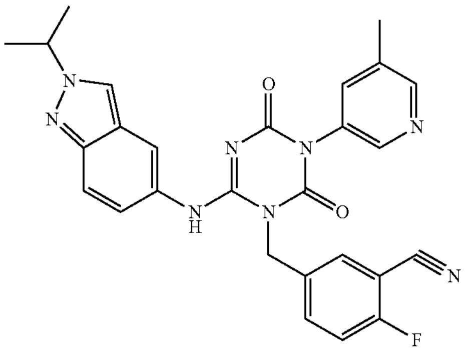 [SMILES: Cc1cncc(-n2c(=O)nc(Nc3ccc4nn(C(C)C)cc4c3)n(Cc3ccc(F)c(C#N)c3)c2=O)c1] | 1 | 1.59 | 511 | |
| II-0039 | 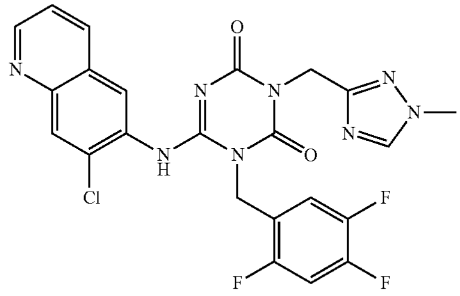 [SMILES: Cn1cnc(Cn2c(=O)nc(Nc3cc4cccnc4cc3Cl)n(Cc3cc(F)c(F)cc3F)c2=O)n1] | 1 | 1.72 | 529 | |
| II-0040 | 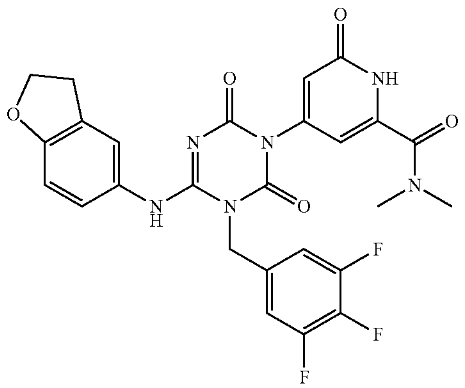 [SMILES: CN(C)C(=O)c1cc(-n2c(=O)nc(Nc3ccc4c(c3)CCO4)n(Cc3cc(F)c(F)c(F)c3)c2=O)cc(=O)[nH]1] | 1 | 1.79 | 569 | |

TABLE 60
| Compound No. | Structure | LC/MS Measured condition | Retention time (min) | m/z | Con- figration |
|---|---|---|---|---|---|
| II-0041 | 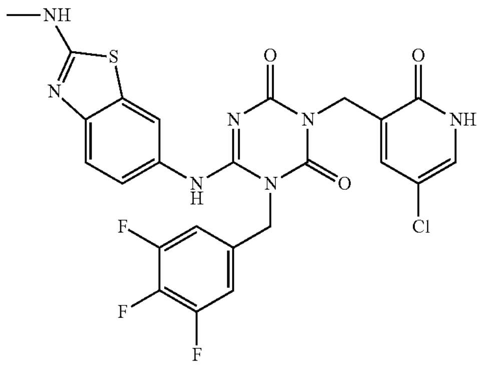 [SMILES: CNc1nc2ccc(Nc3nc(=O)n(Cc4cc(Cl)c[nH]c4=O)c(=O)n3Cc3cc(F)c(F)c(F)c3)cc2s1] | 1 | 1.65 | 576 | |
| II-0042 | 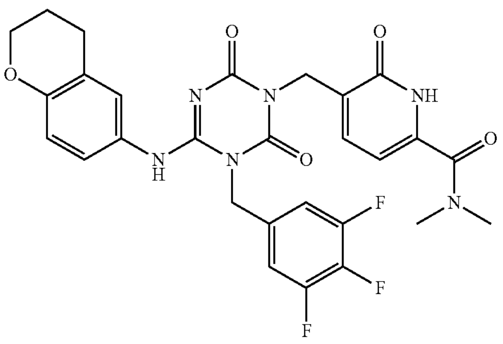 [SMILES: CN(C)C(=O)c1ccc(Cn2c(=O)nc(Nc3ccc4c(c3)CCCO4)n(Cc3cc(F)c(F)c(F)c3)c2=O)c(=O)[nH]1] | 1 | 1.88 | 583 | |
| II-0043 | 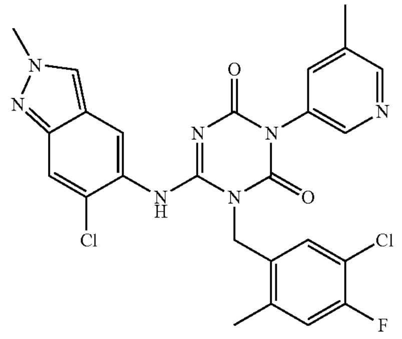 [SMILES: Cc1cncc(-n2c(=O)nc(Nc3cc4cn(C)nc4cc3Cl)n(Cc3cc(Cl)c(F)cc3C)c2=O)c1] | 1 | 2.12 | 540 | |
| II-0044 | 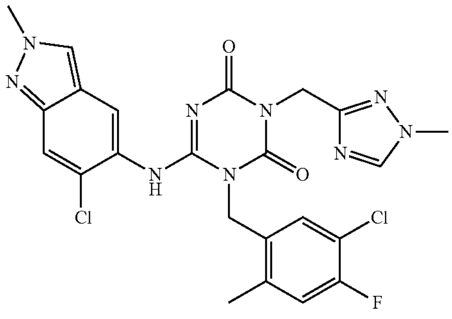 | 1 | 1.94 | 544 | |

TABLE 60-continued
| Compound No. | Structure | LC/MS Measured condition | Retention time (min) | m/z | Con-figration |
|---|---|---|---|---|---|
| II-0045 | 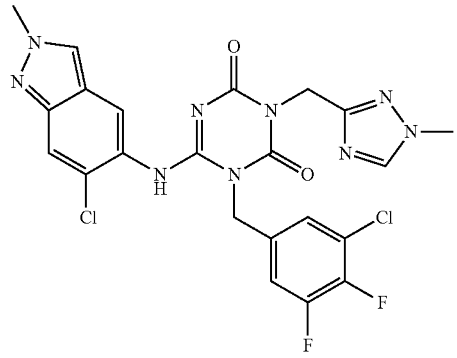 | 1 | 2.01 | 548 | |
TABLE 61
| Compound No. | Structure | LC/MS Measured condition | Retention time (min) | m/z | Con-figration |
|---|---|---|---|---|---|
| II-0046 | 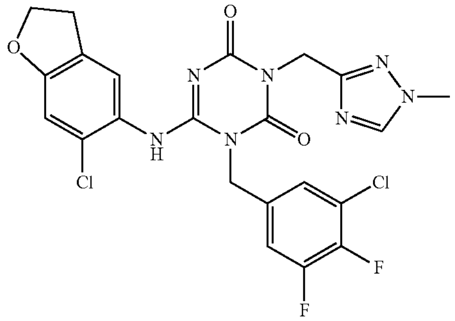 [SMILES: Cn1cnc(Cn2c(=O)nc(Nc3cc4c(cc3Cl)OCC4)n(Cc3cc(F)c(F)c(Cl)c3)c2=O)n1] | 1 | 2.23 | 536 | |
| II-0047 | 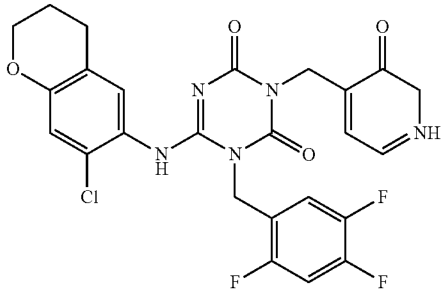 [SMILES: O=C1CN=CC=C1Cn1c(=O)nc(Nc2cc3c(cc2Cl)OCCC3)n(Cc2cc(F)c(F)cc2F)c1=O] | 1 | 2.17 | 546 | |

TABLE 61-continued
| Compound No. | Structure | LC/MS Measured condition | Retention time (min) | m/z | Con-figration |
|---|---|---|---|---|---|
| II-0048 | 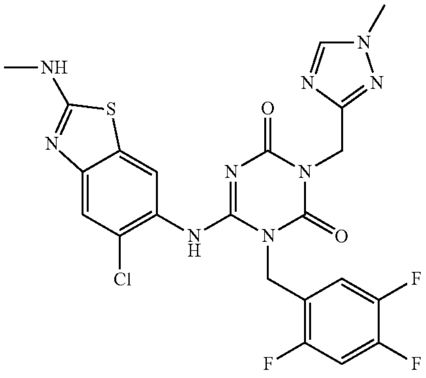 [SMILES: CNc1nc2cc(Cl)c(Nc3nc(=O)n(Cc4ncn(C)n4)c(=O)n3Cc3cc(F)c(F)cc3F)cc2s1] | 1 | 1.88 | 564.1 | |
| II-0049 | 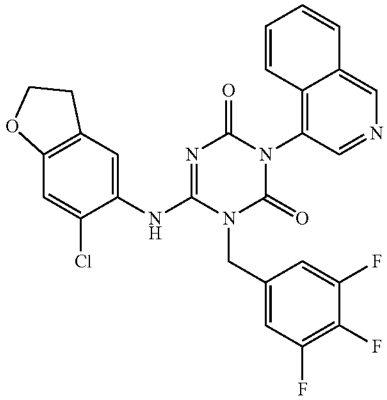 [SMILES: O=c1nc(Nc2cc3c(cc2Cl)OCC3)n(Cc2cc(F)c(F)c(F)c2)c(=O)n1-c1cncc2ccccc12] | 4 | 2.36 | 552 | |
| II-0050 | 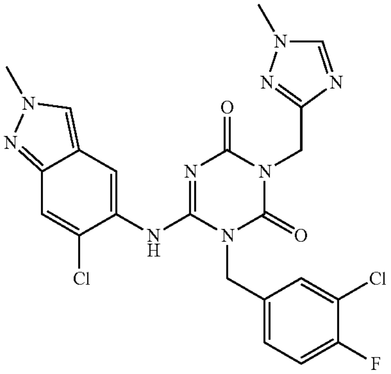 [SMILES: Cn1cnc(Cn2c(=O)nc(Nc3cc4cn(C)nc4cc3Cl)n(Cc3ccc(F)c(Cl)c3)c2=O)n1] | 1 | 1.94 | 530 | |

TABLE 62
| Compound No. | Structure | LC/MS Measured condition | Retention time (min) | m/z | Con-figration |
|---|---|---|---|---|---|
| II-0051 | 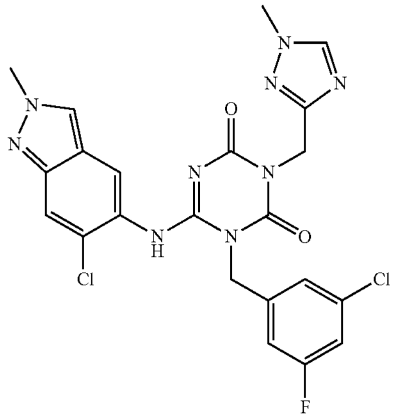 [SMILES: Cn1cnc(Cn2c(=O)nc(Nc3cc4cn(C)nc4cc3Cl)n(Cc3cc(F)cc(Cl)c3)c2=O)n1] | 1 | 1.96 | 530 | |
| II-0052 | 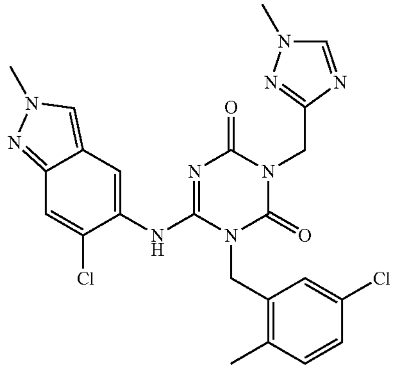 [SMILES: Cc1ccc(Cl)cc1Cn1c(Nc2cc3cn(C)nc3cc2Cl)nc(=O)n(Cc2ncn(C)n2)c1=O] | 3 | 1.93 | 526 | |
| II-0053 | 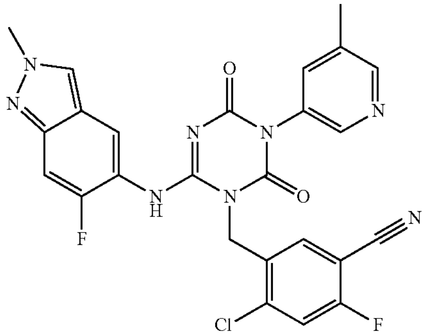 [SMILES: Cc1cncc(-n2c(=O)nc(Nc3cc4cn(C)nc4cc3F)n(Cc3cc(C#N)c(F)cc3Cl)c2=O)c1] | 1 | 1.71 | 535.3 | |
| II-0054 | 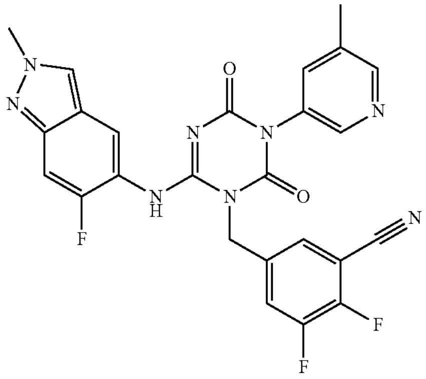 [SMILES: Cc1cncc(-n2c(=O)nc(Nc3cc4cn(C)nc4cc3F)n(Cc3cc(F)c(F)c(C#N)c3)c2=O)c1] | 1 | 1.66 | 519.4 | |

TABLE 62-continued
| Compound No. | Structure | LC/MS Measured condition | Retention time (min) | m/z | Con-figration |
|---|---|---|---|---|---|
| II-0055 | 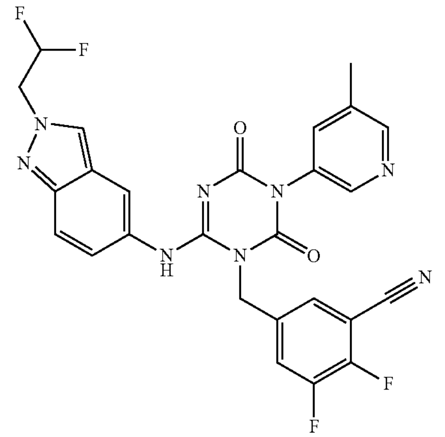 [SMILES: Cc1cncc(-n2c(=O)nc(Nc3ccc4nn(CC(F)F)cc4c3)n(Cc3cc(F)c(F)c(C#N)c3)c2=O)c1] | 1 | 1.69 | 551.4 | |
TABLE 63
| Compound No. | Structure | LC/MS Measured condition | Retention time (min) | m/z | Con-figration |
|---|---|---|---|---|---|
| II-0056 | 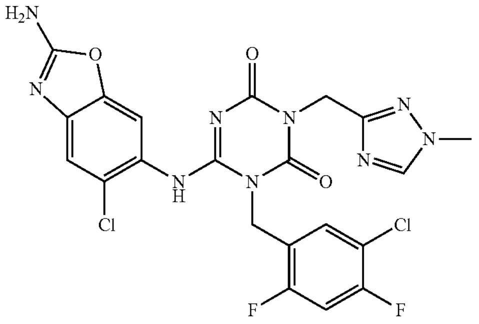 [SMILES: Cn1cnc(Cn2c(=O)nc(Nc3cc4oc(N)nc4cc3Cl)n(Cc3cc(Cl)c(F)cc3F)c2=O)n1] | 1 | 1.64 | 550.3 | |
| II-0057 | 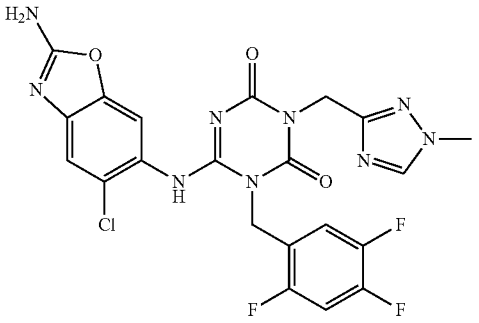 [SMILES: Cn1cnc(Cn2c(=O)nc(Nc3cc4oc(N)nc4cc3Cl)n(Cc3cc(F)c(F)cc3F)c2=O)n1] | 1 | 1.55 | 534.3 | |

TABLE 63-continued
| Compound No. | Structure | LC/MS Measured condition | Retention time (min) | m/z | Con-figration |
|---|---|---|---|---|---|
| II-0058 | 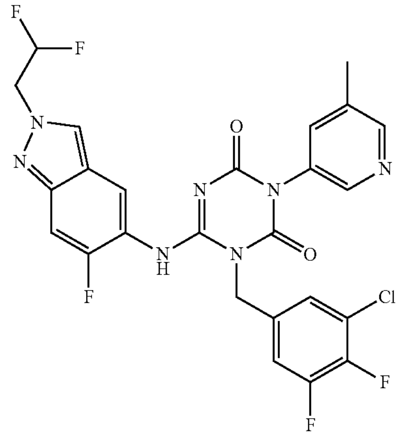 [SMILES: Cc1cncc(-n2c(=O)nc(Nc3cc4cn(CC(F)F)nc4cc3F)n(Cc3cc(F)c(F)c(Cl)c3)c2=O)c1] | 1 | 2.04 | 578.2 | |
| II-0059 | 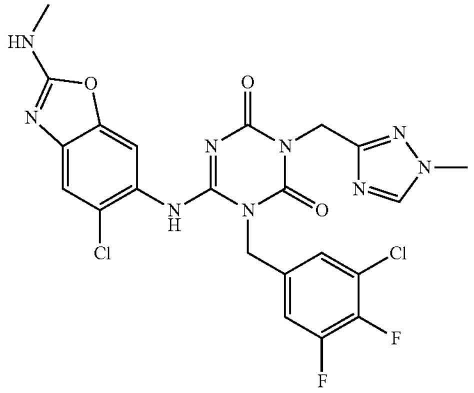 | 1 | 1.81 | 564.3 | |
| II-0060 | 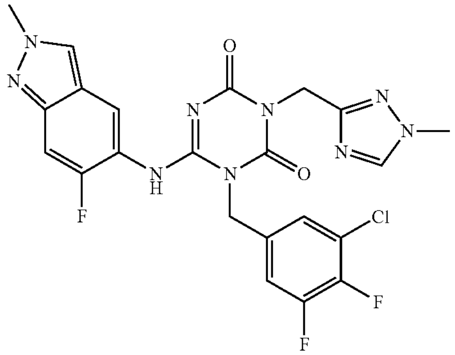 | 1 | 1.69 | 532.3 | |

TABLE 64
| Compound No. | Structure | LC/MS Measured condition | Retention time (min) | m/z | Con-figration |
|---|---|---|---|---|---|
| II-0061 | 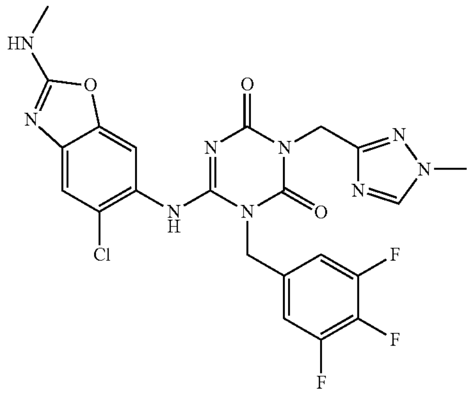 [SMILES: CNc1nc2cc(Cl)c(Nc3nc(=O)n(Cc4ncn(C)n4)c(=O)n3Cc3cc(F)c(F)c(F)c3)cc2o1] | 1 | 1.70 | 548.3 | |
| II-0062 | 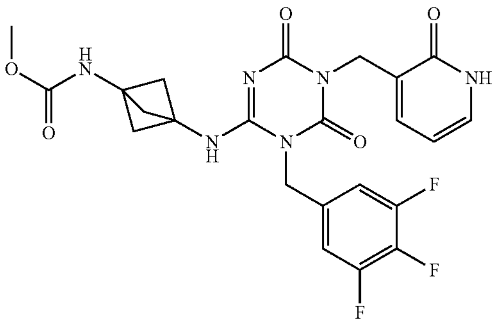 [SMILES: COC(=O)NC12CC(Nc3nc(=O)n(Cc4ccc[nH]c4=O)c(=O)n3Cc3cc(F)c(F)c(F)c3)(C1)C2] | 1 | 1.41 | 519.3 | |
| II-0063 | 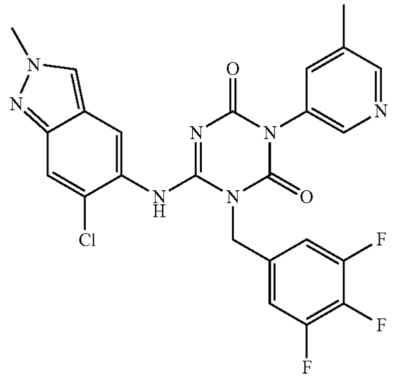 [SMILES: Cc1cncc(-n2c(=O)nc(Nc3cc4cn(C)nc4cc3Cl)n(Cc3cc(F)c(F)c(F)c3)c2=O)c1] | 1 | 2.16 | 562.2 | |
| II-0064 | 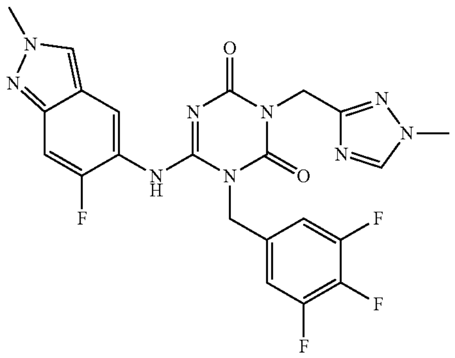 | 1 | 1.59 | 516.3 | |

TABLE 64-continued
| Compound No. | Structure | LC/MS Measured condition | Retention time (min) | m/z | Con- figration |
|---|---|---|---|---|---|
| II-0065 | 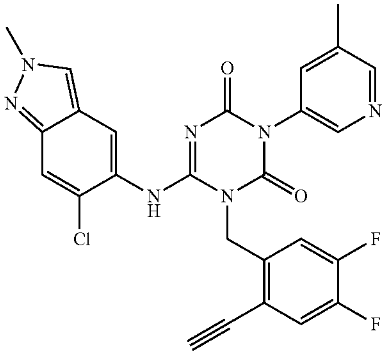 [SMILES: C#Cc1cc(F)c(F)cc1Cn1c(Nc2cc3cn(C)nc3cc2Cl)nc(=O)n(-c2cncc(C)c2)c1=O] | 1 | 2.02 | 534.1 | |
TABLE 65
| Compound No. | Structure | LC/MS Measured condition | Retention time (min) | m/z | Con- figration |
|---|---|---|---|---|---|
| II-0066 | 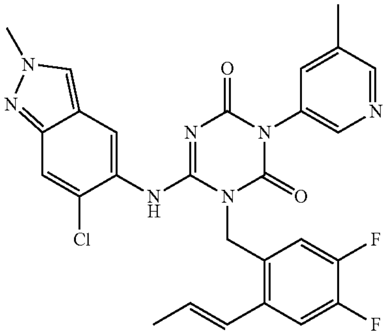 [SMILES: C/C=C/c1cc(F)c(F)cc1Cn1c(Nc2cc3cn(C)nc3cc2Cl)nc(=O)n(-c2cncc(C)c2)c1=O] | 1 | 2.21 | 550.1 | |
| II-0067 | 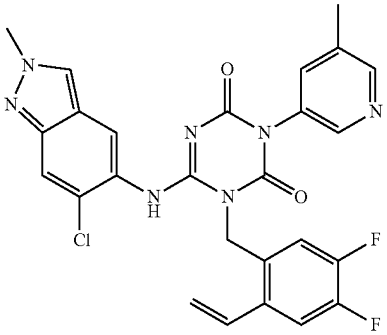 [SMILES: C=Cc1cc(F)c(F)cc1Cn1c(Nc2cc3cn(C)nc3cc2Cl)nc(=O)n(-c2cncc(C)c2)c1=O] | 1 | 2.09 | 536.1 | |

TABLE 65-continued
| Compound No. | Structure | LC/MS Measured condition | Retention time (min) | m/z | Con-figration |
|---|---|---|---|---|---|
| II-0068 | 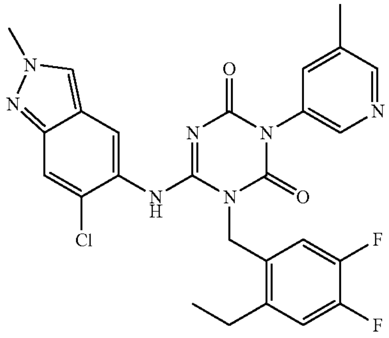 | 1 | 2.13 | 538.1 | |
| II-0069 | 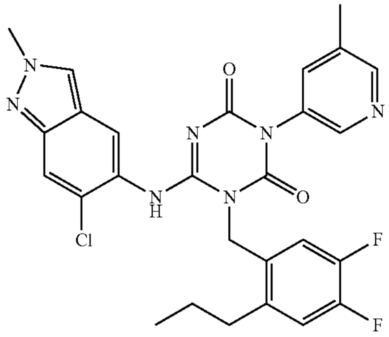 [SMILES: CCCc1cc(F)c(F)cc1Cn1c(Nc2cc3cn(C)nc3cc2Cl)nc(=O)n(-c2cncc(C)c2)c1=O] | 1 | 2.28 | 552.1 | |
| II-0070 | 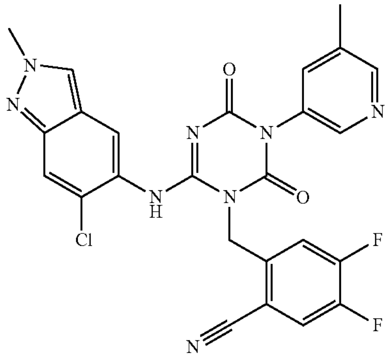 [SMILES: Cc1cncc(-n2c(=O)nc(Nc3cc4cn(C)nc4cc3Cl)n(Cc3cc(F)c(F)cc3C#N)c2=O)c1] | 1 | 1.92 | 535.1 | |

TABLE 66
| Compound No. | Structure | LC/MS Measured condition | Retention time (min) | m/z | Con-figration |
|---|---|---|---|---|---|
| II-0071 | 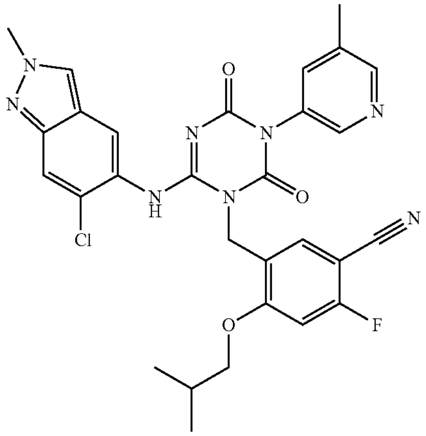 [SMILES: Cc1cncc(-n2c(=O)nc(Nc3cc4cn(C)nc4cc3Cl)n(Cc3cc(C#N)c(F)cc3OCC(C)C)c2=O)c1] | 1 | 2.15 | 589.4 | |
| II-0072 | 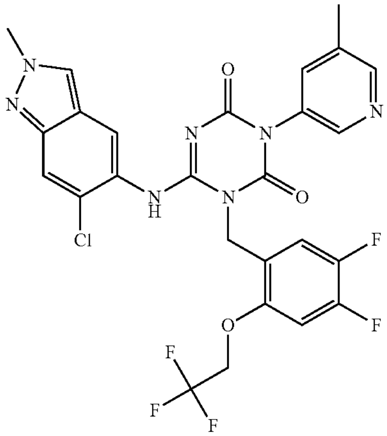 [SMILES: Cc1cncc(-n2c(=O)nc(Nc3cc4cn(C)nc4cc3Cl)n(Cc3cc(F)c(F)cc3OCC(F)(F)F)c2=O)c1] | 1 | 1.95 | 615.3 | |
| II-0073 | 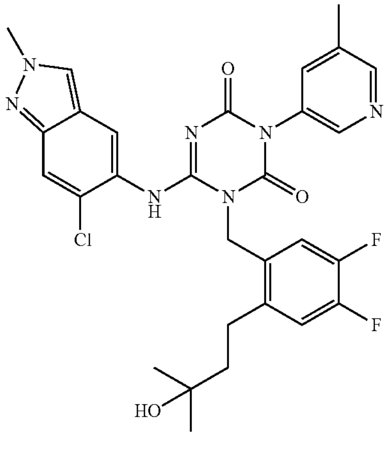 [SMILES: Cc1cncc(-n2c(=O)nc(Nc3cc4cn(C)nc4cc3Cl)n(Cc3cc(F)c(F)cc3CCC(C)(C)O)c2=O)c1] | 1 | 1.92 | 597 | |

TABLE 66-continued
| Compound No. | Structure | LC/MS Measured condition | Retention time (min) | m/z | Con- figration |
|---|---|---|---|---|---|
| II-0074 | 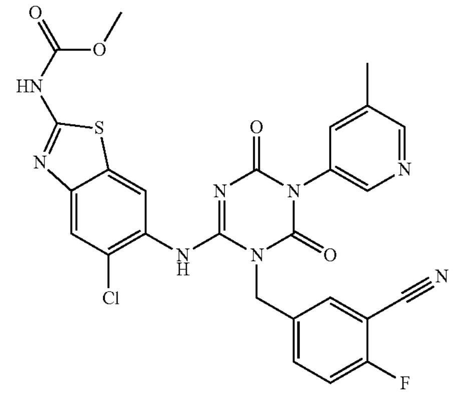 [SMILES: COC(=O)Nc1nc2cc(Cl)c(Nc3nc(=O)n(-c4cncc(C)c4)c(=O)n3Cc3ccc(F)c(C#N)c3)cc2s1] | 1 | 2.11 | 593 | |
| II-0075 | 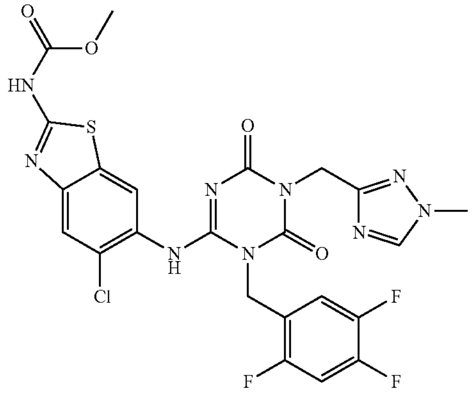 [SMILES: COC(=O)Nc1nc2cc(Cl)c(Nc3nc(=O)n(Cc4ncn(C)n4)c(=O)n3Cc3cc(F)c(F)cc3F)cc2s1] | 1 | 1.94 | 608.1 | |
TABLE 67
| Compound No. | Structure | LC/MS Measured condition | Retention time (min) | m/z | Con- figration |
|---|---|---|---|---|---|
| II-0076 | 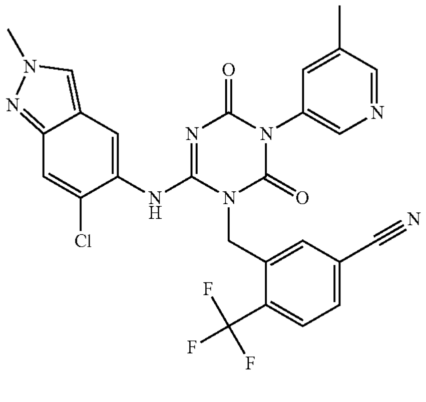 [SMILES: Cc1cncc(-n2c(=O)nc(Nc3cc4cn(C)nc4cc3Cl)n(Cc3cc(C#N)ccc3C(F)(F)F)c2=O)c1] | 1 | 2.07 | 567 | |

TABLE 67-continued
| Compound No. | Structure | LC/MS Measured condition | Retention time (min) | m/z | Con-figration |
|---|---|---|---|---|---|
| II-0077 | 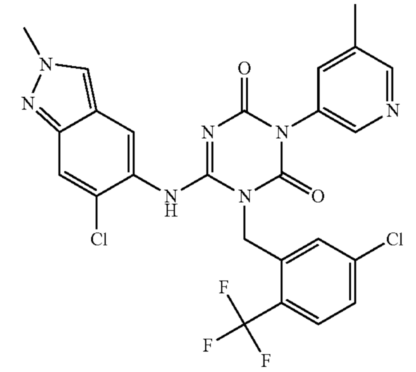 [SMILES: Cc1cncc(-n2c(=O)nc(Nc3cc4cn(C)nc4cc3Cl)n(Cc3cc(Cl)ccc3C(F)(F)F)c2=O)c1] | 1 | 2.21 | 576 | |
| II-0078 | 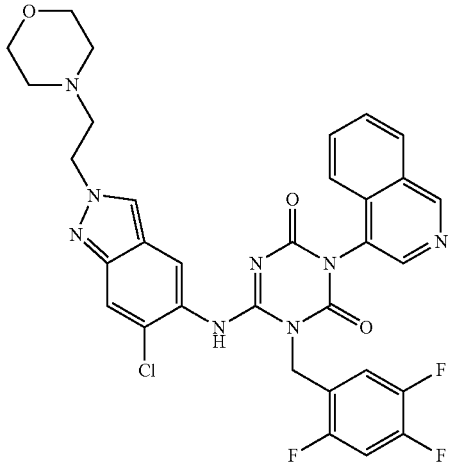 [SMILES: O=c1nc(Nc2cc3cn(CCN4CCOCC4)nc3cc2Cl)n(Cc2cc(F)c(F)cc2F)c(=O)n1-c1cncc2ccccc12] | 1 | 1.65 | 663.3 | |
| II-0079 | 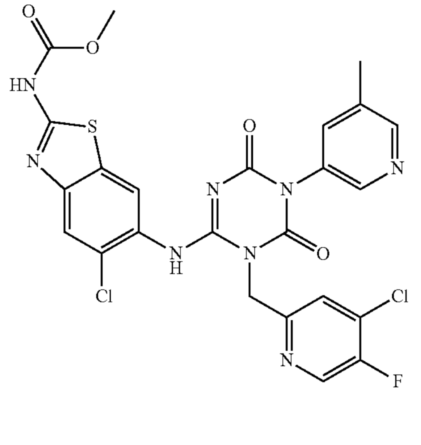 [SMILES: COC(=O)Nc1nc2cc(Cl)c(Nc3nc(=O)n(-c4cncc(C)c4)c(=O)n3Cc3cc(Cl)c(F)cn3)cc2s1] | 1 | 1.86 | 603 | |

TABLE 67-continued
| Compound No. | Structure | LC/MS Measured condition | Retention time (min) | m/z | Con-figration |
|---|---|---|---|---|---|
| II-0080 | 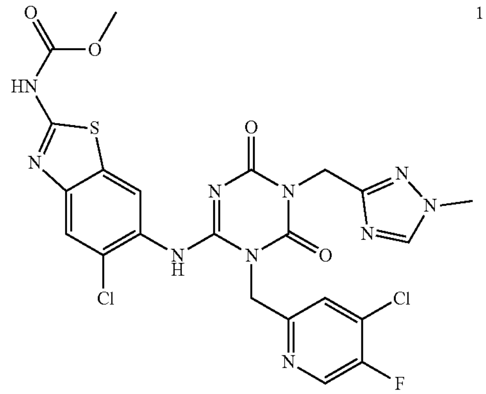 | 1 | 1.76 | 607.3 | |
TABLE 68
| Compound No. | Structure | LC/MS Measured condition | Retention time (min) | m/z | Con-figration |
|---|---|---|---|---|---|
| II-0081 | 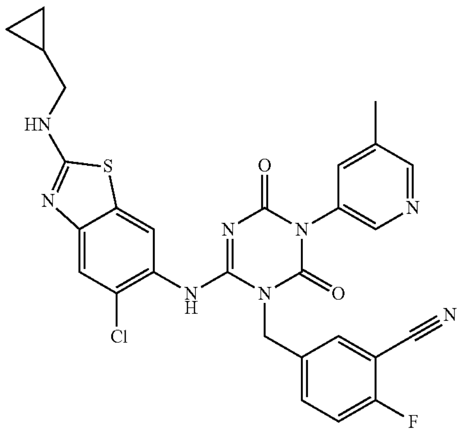 [SMILES: Cc1cncc(-n2c(=O)nc(Nc3cc4sc(NCC5CC5)nc4cc3Cl)n(Cc3ccc(F)c(C#N)c3)c2=O)c1] | 1 | 2.04 | 589.2 | |
| II-0082 | 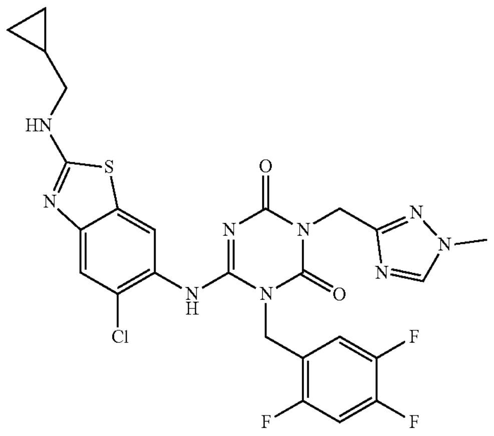 [SMILES: Cn1cnc(Cn2c(=O)nc(Nc3cc4sc(NCC5CC5)nc4cc3Cl)n(Cc3cc(F)c(F)cc3F)c2=O)n1] | 1 | 2.02 | 604.2 | |

TABLE 68-continued
| Compound No. | Structure | LC/MS Measured condition | Retention time (min) | m/z | Con-figration |
|---|---|---|---|---|---|
| II-0083 | 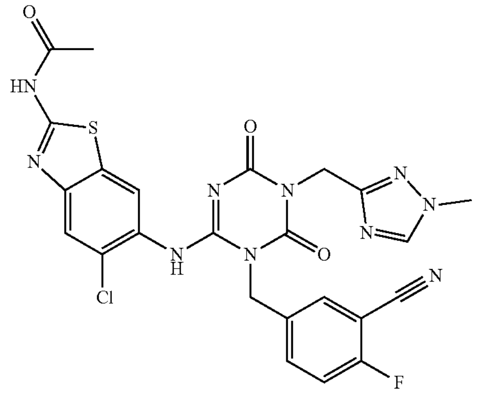 [SMILES: CC(=O)Nc1nc2cc(Cl)c(Nc3nc(=O)n(Cc4ncn(C)n4)c(=O)n3Cc3ccc(F)c(C#N)c3)cc2s1] | 1 | 1.90 | 581 | |
| II-0084 | 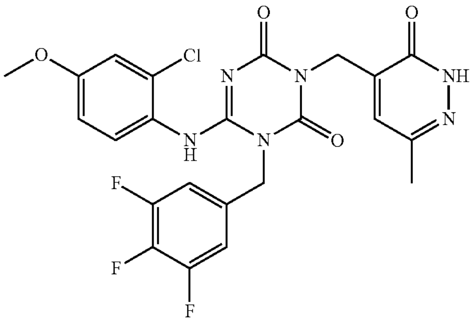 [SMILES: COc1ccc(Nc2nc(=O)n(Cc3cc(C)n[nH]c3=O)c(=O)n2Cc2cc(F)c(F)c(F)c2)c(Cl)c1] | 1 | 2.10 | 535.2 | |
| II-0085 | 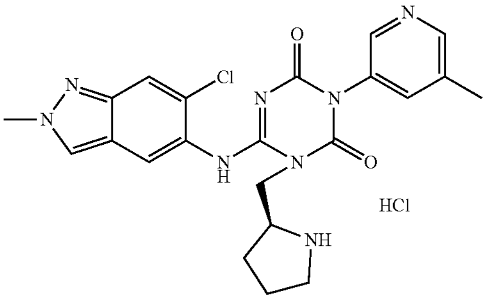 | HCl1 | 0.98 | 467 | a |
TABLE 69
| Compound No. | Structure | LC/MS Measured condition | Retention time (min) | m/z | Con-figration |
|---|---|---|---|---|---|
| II-0086 | 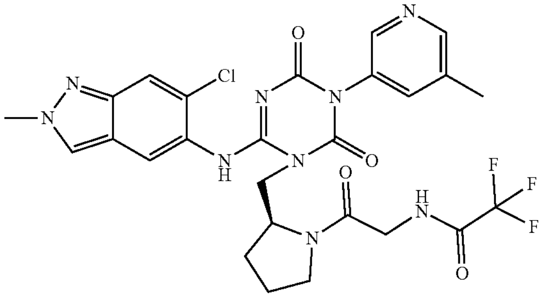 [SMILES: Cc1cncc(-n2c(=O)nc(Nc3cc4cn(C)nc4cc3Cl)n(C[C@@H]3CCCN3C(=O)CNC(=O)C(F)(F)F)c2=O)c1] | 1 | 1.48 | 620 | a |

TABLE 69-continued
| Compound No. | Structure | LC/MS Measured condition | Retention time (min) | m/z | Con-figration |
|---|---|---|---|---|---|
| II-0087 | 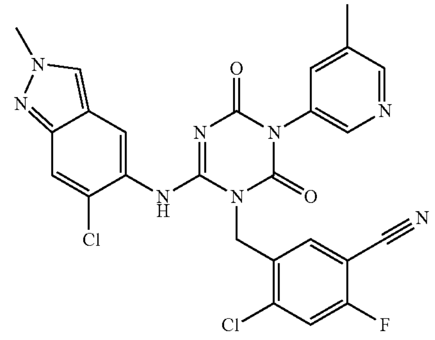 | 1 | 2.02 | 551.1 | |
| II-0088 | 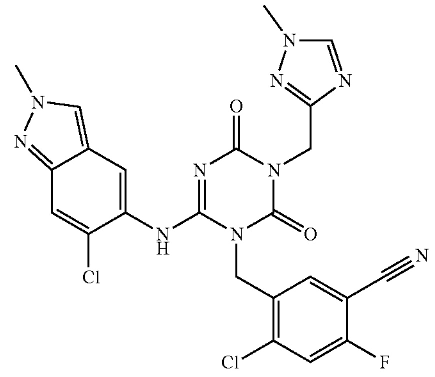 [SMILES: Cn1cnc(Cn2c(=O)nc(Nc3cc4cn(C)nc4cc3Cl)n(Cc3cc(C#N)c(F)cc3Cl)c2=O)n1] | 1 | 1.89 | 555.1 | |
| II-0089 | 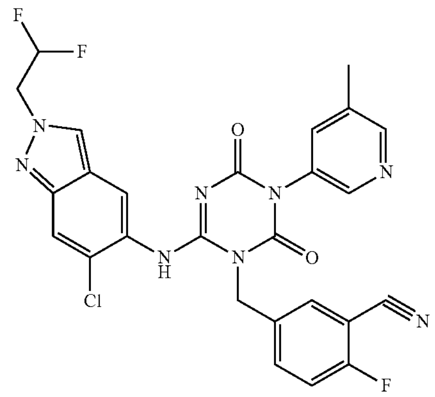 [SMILES: Cc1cncc(-n2c(=O)nc(Nc3cc4cn(CC(F)F)nc4cc3Cl)n(Cc3ccc(F)c(C#N)c3)c2=O)c1] | 1 | 2.02 | 566 | |

TABLE 69-continued
| Compound No. | Structure | LC/MS Measured condition | Retention time (min) | m/z | Con-figration |
|---|---|---|---|---|---|
| II-0090 | 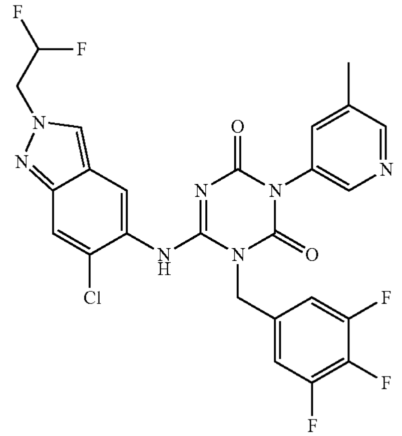 | 1 | 2.22 | 577 | |
TABLE 70
| Compound No. | Structure | LC/MS Measured condition | Retention time (min) | m/z | Con-figration |
|---|---|---|---|---|---|
| II-0091 | 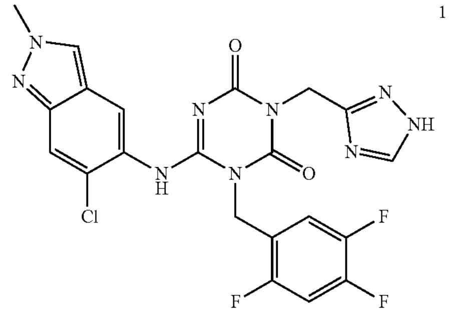 | 1 | 1.55 | 518 | |
| II-0092 | 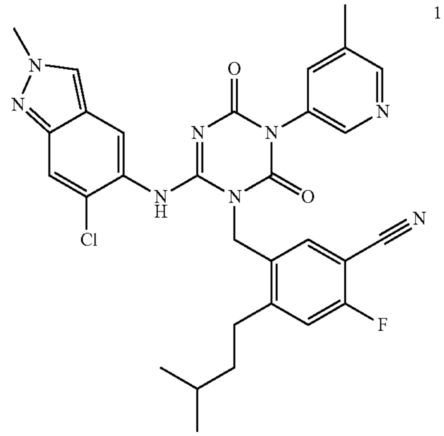 | 1 | 2.43 | 587 | |

TABLE 70-continued
| Compound No. | Structure | LC/MS Measured condition | Retention time (min) | m/z | Con-figration |
|---|---|---|---|---|---|
| II-0093 | 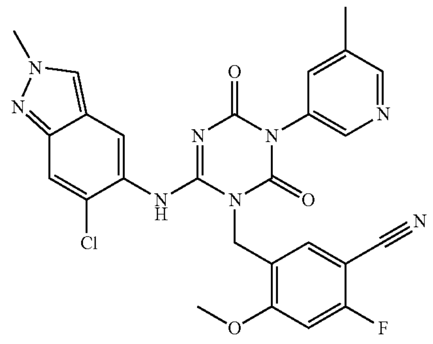 [SMILES: COc1cc(F)c(C#N)cc1Cn1c(Nc2cc3cn(C)nc3cc2Cl)nc(=O)n(-c2cncc(C)c2)c1=O] | 1 | 1.72 | 547 | |
| II-0094 | 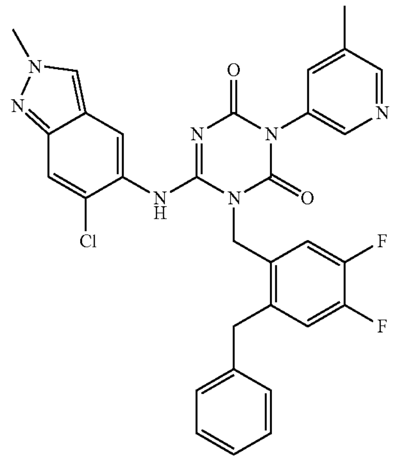 [SMILES: Cc1cncc(-n2c(=O)nc(Nc3cc4cn(C)nc4cc3Cl)n(Cc3cc(F)c(F)cc3Cc3ccccc3)c2=O)c1] | 1 | 2.38 | 600 | |
| II-0095 | 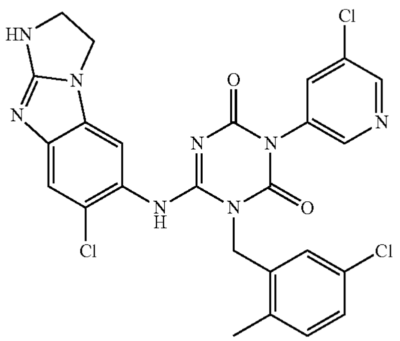 [SMILES: Cc1ccc(Cl)cc1Cn1c(Nc2cc3c(cc2Cl)nc2n3CCN2)nc(=O)n(-c2cncc(Cl)c2)c1=O] | 3 | 1.55 | 568.9 | |

TABLE 71
| Compound No. | Structure | LC/MS Measured condition | Retention time (min) | m/z | Con-figration |
|---|---|---|---|---|---|
| II-0096 | 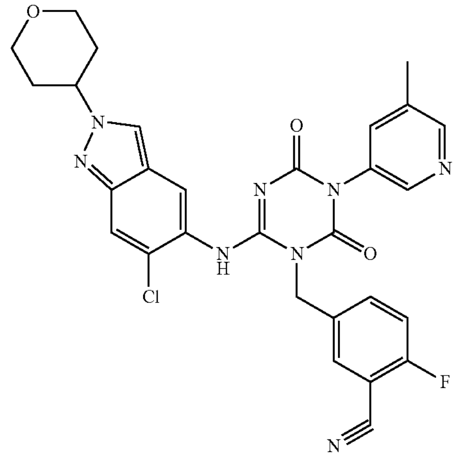 [SMILES: Cc1cncc(-n2c(=O)nc(Nc3cc4cn(C5CCOCC5)nc4cc3Cl)n(Cc3ccc(F)c(C#N)c3)c2=O)c1] | 1 | 1.92 | 587.2 | |
| II-0097 | 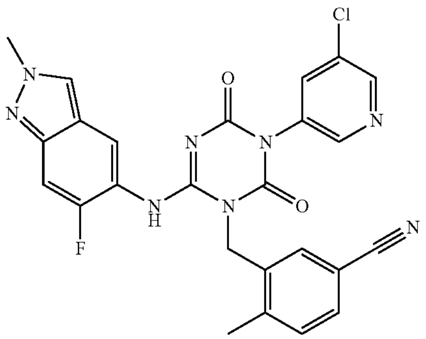 [SMILES: Cc1ccc(C#N)cc1Cn1c(Nc2cc3cn(C)nc3cc2F)nc(=O)n(-c2cncc(Cl)c2)c1=O] | 1 | 1.85 | 517.2 | |
| II-0098 | 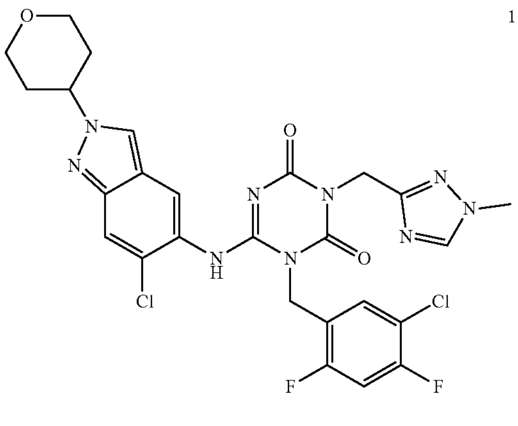 | 1 | 1.90 | 618.2 | |

TABLE 71-continued
| Compound No. | Structure | LC/MS Measured condition | Retention time (min) | m/z | Con-figration |
|---|---|---|---|---|---|
| II-0099 | 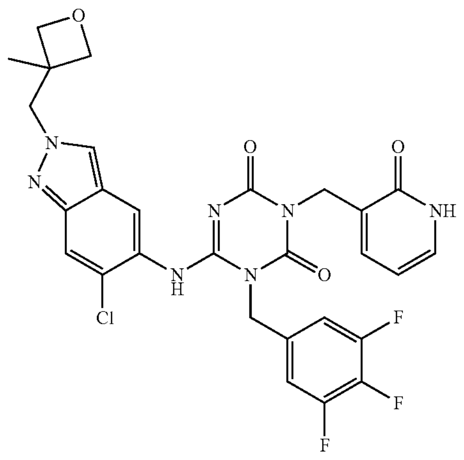 [SMILES: CC1(Cn2cc3cc(Nc4nc(=O)n(Cc5ccc[nH]c5=O)c(=O)n4Cc4cc(F)c(F)c(F)c4)c(Cl)cc3n2)COC1] | 1 | 1.91 | 614.2 | |
| II-0100 | 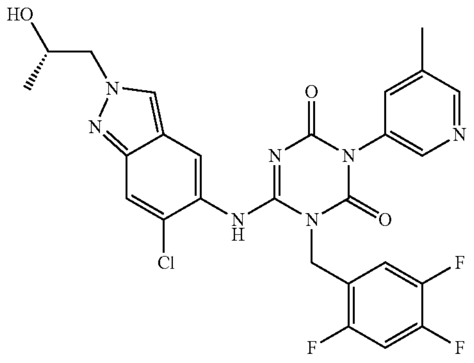 [SMILES: Cc1cncc(-n2c(=O)nc(Nc3cc4cn(C[C@H](C)O)nc4cc3Cl)n(Cc3cc(F)c(F)cc3F)c2=O)c1] | 1 | 1.80 | 572.2 | |
TABLE 72
| Compound No. | Structure | LC/MS Measured condition | Retention time (min) | m/z | Con-figration |
|---|---|---|---|---|---|
| II-0101 | 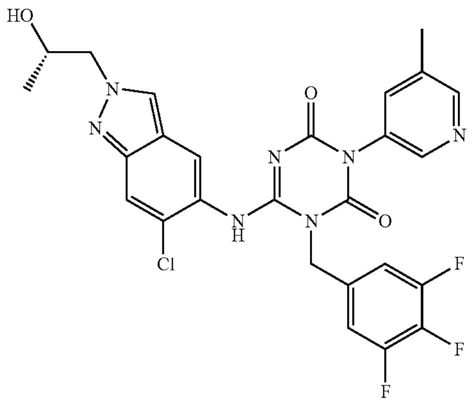 [SMILES: Cc1cncc(-n2c(=O)nc(Nc3cc4cn(C[C@H](C)O)nc4cc3Cl)n(Cc3cc(F)c(F)c(F)c3)c2=O)c1] | 1 | 1.86 | 572.3 | |

TABLE 72-continued
| Compound No. | Structure | LC/MS Measured condition | Retention time (min) | m/z | Con-figration |
|---|---|---|---|---|---|
| II-0102 | 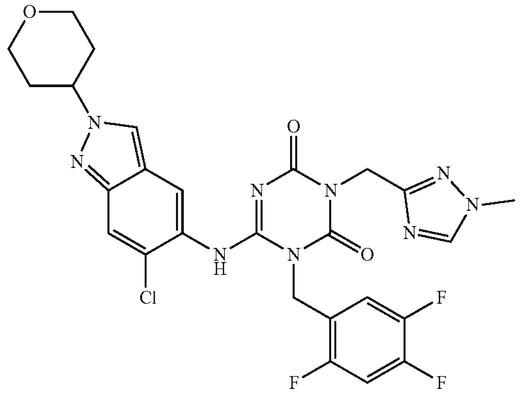 [SMILES: Cn1cnc(Cn2c(=O)nc(Nc3cc4cn(C5CCOCC5)nc4cc3Cl)n(Cc3cc(F)c(F)cc3F)c2=O)n1] | 1 | 1.85 | 602.2 | |
| II-0103 | 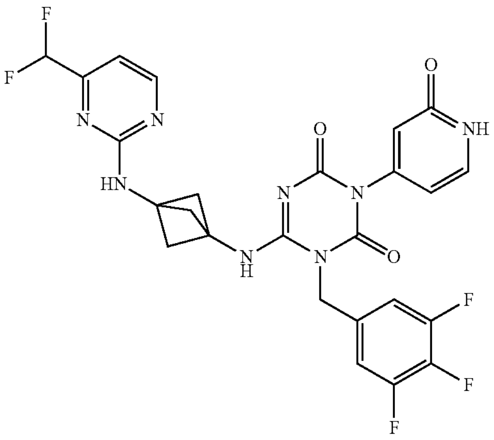 | 3 | 1.70 | 589 | |
| II-0104 | 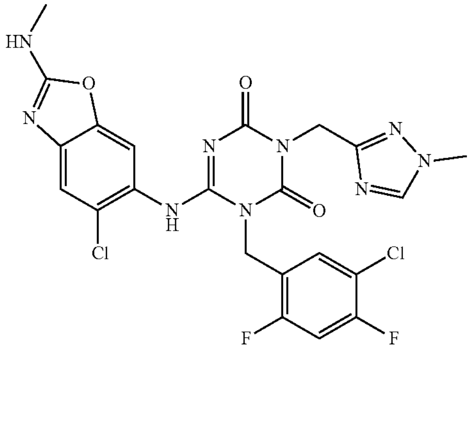 [SMILES: CNc1nc2cc(Cl)c(Nc3nc(=O)n(Cc4ncn(C)n4)c(=O)n3Cc3cc(Cl)c(F)cc3F)cc2o1] | 1 | 1.81 | 564.1 | |

TABLE 72-continued
| Compound No. | Structure | LC/MS Measured condition | Retention time (min) | m/z | Con-figration |
|---|---|---|---|---|---|
| II-0105 | 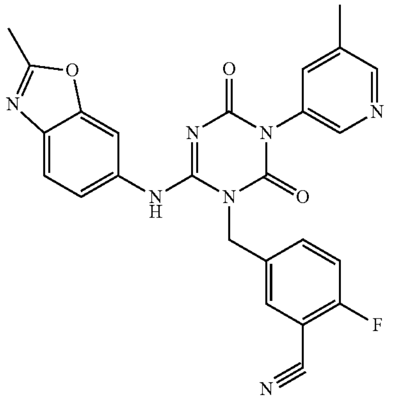 [SMILES: Cc1cncc(-n2c(=O)nc(Nc3ccc4nc(C)oc4c3)n(Cc3ccc(F)c(C#N)c3)c2=O)c1] | 1 | 1.69 | 484.2 | |
TABLE 73
| Compound No. | Structure | LC/MS Measured condition | Retention time (min) | m/z | Con-figration |
|---|---|---|---|---|---|
| II-0106 | 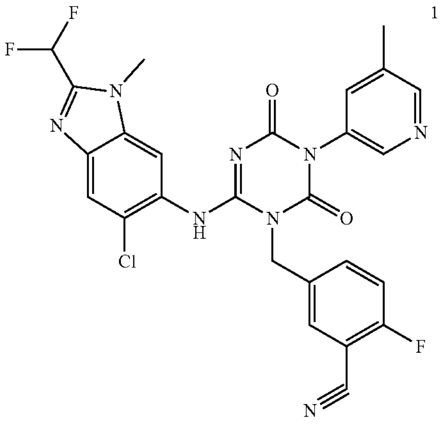 | 1 | 1.69 | 567.1 | |
| II-0107 | 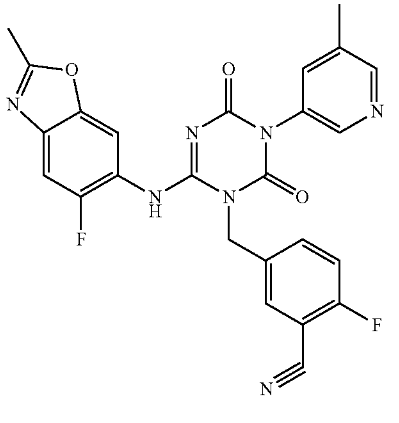 [SMILES: Cc1cncc(-n2c(=O)nc(Nc3cc4oc(C)nc4cc3F)n(Cc3ccc(F)c(C#N)c3)c2=O)c1] | 1 | 1.83 | 502.2 | |

TABLE 73-continued
| Compound No. | Structure | LC/MS Measured condition | Retention time (min) | m/z | Con-figration |
|---|---|---|---|---|---|
| II-0108 | 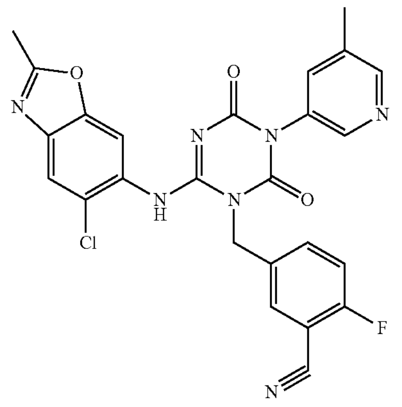 | 1 | 1.93 | 517.2 | |
| II-0109 | 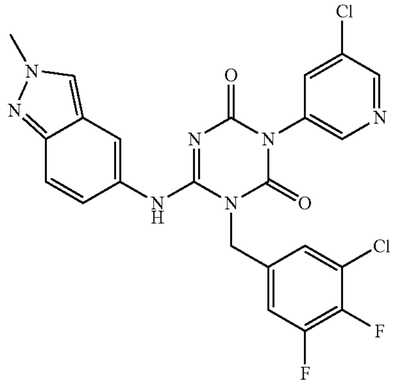 [SMILES: Cn1cc2cc(Nc3nc(=O)n(-c4cncc(Cl)c4)c(=O)n3Cc3cc(F)c(F)c(Cl)c3)ccc2n1] | 1 | 2.03 | 530.1 | |
| II-0110 | 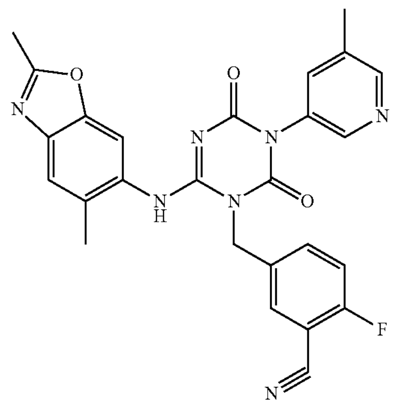 | 1 | 1.76 | 498.2 | |

TABLE 74
| Compound No. | Structure | LC/MS Measured condition | Retention time (min) | m/z | Con-figration |
|---|---|---|---|---|---|
| II-0111 | 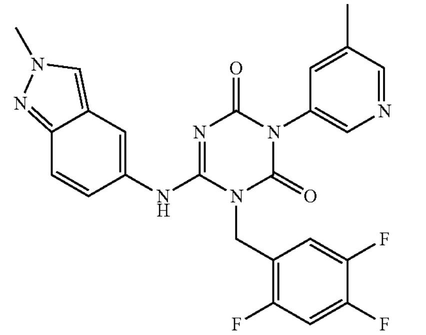 [SMILES: Cc1cncc(-n2c(=O)nc(Nc3ccc4nn(C)cc4c3)n(Cc3cc(F)c(F)cc3F)c2=O)c1] | 1 | 1.65 | 494.2 | |
| II-0112 | 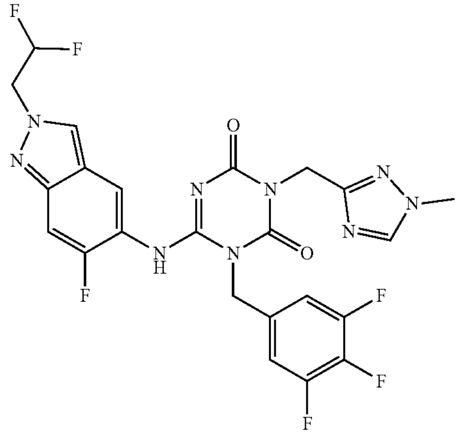 [SMILES: Cn1cnc(Cn2c(=O)nc(Nc3cc4cn(CC(F)F)nc4cc3F)n(Cc3cc(F)c(F)c(F)c3)c2=O)n1] | 1 | 1.89 | 566.2 | |
| II-0113 | 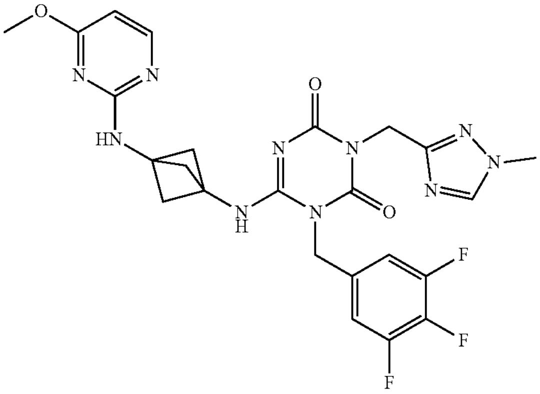 | 1 | 1.47 | 557.2 | |
| II-0114 | 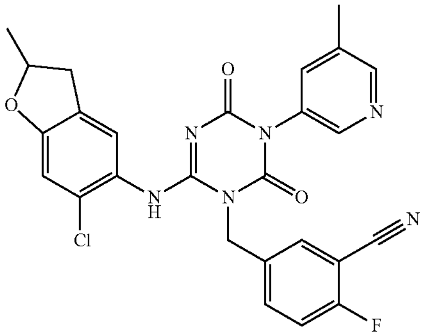 [SMILES: Cc1cncc(-n2c(=O)nc(Nc3cc4c(cc3Cl)OC(C)C4)n(Cc3ccc(F)c(C#N)c3)c2=O)c1] | 1 | 2.05 | 519.2 | |

TABLE 74-continued
| Compound No. | Structure | LC/MS Measured condition | Retention time (min) | m/z | Con-figration |
|---|---|---|---|---|---|
| II-0115 | 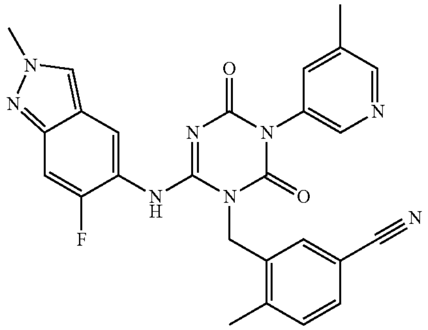 [SMILES: Cc1cncc(-n2c(=O)nc(Nc3cc4cn(C)nc4cc3F)n(Cc3cc(C#N)ccc3C)c2=O)c1] | 3 | 1.48 | 497.1 | |
TABLE 75
| Compound No. | Structure | LC/MS Measured condition | Retention time (min) | m/z | Con-figration |
|---|---|---|---|---|---|
| II-0116 | 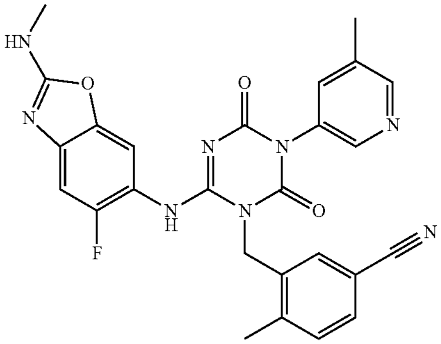 [SMILES: CNc1nc2cc(F)c(Nc3nc(=O)n(-c4cncc(C)c4)c(=O)n3Cc3cc(C#N)ccc3C)cc2o1] | 3 | 1.59 | 529 | |
| II-0117 | 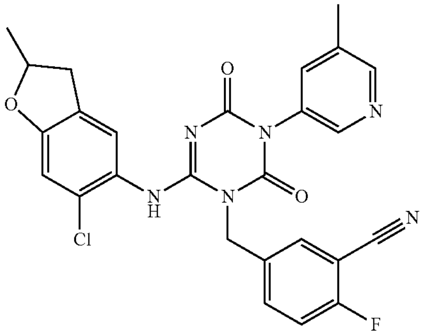 [SMILES: Cc1cncc(-n2c(=O)nc(Nc3cc4c(cc3Cl)OC(C)C4)n(Cc3ccc(F)c(C#N)c3)c2=O)c1] | 1 | 2.05 | 519 | |

TABLE 75-continued
| Compound No. | Structure | LC/MS Measured condition | Retention time (min) | m/z | Con-figration |
|---|---|---|---|---|---|
| II-0118 | 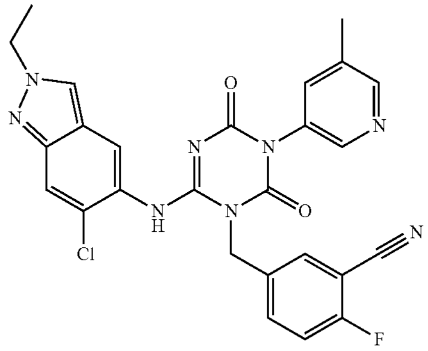 [SMILES: CCn1cc2cc(Nc3nc(=O)n(-c4cncc(C)c4)c(=O)n3Cc3ccc(F)c(C#N)c3)c(Cl)cc2n1] | 1 | 1.86 | 531.2 | |
| II-0119 | 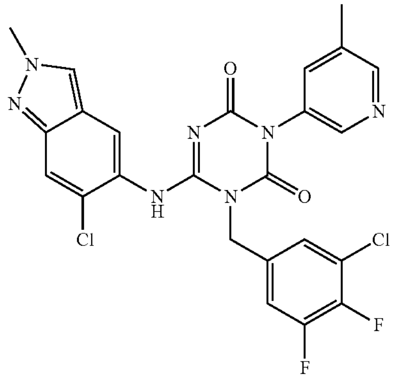 [SMILES: Cc1cncc(-n2c(=O)nc(Nc3cc4cn(C)nc4cc3Cl)n(Cc3cc(F)c(F)c(Cl)c3)c2=O)c1] | 1 | 2.02 | 544.1 | |
| II-0120 | 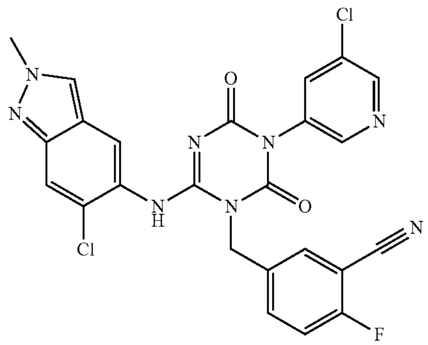 [SMILES: Cn1cc2cc(Nc3nc(=O)n(-c4cncc(Cl)c4)c(=O)n3Cc3ccc(F)c(C#N)c3)c(Cl)cc2n1] | 1 | 1.98 | 537.1 | |

TABLE 76
| Compound No. | Structure | LC/MS Measured condition | Retention time (min) | m/z | Con-figration |
|---|---|---|---|---|---|
| II-0121 | 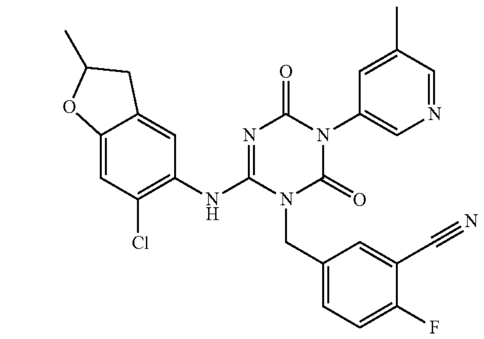 [SMILES: Cc1cncc(-n2c(=O)nc(Nc3cc4c(cc3Cl)OC(C)C4)n(Cc3ccc(F)c(C#N)c3)c2=O)c1] | 1 | 2.04 | 519.2 | |
| II-0122 | 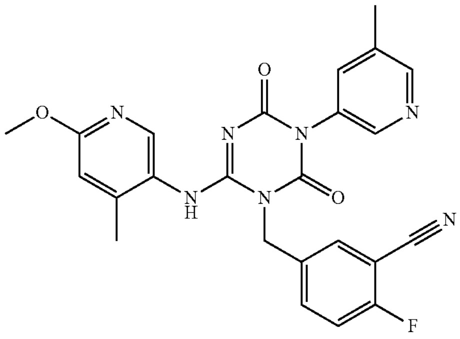 [SMILES: COc1cc(C)c(Nc2nc(=O)n(-c3cncc(C)c3)c(=O)n2Cc2ccc(F)c(C#N)c2)cn1] | 1 | 1.69 | 474.2 | |
| II-0123 | 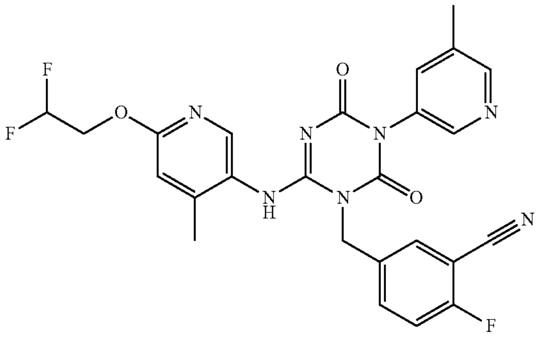 [SMILES: Cc1cncc(-n2c(=O)nc(Nc3cnc(OCC(F)F)cc3C)n(Cc3ccc(F)c(C#N)c3)c2=O)c1] | 1 | 1.96 | 524.2 | |
| II-0124 | 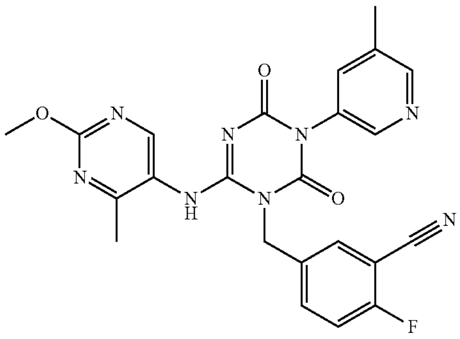 | 1 | 1.63 | 475.2 | |

TABLE 76-continued
| Compound No. | Structure | LC/MS Measured condition | Retention time (min) | m/z | Con-figration |
|---|---|---|---|---|---|
| II-0125 | 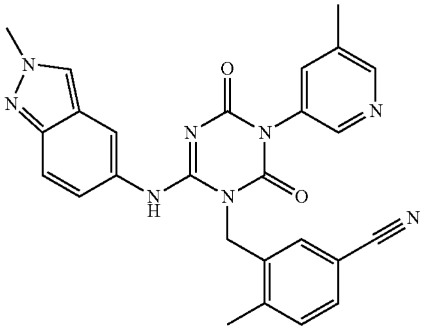 [SMILES: Cc1cncc(-n2c(=O)nc(Nc3ccc4nn(C)cc4c3)n(Cc3cc(C#N)ccc3C)c2=O)c1] | 3 | 1.36 | 479.1 | |
TABLE 77
| Compound No. | Structure | LC/MS Measured condition | Retention time (min) | m/z | Con-figration |
|---|---|---|---|---|---|
| II-0126 | 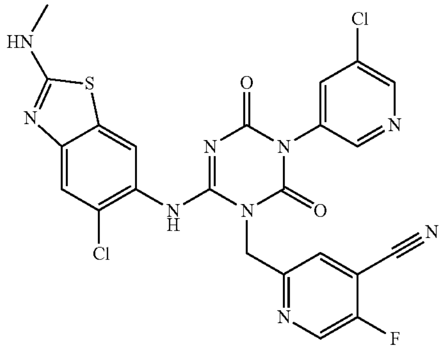 [SMILES: CNc1nc2cc(Cl)c(Nc3nc(=O)n(-c4cncc(Cl)c4)c(=O)n3Cc3cc(C#N)c(F)cn3)cc2s1] | 3 | 1.71 | 570.1 | |
| II-0127 | 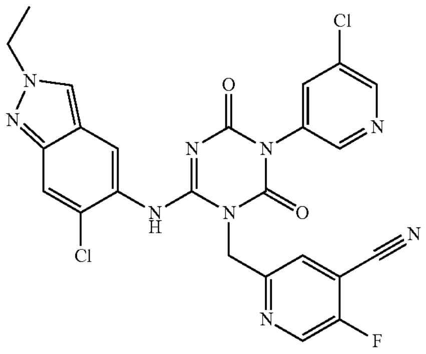 [SMILES: CCn1cc2cc(Nc3nc(=O)n(-c4cncc(Cl)c4)c(=O)n3Cc3cc(C#N)c(F)cn3)c(Cl)cc2n1] | 3 | 1.78 | 552 | |

TABLE 77-continued
| Compound No. | Structure | LC/MS Measured condition | Retention time (min) | m/z | Con-figration |
|---|---|---|---|---|---|
| II-0128 | 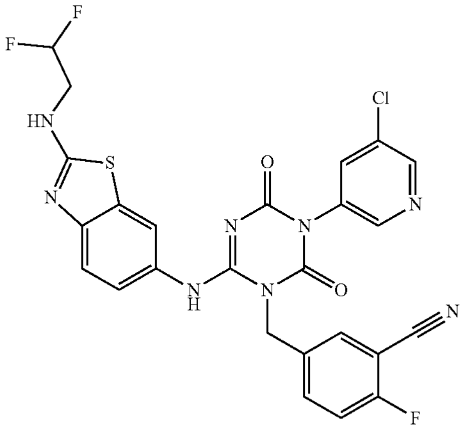 [SMILES: N#Cc1cc(Cn2c(Nc3ccc4nc(NCC(F)F)sc4c3)nc(=O)n(-c3cncc(Cl)c3)c2=O)ccc1F] | 3 | 1.63 | 565 | |
| II-0129 | 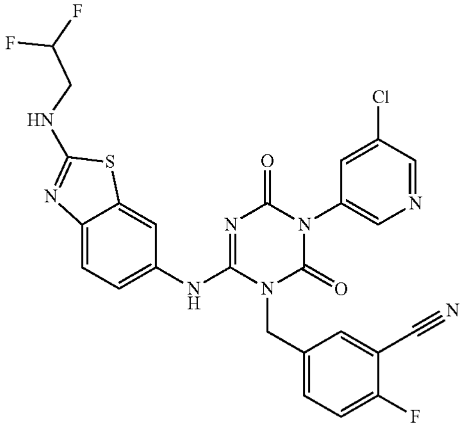 [SMILES: N#Cc1cc(Cn2c(Nc3ccc4nc(NCC(F)F)sc4c3)nc(=O)n(-c3cncc(Cl)c3)c2=O)ccc1F] | 3 | 1.84 | 585.2 | |
| II-0130 | 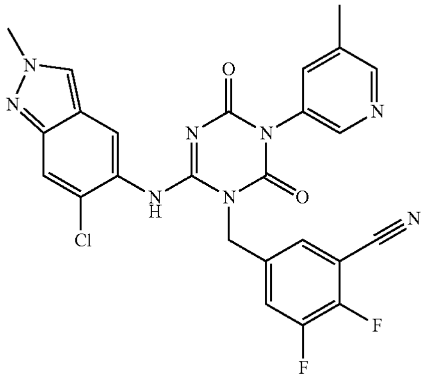 | 1 | 1.98 | 535 | |

TABLE 78
| Compound No. | Structure | LC/MS Measured condition | Retention time (min) | m/z | Con-figuration |
|---|---|---|---|---|---|
| II-0131 | 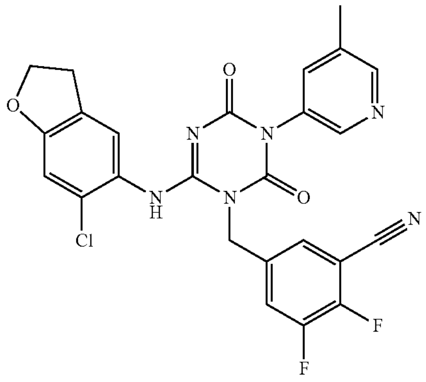 [SMILES: Cc1cncc(-n2c(=O)nc(Nc3cc4c(cc3Cl)OCC4)n(Cc3cc(F)c(F)c(C#N)c3)c2=O)c1] | 1 | 2.20 | 523 | |
| II-0132 | 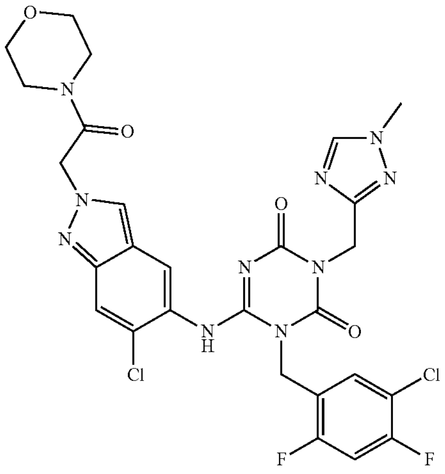 [SMILES: Cn1cnc(Cn2c(=O)nc(Nc3cc4cn(CC(=O)N5CCOCC5)nc4cc3Cl)n(Cc3cc(Cl)c(F)cc3F)c2=O)n1] | 1 | 1.84 | 661 | |
| II-0134 | 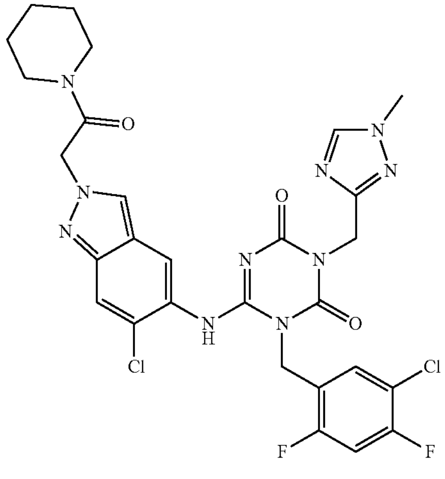 [SMILES: Cn1cnc(Cn2c(=O)nc(Nc3cc4cn(CC(=O)N5CCCCC5)nc4cc3Cl)n(Cc3cc(Cl)c(F)cc3F)c2=O)n1] | 1 | 2.05 | 659 | |

TABLE 78-continued
| Compound No. | Structure | LC/MS Measured condition | Retention time (min) | m/z | Con-figration |
|---|---|---|---|---|---|
| II-0135 | 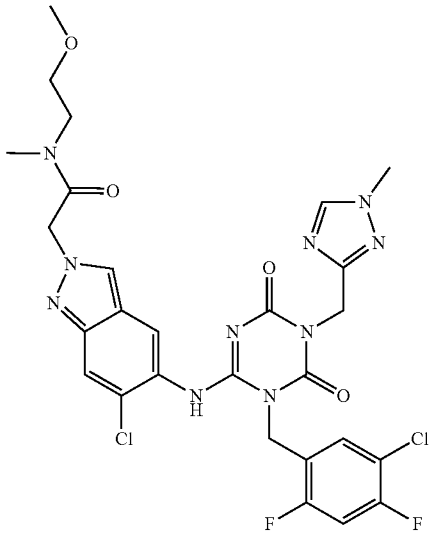 [SMILES: COCCN(C)C(=O)Cn1cc2cc(Nc3nc(=O)n(Cc4ncn(C)n4)c(=O)n3Cc3cc(Cl)c(F)cc3F)c(Cl)cc2n1] | 1 | 1.90 | 663 | |
TABLE 79
| Compound No. | Structure | LC/MS Measured condition | Retention time (min) | m/z | Con-figration |
|---|---|---|---|---|---|
| II-0136 | 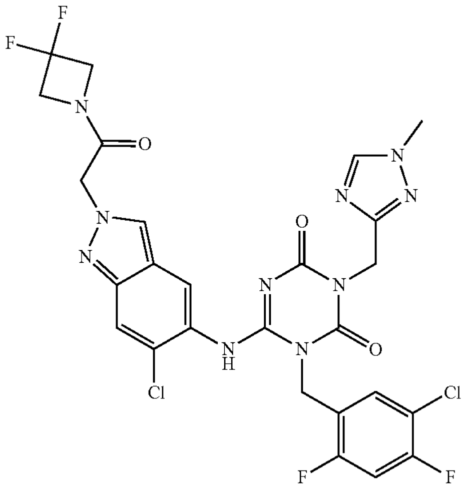 [SMILES: Cn1cnc(Cn2c(=O)nc(Nc3cc4cn(CC(=O)N5CC(F)(F)C5)nc4cc3Cl)n(Cc3cc(Cl)c(F)cc3F)c2=O)n1] | 1 | 2.00 | 667 | |

TABLE 79-continued
| Compound No. | Structure | LC/MS Measured condition | Retention time (min) | m/z | Con-figration |
|---|---|---|---|---|---|
| II-0137 | 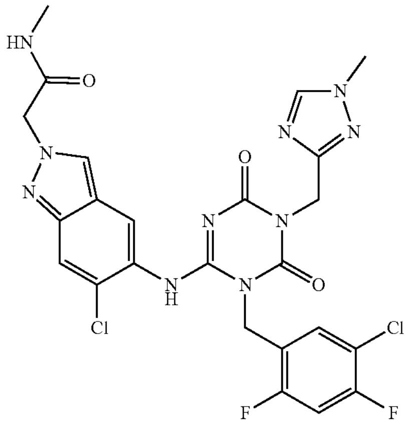 [SMILES: CNC(=O)Cn1cc2cc(Nc3nc(=O)n(Cc4ncn(C)n4)c(=O)n3Cc3cc(Cl)c(F)cc3F)c(Cl)cc2n1] | 1 | 1.78 | 605 | |
| II-0138 | 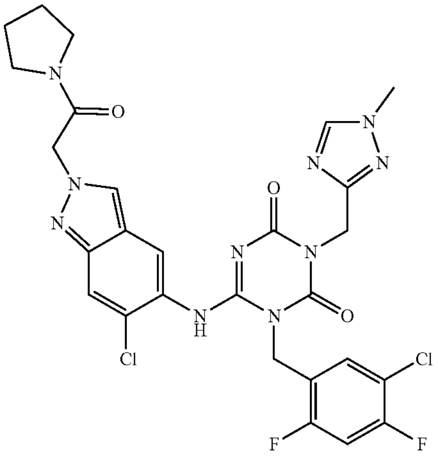 [SMILES: Cn1cnc(Cn2c(=O)nc(Nc3cc4cn(CC(=O)N5CCCC5)nc4cc3Cl)n(Cc3cc(Cl)c(F)cc3F)c2=O)n1] | 1 | 1.93 | 645 | |
| II-0139 | 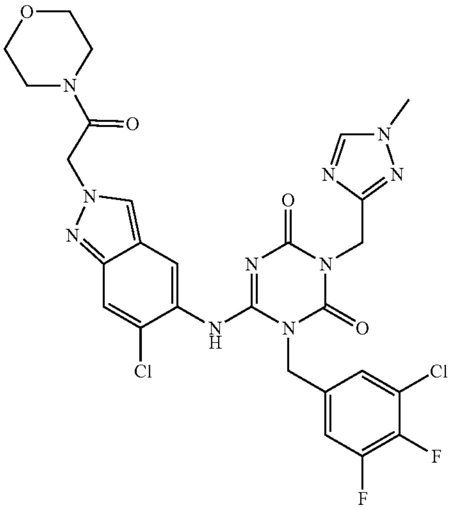 [SMILES: Cn1cnc(Cn2c(=O)nc(Nc3cc4cn(CC(=O)N5CCOCC5)nc4cc3Cl)n(Cc3cc(F)c(F)c(Cl)c3)c2=O)n1] | 1 | 1.91 | 661 | |

TABLE 80
| Compound No. | Structure | LC/MS Measured condition | Retention time (min) | m/z | Con-figration |
|---|---|---|---|---|---|
| II-0140 | 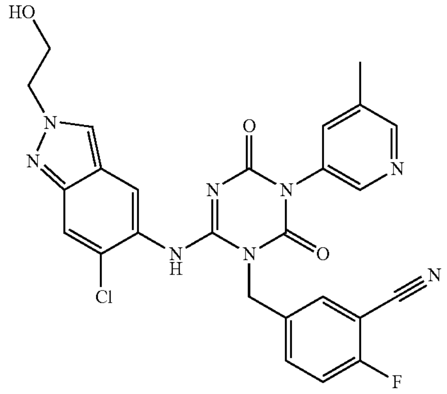 [SMILES: Cc1cncc(-n2c(=O)nc(Nc3cc4cn(CCO)nc4cc3Cl)n(Cc3ccc(F)c(C#N)c3)c2=O)c1] | 1 | 1.75 | 547 | |
| II-0141 | 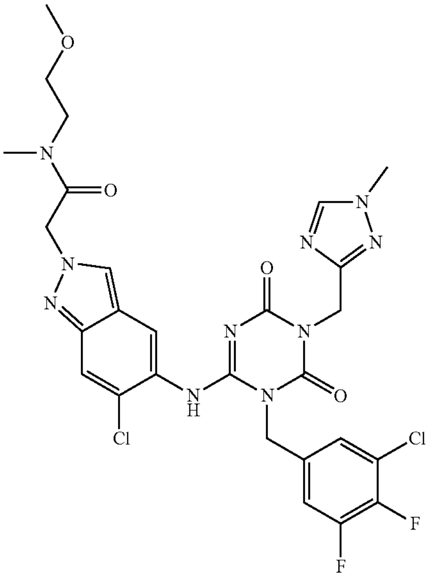 [SMILES: COCCN(C)C(=O)Cn1cc2cc(Nc3nc(=O)n(Cc4ncn(C)n4)c(=O)n3Cc3cc(F)c(F)c(Cl)c3)c(Cl)cc2n1] | 1 | 1.97 | 663 | |
| II-0142 | 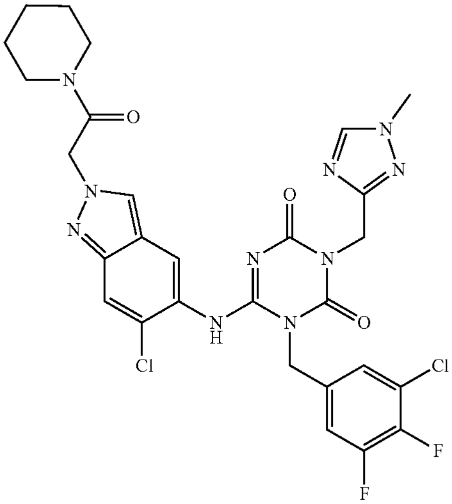 [SMILES: Cn1cnc(Cn2c(=O)nc(Nc3cc4cn(CC(=O)N5CCCCC5)nc4cc3Cl)n(Cc3cc(F)c(F)c(Cl)c3)c2=O)n1] | 1 | 2.13 | 659 | |

TABLE 80-continued
| Compound No. | Structure | LC/MS Measured condition | Retention time (min) | m/z | Configuration |
|---|---|---|---|---|---|
| II-0143 | 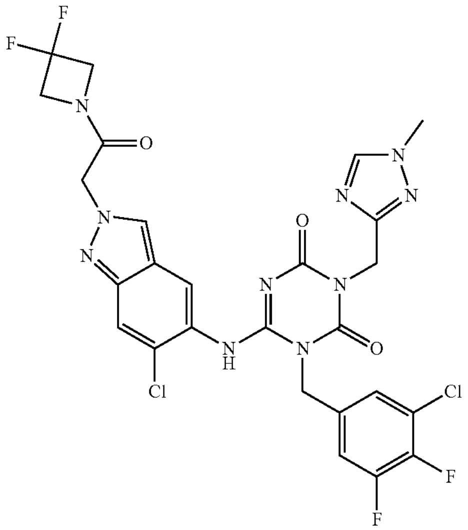 [SMILES: Cn1cnc(Cn2c(=O)nc(Nc3cc4cn(CC(=O)N5CC(F)(F)C5)nc4cc3Cl)n(Cc3cc(F)c(F)c(Cl)c3)c2=O)n1] | 1 | 2.07 | 667 | |
TABLE 811
| Compound No. | Structure | LC/MS Measured condition | Retention time (min) | m/z | Configuration |
|---|---|---|---|---|---|
| II-0144 | 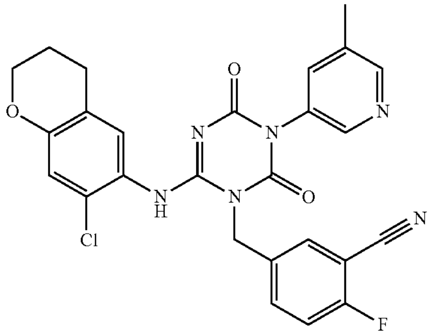 [SMILES: Cc1cncc(-n2c(=O)nc(Nc3cc4c(cc3Cl)OCCC4)n(Cc3ccc(F)c(C#N)c3)c2=O)c1] | 1 | 2.19 | 519 | |
| II-0145 | 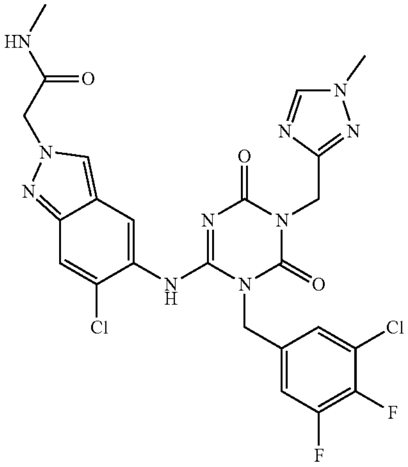 [SMILES: CNC(=O)Cn1cc2cc(Nc3nc(=O)n(Cc4ncn(C)n4)c(=O)n3Cc3cc(F)c(F)c(Cl)c3)c(Cl)cc2n1] | 1 | 1.85 | 605 | |

TABLE 811-continued
| Compound No. | Structure | LC/MS Measured condition | Retention time (min) | m/z | Con-figration |
|---|---|---|---|---|---|
| II-0146 | 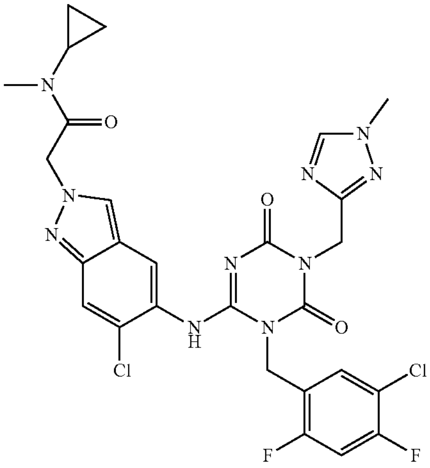 [SMILES: CN(C(=O)Cn1cc2cc(Nc3nc(=O)n(Cc4ncn(C)n4)c(=O)n3Cc3cc(Cl)c(F)cc3F)c(Cl)cc2n1)C1CC1] | 1 | 2.00 | 645 | |
| II-0147 | 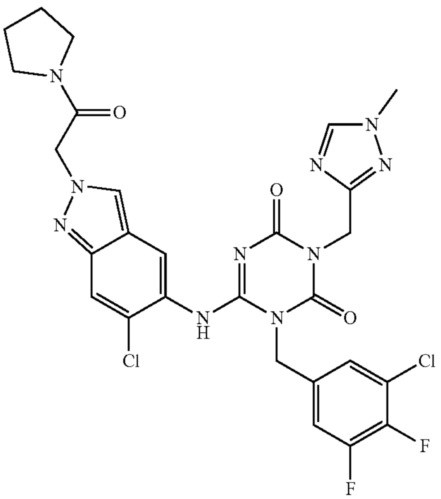 [SMILES: Cn1cnc(Cn2c(=O)nc(Nc3cc4cn(CC(=O)N5CCCC5)nc4cc3Cl)n(Cc3cc(F)c(F)c(Cl)c3)c2=O)n1] | 1 | 2.00 | 645 | |

TABLE 82
| Compound No. | Structure | LC/MS Measured condition | Retention time (min) | m/z | Con-figration |
|---|---|---|---|---|---|
| II-0148 | 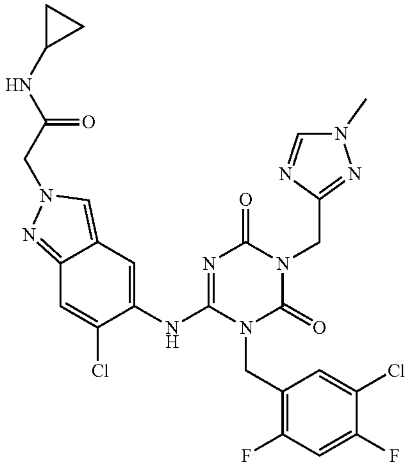 [SMILES: Cn1cnc(Cn2c(=O)nc(Nc3cc4cn(CC(=O)NC5CC5)nc4cc3Cl)n(Cc3cc(Cl)c(F)cc3F)c2=O)n1] | 1 | 1.87 | 631 | |
| II-0149 | 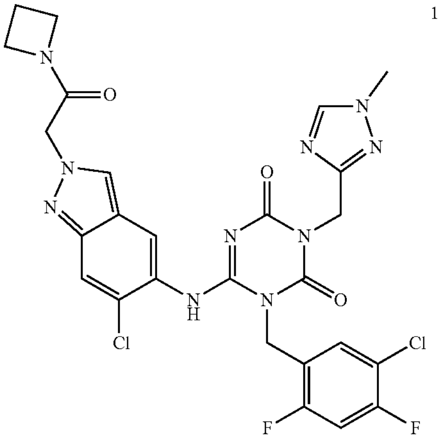 | 1 | 1.85 | 631 | |
| II-0150 | 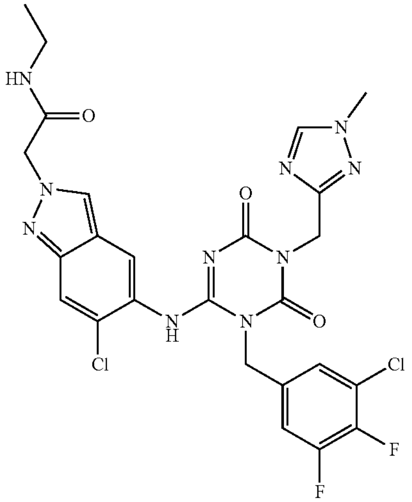 [SMILES: CCNC(=O)Cn1cc2cc(Nc3nc(=O)n(Cc4ncn(C)n4)c(=O)n3Cc3cc(F)c(F)c(Cl)c3)c(Cl)cc2n1] | 1 | 1.92 | 619 | |

TABLE 82-continued
| Compound No. | Structure | LC/MS Measured condition | Retention time (min) | m/z | Con-figration |
|---|---|---|---|---|---|
| II-0151 | 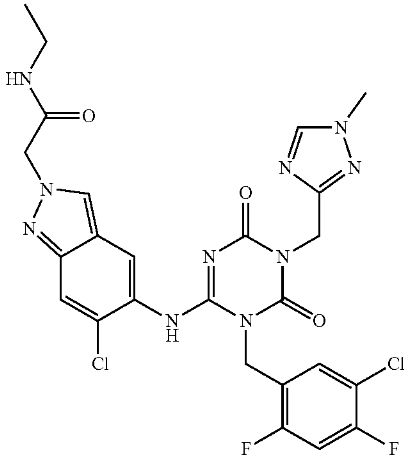 [SMILES: CCNC(=O)Cn1cc2cc(Nc3nc(=O)n(Cc4ncn(C)n4)c(=O)n3Cc3cc(Cl)c(F)cc3F)c(Cl)cc2n1] | 1 | 1.85 | 619 | |
TABLE 83
| Compound No. | Structure | LC/MS Measured condition | Retention time (min) | m/z | Con-figration |
|---|---|---|---|---|---|
| II-0152 | 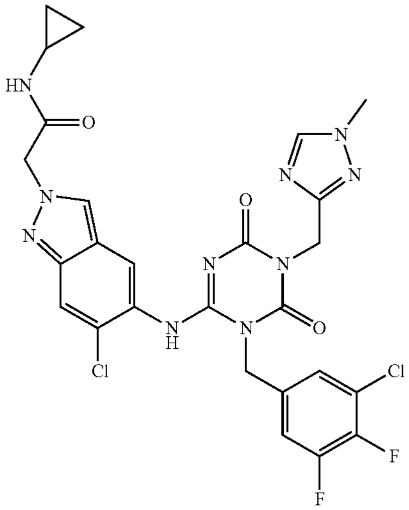 [SMILES: Cn1cnc(Cn2c(=O)nc(Nc3cc4cn(CC(=O)NC5CC5)nc4cc3Cl)n(Cc3cc(F)c(F)c(Cl)c3)c2=O)n1] | 1 | 1.94 | 631 | |

TABLE 83-continued
| Compound No. | Structure | LC/MS Measured condition | Retention time (min) | m/z | Con-figration |
|---|---|---|---|---|---|
| II-0153 | 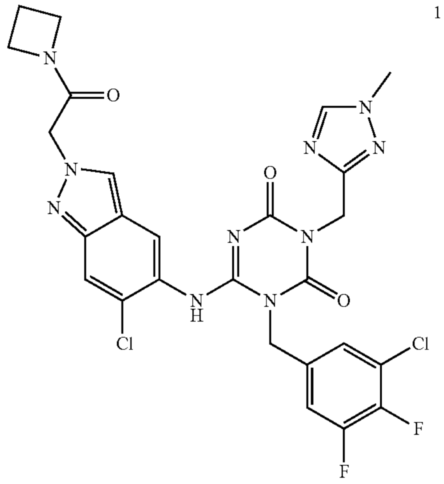 | 1 | 1.92 | 631 | |
| II-0154 | 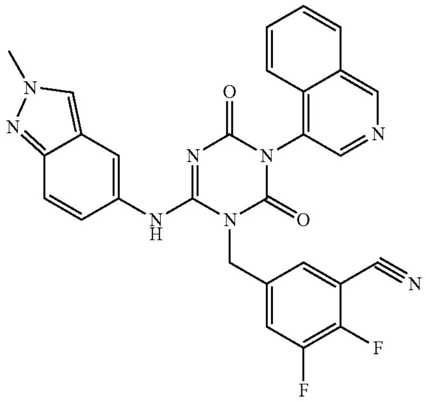 [SMILES: Cn1cc2cc(Nc3nc(=O)n(-c4cncc5ccccc45)c(=O)n3Cc3cc(F)c(F)c(C#N)c3)ccc2n1] | 1 | 1.87 | 537 | |
| II-0155 | 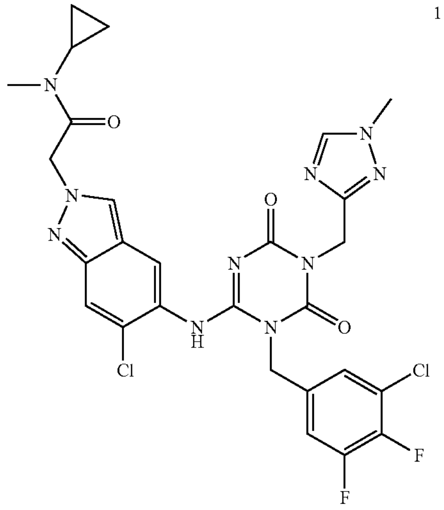 | 1 | 2.07 | 645 | |

TABLE 84
| Compound No. | Structure | LC/MS Measured condition | Retention time (min) | m/z | Con-figration |
|---|---|---|---|---|---|
| II-0156 | 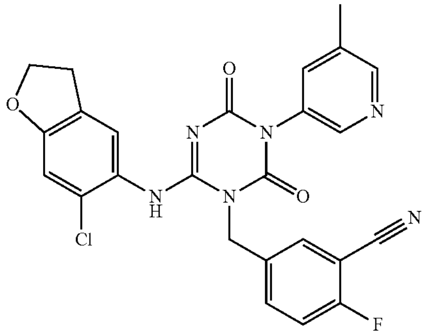 [SMILES: Cc1cncc(-n2c(=O)nc(Nc3cc4c(cc3Cl)OCC4)n(Cc3ccc(F)c(C#N)c3)c2=O)c1] | 1 | 2.06 | 505 | |
| II-0158 | 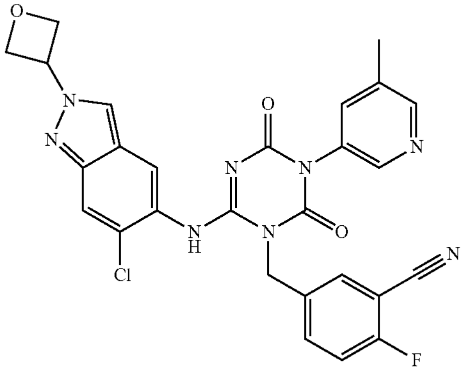 [SMILES: Cc1cncc(-n2c(=O)nc(Nc3cc4cn(C5COC5)nc4cc3Cl)n(Cc3ccc(F)c(C#N)c3)c2=O)c1] | 1 | 1.88 | 559 | |
| II-0159 | 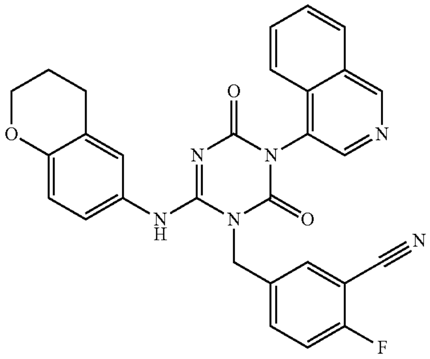 [SMILES: N#Cc1cc(Cn2c(Nc3ccc4c(c3)CCCO4)nc(=O)n(-c3cncc4ccccc34)c2=O)ccc1F] | 1 | 2.02 | 521 | |
| II-0160 | 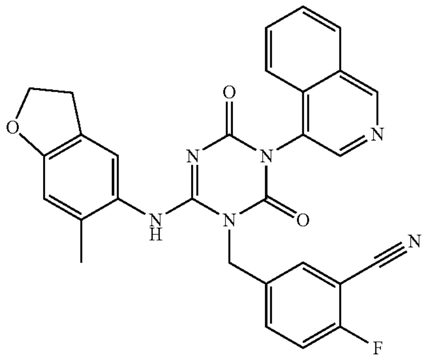 [SMILES: Cc1cc2c(cc1Nc1nc(=O)n(-c3cncc4ccccc34)c(=O)n1Cc1ccc(F)c(C#N)c1)CCO2] | 1 | 1.99 | 521 | |

TABLE 84-continued
| Compound No. | Structure | LC/MS Measured condition | Retention time (min) | m/z | Con-figration |
|---|---|---|---|---|---|
| II-0161 | 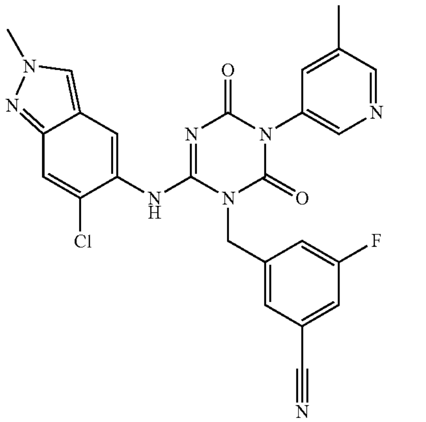 [SMILES: Cc1cncc(-n2c(=O)nc(Nc3cc4cn(C)nc4cc3Cl)n(Cc3cc(F)cc(C#N)c3)c2=O)c1] | 4 | 1.45 | 517 | |
TABLE 85
| Compound No. | Structure | LC/MS Measured condition | Retention time (min) | m/z | Con-figration |
|---|---|---|---|---|---|
| II-0162 | 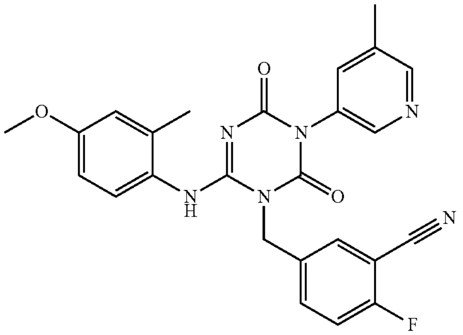 [SMILES: COc1ccc(Nc2nc(=O)n(-c3cncc(C)c3)c(=O)n2Cc2ccc(F)c(C#N)c2)c(C)c1] | 1 | 1.83 | 473 | |
| II-0163 | 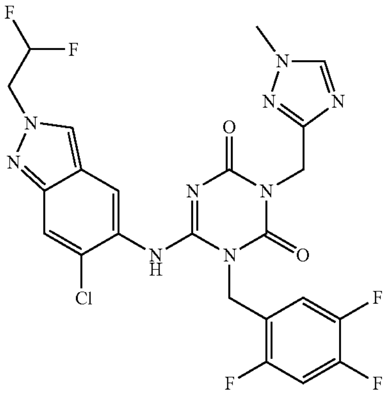 [SMILES: Cn1cnc(Cn2c(=O)nc(Nc3cc4cn(CC(F)F)nc4cc3Cl)n(Cc3cc(F)c(F)cc3F)c2=O)n1] | 1 | 2.04 | 582 | |

TABLE 85-continued
| Compound No. | Structure | LC/MS Measured condition | Retention time (min) | m/z | Con-figration |
|---|---|---|---|---|---|
| II-0164 | 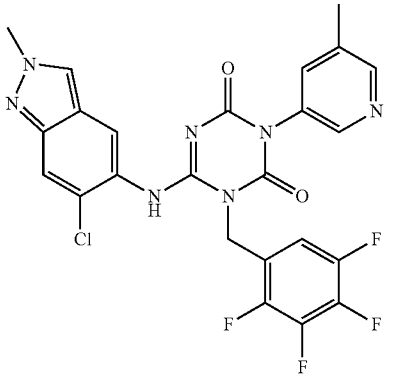 [SMILES: Cc1cncc(-n2c(=O)nc(Nc3cc4cn(C)nc4cc3Cl)n(Cc3cc(F)c(F)c(F)c3F)c2=O)c1] | 1 | 2.09 | 546 | |
| II-0165 | 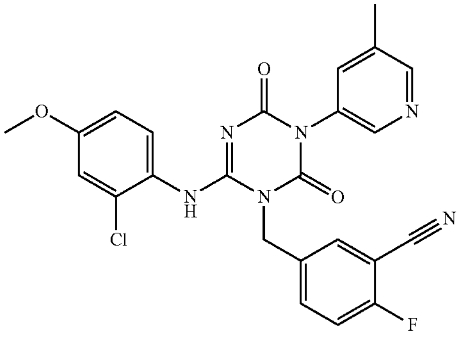 [SMILES: COc1ccc(Nc2nc(=O)n(-c3cncc(C)c3)c(=O)n2Cc2ccc(F)c(C#N)c2)c(Cl)c1] | 1 | 2.09 | 493 | |
| II-0166 | 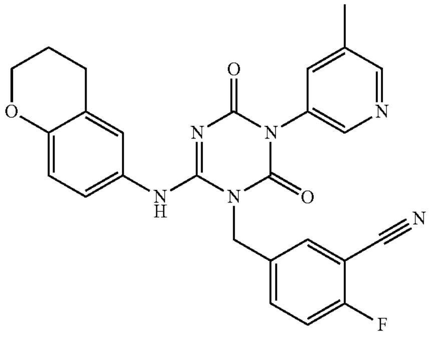 [SMILES: Cc1cncc(-n2c(=O)nc(Nc3ccc4c(c3)CCCO4)n(Cc3ccc(F)c(C#N)c3)c2=O)c1] | 1 | 1.85 | 485 | |

TABLE 86
| Compound No. | Structure | LC/MS Measured condition | Retention time (min) | m/z | Con-figration |
|---|---|---|---|---|---|
| II-0167 | 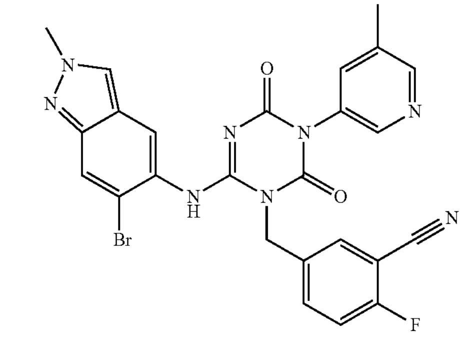 | 1 | 1.91 | 561 | |
| II-0168 | 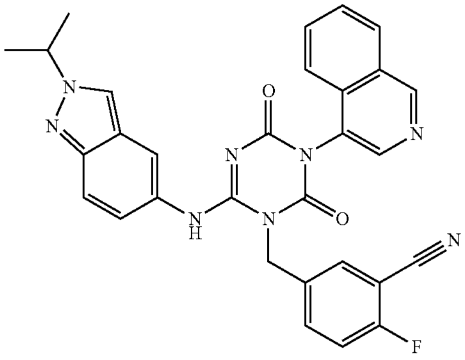 [SMILES: CC(C)n1cc2cc(Nc3nc(=O)n(-c4cncc5ccccc45)c(=O)n3Cc3ccc(F)c(C#N)c3)ccc2n1] | 1 | 1.92 | 547 | |
| II-0169 | 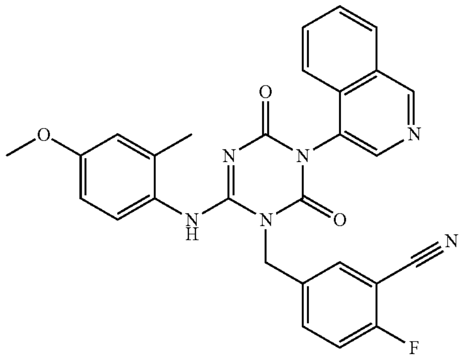 [SMILES: COc1ccc(Nc2nc(=O)n(-c3cncc4ccccc34)c(=O)n2Cc2ccc(F)c(C#N)c2)c(C)c1] | 1 | 2.00 | 509 | |
| II-0170 | 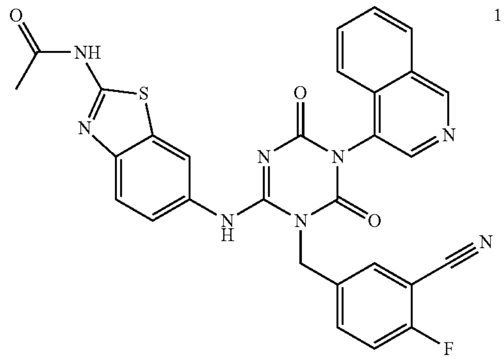 | 1 | 1.87 | 579 | |

TABLE 86-continued
| Compound No. | Structure | LC/MS Measured condition | Retention time (min) | m/z | Con-figration |
|---|---|---|---|---|---|
| II-0171 | 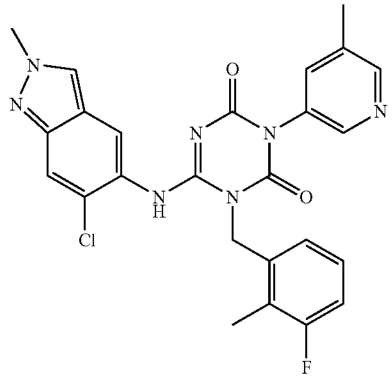 [SMILES: Cc1cncc(-n2c(=O)nc(Nc3cc4cn(C)nc4cc3Cl)n(Cc3cccc(F)c3C)c2=O)c1] | 1 | 1.88 | 506.1 | |
TABLE 87
| Compound No. | Structure | LC/MS Measured condition | Retention time (min) | m/z | Con-figration |
|---|---|---|---|---|---|
| II-0172 | 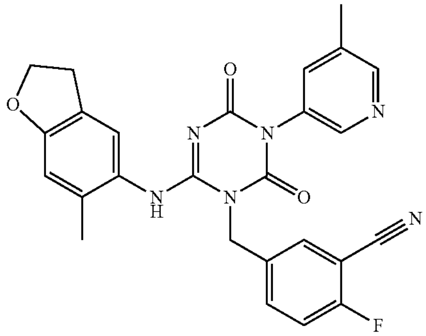 [SMILES: Cc1cncc(-n2c(=O)nc(Nc3cc4c(cc3C)OCC4)n(Cc3ccc(F)c(C#N)c3)c2=O)c1] | 1 | 1.81 | 485 | |
| II-0173 | 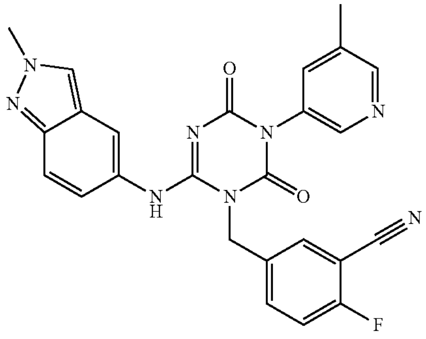 [SMILES: Cc1cncc(-n2c(=O)nc(Nc3ccc4nn(C)cc4c3)n(Cc3ccc(F)c(C#N)c3)c2=O)c1] | 1 | 1.57 | 483 | |

TABLE 87-continued
| Compound No. | Structure | LC/MS Measured condition | Retention time (min) | m/z | Con-figration |
|---|---|---|---|---|---|
| II-0174 | 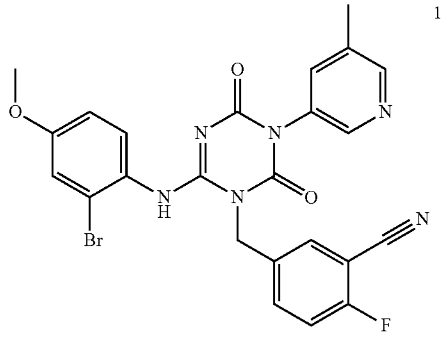 | 1 | 2.14 | 537 | |
| II-0175 | 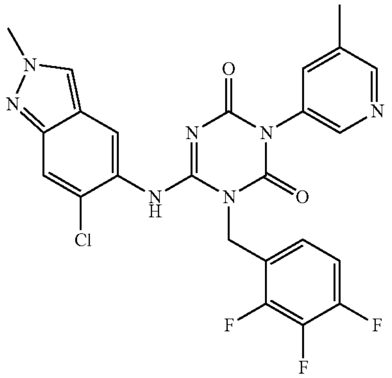 [SMILES: Cc1cncc(-n2c(=O)nc(Nc3cc4cn(C)nc4cc3Cl)n(Cc3ccc(F)c(F)c3F)c2=O)c1] | 4 | 1.62 | 528 | |
| II-0176 | 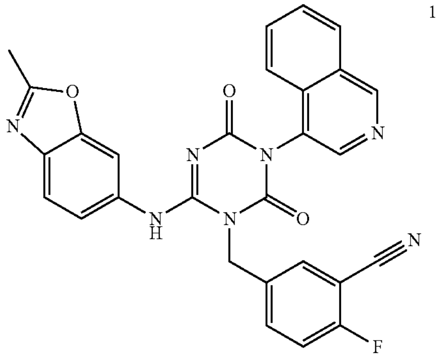 | 1 | 1.91 | 520 | |

TABLE 88
| Compound No. | Structure | LC/MS Measured condition | Retention time (min) | m/z | Con-figration |
|---|---|---|---|---|---|
| II-0177 | 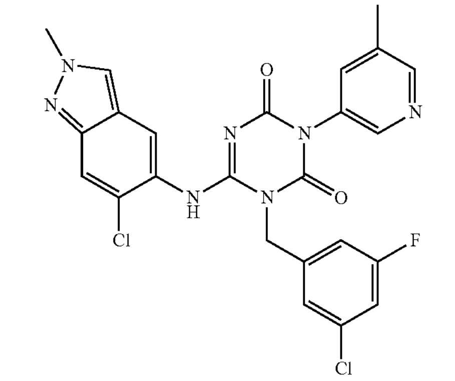 | 4 | 1.71 | 526 | |
| II-0178 | 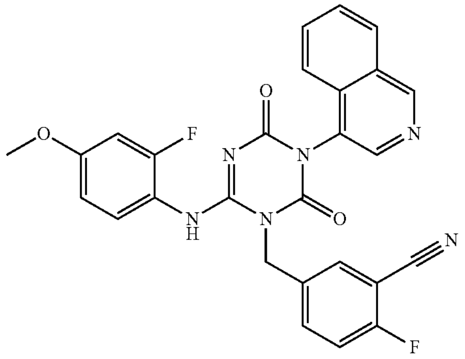 [SMILES: COc1ccc(Nc2nc(=O)n(-c3cncc4ccccc34)c(=O)n2Cc2ccc(F)c(C#N)c2)c(F)c1] | 1 | 2.06 | 513 | |
| II-0179 | 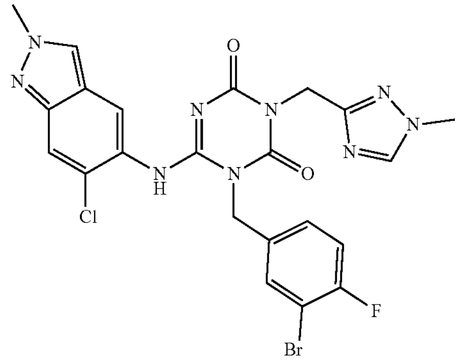 | 1 | 1.90 | 574 | |
| II-0180 | 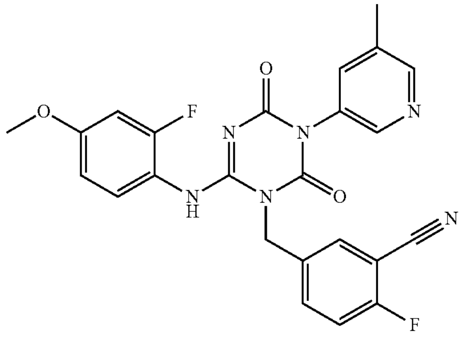 | 1 | 1.89 | 477 | |

TABLE 88-continued
| Compound No. | Structure | LC/MS Measured condition | Retention time (min) | m/z | Con-figration |
|---|---|---|---|---|---|
| II-0181 | 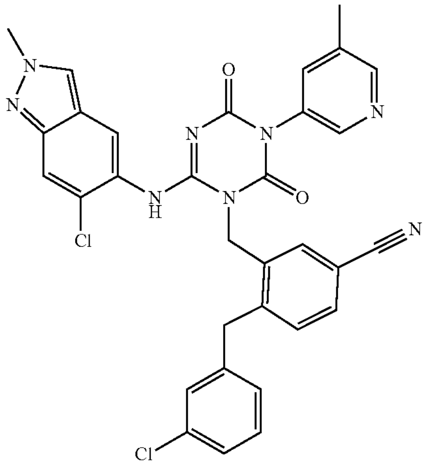 [SMILES: Cc1cncc(-n2c(=O)nc(Nc3cc4cn(C)nc4cc3Cl)n(Cc3cc(C#N)ccc3Cc3cccc(Cl)c3)c2=O)c1] | 1 | 2.34 | 623 | |
TABLE 89
| Compound No. | Structure | LC/MS Measured condition | Retention time (min) | m/z | Con-figration |
|---|---|---|---|---|---|
| II-0182 | 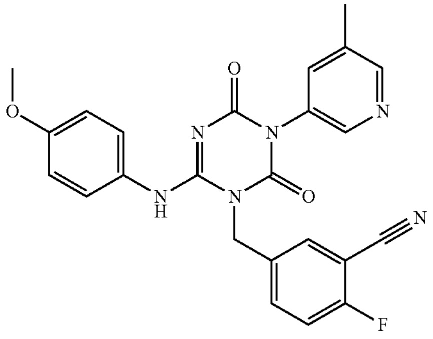 [SMILES: COc1ccc(Nc2nc(=O)n(-c3cncc(C)c3)c(=O)n2Cc2ccc(F)c(C#N)c2)cc1] | 1 | 1.75 | 459 | |
| II-0183 | 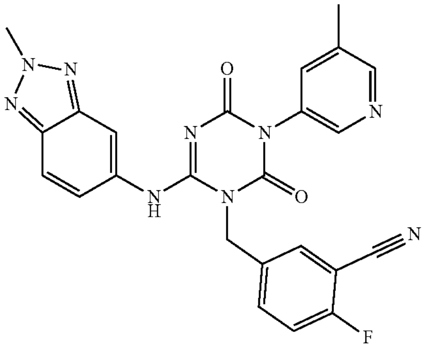 [SMILES: Cc1cncc(-n2c(=O)nc(Nc3ccc4nn(C)nc4c3)n(Cc3ccc(F)c(C#N)c3)c2=O)c1] | 1 | 1.73 | 484 | |

TABLE 89-continued
| Compound No. | Structure | LC/MS Measured condition | Retention time (min) | m/z | Con-figration |
|---|---|---|---|---|---|
| II-0184 | 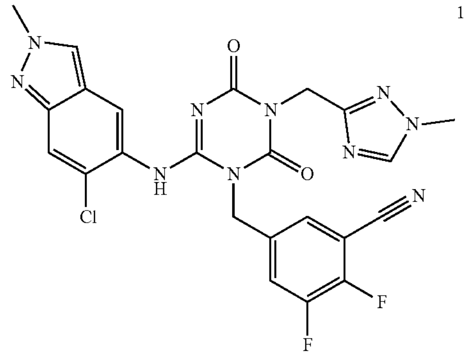 | 1 | 1.85 | 539 | |
| II-0185 | 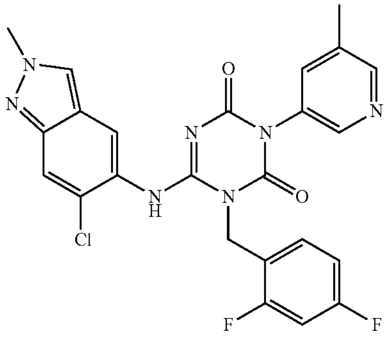 [SMILES: Cc1cncc(-n2c(=O)nc(Nc3cc4cn(C)nc4cc3Cl)n(Cc3ccc(F)cc3F)c2=O)c1] | 1 | 1.85 | 510.1 | |
| II-0186 | 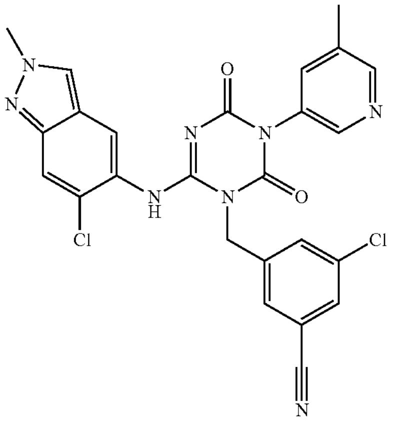 [SMILES: Cc1cncc(-n2c(=O)nc(Nc3cc4cn(C)nc4cc3Cl)n(Cc3cc(Cl)cc(C#N)c3)c2=O)c1] | 1 | 1.95 | 533 | |

TABLE 90
| Compound No. | Structure | LC/MS Measured condition | Retention time (min) | m/z | Con-figration |
|---|---|---|---|---|---|
| II-0187 | 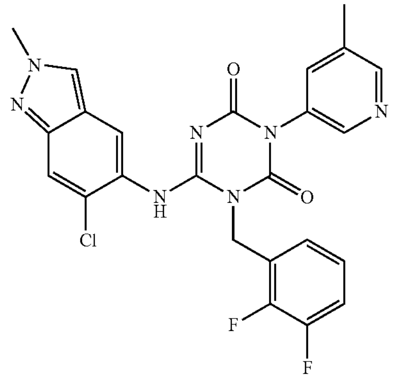 [SMILES: Cc1cncc(-n2c(=O)nc(Nc3cc4cn(C)nc4cc3Cl)n(Cc3cccc(F)c3F)c2=O)c1] | 1 | 1.85 | 510.1 | |
| II-0188 | 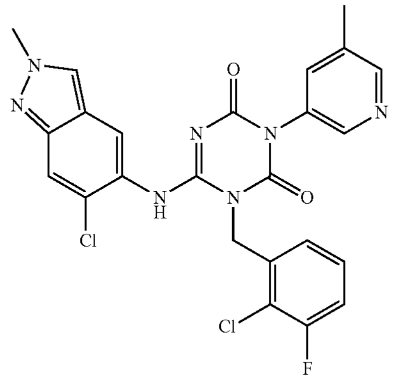 [SMILES: Cc1cncc(-n2c(=O)nc(Nc3cc4cn(C)nc4cc3Cl)n(Cc3cccc(F)c3Cl)c2=O)c1] | 1 | 1.95 | 526.1 | |
| II-0189 | 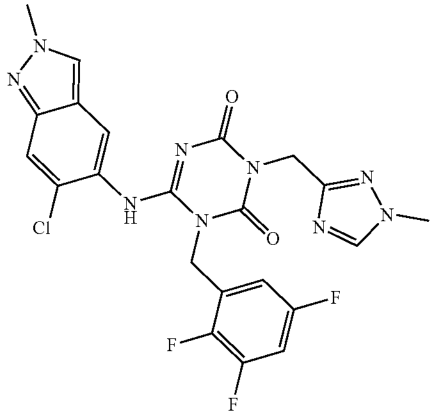 [SMILES: Cn1cnc(Cn2c(=O)nc(Nc3cc4cn(C)nc4cc3Cl)n(Cc3cc(F)cc(F)c3F)c2=O)n1] | 1 | 1.83 | 532 | |
| II-0190 | 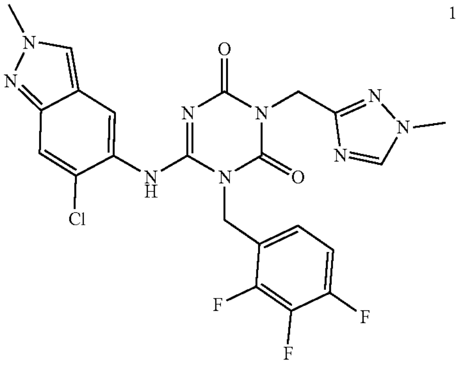 | 1 | 1.85 | 532 | |

TABLE 90-continued
| Compound No. | Structure | LC/MS Measured condition | Retention time (min) | m/z | Con-figration |
|---|---|---|---|---|---|
| II-0191 | 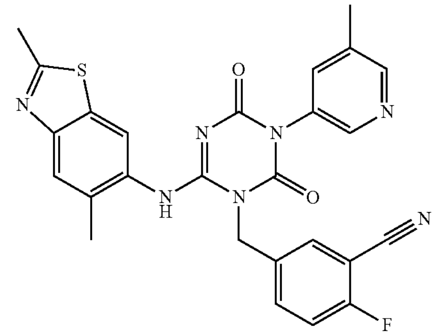 [SMILES: Cc1cncc(-n2c(=O)nc(Nc3cc4sc(C)nc4cc3C)n(Cc3ccc(F)c(C#N)c3)c2=O)c1] | 1 | 1.93 | 514 | |
TABLE 91
| Compound No. | Structure | LC/MS Measured condition | Retention time (min) | m/z | Con-figration |
|---|---|---|---|---|---|
| II-0192 | 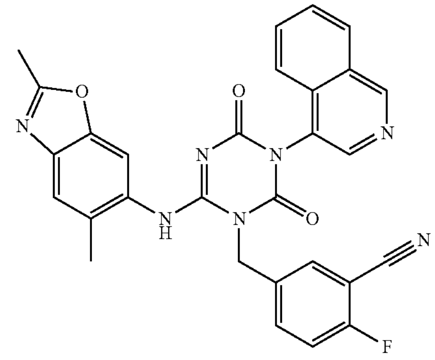 | 1 | 2.00 | 534 | |
| II-0193 | 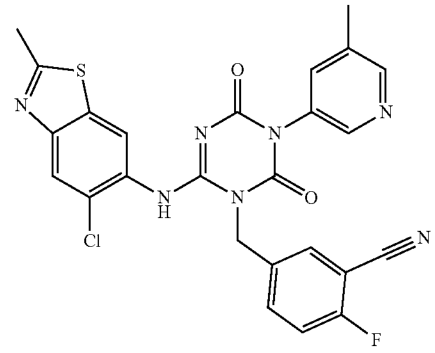 [SMILES: Cc1cncc(-n2c(=O)nc(Nc3cc4sc(C)nc4cc3Cl)n(Cc3ccc(F)c(C#N)c3)c2=O)c1] | 1 | 2.19 | 534 | |

TABLE 91-continued
| Compound No. | Structure | LC/MS Measured condition | Retention time (min) | m/z | Con-figration |
|---|---|---|---|---|---|
| II-0194 | 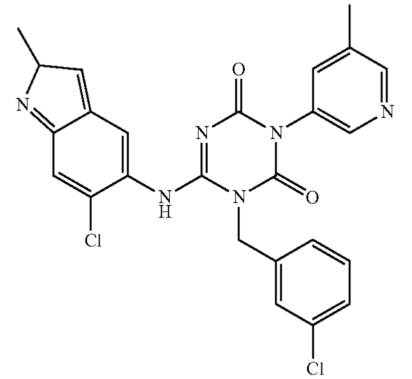 [SMILES: Cc1cncc(-n2c(=O)nc(Nc3cc4c(cc3Cl)=NC(C)C=4)n(Cc3cccc(Cl)c3)c2=O)c1] | 4 | 1.65 | 508 | |
| II-0195 | 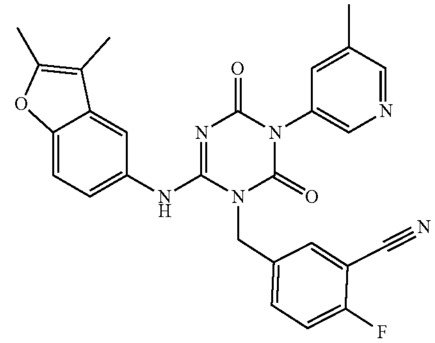 [SMILES: Cc1cncc(-n2c(=O)nc(Nc3ccc4oc(C)c(C)c4c3)n(Cc3ccc(F)c(C#N)c3)c2=O)c1] | 1 | 2.11 | 497 | |
| II-0196 | 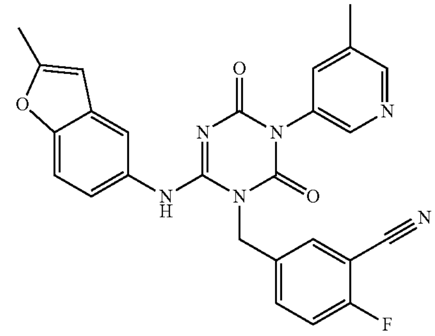 [SMILES: Cc1cncc(-n2c(=O)nc(Nc3ccc4oc(C)cc4c3)n(Cc3ccc(F)c(C#N)c3)c2=O)c1] | 1 | 2.00 | 483 | |

TABLE 92
| Compound No. | Structure | LC/MS Measured condition | Retention time (min) | m/z | Con-figration |
|---|---|---|---|---|---|
| II-0197 | 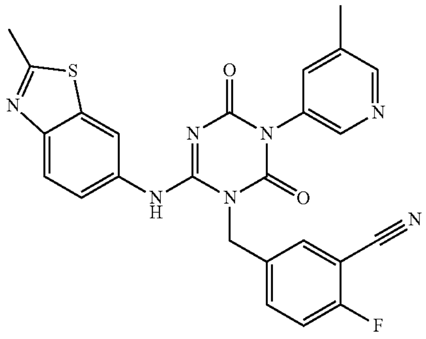 [SMILES: Cc1cncc(-n2c(=O)nc(Nc3ccc4nc(C)sc4c3)n(Cc3ccc(F)c(C#N)c3)c2=O)c1] | 1 | 1.82 | 500 | |
| II-0198 | 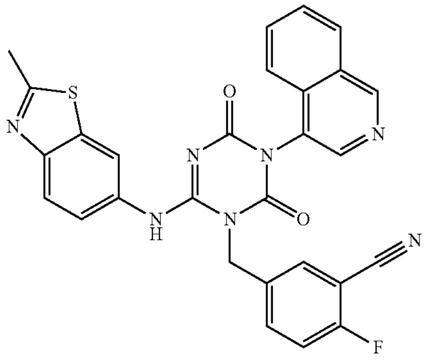 [SMILES: Cc1nc2ccc(Nc3nc(=O)n(-c4cncc5ccccc45)c(=O)n3Cc3ccc(F)c(C#N)c3)cc2s1] | 1 | 1.99 | 536 | |
| II-0199 | 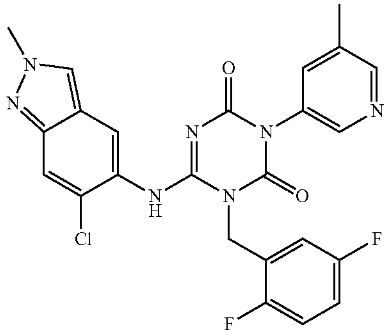 [SMILES: Cc1cncc(-n2c(=O)nc(Nc3cc4cn(C)nc4cc3Cl)n(Cc3cc(F)ccc3F)c2=O)c1] | 1 | 1.84 | 510.1 | |
| II-0200 | 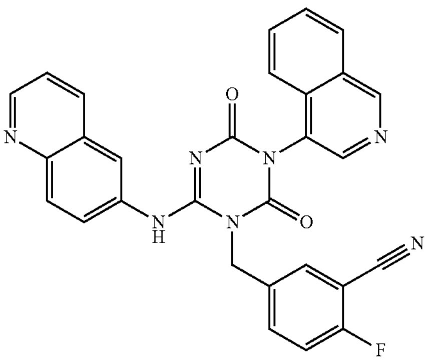 [SMILES: N#Cc1cc(Cn2c(Nc3ccc4ncccc4c3)nc(=O)n(-c3cncc4ccccc34)c2=O)ccc1F] | 1 | 1.63 | 516 | |

TABLE 92-continued
| Compound No. | Structure | LC/MS Measured condition | Retention time (min) | m/z | Con-figration |
|---|---|---|---|---|---|
| II-0201 | 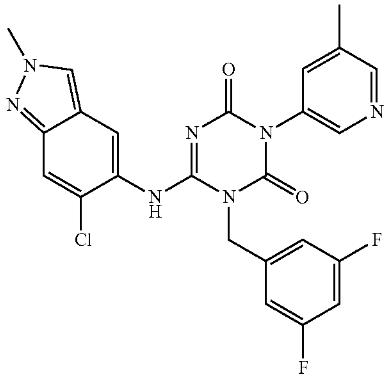 [SMILES: Cc1cncc(-n2c(=O)nc(Nc3cc4cn(C)nc4cc3Cl)n(Cc3cc(F)cc(F)c3)c2=O)c1] | 4 | 1.57 | 510 | |
TABLE 93
| Compound No. | Structure | LC/MS Measured condition | Retention time (min) | m/z | Con-figration |
|---|---|---|---|---|---|
| II-0202 | 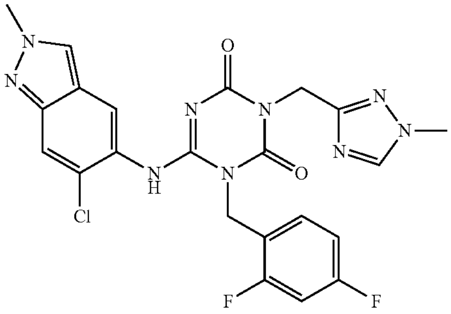 | 1 | 1.75 | 514 | |
| II-0203 | 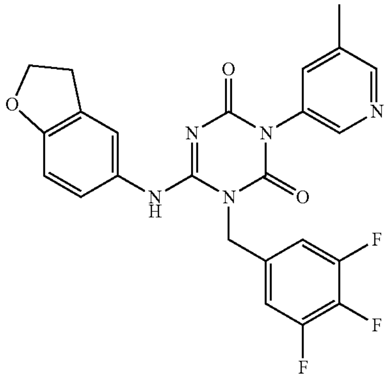 [SMILES: Cc1cncc(-n2c(=O)nc(Nc3ccc4c(c3)CCO4)n(Cc3cc(F)c(F)c(F)c3)c2=O)c1] | 1 | 1.99 | 482 | |

TABLE 93-continued
| Compound No. | Structure | LC/MS Measured condition | Retention time (min) | m/z | Con-figration |
|---|---|---|---|---|---|
| II-0204 | 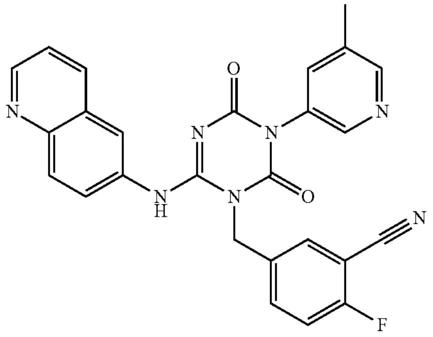 [SMILES: Cc1cncc(-n2c(=O)nc(Nc3ccc4ncccc4c3)n(Cc3ccc(F)c(C#N)c3)c2=O)c1] | 1 | 1.47 | 480 | |
| II-0205 | 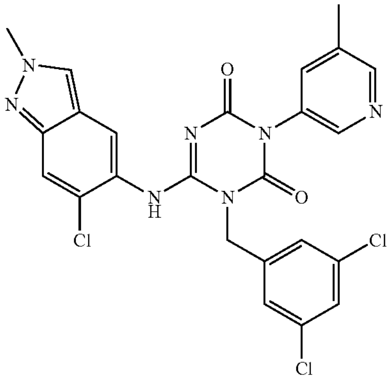 | 1 | 2.20 | 542 | |
| II-0206 | 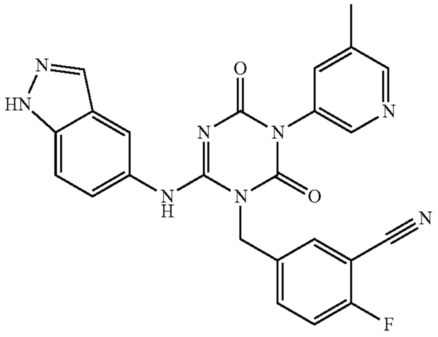 [SMILES: Cc1cncc(-n2c(=O)nc(Nc3ccc4[nH]ncc4c3)n(Cc3ccc(F)c(C#N)c3)c2=O)c1] | 1 | 1.56 | 469 | |

TABLE 94
| Compound No. | Structure | LC/MS Measured condition | Retention time (min) | m/z | Con-figuration |
|---|---|---|---|---|---|
| II-0207 | 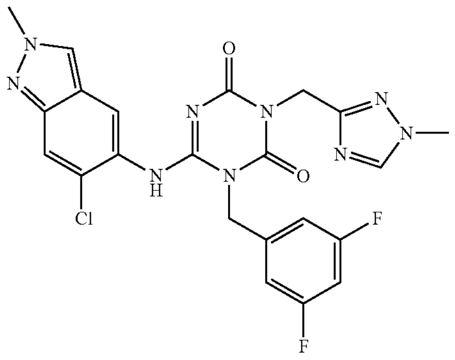 | 1 | 1.78 | 514 | |
| II-0208 | 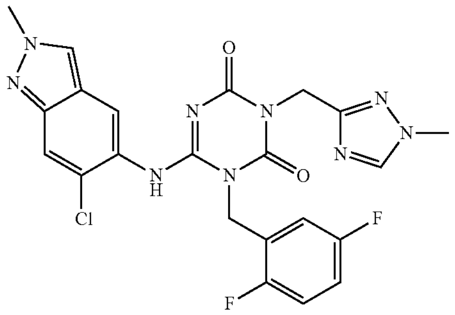 | 1 | 1.73 | 514 | |
| II-0209 | 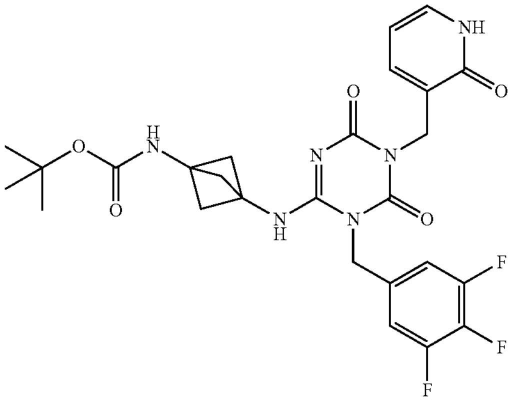 [SMILES: CC(C)(C)OC(=O)NC12CC(Nc3nc(=O)n(Cc4ccc[nH]c4=O)c(=O)n3Cc3cc(F)c(F)c(F)c3)(C1)C2] | 1 | 1.94 | 561 | |
| II-0210 | 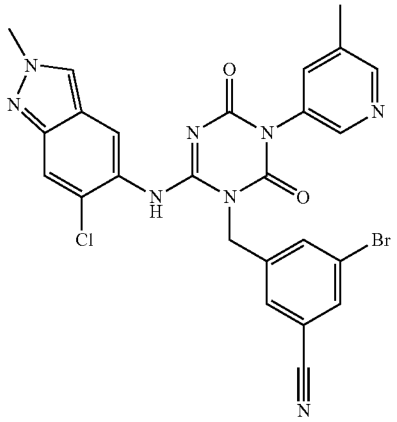 [SMILES: Cc1cncc(-n2c(=O)nc(Nc3cc4cn(C)nc4cc3Cl)n(Cc3cc(Br)cc(C#N)c3)c2=O)c1] | 1 | 1.98 | 577 | |

TABLE 94-continued
| Compound No. | Structure | LC/MS Measured condition | Retention time (min) | m/z | Con-figuration |
|---|---|---|---|---|---|
| II-0211 | 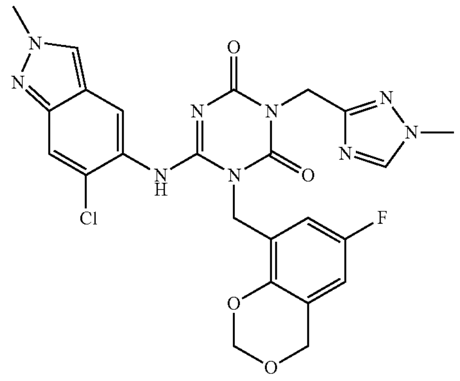 | 1 | 1.63 | 554 | |
TABLE 95
| Compound No. | Structure | LC/MS Measured condition | Retention time (min) | m/z | Con-figuration |
|---|---|---|---|---|---|
| II-0212 | 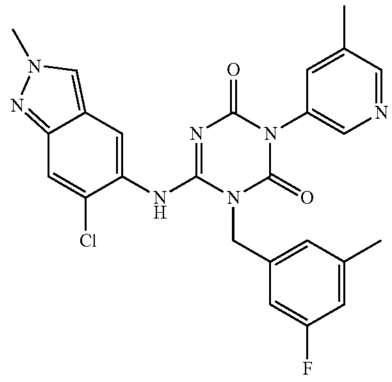 [SMILES: Cc1cc(F)cc(Cn2c(Nc3cc4cn(C)nc4cc3Cl)nc(=O)n(-c3cncc(C)c3)c2=O)c1] | 4 | 1.67 | 506 | |
| II-0213 | 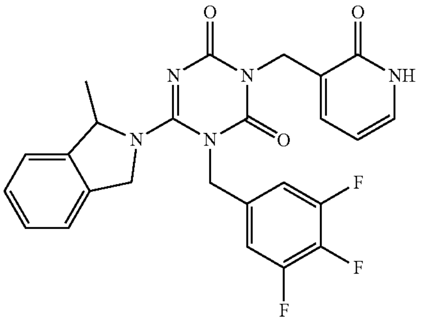 [SMILES: CC1c2ccccc2CN1c1nc(=O)n(Cc2ccc[nH]c2=O)c(=O)n1Cc1cc(F)c(F)c(F)c1] | 1 | 2.13 | 496 | |

TABLE 95-continued
| Compound No. | Structure | LC/MS Measured condition | Retention time (min) | m/z | Con-figration |
|---|---|---|---|---|---|
| II-0214 | 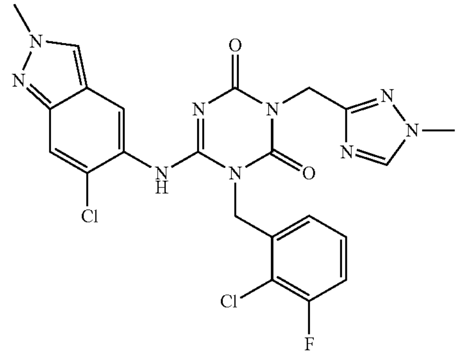 | 1 | 1.84 | 530 | |
| II-0215 | 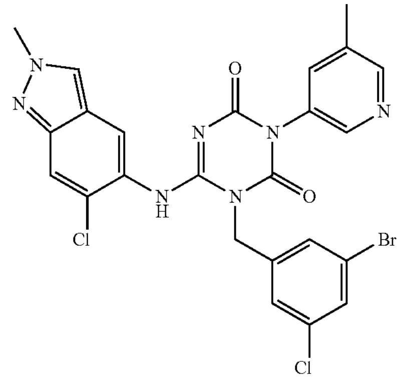 [SMILES: Cc1cncc(-n2c(=O)nc(Nc3cc4cn(C)nc4cc3Cl)n(Cc3cc(Cl)cc(Br)c3)c2=O)c1] | 1 | 2.24 | 586 | |
| II-0216 | 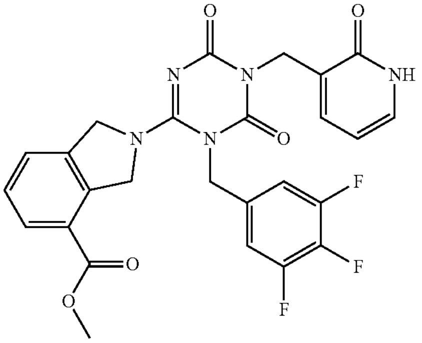 [SMILES: COC(=O)c1cccc2c1CN(c1nc(=O)n(Cc3ccc[nH]c3=O)c(=O)n1Cc1cc(F)c(F)c(F)c1)C2] | 1 | 2.01 | 540 | |

TABLE 96
| Compound No. | Structure | LC/MS Measured condition | Retention time (min) | m/z | Con-figration |
|---|---|---|---|---|---|
| II-0217 | 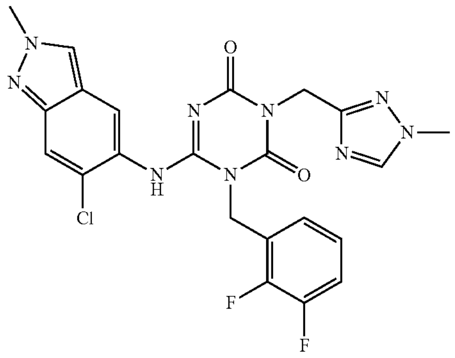 | 1 | 1.75 | 514 | |
| II-0218 | 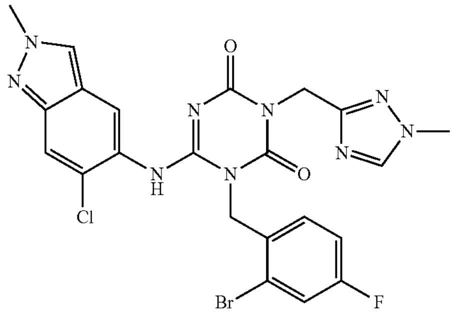 | 1 | 1.90 | 574 | |
| II-0219 | 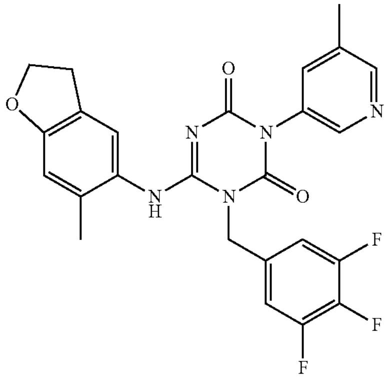 [SMILES: Cc1cncc(-n2c(=O)nc(Nc3cc4c(cc3C)OCC4)n(Cc3cc(F)c(F)c(F)c3)c2=O)c1] | 1 | 2.06 | 496 | |
| II-0220 | 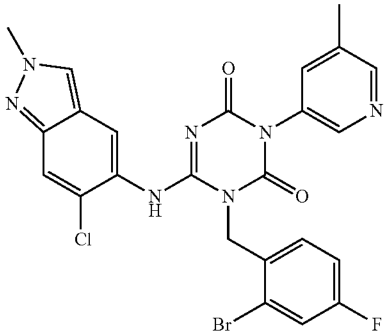 | 1 | 2.02 | 570 | |

TABLE 96-continued
| Compound No. | Structure | LC/MS Measured condition | Retention time (min) | m/z | Con-figration |
|---|---|---|---|---|---|
| II-0221 | 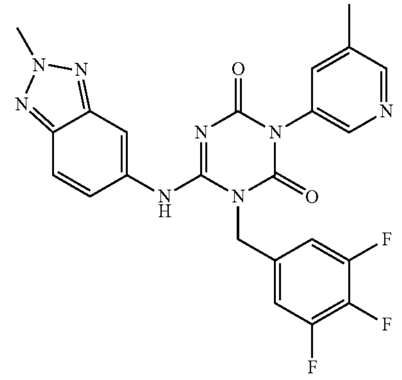 [SMILES: Cc1cncc(-n2c(=O)nc(Nc3ccc4nn(C)nc4c3)n(Cc3cc(F)c(F)c(F)c3)c2=O)c1] | 1 | 1.99 | 495 | |
TABLE 97
| Compound No. | Structure | LC/MS Measured condition | Retention time (min) | m/z | Con-figration |
|---|---|---|---|---|---|
| II-0222 | 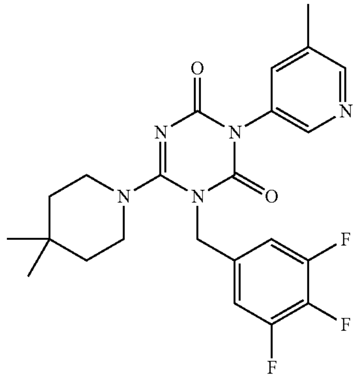 [SMILES: Cc1cncc(-n2c(=O)nc(N3CCC(C)(C)CC3)n(Cc3cc(F)c(F)c(F)c3)c2=O)c1] | 1 | 2.24 | 460 | |
| II-0223 | 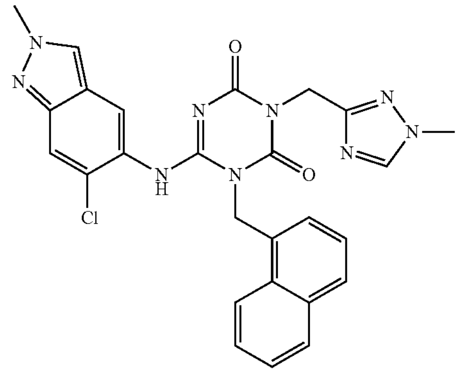 | 1 | 1.84 | 528 | |

TABLE 97-continued
| Compound No. | Structure | LC/MS Measured condition | Retention time (min) | m/z | Con-figration |
|---|---|---|---|---|---|
| II-0224 | 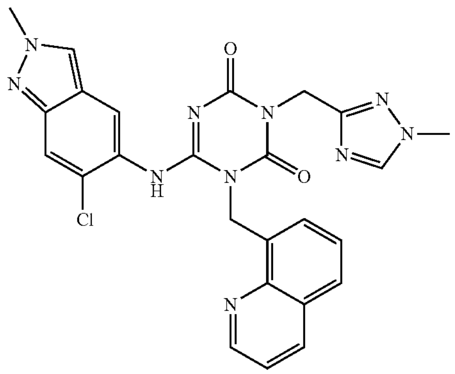 | 1 | 1.68 | 529 | |
| II-0225 | 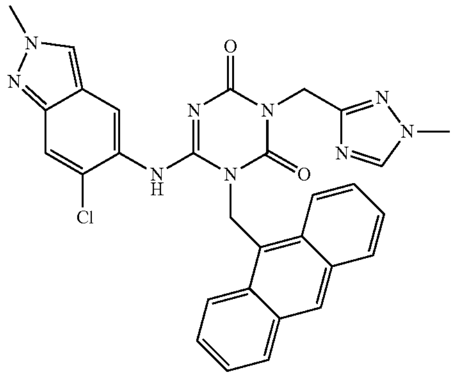 | 1 | 2.22 | 578 | |
| II-0226 | 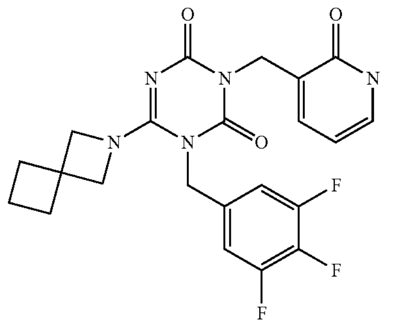 [SMILES: O=c1[nH]cccc1Cn1c(=O)nc(N2CC3(CCC3)C2)n(Cc2cc(F)c(F)c(F)c2)c1=O] | 1 | 1.92 | 460 | |

TABLE 98
| Compound No. | Structure | LC/MS Measured condition | Retention time (min) | m/z | Con-figration |
|---|---|---|---|---|---|
| II-0227 | 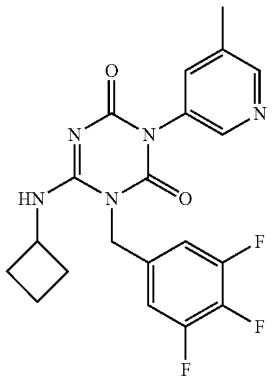 [SMILES: Cc1cncc(-n2c(=O)nc(NC3CCC3)n(Cc3cc(F)c(F)c(F)c3)c2=O)c1] | 1 | 1.85 | 418 | |
| II-0228 | 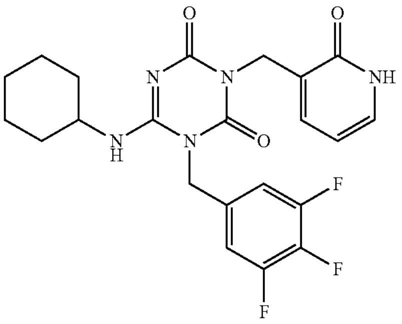 [SMILES: O=c1[nH]cccc1Cn1c(=O)nc(NC2CCCCC2)n(Cc2cc(F)c(F)c(F)c2)c1=O] | 1 | 1.96 | 462 | |
| II-0229 | 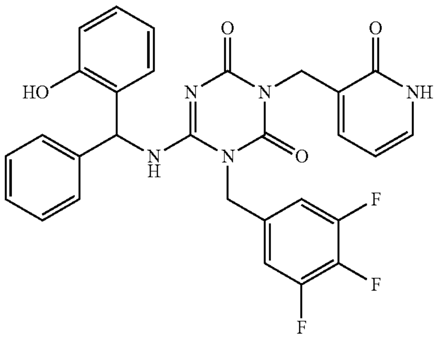 [SMILES: O=c1[nH]cccc1Cn1c(=O)nc(NC(c2ccccc2)c2ccccc2O)n(Cc2cc(F)c(F)c(F)c2)c1=O] | 1 | 2.03 | 562 | |
| II-0230 | 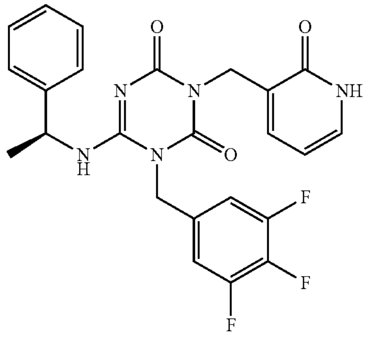 [SMILES: C[C@H](Nc1nc(=O)n(Cc2ccc[nH]c2=O)c(=O)n1Cc1cc(F)c(F)c(F)c1)c1ccccc1] | 1 | 1.94 | 484 | |

TABLE 98-continued
| Compound No. | Structure | LC/MS Measured condition | Retention time (min) | m/z | Con-figration |
|---|---|---|---|---|---|
| II-0231 | 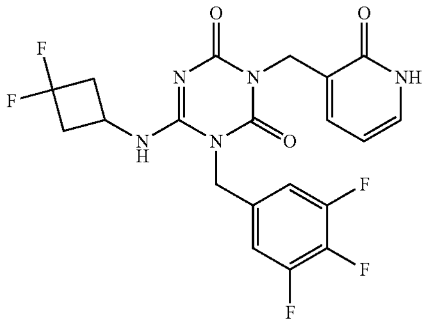 [SMILES: O=c1[nH]cccc1Cn1c(=O)nc(NC2CC(F)(F)C2)n(Cc2cc(F)c(F)c(F)c2)c1=O] | 1 | 1.79 | 470 | |
TABLE 99
| Compound No. | Structure | LC/MS Measured condition | Retention time (min) | m/z | Con-figration |
|---|---|---|---|---|---|
| II-0232 | 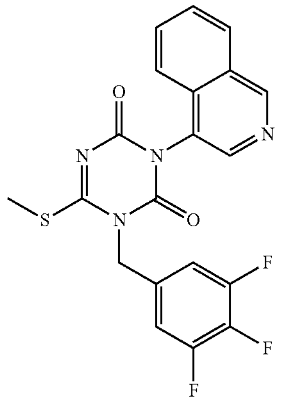 [SMILES: CSc1nc(=O)n(-c2cncc3ccccc23)c(=O)n1Cc1cc(F)c(F)c(F)c1] | 1 | 1.98 | 431 | |
| II-0233 | 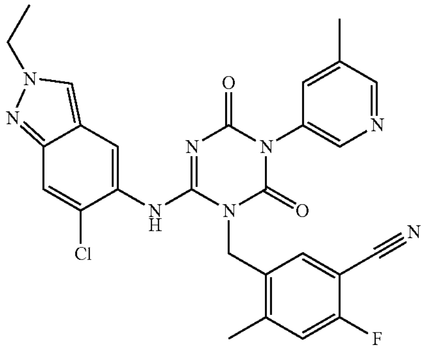 [SMILES: CCn1cc2cc(Nc3nc(=O)n(-c4cncc(C)c4)c(=O)n3Cc3cc(C#N)c(F)cc3C)c(Cl)cc2n1] | 3 | 1.79 | 545 | |

TABLE 99-continued
| Compound No. | Structure | LC/MS Measured condition | Retention time (min) | m/z | Con-figration |
|---|---|---|---|---|---|
| II-0234 | 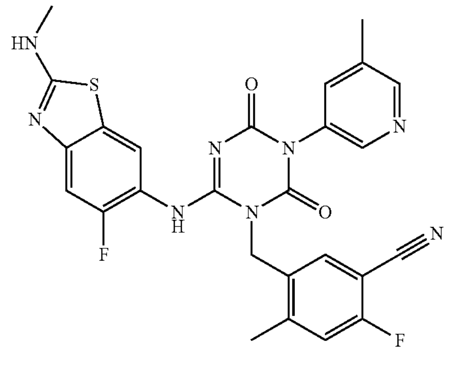 [SMILES: CNc1nc2cc(F)c(Nc3nc(=O)n(-c4cncc(C)c4)c(=O)n3Cc3cc(C#N)c(F)cc3C)cc2s1] | 3 | 1.60 | 547 | |
| II-0235 | 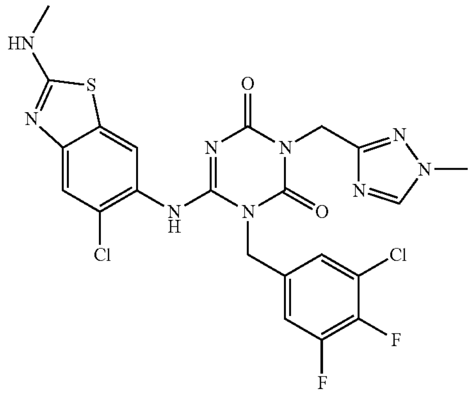 [SMILES: CNc1nc2cc(Cl)c(Nc3nc(=O)n(Cc4ncn(C)n4)c(=O)n3Cc3cc(F)c(F)c(Cl)c3)cc2s1] | 3 | 1.80 | 581 | |
| II-0236 | 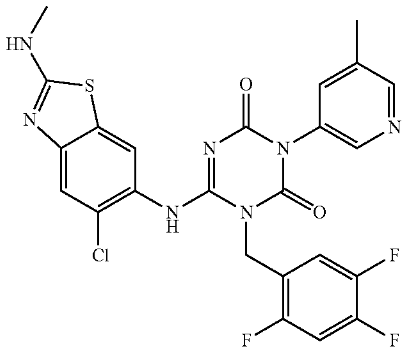 [SMILES: CNc1nc2cc(Cl)c(Nc3nc(=O)n(-c4cncc(C)c4)c(=O)n3Cc3cc(F)c(F)cc3F)cc2s1] | 3 | 1.88 | 560 | |

TABLE 100
| Compound No. | Structure | LC/MS Measured condition | Retention time (min) | m/z | Con-figration |
|---|---|---|---|---|---|
| II-0237 | 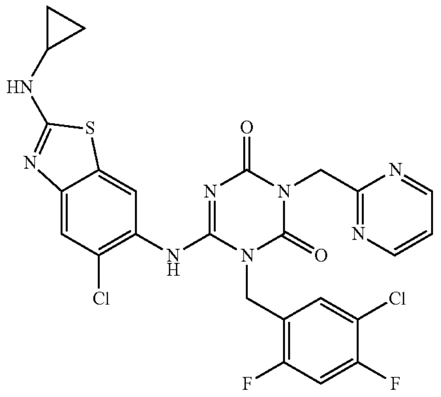 [SMILES: O=c1nc(Nc2cc3sc(NC4CC4)nc3cc2Cl)n(Cc2cc(Cl)c(F)cc2F)c(=O)n1Cc1ncccn1] | 3 | 2.08 | 604 | |
| II-0238 | 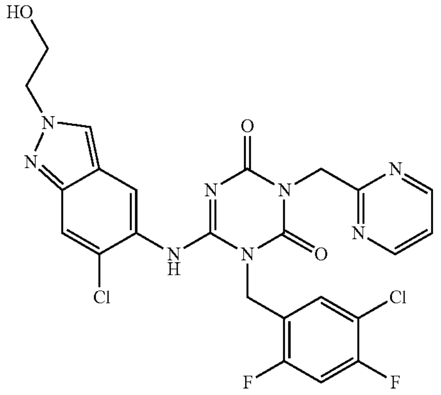 [SMILES: O=c1nc(Nc2cc3cn(CCO)nc3cc2Cl)n(Cc2cc(Cl)c(F)cc2F)c(=O)n1Cc1ncccn1] | 3 | 1.72 | 576 | |
| II-0239 | 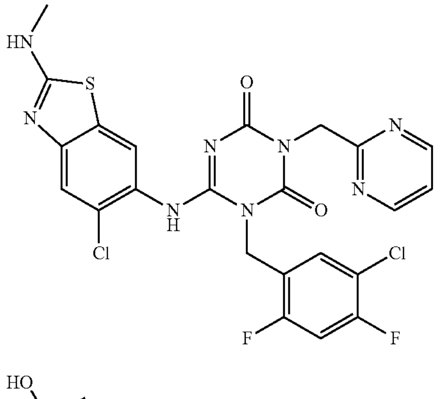 | 3 | 1.90 | 578 | |
| II-0240 | 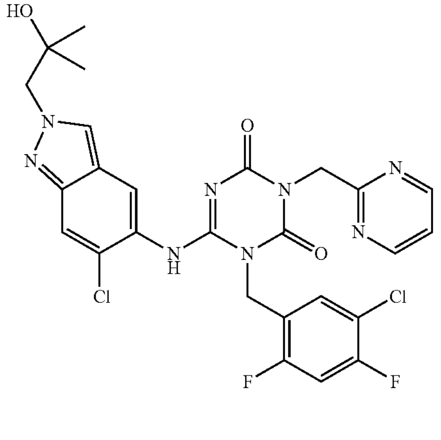 [SMILES: CC(C)(O)Cn1cc2cc(Nc3nc(=O)n(Cc4ncccn4)c(=O)n3Cc3cc(Cl)c(F)cc3F)c(Cl)cc2n1] | 3 | 1.88 | 604 | |

TABLE 100-continued
| Compound No. | Structure | LC/MS Measured condition | Retention time (min) | m/z | Con-figration |
|---|---|---|---|---|---|
| II-0241 | 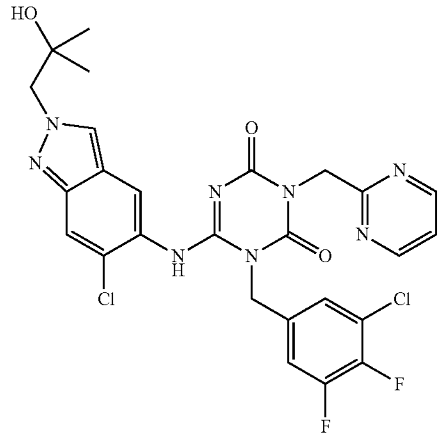 [SMILES: CC(C)(O)Cn1cc2cc(Nc3nc(=O)n(Cc4ncccn4)c(=O)n3Cc3cc(F)c(F)c(Cl)c3)c(Cl)cc2n1] | 3 | 1.95 | 604 | |
TABLE 101
| Compound No. | Structure | LC/MS Measured condition | Retention time (min) | m/z | Con-figration |
|---|---|---|---|---|---|
| II-0242 | 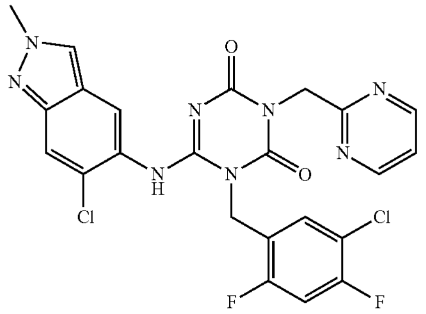 | 3 | 1.86 | 546 | |
| II-0243 | 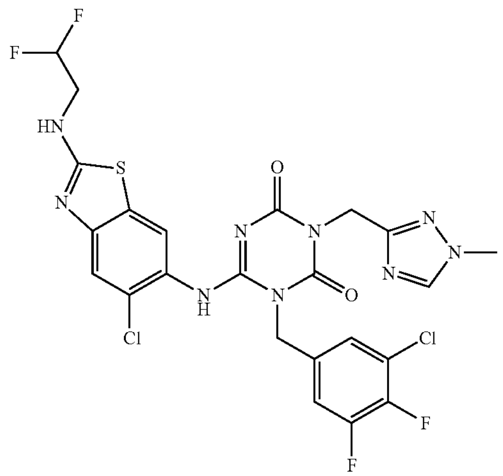 [SMILES: Cn1cnc(Cn2c(=O)nc(Nc3cc4sc(NCC(F)F)nc4cc3Cl)n(Cc3cc(F)c(F)c(Cl)c3)c2=O)n1] | 3 | 2.07 | 631 | |

TABLE 101-continued
| Compound No. | Structure | LC/MS Measured condition | Retention time (min) | m/z | Con-figration |
|---|---|---|---|---|---|
| II-0244 | 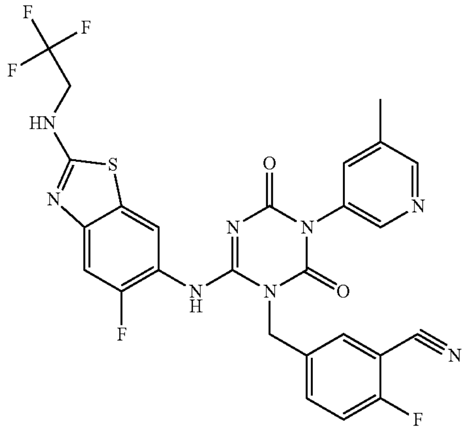 [SMILES: Cc1cncc(-n2c(=O)nc(Nc3cc4sc(NCC(F)(F)F)nc4cc3F)n(Cc3ccc(F)c(C#N)c3)c2=O)c1] | 3 | 1.90 | 601 | |
| II-0245 | 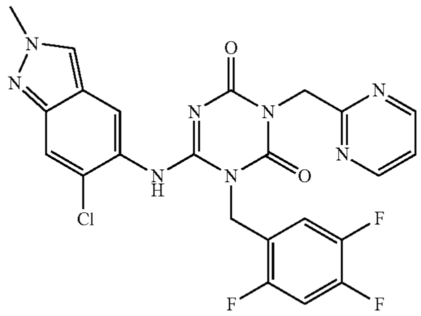 [SMILES: Cn1cc2cc(Nc3nc(=O)n(Cc4ncccn4)c(=O)n3Cc3cc(F)c(F)cc3F)c(Cl)cc2n1] | 3 | 1.78 | 529 | |
| II-0246 | 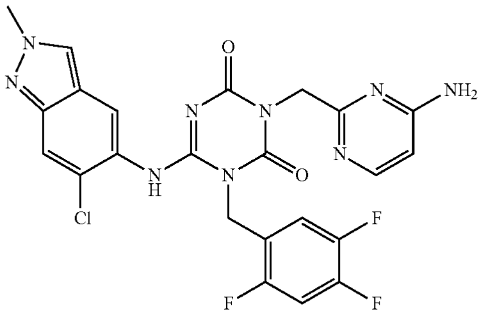 [SMILES: Cn1cc2cc(Nc3nc(=O)n(Cc4nccc(N)n4)c(=O)n3Cc3cc(F)c(F)cc3F)c(Cl)cc2n1] | 3 | 1.30 | 544 | |

TABLE 102
| Compound No. | Structure | LC/MS Measured condition | Retention time (min) | m/z | Con-figration |
|---|---|---|---|---|---|
| II-0247 | 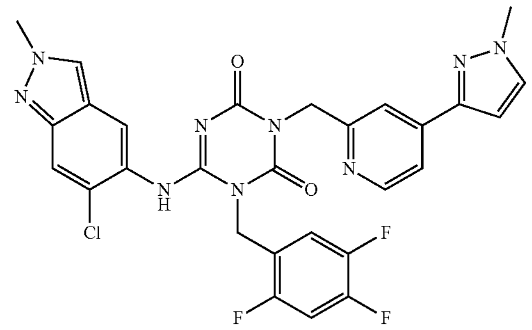 | 3 | 1.73 | 608 | |
| II-0248 | 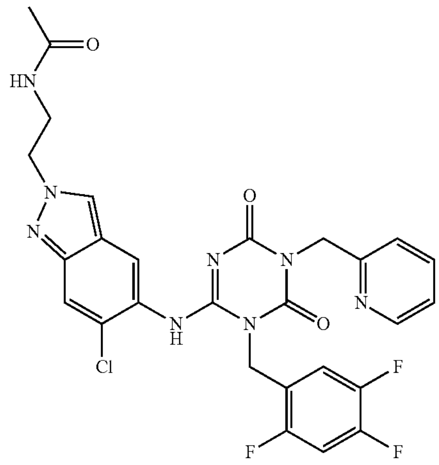 [SMILES: CC(=O)NCCn1cc2cc(Nc3nc(=O)n(Cc4ccccn4)c(=O)n3Cc3cc(F)c(F)cc3F)c(Cl)cc2n1] | 3 | 1.63 | 599 | |
| II-0249 | 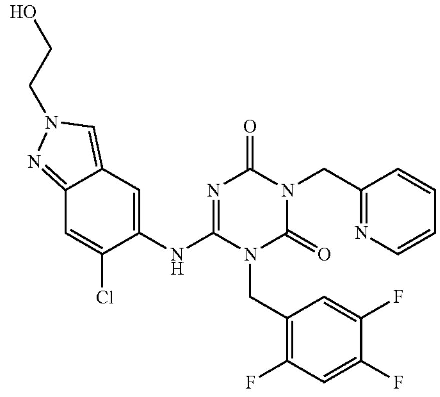 [SMILES: O=c1nc(Nc2cc3cn(CCO)nc3cc2Cl)n(Cc2cc(F)c(F)cc2F)c(=O)n1Cc1ccccn1] | 3 | 1.64 | 558 | |
| II-0250 | 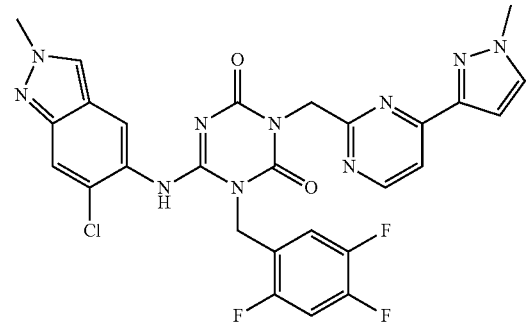 [SMILES: Cn1ccc(-c2ccnc(Cn3c(=O)nc(Nc4cc5cn(C)nc5cc4Cl)n(Cc4cc(F)c(F)cc4F)c3=O)n2)n1] | 3 | 1.88 | 609 | |

TABLE 102-continued
| Compound No. | Structure | LC/MS Measured condition | Retention time (min) | m/z | Con-figration |
|---|---|---|---|---|---|
| II-0251 | 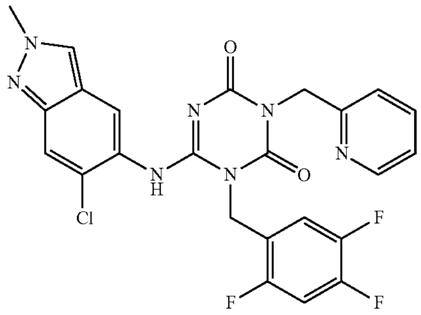 [SMILES: Cn1cc2cc(Nc3nc(=O)n(Cc4ccccn4)c(=O)n3Cc3cc(F)c(F)cc3F)c(Cl)cc2n1] | 3 | 1.78 | 528 | |
TABLE 103
| Compound No. | Structure | LC/MS Measured condition | Retention time (min) | m/z | Con-figration |
|---|---|---|---|---|---|
| II-0252 | 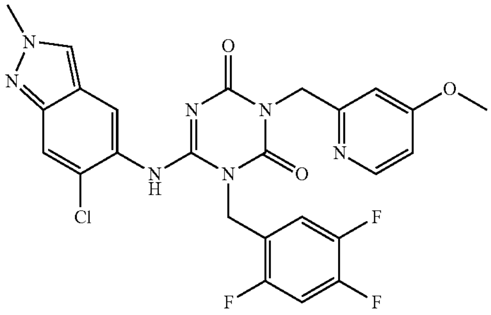 | 3 | 1.44 | 558 | |
| II-0253 | 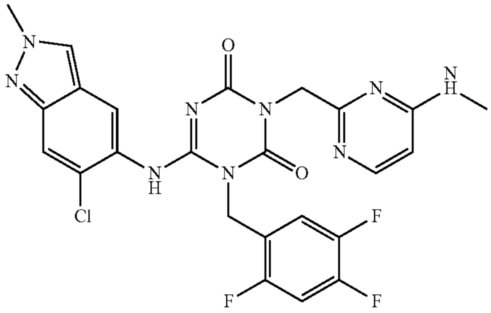 | 3 | 1.33 | 558 | |
| II-0254 | 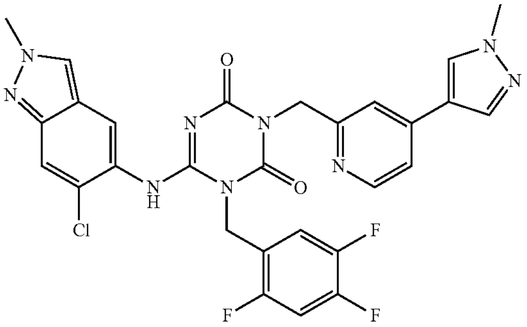 [SMILES: Cn1cc(-c2ccnc(Cn3c(=O)nc(Nc4cc5cn(C)nc5cc4Cl)n(Cc4cc(F)c(F)cc4F)c3=O)c2)cn1] | 3 | 1.54 | 608 | |

TABLE 103-continued
| Compound No. | Structure | LC/MS Measured condition | Retention time (min) | m/z | Con-figration |
|---|---|---|---|---|---|
| II-0255 | 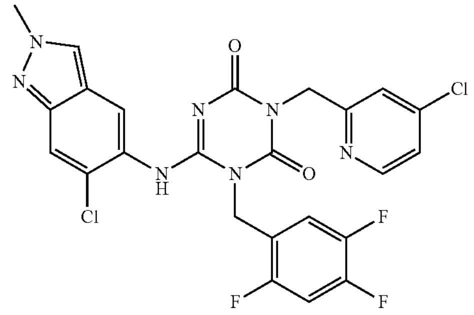 [SMILES: Cn1cc2cc(Nc3nc(=O)n(Cc4cc(Cl)ccn4)c(=O)n3Cc3cc(F)c(F)cc3F)c(Cl)cc2n1] | 3 | 2.10 | 563 | |
| II-0256 | 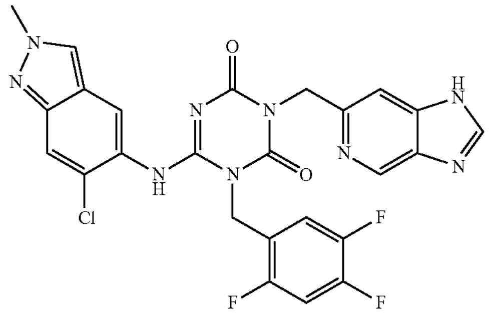 [SMILES: Cn1cc2cc(Nc3nc(=O)n(Cc4cc5[nH]cnc5cn4)c(=O)n3Cc3cc(F)c(F)cc3F)c(Cl)cc2n1] | 3 | 1.47 | 568 | |
TABLE 104
| Compound No. | Structure | LC/MS Measured condition | Retention time (min) | m/z | Con-figration |
|---|---|---|---|---|---|
| II-0257 | 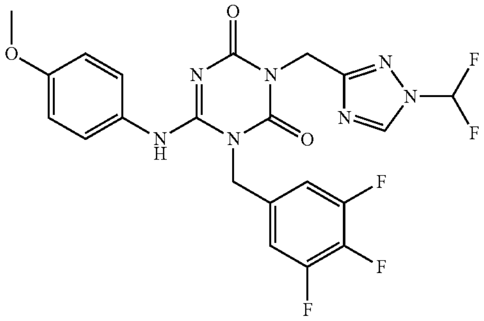 [SMILES: COc1ccc(Nc2nc(=O)n(Cc3ncn(C(F)F)n3)c(=O)n2Cc2cc(F)c(F)c(F)c2)cc1] | 3 | 1.85 | 510 | |
| II-0258 | 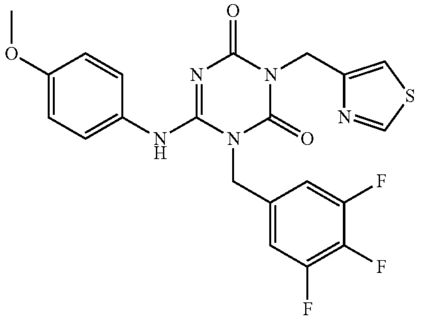 [SMILES: COc1ccc(Nc2nc(=O)n(Cc3cscn3)c(=O)n2Cc2cc(F)c(F)c(F)c2)cc1] | 5 | 1.91 | 476 | |

TABLE 104-continued
| Compound No. | Structure | LC/MS Measured condition | Retention time (min) | m/z | Con-figration |
|---|---|---|---|---|---|
| II-0259 | 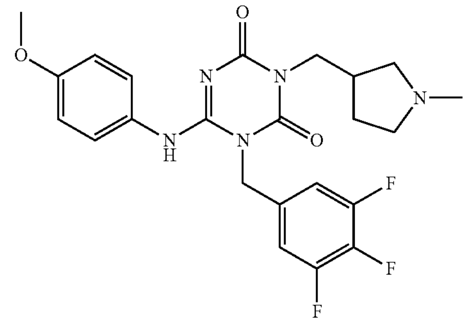 [SMILES: COc1ccc(Nc2nc(=O)n(CC3CCN(C)C3)c(=O)n2Cc2cc(F)c(F)c(F)c2)cc1] | 3 | 1.28 | 476 | |
| II-0260 | 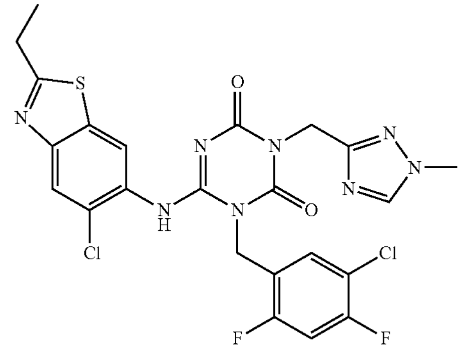 [SMILES: CCc1nc2cc(Cl)c(Nc3nc(=O)n(Cc4ncn(C)n4)c(=O)n3Cc3cc(Cl)c(F)cc3F)cc2s1] | 1 | 1.81 | 580 | |
| II-0261 | 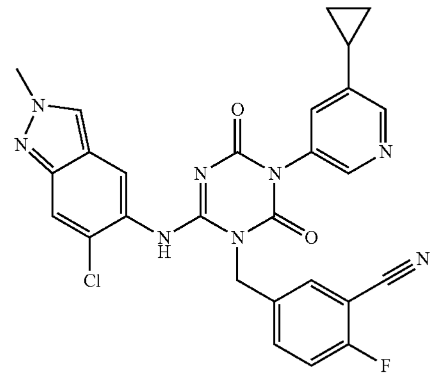 [SMILES: Cn1cc2cc(Nc3nc(=O)n(-c4cncc(C5CC5)c4)c(=O)n3Cc3ccc(F)c(C#N)c3)c(Cl)cc2n1] | 1 | 2.01 | 543.1 | |

TABLE 105
| Compound No. | Structure | LC/MS Measured condition | Retention time (min) | m/z | Con-figration |
|---|---|---|---|---|---|
| II-0262 | 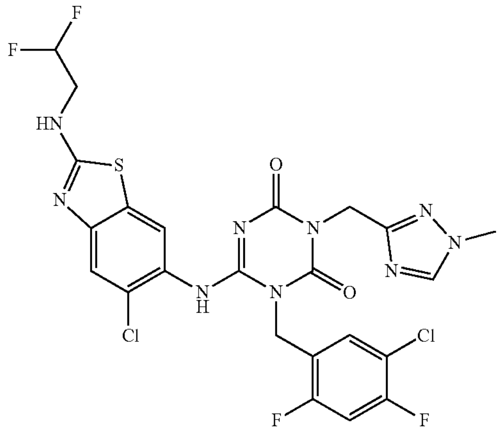 [SMILES: Cn1cnc(Cn2c(=O)nc(Nc3cc4sc(NCC(F)F)nc4cc3Cl)n(Cc3cc(Cl)c(F)cc3F)c2=O)n1] | 1 | 2.11 | 630 | |
| II-0263 | 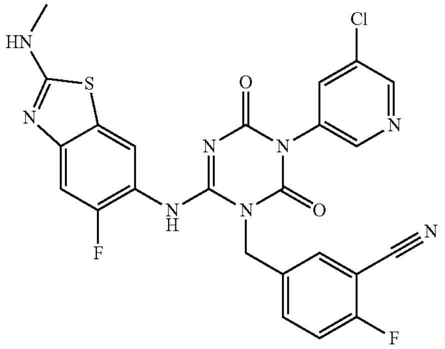 [SMILES: CNc1nc2cc(F)c(Nc3nc(=O)n(-c4cncc(Cl)c4)c(=O)n3Cc3ccc(F)c(C#N)c3)cc2s1] | 1 | 1.88 | 553 | |
| II-0264 | 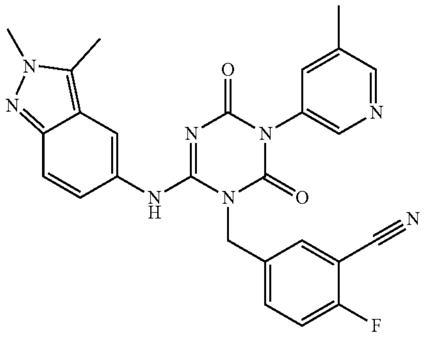 [SMILES: Cc1cncc(-n2c(=O)nc(Nc3ccc4nn(C)c(C)c4c3)n(Cc3ccc(F)c(C#N)c3)c2=O)c1] | 1 | 1.59 | 497.2 | |
| II-0265 | 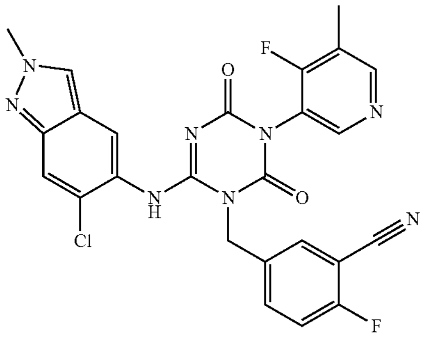 [SMILES: Cc1cncc(-n2c(=O)nc(Nc3cc4cn(C)nc4cc3Cl)n(Cc3ccc(F)c(C#N)c3)c2=O)c1F] | 1 | 1.88 | 535.1 | |

TABLE 105-continued
| Compound No. | Structure | LC/MS Measured condition | Retention time (min) | m/z | Con-figration |
|---|---|---|---|---|---|
| II-0266 | 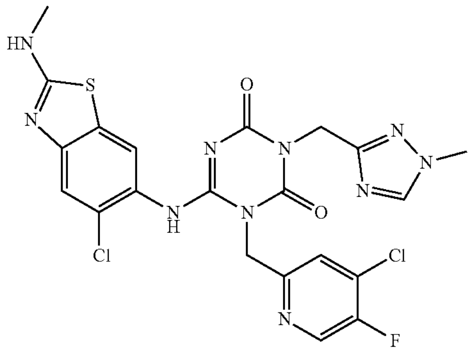 [SMILES: CNc1nc2cc(Cl)c(Nc3nc(=O)n(Cc4ncn(C)n4)c(=O)n3Cc3cc(Cl)c(F)cn3)cc2s1] | 1 | 1.57 | 563.1 | |
TABLE 106
| Compound No. | Structure | LC/MS Measured condition | Retention time (min) | m/z | Con-figration |
|---|---|---|---|---|---|
| II-0267 | 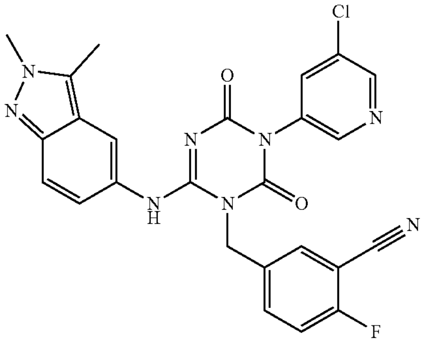 [SMILES: Cc1c2cc(Nc3nc(=O)n(-c4cncc(Cl)c4)c(=O)n3Cc3ccc(F)c(C#N)c3)ccc2nn1C] | 1 | 1.81 | 517.2 | |
| II-0268 | 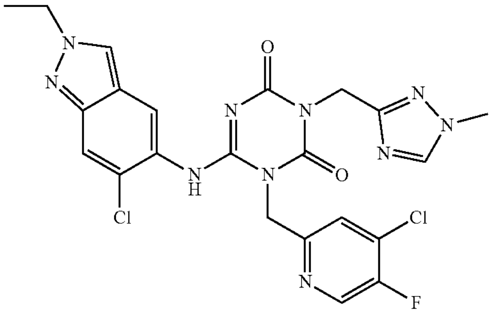 [SMILES: CCn1cc2cc(Nc3nc(=O)n(Cc4ncn(C)n4)c(=O)n3Cc3cc(Cl)c(F)cn3)c(Cl)cc2n1] | 1 | 1.70 | 545.1 | |
| II-0269 | 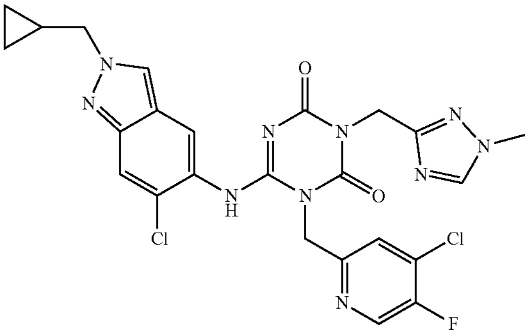 [SMILES: Cn1cnc(Cn2c(=O)nc(Nc3cc4cn(CC5CC5)nc4cc3Cl)n(Cc3cc(Cl)c(F)cn3)c2=O)n1] | 1 | 1.83 | 571 | |

TABLE 106-continued
| Compound No. | Structure | LC/MS Measured condition | Retention time (min) | m/z | Con-figration |
|---|---|---|---|---|---|
| II-0270 | 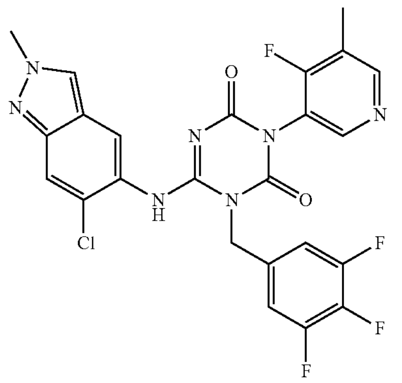 [SMILES: Cc1cncc(-n2c(=O)nc(Nc3cc4cn(C)nc4cc3Cl)n(Cc3cc(F)c(F)c(F)c3)c2=O)c1F] | 1 | 2.05 | 546.2 | |
| II-0271 | 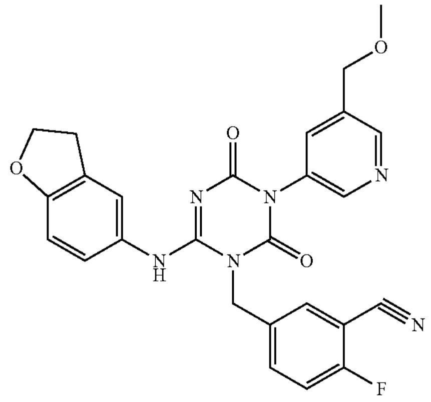 [SMILES: COCc1cncc(-n2c(=O)nc(Nc3ccc4c(c3)CCO4)n(Cc3ccc(F)c(C#N)c3)c2=O)c1] | 1 | 1.76 | 501.2 | |
TABLE 107
| Compound No. | Structure | LC/MS Measured condition | Retention time (min) | m/z | Con-figration |
|---|---|---|---|---|---|
| II-0272 | 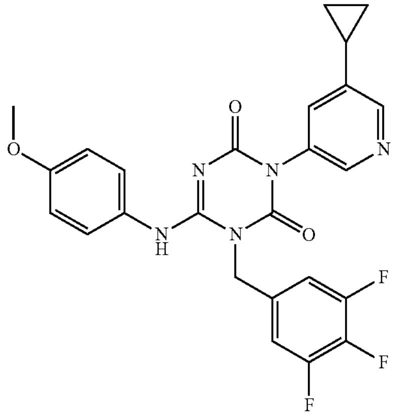 [SMILES: COc1ccc(Nc2nc(=O)n(-c3cncc(C4CC4)c3)c(=O)n2Cc2cc(F)c(F)c(F)c2)cc1] | 1 | 2.03 | 496.2 | |

TABLE 107-continued
| Compound No. | Structure | LC/MS Measured condition | Retention time (min) | m/z | Con-figration |
|---|---|---|---|---|---|
| II-0273 | 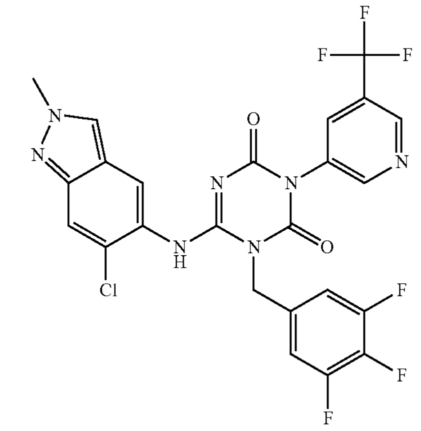 [SMILES: Cn1cc2cc(Nc3nc(=O)n(-c4cncc(C(F)(F)F)c4)c(=O)n3Cc3cc(F)c(F)c(F)c3)c(Cl)cc2n1] | 1 | 2.26 | 582.1 | |
| II-0274 | 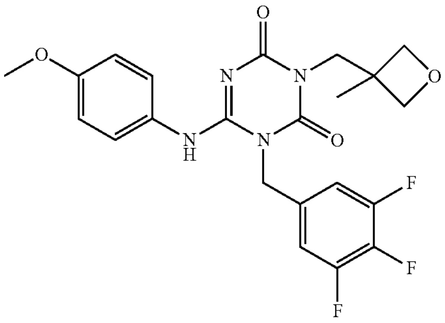 [SMILES: COc1ccc(Nc2nc(=O)n(CC3(C)COC3)c(=O)n2Cc2cc(F)c(F)c(F)c2)cc1] | 1 | 2.19 | 463 | |
| II-0275 | 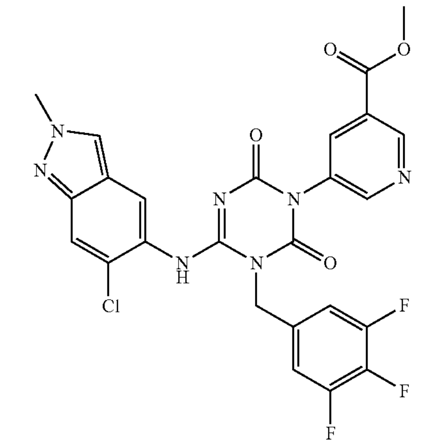 | 1 | 1.98 | 572 | |

TABLE 107-continued
| Compound No. | Structure | LC/MS Measured condition | Retention time (min) | m/z | Con-figration |
|---|---|---|---|---|---|
| II-0276 | 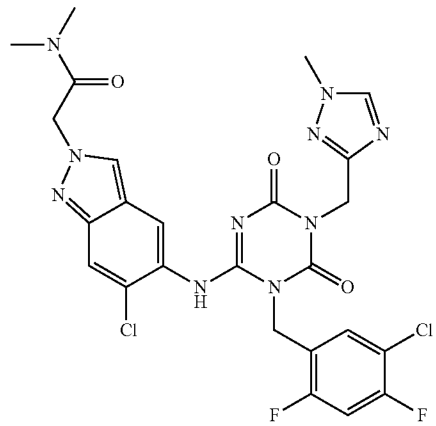 [SMILES: CN(C)C(=O)Cn1cc2cc(Nc3nc(=O)n(Cc4ncn(C)n4)c(=O)n3Cc3cc(Cl)c(F)cc3F)c(Cl)cc2n1] | 1 | 1.67 | 619.4 | |
TABLE 108
| Compound No. | Structure | LC/MS Measured condition | Retention time (min) | m/z | Con-figration |
|---|---|---|---|---|---|
| II-0277 | 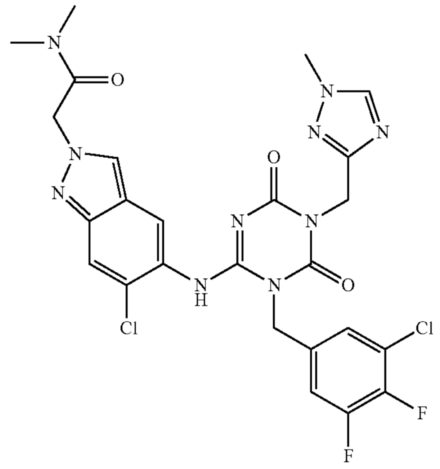 [SMILES: CN(C)C(=O)Cn1cc2cc(Nc3nc(=O)n(Cc4ncn(C)n4)c(=O)n3Cc3cc(F)c(F)c(Cl)c3)c(Cl)cc2n1] | 1 | 1.74 | 619.4 | |
| II-0278 | 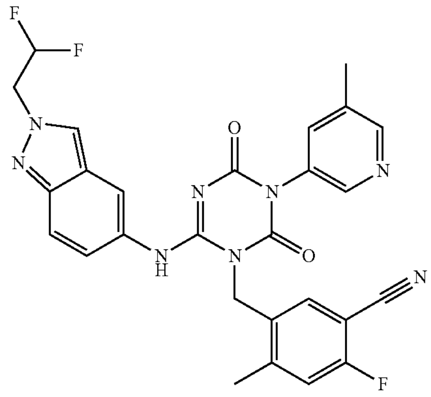 [SMILES: Cc1cncc(-n2c(=O)nc(Nc3ccc4nn(CC(F)F)cc4c3)n(Cc3cc(C#N)c(F)cc3C)c2=O)c1] | 1 | 1.64 | 546.5 | |

TABLE 108-continued
| Compound No. | Structure | LC/MS Measured condition | Retention time (min) | m/z | Con-figration |
|---|---|---|---|---|---|
| II-0279 | 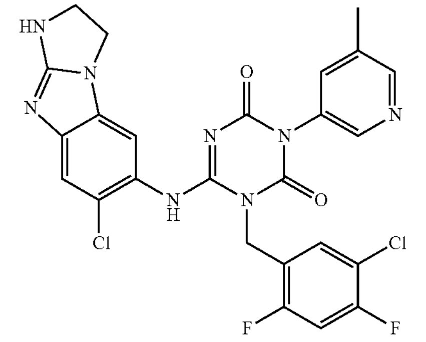 [SMILES: Cc1cncc(-n2c(=O)nc(Nc3cc4c(cc3Cl)nc3n4CCN3)n(Cc3cc(Cl)c(F)cc3F)c2=O)c1] | 1 | 1.61 | 571.3 | |
| II-0280 | 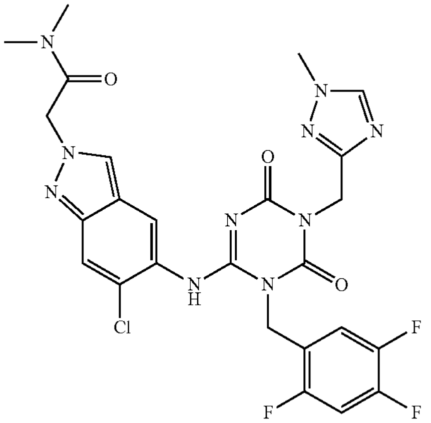 [SMILES: CN(C)C(=O)Cn1cc2cc(Nc3nc(=O)n(Cc4ncn(C)n4)c(=O)n3Cc3cc(F)c(F)cc3F)c(Cl)cc2n1] | 1 | 1.58 | 603.4 | |
| II-0281 | 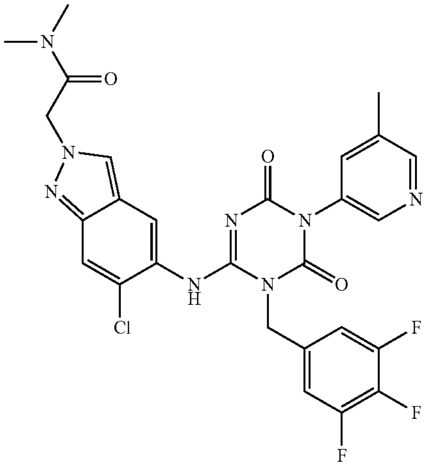 [SMILES: Cc1cncc(-n2c(=O)nc(Nc3cc4cn(CC(=O)N(C)C)nc4cc3Cl)n(Cc3cc(F)c(F)c(F)c3)c2=O)c1] | 4 | 1.80 | 599 | |

TABLE 109
| Compound No. | Structure | LC/MS Measured condition | Retention time (min) | m/z | Con-figration |
|---|---|---|---|---|---|
| II-0282 | 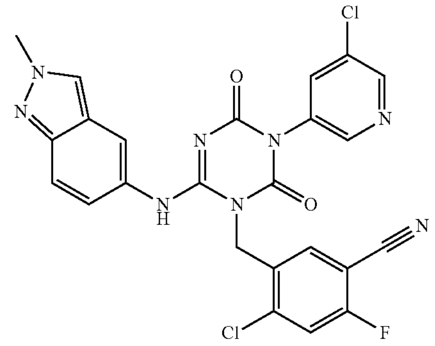 | 1 | 1.82 | 537.3 | |
| II-0283 | 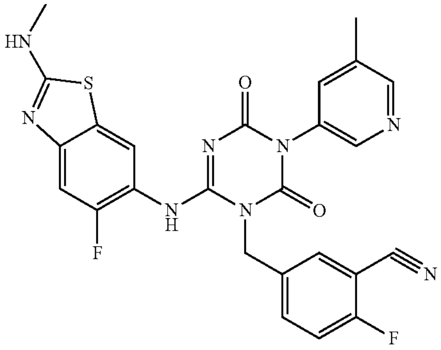 [SMILES: CNc1nc2cc(F)c(Nc3nc(=O)n(-c4cncc(C)c4)c(=O)n3Cc3ccc(F)c(C#N)c3)cc2s1] | 1 | 1.57 | 533 | |
| II-0284 | 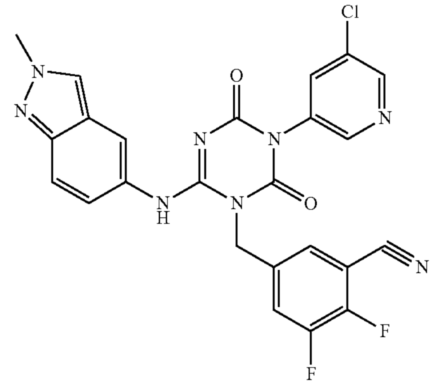 [SMILES: Cn1cc2cc(Nc3nc(=O)n(-c4cncc(Cl)c4)c(=O)n3Cc3cc(F)c(F)c(C#N)c3)ccc2n1] | 1 | 1.77 | 521.3 | |
| II-0285 | 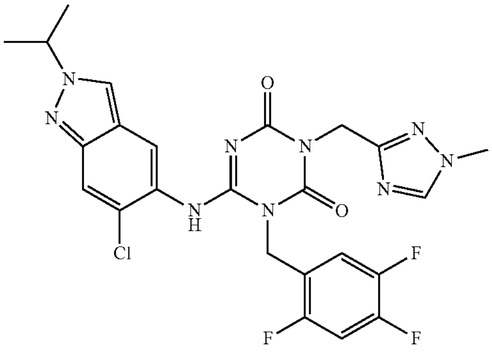 [SMILES: CC(C)n1cc2cc(Nc3nc(=O)n(Cc4ncn(C)n4)c(=O)n3Cc3cc(F)c(F)cc3F)c(Cl)cc2n1] | 1 | 1.88 | 560.4 | |

TABLE 109-continued
| Compound No. | Structure | LC/MS Measured condition | Retention time (min) | m/z | Con-figration |
|---|---|---|---|---|---|
| II-0286 | 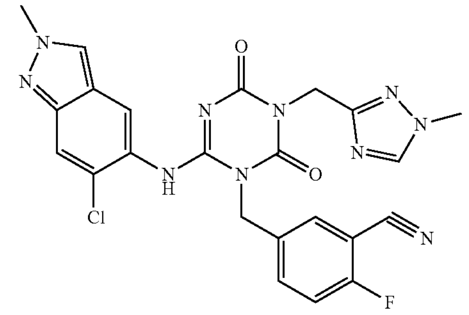 | 1 | 1.51 | 521.3 | |
TABLE 110
| Compound No. | Structure | LC/MS Measured condition | Retention time (min) | m/z | Con-figration |
|---|---|---|---|---|---|
| II-0287 | 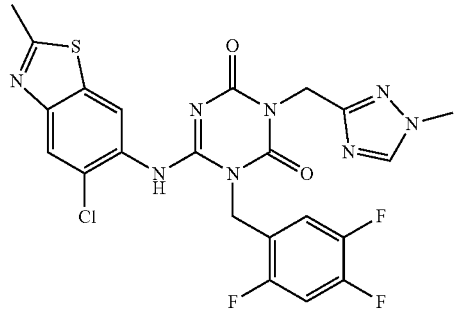 | 1 | 1.98 | 549 | |
| II-0288 | 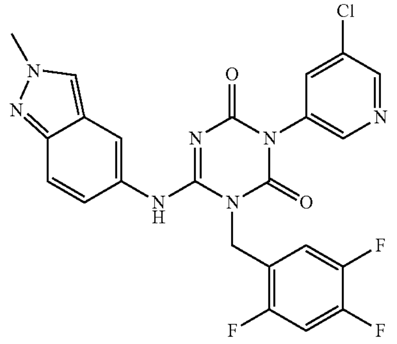 [SMILES: Cn1cc2cc(Nc3nc(=O)n(-c4cncc(Cl)c4)c(=O)n3Cc3cc(F)c(F)cc3F)ccc2n1] | 1 | 1.77 | 514.3 | |
| II-0289 | 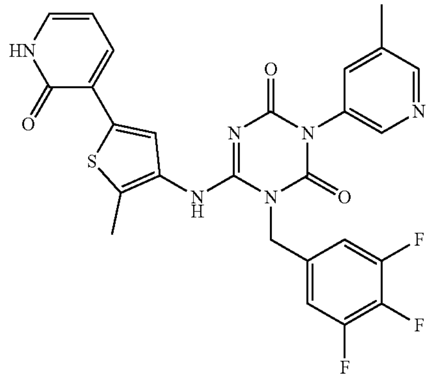 [SMILES: Cc1cncc(-n2c(=O)nc(Nc3cc(-c4ccc[nH]c4=O)sc3C)n(Cc3cc(F)c(F)c(F)c3)c2=O)c1] | 1 | 1.71 | 553.3 | |

TABLE 110-continued
| Compound No. | Structure | LC/MS Measured condition | Retention time (min) | m/z | Con-figration |
|---|---|---|---|---|---|
| II-0290 | 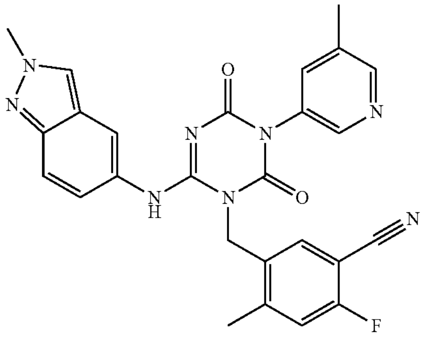 [SMILES: Cc1cncc(-n2c(=O)nc(Nc3ccc4nn(C)cc4c3)n(Cc3cc(C#N)c(F)cc3C)c2=O)c1] | 1 | 1.46 | 497.4 | |
| II-0291 | 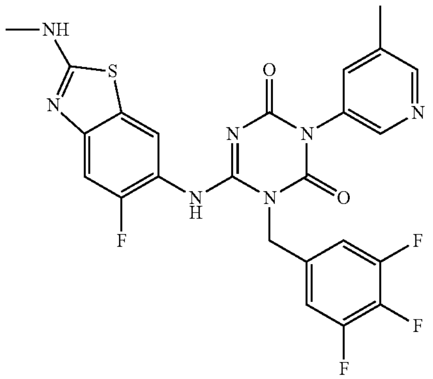 [SMILES: CNc1nc2cc(F)c(Nc3nc(=O)n(-c4cncc(C)c4)c(=O)n3Cc3cc(F)c(F)c(F)c3)cc2s1] | 1 | 1.77 | 544.2 | |
TABLE 111
| Compound No. | Structure | LC/MS Measured condition | Retention time (min) | m/z | Con-figration |
|---|---|---|---|---|---|
| II-0292 | 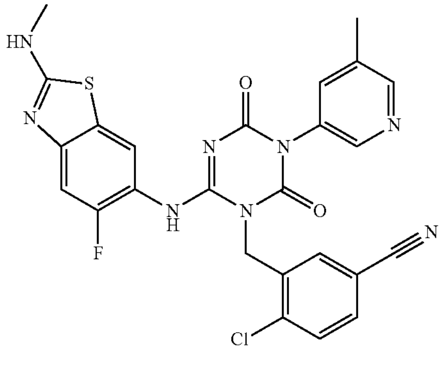 [SMILES: CNc1nc2cc(F)c(Nc3nc(=O)n(-c4cncc(C)c4)c(=O)n3Cc3cc(C#N)ccc3Cl)cc2s1] | 3 | 1.62 | 549 | |

TABLE 111-continued
| Compound No. | Structure | LC/MS Measured condition | Retention time (min) | m/z | Con-figration |
|---|---|---|---|---|---|
| II-0293 | 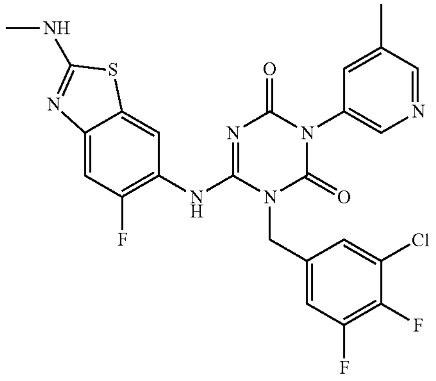 [SMILES: CNc1nc2cc(F)c(Nc3nc(=O)n(-c4cncc(C)c4)c(=O)n3Cc3cc(F)c(F)c(Cl)c3)cc2s1] | 1 | 1.92 | 560 | |
| II-0294 | 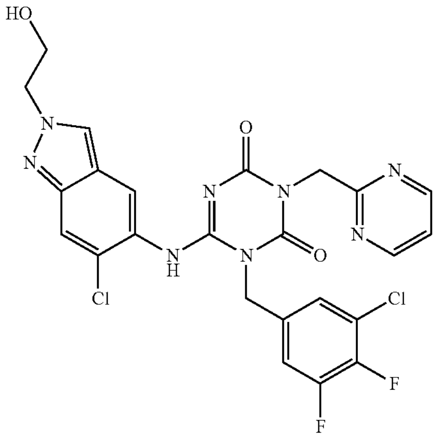 [SMILES: O=c1nc(Nc2cc3cn(CCO)nc3cc2Cl)n(Cc2cc(F)c(F)c(Cl)c2)c(=O)n1Cc1ncccn1] | 3 | 1.79 | 575 | |
| II-0295 | 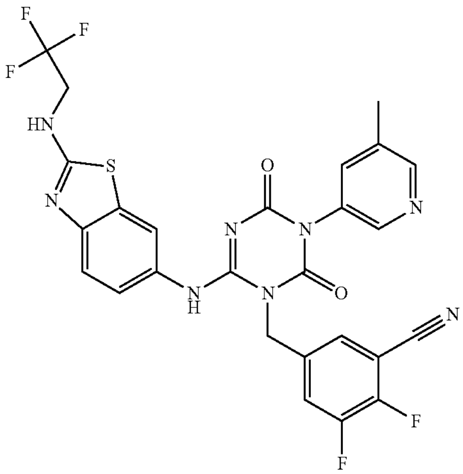 [SMILES: Cc1cncc(-n2c(=O)nc(Nc3ccc4nc(NCC(F)(F)F)sc4c3)n(Cc3cc(F)c(F)c(C#N)c3)c2=O)c1] | 1 | 1.98 | 601 | |

TABLE 111-continued
| Compound No. | Structure | LC/MS Measured condition | Retention time (min) | m/z | Con-figration |
|---|---|---|---|---|---|
| II-0296 | 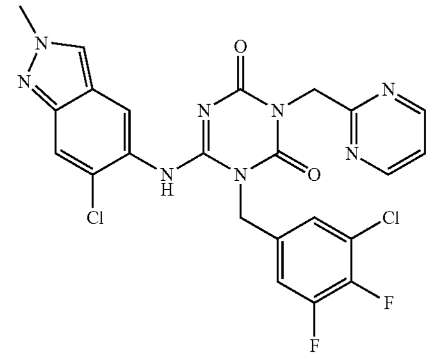 [SMILES: Cn1cc2cc(Nc3nc(=O)n(Cc4ncccn4)c(=O)n3Cc3cc(F)c(F)c(Cl)c3)c(Cl)cc2n1] | 1 | 2.00 | 545 | |
TABLE 112
| Compound No. | Structure | LC/MS Measured condition | Retention time (min) | m/z | Con-figration |
|---|---|---|---|---|---|
| II-0297 | 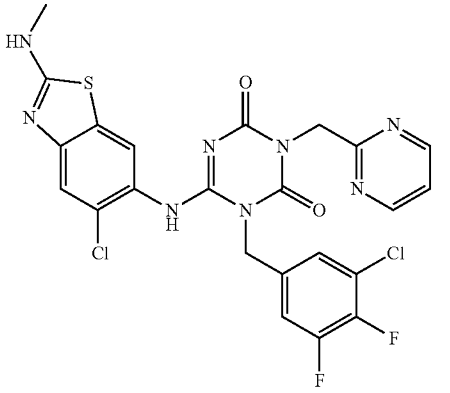 [SMILES: CNc1nc2cc(Cl)c(Nc3nc(=O)n(Cc4ncccn4)c(=O)n3Cc3cc(F)c(F)c(Cl)c3)cc2s1] | 3 | 1.98 | 577 | |
| II-0298 | 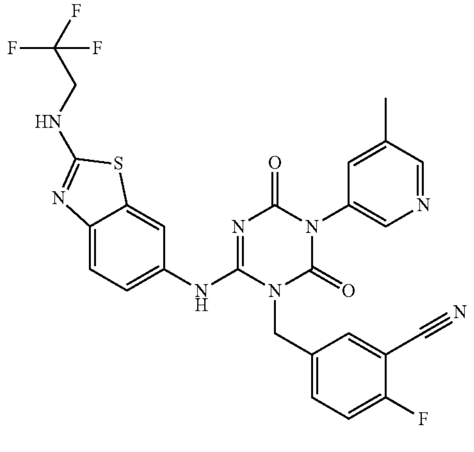 [SMILES: Cc1cncc(-n2c(=O)nc(Nc3ccc4nc(NCC(F)(F)F)sc4c3)n(Cc3ccc(F)c(C#N)c3)c2=O)c1] | 1 | 1.89 | 583 | |

TABLE 112-continued
| Compound No. | Structure | LC/MS Measured condition | Retention time (min) | m/z | Con-figration |
|---|---|---|---|---|---|
| II-0299 | 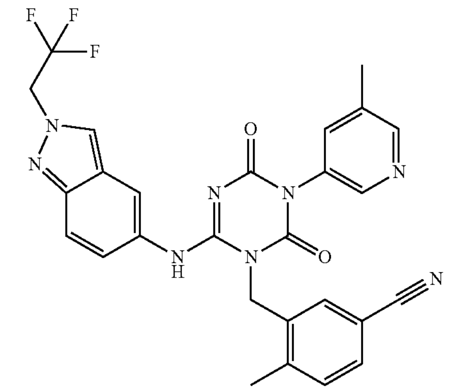 [SMILES: Cc1cncc(-n2c(=O)nc(Nc3ccc4nn(CC(F)(F)F)cc4c3)n(Cc3cc(C#N)ccc3C)c2=O)c1] | 2 | 1.81 | 547.2 | |
| II-0300 | 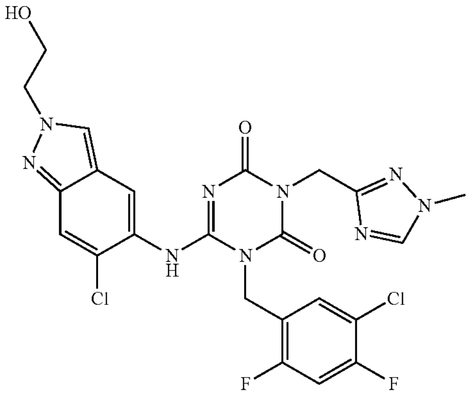 [SMILES: Cn1cnc(Cn2c(=O)nc(Nc3cc4cn(CCO)nc4cc3Cl)n(Cc3cc(Cl)c(F)cc3F)c2=O)n1] | 2 | 1.78 | 578.1 | |
| II-0301 | 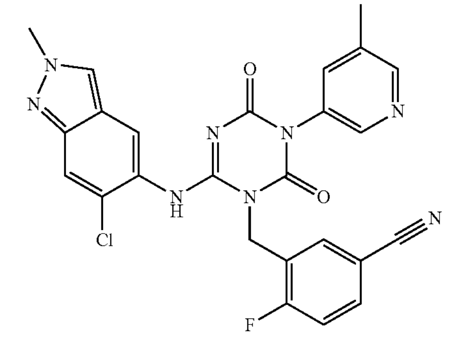 | 2 | 1.74 | 517.2 | |

TABLE 113
| Compound No. | Structure | LC/MS Measured condition | Retention time (min) | m/z | Con-figration |
|---|---|---|---|---|---|
| II-0302 | 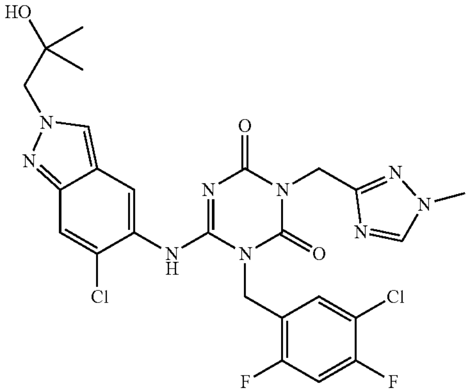 [SMILES: Cn1cnc(Cn2c(=O)nc(Nc3cc4cn(CC(C)(C)O)nc4cc3Cl)n(Cc3cc(Cl)c(F)cc3F)c2=O)n1] | 2 | 1.91 | 606.2 | |
| II-0303 | 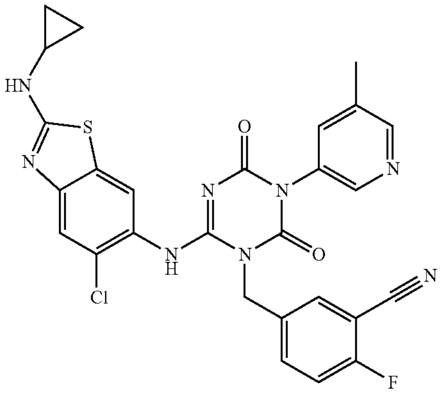 [SMILES: Cc1cncc(-n2c(=O)nc(Nc3cc4sc(NC5CC5)nc4cc3Cl)n(Cc3ccc(F)c(C#N)c3)c2=O)c1] | 2 | 1.95 | 575.1 | |
| II-0304 | 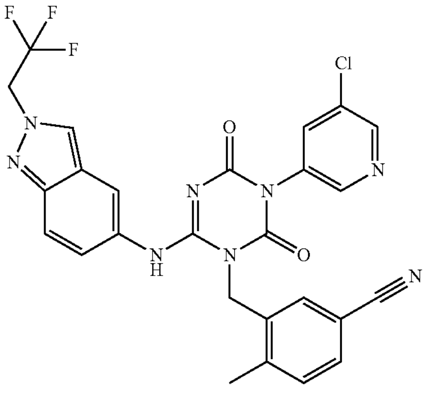 [SMILES: Cc1ccc(C#N)cc1Cn1c(Nc2ccc3nn(CC(F)(F)F)cc3c2)nc(=O)n(-c2cncc(Cl)c2)c1=O] | 2 | 2.00 | 567.2 | |

TABLE 113-continued
| Compound No. | Structure | LC/MS Measured condition | Retention time (min) | m/z | Con-figration |
|---|---|---|---|---|---|
| II-0305 | 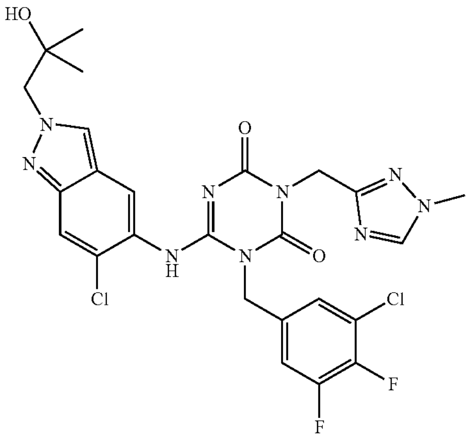 [SMILES: Cn1cnc(Cn2c(=O)nc(Nc3cc4cn(CC(C)(C)O)nc4cc3Cl)n(Cc3cc(F)c(F)c(Cl)c3)c2=O)n1] | 2 | 1.97 | 606.2 | |
| II-0306 | 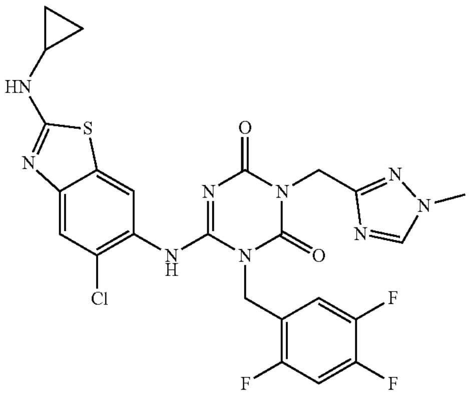 [SMILES: Cn1cnc(Cn2c(=O)nc(Nc3cc4sc(NC5CC5)nc4cc3Cl)n(Cc3cc(F)c(F)cc3F)c2=O)n1] | 2 | 1.94 | 590.1 | |
TABLE 114
| Compound No. | Structure | LC/MS Measured condition | Retention time (min) | m/z | Con-figration |
|---|---|---|---|---|---|
| II-0307 | 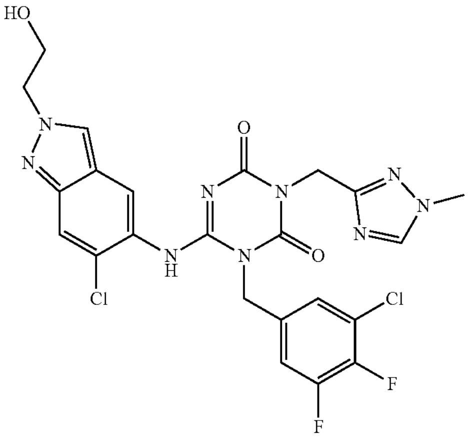 [SMILES: Cn1cnc(Cn2c(=O)nc(Nc3cc4cn(CCO)nc4cc3Cl)n(Cc3cc(F)c(F)c(Cl)c3)c2=O)n1] | 2 | 1.84 | 578.1 | |

TABLE 114-continued
| Compound No. | Structure | LC/MS Measured condition | Retention time (min) | m/z | Con-figration |
|---|---|---|---|---|---|
| II-0308 | 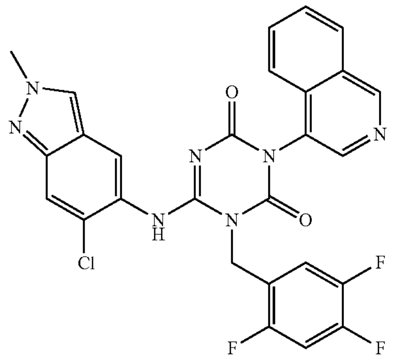 [SMILES: Cn1cc2cc(Nc3nc(=O)n(-c4cncc5ccccc45)c(=O)n3Cc3cc(F)c(F)cc3F)c(Cl)cc2n1] | 2 | 2.01 | 564.2 | |
| II-0309 | 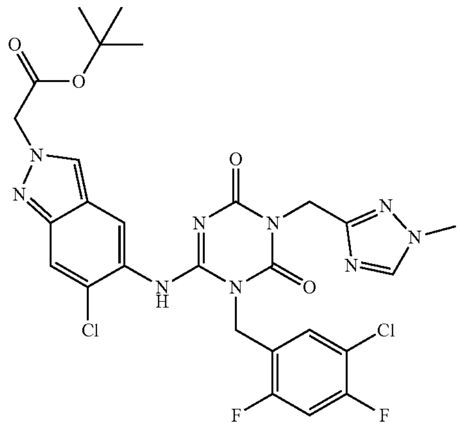 [SMILES: Cn1cnc(Cn2c(=O)nc(Nc3cc4cn(CC(=O)OC(C)(C)C)nc4cc3Cl)n(Cc3cc(Cl)c(F)cc3F)c2=O)n1] | 2 | 2.21 | 648.2 | |
| II-0310 | 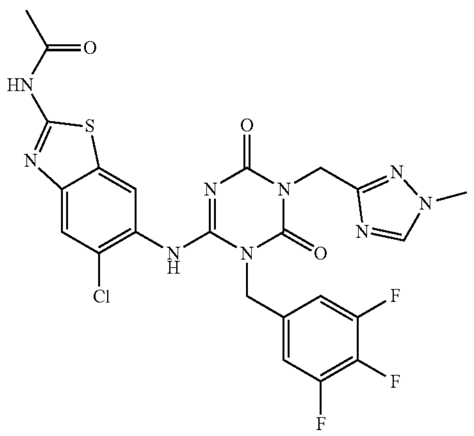 [SMILES: CC(=O)Nc1nc2cc(Cl)c(Nc3nc(=O)n(Cc4ncn(C)n4)c(=O)n3Cc3cc(F)c(F)c(F)c3)cc2s1] | 2 | 1.94 | 592.1 | |

TABLE 114-continued
| Compound No. | Structure | LC/MS Measured condition | Retention time (min) | m/z | Con-figration |
|---|---|---|---|---|---|
| II-0311 | 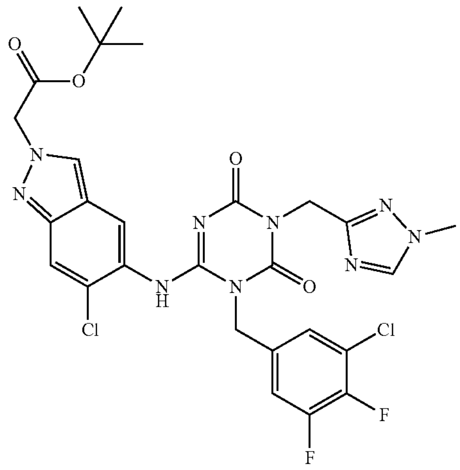 [SMILES: Cn1cnc(Cn2c(=O)nc(Nc3cc4cn(CC(=O)OC(C)(C)C)nc4cc3Cl)n(Cc3cc(F)c(F)c(Cl)c3)c2=O)n1] | 2 | 2.26 | 648.2 | |
TABLE 115
| Compound No. | Structure | LC/MS Measured condition | Retention time (min) | m/z | Con-figration |
|---|---|---|---|---|---|
| II-0312 | 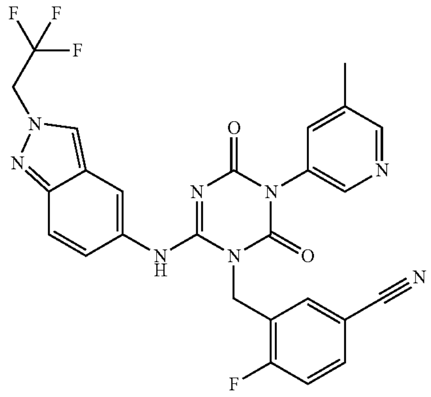 [SMILES: Cc1cncc(-n2c(=O)nc(Nc3ccc4nn(CC(F)(F)F)cc4c3)n(Cc3cc(C#N)ccc3F)c2=O)c1] | 2 | 1.78 | 551.2 | |
| II-0313 | 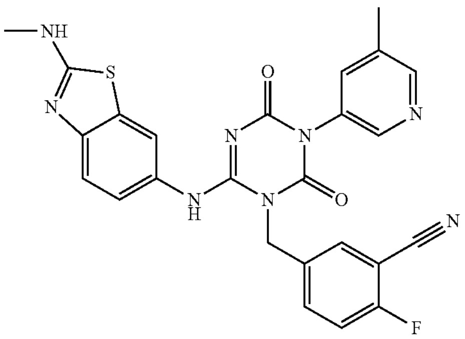 [SMILES: CNc1nc2ccc(Nc3nc(=O)n(-c4cncc(C)c4)c(=O)n3Cc3ccc(F)c(C#N)c3)cc2s1] | 2 | 1.50 | 515.2 | |

TABLE 115-continued
| Compound No. | Structure | LC/MS Measured condition | Retention time (min) | m/z | Con-figuration |
|---|---|---|---|---|---|
| II-0314 | 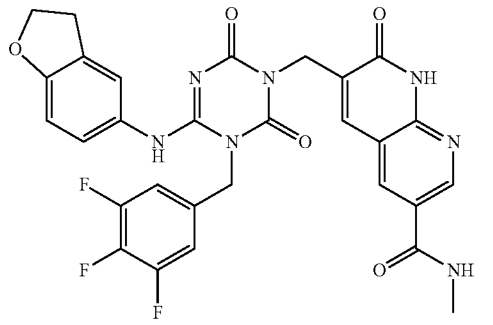 [SMILES: CNC(=O)c1cnc2[nH]c(=O)c(Cn3c(=O)nc(Nc4ccc5c(c4)CCO5)n(Cc4cc(F)c(F)c(F)c4)c3=O)cc2c1] | 2 | 1.81 | 606.2 | |
| II-0315 | 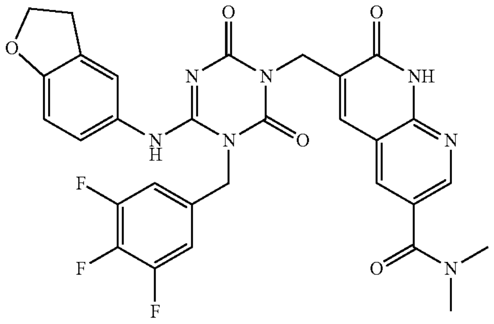 [SMILES: CN(C)C(=O)c1cnc2[nH]c(=O)c(Cn3c(=O)nc(Nc4ccc5c(c4)CCO5)n(Cc4cc(F)c(F)c(F)c4)c3=O)cc2c1] | 2 | 1.84 | 620.3 | |
| II-0316 | 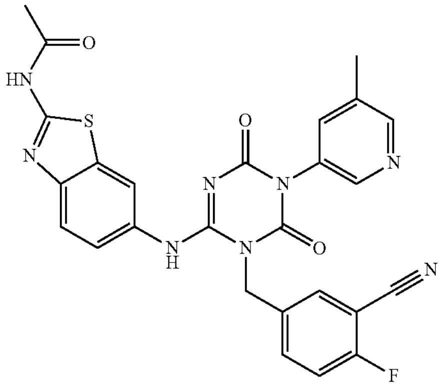 [SMILES: CC(=O)Nc1nc2ccc(Nc3nc(=O)n(-c4cncc(C)c4)c(=O)n3Cc3ccc(F)c(C#N)c3)cc2s1] | 1 | 1.76 | 543.1 | |
TABLE 116
| Compound No. | Structure | LC/MS Measured condition | Retention time (min) | m/z | Con-figuration |
|---|---|---|---|---|---|
| II-0317 | 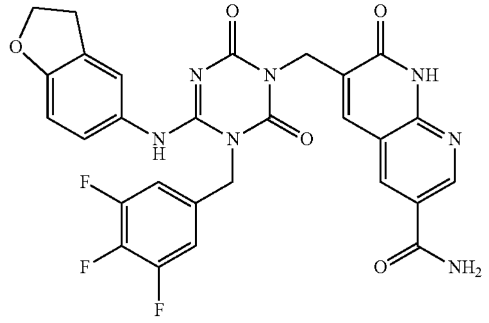 [SMILES: NC(=O)c1cnc2[nH]c(=O)c(Cn3c(=O)nc(Nc4ccc5c(c4)CCO5)n(Cc4cc(F)c(F)c(F)c4)c3=O)cc2c1] | 2 | 1.75 | 592.2 | |

TABLE 116-continued
| Compound No. | Structure | LC/MS Measured condition | Retention time (min) | m/z | Con-figration |
|---|---|---|---|---|---|
| II-0318 | 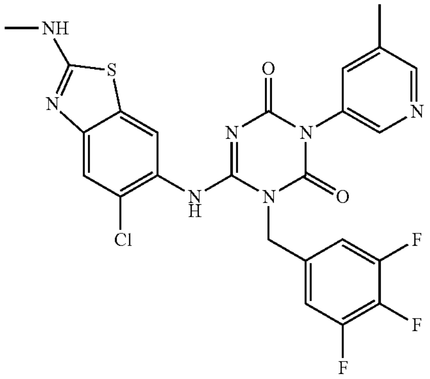 | 2 | 1.99 | 560.2 | |
| II-0319 | 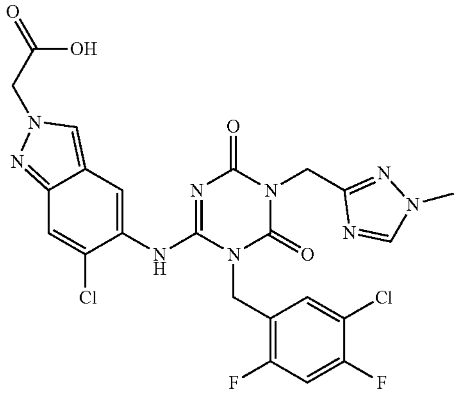 [SMILES: Cn1cnc(Cn2c(=O)nc(Nc3cc4cn(CC(=O)O)nc4cc3Cl)n(Cc3cc(Cl)c(F)cc3F)c2=O)n1] | 2 | 1.87 | 592.1 | |
| II-0320 | 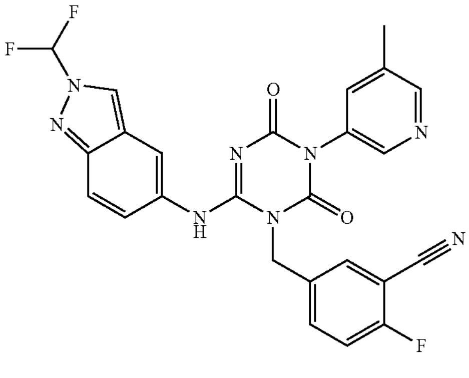 [SMILES: Cc1cncc(-n2c(=O)nc(Nc3ccc4nn(C(F)F)cc4c3)n(Cc3ccc(F)c(C#N)c3)c2=O)c1] | 2 | 1.81 | 519.2 | |

TABLE 116-continued
| Compound No. | Structure | LC/MS Measured condition | Retention time (min) | m/z | Con-figuration |
|---|---|---|---|---|---|
| II-0321 | 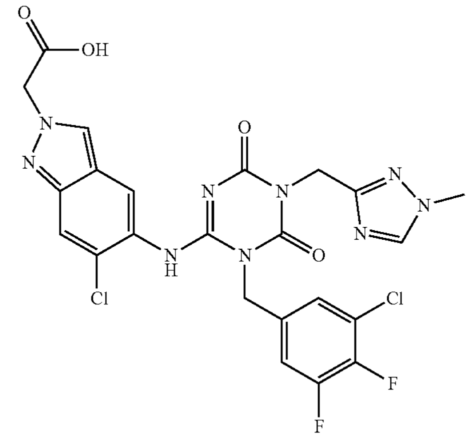 [SMILES: Cn1cnc(Cn2c(=O)nc(Nc3cc4cn(CC(=O)O)nc4cc3Cl)n(Cc3cc(F)c(F)c(Cl)c3)c2=O)n1] | 2 | 1.92 | 592.1 | |
TABLE 117
| Compound No. | Structure | LC/MS Measured condition | Retention time (min) | m/z | Con-figuration |
|---|---|---|---|---|---|
| II-0322 | 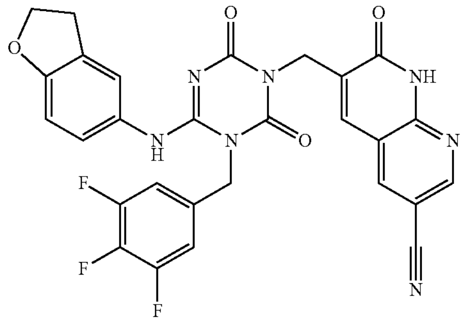 [SMILES: N#Cc1cnc2[nH]c(=O)c(Cn3c(=O)nc(Nc4ccc5c(c4)CCO5)n(Cc4cc(F)c(F)c(F)c4)c3=O)cc2c1] | 2 | 1.96 | 574.2 | |
| II-0323 | 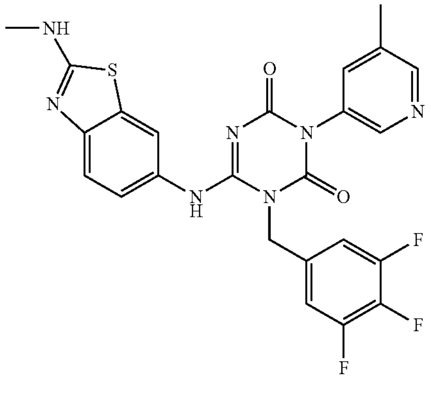 [SMILES: CNc1nc2ccc(Nc3nc(=O)n(-c4cncc(C)c4)c(=O)n3Cc3cc(F)c(F)c(F)c3)cc2s1] | 2 | 1.67 | 526.2 | |

TABLE 117-continued
| Compound No. | Structure | LC/MS Measured condition | Retention time (min) | m/z | Con-figration |
|---|---|---|---|---|---|
| II-0324 | 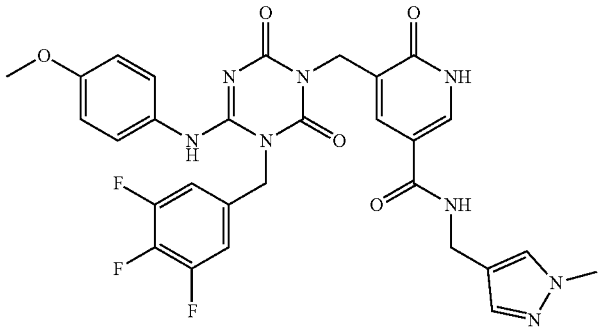 | 2 | 1.77 | 623.3 | |
| II-0325 | 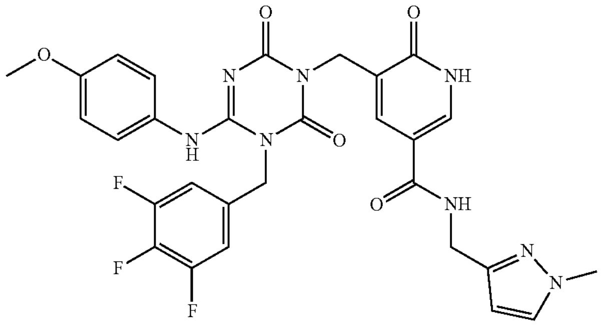 | 2 | 1.80 | 623.3 | |
| II-0326 | 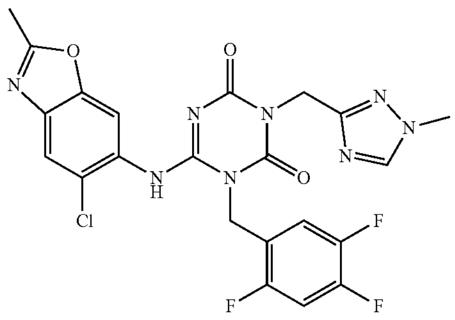 | 2 | 1.97 | 533.2 | |

TABLE 118
| Compound No. | Structure | LC/MS Measured condition | Retention time (min) | m/z | Con-figration |
|---|---|---|---|---|---|
| II-0327 | 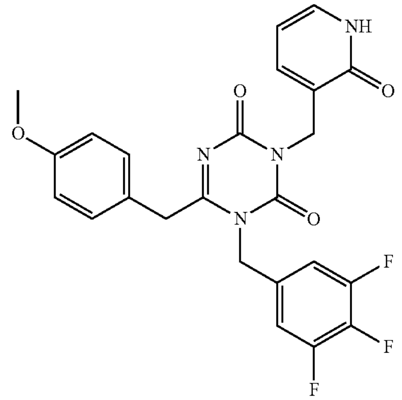 [SMILES: COc1ccc(Cc2nc(=O)n(Cc3ccc[nH]c3=O)c(=O)n2Cc2cc(F)c(F)c(F)c2)cc1] | 1 | 1.92 | 485 | |
| II-0328 | 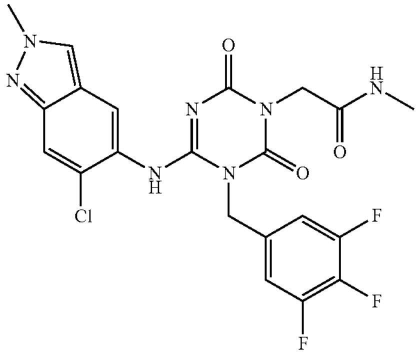 | 1 | 1.85 | 508.1 | |
| II-0329 | 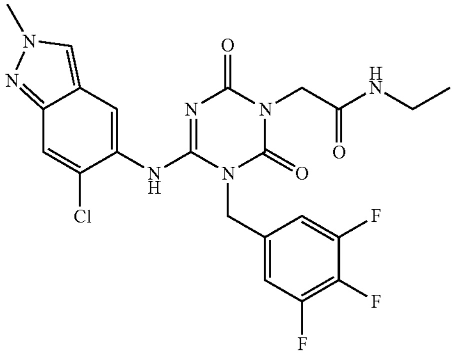 [SMILES: CCNC(=O)Cn1c(=O)nc(Nc2cc3cn(C)nc3cc2Cl)n(Cc2cc(F)c(F)c(F)c2)c1=O] | 1 | 1.98 | 522 | |
| II-0330 | 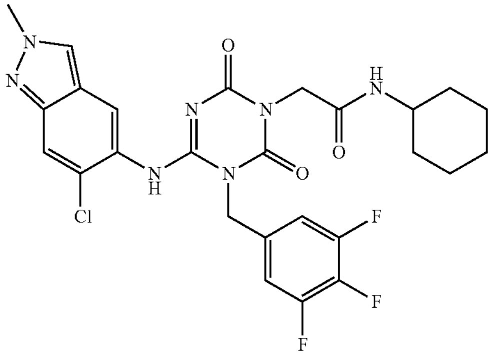 [SMILES: Cn1cc2cc(Nc3nc(=O)n(CC(=O)NC4CCCCC4)c(=O)n3Cc3cc(F)c(F)c(F)c3)c(Cl)cc2n1] | 1 | 2.29 | 576.2 | |

TABLE 118-continued
| Compound No. | Structure | LC/MS Measured condition | Retention time (min) | m/z | Con-figration |
|---|---|---|---|---|---|
| II-0331 | 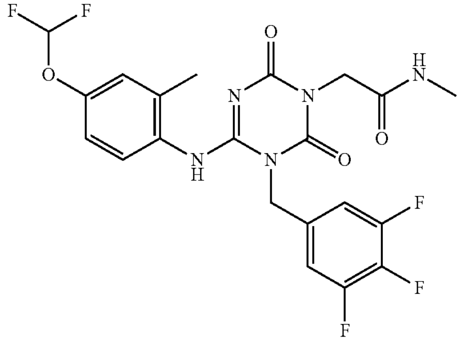 [SMILES: CNC(=O)Cn1c(=O)nc(Nc2ccc(OC(F)F)cc2C)n(Cc2cc(F)c(F)c(F)c2)c1=O] | | 2.13 | 500 | |
TABLE 119
| Compound No. | Structure | LC/MS Measured condition | Retention time (min) | m/z | Con-figration |
|---|---|---|---|---|---|
| II-0332 | 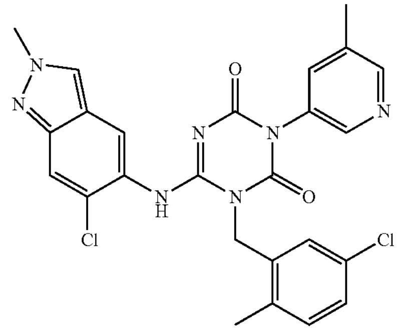 [SMILES: Cc1cncc(-n2c(=O)nc(Nc3cc4cn(C)nc4cc3Cl)n(Cc3cc(Cl)ccc3C)c2=O)c1] | 3 | 2.04 | 522 | |
| II-0333 | 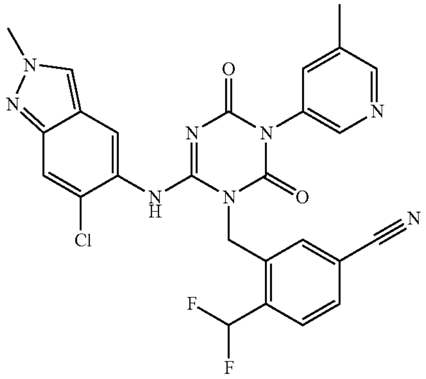 [SMILES: Cc1cncc(-n2c(=O)nc(Nc3cc4cn(C)nc4cc3Cl)n(Cc3cc(C#N)ccc3C(F)F)c2=O)c1] | 1 | 1.84 | 549 | |

TABLE 119-continued
| Compound No. | Structure | LC/MS Measured condition | Retention time (min) | m/z | Con-figration |
|---|---|---|---|---|---|
| II-0334 | 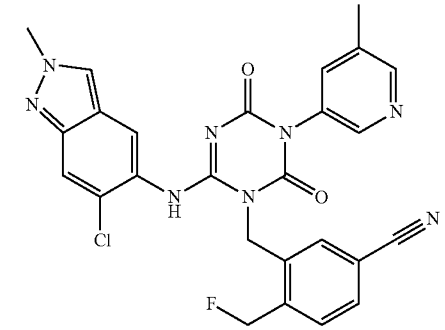 [SMILES: Cc1cncc(-n2c(=O)nc(Nc3cc4cn(C)nc4cc3Cl)n(Cc3cc(C#N)ccc3CF)c2=O)c1] | 1 | 1.72 | 531 | |
| II-0335 | 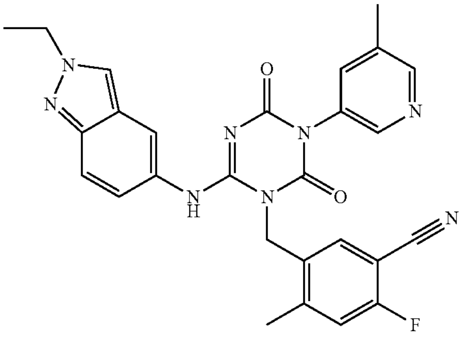 [SMILES: CCn1cc2cc(Nc3nc(=O)n(-c4cncc(C)c4)c(=O)n3Cc3cc(C#N)c(F)cc3C)ccc2n1] | 1 | 1.66 | 511 | |
| II-0336 | 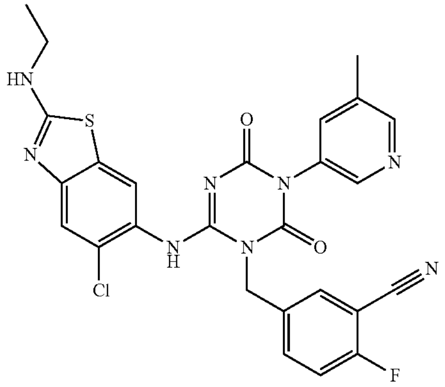 [SMILES: CCNc1nc2cc(Cl)c(Nc3nc(=O)n(-c4cncc(C)c4)c(=O)n3Cc3ccc(F)c(C#N)c3)cc2s1] | 1 | 1.75 | 563 | |

TABLE 120
| Compound No. | Structure | LC/MS Measured condition | Retention time (min) | m/z | Con-figration |
|---|---|---|---|---|---|
| II-0337 | 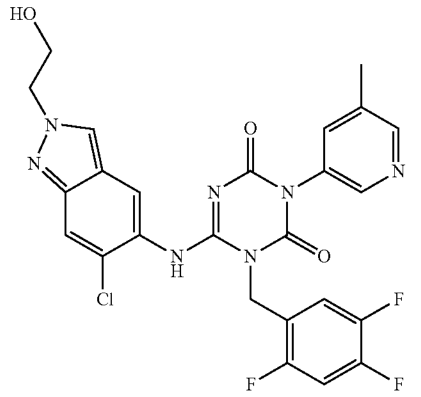 [SMILES: Cc1cncc(-n2c(=O)nc(Nc3cc4cn(CCO)nc4cc3Cl)n(Cc3cc(F)c(F)cc3F)c2=O)c1] | 1 | 1.74 | 558 | |
| II-0338 | 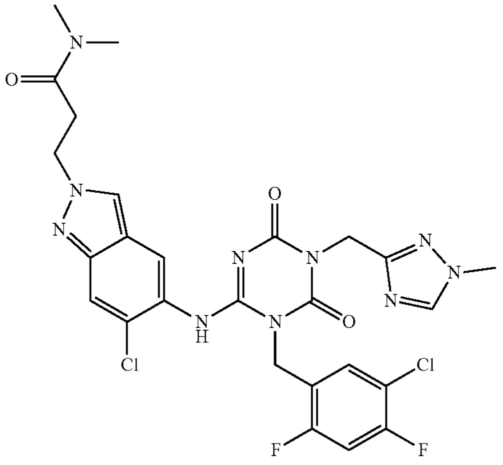 [SMILES: CN(C)C(=O)CCn1cc2cc(Nc3nc(=O)n(Cc4ncn(C)n4)c(=O)n3Cc3cc(Cl)c(F)cc3F)c(Cl)cc2n1] | 1 | 1.78 | 633 | |
| II-0339 | 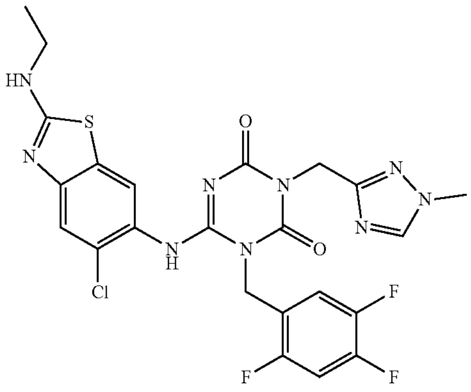 [SMILES: CCNc1nc2cc(Cl)c(Nc3nc(=O)n(Cc4ncn(C)n4)c(=O)n3Cc3cc(F)c(F)cc3F)cc2s1] | 1 | 1.73 | 578 | |

TABLE 120-continued
| Compound No. | Structure | LC/MS Measured condition | Retention time (min) | m/z | Con-figration |
|---|---|---|---|---|---|
| II-0340 | 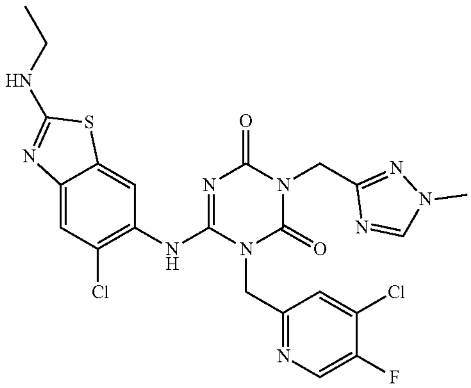 [SMILES: CCNc1nc2cc(Cl)c(Nc3nc(=O)n(Cc4ncn(C)n4)c(=O)n3Cc3cc(Cl)c(F)cn3)cc2s1] | 1 | 1.65 | 577 | |
| II-0341 | 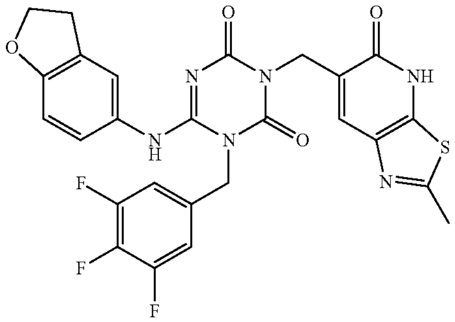 [SMILES: Cc1nc2cc(Cn3c(=O)nc(Nc4ccc5c(c4)CCO5)n(Cc4cc(F)c(F)c(F)c4)c3=O)c(=O)[nH]c2s1] | 1 | 1.90 | 569 | |
TABLE 121
| Compound No. | Structure | LC/MS Measured condition | Retention time (min) | m/z | Con-figration |
|---|---|---|---|---|---|
| II-0342 | 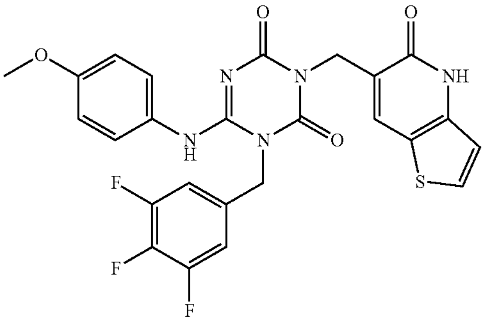 [SMILES: COc1ccc(Nc2nc(=O)n(Cc3cc4sccc4[nH]c3=O)c(=O)n2Cc2cc(F)c(F)c(F)c2)cc1] | 1 | 2.04 | 542 | |
| II-0343 | 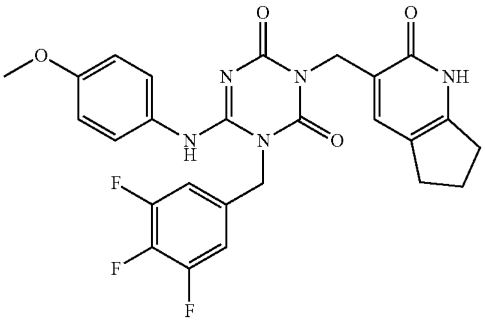 [SMILES: COc1ccc(Nc2nc(=O)n(Cc3cc4c([nH]c3=O)CCC4)c(=O)n2Cc2cc(F)c(F)c(F)c2)cc1] | 1 | 2.03 | 526.1 | |

TABLE 121-continued
| Compound No. | Structure | LC/MS Measured condition | Retention time (min) | m/z | Con-figuration |
|---|---|---|---|---|---|
| II-0344 | 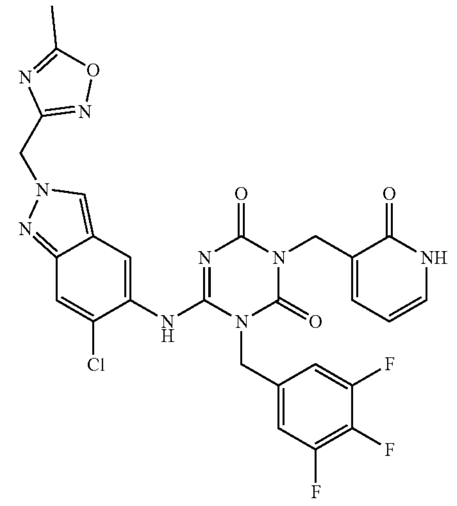 [SMILES: Cc1nc(Cn2cc3cc(Nc4nc(=O)n(Cc5ccc[nH]c5=O)c(=O)n4Cc4cc(F)c(F)c(F)c4)c(Cl)cc3n2)no1] | 1 | 1.83 | 626.3 | |
| II-0345 | 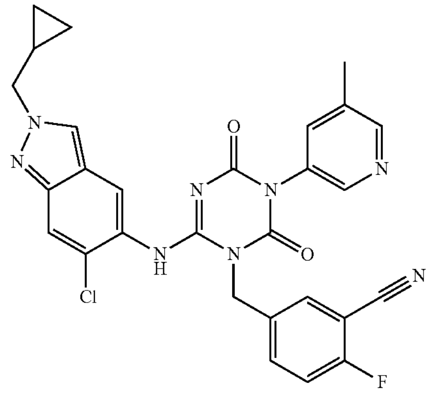 [SMILES: Cc1cncc(-n2c(=O)nc(Nc3cc4cn(CC5CC5)nc4cc3Cl)n(Cc3ccc(F)c(C#N)c3)c2=O)c1] | 1 | 2.16 | 557.4 | |
| II-0346 | 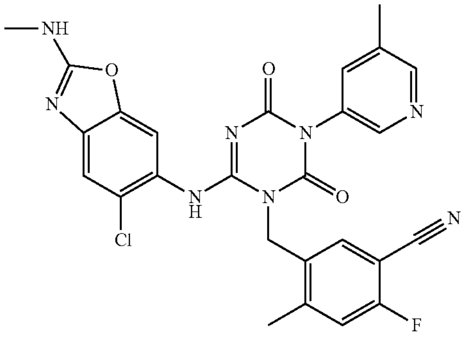 [SMILES: CNc1nc2cc(Cl)c(Nc3nc(=O)n(-c4cncc(C)c4)c(=O)n3Cc3cc(C#N)c(F)cc3C)cc2o1] | 1 | 1.74 | 547.3 | |

TABLE 122
| Compound No. | Structure | LC/MS Measured condition | Retention time (min) | m/z | Con-figration |
|---|---|---|---|---|---|
| II-0347 | 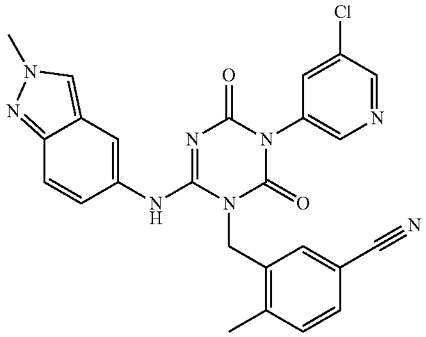 [SMILES: Cc1ccc(C#N)cc1Cn1c(Nc2ccc3nn(C)cc3c2)nc(=O)n(-c2cncc(Cl)c2)c1=O] | 1 | 1.62 | 499.3 | |
| II-0348 | 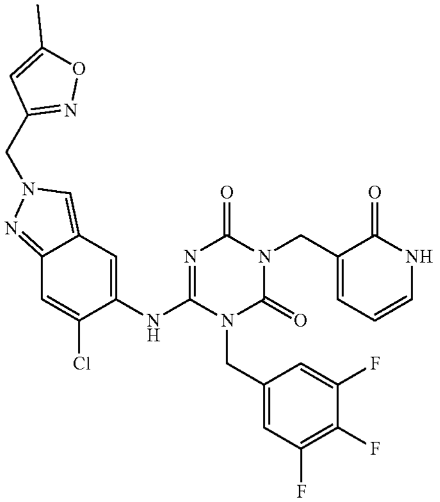 [SMILES: Cc1cc(Cn2cc3cc(Nc4nc(=O)n(Cc5ccc[nH]c5=O)c(=O)n4Cc4cc(F)c(F)c(F)c4)c(Cl)cc3n2)no1] | 1 | 1.93 | 625 | |
| II-0349 | 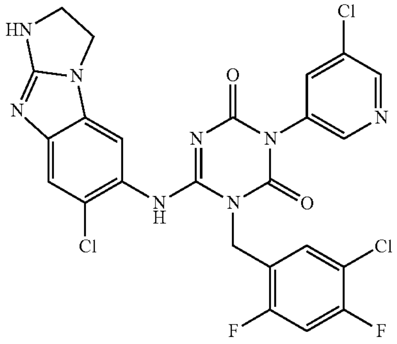 [SMILES: O=c1nc(Nc2cc3c(cc2Cl)nc2n3CCN2)n(Cc2cc(Cl)c(F)cc2F)c(=O)n1-c1cncc(Cl)c1] | 1 | 1.85 | 589.2 | |
| II-0350 | 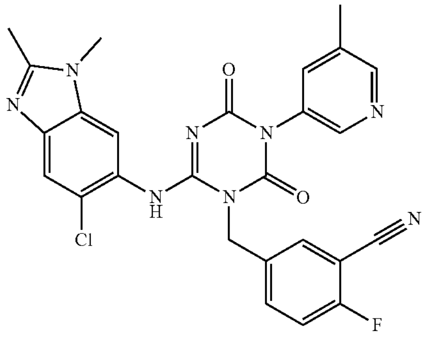 [SMILES: Cc1cncc(-n2c(=O)nc(Nc3cc4c(cc3Cl)nc(C)n4C)n(Cc3ccc(F)c(C#N)c3)c2=O)c1] | 1 | 1.41 | 531.3 | |

TABLE 122-continued
| Compound No. | Structure | LC/MS Measured condition | Retention time (min) | m/z | Con-figration |
|---|---|---|---|---|---|
| II-0351 | 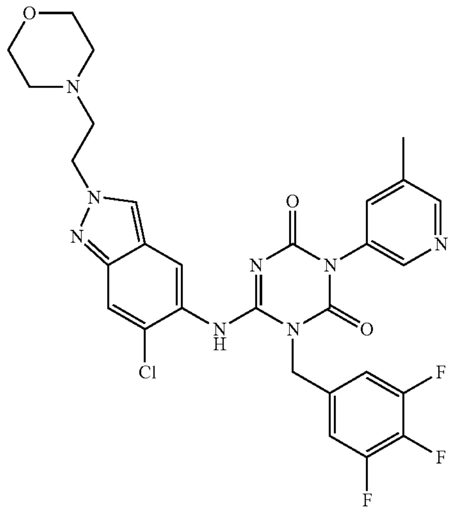 [SMILES: Cc1cncc(-n2c(=O)nc(Nc3cc4cn(CCN5CCOCC5)nc4cc3Cl)n(Cc3cc(F)c(F)c(F)c3)c2=O)c1] | 1 | 1.64 | 627.4 | |
TABLE 123
| Compound No. | Structure | LC/MS Measured condition | Retention time (min) | m/z | Con-figration |
|---|---|---|---|---|---|
| II-0352 | 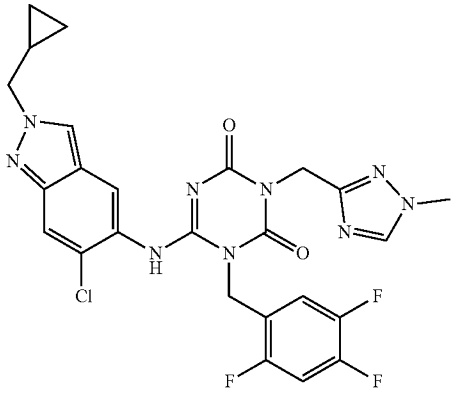 [SMILES: Cn1cnc(Cn2c(=O)nc(Nc3cc4cn(CC5CC5)nc4cc3Cl)n(Cc3cc(F)c(F)cc3F)c2=O)n1] | 1 | 2.16 | 572.4 | |
| II-0353 | 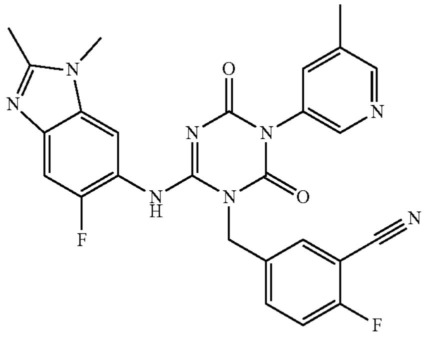 [SMILES: Cc1cncc(-n2c(=O)nc(Nc3cc4c(cc3F)nc(C)n4C)n(Cc3ccc(F)c(C#N)c3)c2=O)c1] | 1 | 1.38 | 515.3 | |

TABLE 123-continued
| Compound No. | Structure | LC/MS Measured condition | Retention time (min) | m/z | Con-figration |
|---|---|---|---|---|---|
| II-0354 | 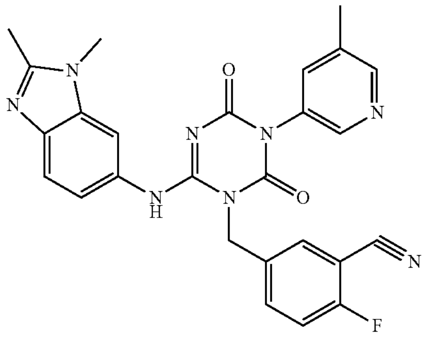 [SMILES: Cc1cncc(-n2c(=O)nc(Nc3ccc4nc(C)n(C)c4c3)n(Cc3ccc(F)c(C#N)c3)c2=O)c1] | 1 | 1.26 | 497.3 | |
| II-0355 | 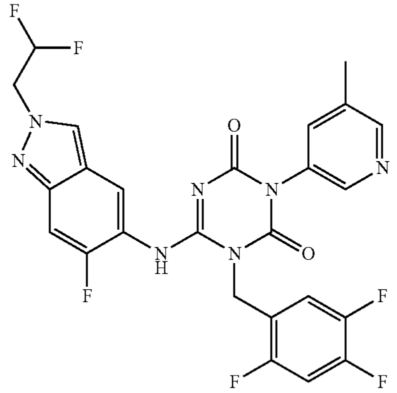 [SMILES: Cc1cncc(-n2c(=O)nc(Nc3cc4cn(CC(F)F)nc4cc3F)n(Cc3cc(F)c(F)cc3F)c2=O)c1] | 1 | 1.85 | 562.3 | |
| II-0356 | 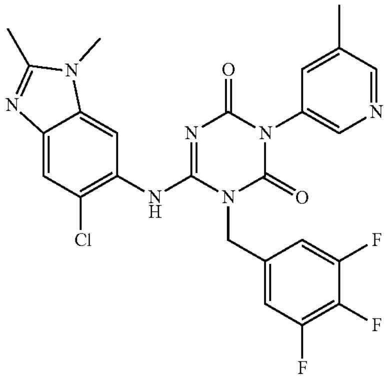 [SMILES: Cc1cncc(-n2c(=O)nc(Nc3cc4c(cc3Cl)nc(C)n4C)n(Cc3cc(F)c(F)c(F)c3)c2=O)c1] | 1 | 1.62 | 542.3 | |

TABLE 124
| Compound No. | Structure | LC/MS Measured condition | Retention time (min) | m/z | Con-figration |
|---|---|---|---|---|---|
| II-0357 | 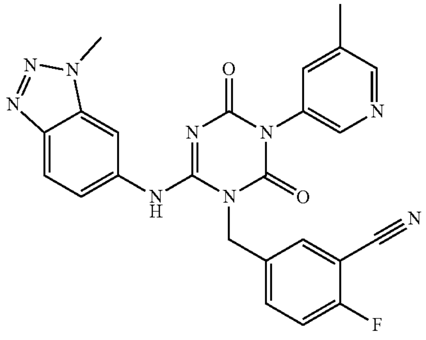 [SMILES: Cc1cncc(-n2c(=O)nc(Nc3ccc4nnn(C)c4c3)n(Cc3ccc(F)c(C#N)c3)c2=O)c1] | 1 | 1.65 | 484.4 | |
| II-0358 | 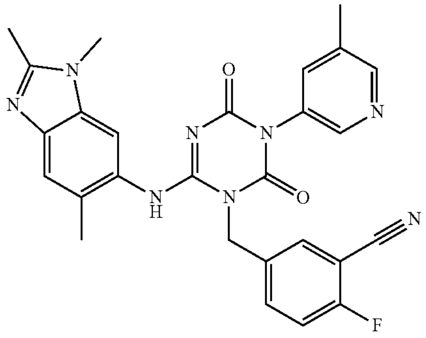 [SMILES: Cc1cncc(-n2c(=O)nc(Nc3cc4c(cc3C)nc(C)n4C)n(Cc3ccc(F)c(C#N)c3)c2=O)c1] | 1 | 1.36 | 511.4 | |
| II-0359 | 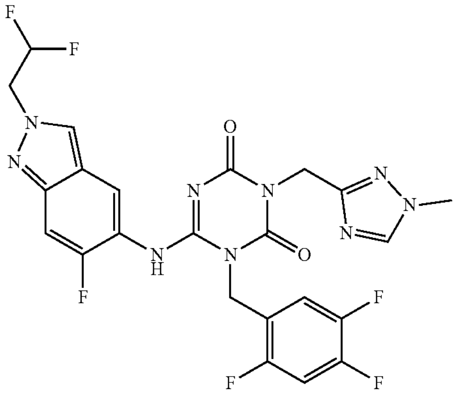 [SMILES: Cn1cnc(Cn2c(=O)nc(Nc3cc4cn(CC(F)F)nc4cc3F)n(Cc3cc(F)c(F)cc3F)c2=O)n1] | 1 | 1.71 | 566.3 | |
| II-0360 | 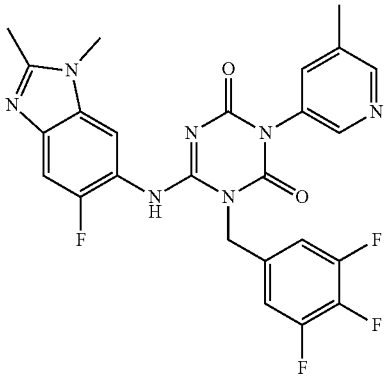 [SMILES: Cc1cncc(-n2c(=O)nc(Nc3cc4c(cc3F)nc(C)n4C)n(Cc3cc(F)c(F)c(F)c3)c2=O)c1] | 1 | 1.49 | 526.3 | |

TABLE 124-continued
| Compound No. | Structure | LC/MS Measured condition | Retention time (min) | m/z | Con-figuration |
|---|---|---|---|---|---|
| II-0361 | 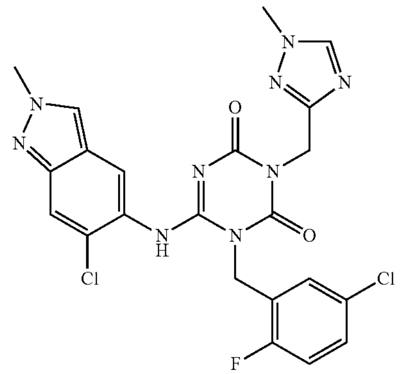 [SMILES: Cn1cnc(Cn2c(=O)nc(Nc3cc4cn(C)nc4cc3Cl)n(Cc3cc(Cl)ccc3F)c2=O)n1] | 1 | 2.14 | 530.2 | |
TABLE 125
| Compound No. | Structure | LC/MS Measured condition | Retention time (min) | m/z | Con-figuration |
|---|---|---|---|---|---|
| II-0362 | 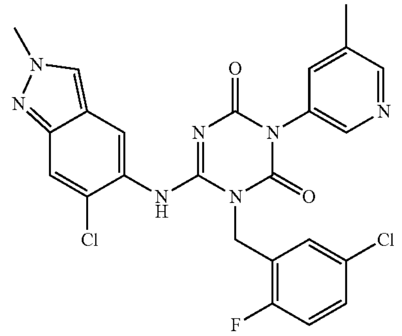 [SMILES: Cc1cncc(-n2c(=O)nc(Nc3cc4cn(C)nc4cc3Cl)n(Cc3cc(Cl)ccc3F)c2=O)c1] | 1 | 2.27 | 528.2 | |
| II-0363 | 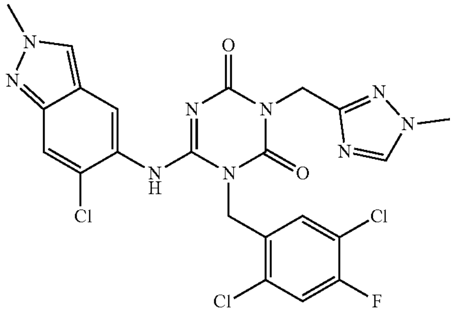 | 3 | 2.08 | 565 | |

TABLE 125-continued
| Compound No. | Structure | LC/MS Measured condition | Retention time (min) | m/z | Con-figration |
|---|---|---|---|---|---|
| II-0364 | 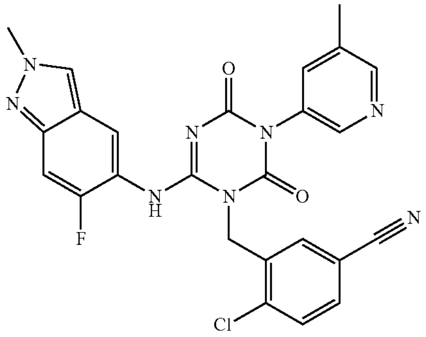 [SMILES: Cc1cncc(-n2c(=O)nc(Nc3cc4cn(C)nc4cc3F)n(Cc3cc(C#N)ccc3Cl)c2=O)c1] | 1 | 1.60 | 517.4 | |
| II-0365 | 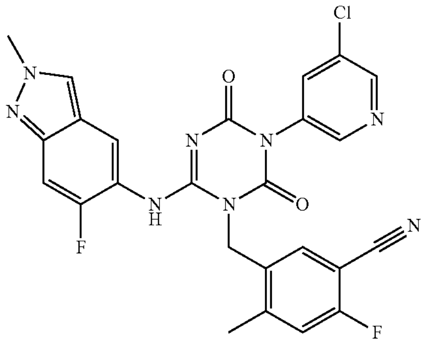 [SMILES: Cc1cc(F)c(C#N)cc1Cn1c(Nc2cc3cn(C)nc3cc2F)nc(=O)n(-c2cncc(Cl)c2)c1=O] | 1 | 1.82 | 535.4 | |
| II-0366 | 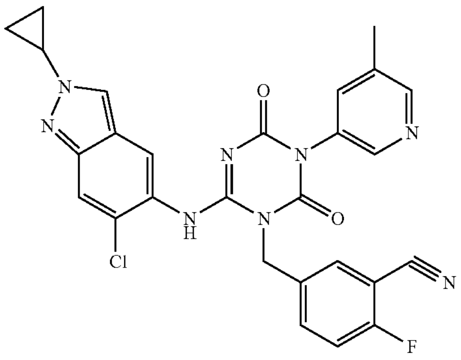 [SMILES: Cc1cncc(-n2c(=O)nc(Nc3cc4cn(C5CC5)nc4cc3Cl)n(Cc3ccc(F)c(C#N)c3)c2=O)c1] | 1 | 1.83 | 543.4 | |

TABLE 126
| Compound No. | Structure | LC/MS Measured condition | Retention time (min) | m/z | Con-figration |
|---|---|---|---|---|---|
| II-0367 | 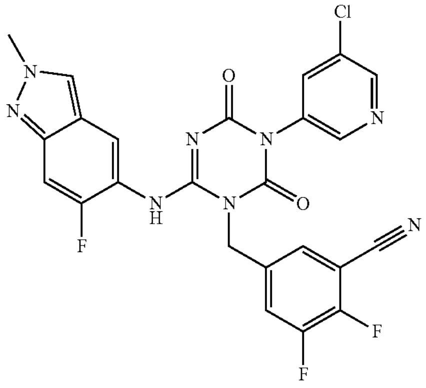 [SMILES: Cn1cc2cc(Nc3nc(=O)n(-c4cncc(Cl)c4)c(=O)n3Cc3cc(F)c(F)c(C#N)c3)c(F)cc2n1] | 1 | 1.89 | 539.3 | |
| II-0368 | 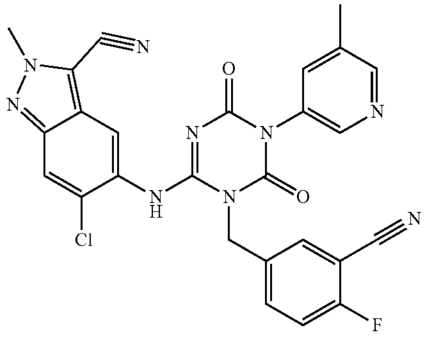 [SMILES: Cc1cncc(-n2c(=O)nc(Nc3cc4c(C#N)n(C)nc4cc3Cl)n(Cc3ccc(F)c(C#N)c3)c2=O)c1] | 1 | 2.01 | 542.3 | |
| II-0369 | 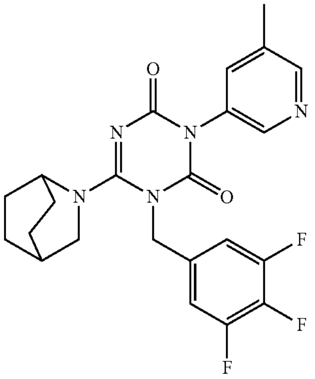 [SMILES: Cc1cncc(-n2c(=O)nc(N3CC4CCC3CC4)n(Cc3cc(F)c(F)c(F)c3)c2=O)c1] | 1 | 2.00 | 458 | |
| II-0370 | 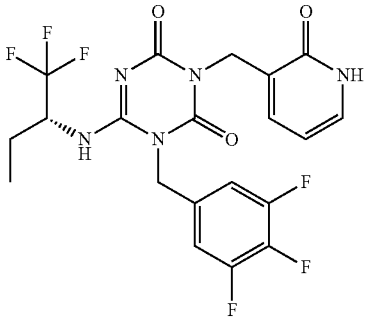 [SMILES: CC[C@@H](Nc1nc(=O)n(Cc2ccc[nH]c2=O)c(=O)n1Cc1cc(F)c(F)c(F)c1)C(F)(F)F] | 1 | 1.88 | 490.1 | a |

TABLE 126-continued
| Compound No. | Structure | LC/MS Measured condition | Retention time (min) | m/z | Con- figration |
|---|---|---|---|---|---|
| II-0371 | 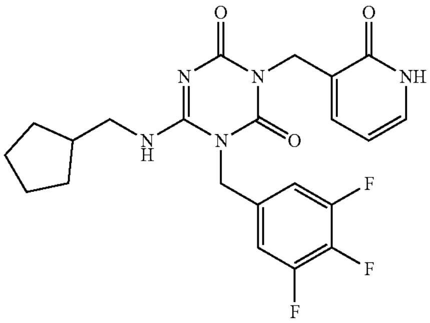 [SMILES: O=c1[nH]cccc1Cn1c(=O)nc(NCC2CCCC2)n(Cc2cc(F)c(F)c(F)c2)c1=O] | 1 | 1.91 | 462.1 | |
TABLE 127
| Compound No. | Structure | LC/MS Measured condition | Retention time (min) | m/z | Con- figration |
|---|---|---|---|---|---|
| II-0372 | 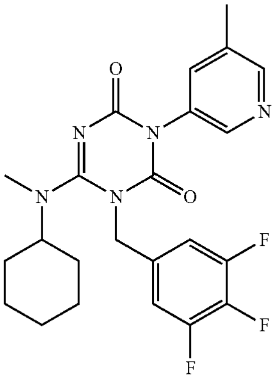 [SMILES: Cc1cncc(-n2c(=O)nc(N(C)C3CCCCC3)n(Cc3cc(F)c(F)c(F)c3)c2=O)c1] | 1 | 2.14 | 460 | |
| II-0373 | 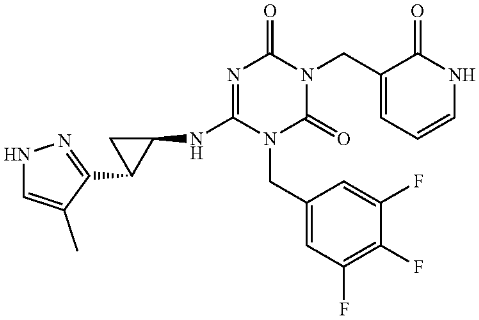 [SMILES: Cc1c[nH]nc1[C@@H]1C[C@H]1Nc1nc(=O)n(Cc2ccc[nH]c2=O)c(=O)n1Cc1cc(F)c(F)c(F)c1] | 1 | 1.44 | 500.3 | b |

TABLE 127-continued
| Compound No. | Structure | LC/MS Measured condition | Retention time (min) | m/z | Con-figration |
|---|---|---|---|---|---|
| II-0374 | 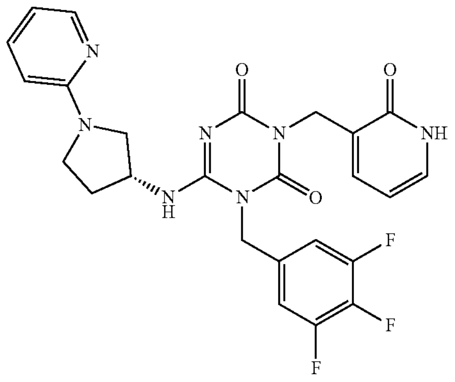 [SMILES: O=c1[nH]cccc1Cn1c(=O)nc(N[C@@H]2CCN(c3ccccn3)C2)n(Cc2cc(F)c(F)c(F)c2)c1=O] | 1 | 1.09 | 526.4 | a |
| II-0375 | 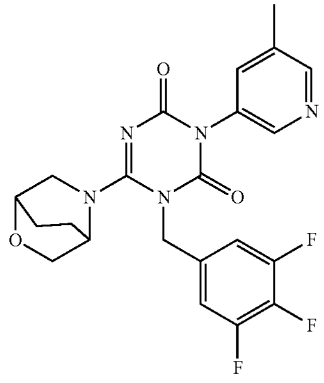 [SMILES: Cc1cncc(-n2c(=O)nc(N3CC4CCC3CO4)n(Cc3cc(F)c(F)c(F)c3)c2=O)c1] | 1 | 1.69 | 460 | |
| II-0376 | 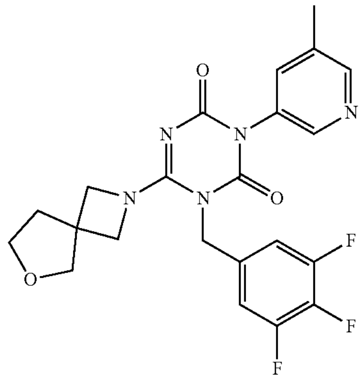 [SMILES: Cc1cncc(-n2c(=O)nc(N3CC4(CCOC4)C3)n(Cc3cc(F)c(F)c(F)c3)c2=O)c1] | 1 | 1.61 | 460 | |

TABLE 128
| Compound No. | Structure | LC/MS Measured condition | Retention time (min) | m/z | Con-figration |
|---|---|---|---|---|---|
| II-0377 | 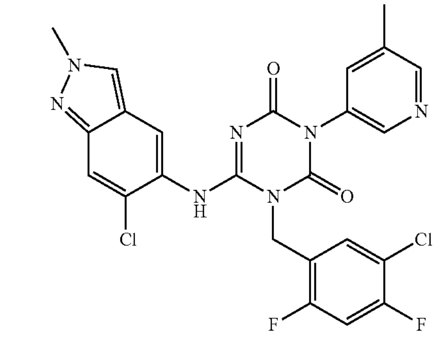 [SMILES: Cc1cncc(-n2c(=O)nc(Nc3cc4cn(C)nc4cc3Cl)n(Cc3cc(Cl)c(F)cc3F)c2=O)c1] | 1 | 1.89 | 544 | |
| II-0378 | 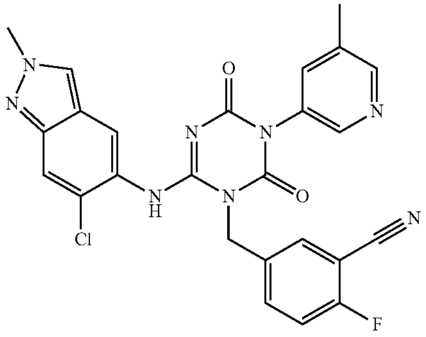 [SMILES: Cc1cncc(-n2c(=O)nc(Nc3cc4cn(C)nc4cc3Cl)n(Cc3ccc(F)c(C#N)c3)c2=O)c1] | 3 | 1.61 | 516 | |
| II-0379 | 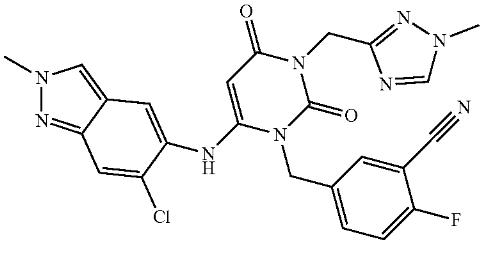 | 3 | 1.58 | 520 | |
| II-0380 | 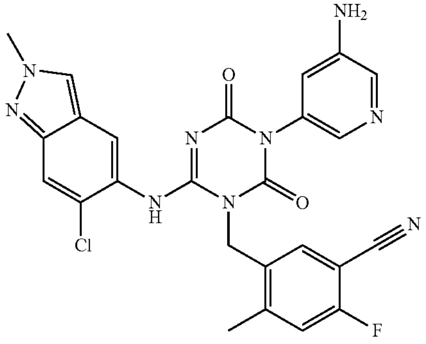 [SMILES: Cc1cc(F)c(C#N)cc1Cn1c(Nc2cc3cn(C)nc3cc2Cl)nc(=O)n(-c2cncc(N)c2)c1=O] | 3 | 1.35 | 532 | |

TABLE 128-continued
| Compound No. | Structure | LC/MS Measured condition | Retention time (min) | m/z | Con-figration |
|---|---|---|---|---|---|
| II-0381 | 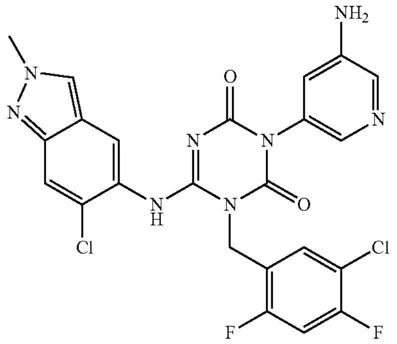 [SMILES: Cn1cc2cc(Nc3nc(=O)n(-c4cncc(N)c4)c(=O)n3Cc3cc(Cl)c(F)cc3F)c(Cl)cc2n1] | 1 | 1.63 | 545 | |
TABLE 129
| Compound No. | Structure | LC/MS Measured condition | Retention time (min) | m/z | Con-figration |
|---|---|---|---|---|---|
| II-0382 | 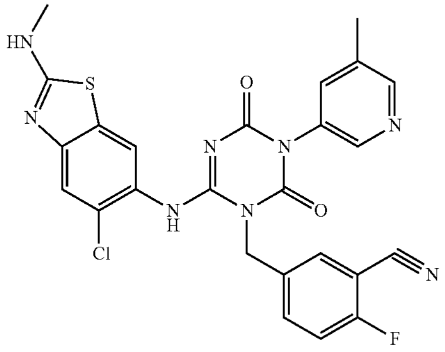 | 3 | 1.66 | 549 | |
| II-0383 | 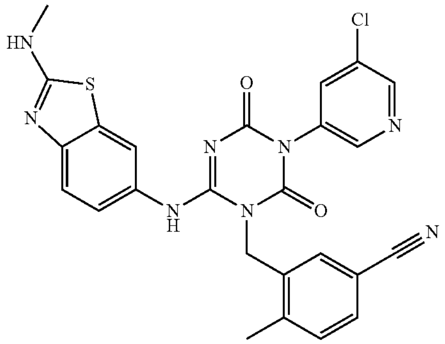 [SMILES: CNc1nc2ccc(Nc3nc(=O)n(-c4cncc(Cl)c4)c(=O)n3Cc3cc(C#N)ccc3C)cc2s1] | 1 | 1.74 | 531 | |

TABLE 129-continued
| Compound No. | Structure | LC/MS Measured condition | Retention time (min) | m/z | Con-figration |
|---|---|---|---|---|---|
| II-0384 | 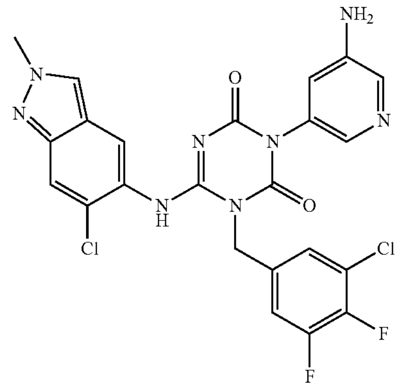 [SMILES: Cn1cc2cc(Nc3nc(=O)n(-c4cncc(N)c4)c(=O)n3Cc3cc(F)c(F)c(Cl)c3)c(Cl)cc2n1] | 3 | 1.56 | 545 | |
| II-0385 | 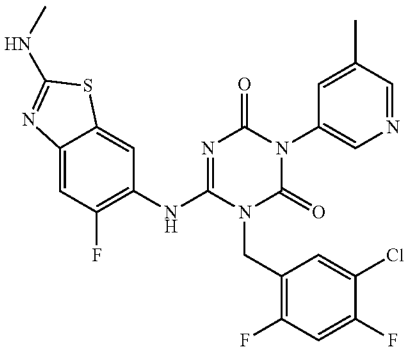 [SMILES: CNc1nc2cc(F)c(Nc3nc(=O)n(-c4cncc(C)c4)c(=O)n3Cc3cc(Cl)c(F)cc3F)cc2s1] | 3 | 1.77 | 560 | |
| II-0386 | 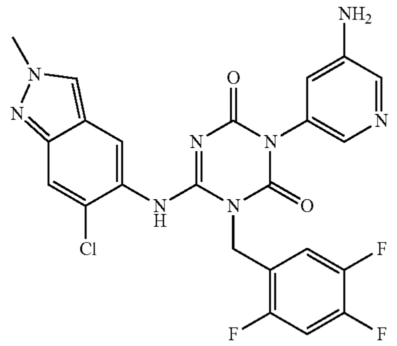 [SMILES: Cn1cc2cc(Nc3nc(=O)n(-c4cncc(N)c4)c(=O)n3Cc3cc(F)c(F)cc3F)c(Cl)cc2n1] | 3 | 1.41 | 529 | |

TABLE 130
| Compound No. | Structure | LC/MS Measured condition | Retention time (min) | m/z | Con-figration |
|---|---|---|---|---|---|
| II-0387 | 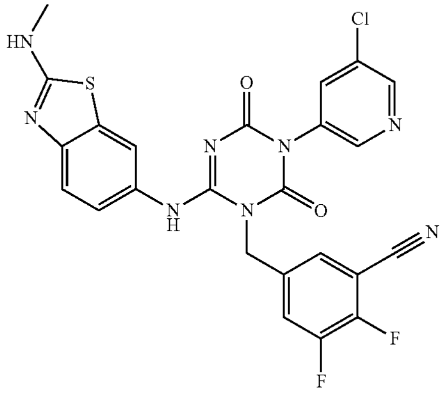 [SMILES: CNc1nc2ccc(Nc3nc(=O)n(-c4cncc(Cl)c4)c(=O)n3Cc3cc(F)c(F)c(C#N)c3)cc2s1] | 1 | 1.79 | 553 | |
| II-0388 | 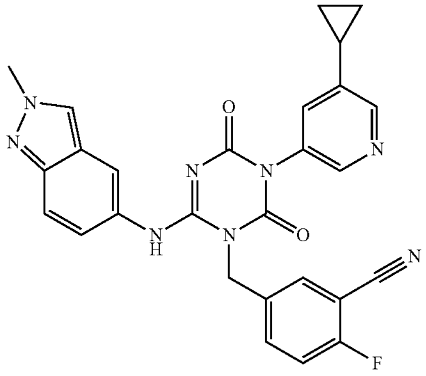 [SMILES: Cn1cc2cc(Nc3nc(=O)n(-c4cncc(C5CC5)c4)c(=O)n3Cc3ccc(F)c(C#N)c3)ccc2n1] | 1 | 1.76 | 509 | |
| II-0389 | 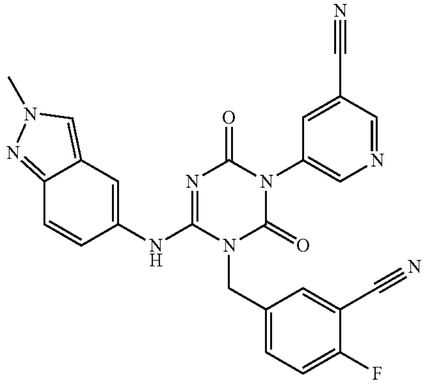 [SMILES: Cn1cc2cc(Nc3nc(=O)n(-c4cncc(C#N)c4)c(=O)n3Cc3ccc(F)c(C#N)c3)ccc2n1] | 1 | 1.76 | 494 | |
| II-0390 | 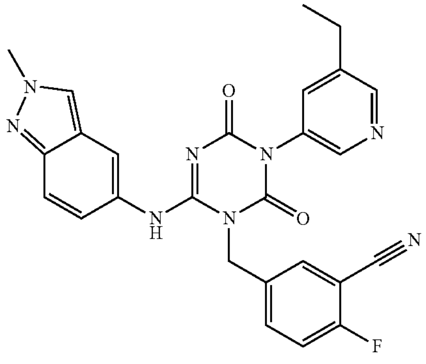 [SMILES: CCc1cncc(-n2c(=O)nc(Nc3ccc4nn(C)cc4c3)n(Cc3ccc(F)c(C#N)c3)c2=O)c1] | 1 | 1.71 | 497 | |

TABLE 130-continued
| Compound No. | Structure | LC/MS Measured condition | Retention time (min) | m/z | Con-figration |
|---|---|---|---|---|---|
| II-0391 | 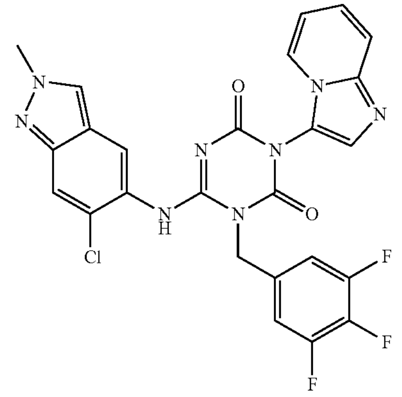 [SMILES: Cn1cc2cc(Nc3nc(=O)n(-c4cnc5ccccn45)c(=O)n3Cc3cc(F)c(F)c(F)c3)c(Cl)cc2n1] | 3 | 1.45 | 553 | |
TABLE 131
| Compound No. | Structure | LC/MS Measured condition | Retention time (min) | m/z | Con-figration |
|---|---|---|---|---|---|
| II-0392 | 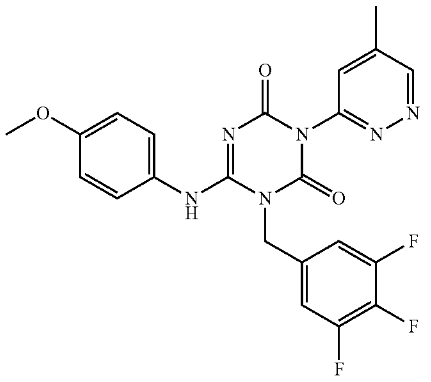 [SMILES: COc1ccc(Nc2nc(=O)n(-c3cc(C)cnn3)c(=O)n2Cc2cc(F)c(F)c(F)c2)cc1] | 3 | 1.73 | 471 | |
| II-0393 | 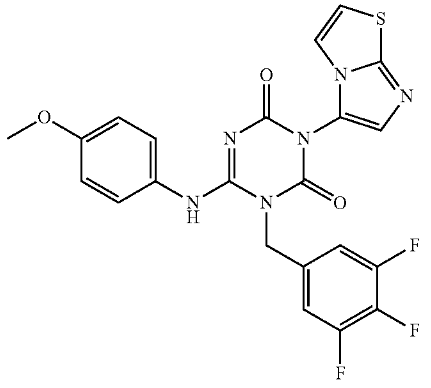 [SMILES: COc1ccc(Nc2nc(=O)n(-c3cnc4sccn34)c(=O)n2Cc2cc(F)c(F)c(F)c2)cc1] | 4 | 1.96 | 501 | |

TABLE 131-continued
| Compound No. | Structure | LC/MS Measured condition | Retention time (min) | m/z | Con-figration |
|---|---|---|---|---|---|
| II-0394 | 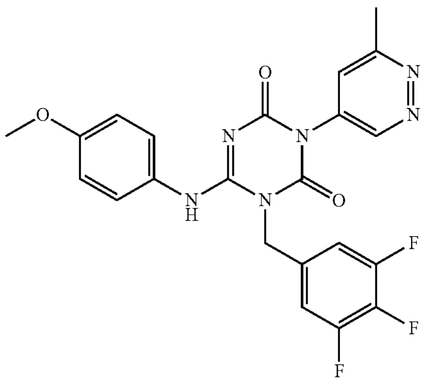 [SMILES: COc1ccc(Nc2nc(=O)n(-c3cnnc(C)c3)c(=O)n2Cc2cc(F)c(F)c(F)c2)cc1] | 3 | 1.70 | 471 | |
| II-0395 | 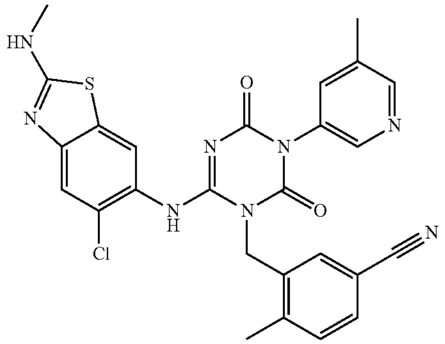 | 1 | 1.71 | 543 | |
| II-0396 | 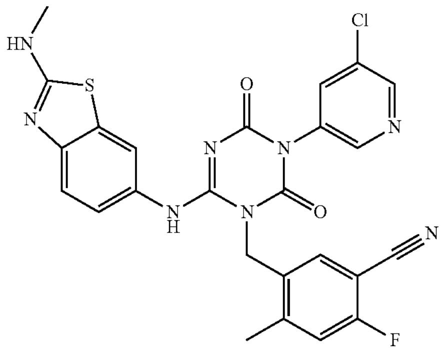 [SMILES: CNc1nc2ccc(Nc3nc(=O)n(-c4cncc(Cl)c4)c(=O)n3Cc3cc(C#N)c(F)cc3C)cc2s1] | 1 | 1.72 | 549 | |

TABLE 132
| Compound No. | Structure | LC/MS Measured condition | Retention time (min) | m/z | Con-figration |
|---|---|---|---|---|---|
| II-0397 | 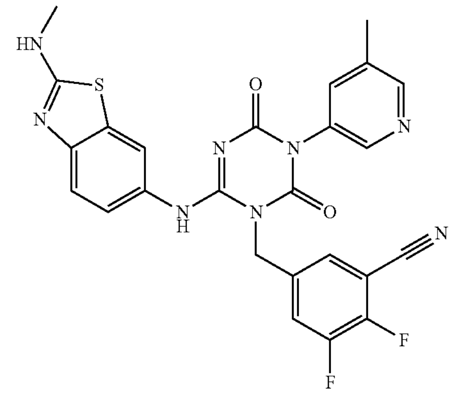 [SMILES: CNc1nc2ccc(Nc3nc(=O)n(-c4cncc(C)c4)c(=O)n3Cc3cc(F)c(F)c(C#N)c3)cc2s1] | 1 | 1.58 | 533 | |
| II-0398 | 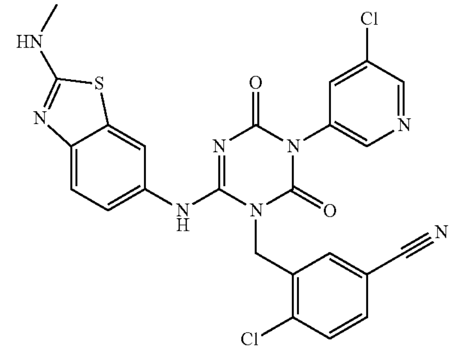 [SMILES: CNc1nc2ccc(Nc3nc(=O)n(-c4cncc(Cl)c4)c(=O)n3Cc3cc(C#N)ccc3Cl)cc2s1] | 3 | 1.59 | 551 | |
| II-0399 | 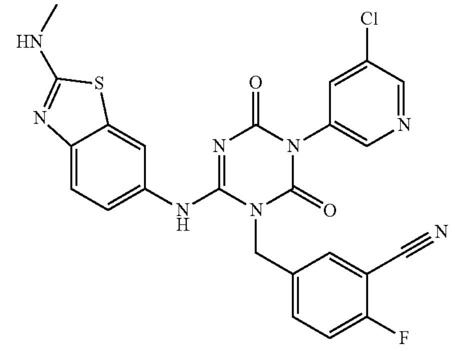 [SMILES: CNc1nc2ccc(Nc3nc(=O)n(-c4cncc(Cl)c4)c(=O)n3Cc3ccc(F)c(C#N)c3)cc2s1] | 3 | 1.52 | 535 | |
| II-0400 | 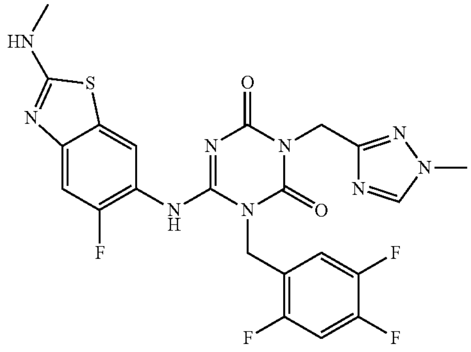 [SMILES: CNc1nc2cc(F)c(Nc3nc(=O)n(Cc4ncn(C)n4)c(=O)n3Cc3cc(F)c(F)cc3F)cc2s1] | 1 | 1.64 | 548 | |

TABLE 132-continued
| Compound No. | Structure | LC/MS Measured condition | Retention time (min) | m/z | Con-figration |
|---|---|---|---|---|---|
| II-0401 | 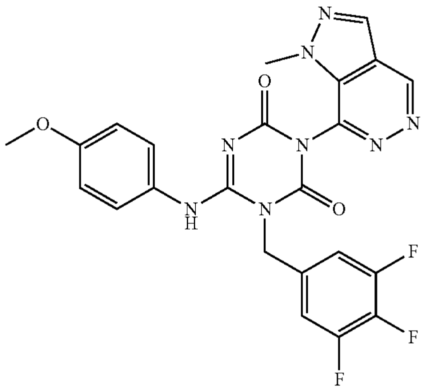 [SMILES: COc1ccc(Nc2nc(=O)n(-c3nncc4cnn(C)c34)c(=O)n2Cc2cc(F)c(F)c(F)c2)cc1] | 1 | 1.57 | 510 | |
TABLE 133
| Compound No. | Structure | LC/MS Measured condition | Retention time (min) | m/z | Con-figration |
|---|---|---|---|---|---|
| II-0402 | 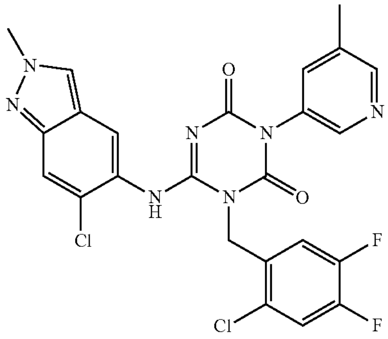 [SMILES: Cc1cncc(-n2c(=O)nc(Nc3cc4cn(C)nc4cc3Cl)n(Cc3cc(F)c(F)cc3Cl)c2=O)c1] | 1 | 2.09 | 544 | |
| II-0403 | 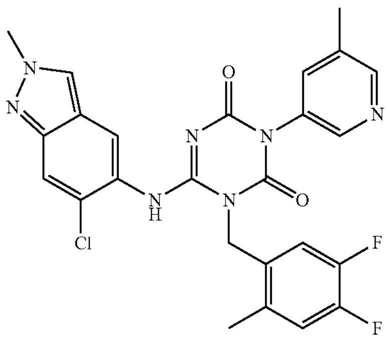 [SMILES: Cc1cncc(-n2c(=O)nc(Nc3cc4cn(C)nc4cc3Cl)n(Cc3cc(F)c(F)cc3C)c2=O)c1] | 1 | 1.98 | 524.1 | |

TABLE 133-continued
| Compound No. | Structure | LC/MS Measured condition | Retention time (min) | m/z | Con-figration |
|---|---|---|---|---|---|
| II-0404 | 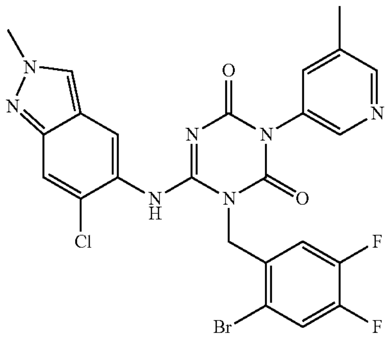 [SMILES: Cc1cncc(-n2c(=O)nc(Nc3cc4cn(C)nc4cc3Cl)n(Cc3cc(F)c(F)cc3Br)c2=O)c1] | 1 | 2.13 | 588 | |
| II-0405 | 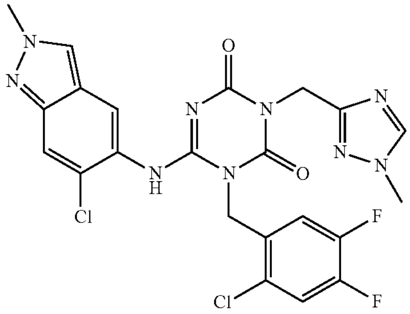 [SMILES: Cn1cnc(Cn2c(=O)nc(Nc3cc4cn(C)nc4cc3Cl)n(Cc3cc(F)c(F)cc3Cl)c2=O)n1] | 1 | 1.95 | 548 | |
| II-0406 | 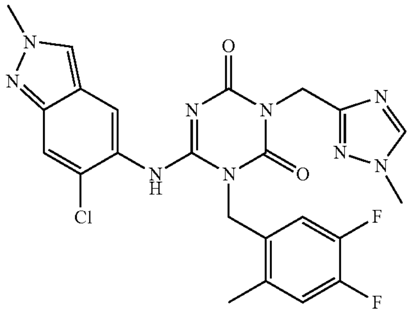 [SMILES: Cc1cc(F)c(F)cc1Cn1c(Nc2cc3cn(C)nc3cc2Cl)nc(=O)n(Cc2ncn(C)n2)c1=O] | 1 | 1.86 | 528 | |
TABLE 134
| Compound No. | Structure | LC/MS Measured condition | Retention time (min) | m/z | Con-figration |
|---|---|---|---|---|---|
| II-0407 | 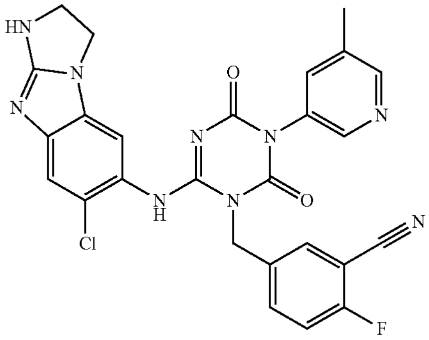 [SMILES: Cc1cncc(-n2c(=O)nc(Nc3cc4c(cc3Cl)nc3n4CCN3)n(Cc3ccc(F)c(C#N)c3)c2=O)c1] | 4 | 1.54 | 544.2 | |

TABLE 134-continued
| Compound No. | Structure | LC/MS Measured condition | Retention time (min) | m/z | Con-figration |
|---|---|---|---|---|---|
| II-0408 | 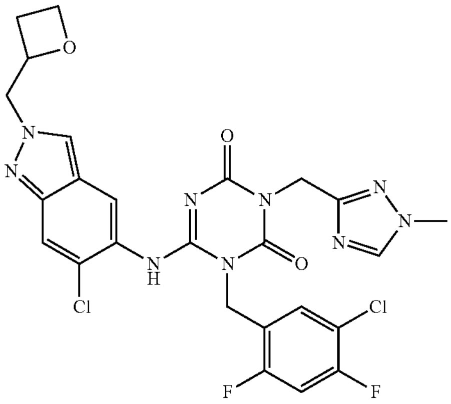 [SMILES: Cn1cnc(Cn2c(=O)nc(Nc3cc4cn(CC5CCO5)nc4cc3Cl)n(Cc3cc(Cl)c(F)cc3F)c2=O)n1] | 3 | 1.74 | 604.1 | b |
| II-0409 | 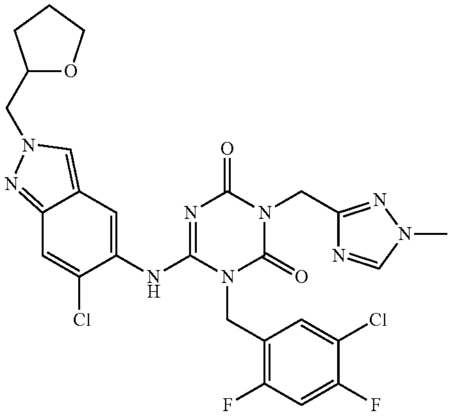 [SMILES: Cn1cnc(Cn2c(=O)nc(Nc3cc4cn(CC5CCCO5)nc4cc3Cl)n(Cc3cc(Cl)c(F)cc3F)c2=O)n1] | 3 | 1.87 | 618 | b |
| II-0410 | 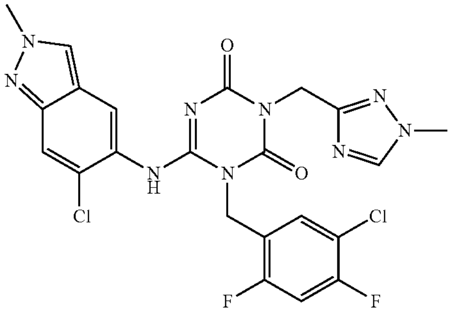 | 1 | 1.84 | 548 | |

TABLE 134-continued
| Compound No. | Structure | LC/MS Measured condition | Retention time (min) | m/z | Con-figration |
|---|---|---|---|---|---|
| II-0411 | 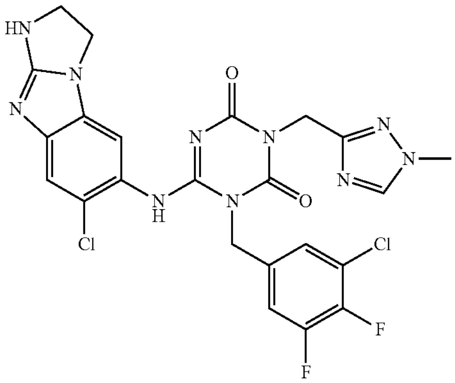 [SMILES: Cn1cnc(Cn2c(=O)nc(Nc3cc4c(cc3Cl)nc3n4CCN3)n(Cc3cc(F)c(F)c(Cl)c3)c2=O)n1] | 3 | 1.36 | 574.9 | |
TABLE 135
| Compound No. | Structure | LC/MS Measured condition | Retention time (min) | m/z | Con-figration |
|---|---|---|---|---|---|
| II-0412 | 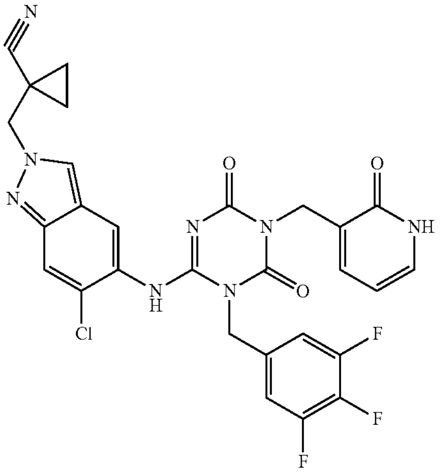 [SMILES: N#CC1(Cn2cc3cc(Nc4nc(=O)n(Cc5ccc[nH]c5=O)c(=O)n4Cc4cc(F)c(F)c(F)c4)c(Cl)cc3n2)CC1] | 1 | 1.96 | 609 | |
| II-0413 | 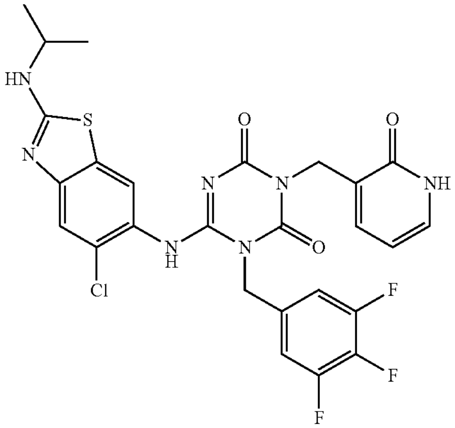 [SMILES: CC(C)Nc1nc2cc(Cl)c(Nc3nc(=O)n(Cc4ccc[nH]c4=O)c(=O)n3Cc3cc(F)c(F)c(F)c3)cc2s1] | 1 | 2.01 | 604.2 | |

TABLE 135-continued
| Compound No. | Structure | LC/MS Measured condition | Retention time (min) | m/z | Con-figration |
|---|---|---|---|---|---|
| II-0414 | 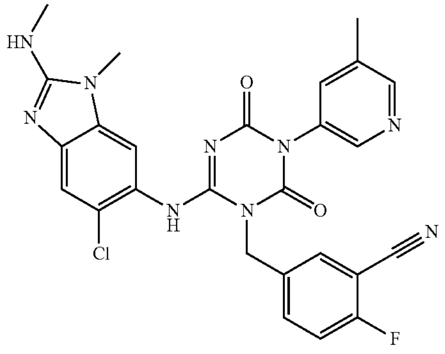 [SMILES: CNc1nc2cc(Cl)c(Nc3nc(=O)n(-c4cncc(C)c4)c(=O)n3Cc3ccc(F)c(C#N)c3)cc2n1C] | 3 | 1.27 | 546 | |
| II-0415 | 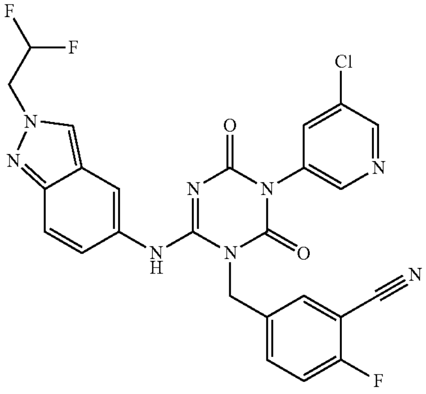 [SMILES: N#Cc1cc(Cn2c(Nc3ccc4nn(CC(F)F)cc4c3)nc(=O)n(-c3cncc(Cl)c3)c2=O)ccc1F] | 1 | 1.94 | 553 | |
| II-0416 | 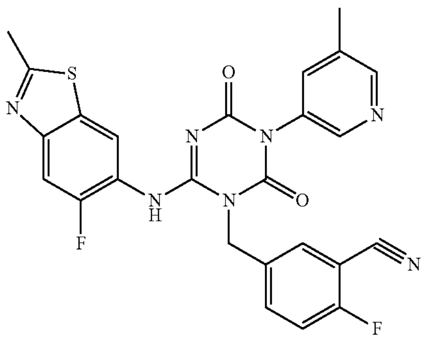 [SMILES: Cc1cncc(-n2c(=O)nc(Nc3cc4sc(C)nc4cc3F)n(Cc3ccc(F)c(C#N)c3)c2=O)c1] | 1 | 1.92 | 518.2 | |

TABLE 136
| Compound No. | Structure | LC/MS Measured condition | Retention time (min) | m/z | Con-figuration |
|---|---|---|---|---|---|
| II-0417 | 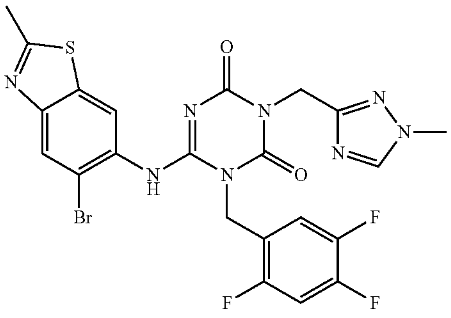 | 3 | 1.97 | 592.9 | |
| II-0418 | 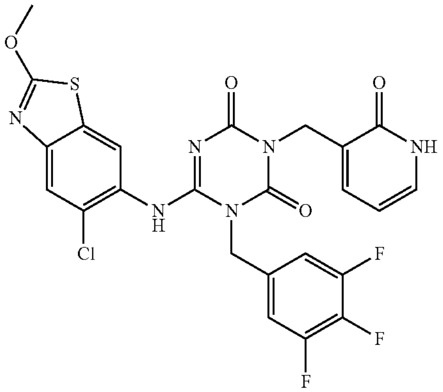 [SMILES: COc1nc2cc(Cl)c(Nc3nc(=O)n(Cc4ccc[nH]c4=O)c(=O)n3Cc3cc(F)c(F)c(F)c3)cc2s1] | 1 | 2.19 | 577 | |
| II-0419 | 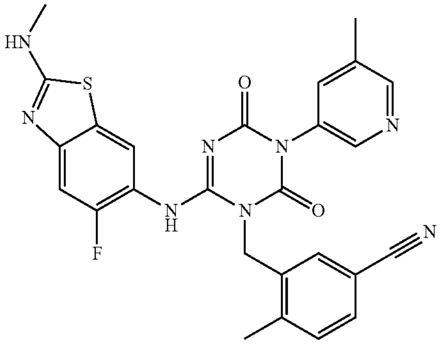 | 3 | 1.52 | 529 | |
| II-0420 | 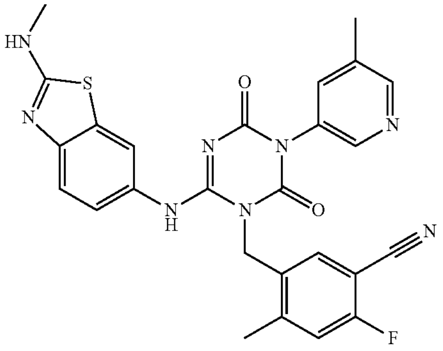 [SMILES: CNc1nc2ccc(Nc3nc(=O)n(-c4cncc(C)c4)c(=O)n3Cc3cc(C#N)c(F)cc3C)cc2s1] | 3 | 1.38 | 529 | |

TABLE 136-continued
| Compound No. | Structure | LC/MS Measured condition | Retention time (min) | m/z | Con-figuration |
|---|---|---|---|---|---|
| II-0421 | 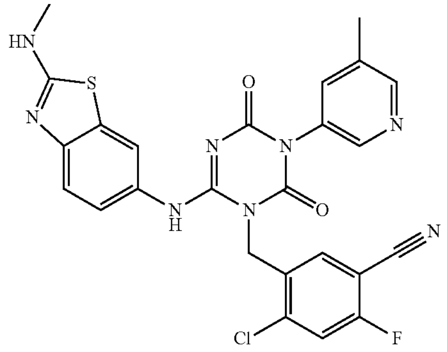 [SMILES: CNc1nc2ccc(Nc3nc(=O)n(-c4cncc(C)c4)c(=O)n3Cc3cc(C#N)c(F)cc3Cl)cc2s1] | 3 | 1.48 | 549 | |
TABLE 137
| Compound No. | Structure | LC/MS Measured condition | Retention time (min) | m/z | Con-figuration |
|---|---|---|---|---|---|
| II-0422 | 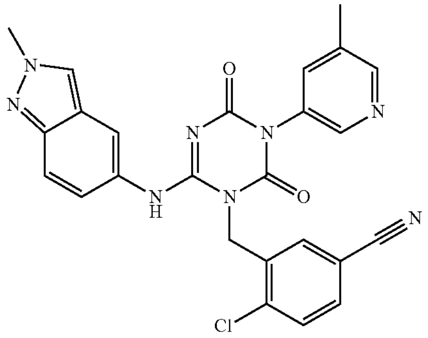 [SMILES: Cc1cncc(-n2c(=O)nc(Nc3ccc4nn(C)cc4c3)n(Cc3cc(C#N)ccc3Cl)c2=O)c1] | 3 | 1.45 | 499 | |
| II-0423 | 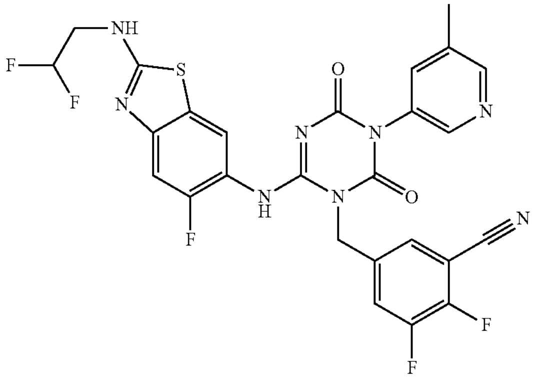 | 3 | 1.90 | 601 | |

TABLE 137-continued
| Compound No. | Structure | LC/MS Measured condition | Retention time (min) | m/z | Con-figration |
|---|---|---|---|---|---|
| II-0424 | 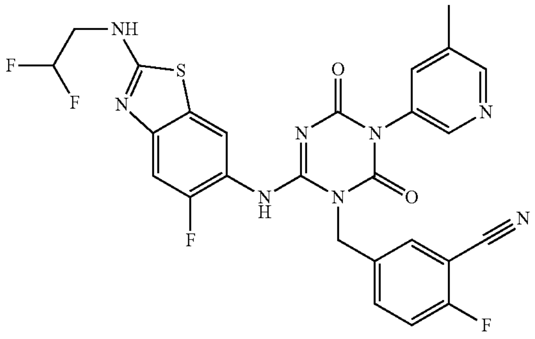 [SMILES: Cc1cncc(-n2c(=O)nc(Nc3cc4sc(NCC(F)F)nc4cc3F)n(Cc3ccc(F)c(C#N)c3)c2=O)c1] | 3 | 1.78 | 583 | |
| II-0425 | 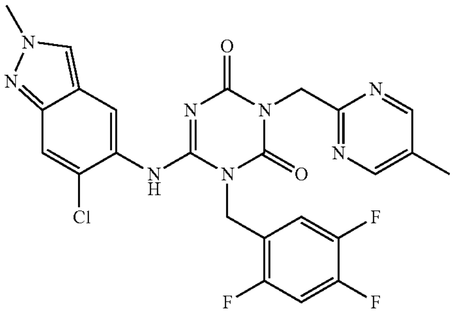 | 1 | 1.99 | 543 | |
| II-0426 | 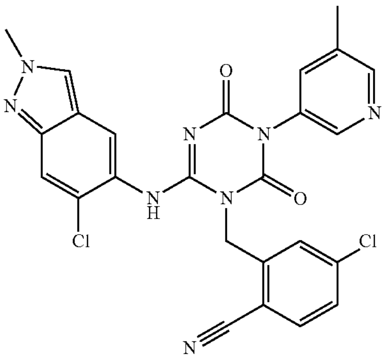 [SMILES: Cc1cncc(-n2c(=O)nc(Nc3cc4cn(C)nc4cc3Cl)n(Cc3cc(Cl)ccc3C#N)c2=O)c1] | 1 | 2.30 | 533 | |

TABLE 138
| Compound No. | Structure | LC/MS Measured condition | Retention time (min) | m/z | Con-figration |
|---|---|---|---|---|---|
| II-0427 | 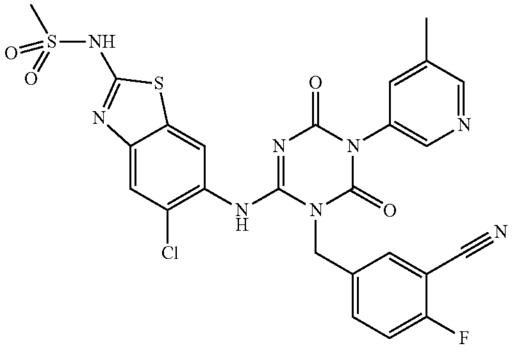 [SMILES: Cc1cncc(-n2c(=O)nc(Nc3cc4sc(NS(C)(=O)=O)nc4cc3Cl)n(Cc3ccc(F)c(C#N)c3)c2=O)c1] | 1 | 2.42 | 613 | |
| II-0428 | 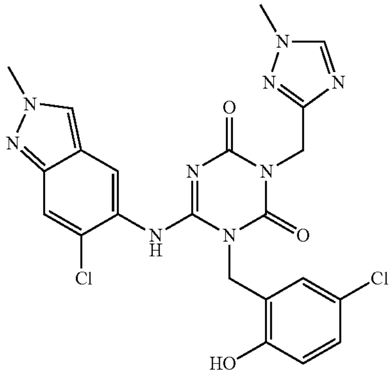 [SMILES: Cn1cnc(Cn2c(=O)nc(Nc3cc4cn(C)nc4cc3Cl)n(Cc3cc(Cl)ccc3O)c2=O)n1] | 1 | 1.51 | 528 | |
| II-0429 | 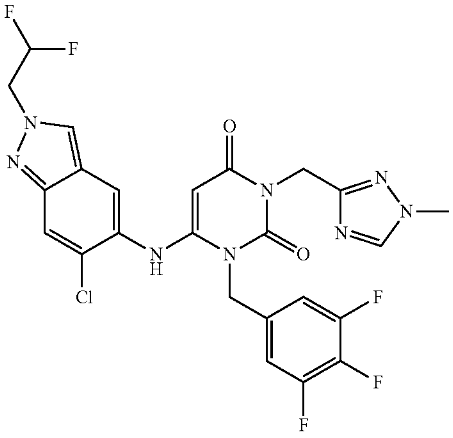 [SMILES: Cn1cnc(Cn2c(=O)cc(Nc3cc4cn(CC(F)F)nc4cc3Cl)n(Cc3cc(F)c(F)c(F)c3)c2=O)n1] | 1 | 1.87 | 581.1 | |
| II-0430 | 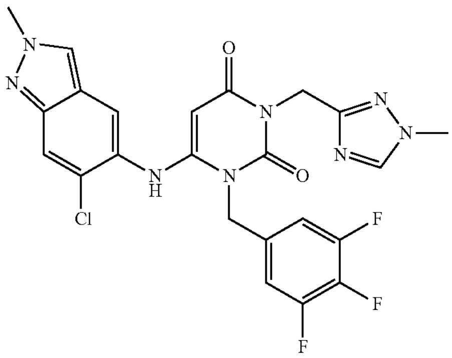 | 3 | 1.73 | 531.1 | |

TABLE 138-continued
| Compound No. | Structure | LC/MS Measured condition | Retention time (min) | m/z | Con-figration |
|---|---|---|---|---|---|
| II-0431 | 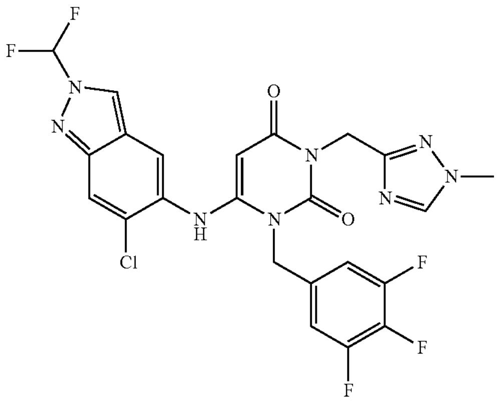 [SMILES: Cn1cnc(Cn2c(=O)cc(Nc3cc4cn(C(F)F)nc4cc3Cl)n(Cc3cc(F)c(F)c(F)c3)c2=O)n1] | 1 | 1.91 | 567.1 | |
TABLE 139
| Compound No. | Structure | LC/MS Measured condition | Retention time (min) | m/z | Con-figration |
|---|---|---|---|---|---|
| II-0432 | 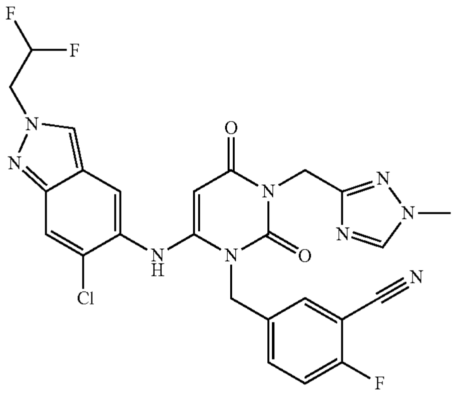 [SMILES: Cn1cnc(Cn2c(=O)cc(Nc3cc4cn(CC(F)F)nc4cc3Cl)n(Cc3ccc(F)c(C#N)c3)c2=O)n1] | 1 | 1.69 | 570.1 | |
| II-0433 | 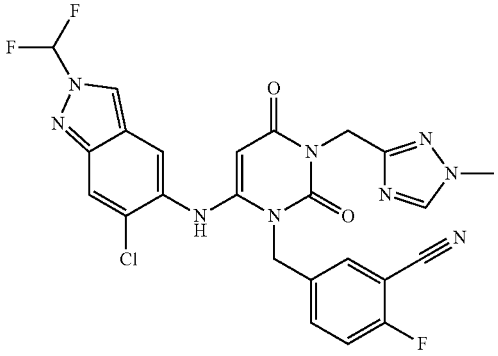 [SMILES: Cn1cnc(Cn2c(=O)cc(Nc3cc4cn(C(F)F)nc4cc3Cl)n(Cc3ccc(F)c(C#N)c3)c2=O)n1] | 1 | 1.75 | 556.1 | |

TABLE 139-continued
| Compound No. | Structure | LC/MS Measured condition | Retention time (min) | m/z | Con-figration |
|---|---|---|---|---|---|
| II-0434 | 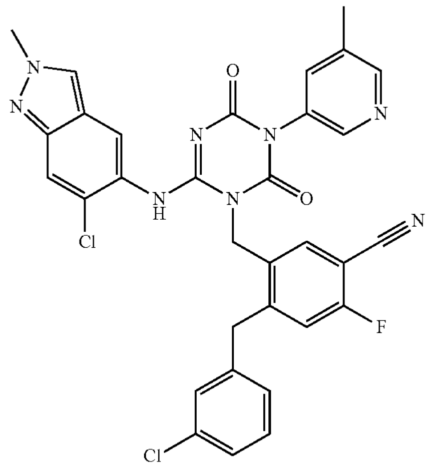 [SMILES: Cc1cncc(-n2c(=O)nc(Nc3cc4cn(C)nc4cc3Cl)n(Cc3cc(C#N)c(F)cc3Cc3cccc(Cl)c3)c2=O)c1] | 1 | 2.43 | 641 | |
| II-0435 | 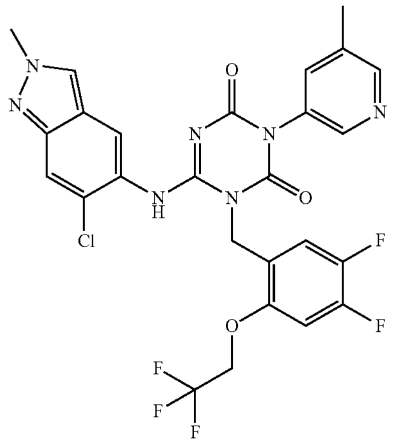 [SMILES: Cc1cncc(-n2c(=O)nc(Nc3cc4cn(C)nc4cc3Cl)n(Cc3cc(F)c(F)cc3OCC(F)(F)F)c2=O)c1] | 1 | 2.10 | 304.6 | |
| II-0436 | 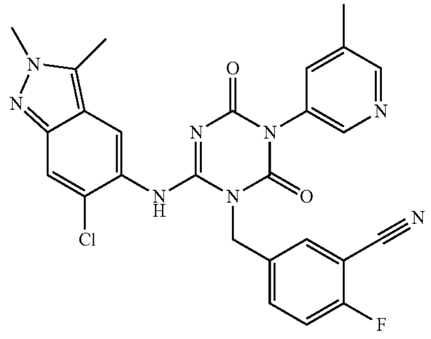 [SMILES: Cc1cncc(-n2c(=O)nc(Nc3cc4c(C)n(C)nc4cc3Cl)n(Cc3ccc(F)c(C#N)c3)c2=O)c1] | 1 | 1.76 | 531.2 | |

TABLE 140
| Compound No. | Structure | LC/MS Measured condition | Retention time (min) | m/z | Con-figration |
|---|---|---|---|---|---|
| II-0437 | 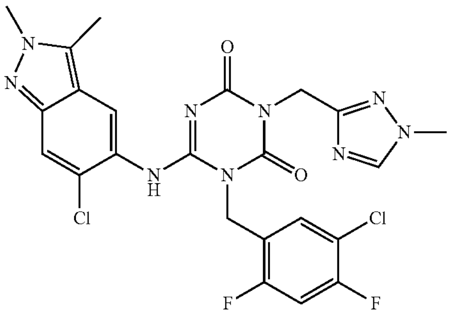 | 1 | 1.73 | 562 | |
| II-0438 | 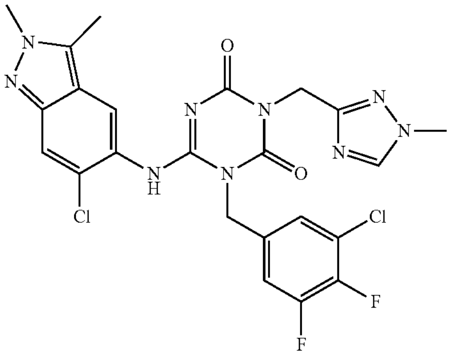 | 1 | 1.80 | 562 | |
| II-0439 | 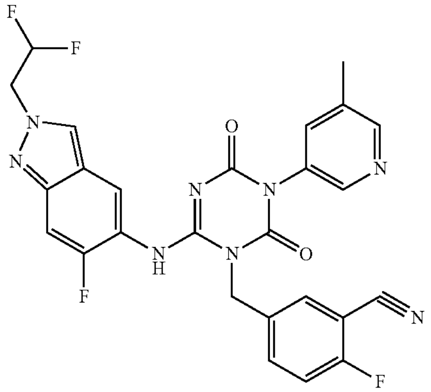 [SMILES: Cc1cncc(-n2c(=O)nc(Nc3cc4cn(CC(F)F)nc4cc3F)n(Cc3ccc(F)c(C#N)c3)c2=O)c1] | 1 | 1.84 | 551.2 | |

TABLE 140-continued
| Compound No. | Structure | LC/MS Measured condition | Retention time (min) | m/z | Con-figuration |
|---|---|---|---|---|---|
| II-0440 | 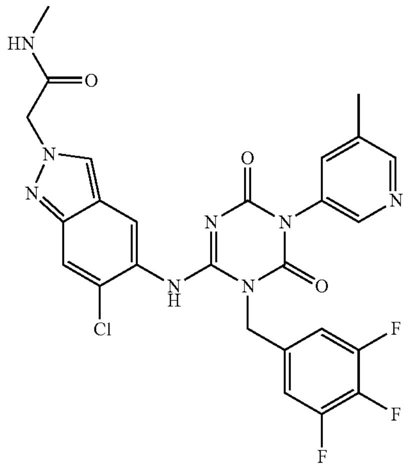 [SMILES: CNC(=O)Cn1cc2cc(Nc3nc(=O)n(-c4cncc(C)c4)c(=O)n3Cc3cc(F)c(F)c(F)c3)c(Cl)cc2n1] | 1 | 1.81 | 585.2 | |
| II-0441 | 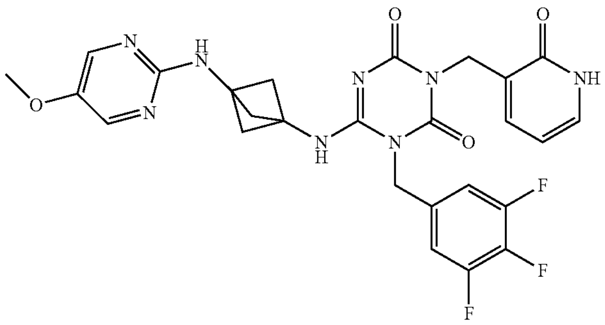 [SMILES: COc1cnc(NC23CC(Nc4nc(=O)n(Cc5ccc[nH]c5=O)c(=O)n4Cc4cc(F)c(F)c(F)c4)(C2)C3)nc1] | 1 | 1.55 | 569.1 | |
TABLE 141
| Compound No. | Structure | LC/MS Measured condition | Retention time (min) | m/z | Con-figuration |
|---|---|---|---|---|---|
| II-0442 | 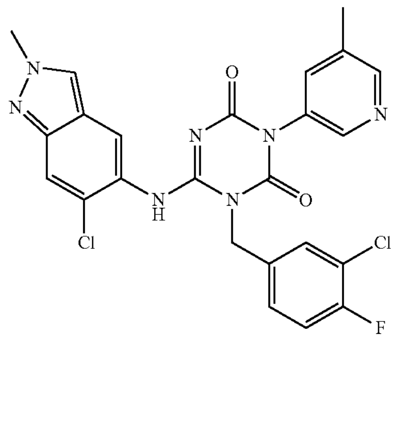 | 1 | 1.93 | 526.1 | |

TABLE 141-continued
| Compound No. | Structure | LC/MS Measured condition | Retention time (min) | m/z | Con-figration |
|---|---|---|---|---|---|
| II-0443 | 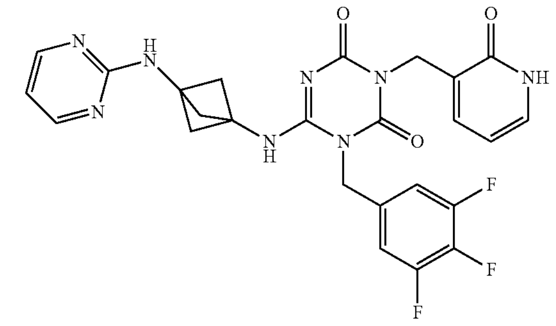 [SMILES: O=c1[nH]cccc1Cn1c(=O)nc(NC23CC(Nc4ncccn4)(C2)C3)n(Cc2cc(F)c(F)c(F)c2)c1=O] | 1 | 1.60 | 539.2 | |
| II-0444 | 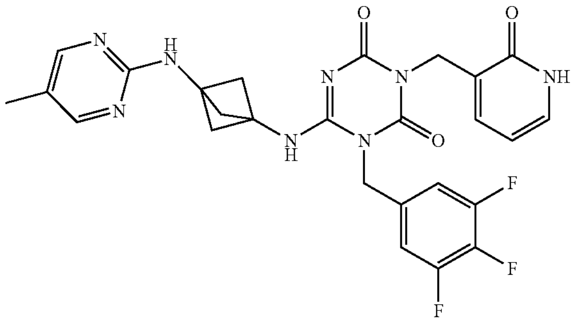 [SMILES: Cc1cnc(NC23CC(Nc4nc(=O)n(Cc5ccc[nH]c5=O)c(=O)n4Cc4cc(F)c(F)c(F)c4)(C2)C3)nc1] | 1 | 1.52 | 553 | |
| II-0445 | 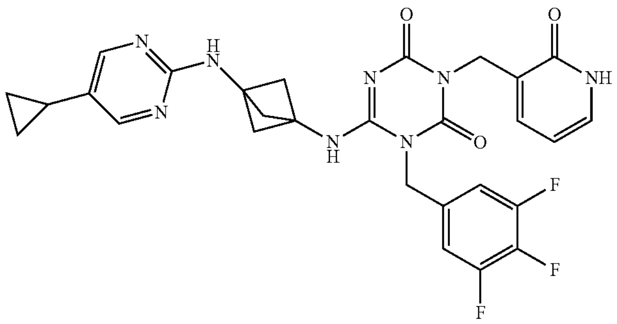 [SMILES: O=c1[nH]cccc1Cn1c(=O)nc(NC23CC(Nc4ncc(C5CC5)cn4)(C2)C3)n(Cc2cc(F)c(F)c(F)c2)c1=O] | 1 | 1.67 | 579.4 | |
| II-0446 | 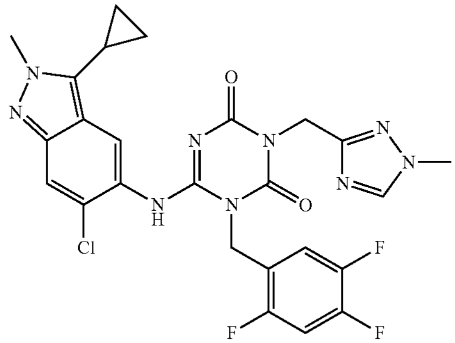 | 1 | 1.93 | 572.2 | |

TABLE 142
| Compound No. | | LC/MS Measured condition | Retention time (min) | m/z | Con-figraton |
|---|---|---|---|---|---|
| II-0447 | 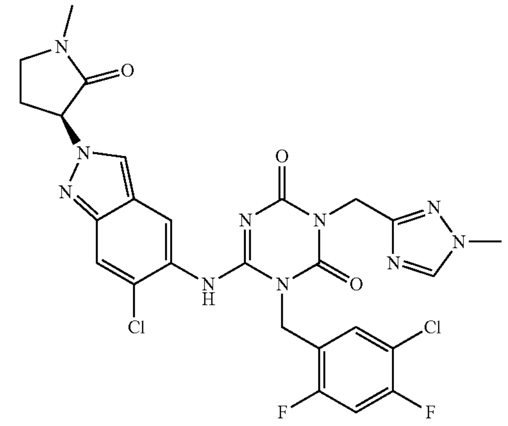 [SMILES: CN1CC[C@H](n2cc3cc(Nc4nc(=O)n(Cc5ncn(C)n5)c(=O)n4Cc4cc(Cl)c(F)cc4F)c(Cl)cc3n2)C1=O] | 1 | 1.69 | 630.9 | a |
| II-0448 | 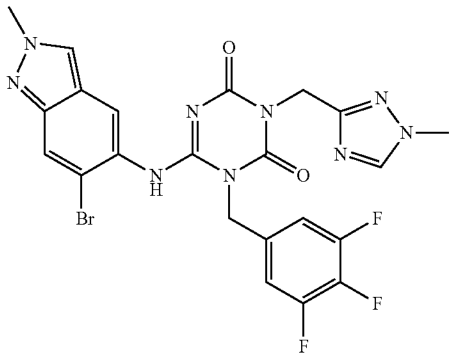 | 1 | 1.83 | 576.2 | |
| II-0449 | 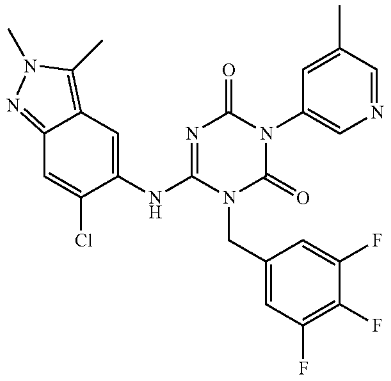 | 1 | 1.96 | 542.2 | |
| II-0450 | 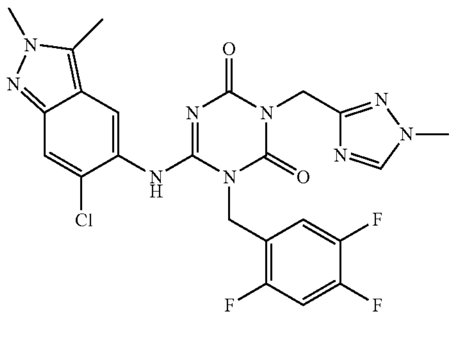 | 1 | 1.65 | 546.2 | |

TABLE 142-continued
| Compound No. | | LC/MS Measured condition | Retention time (min) | m/z | Con-figraton |
|---|---|---|---|---|---|
| II-0451 | 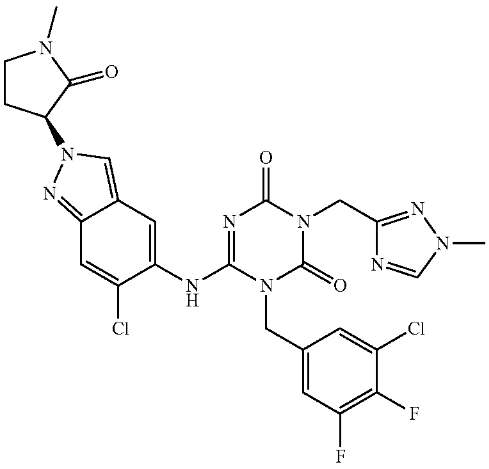 [SMILES: CN1CC[C@H](n2cc3cc(Nc4nc(=O)n(Cc5ncn(C)n5)c(=O)n4Cc4cc(F)c(F)c(Cl)c4)c(Cl)cc3n2)C1=O] | 1 | 1.76 | 631 | a |
TABLE 143
| Compound No. | Structure | LC/MS Measured condition | Retention time (min) | m/z | Con-figration |
|---|---|---|---|---|---|
| II-0452 | 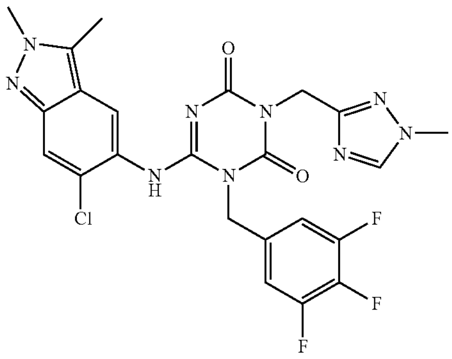 | 1 | 1.81 | 546.2 | |
| II-0453 | 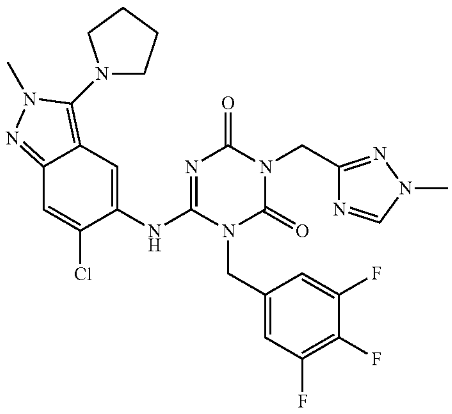 | 1 | 1.73 | 601.2 | |

TABLE 143-continued
| Compound No. | Structure | LC/MS Measured condition | Retention time (min) | m/z | Con-figration |
|---|---|---|---|---|---|
| II-0454 | 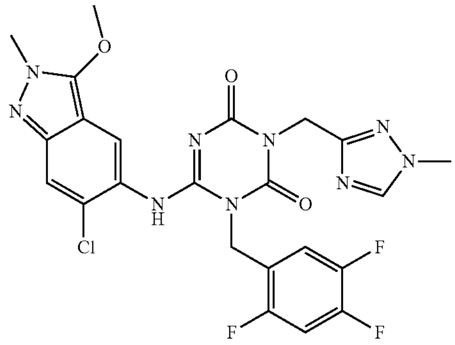 | 1 | 1.67 | 562.2 | |
| II-0455 | 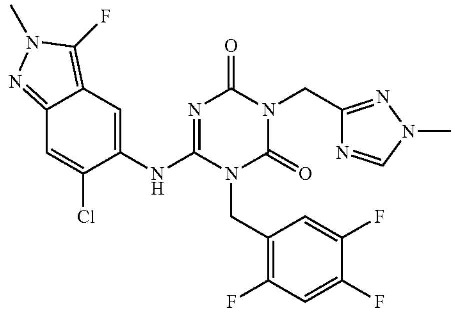 | 1 | 1.95 | 550.1 | |
| II-0456 | 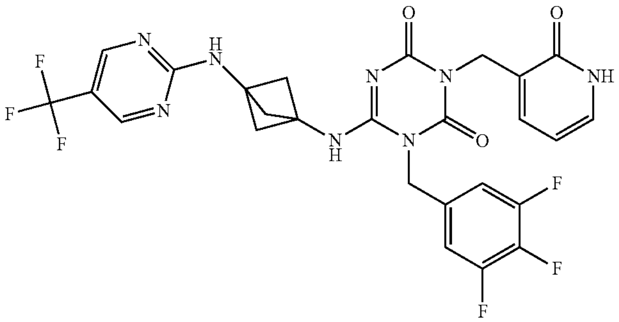 [SMILES: O=c1[nH]cccc1Cn1c(=O)nc(NC23CC(Nc4ncc(C(F)(F)F)cn4)(C2)C3)n(Cc2cc(F)c(F)c(F)c2)c1=O] | 1 | 2.01 | 607.2 | |
TABLE 144
| Compound No. | Structure | LC/MS Measured condition | Retention time (min) | m/z | Con-figration |
|---|---|---|---|---|---|
| II-0457 | 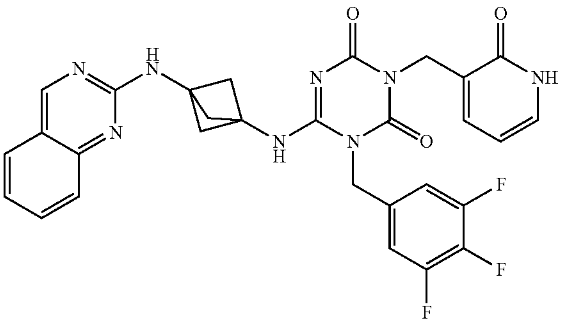 [SMILES: O=c1[nH]cccc1Cn1c(=O)nc(NC23CC(Nc4ncc5ccccc5n4)(C2)C3)n(Cc2cc(F)c(F)c(F)c2)c1=O] | 1 | 1.58 | 589.4 | |

TABLE 144-continued
| Compound No. | Structure | LC/MS Measured condition | Retention time (min) | m/z | Con-figration |
|---|---|---|---|---|---|
| II-0458 | 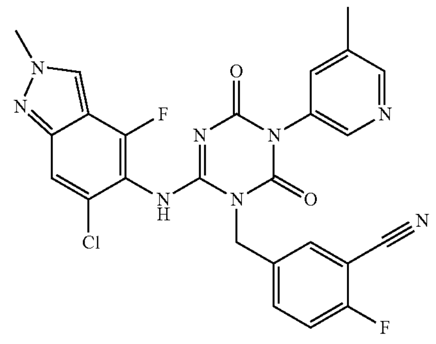 [SMILES: Cc1cncc(-n2c(=O)nc(Nc3c(Cl)cc4nn(C)cc4c3F)n(Cc3ccc(F)c(C#N)c3)c2=O)c1] | 1 | 1.89 | 535.2 | |
| II-0459 | 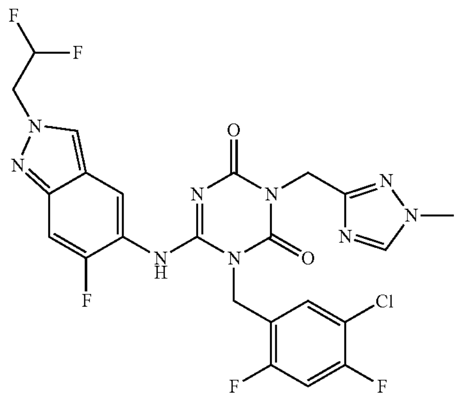 [SMILES: Cn1cnc(Cn2c(=O)nc(Nc3cc4cn(CC(F)F)nc4cc3F)n(Cc3cc(Cl)c(F)cc3F)c2=O)n1] | 1 | 1.92 | 582.1 | |
| II-460 | 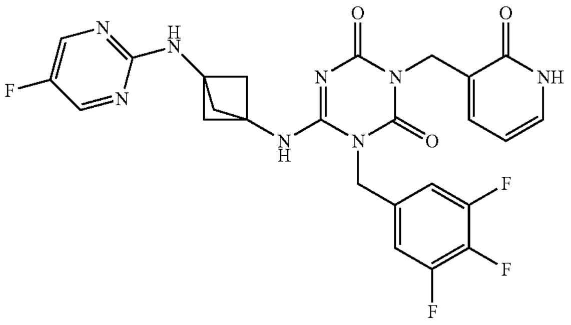 [SMILES: O=c1[nH]cccc1Cn1c(=O)nc(NC23CC(Nc4ncc(F)cn4)(C2)C3)n(Cc2cc(F)c(F)c(F)c2)c1=O] | 1 | 1.62 | 557.3 | |
| II-0461 | 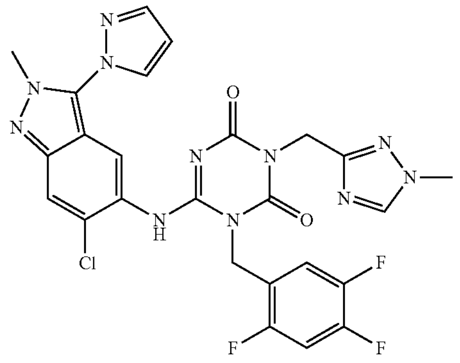 | 1 | 2.02 | 599 | |

TABLE 145
| Compound No. | Structure | LC/MS Measured condition | Retention time (min) | m/z | Con-figration |
|---|---|---|---|---|---|
| II-0462 | 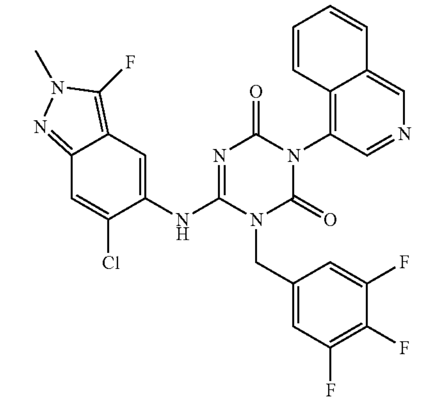 [SMILES: Cn1nc2cc(Cl)c(Nc3nc(=O)n(-c4cncc5ccccc45)c(=O)n3Cc3cc(F)c(F)c(F)c3)cc2c1F] | 1 | 2.15 | 582.2 | |
| II-0463 | 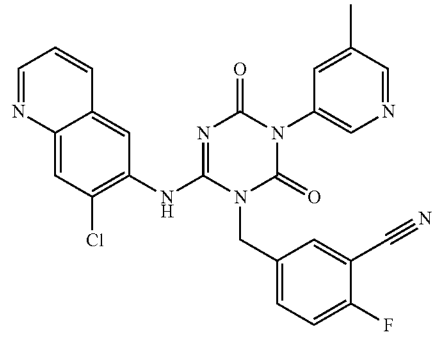 [SMILES: Cc1cncc(-n2c(=O)nc(Nc3cc4cccnc4cc3Cl)n(Cc3ccc(F)c(C#N)c3)c2=O)c1] | 1 | 1.78 | 514.2 | |
| II-0464 | 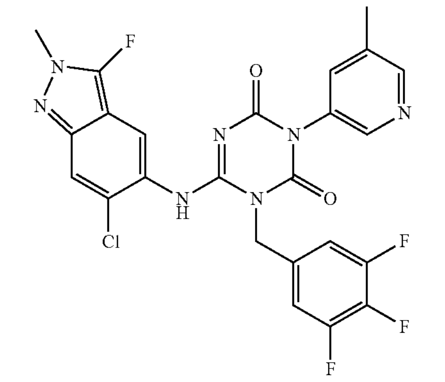 [SMILES: Cc1cncc(-n2c(=O)nc(Nc3cc4c(F)n(C)nc4cc3Cl)n(Cc3cc(F)c(F)c(F)c3)c2=O)c1] | 1 | 2.07 | 546.1 | |

TABLE 145-continued
| Compound No. | Structure | LC/MS Measured condition | Retention time (min) | m/z | Con- figration |
|---|---|---|---|---|---|
| II-0465 | 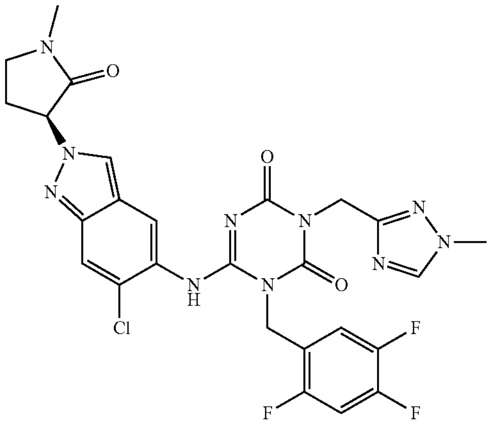 [SMILES: CN1CC[C@H](n2cc3cc(Nc4nc(=O)n(Cc5ncn(C)n5)c(=O)n4Cc4cc(F)c(F)cc4F)c(Cl)cc3n2)C1=O] | 1 | 1.61 | 615 | a |
| II-0466 | 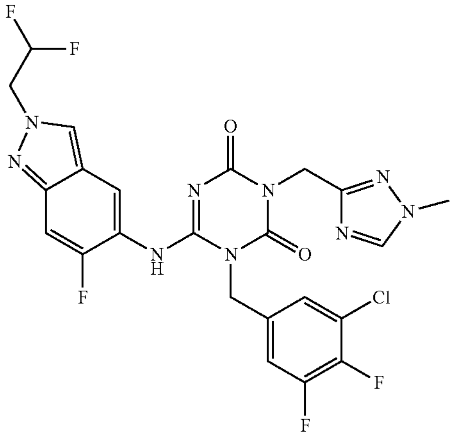 [SMILES: Cn1cnc(Cn2c(=O)nc(Nc3cc4cn(CC(F)F)nc4cc3F)n(Cc3cc(F)c(F)c(Cl)c3)c2=O)n1] | 1 | 1.98 | 582.2 | |
TABLE 146
| Compound No. | Structure | LC/MS Measured condition | Retention time (min) | m/z | Con- figration |
|---|---|---|---|---|---|
| II-0467 | 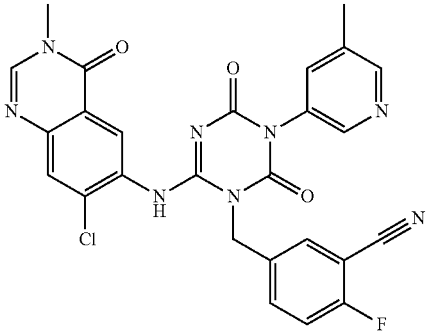 [SMILES: Cc1cncc(-n2c(=O)nc(Nc3cc4c(=O)n(C)cnc4cc3Cl)n(Cc3ccc(F)c(C#N)c3)c2=O)c1] | 1 | 1.81 | 545.2 | |

TABLE 146-continued
| Compound No. | Structure | LC/MS Measured condition | Retention time (min) | m/z | Con-figration |
|---|---|---|---|---|---|
| II-0468 | 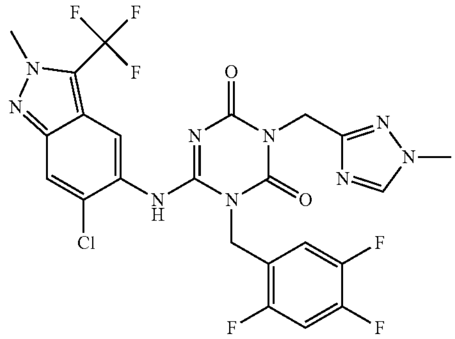 | 1 | 2.24 | 600.1 | |
| II-0469 | 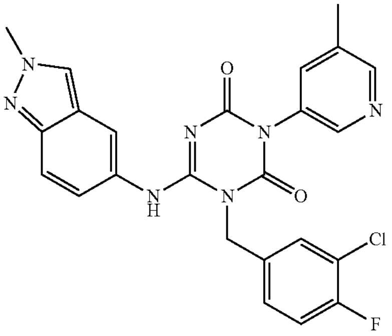 [SMILES: Cc1cncc(-n2c(=O)nc(Nc3ccc4nn(C)cc4c3)n(Cc3ccc(F)c(Cl)c3)c2=O)c1] | 1 | 1.69 | 492.2 | |
| II-0470 | 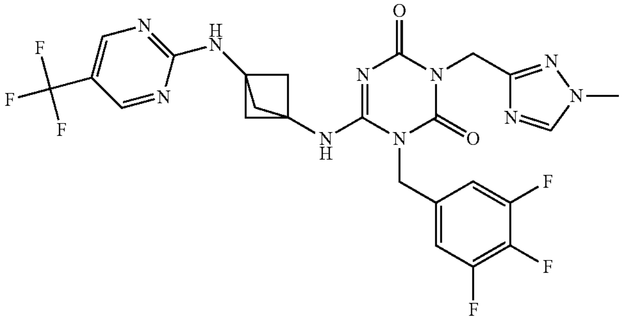 [SMILES: Cn1cnc(Cn2c(=O)nc(NC34CC(Nc5ncc(C(F)(F)F)cn5)(C3)C4)n(Cc3cc(F)c(F)c(F)c3)c2=O)n1] | 3 | 2.06 | 595.2 | |
| II-0471 | 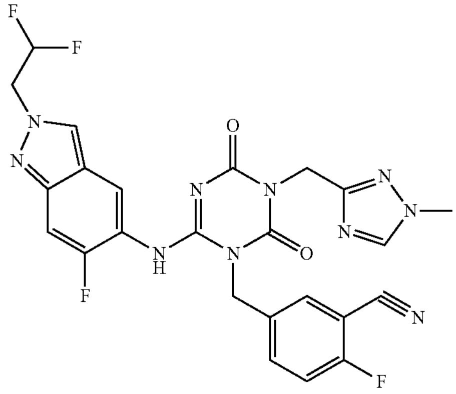 [SMILES: Cn1cnc(Cn2c(=O)nc(Nc3cc4cn(CC(F)F)nc4cc3F)n(Cc3ccc(F)c(C#N)c3)c2=O)n1] | 1 | 1.74 | 555.2 | |

TABLE 147
| Compound No. | Structure | LC/MS Measured condition | Retention time (min) | m/z | Con-figration |
|---|---|---|---|---|---|
| II-0472 | 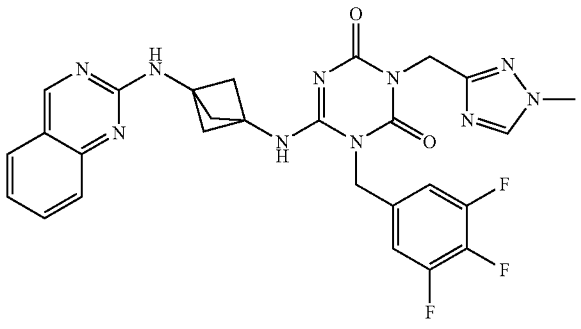 [SMILES: Cn1cnc(Cn2c(=O)nc(NC34CC(Nc5ncc6ccccc6n5)(C3)C4)n(Cc3cc(F)c(F)c(F)c3)c2=O)n1] | 1 | 1.61 | 577.1 | |
| II-0473 | 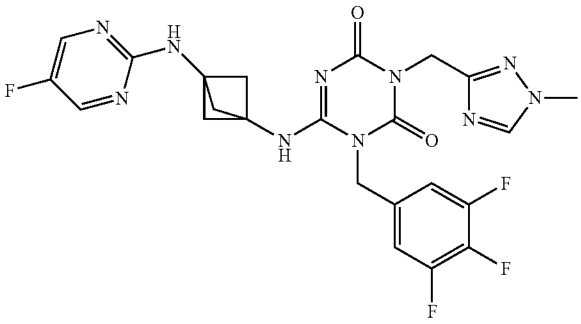 [SMILES: Cn1cnc(Cn2c(=O)nc(NC34CC(Nc5ncc(F)cn5)(C3)C4)n(Cc3cc(F)c(F)c(F)c3)c2=O)n1] | 3 | 1.81 | 545.2 | |
| II-0474 | 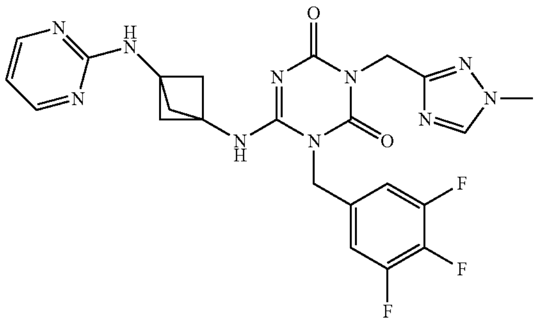 [SMILES: Cn1cnc(Cn2c(=O)nc(NC34CC(Nc5ncccn5)(C3)C4)n(Cc3cc(F)c(F)c(F)c3)c2=O)n1] | 3 | 1.58 | 527.2 | |
| II-0475 | 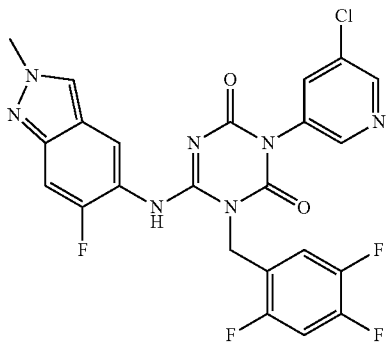 [SMILES: Cn1cc2cc(Nc3nc(=O)n(-c4cncc(Cl)c4)c(=O)n3Cc3cc(F)c(F)cc3F)c(F)cc2n1] | 1 | 2.00 | 532.1 | |

TABLE 147-continued
| Compound No. | Structure | LC/MS Measured condition | Retention time (min) | m/z | Con-figration |
|---|---|---|---|---|---|
| II-0476 | 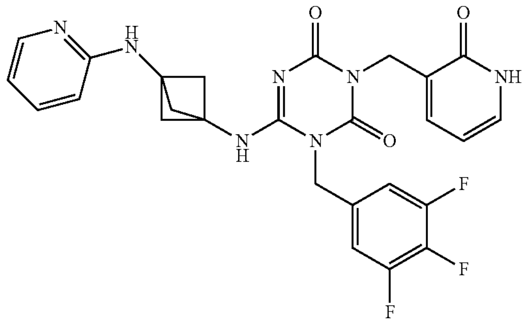 [SMILES: O=c1[nH]cccc1Cn1c(=O)nc(NC23CC(Nc4ccccn4)(C2)C3)n(Cc2cc(F)c(F)c(F)c2)c1=O] | 1 | 1.35 | 538.2 | |
TABLE 148
| Compound No. | Structure | LC/MS Measured condition | Retention time (min) | m/z | Con-figration |
|---|---|---|---|---|---|
| II-0477 | 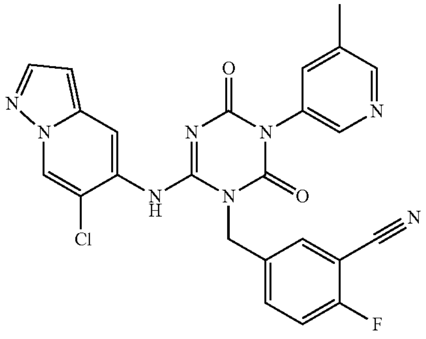 [SMILES: Cc1cncc(-n2c(=O)nc(Nc3cc4ccnn4cc3Cl)n(Cc3ccc(F)c(C#N)c3)c2=O)c1] | 1 | 1.94 | 503.2 | |
| II-0478 | 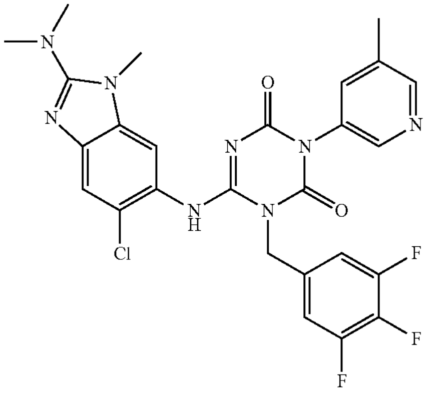 [SMILES: Cc1cncc(-n2c(=O)nc(Nc3cc4c(cc3Cl)nc(N(C)C)n4C)n(Cc3cc(F)c(F)c(F)c3)c2=O)c1] | 1 | 1.63 | 571.2 | |

TABLE 148-continued
| Compound No. | Structure | LC/MS Measured condition | Retention time (min) | m/z | Con-figration |
|---|---|---|---|---|---|
| II-0479 | 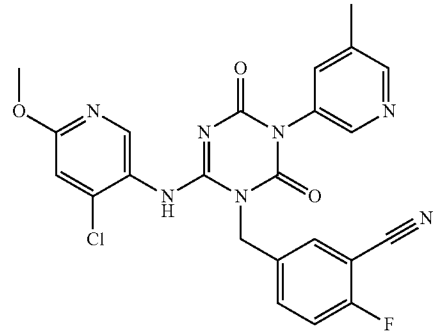 [SMILES: COc1cc(Cl)c(Nc2nc(=O)n(-c3cncc(C)c3)c(=O)n2Cc2ccc(F)c(C#N)c2)cn1] | 1 | 1.93 | 494.2 | |
| II-0480 | 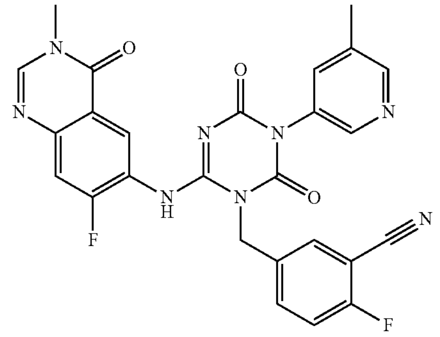 [SMILES: Cc1cncc(-n2c(=O)nc(Nc3cc4c(=O)n(C)cnc4cc3F)n(Cc3ccc(F)c(C#N)c3)c2=O)c1] | 1 | 1.72 | 529.2 | |
| II-0481 | 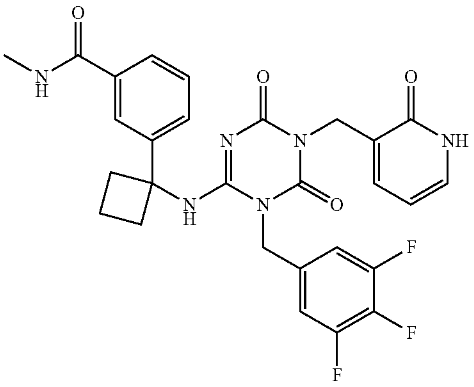 [SMILES: CNC(=O)c1cccc(C2(Nc3nc(=O)n(Cc4ccc[nH]c4=O)c(=O)n3Cc3cc(F)c(F)c(F)c3)CCC2)c1] | 1 | 1.59 | 567.1 | |

TABLE 149
| Compound No. | Structure | LC/MS Measured condition | Retention time (min) | m/z | Con-figration |
|---|---|---|---|---|---|
| II-0482 | 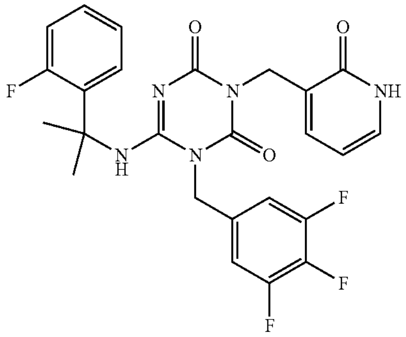 [SMILES: CC(C)(Nc1nc(=O)n(Cc2ccc[nH]c2=O)c(=O)n1Cc1cc(F)c(F)c(F)c1)c1ccccc1F] | 1 | 2.02 | 516.2 | |
| II-0483 | 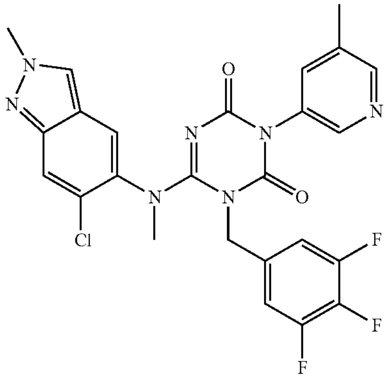 [SMILES: Cc1cncc(-n2c(=O)nc(N(C)c3cc4cn(C)nc4cc3Cl)n(Cc3cc(F)c(F)c(F)c3)c2=O)c1] | 1 | 1.73 | 542.2 | |
| II-0484 | 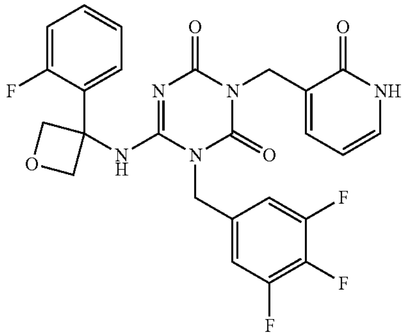 [SMILES: O=c1[nH]cccc1Cn1c(=O)nc(NC2(c3ccccc3F)COC2)n(Cc2cc(F)c(F)c(F)c2)c1=O] | 1 | 1.96 | 530.2 | |
| II-0485 | 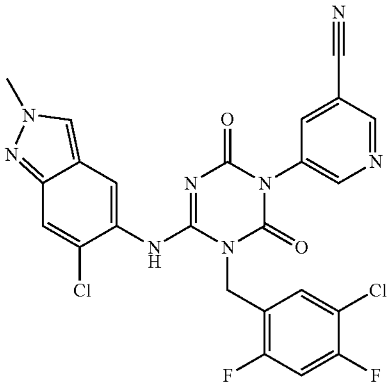 [SMILES: Cn1cc2cc(Nc3nc(=O)n(-c4cncc(C#N)c4)c(=O)n3Cc3cc(Cl)c(F)cc3F)c(Cl)cc2n1] | 1 | 2.19 | 554.1 | |

TABLE 149-continued
| Compound No. | Structure | LC/MS Measured condition | Retention time (min) | m/z | Con-figration |
|---|---|---|---|---|---|
| II-0486 | 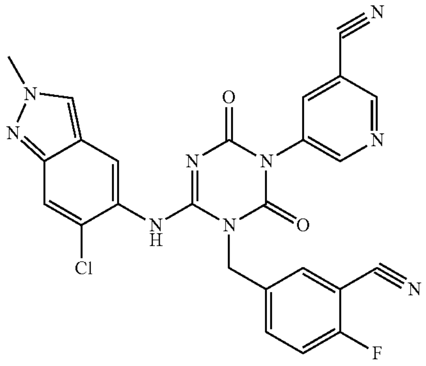 [SMILES: Cn1cc2cc(Nc3nc(=O)n(-c4cncc(C#N)c4)c(=O)n3Cc3ccc(F)c(C#N)c3)c(Cl)cc2n1] | 1 | 1.97 | 527.1 | |
TABLE 150
| Compound No. | Structure | LC/MS Measured condition | Retention time (min) | m/z | Con-figration |
|---|---|---|---|---|---|
| II-0487 | 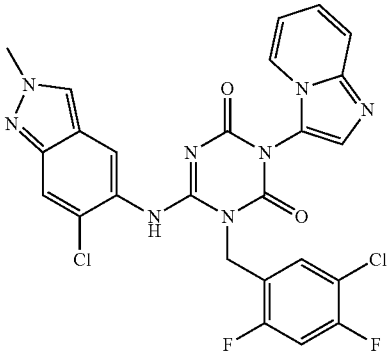 [SMILES: Cn1cc2cc(Nc3nc(=O)n(-c4cnc5ccccn45)c(=O)n3Cc3cc(Cl)c(F)cc3F)c(Cl)cc2n1] | 1 | 1.73 | 568.1 | |
| II-0488 | 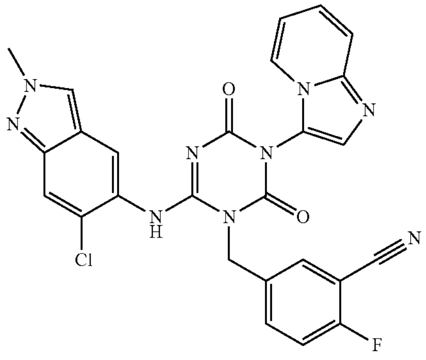 [SMILES: Cn1cc2cc(Nc3nc(=O)n(-c4cnc5ccccn45)c(=O)n3Cc3ccc(F)c(C#N)c3)c(Cl)cc2n1] | 1 | 1.58 | 541.1 | |

TABLE 150-continued
| Compound No. | Structure | LC/MS Measured condition | Retention time (min) | m/z | Con-figuration |
|---|---|---|---|---|---|
| II-0489 | 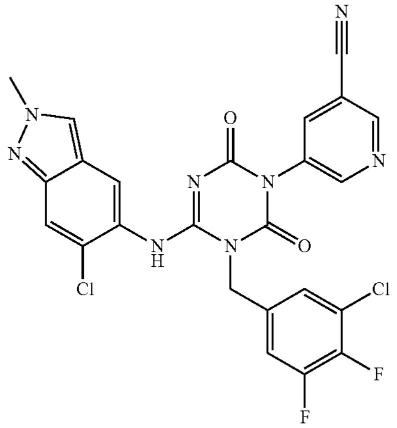 [SMILES: Cn1cc2cc(Nc3nc(=O)n(-c4cncc(C#N)c4)c(=O)n3Cc3cc(F)c(F)c(Cl)c3)c(Cl)cc2n1] | 1 | 2.27 | 554.1 | |
| II-490 | 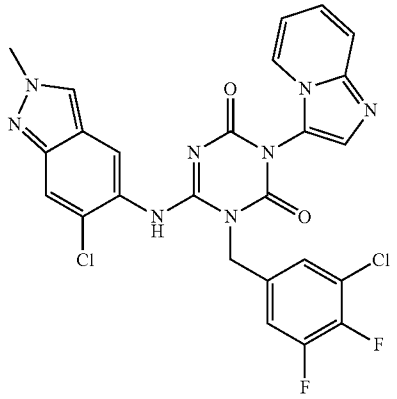 [SMILES: Cn1cc2cc(Nc3nc(=O)n(-c4cnc5ccccn45)c(=O)n3Cc3cc(F)c(F)c(Cl)c3)c(Cl)cc2n1] | 1 | 1.79 | 568.1 | |
| II-0491 | 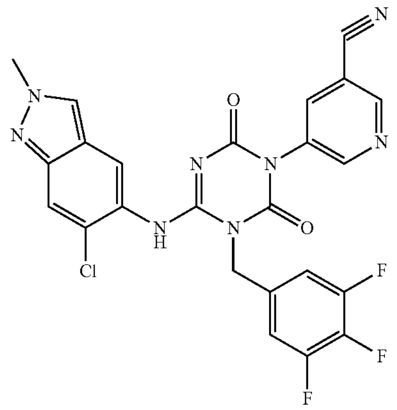 [SMILES: Cn1cc2cc(Nc3nc(=O)n(-c4cncc(C#N)c4)c(=O)n3Cc3cc(F)c(F)c(F)c3)c(Cl)cc2n1] | 1 | 2.16 | 538.1 | |

TABLE 151
| Compound No. | Structure | LC/MS Measured condition | Retention time (min) | m/z | Con-figration |
|---|---|---|---|---|---|
| II-0492 | 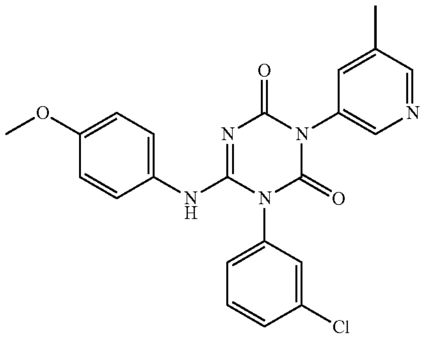 [SMILES: COc1ccc(Nc2nc(=O)n(-c3cncc(C)c3)c(=O)n2-c2cccc(Cl)c2)cc1] | 1 | 1.72 | 435.1 | |
| II-0493 | 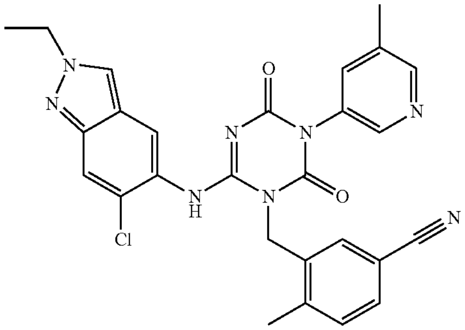 [SMILES: CCn1cc2cc(Nc3nc(=O)n(-c4cncc(C)c4)c(=O)n3Cc3cc(C#N)ccc3C)c(Cl)cc2n1] | 3 | 1.60 | 527 | |
| II-0494 | 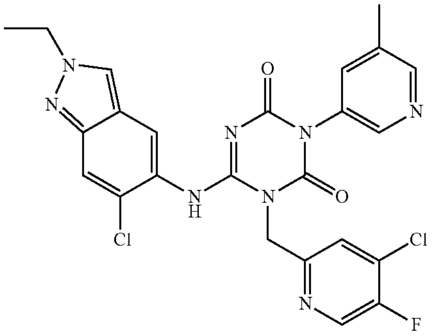 [SMILES: CCn1cc2cc(Nc3nc(=O)n(-c4cncc(C)c4)c(=O)n3Cc3cc(Cl)c(F)cn3)c(Cl)cc2n1] | 3 | 1.70 | 541 | |
| II-0495 | 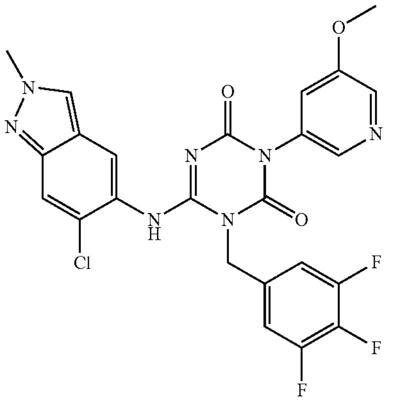 [SMILES: COc1cncc(-n2c(=O)nc(Nc3cc4cn(C)nc4cc3Cl)n(Cc3cc(F)c(F)c(F)c3)c2=O)c1] | 3 | 1.87 | 544 | |

TABLE 151-continued
| Compound No. | Structure | LC/MS Measured condition | Retention time (min) | m/z | Con-figration |
|---|---|---|---|---|---|
| II-0496 | 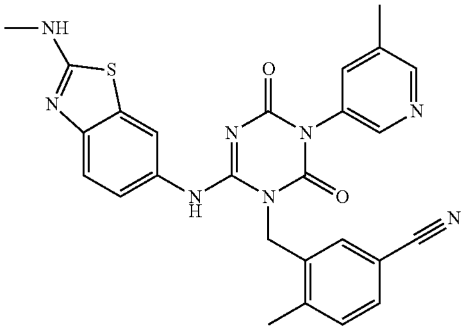 [SMILES: CNc1nc2ccc(Nc3nc(=O)n(-c4cncc(C)c4)c(=O)n3Cc3cc(C#N)ccc3C)cc2s1] | 3 | 1.30 | 511 | |
TABLE 152
| Compound No. | Structure | LC/MS Measured condition | Retention time (min) | m/z | Con-figration |
|---|---|---|---|---|---|
| II-0497 | 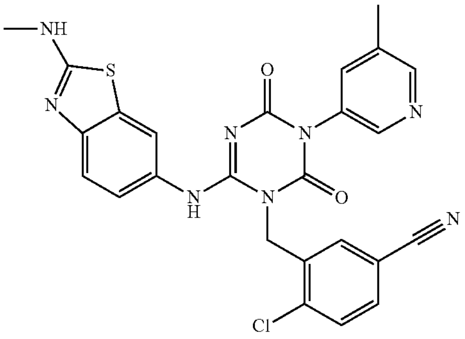 [SMILES: CNc1nc2ccc(Nc3nc(=O)n(-c4cncc(C)c4)c(=O)n3Cc3cc(C#N)ccc3Cl)cc2s1] | 3 | 1.39 | 531 | |
| II-0498 | 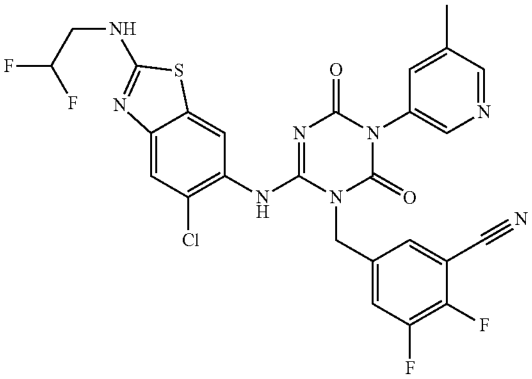 [SMILES: Cc1cncc(-n2c(=O)nc(Nc3cc4sc(NCC(F)F)nc4cc3Cl)n(Cc3cc(F)c(F)c(C#N)c3)c2=O)c1] | 3 | 2.02 | 617 | |

TABLE 152-continued
| Compound No. | Structure | LC/MS Measured condition | Retention time (min) | m/z | Con-figration |
|---|---|---|---|---|---|
| II-0499 | 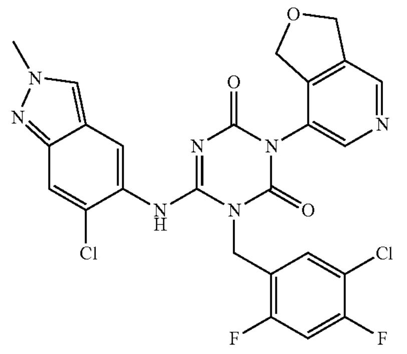 [SMILES: Cn1cc2cc(Nc3nc(=O)n(-c4cncc5c4COC5)c(=O)n3Cc3cc(Cl)c(F)cc3F)c(Cl)cc2n1] | 3 | 1.81 | 572 | |
| II-0500 | 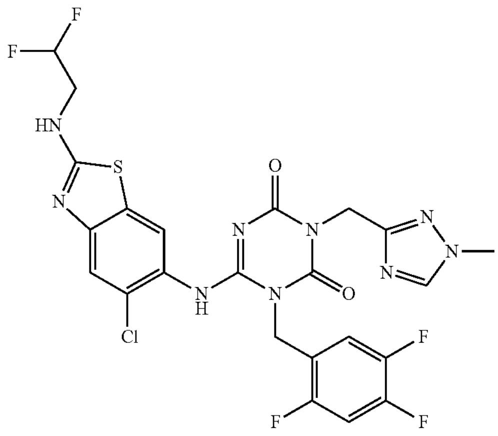 [SMILES: Cn1cnc(Cn2c(=O)nc(Nc3cc4sc(NCC(F)F)nc4cc3Cl)n(Cc3cc(F)c(F)cc3F)c2=O)n1] | 3 | 1.91 | 614 | |
| II-0501 | 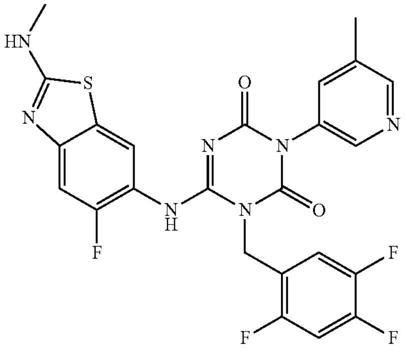 | 3 | 1.67 | 544 | |

TABLE 153
| Compound No. | Structure | LC/MS Measured condition | Retention time (min) | m/z | Con-figration |
|---|---|---|---|---|---|
| II-0502 | 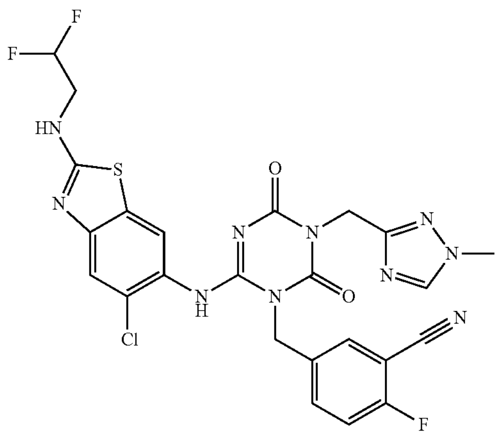 [SMILES: Cn1cnc(Cn2c(=O)nc(Nc3cc4sc(NCC(F)F)nc4cc3Cl)n(Cc3ccc(F)c(C#N)c3)c2=O)n1] | 3 | 1.77 | 603 | |
| II-0503 | 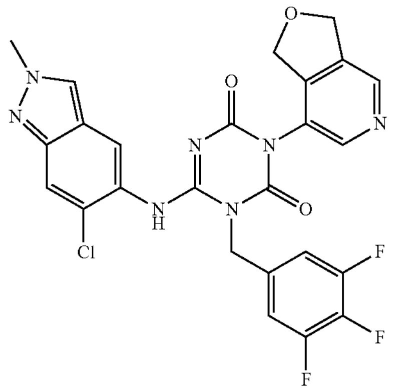 [SMILES: Cn1cc2cc(Nc3nc(=O)n(-c4cncc5c4COC5)c(=O)n3Cc3cc(F)c(F)c(F)c3)c(Cl)cc2n1] | 3 | 1.78 | 556 | |
| II-0504 | 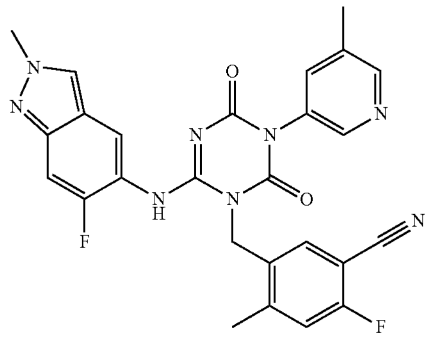 [SMILES: Cc1cncc(-n2c(=O)nc(Nc3cc4cn(C)nc4cc3F)n(Cc3cc(C#N)c(F)cc3C)c2=O)c1] | 3 | 1.57 | 515.1 | |

TABLE 153-continued
| Compound No. | Structure | LC/MS Measured condition | Retention time (min) | m/z | Con- figration |
|---|---|---|---|---|---|
| II-0505 | 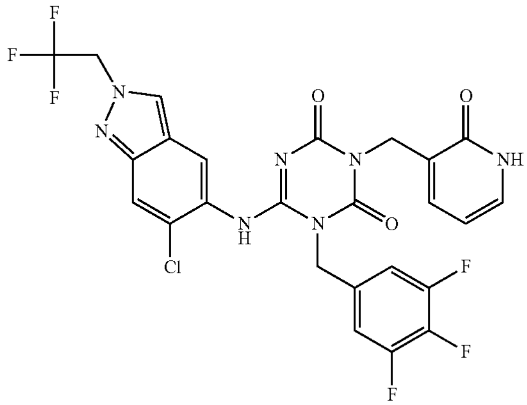 [SMILES: O=c1[nH]cccc1Cn1c(=O)nc(Nc2cc3cn(CC(F)(F)F)nc3cc2Cl)n(Cc2cc(F)c(F)c(F)c2)c1=O] | 1 | 2.12 | 612.2 | |
| II-0506 | 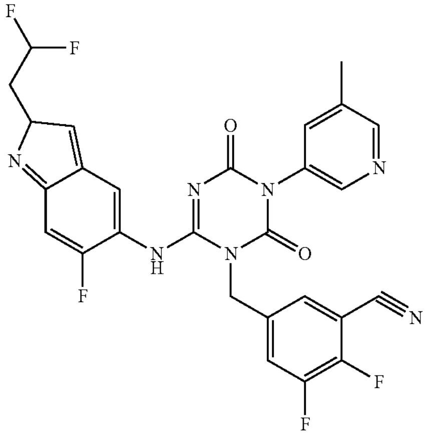 [SMILES: Cc1cncc(-n2c(=O)nc(Nc3cc4c(cc3F)=NC(CC(F)F)C=4)n(Cc3cc(F)c(F)c(C#N)c3)c2=O)c1] | 3 | 1.81 | 569 | |
TABLE 154
| Compound No. | Structure | LC/MS Measured condition | Retention time (min) | m/z | Con- figration |
|---|---|---|---|---|---|
| II-0507 | 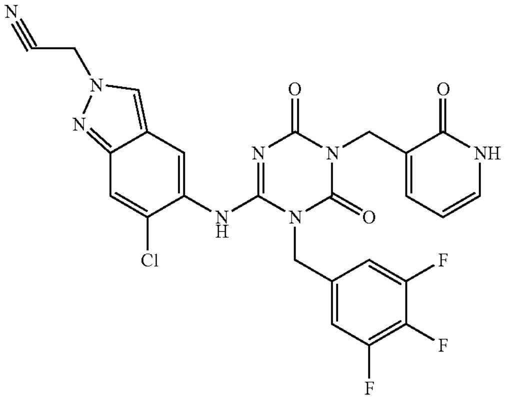 [SMILES: N#CCn1cc2cc(Nc3nc(=O)n(Cc4ccc[nH]c4=O)c(=O)n3Cc3cc(F)c(F)c(F)c3)c(Cl)cc2n1] | 1 | 1.92 | 569.2 | |

TABLE 154-continued
| Compound No. | Structure | LC/MS Measured condition | Retention time (min) | m/z | Con-figration |
|---|---|---|---|---|---|
| II-0508 | 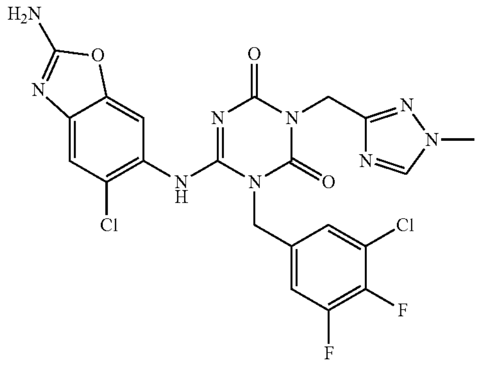 [SMILES: Cn1cnc(Cn2c(=O)nc(Nc3cc4oc(N)nc4cc3Cl)n(Cc3cc(F)c(F)c(Cl)c3)c2=O)n1] | 3 | 1.67 | 550.9 | |
| II-0509 | 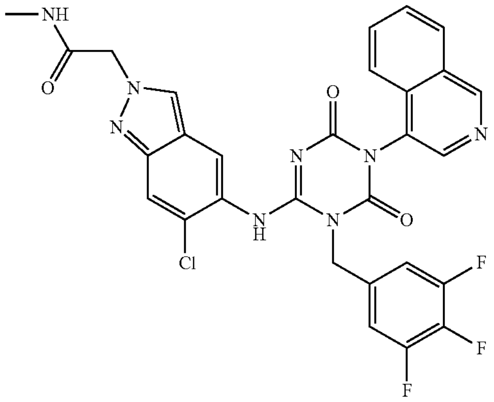 [SMILES: CNC(=O)Cn1cc2cc(Nc3nc(=O)n(-c4cncc5ccccc45)c(=O)n3Cc3cc(F)c(F)c(F)c3)c(Cl)cc2n1] | 1 | 1.92 | 621.2 | |
| II-0510 | 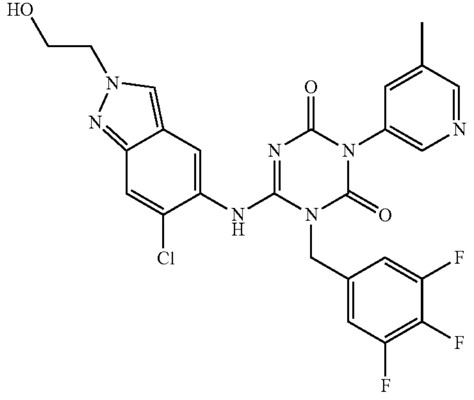 [SMILES: Cc1cncc(-n2c(=O)nc(Nc3cc4cn(CCO)nc4cc3Cl)n(Cc3cc(F)c(F)c(F)c3)c2=O)c1] | 1 | 1.81 | 658.2 | |

TABLE 154-continued
| Compound No. | Structure | LC/MS Measured condition | Retention time (min) | m/z | Con-figuration |
|---|---|---|---|---|---|
| II-0511 | 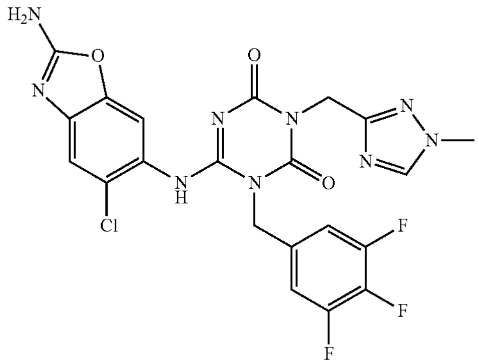 [SMILES: Cn1cnc(Cn2c(=O)nc(Nc3cc4oc(N)nc4cc3Cl)n(Cc3cc(F)c(F)c(F)c3)c2=O)n1] | 1 | 1.73 | 534.1 | |
TABLE 155
| Compound No. | Structure | LC/MS Measured condition | Retention time (min) | m/z | Con-figuration |
|---|---|---|---|---|---|
| II-0512 | 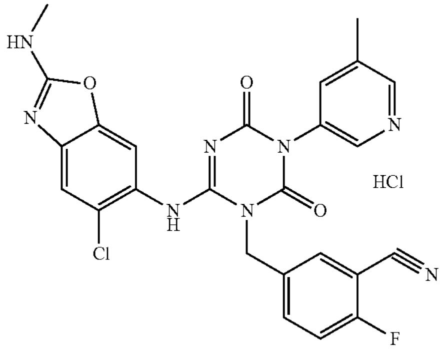 [SMILES: CNc1nc2cc(Cl)c(Nc3nc(=O)n(-c4cncc(C)c4)c(=O)n3Cc3ccc(F)c(C#N)c3)cc2o1 ; Cl] | 1 | 1.77 | 533.1 | |
| II-0513 | 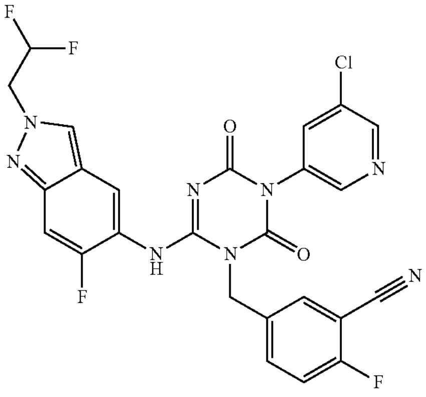 [SMILES: N#Cc1cc(Cn2c(Nc3cc4cn(CC(F)F)nc4cc3F)nc(=O)n(-c3cncc(Cl)c3)c2=O)ccc1F] | 3 | 1.90 | 570.9 | |

TABLE 155-continued
| Compound No. | Structure | LC/MS Measured condition | Retention time (min) | m/z | Con-figuration |
|---|---|---|---|---|---|
| II-0514 | 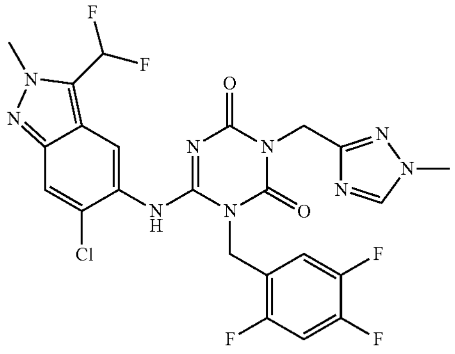 | 1 | 2.05 | 582.2 | |
| II-0515 | 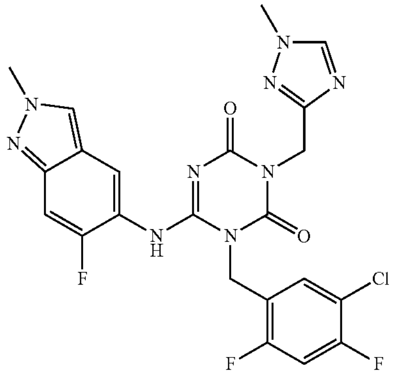 [SMILES: Cn1cnc(Cn2c(=O)nc(Nc3cc4cn(C)nc4cc3F)n(Cc3cc(Cl)c(F)cc3F)c2=O)n1] | 3 | 1.60 | 532.2 | |
| II-0516 | 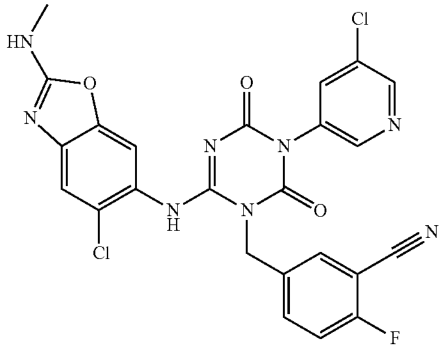 | 3 | 1.83 | 554.6 | |

TABLE 156
| Compound No. | Structure | LC/MS Measured condition | Retention time (min) | m/z | Con-figration |
|---|---|---|---|---|---|
| II-0517 | 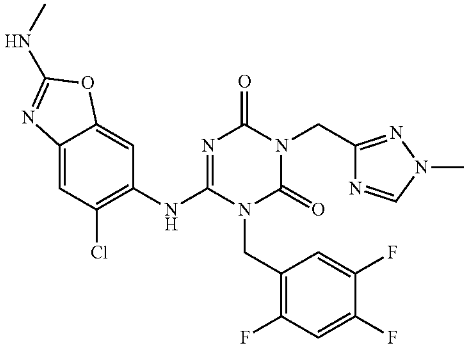 [SMILES: CNc1nc2cc(Cl)c(Nc3nc(=O)n(Cc4ncn(C)n4)c(=O)n3Cc3cc(F)c(F)cc3F)cc2o1] | 3 | 1.62 | 548.1 | |
| II-0518 | 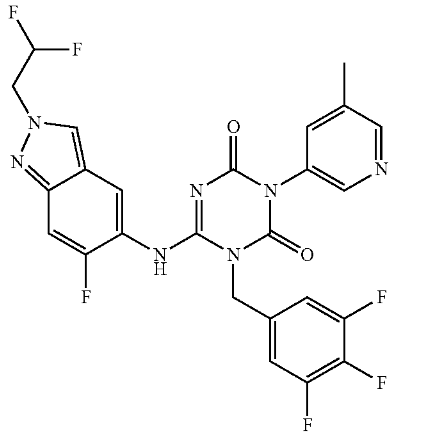 [SMILES: Cc1cncc(-n2c(=O)nc(Nc3cc4cn(CC(F)F)nc4cc3F)n(Cc3cc(F)c(F)c(F)c3)c2=O)c1] | 1 | 2.01 | 562.2 | |
| II-0519 | 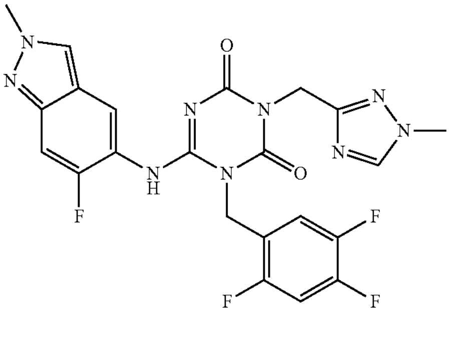 | 3 | 1.51 | 516 | |
| II-0520 | 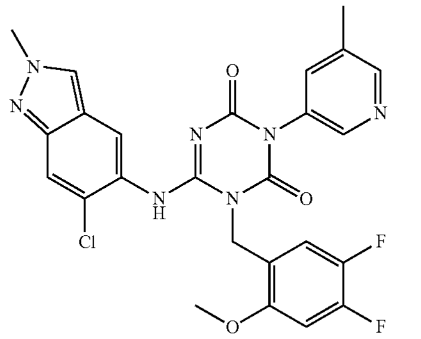 [SMILES: COc1cc(F)c(F)cc1Cn1c(Nc2cc3cn(C)nc3cc2Cl)nc(=O)n(-c2cncc(C)c2)c1=O] | 1 | 1.87 | 540 | |

TABLE 156-continued
| Compound No. | Structure | LC/MS Measured condition | Retention time (min) | m/z | Con-figration |
|---|---|---|---|---|---|
| II-0521 | 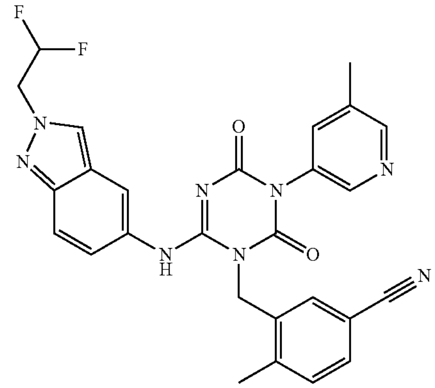 [SMILES: Cc1cncc(-n2c(=O)nc(Nc3ccc4nn(CC(F)F)cc4c3)n(Cc3cc(C#N)ccc3C)c2=O)c1] | 3 | 1.52 | 529 | |
TABLE 157
| Compound No. | Structure | LC/MS Measured condition | Retention time (min) | m/z | Con-figration |
|---|---|---|---|---|---|
| II-0522 | 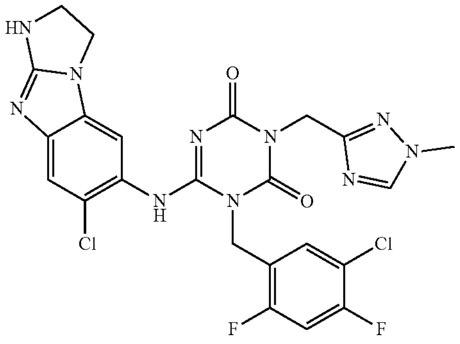 [SMILES: Cn1cnc(Cn2c(=O)nc(Nc3cc4c(cc3Cl)nc3n4CCN3)n(Cc3cc(Cl)c(F)cc3F)c2=O)n1] | 3 | 1.31 | 575 | |
| II-0523 | 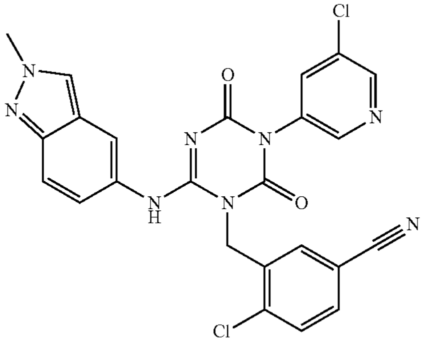 [SMILES: Cn1cc2cc(Nc3nc(=O)n(-c4cncc(Cl)c4)c(=O)n3Cc3cc(C#N)ccc3Cl)ccc2n1] | 3 | 1.69 | 519 | |

TABLE 157-continued
| Compound No. | Structure | LC/MS Measured condition | Retention time (min) | m/z | Con-figration |
|---|---|---|---|---|---|
| II-0524 | 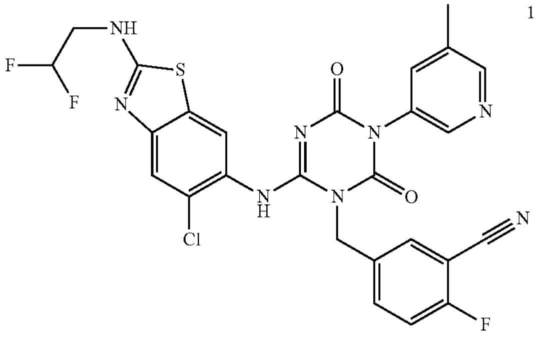 | 1 | 1.91 | 598.9 | |
| II-0525 | 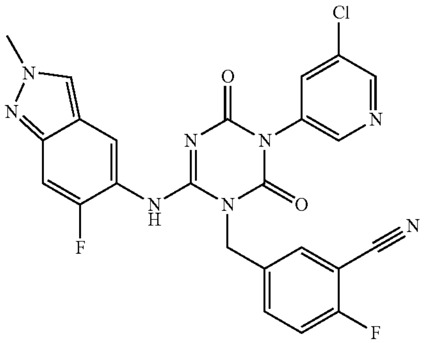 | 3 | 1.74 | 52.1 | |
| II-0526 | 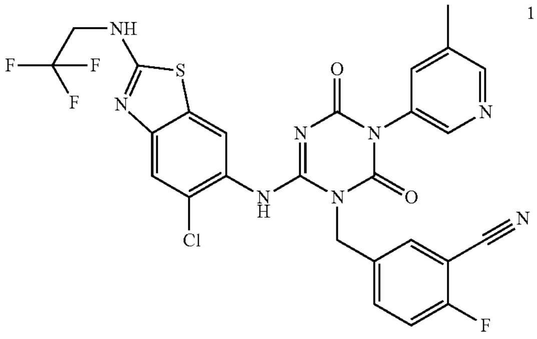 | 1 | 2.03 | 617 | |

TABLE 158
| Compound No. | Structure | LC/MS Measured condition | Retention time (min) | m/z | Con-figration |
|---|---|---|---|---|---|
| II-0527 | 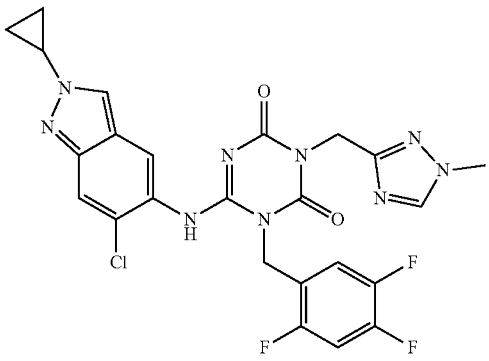 [SMILES: Cn1cnc(Cn2c(=O)nc(Nc3cc4cn(C5CC5)nc4cc3Cl)n(Cc3cc(F)c(F)cc3F)c2=O)n1] | 3 | 1.88 | 558 | |
| II-0528 | 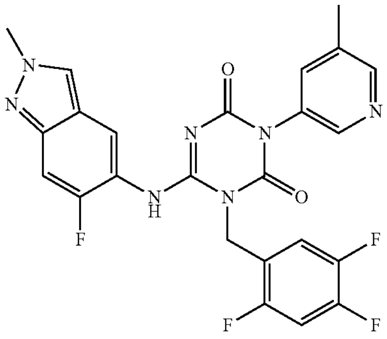 | 3 | 1.64 | 512 | |
| II-0529 | 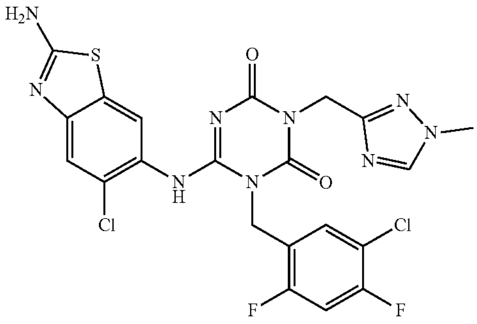 | 1 | 1.82 | 566 | |
| II-0530 | 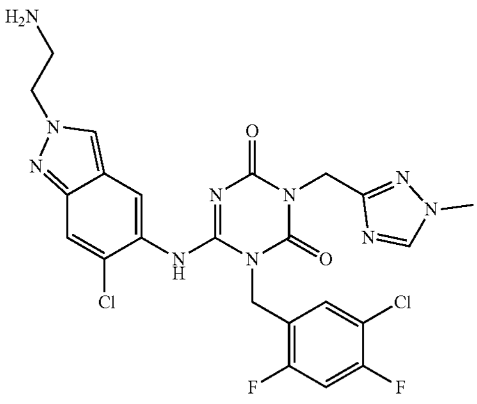 [SMILES: Cn1cnc(Cn2c(=O)nc(Nc3cc4cn(CCN)nc4cc3Cl)n(Cc3cc(Cl)c(F)cc3F)c2=O)n1] | 4 | 1.59 | 577.1 | |

TABLE 158-continued
| Compound No. | Structure | LC/MS Measured condition | Retention time (min) | m/z | Con-figration |
|---|---|---|---|---|---|
| II-0531 | 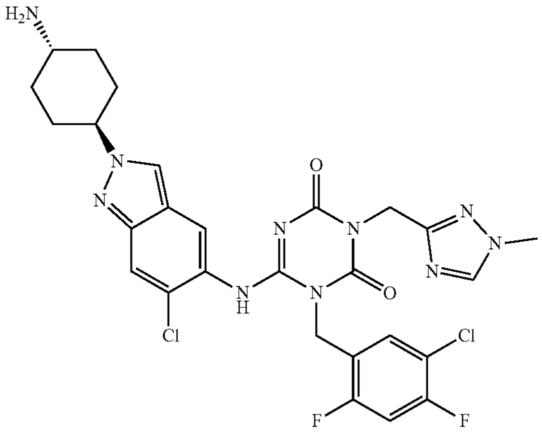 [SMILES: Cn1cnc(Cn2c(=O)nc(Nc3cc4cn([C@H]5CC[C@H](N)CC5)nc4cc3Cl)n(Cc3cc(Cl)c(F)cc3F)c2=O)n1] | 4 | 1.69 | 631.1 | a |
TABLE 159
| Compound No. | Structure | LC/MS Measured condition | Retention time (min) | m/z | Con-figration |
|---|---|---|---|---|---|
| II-0532 | 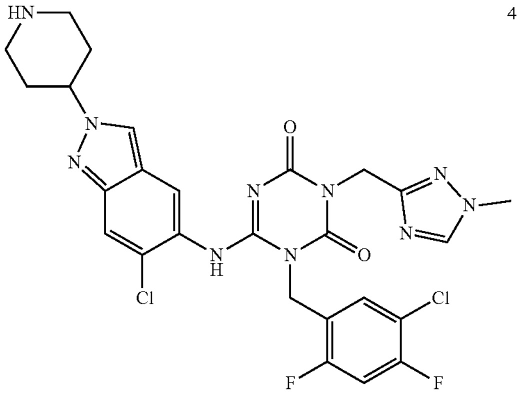 | 4 | 1.67 | 617.1 | |
| II-0533 | 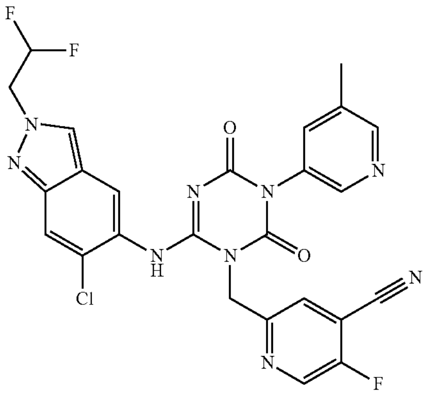 [SMILES: Cc1cncc(-n2c(=O)nc(Nc3cc4cn(CC(F)F)nc4cc3Cl)n(Cc3cc(C#N)c(F)cn3)c2=O)c1] | 1 | 1.86 | 568.1 | |

TABLE 159-continued
| Compound No. | Structure | LC/MS Measured condition | Retention time (min) | m/z | Con-figuration |
|---|---|---|---|---|---|
| II-0534 | 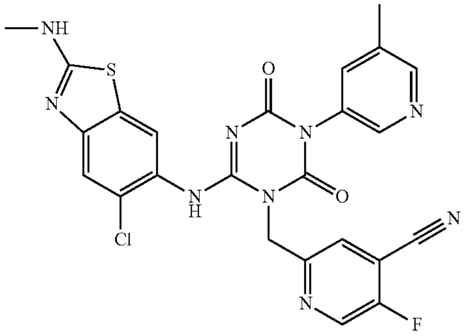 [SMILES: CNc1nc2cc(Cl)c(Nc3nc(=O)n(-c4cncc(C)c4)c(=O)n3Cc3cc(C#N)c(F)cn3)cc2s1] | 1 | 1.68 | 550 | |
| II-0535 | 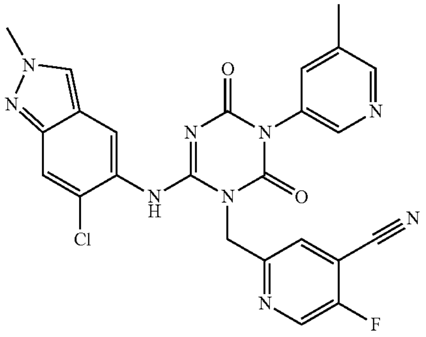 | 1 | 1.68 | 518.1 | |
| II-0536 | 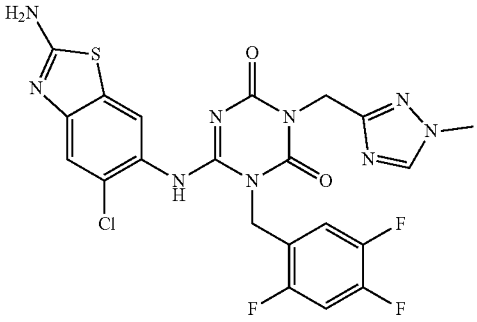 | 1 | 1.68 | 549.1 | |
TABLE 160
| Compound No. | Structure | LC/MS Measured condition | Retention time (min) | m/z | Con-figuration |
|---|---|---|---|---|---|
| II-0537 | 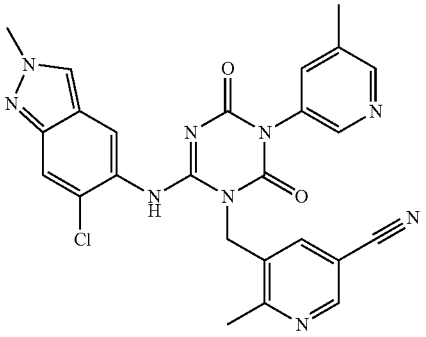 | 1 | 1.56 | 513.1 | |

TABLE 160-continued
| Compound No. | Structure | LC/MS Measured condition | Retention time (min) | m/z | Con-figration |
|---|---|---|---|---|---|
| II-0538 | 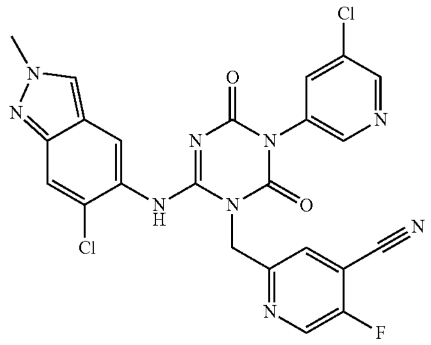 | 1 | 1.86 | 538 | |
| II-0539 | 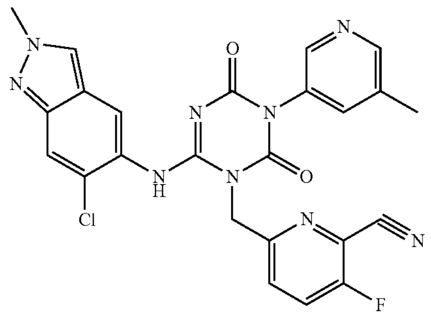 | 4 | 1.64 | 518.1 | |
| II-0540 | 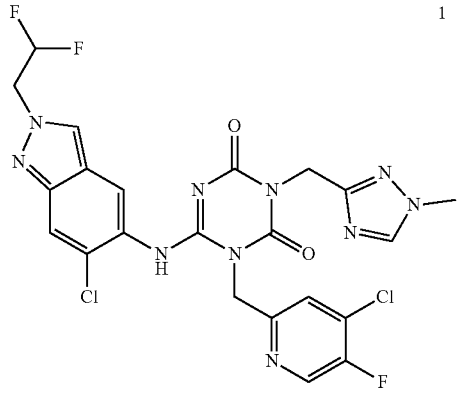 [SMILES: Cn1cnc(Cn2c(=O)nc(Nc3cc4cn(CC(F)F)nc4cc3Cl)n(Cc3cc(Cl)c(F)cn3)c2=O)n1] | 1 | 1.81 | 581 | |
| II-0541 | 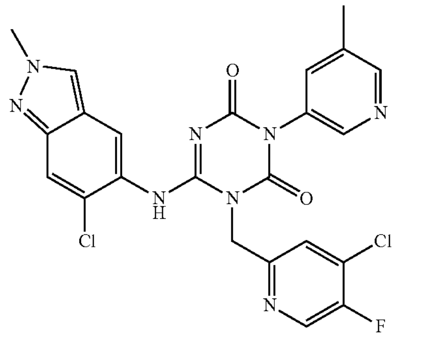 | 1 | 1.78 | 527 | |

TABLE 161
| Compound No. | Structure | LC/MS Measured condition | Retention time (min) | m/z | Con-figration |
|---|---|---|---|---|---|
| II-0542 | 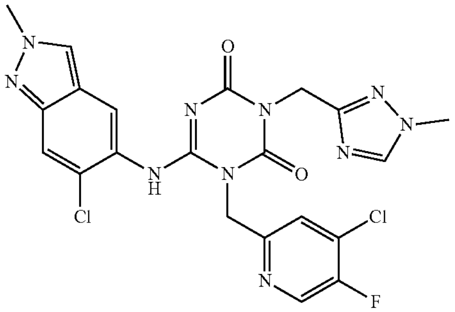 | 1 | 1.63 | 531 | |
| II-0543 | 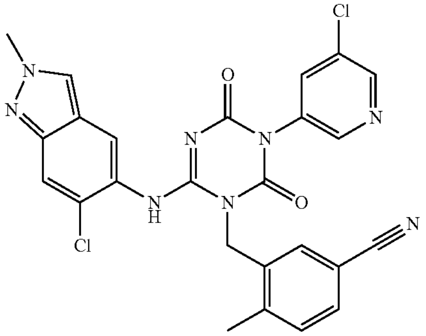 | 1 | 1.92 | 533 | |
| II-0544 | 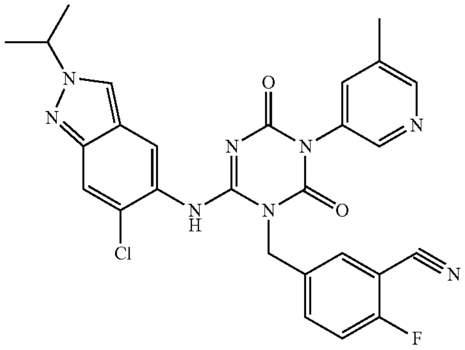 [SMILES: Cc1cncc(-n2c(=O)nc(Nc3cc4cn(C(C)C)nc4cc3Cl)n(Cc3ccc(F)c(C#N)c3)c2=O)c1] | 1 | 1.95 | 545 | |
| II-0545 | 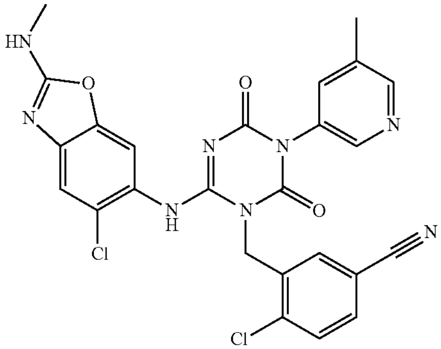 | 3 | 1.80 | 549 | |

TABLE 161-continued
| Compound No. | Structure | LC/MS Measured condition | Retention time (min) | m/z | Con-figration |
|---|---|---|---|---|---|
| II-0546 | 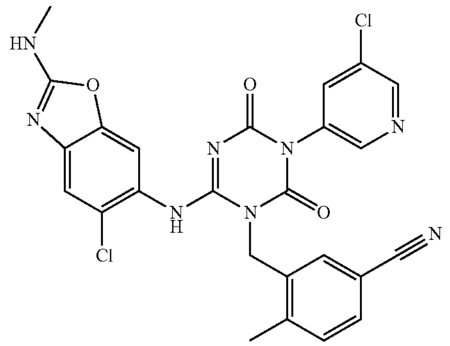 [SMILES: CNc1nc2cc(Cl)c(Nc3nc(=O)n(-c4cncc(Cl)c4)c(=O)n3Cc3cc(C#N)ccc3C)cc2o1] | 3 | 1.93 | 549 | |
TABLE 162
| Compound No. | Structure | LC/MS Measured condition | Retention time (min) | m/z | Con-figration |
|---|---|---|---|---|---|
| II-0547 | 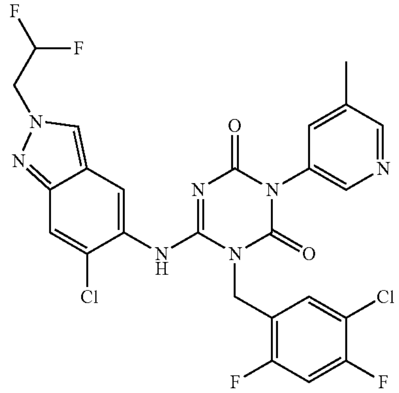 [SMILES: Cc1cncc(-n2c(=O)nc(Nc3cc4cn(CC(F)F)nc4cc3Cl)n(Cc3cc(Cl)c(F)cc3F)c2=O)c1] | 1 | 2.01 | 578 | |
| II-0548 | 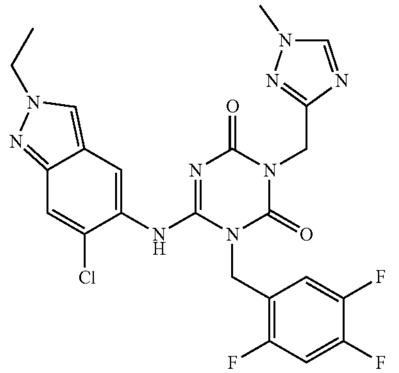 [SMILES: CCn1cc2cc(Nc3nc(=O)n(Cc4ncn(C)n4)c(=O)n3Cc3cc(F)c(F)cc3F)c(Cl)cc2n1] | 1 | 1.86 | 546 | |

TABLE 162-continued
| Compound No. | Structure | LC/MS Measured condition | Retention time (min) | m/z | Con-figration |
|---|---|---|---|---|---|
| II-0549 | 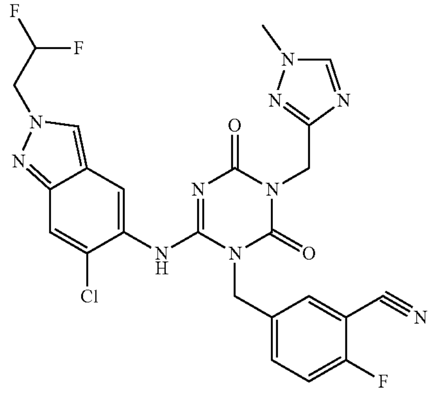 [SMILES: Cn1cnc(Cn2c(=O)nc(Nc3cc4cn(CC(F)F)nc4cc3Cl)n(Cc3ccc(F)c(C#N)c3)c2=O)n1] | 1 | 1.83 | 571 | |
| II-0550 | 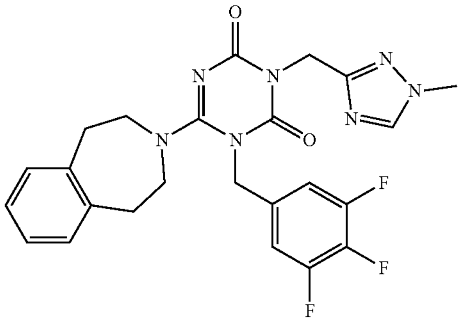 [SMILES: Cn1cnc(Cn2c(=O)nc(N3CCc4ccccc4CC3)n(Cc3cc(F)c(F)c(F)c3)c2=O)n1] | 1 | 2.03 | 498.2 | |
| II-0551 | 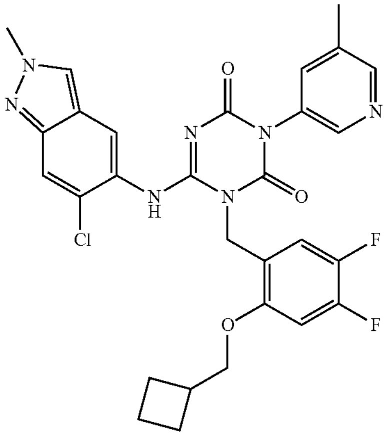 [SMILES: Cc1cncc(-n2c(=O)nc(Nc3cc4cn(C)nc4cc3Cl)n(Cc3cc(F)c(F)cc3OCC3CCC3)c2=O)c1] | 1 | 2.37 | 594.2 | |

TABLE 163
| Compound No. | Structure | LC/MS Measured condition | Retention time (min) | m/z | Con-figration |
|---|---|---|---|---|---|
| II-0552 | 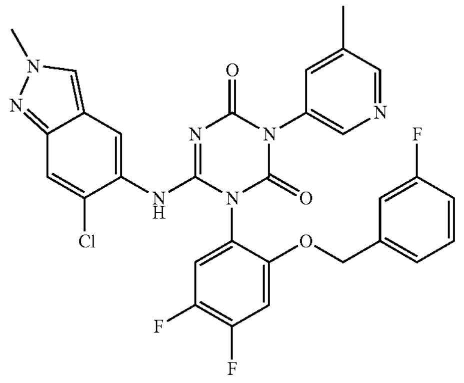 [SMILES: Cc1cncc(-n2c(=O)nc(Nc3cc4cn(C)nc4cc3Cl)n(-c3cc(F)c(F)cc3OCc3cccc(F)c3)c2=O)c1] | 1 | 2.27 | 634.2 | |
| II-0553 | 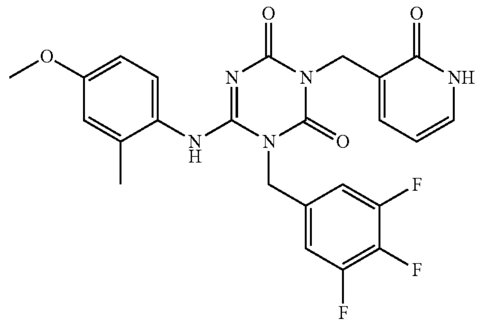 [SMILES: COc1ccc(Nc2nc(=O)n(Cc3ccc[nH]c3=O)c(=O)n2Cc2cc(F)c(F)c(F)c2)c(C)c1] | 1 | 2.21 | 612 | |
| II-0554 | 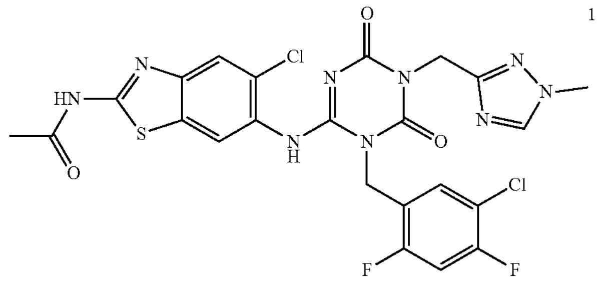 | 1 | 1.87 | 608 | |
| II-0555 | 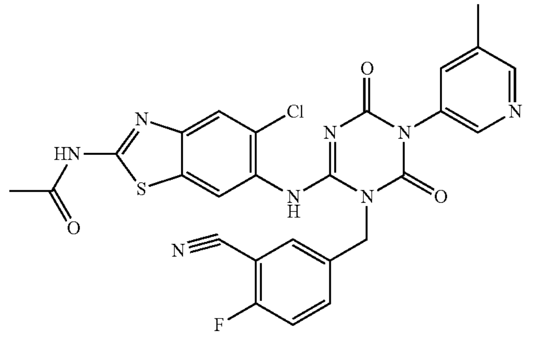 [SMILES: CC(=O)Nc1nc2cc(Cl)c(Nc3nc(=O)n(-c4cncc(C)c4)c(=O)n3Cc3ccc(F)c(C#N)c3)cc2s1] | 1 | 1.80 | 577 | |

TABLE 163-continued
| Compound No. | Structure | LC/MS Measured condition | Retention time (min) | m/z | Con-figration |
|---|---|---|---|---|---|
| II-0556 | 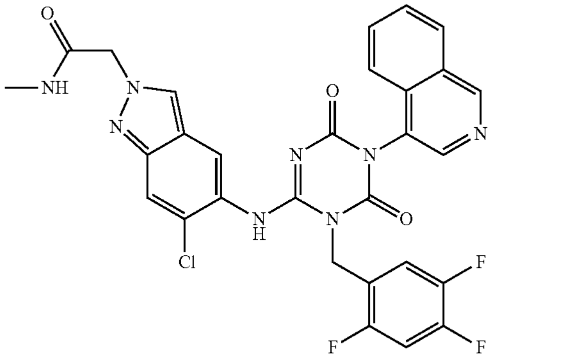 [SMILES: CNC(=O)Cn1cc2cc(Nc3nc(=O)n(-c4cncc5ccccc45)c(=O)n3Cc3cc(F)c(F)cc3F)c(Cl)cc2n1] | 1 | 1.78 | 621 | |
TABLE 164
| Compound No. | Structure | LC/MS Measured condition | Retention time (min) | m/z | Con-figration |
|---|---|---|---|---|---|
| II-0557 | HCl 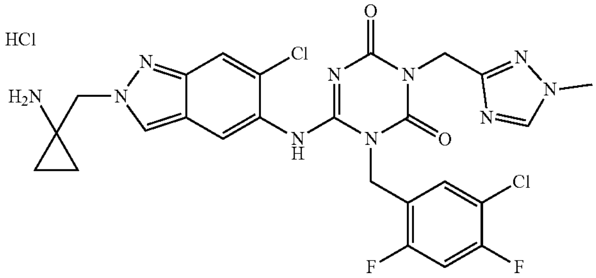 [SMILES: Cl ; Cn1cnc(Cn2c(=O)nc(Nc3cc4cn(CC5(N)CC5)nc4cc3Cl)n(Cc3cc(Cl)c(F)cc3F)c2=O)n1] | 1 | 1.44 | 603 | |
| II-0558 | HCl 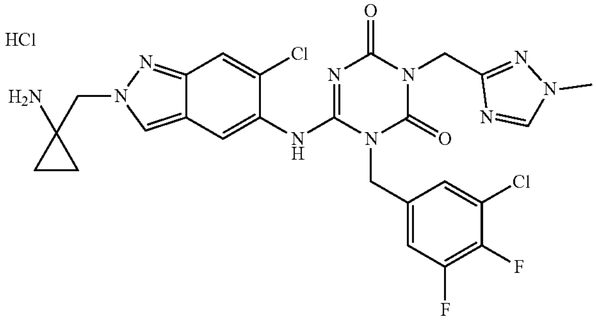 [SMILES: Cl ; Cn1cnc(Cn2c(=O)nc(Nc3cc4cn(CC5(N)CC5)nc4cc3Cl)n(Cc3cc(F)c(F)c(Cl)c3)c2=O)n1] | 1 | 1.50 | 603 | |
| II-0559 | 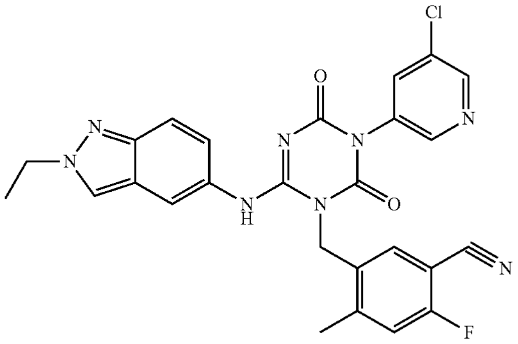 [SMILES: CCn1cc2cc(Nc3nc(=O)n(-c4cncc(Cl)c4)c(=O)n3Cc3cc(C#N)c(F)cc3C)ccc2n1] | 1 | 1.80 | 531 | |

TABLE 164-continued
| Compound No. | Structure | LC/MS Measured condition | Retention time (min) | m/z | Con-figration |
|---|---|---|---|---|---|
| II-0560 | 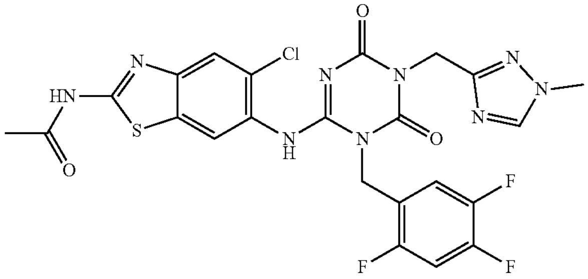 [SMILES: CC(=O)Nc1nc2cc(Cl)c(Nc3nc(=O)n(Cc4ncn(C)n4)c(=O)n3Cc3cc(F)c(F)cc3F)cc2s1] | 1 | 1.79 | 592 | |
| II-0561 | 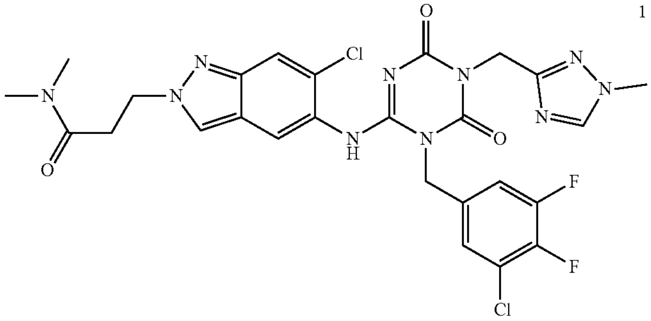 | 1 | 1.78 | 633 | |
TABLE 165
| Compound No. | Structure | LC/MS Measured condition | Retention time (min) | m/z | Con-figration |
|---|---|---|---|---|---|
| II-0562 | 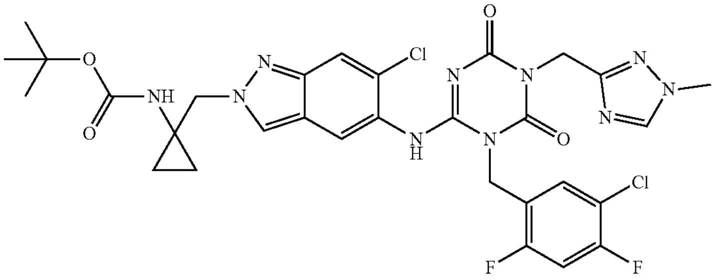 [SMILES: Cn1cnc(Cn2c(=O)nc(Nc3cc4cn(CC5(NC(=O)OC(C)(C)C)CC5)nc4cc3Cl)n(Cc3cc(Cl)c(F)cc3F)c2=O)n1] | 1 | 2.11 | 703 | |
| II-0563 | 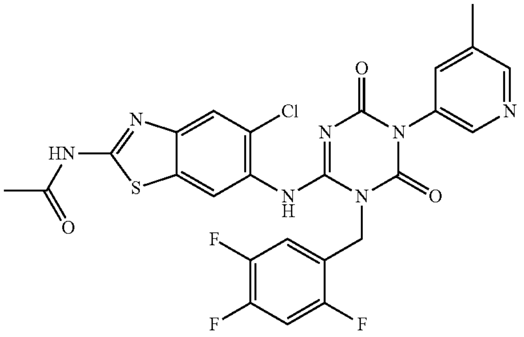 [SMILES: CC(=O)Nc1nc2cc(Cl)c(Nc3nc(=O)n(-c4cncc(C)c4)c(=O)n3Cc3cc(F)c(F)cc3F)cc2s1] | 1 | 1.95 | 588 | |

TABLE 165-continued
| Compound No. | Structure | LC/MS Measured condition | Retention time (min) | m/z | Con-figration |
|---|---|---|---|---|---|
| II-0564 | 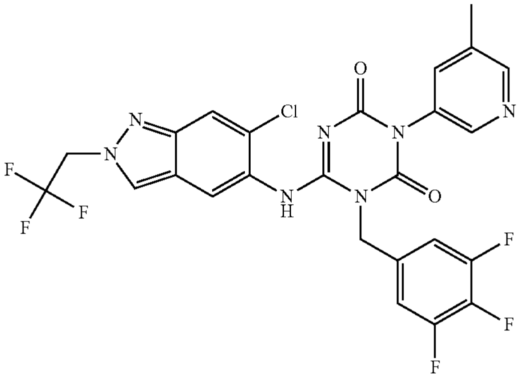 [SMILES: Cc1cncc(-n2c(=O)nc(Nc3cc4cn(CC(F)(F)F)nc4cc3Cl)n(Cc3cc(F)c(F)c(F)c3)c2=O)c1] | 1 | 2.24 | 596 | |
| II-0565 | 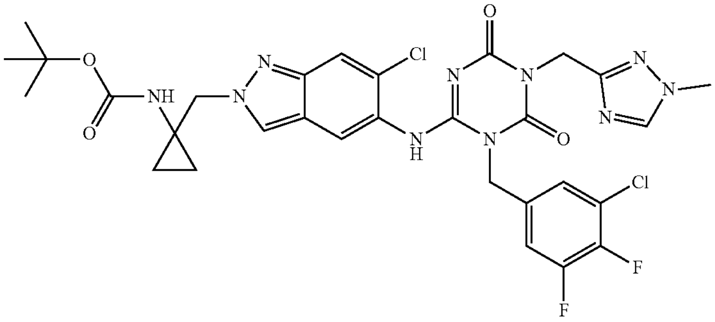 [SMILES: Cn1cnc(Cn2c(=O)nc(Nc3cc4cn(CC5(NC(=O)OC(C)(C)C)CC5)nc4cc3Cl)n(Cc3cc(F)c(F)c(Cl)c3)c2=O)n1] | 1 | 2.18 | 703 | |
| II-0566 | 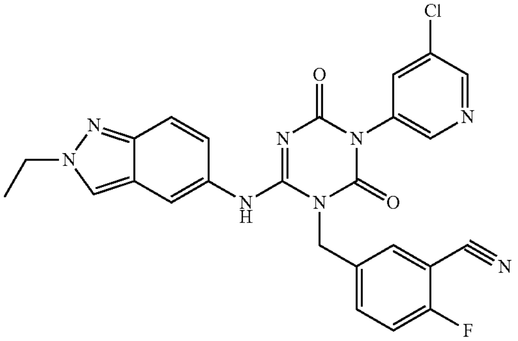 [SMILES: CCn1cc2cc(Nc3nc(=O)n(-c4cncc(Cl)c4)c(=O)n3Cc3ccc(F)c(C#N)c3)ccc2n1] | 1 | 1.73 | 517 | |

TABLE 166
| Compound No. | Structure | LC/MS Measured condition | Retention time (min) | m/z | Con-figration |
|---|---|---|---|---|---|
| II-0567 | 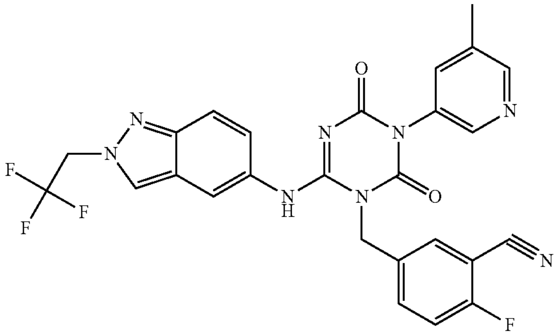 [SMILES: Cc1cncc(-n2c(=O)nc(Nc3ccc4nn(CC(F)(F)F)cc4c3)n(Cc3ccc(F)c(C#N)c3)c2=O)c1] | 1 | 1.68 | 551 | |
| II-0568 | 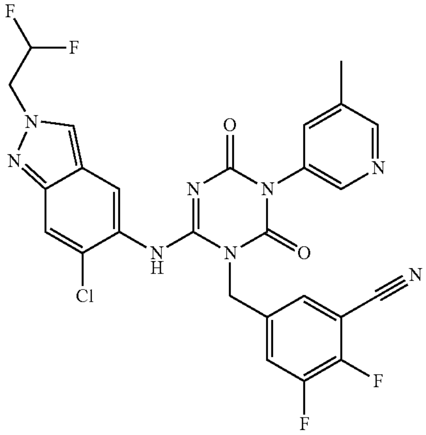 [SMILES: Cc1cncc(-n2c(=O)nc(Nc3cc4cn(CC(F)F)nc4cc3Cl)n(Cc3cc(F)c(F)c(C#N)c3)c2=O)c1] | 1 | 2.05 | 585 | |
| II-0569 | 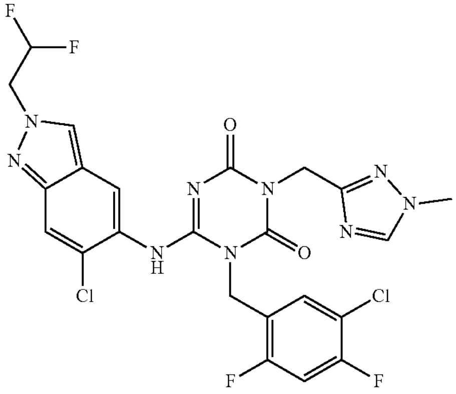 | 3 | 1.89 | 598 | |
| II-0570 | 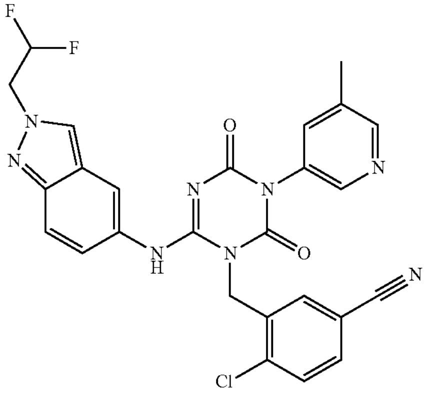 [SMILES: Cc1cncc(-n2c(=O)nc(Nc3ccc4nn(CC(F)F)cc4c3)n(Cc3cc(C#N)ccc3Cl)c2=O)c1] | 1 | 1.74 | 549 | |

TABLE 166-continued
| Compound No. | Structure | LC/MS Measured condition | Retention time (min) | m/z | Con-figration |
|---|---|---|---|---|---|
| II-0571 | 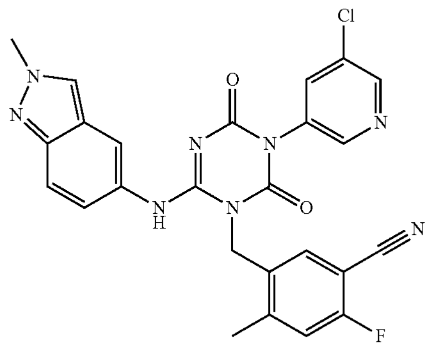 [SMILES: Cc1cc(F)c(C#N)cc1Cn1c(Nc2ccc3nn(C)cc3c2)nc(=O)n(-c2cncc(Cl)c2)c1=O] | 1 | 1.83 | 517 | |
TABLE 167
| Compound No. | Structure | LC/MS Measured condition | Retention time (min) | m/z | Con-figration |
|---|---|---|---|---|---|
| II-0572 | 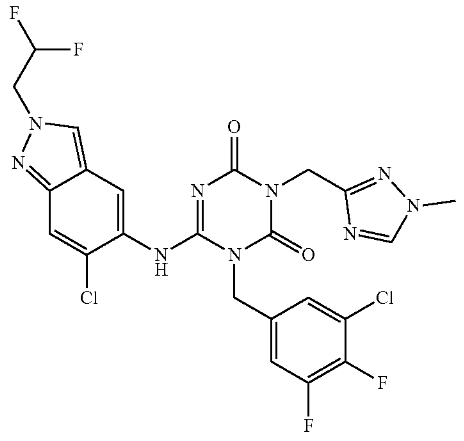 | 1 | 2.07 | 598 | |
| II-0573 | 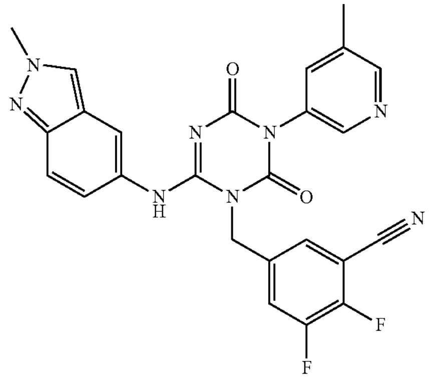 [SMILES: Cc1cncc(-n2c(=O)nc(Nc3ccc4nn(C)cc4c3)n(Cc3cc(F)c(F)c(C#N)c3)c2=O)c1] | 1 | 1.64 | 501 | |

TABLE 167-continued
| Compound No. | Structure | LC/MS Measured condition | Retention time (min) | m/z | Con-figration |
|---|---|---|---|---|---|
| II-0574 | 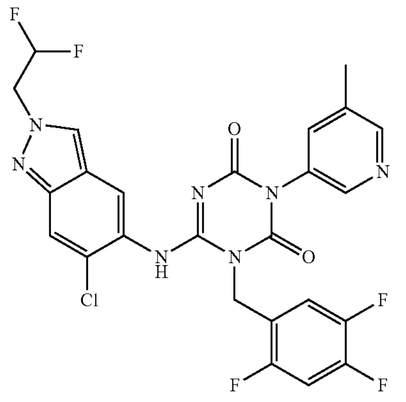 | 3 | 1.95 | 578 | |
| II-0575 | 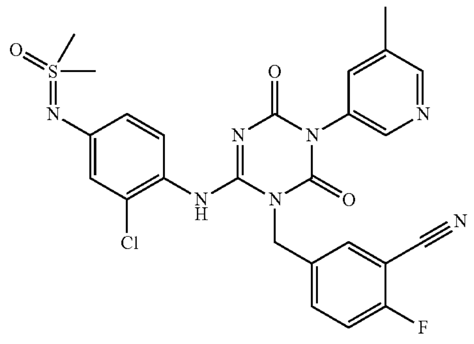 [SMILES: Cc1cncc(-n2c(=O)nc(Nc3ccc(N=S(C)(C)=O)cc3Cl)n(Cc3ccc(F)c(C#N)c3)c2=O)c1] | 3 | 1.54 | 554 | |
| II-0576 | 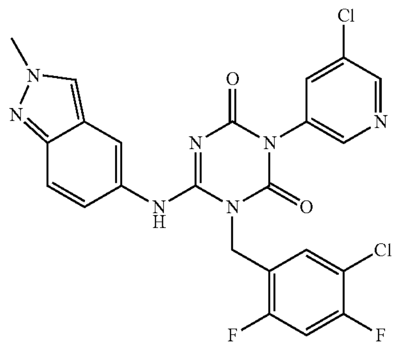 [SMILES: Cn1cc2cc(Nc3nc(=O)n(-c4cncc(Cl)c4)c(=O)n3Cc3cc(Cl)c(F)cc3F)ccc2n1] | 1 | 1.96 | 530 | |

TABLE 168
| Compound No. | Structure | LC/MS Measured condition | Retention time (min) | m/z | Con-figuration |
|---|---|---|---|---|---|
| II-0577 | 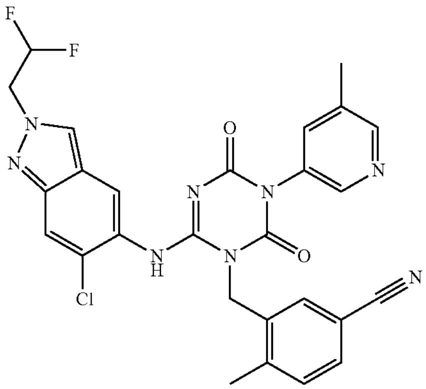 [SMILES: Cc1cncc(-n2c(=O)nc(Nc3cc4cn(CC(F)F)nc4cc3Cl)n(Cc3cc(C#N)ccc3C)c2=O)c1] | 3 | 1.76 | 563 | |
| II-0578 | 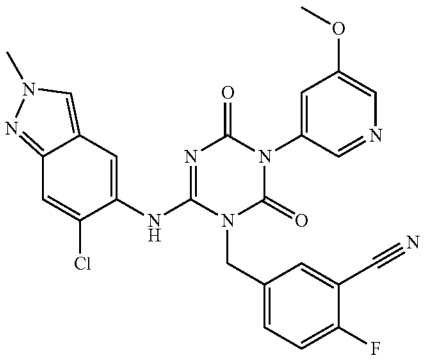 [SMILES: COc1cncc(-n2c(=O)nc(Nc3cc4cn(C)nc4cc3Cl)n(Cc3ccc(F)c(C#N)c3)c2=O)c1] | 3 | 1.83 | 533 | |
| II-0579 | 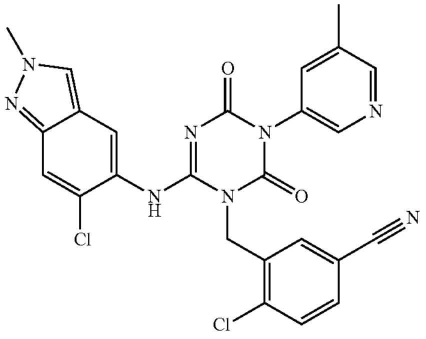 | 1 | 1.91 | 533 | |
| II-0580 | 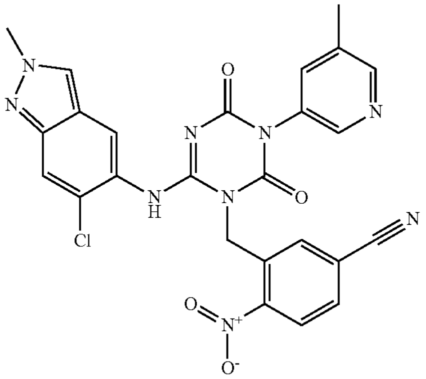 [SMILES: Cc1cncc(-n2c(=O)nc(Nc3cc4cn(C)nc4cc3Cl)n(Cc3cc(C#N)ccc3[N+](=O)[O-])c2=O)c1] | 1 | 1.80 | 544.1 | |

TABLE 168-continued
| Compound No. | Structure | LC/MS Measured condition | Retention time (min) | m/z | Con-figration |
|---|---|---|---|---|---|
| II-0581 | 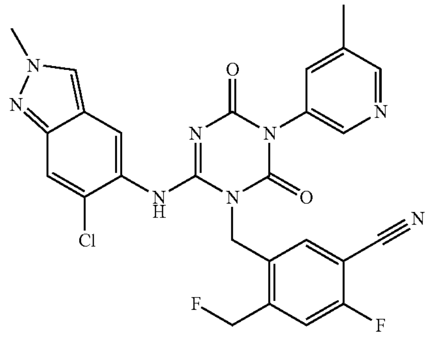 | 1 | 1.89 | 549.1 | |
TABLE 169
| Compound No. | Structure | LC/MS Measured condition | Retention time (min) | m/z | Con-figration |
|---|---|---|---|---|---|
| II-0582 | 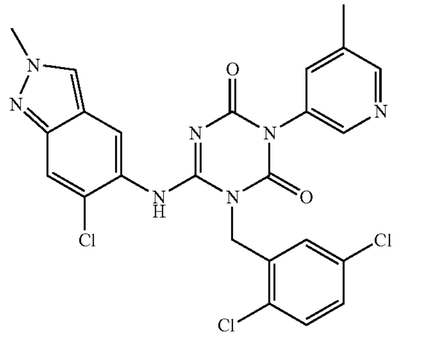 [SMILES: Cc1cncc(-n2c(=O)nc(Nc3cc4cn(C)nc4cc3Cl)n(Cc3cc(Cl)ccc3Cl)c2=O)c1] | 1 | 2.08 | 542 | |
| II-0583 | 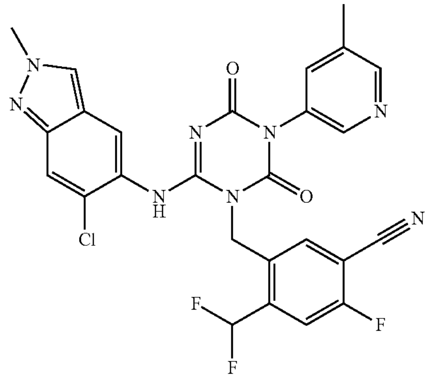 [SMILES: Cc1cncc(-n2c(=O)nc(Nc3cc4cn(C)nc4cc3Cl)n(Cc3cc(C#N)c(F)cc3C(F)F)c2=O)c1] | 1 | 2.03 | 567.1 | |

TABLE 169-continued
| Compound No. | Structure | LC/MS Measured condition | Retention time (min) | m/z | Con-figuration |
|---|---|---|---|---|---|
| II-0584 | 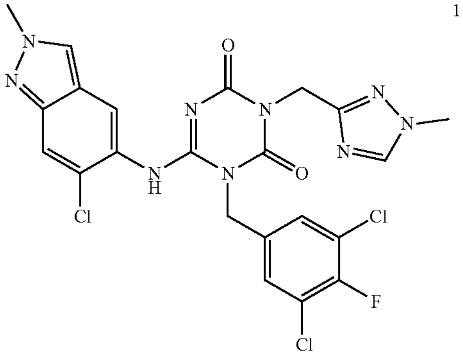 | 1 | 2.07 | 564 | |
| II-0585 | 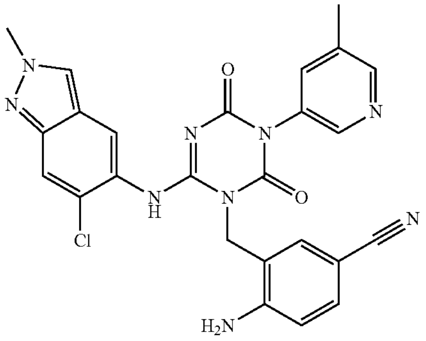 [SMILES: Cc1cncc(-n2c(=O)nc(Nc3cc4cn(C)nc4cc3Cl)n(Cc3cc(C#N)ccc3N)c2=O)c1] | 1 | 1.54 | 514.1 | |
| II-0586 | 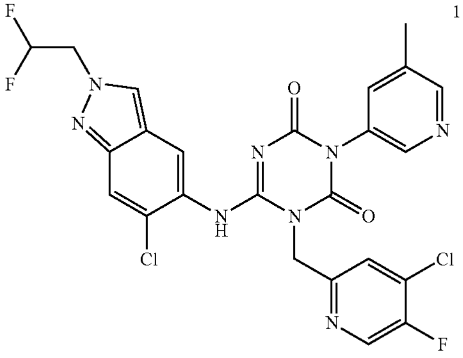 | 1 | 1.97 | 577 | |

TABLE 170
| Compound No. | Structure | LC/MS Measured condition | Retention time (min) | m/z | Con-figration |
|---|---|---|---|---|---|
| II-0587 | 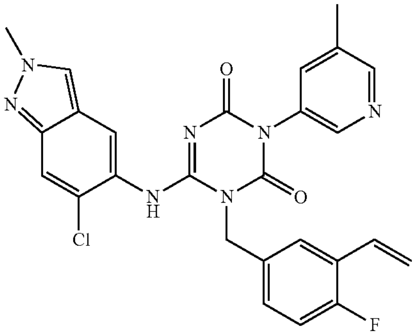 [SMILES: C=Cc1cc(Cn2c(Nc3cc4cn(C)nc4cc3Cl)nc(=O)n(-c3cncc(C)c3)c2=O)ccc1F] | 1 | 2.03 | 518.1 | |
| II-0588 | 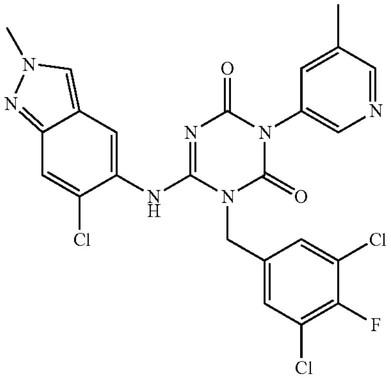 | 1 | 2.23 | 560 | |
| II-0589 | 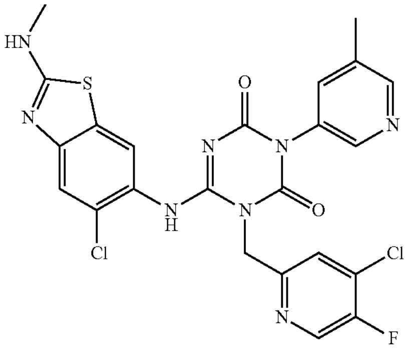 [SMILES: CNc1nc2cc(Cl)c(Nc3nc(=O)n(-c4cncc(C)c4)c(=O)n3Cc3cc(Cl)c(F)cn3)cc2s1] | 1 | 1.75 | 559 | |
| II-0590 | 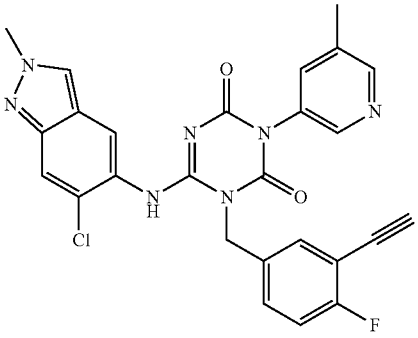 [SMILES: C#Cc1cc(Cn2c(Nc3cc4cn(C)nc4cc3Cl)nc(=O)n(-c3cncc(C)c3)c2=O)ccc1F] | 1 | 1.91 | 516.1 | |

TABLE 170-continued
| Compound No. | Structure | LC/MS Measured condition | Retention time (min) | m/z | Con-figration |
|---|---|---|---|---|---|
| II-0591 | 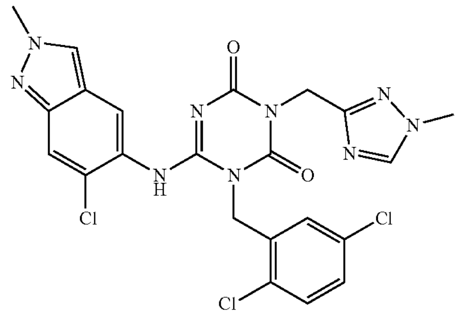 | 1 | 1.95 | 546 | |
TABLE 171
| Compound No. | Structure | LC/MS Measured condition | Retention time (min) | m/z | Con-figration |
|---|---|---|---|---|---|
| II-0592 | 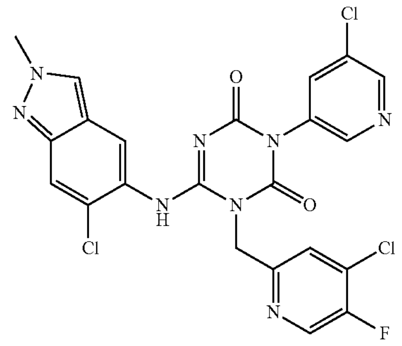 [SMILES: Cn1cc2cc(Nc3nc(=O)n(-c4cncc(Cl)c4)c(=O)n3Cc3cc(Cl)c(F)cn3)c(Cl)cc2n1] | 1 | 2.00 | 547 | |
| II-0593 | 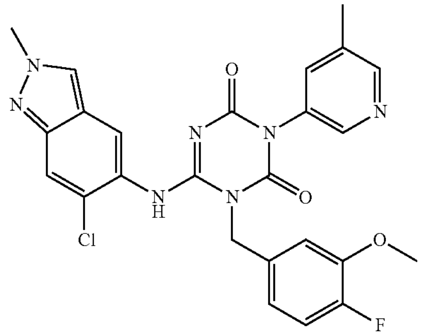 | 3 | 1.82 | 522.1 | |
| II-0594 | 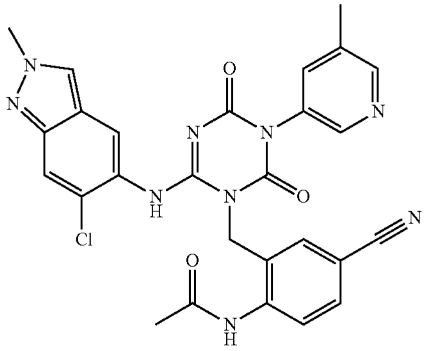 [SMILES: CC(=O)Nc1ccc(C#N)cc1Cn1c(Nc2cc3cn(C)nc3cc2Cl)nc(=O)n(-c2cncc(C)c2)c1=O] | 1 | 1.55 | 556.1 | |

TABLE 171-continued
| Compound No. | Structure | LC/MS Measured condition | Retention time (min) | m/z | Con-figration |
|---|---|---|---|---|---|
| II-0595 | 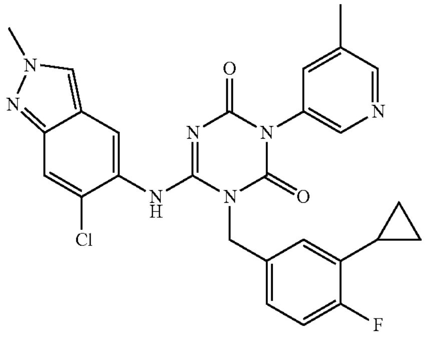 [SMILES: Cc1cncc(-n2c(=O)nc(Nc3cc4cn(C)nc4cc3Cl)n(Cc3ccc(F)c(C4CC4)c3)c2=O)c1] | 1 | 2.09 | 532.1 | |
| II-0596 | 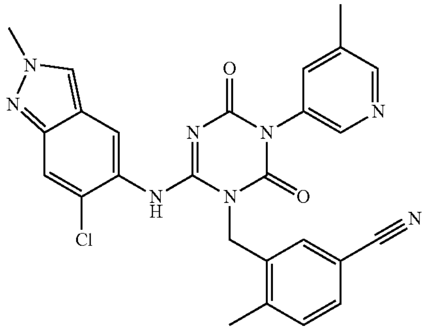 | 1 | 1.78 | 513.1 | |
TABLE 172
| Compound No. | Structure | LC/MS Measured condition | Retention time (min) | m/z | Con-figration |
|---|---|---|---|---|---|
| II-0597 | 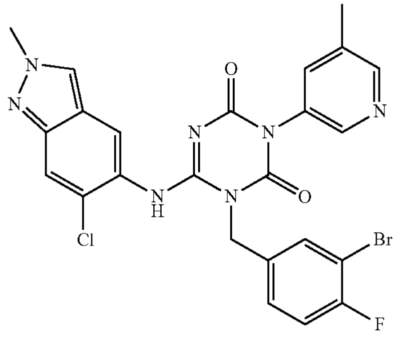 [SMILES: Cc1cncc(-n2c(=O)nc(Nc3cc4cn(C)nc4cc3Cl)n(Cc3ccc(F)c(Br)c3)c2=O)c1] | 1 | 2.04 | 570 | |

TABLE 172-continued
| Compound No. | Structure | LC/MS Measured condition | Retention time (min) | m/z | Con-figration |
|---|---|---|---|---|---|
| II-0598 | 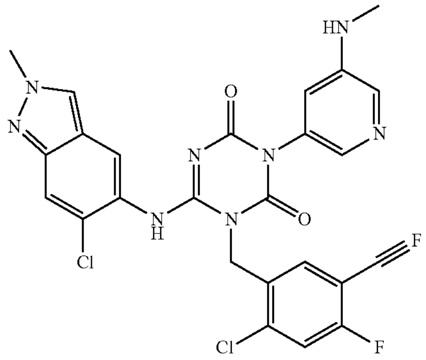 | 1 | 1.51 | 566 | |
| II-0599 | 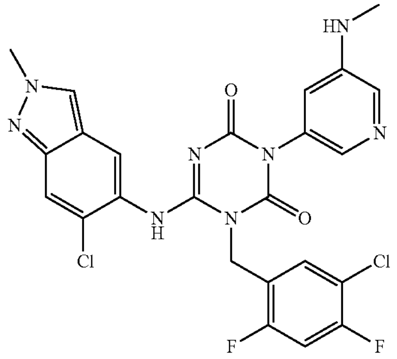 [SMILES: CNc1cncc(-n2c(=O)nc(Nc3cc4cn(C)nc4cc3Cl)n(Cc3cc(Cl)c(F)cc3F)c2=O)c1] | 1 | 1.54 | 559 | |
| II-0600 | 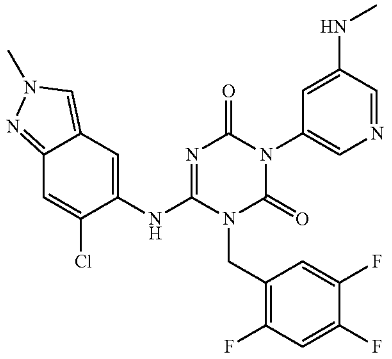 [SMILES: CNc1cncc(-n2c(=O)nc(Nc3cc4cn(C)nc4cc3Cl)n(Cc3cc(F)c(F)cc3F)c2=O)c1] | 1 | 1.46 | 542 | |
| II-0601 | 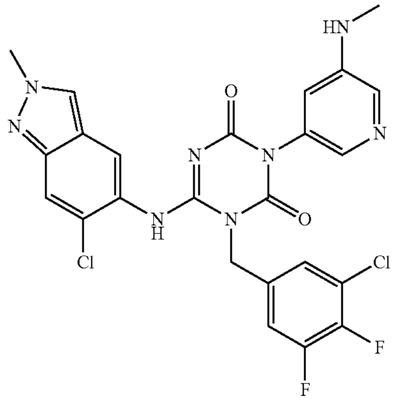 [SMILES: CNc1cncc(-n2c(=O)nc(Nc3cc4cn(C)nc4cc3Cl)n(Cc3cc(F)c(F)c(Cl)c3)c2=O)c1] | 1 | 1.62 | 559 | |

TABLE 173
| Compound No. | Structure | LC/MS Measured condition | Retention time (min) | m/z | Con-figration |
|---|---|---|---|---|---|
| II-0602 | 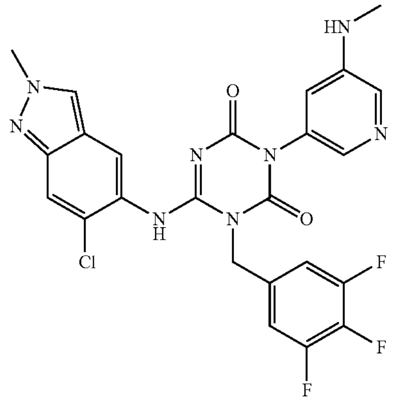 [SMILES: CNc1cncc(-n2c(=O)nc(Nc3cc4cn(C)nc4cc3Cl)n(Cc3cc(F)c(F)c(F)c3)c2=O)c1] | 1 | 1.52 | 543 | |
| II-0603 | 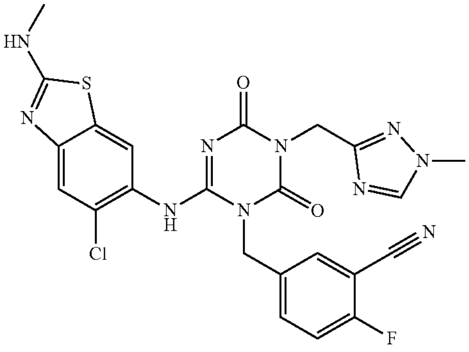 [SMILES: CNc1nc2cc(Cl)c(Nc3nc(=O)n(Cc4ncn(C)n4)c(=O)n3Cc3ccc(F)c(C#N)c3)cc2s1] | 3 | 1.51 | 552 | |
| II-0604 | 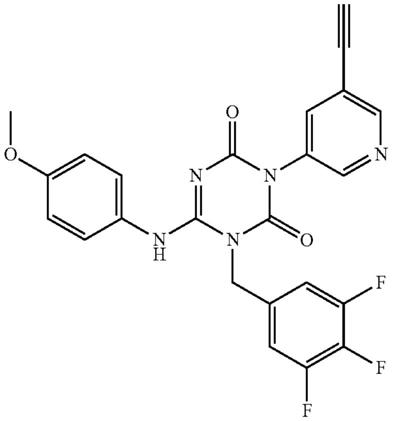 [SMILES: C#Cc1cncc(-n2c(=O)nc(Nc3ccc(OC)cc3)n(Cc3cc(F)c(F)c(F)c3)c2=O)c1] | 3 | 2.08 | 480 | |
| II-0605 | 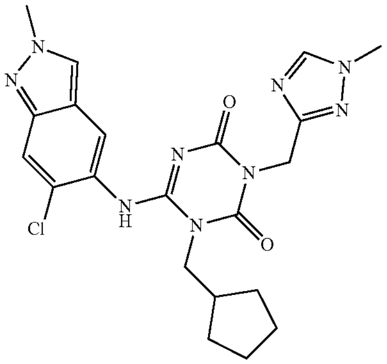 [SMILES: Cn1cnc(Cn2c(=O)nc(Nc3cc4cn(C)nc4cc3Cl)n(CC3CCCC3)c2=O)n1] | 1 | 1.69 | 470 | |

TABLE 173-continued
| Compound No. | Structure | LC/MS Measured condition | Retention time (min) | m/z | Con-figration |
|---|---|---|---|---|---|
| II-0606 | 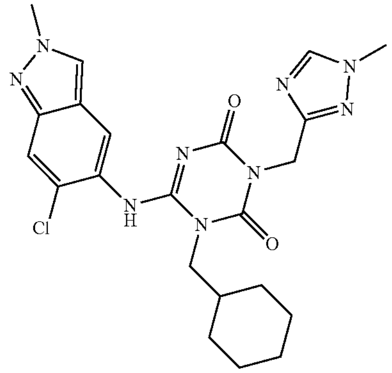 [SMILES: Cn1cnc(Cn2c(=O)nc(Nc3cc4cn(C)nc4cc3Cl)n(CC3CCCCC3)c2=O)n1] | 1 | 1.81 | 484.1 | |
TABLE 174
| Compound No. | Structure | LC/MS Measured condition | Retention time (min) | m/z | Con-figration |
|---|---|---|---|---|---|
| II-0607 | 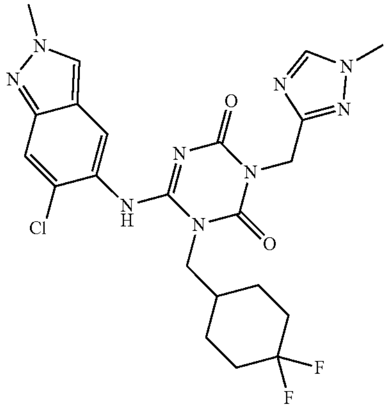 [SMILES: Cn1cnc(Cn2c(=O)nc(Nc3cc4cn(C)nc4cc3Cl)n(CC3CCC(F)(F)CC3)c2=O)n1] | 1 | 1.71 | 520 | |
TABLE 175
| Compound No. | Structure | LC/MS Mesured condition | Retention time (min) | m/z | Con-figration |
|---|---|---|---|---|---|
| II-0608 | 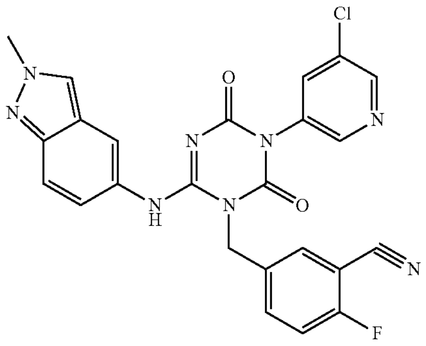 [SMILES: Cn1cc2cc(Nc3nc(=O)n(-c4cncc(Cl)c4)c(=O)n3Cc3ccc(F)c(C#N)c3)ccc2n1] | 3 | 1.65 | 503 | |

TABLE 175-continued
| Compound No. | Structure | LC/MS Mesured condition | Retention time (min) | m/z | Con-figuration |
|---|---|---|---|---|---|
| II-0609 | 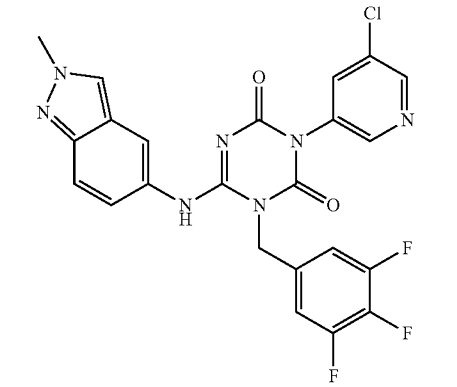 [SMILES: Cn1cc2cc(Nc3nc(=O)n(-c4cncc(Cl)c4)c(=O)n3Cc3cc(F)c(F)c(F)c3)ccc2n1] | 1 | 1.84 | 514.3 | |
| II-0610 | 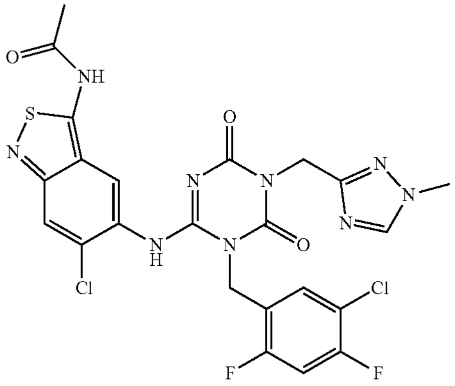 [SMILES: CC(=O)Nc1snc2cc(Cl)c(Nc3nc(=O)n(Cc4ncn(C)n4)c(=O)n3Cc3cc(Cl)c(F)cc3F)cc12] | 3 | 1.86 | 608.2 | |
| II-0611 | 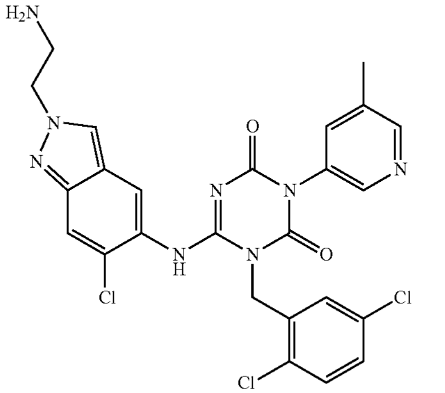 [SMILES: Cc1cncc(-n2c(=O)nc(Nc3cc4cn(CCN)nc4cc3Cl)n(Cc3cc(Cl)ccc3Cl)c2=O)c1] | 1 | 1.58 | 571 | |
| II-0612 | 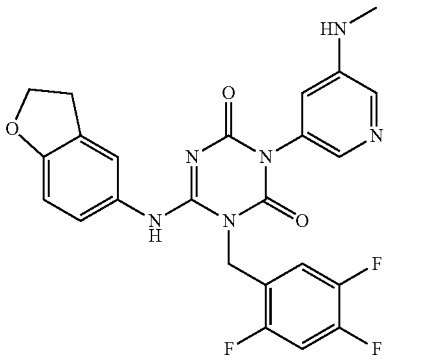 [SMILES: CNc1cncc(-n2c(=O)nc(Nc3ccc4c(c3)CCO4)n(Cc3cc(F)c(F)cc3F)c2=O)c1] | 3 | 1.55 | 497 | |

TABLE 176
| | | | | |
|---|---|---|---|---|
| II-0613 | 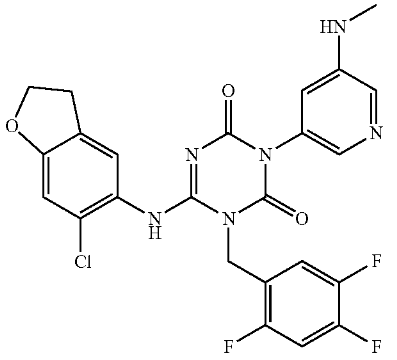 [SMILES: CNc1cncc(-n2c(=O)nc(Nc3cc4c(cc3Cl)OCC4)n(Cc3cc(F)c(F)cc3F)c2=O)c1] | 3 | 1.79 | 531 |
| II-0614 | 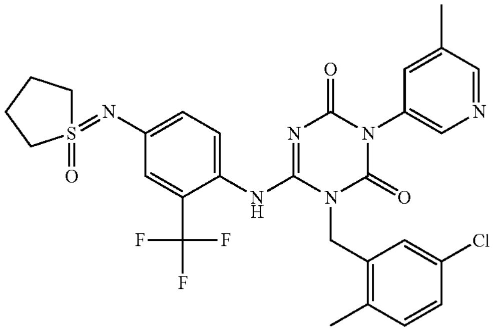 [SMILES: Cc1cncc(-n2c(=O)nc(Nc3ccc(N=S4(=O)CCCC4)cc3C(F)(F)F)n(Cc3cc(Cl)ccc3C)c2=O)c1] | 1 | 2.14 | 619.2 |
| II-0615 | 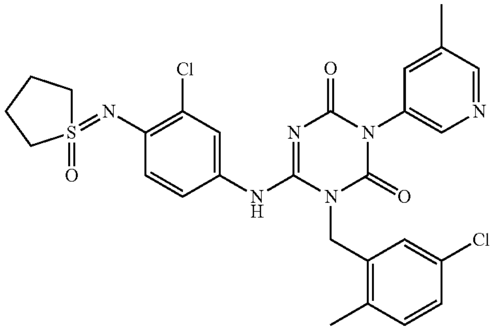 [SMILES: Cc1cncc(-n2c(=O)nc(Nc3ccc(N=S4(=O)CCCC4)c(Cl)c3)n(Cc3cc(Cl)ccc3C)c2=O)c1] | 1 | 1.92 | 585.2 |
| II-0616 | 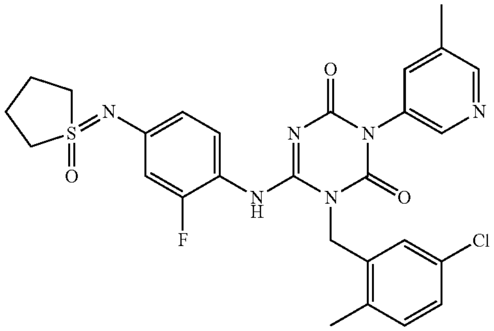 [SMILES: Cc1cncc(-n2c(=O)nc(Nc3ccc(N=S4(=O)CCCC4)cc3F)n(Cc3cc(Cl)ccc3C)c2=O)c1] | 1 | 1.82 | 569.2 |

TABLE 176-continued
| | | | | |
|---|---|---|---|---|
| II-0617 | 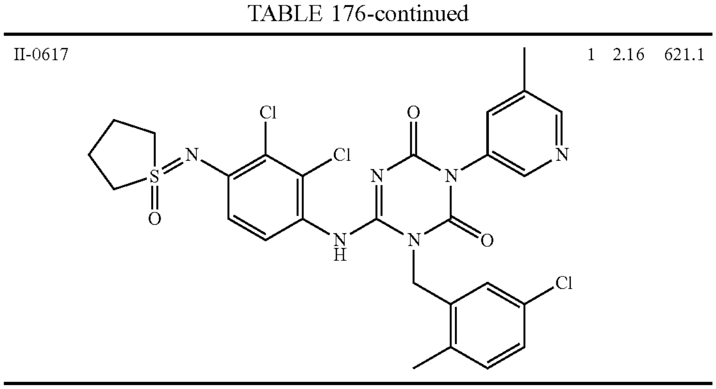 | 1 | 2.16 | 621.1 |
TABLE 177
| | | | | |
|---|---|---|---|---|
| II-0618 | 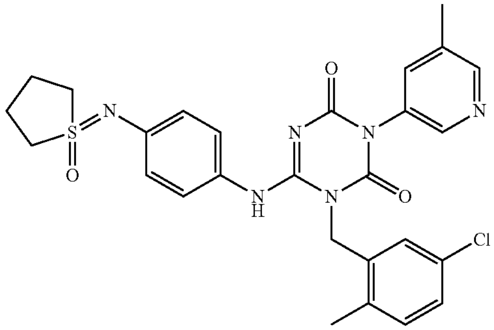 [SMILES: Cc1cncc(-n2c(=O)nc(Nc3ccc(N=S4(=O)CCCC4)cc3)n(Cc3cc(Cl)ccc3C)c2=O)c1] | 1 | 1.71 | 551.2 |
| II-0619 | 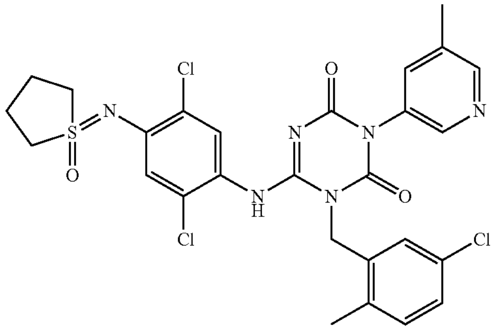 [SMILES: Cc1cncc(-n2c(=O)nc(Nc3cc(Cl)c(N=S4(=O)CCCC4)cc3Cl)n(Cc3cc(Cl)ccc3C)c2=O)c1] | 1 | 2.17 | 621.1 |
| II-0620 | 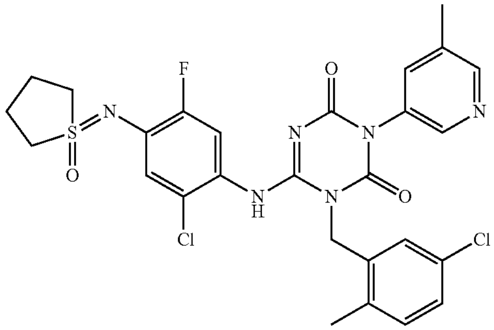 [SMILES: Cc1cncc(-n2c(=O)nc(Nc3cc(F)c(N=S4(=O)CCCC4)cc3Cl)n(Cc3cc(Cl)ccc3C)c2=O)c1] | 1 | 2.06 | 603.1 |

TABLE 177-continued
| | | | | |
|---|---|---|---|---|
| II-0621 | 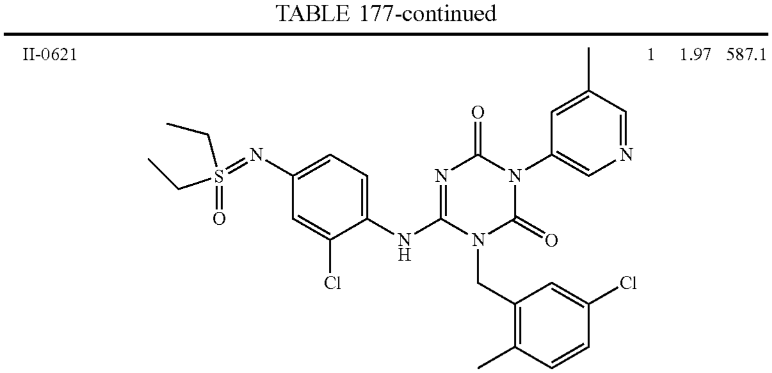 | 1 | 1.97 | 587.1 |
| II-0622 | 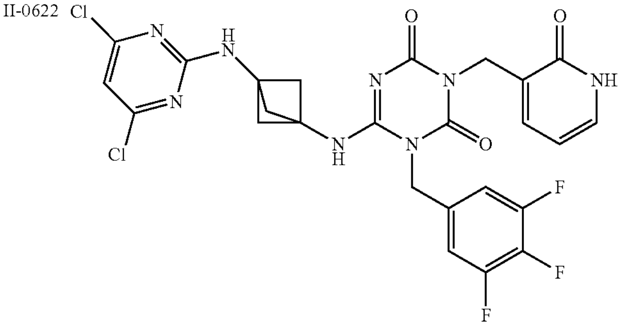 | 1 | 2.15 | 607.1 |
TABLE 178
| | | | | |
|---|---|---|---|---|
| II-0623 | 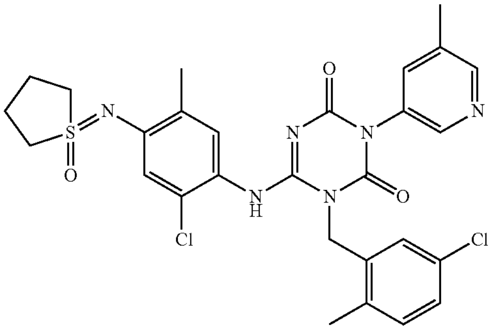 [SMILES: Cc1cncc(-n2c(=O)nc(Nc3cc(C)c(N=S4(=O)CCCC4)cc3Cl)n(Cc3cc(Cl)ccc3C)c2=O)c1] | 1 | 2.03 | 599.2 |
| II-0624 | 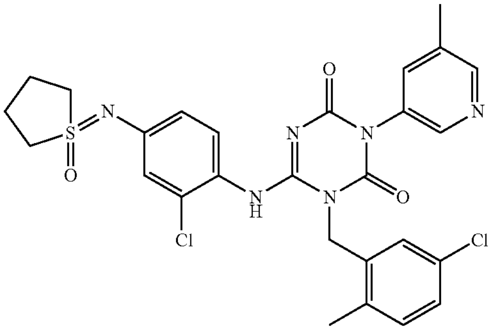 [SMILES: Cc1cncc(-n2c(=O)nc(Nc3ccc(N=S4(=O)CCCC4)cc3Cl)n(Cc3cc(Cl)ccc3C)c2=O)c1] | 1 | 1.93 | 585.2 |

TABLE 178-continued
| | | | | | |
|---|---|---|---|---|---|
| II-0625 | 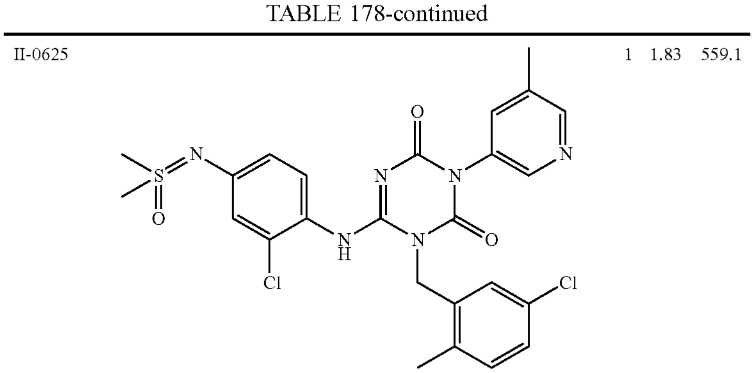 | 1 | 1.83 | 559.1 | |
| II-0626 | 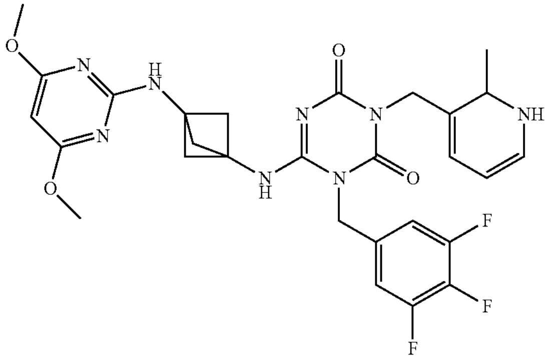 [SMILES: COc1cc(OC)nc(NC23CC(Nc4nc(=O)n(CC5=CC=CNC5C)c(=O)n4Cc4cc(F)c(F)c(F)c4)(C2)C3)n1] | 1 | 1.91 | 599.3 | |
| II-0627 | 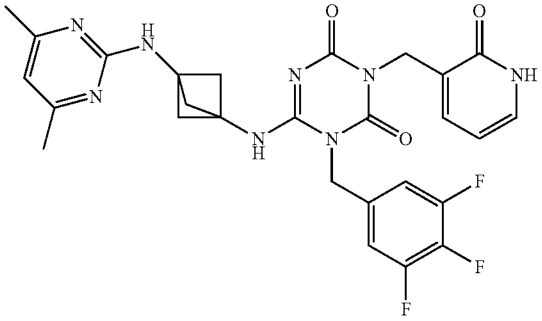 [SMILES: Cc1cc(C)nc(NC23CC(Nc4nc(=O)n(Cc5ccc[nH]c5=O)c(=O)n4Cc4cc(F)c(F)c(F)c4)(C2)C3)n1] | 1 | 1.54 | 567.3 | |
TABLE 179
| | | | | | |
|---|---|---|---|---|---|
| II-0628 | 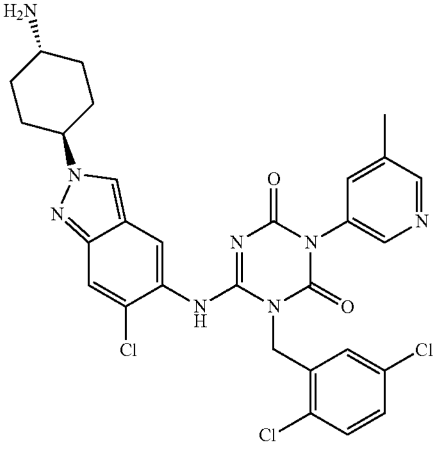 [SMILES: Cc1cncc(-n2c(=O)nc(Nc3cc4cn([C@H]5CC[C@H](N)CC5)nc4cc3Cl)n(Cc3cc(Cl)ccc3Cl)c2=O)c1] | 1 | 1.65 | 625.2 | a |

TABLE 179-continued
| | | | | |
|---|---|---|---|---|
| II-0629 | 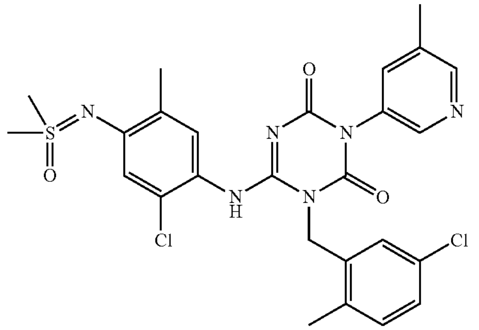 [SMILES: Cc1cncc(-n2c(=O)nc(Nc3cc(C)c(N=S(C)(C)=O)cc3Cl)n(Cc3cc(Cl)ccc3C)c2=O)c1] | 1 | 1.90 | 573.1 |
| II-0630 | 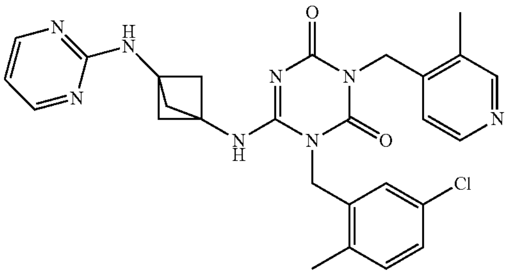 [SMILES: Cc1ccc(Cl)cc1Cn1c(NC23CC(Nc4ncccn4)(C2)C3)nc(=O)n(Cc2ccncc2C)c1=O] | 1 | 1.76 | 517.2 |
| II-0631 | 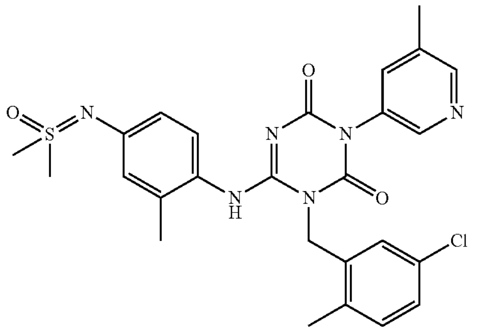 [SMILES: Cc1cncc(-n2c(=O)nc(Nc3ccc(N=S(C)(C)=O)cc3C)n(Cc3cc(Cl)ccc3C)c2=O)c1] | 1 | 1.68 | 539.2 |
| II-0632 | 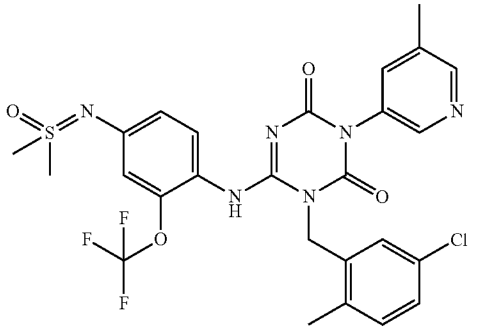 [SMILES: Cc1cncc(-n2c(=O)nc(Nc3ccc(N=S(C)(C)=O)cc3OC(F)(F)F)n(Cc3cc(Cl)ccc3C)c2=O)c1] | 1 | 2.00 | 609.1 |

TABLE 180
| | | | | |
|---|---|---|---|---|
| II-0633 | 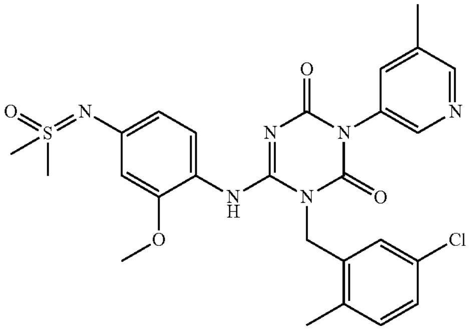 [SMILES: COc1cc(N=S(C)(C)=O)ccc1Nc1nc(=O)n(-c2cncc(C)c2)c(=O)n1Cc1cc(Cl)ccc1C] | 1 | 1.67 | 555.2 |
| II-0634 | 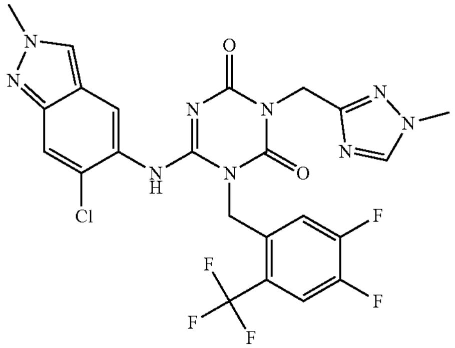 | 1 | 2.13 | 582.1 |
| II-0635 | 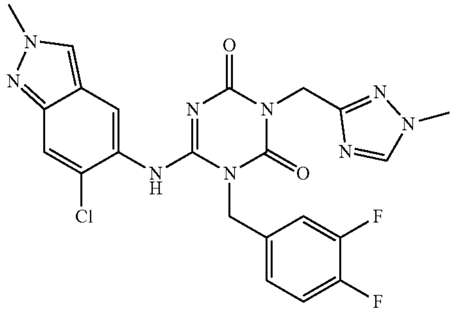 | 1 | 1.87 | 514 |
| II-0636 | 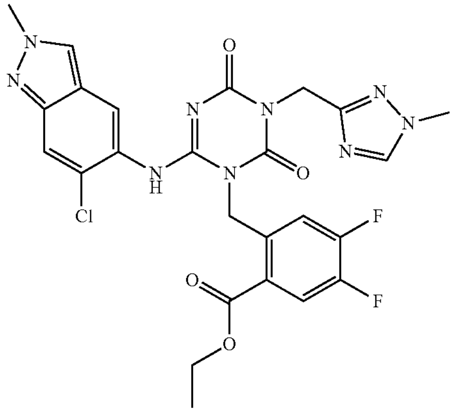 | 1 | 2.03 | 586.1 |

TABLE 180-continued
| | | | | |
|---|---|---|---|---|
| II-0637 | 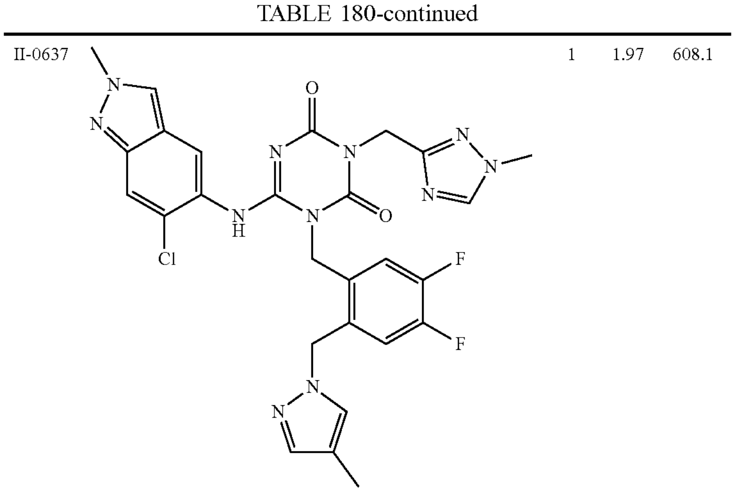 | 1 | 1.97 | 608.1 |
TABLE 181
| | | | | |
|---|---|---|---|---|
| II-0638 | 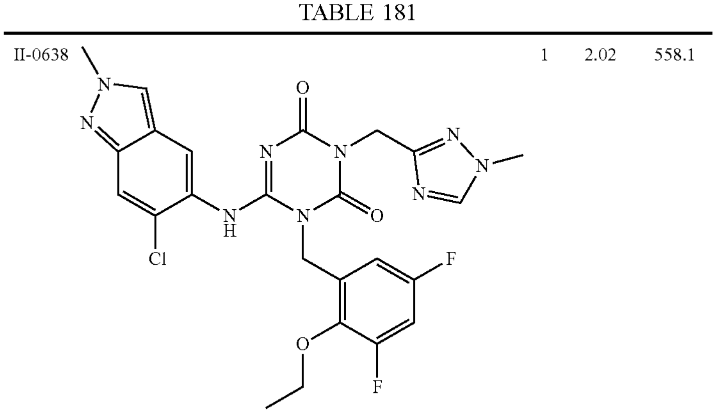 | 1 | 2.02 | 558.1 |
| II-0639 | 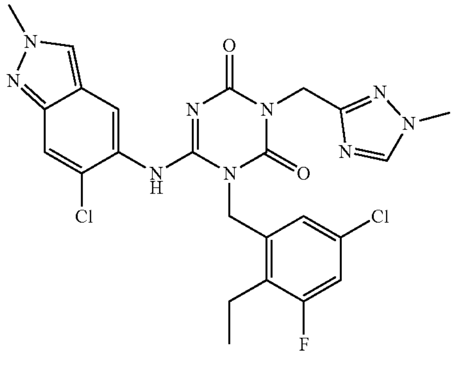 | 1 | 2.21 | 558 |

TABLE 181-continued
| | | | | |
|---|---|---|---|---|
| II-0640 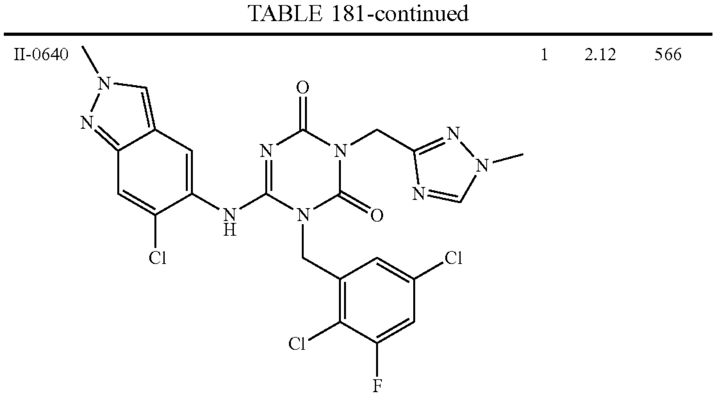 | | 1 | 2.12 | 566 |
| II-0641 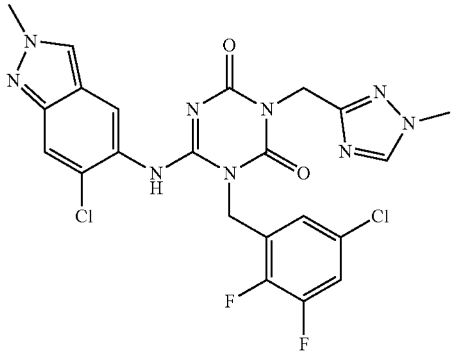 | | 1 | 2.05 | 548.1 |
| II-0642 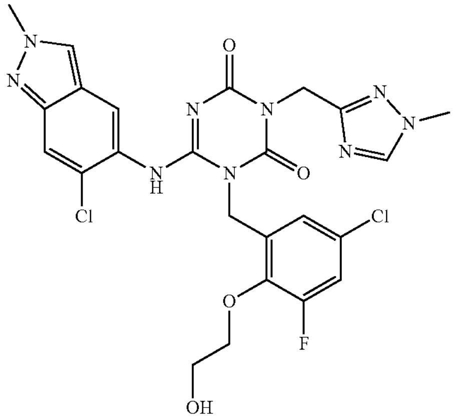 | | 1 | 1.84 | 590.1 |
TABLE 182
| | | | | |
|---|---|---|---|---|
| II-0643 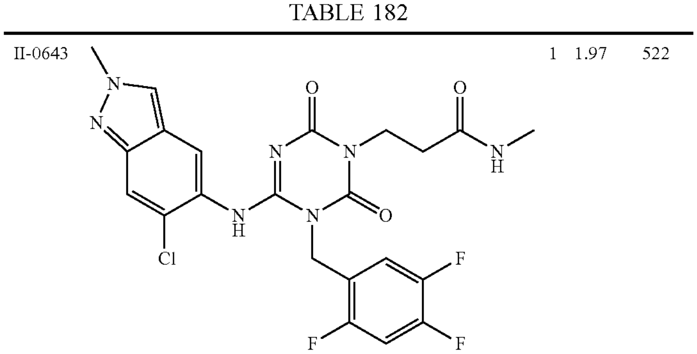 | | 1 | 1.97 | 522 |

TABLE 182-continued

| | | | | |
|---|---|---|---|---|
| II-0644 | 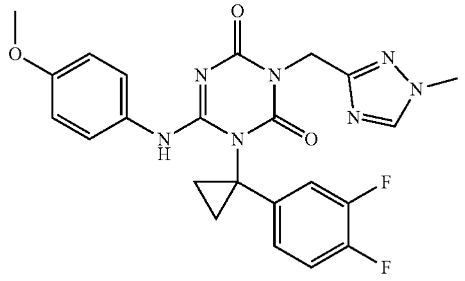 [SMILES: COc1ccc(Nc2nc(=O)n(Cc3ncn(C)n3)c(=O)n2C2(c3ccc(F)c(F)c3)CC2)cc1] | 1 | 1.92 | 482.15 |

TABLE 183

| Compound No. | NMR |
|---|---|
| I-0355 | 1H NMR (400 MHz, CDCI3)6 2.41 (3H, s), 4.77 (2H, td, J = 13.2, 4.3 Hz), 5.30 (2H, s), 6.26 (1H, tt, J = 55.3, 4.3 Hz), 6.90 (1H, dd, J = 9.2, 1.9 Hz), 7.09 (1H, d, J = 1.9 Hz), 7.22 (1H, dd, J = 8.5, 8.5 Hz), 7.42-7.43 (1H, m), 7.71 (1H, br s), 7.79 (1H, d, J = 9.2 Hz), 7.91 (1H, ddd, J = 8.5,5.3, 2.3 Hz), 7.97-7.98 (2H, m), 8.36 (1H, d, J = 2.1 Hz), 8.51 (1H, d, J = 1.1 Hz). |
| I-0361 | 1H-NMR (400 MHz, CDCI3) B: 2.40 (3H, s), 4.22 (3H, s), 5.38 (2H, s), 6.95 (1H, td, J = 9.6, 6.6 Hz), 7.13 (1H, s), 7.46-7.54 (2H, m), 7.84 (2H, d, J = 6.5 Hz), 8.38 (1H, d, J = 2.0 Hz), 8.49(1H, d, J = 1.0 Hz). |
| I-0383 | 1H-NMR (CDCI3) 6: 2.41 (3H, s), 3.49 (1H, s), 4.23 (3H, s), 5.33 (2H, s), 7.14 (1H, s), 7.20 (1H, tJ = 8.4 Hz), 7.45 (1H, s), 7.87 (2H, d, J = 12.0 Hz), 7.92-7.99 (1H, m), 8.04-8.09 (1H, m), 8.37 (1H, s), 8.50 (1H, s). |
| I-0421 | 1H NMR (400 MHz, CDCI3) B 3.89 (3H, s), 4.22 (3H, sj, 5.14 (2H, s), 5.23 (2H, s), 7.08 (1H, s), 7.27-7.32 (2H, m), 7.83 (2H, d, J = 9.8 Hz), 7.96 (1H, s). |
| I-0433 | 1 H-NMR (400 MHz, CDCI3) B: 3.89 (3H, s), 4.74 (2H, td, J = 13.1,4.1 Hz), 5.15 (2H, s), 5.23 (2H, s), 6.24 (1H, tt, J = 55.3,4.1 Hz), 7.11 (1H, s), 7.26-7.31 (2H, m), 7.86 (1H, s), 7.95 (2H, J = 9.9 Hz) |
| I-0483 | 1 H-NMR (400 MHz, CDCI3) B: 3.88 (3H, s), 4.21 (3H, s), 5.16 (2H, s), 5.37 (2H, s), 7.08 (1H, s), 7.18-7.28 (1H, m), 7.53 (1H, s), 7.82 (2H, s), 7.95 (1H, s). |
| II-0001 | 1 H-NMR (400 MHz, CDCI3) 6: 2.40 (3H, s), 5.01 (2H, q, J = 8.2 Hz), 5.46 (2H, s), 6.84 (1H, dd, J = 9.0,1.8 Hz), 7.05 (1H, s), 7.48 (1H, s), 7.52-7.58 (2H, m), 7.66 (1H, s), 7.77 (1H, d, J = 9.0 Hz), 7.98-8.00 (2H, br m), 8.39 (1H, d, J = 2.3 Hz), 8.48 (1H, d, J = 1.0 Hz). |
| II-0010 | 1H NMR (CDCI3) 5:1.13 (3H, t, J = 6.1 Hz), 2.40 (3H, s), 4.50 (2H, q, J = 7.3 Hz), 5.30 (2H, s), 6.86 (1H, dd, J = 9.0,1.9 Hz), 7.08 (1H, s), 7.21 (1H, t, J = 8.7 Hz), 7.43 (1H, s), 7.79 (1H, d, J = 9.0 Hz), 7.92 (2H, dt, J = 9.5, 3.4 Hz), 7.98 (1H, dd, J = 6.0,1.8 Hz), 8.35 (1H, d, J = 2.1 Hz), 8.48 (1H, d, J = 1.0 Hz). |
| II-0015 | 1 H-NMR (400 MHz, CDCI3) B: 2.40 (3H, s), 2.54 (3H, s), 4.21 (3H, s), 5.32 (2H, s), 7.04 (1H, d, J = 9.4 Hz), 7.12 (1H, s), 7.49 (1H, s), 7.77-7.88 (3H, m), 8.38 (1H, s), 8.48 (1H, s). |
| II-0034 | 1 H-NMR (400 MHz, CDCI3) B:1.65 (3H, t, J = 7.3 Hz), 2.53 (3H, s), 4.49 (2H, q, J = 7.3 Hz), 5.34 (2H, s), 6.80 (1H, dd, J = 9.0,1.8 Hz), 7.05 (1H, d, J = 1.0 Hz), 7.30 (1H, d, J = 7.8 Hz), 7.52 (1H, dd, J = 7.8, 1.0 Hz), 7.66 (1H, s), 7.71 (1H, t, J = 2.0 Hz), 7.76 (1H, d, J = 9.0 Hz), 7.85-7.88 (2H, m), 8.48 (1H, d, J = 2.3 Hz), 8.63 (1H, d, J = 2.0 Hz). |
| II-0036 | 1 H-NMR (400 MHz, CDCI3) 6: 1.65 (3H, t, J = 7.3 Hz), 4.49 (2H, q, J = 7.3 Hz), 5.47 (2H, s), 6.79 (1H, dd, J = 9.0, 2.0 Hz), 7.04 (1H, br s), 7.54-7.57 (2H, m), 7.67 (1H, s), 7.71 (1H, t, J = 2.1 Hz), 7.76 (1H, d, J = 9.0 Hz), 7.89 (2H, s), 8.49 (1H, d, J = 2.3 Hz), 8.63 (1H, d, J = 2.0 Hz). |
| II-0043 | 1H NMR (400 MHz, CDCI3) B 2.41 (3H, s), 2.43 (3H, s), 4.23 (3H, s), 5.30 (2H, s), 6.95-6.97 (1H, m), 7.13 (1H, s), 7.50-7.52 (1H, m), 7.59 (1H, d, J = 7.2 Hz), 7.65 (1H, s), 7.86 (2H, d, J = 10.8 Hz), 8.02 (1H, s), 8.41 (1H, s), 8.51 (1H, s). |
| II-0045 | 1 H-NMR (400 MHz, CDCI3) B: 3.88 (3H, s), 4.22 (3H, s), 5.13 (2H, s), 5.22 (2H, s), 7.08 (1H, s), 7.39-7.45 (1H, m), 7.50-7.54 (1H, m), 7.82 (1H, s), 7.84 (1H, s), 7.94 (1H, s) |
| II-0055 | 1 H-NMR (DMSO-D6) B: 2.55 (3H, s), 4.97 (2H, td, J = 15.0, 3.6 Hz), 5.45 (2H, s), 6.52 (1H, t, J = 54.7 Hz), 7.18 (1H, d, J = 8.0 Hz), 7.62 (1H, s), 7.64 (1H, d, J = 9.0 Hz), 7.96 (1H, s), 8.06 (1H, t, J = 8.7 Hz), 8.47 (2H, s), 8.87 (1H, s), 8.88 (1H, s). |
| II-0087 | 1 H-NMR (CDCI3) B: 2.41 (3H, s), 4.23 (3H, s), 5.46 (2H, s), 7.12 (1H, s), 7.32 (1H, d, J = 8.4 Hz), 7.50 (1H, s), 7.83-7.88 (3H, m), 8.41 (1H, d, J = 2.3 Hz), 8.52 (1H, s). |
| II-0089 | 1 H-NMR (400 MHz, CDCI3) B: 2.41 (3H, s), 4.76 (2H, td, J = 13.3, 4.2 Hz), 5.33 (2H, s), 6.25 (1H, tt, J = 55.3,4.2 Hz), 7.16 (1H, s), 7.20 (1H, t, J = 8.7 Hz), 7.45 (1H, s), 7.63 (1H, br s), 7.91 (1H, s), 7.92-7.95 (1H, m), 7.97 (1H, s), 8.06 (1H, dd, J = 6.1, 2.2 Hz), 8.37 (1H, d, J-2.3 Hz), 8.51 (1H, s). |

TABLE 184

| | |
|---|---|
| II-0090 | 1H-NMR (400 MHz, CDCI3) 6: 2,41 (3H, s), 4.76 (2H, td, J = 13.3,4.2 Hz), 5.27 (2H, s), 6.24 (1H, tt, J = 55.2, 4.2 Hz), 7.16 (1H, s), 7.33-7.39 (2H, m), 7.45 (1H, s), 7.65 (1H, s), 7.89 (1H, d, J = 5.4 Hz), 7.96 (1H, s), 8.37 (1H, d, J = 2.1 Hz), 8.50 (1H, s). |

TABLE 184-continued

| | |
|---|---|
| II-0093 | 1H-NMR (400 MHz, CDCI3) 6: 2.41 (3H, s), 3.94 (3H, s), 4.22 (3H, s), 5.32 (2H, s), 6.75 (1H, br s), 7.12 (1H, br s), 7.50 (1H, s), 7.65 (1H, br s), 7.79-7.92 (2H, m), 8.40 (1H, d, J = 2.3 Hz), 8.50 (1H,s). |
| II-0109 | 1H NMR (400 MHz, DMSO-d6) 6 4.16 (3H, s), 5.30 (2H, s), 7.15 (1H, d, J = 9.5 Hz), 7.61 (4H, m), 8.05 (1H, m), 8.36 (1H, s), 8.54 (1H, s), 8.67 (1H, s), 9.51 (1H, s) |
| II-0111 | 1H NMR (400 MHz, DMSO-d6) 6 2.34 (3H, s), 4.17 (3H, s), 5.26 (2H, s), 7.22 (1H, d, J = 8.9 Hz), 7.60 (4H, m), 7.79 (1H, dd, J = 18.1 Hz, 8.7 Hz), 8.30 (1H, s), 8.36 (1H, s), 8.40 (1H, s), 9.60 (1H, s) |
| II-0118 | 1H NMR (400 MHz, DMSO-d6) 6:1.49 (3H, t, J = 7.2 Hz), 2.34 (3H, s), 4.40-4.48 (2H, m), 5.23 (1.2H, s), 5.34 (0.8H, s), 7.15-7.95 (5H, m), 8.13-8.15 (1H, m), 8.32-8.51 (3H, m), 9.58 (0.4H, s), 11.16 (0.6H,s). |
| II-0119 | 1H NMR (400 MHz, CDCI3) 5: 2.40 (3H, s), 4.23 (3H, s), 5.27 (2H, s), 7.14 (1H, s), 7.45-7.51 (2H, m), 7.58-7.61 (1H, m), 7.85 (1H, s), 7.88 (1H, s), 8.37 (1H, d, J = 2.3 Hz), 8.50 (1H,d, J = 1.0 Hz). |
| II-0120 | 1H NMR (400 MHz, DMSO-d6) 5: 4.14 (1.8H, s), 4.19 (1.2H, s), 5.24 (1.2H, s), 5.35 (0.8H, s), 7.13-8.74 (9H, m), 9.64 (0.4H, s), 11.29 (0.6H, s). |
| II-0125 | 1H NMR (400 MHz, CDCI3) 5 2.41 (3H, s), 2.53 (3H, s), 4.24 (3H, s), 5.33 (2H, s), 6.79-6.82 (1H, m), 7.05-7.05 (1H, m), 7.30 (1H, d, J = 7.9 Hz), 7.47-7.49 (1H, m), 7.51 (1H, dd, J = 8.2,1.3 Hz), 7.64-7.66 (1H, m), 7.74 (1H, d, J = 9.0 Hz), 7.78-7.81 (1H, m), 7.85 (1H, s), 8.39 (1H, d, J = 2.4 Hz), 8.49-8.52 (1H, m). |
| II-0130 | 1H-NMR (400 MHz, CDCI3) 5: 2.41 (3H, s), 4.24 (3H, s), 5.31 (2H, s), 7.15 (1H, s), 7.45 (1H, s), 7.69 (1H, brs), 7.81-7.91 (4H, m), 8.37 (1H, d, J = 2.3 Hz), 8.51 (1H, s). |
| II-0163 | IH-NMR (400 MHz, CDCI3) 6: 3.88 (3H, s), 4.73 (1H, td, J = 13.2,4.2 Hz), 5.13 (2H, s), 5.34 (2H, s), 6.23 (1H, tt, J = 55.3, 4.2 Hz), 6.92 (1H, td, J = 9.6, 6.6 Hz), 7.09 (1H, s), 7.36-7.44 (1H, m), 7.66 (1H, brs), 7.81 (1H, s), 7.92 (1H, s), 7.94 (1H, s). |
| II-0164 | 1H-NMR (400 MHz, DMSO-d6) 5: 2.09 (3H, s), 3.57 (3H, s), 4.16 (2H, s), 5.90 (1H, s), 7.74 (1H, s), 7.96 (1H, s), 8.07 (1H, s), 8.35 (1H, s), 8.46 (1H, s), 8.89 (1H, S), 9.12 (1H, s). |
| II-0173 | 1H-NMR(400 MHz, DMSO-d6) 6: 2.34 (3H, s), 4.15 (3H, s), 5.30 (2H, s), 7.10 (1H, brs), 7.44-7.61 (4H, m), 7.85-7.91 (1H, m), 8.04-8.09 (1H, m), 8.29 (1H, brs), 8.32 (1H, s), 8.40 (1H,s). |
| II-0233 | 1H NMR (400 MHz, CDCI3J5 1.65 (3H, t, J = 7.3 Hz), 2.41 (3H, s), 2.54 (3H, s), 4.48 (2H, q, J = 7.3 Hz), 5.32 (2H, s), 7.04 (1H, d, J = 9.5 Hz), 7.12 (1H, s), 7.50 (1H, brs), 7.66 (1H, brs), 7.82 (1H, d, J = 6.5 Hz), 7.88-7.90 (2H, m), 8.40 (1H, d, J = 2.3 Hz), 8.51 (1H, s). |
| II-0278 | 1H-NMR (400 MHz, CDCI3) 5: 2.41 (3H, s), 2.55 (3H, s), 4.77 (2H, td, J = 13.3, 4.4 Hz), 5.29 (2H, s), 6.25 (1H, tt, J = 55.2,13.3 Hz), 6.85 (1H, d, J = 10.8 Hz), 7.07 (2H, s), 7.47 (1H, s), 7.69 (1H, d, J = 6.3 Hz), 7.76 (1H, d, J = 9.3 Hz), 7.97 (1H, s), 8.38 (1H, d, J = 1.5 Hz), 8.51 (1H,s). |
| II-0282 | 1H-NMR (400 MHz, CDCI3) 5: 4.24 (3H, s), 5.43 (2H, s), 6.80 (1H, d, J = 9.0 Hz), 7.04 (1H, brs), 7.35 (1H, d, J = 8.3 Hz), 7.68-7.72 (2H, m), 7.76 (1H, d, J = 9.0 Hz), 7.87 (1H, s), 8.48 (1H, d, J = 2.0 Hz), 8.65 (1H, d, J = 2.0 Hz). |
| II-0284 | 1 H-NMR (400 MHz, CDCI3) 5: 4.18 (3H, s), 5.22 (2H, s), 6.79 (1H, dd, J = 9.0,1.8 Hz), 7.00 (1H, s), 7.59 (1H, t, J = 2.1 Hz), 7.65-7.69 (1H, m), 7.70-7.77 (3H, m), 7.81 (1H, s), 8.38 (1H, d, J = 2.0 Hz), 8.58 (1H, d, J = 2.0 Hz). |
| II-0285 | 1 H-NMR (400 MHz, CDCI3) 5:1.58 (6H, d, J = 6.5 Hz), 3.81 (3H, s), 4.71 (1H, sext, J = 6.5 Hz), 5.09 (2H, s), 5.28 (2H, s), 6.85 (1H, td, J = 9.6, 6.4 Hz), 7.01 (1H, s), 7.31-7.39 (1H, m), 7.46 (1H, brs), 7.78 (1H, d, J = 9.0 Hz), 7.88 (1H, s). |

TABLE 185

| | |
|---|---|
| II-0288 | 1H-NMR (400 MHz, CDCI3) 5: 4.24 (3H, s), 5.35 (2H, s), 6.80 (1H, dd, J = 9.0, 2.0 Hz), 6.93-7.01 (1H, m), 7.06 (1H, s), 7.38-7.46 (1H, m), 7.66 (1H, t, J = 2.1 Hz), 7.76 (1H, d, J = 8.8 Hz), 7.80 (1H, brs), 7.86 (1H, s), 8.46 (1H, d, J = 2.3 Hz), 8.63 (1H, d, J = 2.3 Hz). |
| II-0290 | 1 H-NMR (400 MHz, CDCI3) 5: 2.41 (3H, sj, 2.55 (3H, s), 4.24 (3H, s), 5.29 (2H, s), 6.81 (1H, dd, J = 8.9,1.7 Hz), 7.05 (1H, s), 7.06 (1H, d, J = 7.5 Hz), 7.47 (1H, s), 7.69 (1H, d, J = 6.5 Hz), 7.75 (1H, d, J = 9.1 Hz), 7.85 (1H, s), 8.38 (1H, s), 8.50 (1H, s). |
| II-0299 | 1 H-NMR (CDCI3) 5: 2.41 (s, 3H), 2.53 (s, 3H), 5.01 (q, 2H, J = 8.2 Hz), 5.33 (s, 2H), 6.85 (dd, 1H, J = 9.2,1.9 Hz), 7.06 (m, 1H), 7.30 (d, 1H, J = 7.9 Hz), 7.48 (m, 1H), 7.51 (dd, 1H, J = 7.8,1.6 Hz), 7.65 (s, 1H), 7.78 (d, 1H, J = 9.2 Hz), 7.84 (s, 1H), 7.99 (s, 1H), 8.39 (d, 1H, 3 = 2.3 Hz), 8.49 (d, 1H, J = 1.1 Hz). |
| II-0304 | 1 H-NMR (CDCI3) 6: 2.53 (s, 3H), 5.02 (q, 2H, J = 8.2 Hz), 5.33 (s, 2H), 6.85 (dd, 1H, J = 9.1,1.9 Hz), 7.05 (d, 1H, J = 1.1 Hz), 7.31 (d, 1H, J = 7.9 Hz), 7.52 (dd, 1H, J = 7.9,1.5 Hz), 7.65 (s, 1H), 7.71 (t, 1H, J = 2.1 Hz), 7.74-7.92 (m, 2H), 8.00 (s, 1H), 8.48 (d, 1H, J = 2.0 Hz), 8.63 (d, 1H, J = 2.1 Hz). |
| II-0332 | 1 H-NMR (CDCI3) 5: 2.40 (s, 3H), 2.41 (s, 3H),4.22 (s, 3H), 5.33 (s, 2H), 7.09-7.18 (m, 3H), 7.46-7.49 (m, 2H), 7.85 (d, 2H, J = 8.8 Hz), 7.64 (s, 1H), 8.40 (d, 1H, J = 2.0 Hz), 8.50 (s, 1H) |
| II-0334 | 1 H-NMR (400 MHz, CDCI3) 5: 2.42 (3H, s), 4.23 (3H, s), 5.40 (2H, s), 5.66 (1H, s), 5.77 (1H, s), 7.12 (1H, s), 7.51 (2H, t, J = 5.4 Hz), 7.66 (2H, t, J = 7.8 Hz), 7.86 (2H, d, J = 3.8 Hz), 8.01 (1H, s), 8.40 (1H, d, J = 2.3 Hz), 8.52 (1H, s). |
| II-0335 | 1 H-NMR (400 MHz, CDC13) 5:1.66 (3H, t, J = 7.3 Hz), 2.41 (3H, s), 2.55 (3H, s), 4.49 (2H, q, J = 7.4 Hz), 5.29 (2H, s), 6.81 (1H, dd, J = 9.0, 2.0 Hz), 7.06 (2H, dd, J = 5.4,4.1 Hz), 7.47 (1H, s), 7.69 (1H, d, J = 6.5 Hz), 7.77 (2H, d, J = 9.0 Hz), 7.89 (1H, s), 8.38 (1H, d, J = 2.3 Hz), 8.51 (1H, d, J = 1.3 Hz). |

TABLE 185-continued

| | |
|---|---|
| II-0347 | 1 H-NMR (400 MHz, CDCI3) 5: 2.53 (3H, s), 4.24 (3H, s), 5.34 (2H, s), 6.80 (1H, dd, J = 9.0, 2.0 Hz), 7.04 (1H, d, J = 1.3 Hz), 7.30 (1H, d, J = 7.8 Hz), 7.52 (1H, dd, J = 7.9,1.4 Hz), 7.65 (1H, s), 7.71 (1H, t, J = 2.3 Hz), 7.75 (1H, d, J = 8.8 Hz), 7.85 (2H, s), 8.49 (1H, d, J = 2.0 Hz), 8.64 (1H, d, J = 2.3 Hz). |
| II-0377 | 1H-NMR (CDCI3) 5: 2.40 (3H, s), 4.23 (3H, s), 5.38 (2H, s), 6.93 (1H, t, J = 9.0 Hz), 7.13 (1H, s), 7.47 (1H, m), 7.66 (1H, s), 7.77 (1H, t, J = 7.7 Hz), 7.85 (1H, s), 7.87 (1H, s), 8.38 (1H,d, J = 2.3 Hz), 8.50 (1H, s). |
| II-0410 | 1H-NMR (CDCI3) 5: 3.88 (3H, s), 4.21 (3H, s), 5.14 (2H, s), 5.34 (2H, s), 6.91 (1H, t, J = 9.0 Hz), 7.08 (1H, s), 7.60 (1H, s), 7.64 (1H, t, J = 7.8 Hz), 7.81 (1H, s), 7.95 (1H, s). |
| II-0415 | 1H-NMR (CDCI3) 5: 4.77 (2H, dd, J = 13.3, 4.2 Hz), 5.30 (2H, s), 6.25 (1H, tt, J = 55.2, 4.24 Hz), 6.90 (1H, dd, J = 9.0, 2.0 Hz), 7.09 (1H, s),7.23 (1H, t, J = 8.8 Hz), 7.66 (1H, t, J = 2.0 Hz),7.78 (1H, d, J = 9.0 Hz) 7.90 (1H, m), 7.96 (1H, m), 7.97 (1H, s), 8.44 (1H, d, J = 2.0 Hz), 8.63 (1H,d, J = 2.0 Hz). |
| II-0422 | 1H-NMR (CDCI3) 6: 2.40 (3H, s), 4.23 (3H, s), 5.46 (2H, s), 6.80 (1H, dd, J = 9.0,1.8 Hz), 7.04 (1H, s, J = 1.3 Hz), 7.48 (1H, s), 7.51-7.58, 2H, m), 7.66 (1H, s), 7.73 (1H, d, J = 9.0 Hz), 7.84 (1H, s), 7.94 (1H, s), 8.39 (1H, d, J = 2.3 Hz), 8.49 (1H, s). |
| II-0493 | 1H-NMR (CDCI3) 5: 1.64 (3H, t, J = 7.3 Hz), 2.41 (3H, s), 2.52 (3H, s), 4.48 (2H, q, J = 7.3 Hz), 5.37 (2H, s), 7.12 (1H, s), 7.28 (1H, d, J = 8.0 Hz), 7.50 (2H, d, J = 8.3 Hz), 7.77 (1H, s), 7.87 (2H, d, J = 1.8 Hz), 8.41 (1H, d, J = 2.0 Hz), 8.50 (1H, s). |
| II-0521 | 1H-NMR (DMSO-D6) 5: 2.34 (3H, s), 2.42 (3H, s), 4.97 (2H, td, J = 14.8, 3.1 Hz), 5.19 (2H, s), 6.53 (1H, tt, J = 54.8, 3.4 Hz), 7.24 (1H, d, J = 9.4 Hz), 7.46 (1H, d, J = 7.9 Hz), 7.62-7.71 (4H, m), 7.95 (1H, s), 8.34 (1H, s), 8.40 (1H, s), 8.47 (1H, s), 9.49 (1H, s). |
| II-0523 | 1H-NMR (DMSO-D6) 6: 4.16 (3H, s), 5.26 (2H, s), 7.21 (1H, d, J = 8.5 Hz), 7.62 (2H, d, J = 8.4 Hz), 7.78 (1H, d, J = 8.0 Hz), 7.87 (1H, d, J = 8.0 Hz), 8.00 (1H, s), 8.17 (1H, s), 8.36 (1H, s), 8.53 (1H, s), 8.67 (1H, s), 9.72 (1H, s). |
| II-0543 | 1H-NMR (CDCI3) 6: 2.52(3H, s), 4.22 (3H, s), 5.37 (2H, s), 7.10 (1H, s), 7.29 (1H, d, J = 8.0 Hz), 7.50 (1H, d, J = 6.8 Hz), 7.74 (1H, m), 7.77 (1H, brs), 7.81-7.86 (2H, m), 8.50 (1H, d, J = 2.0 Hz), 8.63 (1H, d, J = 2.0 Hz) |

TABLE 186

| | |
|---|---|
| II-0548 | 1H-NMR (CDCI3) 5:1.64 (3H, t, J = 7.2 Hz), 2.92 (3H, s), 4.46 (2H, q, 7.2 Hz), 5.15 (2H, s), 5.35 (2H, s), 6.92 (1H, m), 7.08 (1H, s), 7.41 (1H, m), 7.63 (1H, s), 7.82 (1H, s), 7.84 (1H, s), 7.94 (1H, s) |
| II-0559 | 1H NMR (DMSO-d6) 5 ppm 1.50 (3 H, t, J = 7.28 Hz) 2.43 - 2.47 (3 H, m) 4.45 (2 H, q, J = 7.19 Hz) 5.16 (2 H, brs)7.15(1 H, brd, J = 9.29 Hz) 7.46 - 7.55 (1 H, m) 7.58(1 H, br s) 7.61 (1 H, br s) 7.94 - 7.97 (1 H, m) 7.97 - 8.05 (2 H, m) 8.41 (1 H, br s) 8.54 (1 H, s) 8.67(1 H, s) 9.53(1 H, brs) |
| II-0566 | 1H NMR (DMSO-d6) 5 ppm 1.50 (3 H, t, J = 7.28 Hz) 4.44 (2 H, q, J = 7.03 Hz) 5.33 (2 H, br<br>br<br>s) 7.13 (1 H, br s) 7.59 (3 H, br d, J = 8.66 Hz) 7.87 - 7.92 (1 H, m) 8.02 - 8.08 (2 H, m) 8.39 (1 H, br s) 8.54 (1 H, s) 8.67 (1 H, d, J = 1.76 Hz) 9.55 (1 H, br s) |
| II-0567 | 1H NMR (DMSO-d6) 5 ppm 2.22 - 2.42 (3 H, tn) 5.05 - 5.70 (4 H, m) 6.56 - 7.38 (1 H, m) 7.62 (4 H, br s) 7.82 - 8.19 (2 H, m) 8.42 (3 H, br s) 9.24 - 9.76 (1 H, m) |
| II-0568 | 1H-NMR (CKJI3) 6: 2.41 (3H, s), 4.72-4.80 (2H, m), 5.31 (2H, s), 6.10-6.40 (1H, m),7.17 (1H, s), 7.45 (1H, s), 7.73 (1H, s), 7.82-7.91 (3H, m), 7.97 (1H, s), 8.37 (1H, d, J = 2.3 Hz), 8.51 (1H, d, J = 0.8 Hz). |
| II-0569 | 1H-NMR (CDC13) 5: 3.89 (3H, s), 4.70-4.78 (2H, m), 5.15 (2H, s), 5.34 (2H, s), 6.08-6.37 (1H, m), 6.91 (1H, t, J = 9.0 Hz), 7.11 (1H, s), 7.55 (1H, s), 7.63 (1H, t, J = 7.8 Hz), 7.83 (1H,s), 7.93 (1H, s),7.96(1H, s). |
| II-0570 | 1H-NMR(CDCI3) 5: 2.40 (3H, s), 4.72-4.80 (2H, mj, 5.47 (2H, s), 6.10-6.39 (1H, m), 6.83 (1H, dd, J = 9.2,1.9 Hz), 7.06 (1H, d, J = 1.3 Hz), 7.48 (1H, s), 7.52-7.58 (2H, m), 7.66 (1H, s), 7.75 (1H, d, J = 9.0 Hz), 7.82 (1H, s), 7.95 (1H, s), 8.40 (1H, d, J = 2.0 Hz), 8.50 (1H, s). |
| II-0571 | 1H-NMR(CDCI3) 5: 2.55 (3H, s), 4.24 (3H, s), 5.29 (2H, s), 6.81 (1H, dd, J = 9.0,1.9 Hz), 7.04-7.08 (2H, m), 7.69-7.70 (2H, m), 7.75 (1H, d, J = 8.9 Hz), 7.85 (2H, s), 8.47 (1H, d, J = 2.1 Hz), 8.63 (1H, d, 4 = 2.0 Hz). |
| II-0572 | 1H-NMR (CDCI3) 6: 3.97 (3H, s), 4.71-4.78 (2H, m), 5.14 (2H, s), 5.23 (2H, s), 6.10-6.38 (1H, m), 7.11 (1H, s), 7.39-7.52 (3H, m), 7.86 (1H, s), 7.94 (1H, s), 7.96 (1H, s). |
| II-0573 | 1H-NMR (CDCI3) 6: 2.41 (3H, s), 4.25 (3H, s), 5.28 (2H, s), 6.85-6.88 (1H, m), 7.08 (1H, s), 7.43 (1H, s), 7.74-7.87 (5H, m), 8.36 (1H, br-s), 8.51 (1H, br-s). |
| II-0574 | 1H-NMR(CDCI3) 5: 2.40 (3H, s), 4.72-4.79 (2H, m), 5.38 (2H, s), 6.10-6.38 (1H, m), 6.92-6.98 (1H, m), 7.15 (1H, s), 7.46-7.53 (2H, m), 7.88 (1H, s), 7.96 (1H, s), 8.38 (1H, d, J = 2.3 Hz), 8.50 (1H, br-s). |
| II-0576 | 1H-NMR (CDCI3) 5: 4.24 (3H, s), 5.35 (2H, s), 6.83-6.85 (1H, m), 6.96 (1H, t, J = 9.0 Hz), 7.06 (1H, s), 7.63-7.85 (5H,m), 8.45 (1H, d, J = 2.0 Hz), 8.62 (1H, d, J = 2.0 Hz). |
| II-0577 | 1 H-NMR (CDCI3) 5: 2.41 (3H, s), 2.52 (3H, s), 4.71-4.79 (2H, m), 5.36 (2H, s), 6.09-6.37 (1H, m), 7.14 (1H, s), 7.28 (1H, d, J = 8.0 Hz), 7.49-7.51 (2H, m), 7.76 (1H, s), 7.86 (1H, s), 7.95 (1H, s), 8.41 (1H, d, J = 2.3 Hz), 8.51 (1H, s). |
| II-0579 | 1H-NMR (CDCI3) 5: 2.41 (3H, s), 4.22 (3H, s), 5.50 (2H, s), 7.11 (1H, s), 7.48-7.57 (3H, m), 7.70 (1H, s), 7.78 (1H, s), 7.82-7.86 (2H, m), 8.41 (1H, s), 8.51 (1H, s). |
| II-0584 | 1H-NMR (CDCI3) 5: 3.88 (3H, s), 4.22 (3H, s), 5.13 (2H, s), 5.22 (2H, s), 7.09 (1H, s), 7.56 (1H, s), 7.65 (2H, d, J = 6.3 Hz), 7.82 (1H, s), 7.85 (1H, s), 7.95 (1H, s). |
| II-0596 | 1H-NMR (CDCI3) 5: 2.41 (3H, s), 2.52 (3H, s), 4.22 (3H, s), 5.37 (2H, s), 7.11 (1H, s), 7.24-7.31 (1H, m), 7.47-7.53 (2H, m), 7.69 (1H, s), 7.76 (1H, s), 7.81-7.87 (2H, m), 8.40 (1H,s), 8.50 (1H, s). |

TABLE 186-continued

| | |
|---|---|
| II-0608 | 1H NMR (400 MHz, CDCI3)6 4.25 (3H, s), 5.31 (2H, s), 6.86 (1H, dd, J = 9.0,1.6 Hz), 7.07 (1H, s), 7.22 (1H, dd, J = 8.6, 8.3 Hz), 7.66 (1H, dd, J = 1.9, 1.9 Hz), 7.78 (2H, d, J = 9.0 Hz), 7.87 (1H, s), 7.91 (1H, ddd, J * 8.3, 5.9, 2.0 Hz), 7.98 (1H, dd, J = 5.9, 2.0 Hz), 8.45 (1H, d, J = 1.9 Hz), 8.64 (1H, d, J = 1.9 Hz). |
| II-0609 | 1H-NMR (400 MHz, CDCI3) 5: 4.25 (3H, s), 5.24 (2H, s), 6.87 (1H, dd, J = 9.0,1.8 Hz), 7.08 (1H, d, J = 1.3 Hz), 7.30 (2H, t, J = 7.3 Hz), 7.66 (1H, t, J = 2.1 Hz), 7.78 (1H, d, J = 9.0 Hz), 7.81 (1H, brs), 7.87 (1H, s), 8.45 (1H, d, J = 2.3 Hz), 8.64 (1H, d, J = 2.0 Hz). |

Example 81

To 1400 mg of Compound (1-0113), 7 mL of ethyl acetate and 557 μL (1.05 eq) of a 5 mol/L aqueous solution of p-toluenesulfonic acid was added. The mixture was stirred at 60° C. for 15 minutes and then was stirred at 25° C. for 2 hours. Solids were collected by filtration and dried to give a crystalline form of p-toluenesulfonate Form I of a compound represented by Formula (I-A) (1289.6 mg, 69%).

The results of single crystal structure analysis of the crystalline form of p-toluenesulfonate Form I of the compound represented by Formula (I-A) are shown below.

R1 (I>2.00 s (I)) was 0.0444, and it was confirmed from the final difference Fourier that there was neither inadequacy nor misplacement of electron density.

Crystallographic data are shown in Table 187.

TABLE 187

| Space Group | P-1 |
|---|---|
| a (Å) | 8.7844(2) |
| b (Å) | 10.2991(2) |
| c (Å) | 18.0182(3) |
| α (°) | 103.727(2) |
| β (°) | 97.411(2) |
| γ (°) | 100.358(2) |
| Volume ($Å^3$) | 1532.43(6) |
| Z | 2 |
| Density (calculated value) ($g/cm^3$) | 1.517 |
| Measured temperature(K) | 298 |

Here, Volume means the unit lattice volume, and Z means the number of molecules in a unit lattice.

Furthermore, the atomic coordinates of non-hydrogen atoms are indicated in Table 188 to Table 189. Here, U(eq) means the equivalent isotropic temperature factor.

TABLE 188

| Atom | X | y | z | U(eq) |
|---|---|---|---|---|
| S1 | 5557.0(7) | 5570.9(7) | 3382.5(3) | 58.54(18) |
| Cl1 | 9613.3(8) | 973.2(6) | 9196.1(4) | 65.77(19) |
| O0AA | 9535.3(19) | 4701.0(16) | 6926.8(8) | 53.6(4) |
| O2 | 6849(2) | 439.0(17) | 5545.6(8) | 60.9(4) |
| N6 | 8276(2) | 2541.7(17) | 6223.6(9) | 40.7(4) |
| N5 | 7041.4(19) | 1025.1(16) | 6857.9(9) | 39.7(4) |
| F2 | −141.7(19) | −251.9(19) | 7226.8(11) | 92.1(6) |
| N2 | 8829(2) | 5271.5(19) | 11119.0(9) | 48.5(4) |
| N3 | 7195(2) | 1663.4(19) | 8176.4(9) | 48.2(4) |
| N4 | 8541(2) | 3184.9(17) | 7562.2(9) | 42.4(4) |
| F3 | 887(2) | 430(2) | 5999.5(12) | 97.1(6) |
| N1 | 7812(2) | 6077.8(19) | 11018(1) | 50.4(4) |
| O4 | 4537(2) | 6507(2) | 3385.2(11) | 77.0(5) |
| N7 | 7564(2) | 3712.1(19) | 4481.8(10) | 51.8(5) |
| Fl | 1789(2) | −1005(2) | 8247.6(11) | 106.2(7) |
| O3 | 5276(3) | 4797(2) | 3958.3(11) | 84.0(6) |
| O5 | 7190(2) | 6153(3) | 3452.2(12) | 88.9(7) |
| C9 | 7583(2) | 1982(2) | 7574.6(11) | 40.1(4) |
| C11 | 7341(2) | 1270(2) | 6163.6(11) | 42.9(5) |
| C7 | 7658(2) | 2633(2) | 8912.6(11) | 43.2(5) |
| C10 | 8834(2) | 3579(2) | 6910.2(11) | 40.9(4) |

TABLE 188-continued

| Atom | X | y | z | U(eq) |
|---|---|---|---|---|
| C13 | 4424(2) | −281(2) | 6933.5(11) | 41.9(4) |
| C4 | 8567(2) | 4339(2) | 10420.3(11) | 42.0(4) |
| C3 | 7411(2) | 4585(2) | 9881.8(11) | 43.7(5) |
| C19 | 8494(2) | 2887(2) | 5509.3(11) | 41.9(4) |
| C12 | 6089(2) | −316(2) | 6838.6(12) | 43.8(5) |
| C6 | 8796(3) | 2385(2) | 9477.2(12) | 45.7(5) |
| C8 | 6978(3) | 3725(2) | 9112.3(12) | 46.5(5) |
| C23 | 9844(3) | 2769(2) | 5216.8(11) | 45.0(5) |
| C21 | 8868(3) | 3604(2) | 4179.9(12) | 50.6(5) |
| C22 | 10048(3) | 3130(2) | 4531.1(12) | 48.5(5) |
| C5 | 9266(3) | 3215(2) | 10214.4(11) | 46.2(5) |
| C20 | 7340(3) | 3359(2) | 5136.1(12) | 48.6(5) |
| C25 | 5003(3) | 4321(2) | 2476.2(13) | 50.7(5) |
| C2 | 6957(3) | 5725(2) | 10300.8(13) | 51.0(5) |
| C18 | 3415(3) | 91(2) | 6402.6(14) | 54.5(6) |

TABLE 189

| Atom | X | y | z | U(eq) |
|---|---|---|---|---|
| C14 | 3868(3) | −662(2) | 7553.5(13) | 53.7(5) |
| C16 | 1347(3) | −281(3) | 7124.4(16) | 60.7(6) |
| C17 | 1900(3) | 94(2) | 6512.6(16) | 61.2(6) |
| C30 | 6119(3) | 3983(3) | 2035.5(14) | 55.9(6) |
| C26 | 3439(3) | 3640(3) | 2211.0(15) | 61.5(6) |
| C15 | 2335(3) | -663(3) | 7636.1(15) | 62.9(6) |
| C29 | 5673(3) | 3002(3) | 1334.5(15) | 61.3(6) |
| C28 | 4124(3) | 2306(3) | 1062.3(15) | 60.2(6) |
| C1 | 7696(3) | 7183(3) | 11670.0(15) | 66.2(7) |
| C27 | 3021(3) | 2642(3) | 1519.6(17) | 66.8(7) |
| C24 | 11523(3) | 3005(3) | 4204.0(16) | 68.8(7) |
| C31 | 3666(4) | 1199(3) | 313.7(19) | 86.6(9) |

Next, the atomic coordinates of hydrogen atoms are shown in Table 190. Here, U(iso) means the isotropic temperature factor. Furthermore, the numbers of hydrogen atoms in Table 190 are assigned in relation to the numbers of non-hydrogen atoms that are bonded.

TABLE 190

| Atom | X | y | z | U (iso) |
|---|---|---|---|---|
| H4 | 8997.31 | 3740.96 | 8003.33 | 51 |
| H7 | 6846.9 | 4018.17 | 4247.85 | 62 |
| H12A | 6580 | −646.73 | 7249.93 | 53 |
| H12B | 6080.56 | −961.06 | 6347.82 | 53 |
| H8 | 6243.08 | 3903.21 | 8750.78 | 56 |
| H23 | 10622.43 | 2448.15 | 5474.97 | 54 |
| H21 | 8972.67 | 3855.23 | 3723.18 | 61 |
| H5 | 10022.27 | 3041.45 | 10567.4 | 55 |
| H20 | 6421.35 | 3433.73 | 5331.94 | 58 |
| H2 | 6205.25 | 6159.69 | 10118.28 | 61 |
| H18 | 3760.99 | 335.18 | 5978 | 65 |
| H14 | 4530.93 | −915.45 | 7912.92 | 64 |
| H30 | 7172.24 | 4418.9 | 2212.04 | 67 |
| H26 | 2676.66 | 3860.81 | 2502.17 | 74 |
| H29 | 6431.77 | 2800.81 | 1036.17 | 74 |
| HlA | 7407.56 | 6810.87 | 12085.34 | 99 |
| H1B | 6911.8 | 7647.04 | 11507.76 | 99 |
| H1C | 8694.25 | 7819.65 | 11846.48 | 99 |

TABLE 190-continued

| Atom | X | y | z | U (iso) |
|---|---|---|---|---|
| H27 | 1975.25 | 2179.81 | 1353.37 | 80 |
| H24A | 12424.61 | 3497.89 | 4594.3 | 103 |
| H24B | 11517.08 | 3380.23 | 3764.48 | 103 |
| H24C | 11568.94 | 2056.87 | 4044.69 | 103 |
| H31A | 4413.51 | 1353.07 | −17.7 | 130 |
| H31B | 2638.62 | 1210.23 | 61.36 | 130 |
| H31C | 3652.49 | 325.83 | 417.97 | 130 |

In addition, the interatomic bond length (unit: angstrom) is shown in Table 191.

TABLE 191

| Atom | Atom | Length/Å | Atom | Atom | Length/Å |
|---|---|---|---|---|---|
| S1 | O4 | 1.4286(19) | C7 | C6 | 1.432(3) |
| S1 | O3 | 1.4694(19) | C7 | C8 | 1.363(3) |
| S1 | O5 | 1.429(2) | C13 | C12 | 1.500(3) |
| S1 | C25 | 1.770(2) | C13 | C18 | 1.388(3) |
| Cl1 | C6 | 1.734(2) | C13 | C14 | 1.386(3) |
| O0AA | C10 | 1.200(2) | C4 | C3 | 1.412(3) |
| O2 | C11 | 1.204(2) | C4 | C5 | 1.402(3) |
| N6 | C11 | 1.388(3) | C3 | C8 | 1.418(3) |
| N6 | CIO | 1.393(2) | C3 | C2 | 1.390(3) |
| N6 | C19 | 1.441(2) | C19 | C23 | 1.372(3) |
| N5 | C9 | 1.391(2) | C19 | C20 | 1.368(3) |
| N5 | C11 | 1.381(2) | C6 | C5 | 1.363(3) |
| N5 | C12 | 1.471(3) | C23 | C22 | 1.396(3) |
| F2 | C16 | 1.349(3) | C21 | C22 | 1.368(3) |
| N2 | N1 | 1.348(3) | C22 | C24 | 1.505(3) |
| N2 | C4 | 1.354(3) | C25 | C30 | 1.381(3) |
| N3 | C9 | 1.274(2) | C25 | C26 | 1.390(3) |
| N3 | C7 | 1.417(3) | C18 | C17 | 1.371(4) |
| N4 | C9 | 1.373(3) | C14 | C15 | 1.373(3) |
| N4 | C10 | 1.370(2) | C16 | C17 | 1.368(4) |
| F3 | C17 | 1.348(3) | C16 | C15 | 1.359(4) |
| N1 | C2 | 1.339(3) | C30 | C29 | 1.376(4) |
| N1 | Cl | 1.457(3) | C26 | C27 | 1.372(4) |
| N7 | C21 | 1.341(3) | C29 | C28 | 1.385(4) |
| N7 | C20 | 1.341(3) | C28 | C27 | 1.388(4) |
| F1 | C15 | 1.352(3) | C28 | C31 | 1.498(4) |

In the crystalline form of p-toluenesulfonate Form I of a compound represented by Formula (I-A), one molecule of the compound represented by Formula (I-A) exists in an asymmetric unit. The structure of the compound represented by Formula (I-A) in the asymmetric unit is shown in FIG. 2.

The numbers of non-hydrogen atoms in Table 188 to Table 189 and Table 191 correspond to the numbers shown in FIG. 2, respectively.

As shown in Table 191, the bond length of N3-C9 was about 1.27 Å, and the bond length of N4-C9 was about 1.37 Å.

Since the bond length of N3-C9 (about 1.27 Å) was shorter than the bond length of N4-C9 (about 137 Å), the compound represented by Formula (I-A) in the crystalline form of p-toluenesulfonate Form I was identified to have an imino structure:

[Chemical Formula 86]

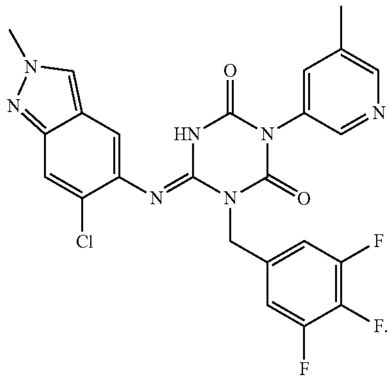

Furthermore, the results of powder X-ray diffraction of the crystalline form of p-toluenesulfonate Form I of the compound represented by Formula (I-A) is shown.

In the powder X-ray diffraction pattern, peaks were observed at the diffraction angles (2θ): 9.1±0.2°, 11.5±0.2°, 14.6±0.2°, 15.2±0.2°, 18.8±0.2°, 20.2±0.2°, 23.6±0.2°, 24.2±0.2°, 24.9±0.2°, and 26.9±0.2°.

Regarding the powder X-ray diffraction peaks, the peaks at the diffraction angles (2θ): 9.1±0.2°, 15.2±0.2°, 18.8±0.2°, 23.6±0.2°, and 24.9±0.2° are particularly characteristic as the crystalline form of p-toluenesulfonate Form 1 of the compound represented by Formula (I-A).

Example 9

To Compound (1-0115, 1170 mg) were added fumaric acid (278 mg, 1.1 eq) and ethyl acetate (5.85 mL). The mixture was stirred at room temperature for 45 minutes. The resulting solids were collected by filtration and dried to give fumaric acid cocrystal Form I of the compound represented by Formula (I-B) (1369.4 mg, 94.6%).

The results of the single crystal structure analysis of the fumaric acid cocrystal Form 1 of the compound represented by the Formula (I-B) are shown below.

R1 (I>2.00 s (I)) was 0.0470, and it was confirmed from the final difference Fourier that there was no lack of electron density or misplacement.

Crystallographic data are shown in Table 192.

TABLE 192

| Space Group | P-1 |
|---|---|
| a (Å) | 8.4374(2) |
| b (Å) | 11.6780(3) |
| c (Å) | 15.1612(4) |
| α (°) | 83.827(2) |
| β (°) | 78.868(2) |
| γ (°) | 77.147(2) |
| Volume ($Å^3$) | 1425.77(6) |
| Z | 2 |
| Density (calculated value) (g/$cm^3$) | 1.509 |
| Measured temperature(K) | 298 |

Wherein Volume indicates the unit lattice volume, Z indicates chemical unit number per unit cell.

In addition, the atomic coordinates of non-hydrogen atoms are indicated in Table 193 to 194. Here, U(eq) means an equivalent isotropic temperature factor.

TABLE 193

| Atom | X | y | z | U(eq) |
|---|---|---|---|---|
| Cl36 | 8115.3(9) | 8341.6(8) | 5010.7(5) | 79.9(3) |
| F32 | 8958.5(19) | 7981.3(17) | 307.5(9) | 78.5(5) |
| O35 | 7267(2) | 5961.4(16) | 1399.9(10) | 56.3(5) |
| O34 | 5322(3) | 4254.8(16) | 4098.2(11) | 63.3(5) |
| O38 | 3536(2) | 9367.5(19) | 8936.3(12) | 64.2(5) |
| N12 | 6506(2) | 7056.8(18) | 2611.0(12) | 44.2(5) |
| F33 | 13870(2) | 7642(2) | 1402.1(13) | 100.3(7) |
| N16 | 5475(2) | 6174.4(18) | 3988.1(12) | 48.2(5) |
| N14 | 6120(3) | 5115.3(18) | 2713.0(12) | 47.3(5) |
| N9 | 2815(3) | 8924(2) | 7397.8(13) | 55.4(6) |
| N10 | 5772(3) | 8146(2) | 3856.1(13) | 55.1(6) |
| N1 | 1276(3) | 8864(2) | 7324.6(14) | 60.2(6) |
| F31 | 12197(3) | 7751(3) | 3084.6(13) | 124.9(9) |
| N23 | 3644(3) | 4434(2) | 1818.7(15) | 64.5(6) |
| N20 | 3122(3) | 4249(2) | 1061.4(15) | 64.9(6) |
| C11 | 6673(3) | 6043(2) | 2193.8(15) | 44.7(6) |
| C9 | 5879(3) | 7178(2) | 3527.6(15) | 44.2(6) |
| C10 | 5619(3) | 5119(2) | 3639.3(15) | 48.4(6) |
| N22 | 5784(3) | 3621(2) | 814.1(15) | 67.8(7) |
| O39 | 6151(3) | 8893(3) | 8285.8(15) | 109.2(10) |
| C12 | 6985(3) | 8068(2) | 2049.4(15) | 47.2(6) |
| C20 | 5248(3) | 4044(2) | 1633.9(16) | 50.7(6) |
| C7 | 5022(3) | 8298(2) | 4770.9(15) | 50.8(6) |
| C4 | 3693(3) | 8762(2) | 6554.3(16) | 49.4(6) |
| C13 | 8823(3) | 7976(2) | 1872.6(16) | 48.8(6) |
| C5 | 5385(3) | 8700(2) | 6267.8(17) | 56.4(7) |
| C19 | 6380(3) | 4009(2) | 2279.5(17) | 54.5(7) |
| C14 | 9741(3) | 7934(2) | 1013.2(16) | 54.7(7) |
| C3 | 2685(3) | 8593(2) | 5965.2(17) | 54.4(7) |
| C6 | 6015(3) | 8469(2) | 5392.0(16) | 54.3(7) |
| C23 | 5121(4) | 9287(3) | 8898.3(18) | 62.1(7) |
| O41 | 1842(3) | 4874(3) | 3529.1(18) | 119.8(10) |
| C8 | 3370(3) | 8376(2) | 5054.8(17) | 57.4(7) |
| C24 | 5542(3) | 9730(3) | 9679.7(17) | 61.9(7) |
| C18 | 9684(4) | 7917(3) | 2570.7(18) | 67.1(8) |
| C15 | 11431(3) | 7827(3) | 831.3(19) | 67.8(8) |
| C16 | 12217(3) | 7760(3) | 1541(2) | 67.9(8) |
| C2 | 1134(4) | 8667(3) | 6497.1(18) | 67.4(8) |

TABLE 194

| Atom | X | y | z | U(eq) |
|---|---|---|---|---|
| C17 | 11360(4) | 7806(3) | 2405(2) | 75.0(9) |
| C21 | 4400(4) | 3767(3) | 485.7(19) | 70.6(8) |
| O43 | −464(4) | 4618(4) | 3203.2(19) | 154.2(15) |
| C1 | 9(4) | 8943(3) | 8139(2) | 81.7(10) |
| C26 | 307(4) | 4766(4) | 3745(2) | 93.6(12) |
| C25 | −384(4) | 4909(4) | 4700(2) | 92.1(11) |
| C22 | 1397(4) | 4562(4) | 963(3) | 102.7(13) |

Next, the atomic coordinates of the hydrogen atom are shown in Table 195. Here, U(iso) means an isotropic temperature factor. In addition, the numbers of hydrogen atoms in Table 195 are assigned in relation to the numbers of non-hydrogen atoms that are bonded.

TABLE 195

| Atom | X | y | z | U(iso) |
|---|---|---|---|---|
| H38 | 3370.9 | 9206.88 | 8452.86 | 96 |
| H16 | 5092.25 | 6215.55 | 4554.71 | 58 |
| H12A | 6452.59 | 8783.45 | 2347.49 | 57 |
| H12B | 6603.63 | 8119.01 | 1479.7 | 57 |
| H5 | 6053.99 | 8811.71 | 6658.45 | 68 |
| H19A | 6229.72 | 3381.57 | 2741.61 | 65 |
| H19B | 7509.94 | 3824.57 | 1962.58 | 65 |
| H41 | 2202.36 | 4700.41 | 3007.94 | 180 |
| H8 | 2702.01 | 8287.11 | 4656.27 | 69 |
| H24 | 6652.83 | 9619.42 | 9719.44 | 74 |
| H18 | 9115.24 | 7953.15 | 3160.4 | 81 |
| H15 | 12010.7 | 7800.84 | 243.55 | 81 |

TABLE 195-continued

| Atom | X | y | z | U(iso) |
|---|---|---|---|---|
| H2 | 176.44 | 8593.16 | 6310.6 | 81 |
| H21 | 4344.44 | 3553.57 | −79.51 | 85 |
| H1A | 260.69 | 8258.79 | 8539.89 | 122 |
| H1B | −1049.48 | 8985.26 | 7978.29 | 122 |
| H1C | −14.15 | 9635.57 | 8433.78 | 122 |
| H25 | −1486.76 | 4863.66 | 4886.06 | 110 |
| H22A | 719.4 | 4375.73 | 1521.91 | 154 |
| H22B | 1225.91 | 4127.33 | 499 | 154 |
| H22C | 1105.77 | 5390.24 | 801.98 | 154 |

Furthermore, the interatomic bond length (unit: angstrom) is shown in Table 196.

TABLE 196

| Atom | Atom | Length/Å | Atom | Atom | Length/Å |
|---|---|---|---|---|---|
| Cl36 | C6 | 1.733(3) | N22 | C20 | 1.345(3) |
| F32 | C14 | 1.352(3) | N22 | C21 | 1.326(4) |
| O35 | C11 | 1.216(3) | O39 | C23 | 1.196(3) |
| O34 | C10 | 1.208(3) | C12 | C13 | 1.503(3) |
| O38 | C23 | 1.310(3) | C20 | C19 | 1.485(4) |
| N12 | C11 | 1.369(3) | C7 | C6 | 1.431(4) |
| N12 | C9 | 1.398(3) | C7 | C8 | 1.362(4) |
| N12 | C12 | 1.465(3) | C4 | C5 | 1.398(4) |
| F33 | C16 | 1.347(3) | C4 | C3 | 1.402(3) |
| N16 | C9 | 1.373(3) | C13 | C14 | 1.381(3) |
| N16 | C10 | 1.365(3) | C13 | C18 | 1.383(4) |
| N14 | C11 | 1.382(3) | C5 | C6 | 1.364(3) |
| N14 | C10 | 1.386(3) | C14 | C15 | 1.379(4) |
| N14 | C19 | 1.466(3) | C3 | C8 | 1.416(3) |
| N9 | N1 | 1.342(3) | C3 | C2 | 1.388(4) |
| N9 | C4 | 1.358(3) | C23 | C24 | 1.475(4) |
| N10 | C9 | 1.262(3) | O41 | C26 | 1.304(4) |
| N10 | C7 | 1.421(3) | C24 | C24[1] | 1.307(5) |
| N1 | C2 | 1.332(3) | C18 | C17 | 1.367(4) |
| N1 | Cl | 1.466(3) | C15 | C16 | 1.355(4) |
| F31 | C17 | 1.345(3) | C16 | C17 | 1.370(4) |
| N23 | N20 | 1.360(3) | 043 | C26 | 1.189(4) |
| N23 | C20 | 1.313(3) | C26 | C25 | 1.466(5) |
| N20 | C21 | 1.309(4) | C25 | C25[2] | 1.273(7) |
| N20 | C22 | 1.453(4) | | | |

In the fumaric acid cocrystal Form I of the compound represented by Formula (I-B), one molecule of the compound represented by Formula (I-B) was present in the asymmetric unit. The structure of the fumaric acid cocrystal Form I of the compound represented by Formula (I-B) in the asymmetric unit is shown in FIG. 4.

The numbers of non-hydrogen atoms in Tables 193 to 194 and 196 correspond to the numbers shown in FIG. 4, respectively.

As shown in Table 196, the bond length of N10-C9 was about 1.26 Å, and the bond length of N16-C9 was about 1.37 Å.

Since the bond length of N10-C9 (about 1.26 Å) is shorter than that of N16-C9 (about 1.37 Å), the fumaric acid cocrystal Form I of the compound represented by Formula (I-B) was identified as imino structure:

[Chemical Formula 87]

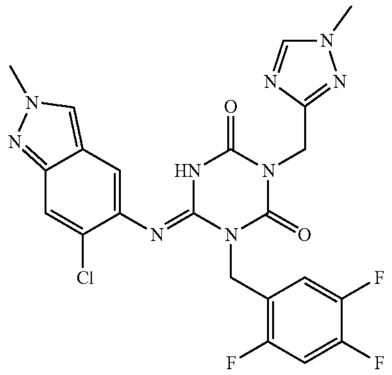

Further, the result of the powder X-ray diffraction of the fumaric acid cocrystal Form I of the compound represented by Formula (I-B) is shown.

In the powder X-ray diffraction pattern, peaks were observed at the diffraction angle (2θ): 7.8±0.2°, 9.5±0.2°, 10.1±0.2°, 10.9±0.2°, 13.8±0.2°, 14.7±0.2°, 18.6±0.2°, 22.6±0.2°, 23.5±0.2° and 24.6±0.2°.

In the powder X-ray diffraction pattern, the peaks of the diffraction angle (2θ): 9.5±0.2°, 10.9±0.2°, 18.6±0.2°, 23.5±0.2° and 24.6±0.2 are particularly characteristic as the fumaric acid cocrystal Form I of the compound represented by Formula (I-B).

Figure 5:
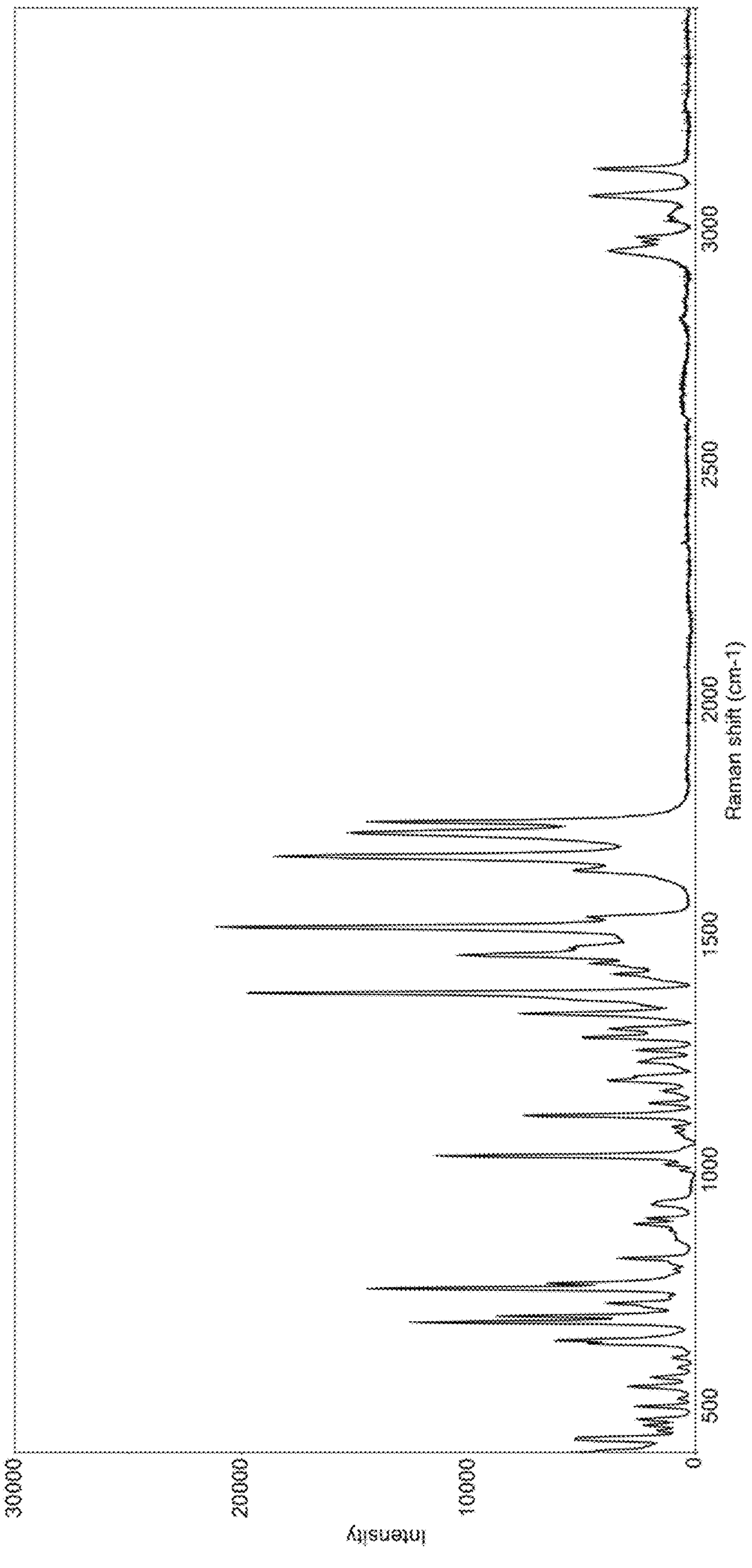
FIG. 5 shows the Raman spectrum of the fumaric acid cocrystal Form I (Form I) of the compound represented by Formula (I-B). The axis of abscissa represents Raman shift ($cm^{-1}$), and the axis of ordinate represents the peak intensity.

The result of the Raman spectrum of fumaric acid cocrystal Form I of the compound represented by Formula (I-B) is shown in FIG. 5.

A major Raman spectrum peaks were observed at 637.3 $cm^{-1}$±2 $cm^{-1}$, 676.3 $cm^{-1}$±2 $cm^{-1}$, 688.8 $cm^{-1}$±2 $cm^{-1}$, 748.0 $cm^{-1}$±2 $cm^{-1}$, 758.1 $cm^{-1}$±2 $cm^{-1}$, 1029.3 $cm^{-1}$±2 $cm^{-1}$, 1114.4 $cm^{-1}$±2 $cm^{-1}$, 1281.3 $cm^{-1}$±2 $cm^{-1}$, 1332.1 $cm^{-1}$±2 $cm^{-1}$, 1374.4 $cm^{-1}$±2 $cm^{-1}$, 1456.0 $cm^{-1}$±2 $cm^{-1}$, 1515.5 $cm^{-1}$±2 $cm^{-1}$, 1636.0 $cm^{-1}$±2 $cm^{-1}$, 1665.7 $cm^{-1}$±2 $cm^{-1}$, 1715.7 $cm^{-1}$±2 $cm^{-1}$, 1739.1 $cm^{-1}$±2 $cm^{-1}$, 2951.2 $cm^{-1}$±2 $cm^{-1}$, 3068.3 $cm^{-1}$±2 $cm^{-1}$ and 3126.2 $cm^{-1}$±2 $cm^{-1}$.

In one embodiment, the fumaric acid cocrystal Form I of the compound represented by Formula (I-B) has a Raman spectrum peaks at 676.3 $cm^{-1}$±2 $cm^{-1}$, 748.0 $cm^{-1}$±2 $cm^{-1}$, 1029.3 $cm^{-1}$±2 $cm^{-1}$, 1374.4 $cm^{-1}$±2 $cm^{-1}$, 1515.5 $cm^{-1}$±2 $cm^{-1}$, 1665.7 $cm^{-1}$±2 $cm^{-1}$, 1715.7 $cm^{-1}$±2 $cm^{-1}$ and 1739.1 $cm^{-1}$±2 $cm^{-1}$.

In one embodiment, the fumaric acid cocrystal Form I of the compound represented by Formula (I-B) has a Raman spectrum peak at 676.3 $cm^{-1}$±2 $cm^{-1}$.

In one embodiment, the fumaric acid cocrystal Form I of the compound represented by Formula (I-B) has a Raman spectrum peak at 748.0 $cm^{-1}$±2 $cm^{-1}$.

In one embodiment, the fumaric acid cocrystal Form I of the compound represented by Formula (I-B) has a Raman spectrum peak at 1029.3 $cm^{-1}$±2 $cm^{-1}$.

In one embodiment, the fumaric acid cocrystal Form I of the compound represented by Formula (I-B) has a Raman spectrum peak at 1374.4 $cm^{-1}$±2 $cm^{-1}$.

In one embodiment, the fumaric acid cocrystal Form I of the compound represented by Formula (I-B) has a Raman spectrum peak at 1515.5 $cm^{-1}$±2 $cm^{-1}$.

In one embodiment, the fumaric acid cocrystal Form I of the compound represented by Formula (I-B) has a Raman spectrum peak at 1665.7 $cm^{-1}$±2 $cm^{-1}$.

In one embodiment, the fumaric acid cocrystal Form I of the compound represented by Formula (I-B) has a Raman spectrum peak at 1715.7 $cm^{-1}$±2 $cm^{-1}$.

In one embodiment, the fumaric acid cocrystal Form I of the compound represented by Formula (I-B) has a Raman spectrum peak at 1739.1 $cm^{-1}$±2 $cm^{-1}$.

In one embodiment, the fumaric acid cocrystal Form I of the compound represented by Formula (I-B) has one or more Raman spectrum peak(s) selected from the group consisting of: Raman spectral peak of 676.3 $cm^{-1}$±2 $cm^{-1}$, Raman spectral peak of 748.0 $cm^{-1}$±2 $cm^{-1}$, Raman spectral peak of 1029.3 $cm^{-1}$±2 $cm^{-1}$, Raman spectral peak of 1374.4 $cm^{-1}$±2 $cm^{-1}$, Raman spectral peak of 1515.5 $cm^{-1}$±2 $cm^{-1}$, Raman spectral peak of 1665.7 $cm^{-1}$±2 $cm^{-1}$, Raman spectral peak of 1715.7 $cm^{-1}$±2 $cm^{-1}$ and Raman spectral peak of 1739.1 $cm^{-1}$±2 $cm^{-1}$.

Figure 6:
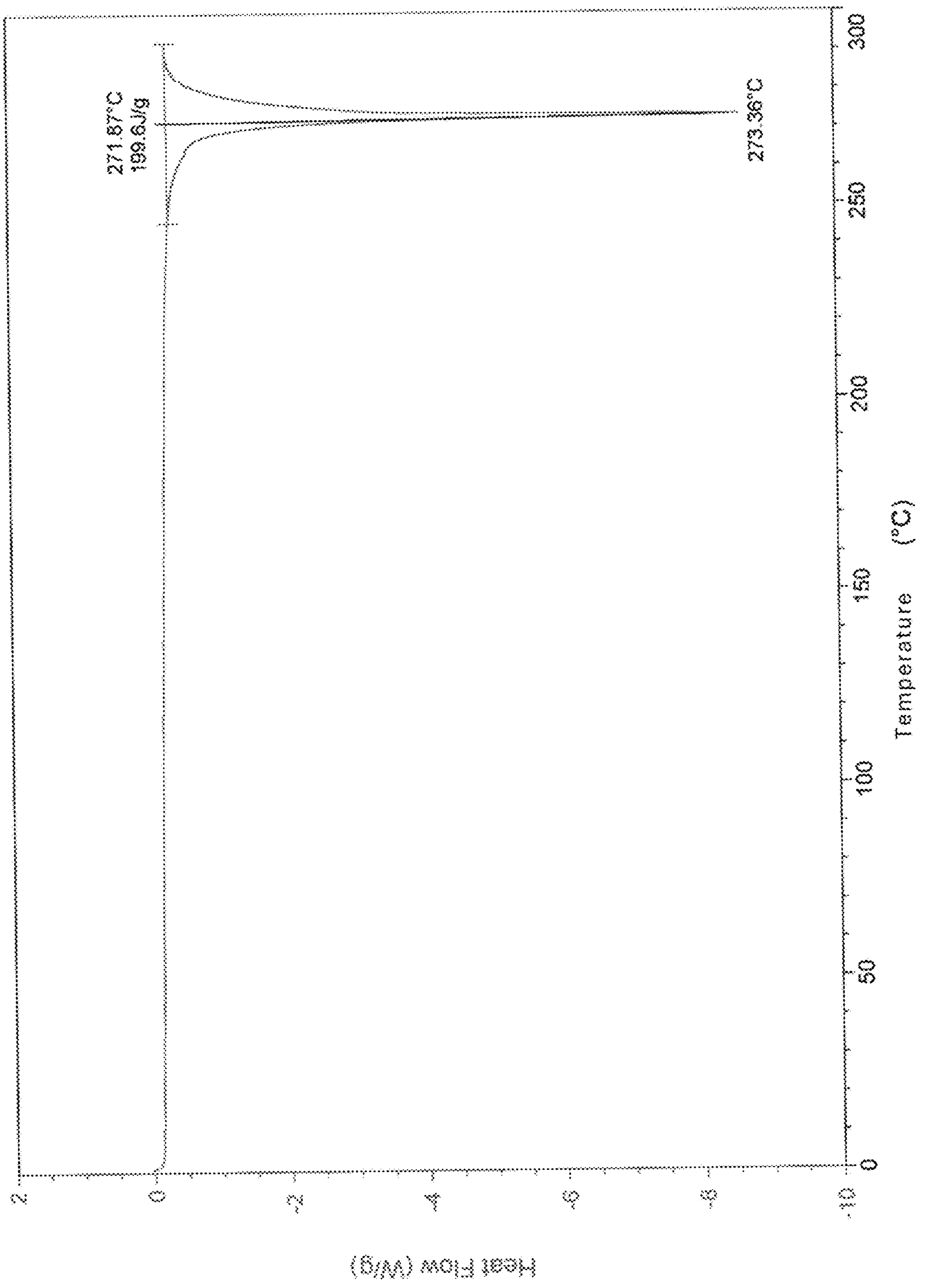
FIG. 6 shows results of a DSC analysis of the fumaric acid cocrystal Form I (Form I) of the compound represented by Formula (I-B). The axis of abscissa represents temperature (° C.), and the axis of ordinate represents the normalized heat flow (W/g).

The DSC analysis result of the fumaric acid cocrystal Form I of the compound represented by Formula (I-B) is shown in FIG. 6. The onset temperature (endothermic peak) was about 272° C.

Example 10

To 200 mg of Compound (1-0115), 395 μL (1.05 eq) of a 1 mol/L aqueous solution of potassium hydroxide and 2 mL of acetonitrile were added, and the solvent was evaporated to dryness. 1 mL of ethyl acetate was added thereto, and the mixture was stirred at 60° C. for 10 minutes and then stirred overnight at 25° C. Solids were collected by filtration and dried to obtain a crystalline form of potassium salt Form I of the compound represented by Formula (I-B). With regard to the crystalline form of potassium salt Form I of the compound represented by Formula (I-B), the molecular structure (amino form/imino form) was not identified.

Figure 7:
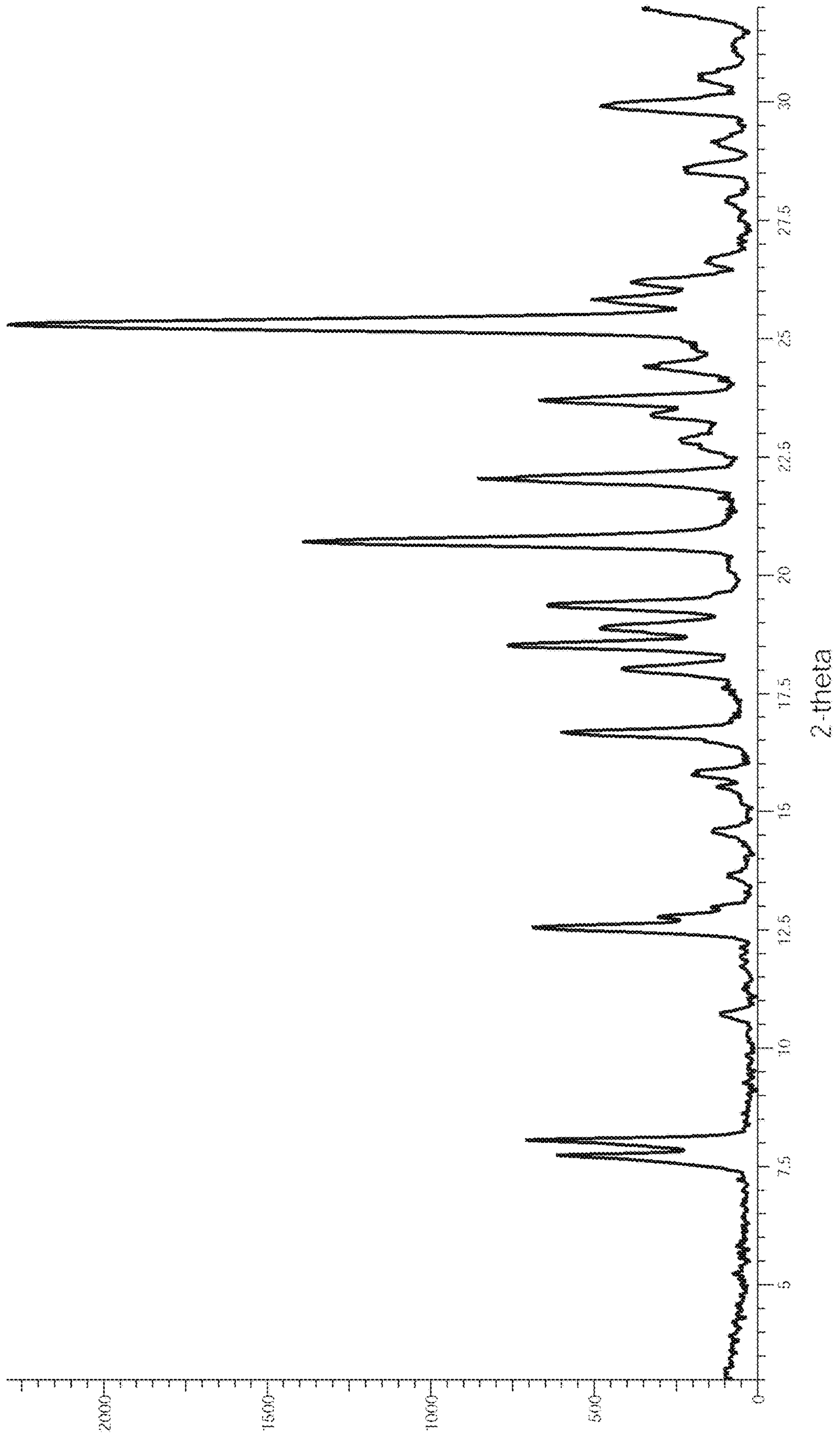
FIG. 7 shows a powder X-ray diffraction pattern of a crystalline form of potassium salt Form I (Form I) of the compound represented by Formula (I-B). The axis of abscissa represents 2θ(°), and the axis of ordinate represents the intensity (Count).

The results of powder X-ray diffraction of the crystalline form of potassium salt Form I of the compound represented by Formula (I-B) are shown in FIG. 7.

In the powder X-ray diffraction pattern, peaks were observed at the diffraction angles (2θ): 7.7±0.2°, 8.1±0.2°, 12.6±0.2°, 16.7±0.2°, 18.5±0.2°, 19.4±0.2°, 20.7±0.2°, 22.0±0.2°, 23.7±0.2°, and 25.3±0.2°.

Regarding the powder X-ray diffraction peaks, the peaks at the diffraction angles (2θ): 8.1±0.2°, 16.7±0.2°, 20.7±0.2°, 22.0±0.2°, 25.3±0.2° are particularly characteristic as the crystalline form of potassium salt Form I of the compound represented by Formula (I-B).

Figure 8:
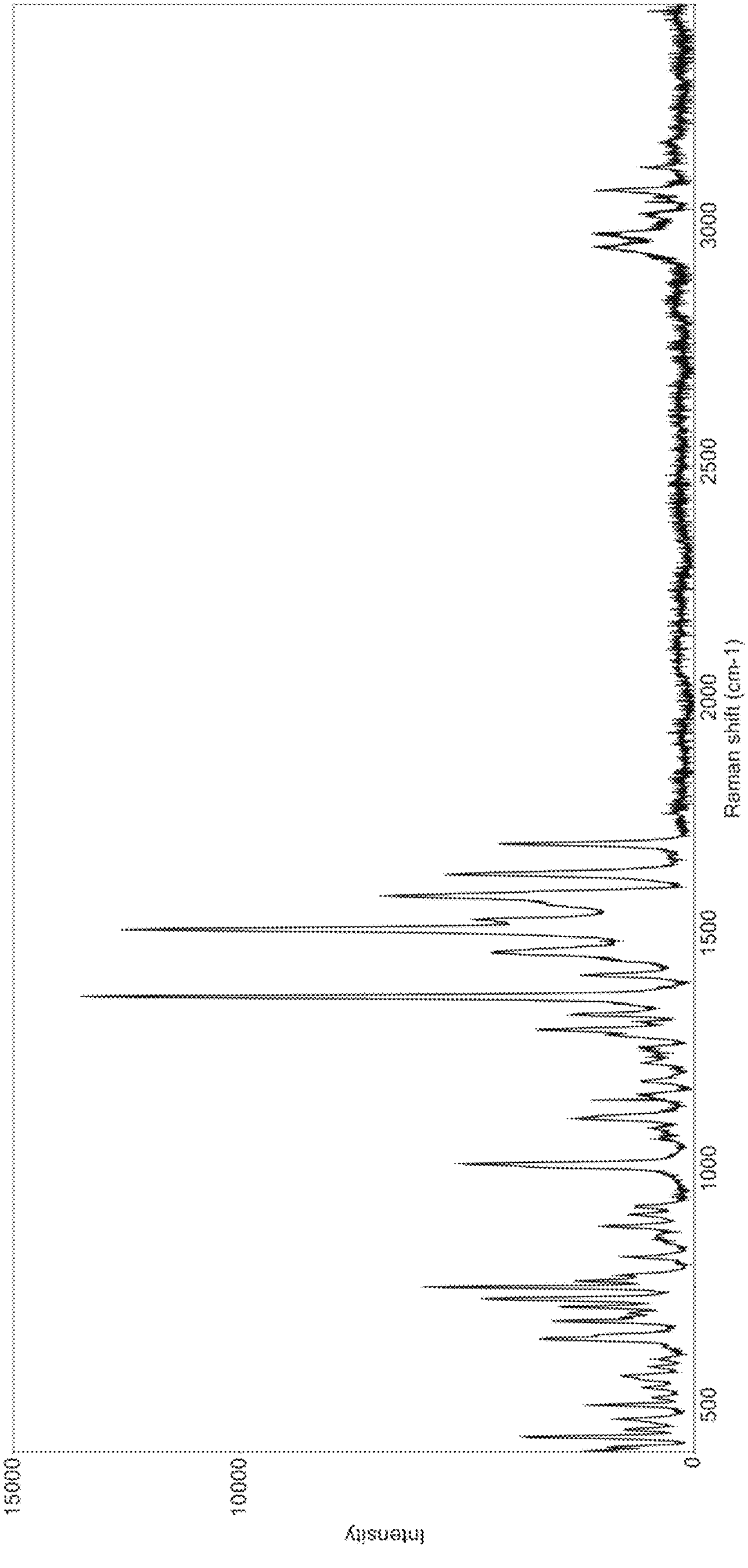
FIG. 8 shows the Raman spectrum of the crystalline form of potassium salt Form I (Form I) of the compound represented by Formula (I-B). The axis of abscissa represents Raman shift ($cm^{-1}$), and the axis of ordinate represents the peak intensity.

The results of Raman spectroscopy of the crystal of potassium salt Form I of the compound represented by Formula (I-B) are shown in FIG. 8.

Major Raman spectrum peaks were observed at 638.4 $cm^{-1}$±2 $cm^{-1}$, 676.3 $cm^{-1}$±2 $cm^{-1}$, 724.1 $cm^{-1}$±2 $cm^{-1}$, 749.1 $cm^{-1}$±2 $cm^{-1}$, 876.9 $cm^{-1}$±2 $cm^{-1}$, 1008.7 $cm^{-1}$±2 $cm^{-1}$, 1105.9 $cm^{-1}$±2 $cm^{-1}$, 1294.8 $cm^{-1}$±2 $cm^{-1}$, 1363.1 $cm^{-1}$±2 $cm^{-1}$, 1409.2 $cm^{-1}$±2 $cm^{-1}$, 1457.0 $cm^{-1}$±2 $cm^{-1}$, 1506.4 $cm^{-1}$±2 $cm^{-1}$, 1526.5 $cm^{-1}$±2 $cm^{-1}$, 1577.4 $cm^{-1}$±2 $cm^{-1}$, 1624.1 $cm^{-1}$±2 $cm^{-1}$, 1688.3 $cm^{-1}$±2 $cm^{-1}$, 2952.0 $cm^{-1}$±2 $cm^{-1}$, 2980.5 $cm^{-1}$±2 $cm^{-1}$, 3073.7 $cm^{-1}$±2 $cm^{-1}$, and 3121.6 $cm^{-1}$±2 $cm^{-1}$.

According to one embodiment, the crystalline form of potassium salt Form I of the compound represented by Formula (I-B) has Raman spectrum peaks at 749.1 $cm^{-1}$±2 $cm^{-1}$, 1008.7 $cm^{-1}$±2 $cm^{-1}$, 1363.1 $cm^{-1}$±2 $cm^{-1}$, 1506.4 $cm^{-1}$±2 $cm^{-1}$, 1577.4 $cm^{-1}$±2 $cm^{-1}$, and 1624.1 $cm^{-1}$±2 $cm^{-1}$.

Example 11

To 190 mg of Compound (I-0115), 46.4 mg (1.1 eq) of succinic acid and 3.8 mL of acetonitrile were added, and the mixture was stirred at room temperature for 1 hour. Solids were collected by filtration and dried to obtain succinic acid cocrystal Form I of the compound represented by Formula (I-B). With regard to the succinic acid cocrystal Form I of the compound represented by Formula (I-B), the molecular structure (amino form/imino form) was not identified.

Figure 9:
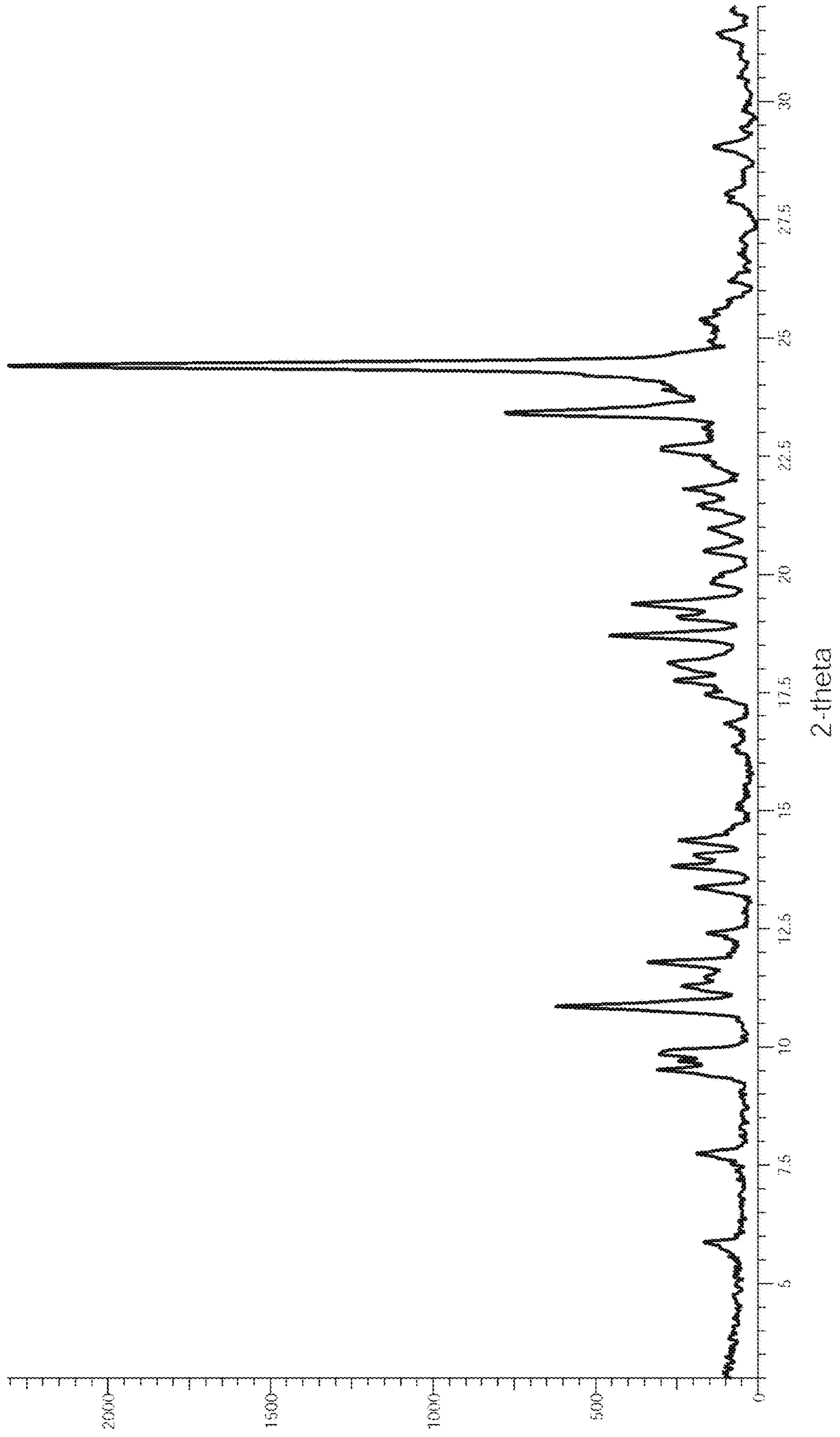
FIG. 9 shows a powder X-ray diffraction pattern of a succinic acid cocrystal Form I (Form I) of the compound represented by Formula (I-B). The axis of abscissa represents 2θ(°), and the axis of ordinate represents the intensity (Count).

The results of powder X-ray diffraction of the succinic acid cocrystal Form I of the compound represented by Formula (I-B) are shown in FIG. 9.

In the powder X-ray diffraction pattern, peaks were observed at the diffraction angles (2θ): 9.5±0.2°, 10.9±0.2°, 11.3±0.2°, 13.4±0.2°, 14.4±0.2°, 18.7±0.2°, 19.4±0.2°, 22.6±0.2°, 23.4±0.2°, and 24.4±0.2°.

Regarding the powder X-ray diffraction peaks, the peaks at the diffraction angles (2θ): 10.9±0.2°, 18.7±0.2°, 22.6±0.2°, 23.4±0.2°, and 24.4±0.2° are particularly characteristic as the succinic acid cocrystal Form I of the compound represented by Formula (I-B).

Figure 10:
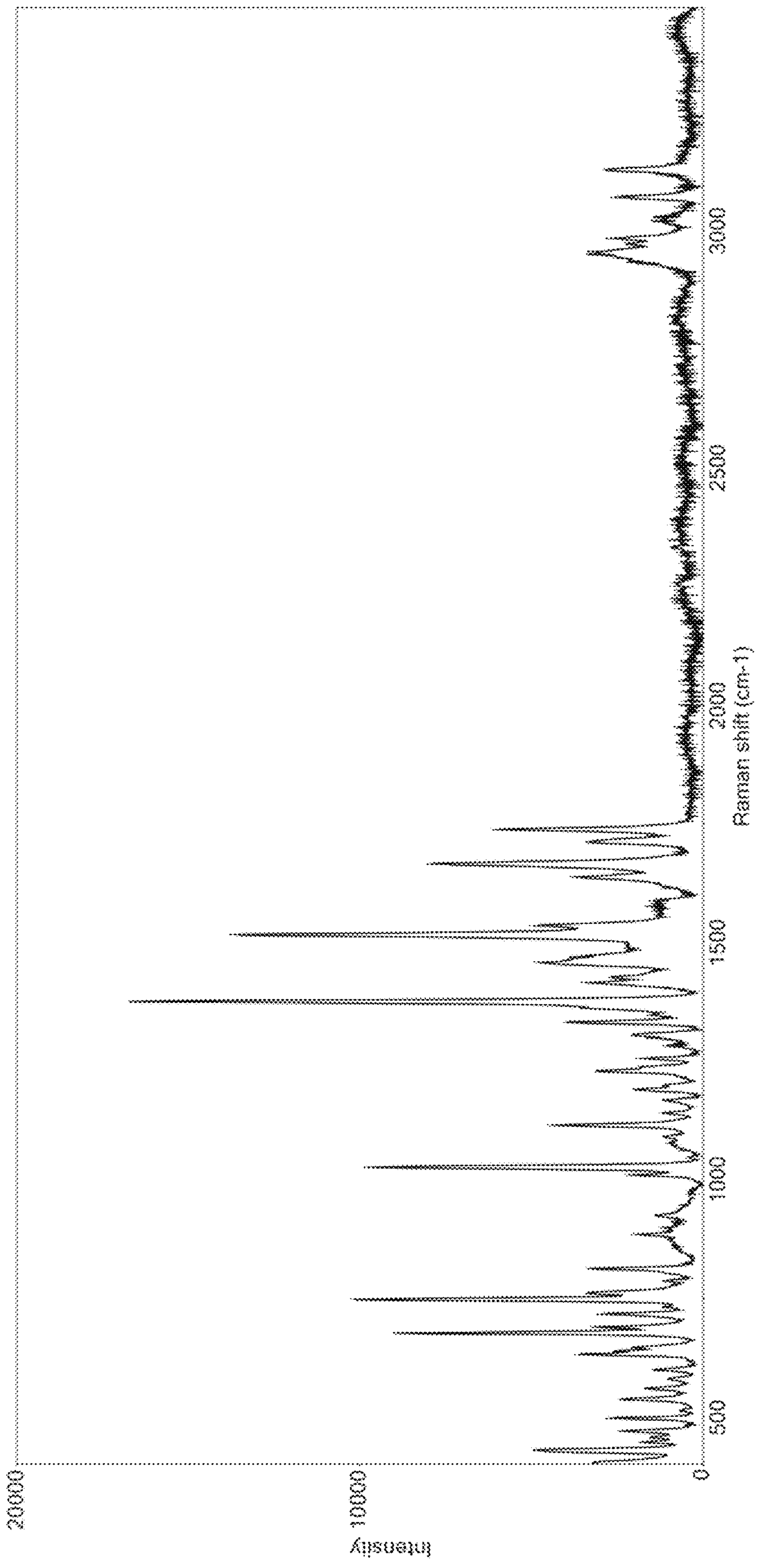
FIG. 10 shows the Raman spectrum of the succinic acid cocrystal Form I (Form I) of the compound represented by Formula (I-B). The axis of abscissa represents Raman shift ($cm^{-1}$), and the axis of ordinate represents the peak intensity.

The results of Raman spectroscopy of succinic acid cocrystal Form I of the compound represented by Formula (I-B) is shown in FIG. 10.

Major Raman spectrum peaks were observed at 631.6 $cm^{-1}$±2 $cm^{-1}$, 676.4 $cm^{-1}$±2 $cm^{-1}$, 748.1 $cm^{-1}$±2 $cm^{-1}$, 812.3 $cm^{-1}$±2 $cm^{-1}$, 1025.2 $cm^{-1}$±2 $cm^{-1}$, 1114.6 $cm^{-1}$±2 $cm^{-1}$, 1229.2 $cm^{-1}$±2 $cm^{-1}$, 1331.3 $cm^{-1}$±2 $cm^{-1}$, 1374.6 $cm^{-1}$±2 $cm^{-1}$, 1515.7 $cm^{-1}$±2 $cm^{-1}$, 1636.3 $cm^{-1}$±2 $cm^{-1}$, 1665.0 $cm^{-1}$±2 $cm^{-1}$, 1712.1 $cm^{-1}$±2 $cm^{-1}$, 1737.5 $cm^{-1}$±2 $cm^{-1}$, 2953.3 $cm^{-1}$±2 $cm^{-1}$, 2982.6 $cm^{-1}$±2 $cm^{-1}$, 3069.5 $cm^{-1}$±2 $cm^{-1}$, and 3127.5 $cm^{-1}$±2 $cm^{-1}$.

According to one exemplary embodiment, the succinic acid cocrystal Form I of the compound represented by Formula (I-B) has Raman spectrum peaks at 676.4 $cm^{-1}$±2 $cm^{-1}$, 748.1 $cm^{-1}$±2 $cm^{-1}$, 1025.2 $cm^{-1}$±2 $cm^{-1}$, 1374.6 $cm^{-1}$±2 $cm^{-1}$, 1515.7 $cm^{-1}$±2 $cm^{-1}$, and 1665.0 $cm^{-1}$±2 $cm^{-1}$.

Example 12

750 μL of ethyl acetate was added to 150 mg of Compound (I-0115), and the mixture was stirred overnight at 60° C. Solids were collected by filtration and dried to obtain a crystalline form of anhydride Form I of the compound represented by Formula (I-B). With regard to the crystalline form of anhydride Form I of the compound represented by Formula (I-B), the molecular structure (amino form/imino form) was not identified.

Figure 11:
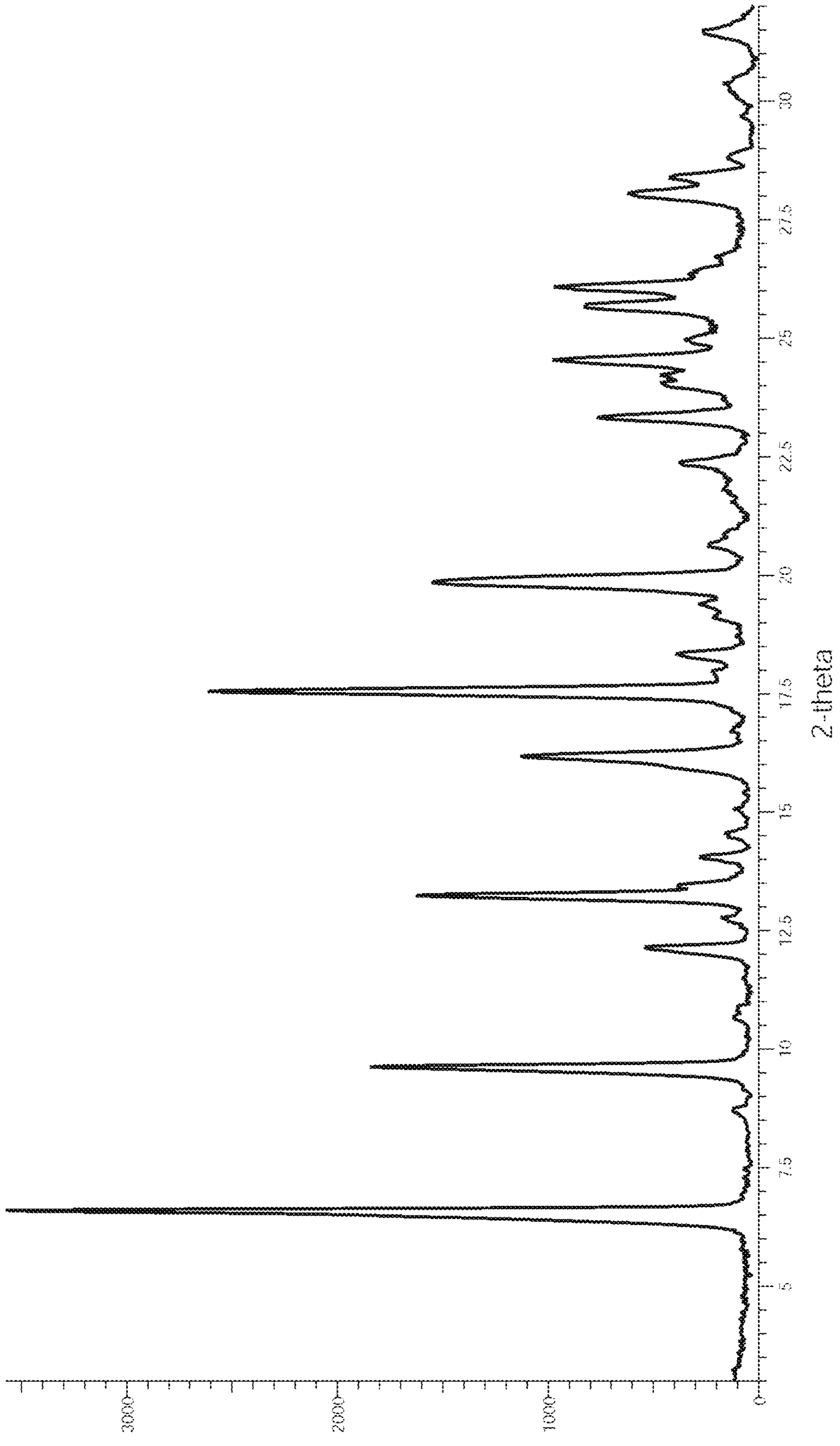
FIG. 11 shows a powder X-ray diffraction pattern of a crystalline form of anhydride Form I (Form I) of the compound represented by Formula (I-B). The axis of abscissa represents 2θ(°), and the axis of ordinate represents the intensity (Count).

The results of powder X-ray diffraction of the crystalline form of anhydride Form I of the compound represented by Formula (I-B) are shown in FIG. 11.

In the powder X-ray diffraction pattern, peaks were observed at the diffraction angles (2θ): 6.6±0.2°, 9.6±0.2°, 12.2±0.2°, 13.2±0.2°, 16.2±0.2°, 17.5±0.2°, 19.8±0.2°, 23.3±0.2°, 24.5±0.2°, and 26.1±0.2°.

Regarding the powder X-ray diffraction peaks, the peaks at the diffraction angles (2θ): 6.6±0.2°, 9.6±0.2°, 13.2±0.2°, 17.5±0.2°, and 19.8±0.2° are particularly characteristic as anhydride Form I of the compound represented by Formula (I-B).

Figure 12:
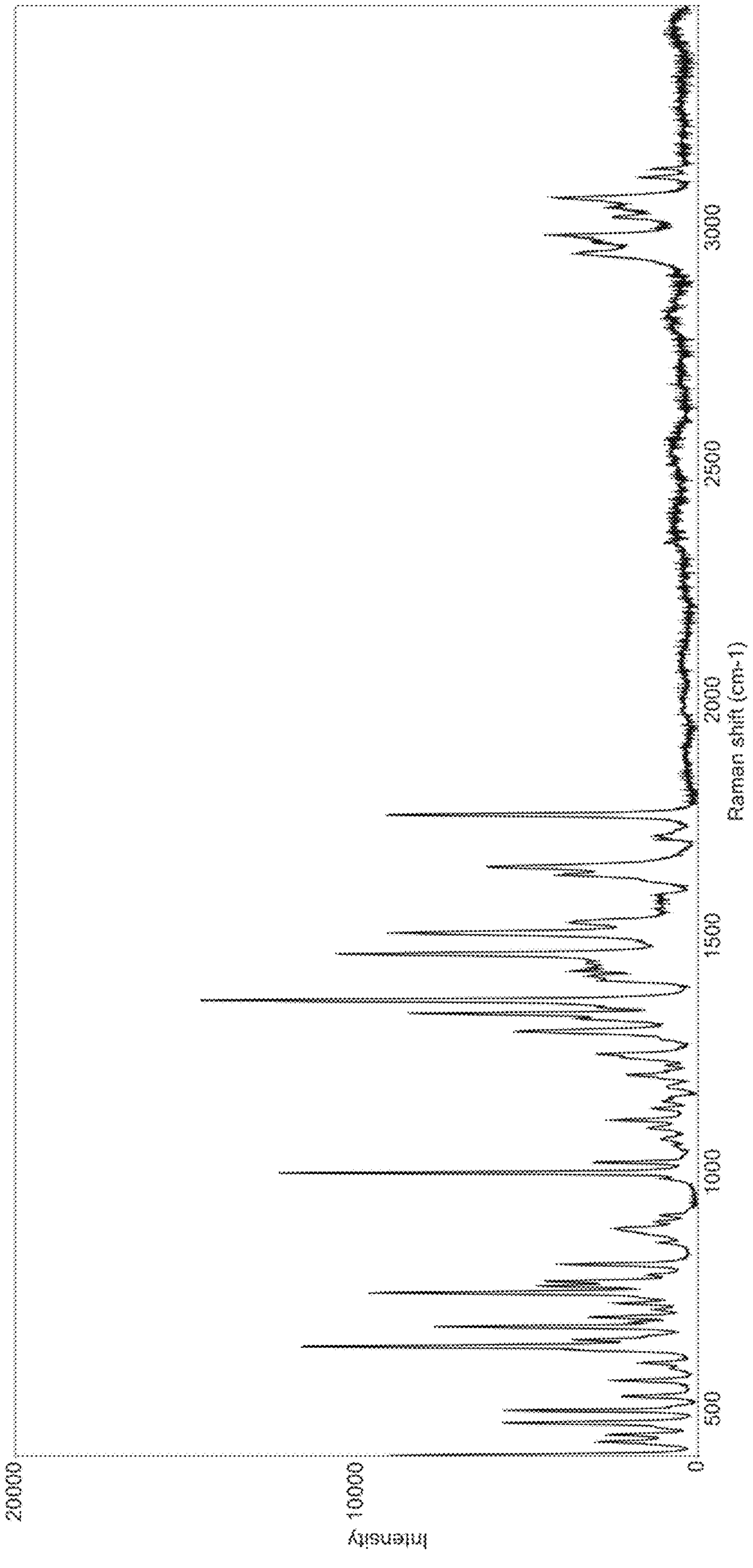
FIG. 12 shows the Raman spectrum of the crystalline form of anhydride Form (Form I) of the compound represented by Formula (I-B). The axis of abscissa represents Raman shift ($cm^{-1}$), and the axis of ordinate represents the peak intensity.

The results of Raman spectroscopy of the crystal of anhydride Form I of the compound represented by Formula (I-B) are shown in FIG. 12.

Major Raman spectrum peaks were observed at 630.4 $cm^{-1}$±2 $cm^{-1}$, 672.8 $cm^{-1}$±2 $cm^{-1}$, 744.6 $cm^{-1}$±2 $cm^{-1}$, 805.4 $cm^{-1}$±2 $cm^{-1}$, 997.8 $cm^{-1}$±2 $cm^{-1}$, 1020.7 $cm^{-1}$±2 $cm^{-1}$, 1297.9 $cm^{-1}$±2 $cm^{-1}$, 1335.2 $cm^{-1}$±2 $cm^{-1}$, 1362.0 $cm^{-1}$±2 $cm^{-1}$, 1461.0 $cm^{-1}$±2 $cm^{-1}$, 1505.4 $cm^{-1}$±2 $cm^{-1}$, 1527.5 $cm^{-1}$±2 $cm^{-1}$, 1629.1 $cm^{-1}$±2 $cm^{-1}$, 1645.9 $cm^{-1}$±2 $cm^{-1}$, 1755.7 $cm^{-1}$±2 $cm^{-1}$, 2943.3 $cm^{-1}$±2 $cm^{-1}$, 2982.1 $cm^{-1}$±2 $cm^{-1}$, 3060.5 $cm^{-1}$±2 $cm^{-1}$, 3104.7 $cm^{-1}$±2 $cm^{-1}$, and 3123.2 $cm^{-1}$±2 $cm^{-1}$.

According to an exemplary embodiment, the crystal of anhydride Form I of the compound represented by Formula (I-B) has Raman spectrum peaks at 630.4 $cm^{-1}$±2 $cm^{-1}$, 744.6 $cm^{-1}$±2 $cm^{-1}$, 997.8 $cm^{-1}$±2 $cm^{-1}$, 1362.0 $cm^{-1}$±2 $cm^{-1}$, 1461.0 $cm^{-1}$±2 $cm^{-1}$, 1505.4 $cm^{-1}$±2 $cm^{-1}$, and 1755.7 $cm^{-1}$±2 $cm^{-1}$.

Example 13

To 95 mg of Compound (I-0115), 187 μL (1.05 eq) of a 1 mol/L aqueous solution of sodium hydroxide and 1 mL of acetonitrile were added, and the solvent was evaporated to dryness. 100 μL of acetonitrile was added to 5 mg of the obtained solids, and the mixture was stirred overnight at 25° C. Solids were collected by filtration and dried to obtain a crystal of sodium salt Form I of the compound represented by Formula (I-B). With regard to the crystal of sodium salt Form I of the compound represented by Formula (I-B), the molecular structure (amino form/imino form) was not identified.

Figure 13:
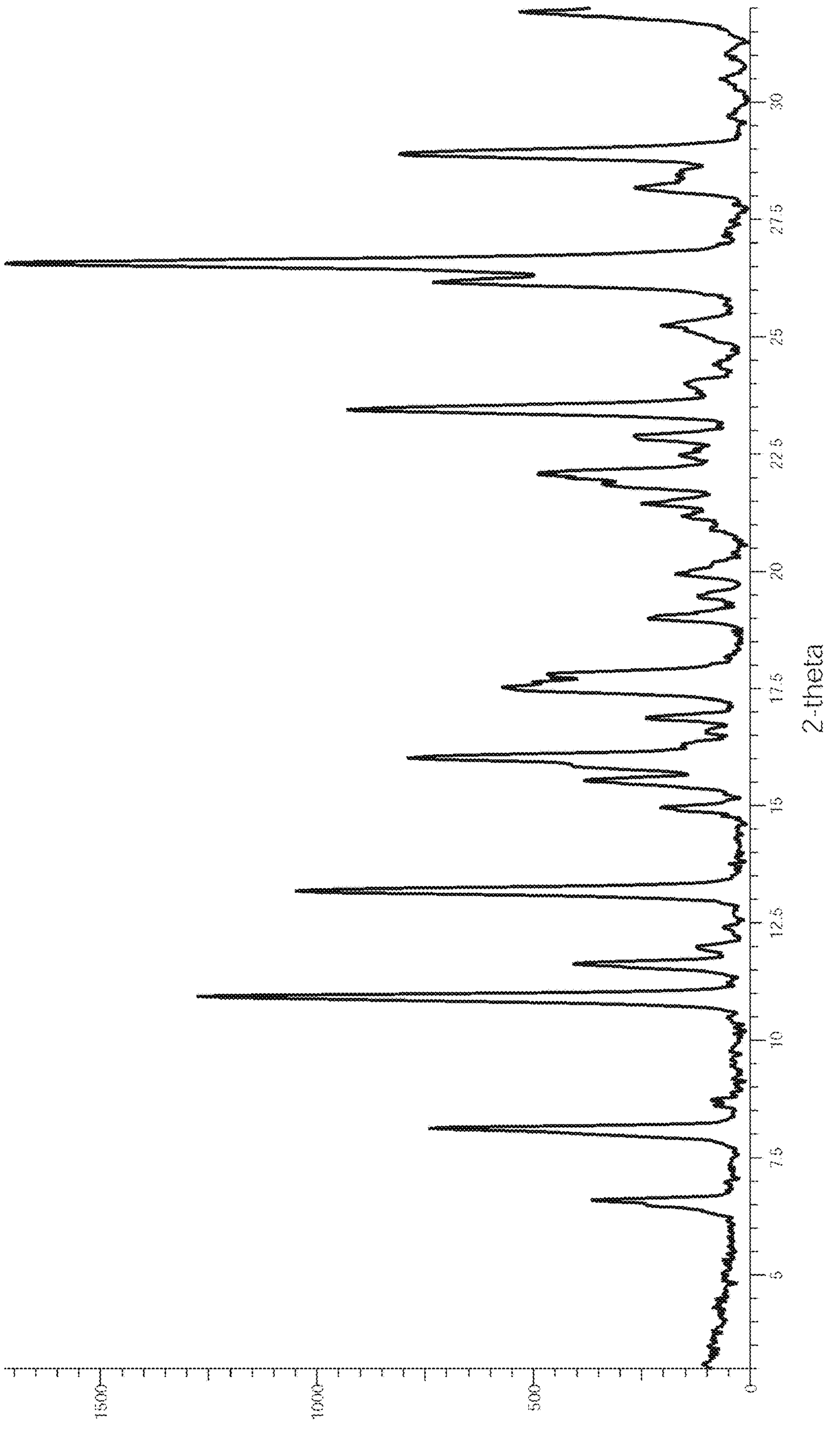
FIG. 13 shows a powder X-ray diffraction pattern of a crystalline form of sodium salt Form I (Form I) of the compound represented by Formula (I-B). The axis of abscissa represents 2θ(°), and the axis of ordinate represents the intensity (Count).

The results of powder X-ray diffraction of the crystal of sodium salt Form I of the compound represented by Formula (I-B) are shown in FIG. 13.

In the powder X-ray diffraction pattern, peaks were observed at the diffraction angles (2θ): 6.6±0.2°, 8.1±0.2°, 10.9±0.2°, 11.6±0.2°, 13.2±0.2°, 16.0±0.2°, 22.1±0.2°, 23.4±0.2°, 26.6±0.2°, and 28.9±0.2°.

Regarding the powder X-ray diffraction peaks, the peaks at the diffraction angles (2θ): 8.1±0.2°, 10.9±0.2°, 13.2±0.2°, 23.4±0.2°, and 26.6±0.2° are particularly characteristic as the crystal of sodium salt Form I of the compound represented by Formula (I-B).

Figure 14:
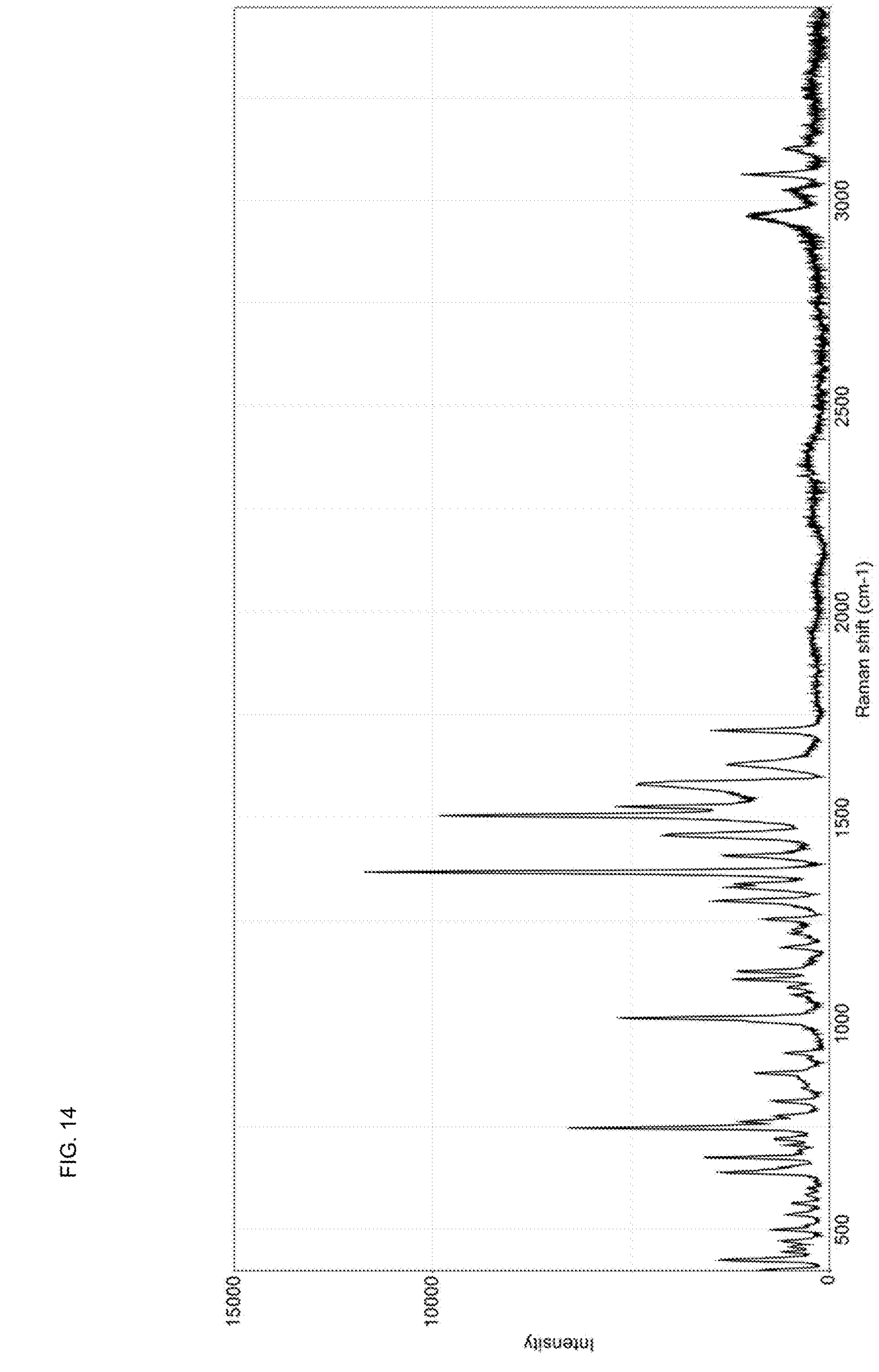
FIG. 14 shows the Raman spectrum of the crystalline form of sodium salt Form I (Form I) of the compound represented by Formula (I-B). The axis of abscissa represents Raman shift ($cm^{-1}$), and the axis of ordinate represents the peak intensity.

The results of Raman spectroscopy of the crystal of sodium salt Form I of the compound represented by Formula (I-B) are shown in FIG. 14.

Major Raman spectrum peaks were observed at 638.4 $cm^{-1}$±2 $cm^{-1}$, 675.1 $cm^{-1}$±2 $cm^{-1}$, 746.8 $cm^{-1}$±2 $cm^{-1}$, 1013.0 $cm^{-1}$, 1106.9 $cm^{-1}$±2 $cm^{-1}$, 1126.2 $cm^{-1}$±2 $cm^{-1}$, 1299.0 $cm^{-1}$±2 $cm^{-1}$, 1367.2 $cm^{-1}$±2 $cm^{-1}$, 1407.1 $cm^{-1}$±2 $cm^{-1}$, 1457.0 $cm^{-1}$±2 $cm^{-1}$, 1504.4 $cm^{-1}$±2 $cm^{-1}$, 1526.5 $cm^{-1}$±2 $cm^{-1}$, 1581.3 $cm^{-1}$±2 $cm^{-1}$, 1629.1 $cm^{-1}$±2 $cm^{-1}$, 1711.8 $cm^{-1}$±2 $cm^{-1}$, 2959.1 $cm^{-1}$±2 $cm^{-1}$, 3062.0 $cm^{-1}$±2 $cm^{-1}$, and 3125.5 $cm^{-1}$±2 $cm^{-1}$.

According to one exemplary embodiment, the crystal of sodium salt Form I of the compound represented by Formula (I-B) has Raman spectrum peaks at 746.8 $cm^{-1}$±2 $cm^{-1}$, 1013.0 $cm^{-1}$±2 $cm^{-1}$, 1367.2 $cm^{-1}$±2 $cm^{-1}$, 1504.4 $cm^{-1}$±2 $cm^{-1}$, 1526.5 $cm^{-1}$±2 $cm^{-1}$, and 1581.3 $cm^{-1}$±2 $cm^{-1}$.

Figure 15:
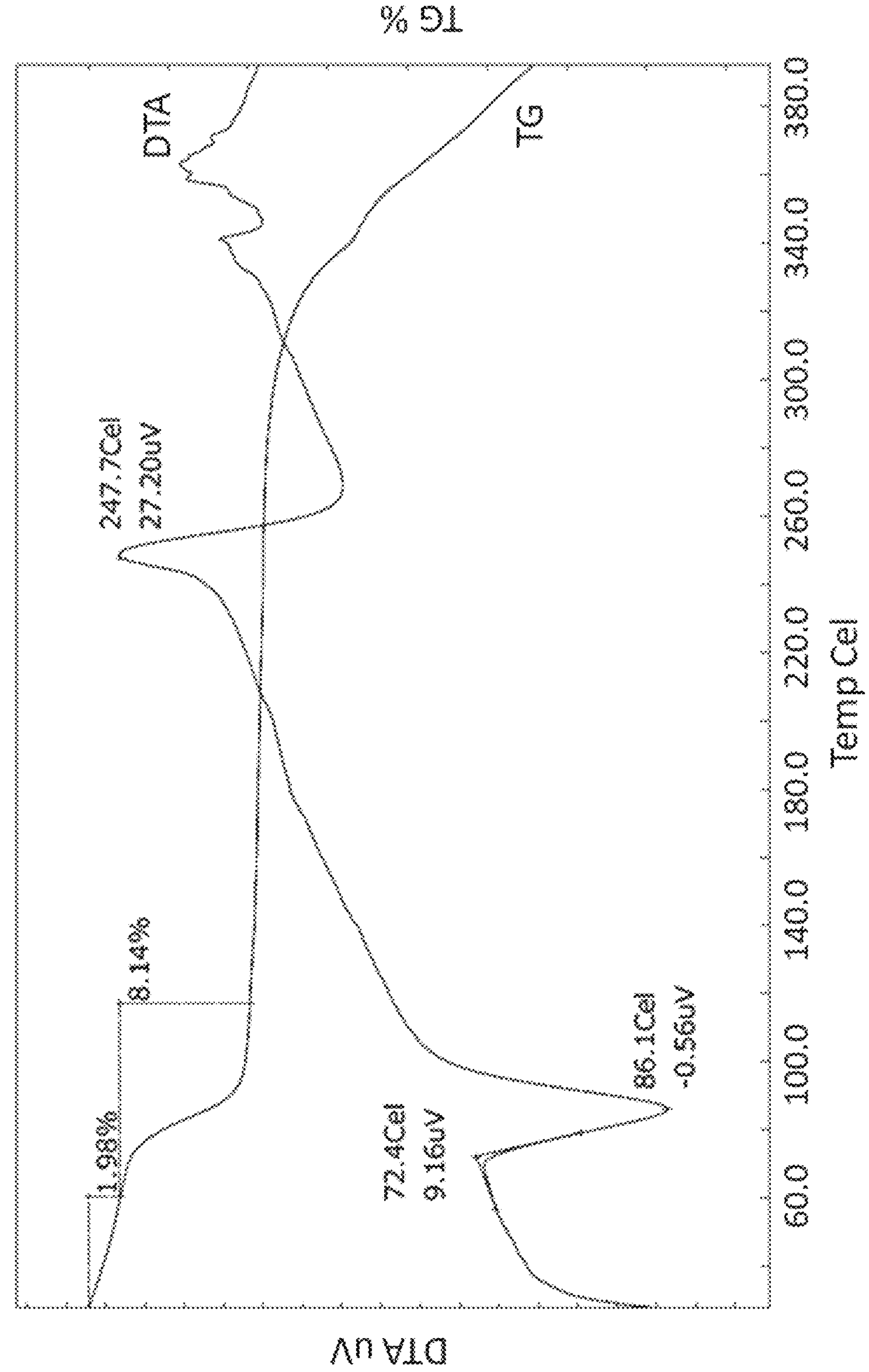
FIG. 15 shows results of a TG/DTA analysis of a crystalline form of sodium salt Form I (Form I) of the compound represented by Formula (I-B). The axis of ordinate represents the heat flow (μV) or the change in weight (%), and the axis of abscissa represents temperature (CC). Cel in the diagram means degree Celsius (° C.).

The results of simultaneous differential thermal analysis and thermogravimetric analysis (TG/DTA) of the crystal of sodium salt Form I of the compound represented by Formula (I-B) are shown in FIG. 15. As a result, a weight loss of 8.1% accompanied by an endothermic peak was confirmed from about 72° C. to about 105° C.

From the above-described measurement results, it is expected that the crystal of sodium salt Form I of the compound represented by Formula (I-B) is a crystal including 2.5 to 3 water equivalents of water.

Biological Test Examples for the compounds of the present invention will be described below.

It is desirable that the compounds represented by Formula (I), Formula (I'), and Formula (I'') according to the present invention are compounds having coronavirus 3CL protease inhibitory activity and inhibiting coronavirus 3CL proteases.

Specifically, in the evaluation method described below, the $IC_{50}$ is preferably 50 μM or less, more preferably 1 μM or less, and even more preferably 100 nM or less.

Test Example 1: Inhibitory Activity of Cytopathic Effect (CPE) in Vero E6 Cells Expressing Human TMPRSS2 (Vero E6/TMPRSS2 Cells)

<Operational Procedure>

Dilution and Dispensing of Sample to be Tested

The sample to be tested is diluted in advance to an appropriate concentration with DMSO, and a 2- to 5-fold series of serial dilutions is prepared and then dispensed into a 384-well plate.

Dilution and Dispensing of Cells and SARS-CoV-2

VeroE6/TMPRSS2 cells (JCRB1819, $5\times10^3$ cells/well) and SARS-CoV-2 (100-300 $TCID_{50}$/well) are mixed in a medium (MEM, 2% FBS, penicillin-streptomycin), the mixture is dispensed into the wells in which the sample to be tested has been introduced, and then the cells are cultured for 3 days in a $CO_2$ incubator.

Dispensing of CellTiter-Glo (Registered Trademark) 2.0 and Measurement of Luminescence Signals The plate that has been cultured for 3 days is returned to room temperature, subsequently CellTiter-Glo (registered trademark) 2.0 is dispensed into each well, and the plate is mixed using a plate mixer. The plate is left to stand for a certain time, and then the luminescence signals (Lum) is measured with a plate reader.

<Calculation of Each Measurement Item Value>

Calculation of 50% SARS-CoV-2 Infected Cell Death Inhibitory Concentration ($EC_{50}$)

When x denotes the logarithmic value of the compound concentration and y denotes % Efficacy, the inhibition curve is approximated by the following Logistic regression equation, and the value of x when y=50(%) is inputted is calculated as $EC_{50}$.

$$y=\min+(\max-\min)/\{1+(X50/x)\hat{}\mathrm{Hill}\}$$

$$\%\ \mathrm{Efficacy}=\{(\mathrm{Sample}-\mathrm{virus\ control})/(\mathrm{cell\ control}-\mathrm{virus\ control})\}*100\%$$

cell control: the average of Lum of cell control wells virus control: the average of Lum of virus control wells min: lower limit value of y-axis, max: upper limit value of y-axis, X50: x-coordinates of inflection point, Hill: slope of curve at midpoint between min and max The compounds of the present invention were tested essentially as described above. The results are shown in the following tables.

Meanwhile, regarding the $EC_{50}$ value, a value of less than 1 μM is denoted by "A", and a value of 1 μM or more and less than 10 μM is denoted by "B".

TABLE 197

| Compound No. | EC50 [μM] |
|---|---|
| I-0031 | 4.06 |
| I-0110 | 0.321 |
| I-0113 | 0.177 |
| I-0115 | 0.328 |
| I-0180 | 6.41 |
| I-0237 | 3.39 |
| I-0239 | 0.225 |
| I-0247 | 3.54 |
| I-0281 | 4.18 |
| I-0288 | 0.747 |

TABLE 197-continued

| Compound No. | EC50 [μM] |
|---|---|
| I-0318 | 1.36 |
| I-0329 | 5.10 |
| I-0339 | 8.00 |
| I-0351 | 0.0747 |
| I-0353 | 0.306 |
| I-0354 | 0.107 |
| I-0355 | 0.339 |
| I-0358 | 7.45 |
| I-0361 | 0.131 |
| I-0377 | 0.0729 |
| I-0383 | 0.0960 |
| I-0390 | 3.16 |
| I-0391 | 0.460 |
| I-0421 | 0.450 |
| I-0426 | 1.03 |
| I-0433 | 0.720 |
| I-0444 | 3.94 |
| I-0457 | 5.30 |
| I-0465 | 3.27 |
| I-0480 | 0.0726 |
| I-0481 | 0.0432 |
| I-0482 | 0.385 |
| I-0483 | 0.395 |
| II-0001 | 0.466 |
| II-0003 | 17.8 |
| II-0010 | 0.940 |
| II-0014 | 22.1 |
| II-0015 | 0.0350 |
| II-0034 | 0.234 |
| II-0036 | 0.355 |
| II-0043 | 0.232 |
| II-0045 | 0.218 |
| II-0055 | 0.180 |
| II-0074 | 0.248 |
| II-0087 | 0.0690 |
| II-0089 | 0.182 |
| II-0090 | 0.355 |
| II-0093 | 0.487 |
| II-0109 | 0.798 |
| II-0111 | 1.91 |
| II-0118 | 0.121 |
| II-0119 | 0.183 |
| II-0120 | 0.127 |
| II-0125 | 0.220 |
| II-0130 | 0.0950 |
| II-0132 | 49.8 |
| II-0163 | 0.342 |
| II-0164 | 0.195 |
| II-0173 | 0.272 |
| II-0192 | 0.454 |
| II-0223 | 22.5 |
| II-0226 | 2.77 |
| II-0228 | 5.00 |
| II-0233 | 0.0650 |
| II-0241 | 1.39 |
| II-0255 | 1.52 |
| II-0257 | 9.14 |
| II-0258 | 7.87 |
| II-0259 | 36.3 |
| II-0272 | 1.59 |
| II-0273 | 6.60 |
| II-0275 | 7.28 |
| II-0278 | 0.170 |
| II-0282 | 0.260 |
| II-0284 | 0.184 |
| II-0288 | 2.40 |
| II-0289 | 16.0 |
| II-0290 | 0.210 |
| II-0292 | 0.434 |
| II-0299 | 0.202 |
| II-0304 | 0.213 |
| II-0306 | 0.410 |
| II-0329 | 11.5 |
| II-0330 | 42.2 |
| II-0332 | 0.0540 |
| II-0334 | 0.620 |
| II-0335 | 0.241 |

TABLE 197-continued

| Compound No. | EC50 [μM] |
|---|---|
| II-0343 | 4.14 |
| II-0347 | 0.190 |
| II-0369 | 1.16 |
| II-0370 | 28.9 |
| II-0371 | 13.3 |
| II-0372 | 6.52 |
| II-0375 | 21.6 |
| II-0376 | 7.13 |
| II-0377 | 0.0490 |
| II-0389 | 4.40 |
| II-0392 | 20.8 |
| II-0393 | 6.08 |
| II-0394 | 44.9 |
| II-0401 | 2.33 |
| II-0407 | 15.0 |
| II-0410 | 0.201 |
| II-0415 | 0.870 |
| II-0418 | 6.24 |
| II-0422 | 0.290 |
| II-0425 | 5.85 |
| II-0455 | 0.750 |
| II-0460 | 19.0 |
| II-0482 | 44.5 |
| II-0483 | 20.9 |
| II-0484 | 14.2 |
| II-0490 | 8.70 |
| II-0493 | 0.0680 |
| II-0494 | 0.878 |
| II-0499 | 0.680 |
| II-0521 | 0.220 |
| II-0522 | 15.0 |
| II-0523 | 0.240 |
| II-0525 | 0.533 |
| II-0543 | 0.0870 |
| II-0545 | 0.750 |
| II-0548 | 0.533 |
| II-0550 | 6.42 |
| II-0559 | 0.246 |
| II-0566 | 0.898 |
| II-0567 | 0.650 |
| II-0568 | 0.132 |
| II-0569 | 0.419 |
| II-0570 | 0.600 |
| II-0571 | 0.190 |
| II-0572 | 0.925 |
| II-0573 | 0.340 |
| II-0574 | 0.200 |
| II-0576 | 0.530 |
| II-0577 | 0.0850 |
| II-0579 | 0.0670 |
| II-0584 | 0.750 |
| II-0595 | 8.22 |
| II-0596 | 0.0620 |
| II-0604 | 9.76 |

TABLE 198

| Compound No. | EC50 [μM] | Compound No. | EC50 [μM] |
|---|---|---|---|
| II-0608 | 0.487 | II-0609 | 2.04 |

TABLE 199

| Compound No. | EC50 |
|---|---|
| I-0007 | B |
| I-0008 | B |
| I-0009 | A |
| I-0011 | A |
| I-0012 | B |

TABLE 199-continued

| Compound No. | EC50 |
|---|---|
| I-0013 | B |
| I-0016 | A |
| I-0019 | B |
| I-0020 | B |
| I-0025 | B |
| I-0026 | B |
| I-0029 | A |
| I-0031 | B |
| I-0033 | A |
| I-0035 | A |
| I-0038 | A |
| I-0042 | B |
| I-0064 | B |
| I-0066 | B |
| I-0069 | B |
| I-0077 | A |
| I-0079 | B |
| I-0081 | A |
| I-0084 | B |
| I-0094 | B |
| I-0095 | B |
| I-0100 | B |
| I-0111 | B |
| I-0112 | A |
| I-0114 | B |
| I-0116 | B |
| I-0128 | A |
| I-0129 | B |
| I-0132 | A |
| I-0133 | A |
| I-0134 | A |
| I-0135 | B |
| I-0136 | B |
| I-0447 | B |
| I-0450 | B |
| I-0451 | B |
| I-0452 | B |
| I-0454 | B |
| I-0455 | B |
| I-0456 | B |
| I-0459 | B |
| I-0460 | B |
| I-0461 | B |
| I-0462 | B |
| I-0465 | B |
| I-0466 | A |
| I-0467 | B |
| I-0468 | B |
| I-0470 | B |
| I-0471 | B |
| I-0472 | A |
| II-0002 | B |
| II-0005 | B |
| II-0006 | B |
| II-0007 | A |
| II-0008 | B |
| II-0011 | B |
| II-0017 | A |
| II-0018 | B |
| II-0020 | B |
| II-0022 | A |
| II-0023 | A |
| II-0024 | B |
| II-0025 | 8 |
| II-0027 | A |
| II-0028 | A |
| II-0029 | B |
| II-0030 | A |
| II-0031 | B |
| II-0032 | A |
| II-0035 | A |
| II-0184 | B |
| II-0185 | A |
| II-0186 | B |
| II-0187 | A |
| II-0188 | A |
| II-0189 | B |

TABLE 199-continued

| Compound No. | EC50 |
|---|---|
| II-0190 | B |
| II-0191 | A |
| II-0193 | B |
| II-0194 | A |
| II-0195 | B |
| II-0196 | A |
| II-0197 | A |
| II-0198 | A |
| II-0199 | A |
| II-0200 | B |
| II-0201 | A |
| II-0202 | B |
| II-0203 | A |
| II-0204 | B |
| II-0205 | B |
| II-0207 | B |
| II-0208 | B |
| II-0210 | B |
| II-0212 | A |
| II-0213 | B |
| II-0214 | B |
| II-0215 | B |
| II-0217 | B |
| II-0218 | B |
| II-0219 | B |
| II-0220 | B |
| II-0221 | B |
| II-0222 | A |
| II-0227 | A |
| II-0232 | A |
| II-0234 | A |
| II-0235 | B |
| II-0391 | B |
| II-0395 | A |
| II-0396 | A |
| II-0397 | A |
| II-0398 | A |
| II-0399 | A |
| II-0400 | B |
| II-0402 | A |
| II-0403 | A |
| II-0404 | A |
| II-0405 | A |
| II-0406 | A |
| II-0408 | B |
| II-0409 | B |
| II-0412 | B |
| II-0413 | B |
| II-0414 | B |
| II-0416 | B |
| II-0417 | B |
| II-0419 | A |
| II-0420 | A |
| II-0421 | A |
| II-0423 | B |
| II-0424 | B |
| II-0426 | A |
| II-0429 | B |
| II-0430 | B |
| II-0431 | A |
| II-0433 | A |
| II-0434 | A |
| II-0435 | B |
| II-0436 | A |
| II-0437 | A |
| II-0438 | B |
| II-0439 | A |
| II-0440 | B |
| II-0442 | A |
| II-0446 | B |

TABLE 200

| Compound No. | EC50 |
|---|---|
| I-0152 | A |
| I-0165 | B |
| I-0166 | A |
| I-0194 | B |
| I-0196 | B |
| I-0213 | B |
| I-0214 | A |
| I-0226 | B |
| I-0227 | B |
| I-0231 | B |
| I-0236 | A |
| I-0242 | A |
| I-0245 | B |
| I-0247 | B |
| I-0248 | B |
| I-0249 | B |
| I-0250 | B |
| I-0251 | B |
| I-0252 | B |
| I-0253 | B |
| I-0254 | B |
| I-0255 | A |
| I-0256 | B |
| I-0260 | B |
| I-0264 | B |
| I-0267 | B |
| I-0269 | B |
| I-0271 | B |
| I-0272 | A |
| I-0279 | B |
| I-0284 | A |
| I-0285 | B |
| I-0286 | B |
| I-0290 | B |
| I-0301 | A |
| I-0306 | B |
| I-0307 | A |
| I-0310 | B |
| II-0037 | B |
| II-0038 | B |
| II-0039 | B |
| II-0041 | B |
| II-0044 | A |
| II-0046 | A |
| II-0047 | A |
| II-0048 | A |
| II-0049 | A |
| II-0050 | A |
| II-0051 | B |
| II-0052 | B |
| II-0053 | A |
| II-0054 | A |
| II-0056 | B |
| II-0057 | B |
| II-0058 | A |
| II-0059 | B |
| II-0060 | B |
| II-0061 | B |
| II-0063 | B |
| II-0064 | B |
| II-0065 | A |
| II-0066 | B |
| II-0067 | A |
| II-0068 | A |
| II-0069 | B |
| II-0070 | B |
| II-0071 | A |
| II-0072 | B |
| II-0073 | B |
| II-0075 | A |
| II-0076 | A |
| II-0077 | A |
| II-0078 | A |
| II-0079 | A |
| II-0080 | B |
| II-0082 | B |
| II-0236 | A |

TABLE 200-continued

| Compound No. | EC50 |
|---|---|
| II-0237 | A |
| II-0238 | B |
| II-0239 | B |
| II-0240 | B |
| II-0242 | A |
| II-0243 | B |
| II-0244 | B |
| II-0245 | A |
| II-0246 | B |
| II-0247 | A |
| II-0249 | B |
| II-0250 | B |
| II-0251 | A |
| II-0252 | B |
| II-0253 | B |
| II-0254 | B |
| II-0260 | A |
| II-0261 | A |
| II-0262 | B |
| II-0263 | B |
| II-0264 | B |
| II-0265 | A |
| II-0267 | B |
| II-0269 | B |
| II-0270 | B |
| II-0271 | B |
| II-0279 | B |
| II-0281 | B |
| II-0283 | A |
| II-0285 | A |
| II-0286 | B |
| II-0287 | B |
| II-0291 | B |
| II-0294 | B |
| II-0295 | B |
| II-0296 | A |
| II-0297 | B |
| II-0448 | A |
| II-0449 | A |
| II-0450 | B |
| II-0452 | B |
| II-0453 | B |
| II-0454 | B |
| II-0458 | A |
| II-0459 | B |
| II-0461 | B |
| II-0462 | A |
| II-0463 | A |
| II-0464 | A |
| II-0466 | B |
| II-0468 | B |
| II-0469 | A |
| II-0475 | B |
| II-0477 | B |
| II-0478 | B |
| II-0479 | B |
| II-0485 | A |
| II-0486 | B |
| II-0487 | B |
| II-0489 | B |
| II-0491 | B |
| II-0492 | A |
| II-0495 | A |
| II-0496 | A |
| II-0497 | A |
| II-0498 | B |
| II-0500 | B |
| II-0501 | A |
| II-0503 | B |
| II-0504 | A |
| II-0505 | B |
| II-0506 | A |
| II-0507 | B |
| II-0508 | B |
| II-0509 | B |

TABLE 201

| Compound No. | EC50 |
|---|---|
| I-0316 | B |
| I-0318 | B |
| I-0320 | B |
| I-0321 | A |
| I-0330 | B |
| I-0331 | B |
| I-0332 | B |
| I-0335 | B |
| I-0339 | B |
| I-0344 | A |
| I-0346 | A |
| I-0348 | A |
| I-0349 | B |
| I-0350 | A |
| I-0352 | A |
| I-0355 | A |
| I-0357 | B |
| I-0359 | B |
| I-0364 | B |
| I-0365 | B |
| I-0366 | B |
| I-0368 | B |
| I-0369 | B |
| I-0370 | B |
| I-0372 | A |
| I-0374 | B |
| I-0378 | A |
| I-0379 | A |
| I-0380 | A |
| I-0381 | B |
| I-0382 | B |
| I-0384 | A |
| I-0385 | A |
| I-0390 | B |
| I-0392 | B |
| I-0400 | B |
| I-0401 | B |
| I-0402 | B |
| II-0084 | A |
| II-0088 | B |
| II-0092 | A |
| II-0094 | B |
| II-0095 | A |
| II-0096 | A |
| II-0097 | A |
| II-0098 | B |
| II-0099 | B |
| II-0100 | A |
| II-0101 | A |
| II-0102 | B |
| II-0104 | B |
| II-0105 | A |
| II-0106 | B |
| II-0107 | B |
| II-0108 | B |
| II-0110 | A |
| II-0112 | B |
| II-0114 | A |
| II-0115 | A |
| II-0116 | A |
| II-0117 | A |
| II-0121 | A |
| II-0122 | B |
| II-0123 | B |
| II-0126 | B |
| II-0127 | B |
| II-0128 | B |
| II-0129 | B |
| II-0131 | A |
| II-0140 | B |
| II-0144 | A |
| II-0154 | A |
| II-0156 | A |
| II-0158 | B |
| II-0159 | A |
| II-0160 | A |
| II-0298 | B |

TABLE 201-continued

| Compound No. | EC50 |
|---|---|
| II-0300 | B |
| II-0301 | A |
| II-0302 | B |
| II-0303 | A |
| II-0305 | B |
| II-0307 | B |
| II-0308 | A |
| II-0309 | B |
| II-0311 | B |
| II-0312 | A |
| II-0313 | A |
| II-0316 | B |
| II-0318 | A |
| II-0320 | A |
| II-0322 | B |
| II-0323 | A |
| II-0326 | B |
| II-0333 | A |
| II-0336 | A |
| II-0337 | A |
| II-0339 | A |
| II-0341 | B |
| II-0342 | B |
| II-0344 | B |
| II-0345 | A |
| II-0346 | A |
| II-0348 | B |
| II-0349 | B |
| II-0350 | B |
| II-0351 | A |
| II-0352 | A |
| II-0353 | B |
| II-0354 | B |
| II-0355 | A |
| II-0356 | B |
| II-0359 | B |
| II-0360 | B |
| II-0510 | B |
| II-0512 | B |
| II-0513 | A |
| II-0514 | B |
| II-0515 | B |
| II-0516 | B |
| II-0517 | B |
| II-0518 | B |
| II-0519 | B |
| II-0520 | B |
| II-0524 | B |
| II-0526 | B |
| II-0527 | A |
| II-0528 | A |
| II-0529 | A |
| II-0533 | B |
| II-0534 | B |
| II-0535 | A |
| II-0536 | B |
| II-0537 | B |
| II-0538 | B |
| II-0539 | B |
| II-0541 | A |
| II-0544 | A |
| II-0546 | A |
| II-0547 | A |
| II-0551 | A |
| II-0552 | A |
| II-0553 | B |
| II-0554 | B |
| II-0555 | B |
| II-0556 | B |
| II-0560 | B |
| II-0562 | B |
| II-0563 | B |
| II-0564 | A |
| II-0565 | B |
| II-0578 | B |

TABLE 202

| Compound No. | EC50 |
|---|---|
| I-0404 | B |
| I-0406 | B |
| I-0408 | B |
| I-0421 | A |
| I-0422 | B |
| I-0423 | B |
| I-0424 | B |
| I-0425 | B |
| I-0428 | A |
| I-0429 | A |
| I-0430 | A |
| I-0431 | A |
| I-0432 | B |
| I-0433 | A |
| I-0434 | B |
| I-0435 | B |
| I-0436 | A |
| I-0437 | B |
| I-0444 | B |
| II-0161 | A |
| II-0162 | A |
| II-0165 | A |
| II-0166 | A |
| II-0167 | A |
| II-0168 | A |
| II-0169 | A |
| II-0171 | A |
| II-0172 | A |
| II-0174 | A |
| II-0175 | A |
| II-0176 | A |
| II-0177 | A |
| II-0178 | A |
| II-0179 | B |
| II-0180 | A |
| II-0181 | A |
| II-0182 | A |
| II-0183 | A |
| II-0361 | A |
| II-0362 | A |
| II-0363 | A |
| II-0364 | A |
| II-0365 | A |
| II-0366 | A |
| II-0367 | A |
| II-0368 | B |
| II-0378 | B |
| II-0380 | B |
| II-0381 | A |
| II-0382 | A |
| II-0383 | A |
| II-0384 | B |
| II-0385 | A |
| II-0386 | B |
| II-0387 | A |
| II-0388 | A |
| II-0390 | B |
| II-0580 | A |
| II-0581 | A |
| II-0582 | A |
| II-0583 | A |
| II-0585 | B |
| II-0586 | A |
| II-0587 | A |
| II-0588 | A |
| II-0589 | B |
| II-0590 | A |
| II-0591 | A |
| II-0592 | B |
| II-0593 | B |
| II-0597 | A |
| II-0598 | A |
| II-0599 | A |
| II-0600 | A |
| II-0601 | A |
| II-0602 | A |

Reference Example 1

Compounds I-0679, I-0683, I-0685 and I-1603 of WO2012/020749A (Patent Document 1), and Compounds I-575 and I-580 of WO2013/089212A (Patent Document 2), and Compound I-066 of WO2010/099266A (Patent Document 3) were tested essentially as described in Test Example 1. The results are shown in the tables below.

TABLE 203

| | Patent Document 3<br>Compound I-066 | Patent Document 1<br>Compound I-1603 |
|---|---|---|
| Structure | 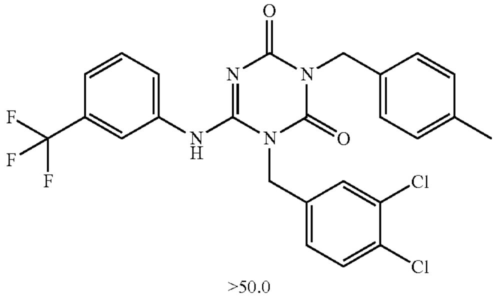 | 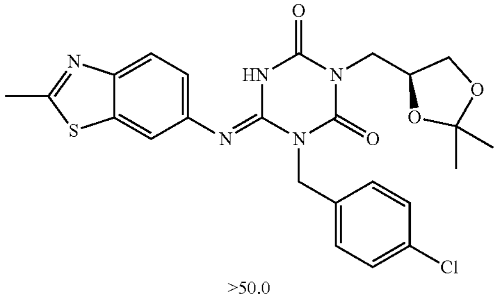 |
| EC50 [μM] | >50.0 | >50.0 |
| | Patent Document 1<br>Compound I-0683 | Patent Document 1<br>Compound I-0685 |
| Structure | 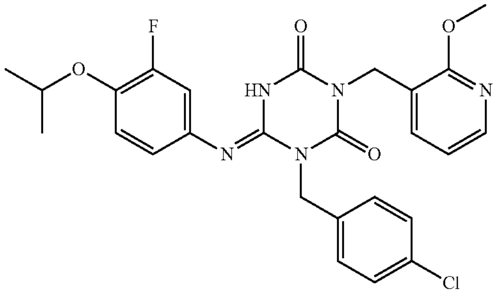 [SMILES: COc1ncccc1Cn1c(=O)[nH]/c(=N\c2ccc(OC(C)C)c(F)c2)n(Cc2ccc(Cl)cc2)c1=O] | 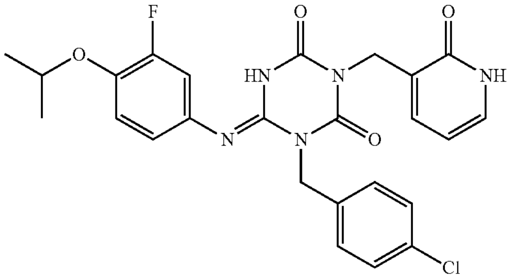 [SMILES: CC(C)Oc1ccc(/N=c2\[nH]c(=O)n(Cc3ccc[nH]c3=O)c(=O)n2Cc2ccc(Cl)cc2)cc1F] |
| EC50 [μM] | >50.0 | >50.0 |

TABLE 204

| | Patent Document 1<br>Compound I-0679 | Patent Document 2<br>Compound I-580 |
|---|---|---|
| Structure | 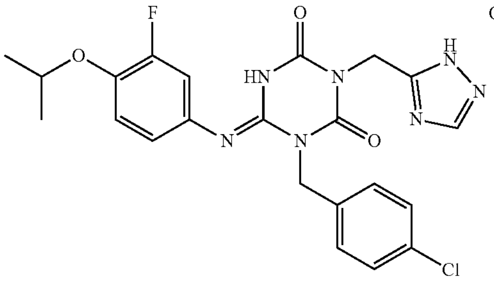 | 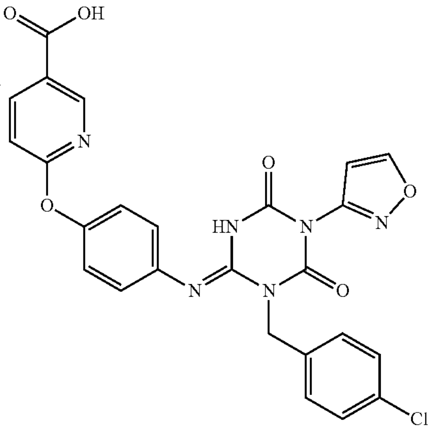 |
| EC50 [μM] | >50.0 | >50.0 |

TABLE 204-continued

| Patent Document 2<br>Compound I-575 | |
|---|---|
| Structure | 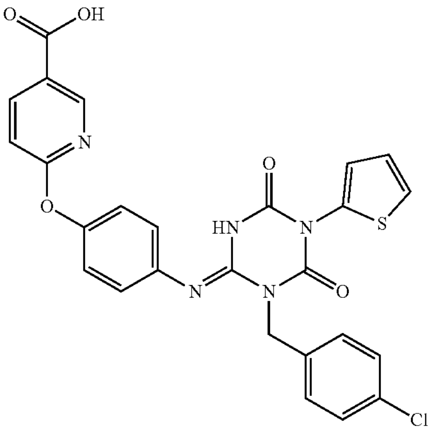 [SMILES: O=C(O)c1ccc(Oc2ccc(/N=c3\[nH]c(=O)n(-c4cccs4)c(=O)n3Cc3ccc(Cl)cc3)cc2)nc1] |
| EC50 [μM] | >50.0 |

Compounds I-0679, I-0683, I-0685 and I-1603 of WO2012/020749A (Patent Document 1), and Compounds I-575 and I-580 of WO2013/089212A (Patent Document 2), and Compound I-066 of WO2010/099266A (Patent Document 3) did not show coronavirus replication inhibitory activity at concentrations up to 50 μM.

Test Example 2: Inhibitory Activity Test Against SARS-CoV-2 3CL Proteases

<Materials>

Commercially Available Recombinant SARS-CoV-2 3CL Protease

Commercially Available Substrate Peptide

Dabcyl-Lys-Thr-Ser-Ala-Val-Leu-Gln-Ser-Gly-Phe-Arg-Lys-Met-Glu(Edans)-NH2 (SEQ ID NO: 1)

Internal Standard Peptide

Dabcyl-Lys-Thr-Ser-Ala-Val-Leu(13C6, 15N)-Gln (SEQ ID NO: 2)

Dabcyl-Lys-Thr-Ser-Ala-Val-Leu(13C6, 15N)-Gln can be synthesized with reference to documents (Atherton, E.; Sheppard, R. C., "In Solid Phase Peptide Synthesis, A Practical Approach", IRL Press at Oxford University Pres, 1989; Bioorg. Med. Chem., Vol. 5, No. 9, 1997, pp. 1883-1891; and the like). An example will be shown below.

H-Lys-Thr-Ser-Ala-Val-Leu(13C6, 15N)-Glu(resin)-OαOtBu (the Lys-side chain is Boc-protected, the Thr-side chain is protected with a tert-butyl group, the Ser-side chain is protected with a tert-butyl group, the C-terminal OH of Glu is protected with a tert-butyl group, and the carboxylic acid of the Glu-side chain is condensed into the resin) is synthesized by Fmoc solid-phase synthesis using a Rink amide resin. Regarding the modification of the N-terminal Dabcyl group, 4-dimethylaminoazobenzene-4'-carboxylic acid. (Dabcyl-OH) is condensed on the resin using EDC/HOBT. Final deprotection and cleavage from the resin are carried out by treatment with TFAIEDT=95:5. Thereafter, purification is performed by reverse phase HPLC.

RapidFire Cartridge C4 Type A

<Operational Procedure>

Preparation of Assay Buffer

In the present test, an assay buffer composed of 20 mM Tris-HCl, 100 mM sodium chloride, 1 mM EDTA, 10 mM DTT, and 0.01% BSA is used. For a compound with an $IC_{50}$ of 10 nM or less, an assay buffer composed of 20 mM Tris-HCl, 1 mM EDTA, 10 mM DTT, and 0.01% BSA is used.

Dilution and Dispensing of Sample to be Tested

The sample to be tested is diluted in advance to an appropriate concentration with DMSO, and a 2- to 5-fold series of serial dilutions is prepared and then dispensed into a 384-well plate.

Addition of Enzyme and Substrate, and Enzymatic Reaction

To a prepared compound plate, 8 μM substrate, and a 6 or 0.6 nM enzyme solution are added, and incubation is carried out for 3 to 5 hours at room temperature. Thereafter, a reaction stopping solution (0.067 μM Internal Standard, 0.1% formic acid, and 10% or 25% acetonitrile) is added to stop the enzymatic reaction.

Measurement of Reaction Product

The plate in which the reaction has been completed is measured using RapidFire System 360 and a mass analyzer (Agilent, 6550 iFunnel Q-TOF), or RapidFire System 365 and a mass analyzer (Agilent, 6495C Triple Quadrupole). Solution A (75% isopropanol, 15% acetonitrile, 5 mM ammonium formate) and solution B (0.01% trifluoroacetic acid, 0.09% formic acid) are used as a mobile phase at the measurement.

The reaction product detected by the mass analyzer is calculated using RapidFire Integrator or an equivalent program capable of analysis and is taken as Product area value. Furthermore, the Internal Standard that has been detected at the same time is also calculated and is designated as Internal Standard area value.

<Calculation of Each Measurement Item Value>

Calculation of P/IS

The area values obtained in the previous items are calculated by the following formula, and P/IS is calculated.

$$P/IS = \text{Product area value}/\text{Internal Standard area value}$$

Calculation of 50% SARS-CoV-2 3 CL Protease Inhibitory Concentration ($IC_{50}$)

When x denotes the logarithmic value of the compound concentration and y denotes % Inhibition, the inhibition curve is approximated by the following Logistic regression equation, and the value of x obtainable when y=50(%) is inputted is calculated as ICH.

$$y=\min+(ma-\min)/\{1+(X50/x)^{\wedge}\mathrm{Hill}\}$$

$$\%\ \mathrm{Inhibition}=\{1-(\mathrm{Sample}-\mathrm{Control}(-))/\mathrm{Control}(+)-\mathrm{Control}(-))\}*100$$

Control(−): the average of P/IS of enzyme inhibited condition wells

Control(+): the average of P/IS of DMSO control wells min: lower limit value of y-axis, max: upper limit value of y-axis, X50: x-coordinates of inflection point, Hill: slope of curve at midpoint between min and max The compounds of the present invention were tested essentially as described above. The results are shown in the following tables.

Incidentally, regarding the $IC_{50}$ value, a value of less than 0.1 μM is denoted by "A", a value of 0.1 μM or more and less than 1 μM is denoted by "B", and a value of 1 μM or more and less than 10 μM is denoted by "C".

TABLE 205

| Compound No. | IC50 [μM] |
|---|---|
| I-0031 | 0.13 |
| I-0033 | 5.6 |
| I-0035 | 3.5 |
| I-0038 | 1.3 |
| I-0048 | 0.44 |
| I-0083 | 1.8 |
| I-0102 | 0.85 |
| I-0106 | 1.9 |
| I-0110 | 0.0042 |
| I-0113 | 0.014 |
| I-0115 | 0.010 |
| I-0128 | 9.7 |
| I-0132 | 2.3 |
| I-0133 | 3.4 |
| I-0134 | 4.0 |
| I-0149 | 3.5 |
| I-0151 | 0.97 |
| I-0154 | 1.3 |
| I-0180 | 0.058 |
| I-0204 | 0.61 |
| I-0207 | 1.9 |
| I-0208 | 0.23 |
| I-0223 | 4.3 |
| I-0237 | 0.0042 |
| I-0239 | 0.0039 |
| I-0247 | 0.025 |
| I-0257 | 2.9 |
| I-0258 | 3.5 |
| I-0281 | 0.0038 |
| I-0288 | 0.0058 |
| I-0301 | 3.8 |
| I-0307 | 0.44 |
| I-0318 | 0.11 |
| I-0321 | 2.1 |
| I-0326 | 0.065 |
| I-0329 | 2.0 |
| I-0334 | 0.87 |
| I-0339 | 0.61 |
| I-0340 | 0.84 |
| I-0351 | 0.0043 |
| I-0353 | 0.0054 |
| I-0354 | 0.0050 |
| I-0396 | 3.1 |
| I-0397 | 0.73 |
| I-0403 | 0.31 |

TABLE 205-continued

| Compound No. | IC50 [μM] |
|---|---|
| I-0412 | 5.1 |
| I-0414 | 0.25 |
| I-0415 | 3.0 |
| I-0416 | 3.5 |
| I-0421 | 0.010 |
| I-0426 | 0.0063 |
| I-0433 | 0.010 |
| I-0438 | 0.74 |
| I-0444 | 0.0051 |
| I-0457 | 0.0072 |
| I-0465 | 0.0042 |
| I-0480 | 0.0065 |
| I-0481 | 0.0027 |
| I-0482 | 0.015 |
| I-0483 | 0.0098 |
| II-0001 | 0.0034 |
| II-0003 | 0.0060 |
| II-0010 | 0.019 |
| II-0014 | 2.4 |
| II-0015 | 0.0015 |
| II-0021 | 3.6 |
| II-0034 | 0.0073 |
| II-0036 | 0.0083 |
| II-0043 | 0.0058 |
| II-0045 | 0.0047 |
| II-0055 | 0.0045 |
| II-0074 | 0.0036 |
| II-0085 | 9.2 |
| II-0086 | 3.4 |
| II-0087 | 0.0025 |
| II-0089 | 0.0036 |
| II-0090 | 0.016 |
| II-0093 | 0.012 |
| II-0109 | 0.040 |
| II-0111 | 0.078 |
| II-0118 | 0.0045 |
| II-0119 | 0.0089 |
| II-0120 | 0.0090 |
| II-0124 | 3.3 |
| II-0223 | 0.78 |
| II-0224 | 1.9 |
| II-0225 | 2.7 |
| II-0226 | 0.13 |
| II-0227 | 0.63 |
| II-0228 | 0.24 |
| II-0229 | 0.25 |
| II-0229 | 0.25 |
| II-0230 | 0.55 |
| II-0231 | 0.88 |
| II-0232 | 3.7 |
| II-0233 | 0.0015 |
| II-0241 | 0.024 |
| II-0255 | 0.10 |
| II-0256 | 0.16 |
| II-0257 | 0.97 |
| II-0258 | 0.95 |
| II-0259 | 3.4 |
| II-0272 | 0.18 |
| II-0273 | 0.36 |
| II-0274 | 3.0 |
| II-0275 | 0.36 |
| II-0278 | 0.0031 |
| II-0282 | 0.0088 |
| II-0284 | 0.0092 |
| II-0288 | 0.099 |
| II-0289 | 0.24 |
| II-0290 | 0.0035 |
| II-0292 | 0.0039 |
| II-0299 | 0.0033 |
| II-0304 | 0.0045 |
| II-0306 | 0.0051 |
| II-0327 | 1.5 |
| II-0329 | 0.14 |
| II-0330 | 3.6 |
| II-0332 | 0.0020 |
| II-0334 | 0.0028 |
| II-0335 | 0.0032 |

TABLE 205-continued

| Compound No. | IC50 [μM] |
|---|---|
| II-0343 | 0.31 |
| II-0347 | 0.0070 |
| II-0369 | 0.63 |
| II-0370 | 0.52 |
| II-0389 | 0.045 |
| II-0392 | 1.0 |
| II-0393 | 3.1 |
| II-0394 | 3.9 |
| II-0401 | 0.29 |
| II-0407 | 0.0038 |
| II-0410 | 0.0047 |
| II-0415 | 0.015 |
| II-0418 | 0.11 |
| II-0422 | 0.0064 |
| II-0425 | 0.26 |
| II-0428 | 0.84 |
| II-0455 | 0.019 |
| II-0460 | 0.022 |
| II-0481 | 0.10 |
| II-0482 | 0.41 |
| II-0483 | 1.8 |
| II-0484 | 3.4 |
| II-0490 | 0.083 |
| II-0492 | 1.0 |
| II-0493 | 0.0013 |
| II-0494 | 0.024 |
| II-0499 | 0.012 |
| II-0521 | 0.0034 |
| II-0522 | 0.0041 |
| II-0523 | 0.011 |
| II-0525 | 0.016 |
| II-0543 | 0.0028 |
| II-0545 | 0.0086 |
| II-0548 | 0.014 |
| II-0550 | 1.1 |
| II-0559 | 0.0064 |
| II-0566 | 0.027 |
| II-0567 | 0.0088 |
| II-0568 | 0.0021 |
| II-0569 | 0.0042 |
| II-0570 | 0.0044 |
| II-0571 | 0.0054 |
| II-0572 | 0.0056 |
| II-0573 | 0.0061 |
| II-0574 | 0.0092 |
| II-0576 | 0.017 |

TABLE 206

| Compound No. | IC50 [μM] |
|---|---|
| I-0355 | 0.0087 |
| I-0358 | 0.12 |
| I-0361 | 0.0091 |
| I-0377 | 0.0080 |
| I-0383 | 0.0034 |
| I-0390 | 0.0040 |
| I-0391 | 0.0076 |
| II-0125 | 0.0048 |
| II-0130 | 0.0019 |
| II-0132 | 0.0025 |
| II-0163 | 0.0088 |
| II-0164 | 0.0090 |
| II-0173 | 0.015 |
| II-0192 | 0.037 |
| II-0371 | 0.54 |
| II-0372 | 3.4 |
| II-0373 | 0.43 |
| II-0374 | 3.5 |
| II-0375 | 3.8 |
| II-0376 | 1.0 |
| II-0377 | 0.0030 |
| II-0577 | 0.0011 |

TABLE 206-continued

| Compound No. | IC50 [μM] |
|---|---|
| II-0579 | 0.0021 |
| II-0584 | 0.0048 |
| II-0594 | 0.27 |
| II-0595 | 0.53 |
| II-0596 | 0.0016 |
| II-0604 | 0.47 |

TABLE 207

| Compound No. | IC50 [μM] |
|---|---|
| II-0608 | 0.019 |
| II-0609 | 0.12 |
| II-0643 | 1.0 |
| II-0644 | 3.5 |

TABLE 208

| Compound No. | IC50 |
|---|---|
| I-0001 | B |
| I-0005 | A |
| I-0006 | A |
| I-0007 | A |
| I-0008 | A |
| I-0009 | A |
| I-0010 | A |
| I-0011 | A |
| I-0012 | A |
| I-0013 | A |
| I-0016 | A |
| I-0019 | A |
| I-0020 | A |
| I-0025 | A |
| I-0026 | A |
| I-0027 | A |
| I-0029 | A |
| I-0031 | B |
| I-0033 | C |
| I-0035 | C |
| I-0038 | C |
| I-0042 | A |
| I-0048 | B |
| I-0056 | A |
| I-0063 | A |
| I-0064 | A |
| I-0066 | A |
| I-0069 | A |
| I-0072 | A |
| I-0074 | A |
| I-0077 | A |
| I-0078 | A |
| I-0079 | A |
| I-0080 | A |
| I-0081 | A |
| I-0083 | C |
| I-0084 | A |
| I-0087 | A |
| I-0421 | A |
| I-0422 | A |
| I-0423 | A |
| I-0424 | A |
| I-0425 | A |
| I-0427 | A |
| I-0428 | A |
| I-0429 | A |
| I-0430 | A |
| I-0431 | A |
| I-0432 | A |
| I-0433 | A |

TABLE 208-continued

| Compound No. | IC50 |
|---|---|
| I-0434 | A |
| I-0435 | A |
| I-0436 | A |
| I-0437 | A |
| I-0438 | B |
| I-0439 | A |
| I-0440 | A |
| I-0441 | A |
| I-0442 | A |
| I-0443 | A |
| I-0444 | A |
| I-0445 | A |
| I-0446 | A |
| I-0447 | A |
| I-0448 | A |
| I-0449 | A |
| I-0450 | A |
| I-0451 | A |
| I-0445 | A |
| I-0446 | A |
| I-0447 | A |
| I-0448 | A |
| I-0449 | A |
| I-0450 | A |
| I-0451 | A |
| I-0452 | A |
| II-0149 | A |
| II-0150 | A |
| II-0151 | A |
| II-0152 | A |
| II-0153 | A |
| II-0154 | A |
| II-0155 | A |
| II-0156 | A |
| II-0158 | A |
| II-0159 | A |
| II-0160 | A |
| II-0161 | A |
| II-0162 | A |
| II-0165 | A |
| II-0166 | A |
| II-0167 | A |
| II-0168 | A |
| II-0169 | A |
| II-0170 | A |
| II-0171 | A |
| II-0172 | A |
| II-0174 | A |
| II-0175 | A |
| II-0176 | A |
| II-0177 | A |
| II-0178 | A |
| II-0179 | A |
| II-0180 | A |
| II-0181 | A |
| II-0182 | A |
| II-0183 | A |
| II-0184 | A |
| II-0185 | A |
| II-0186 | A |
| II-0187 | A |
| II-0188 | A |
| II-0189 | A |
| II-0190 | A |
| II-0380 | A |
| II-0381 | A |
| II-0382 | A |
| II-0383 | A |
| II-0384 | A |
| II-0385 | A |
| II-0386 | A |
| II-0387 | A |
| II-0388 | A |
| II-0390 | A |
| II-0391 | A |
| II-0395 | A |
| II-0396 | A |

TABLE 208-continued

| Compound No. | IC50 |
|---|---|
| II-0397 | A |
| II-0398 | A |
| II-0400 | A |
| II-0402 | A |
| II-0403 | A |
| II-0404 | A |
| II-0405 | A |
| II-0406 | A |
| II-0408 | A |
| II-0409 | A |
| II-0411 | A |
| II-0412 | A |
| II-0413 | A |
| II-0414 | A |
| II-0416 | A |
| II-0417 | A |
| II-0419 | A |
| II-0420 | A |
| II-0421 | A |
| II-0423 | A |
| II-0424 | A |
| II-0426 | A |
| II-0427 | A |
| II-0429 | A |
| II-0430 | A |

TABLE 209

| Compound No. | IC50 |
|---|---|
| I-0088 | A |
| I-0089 | A |
| I-0092 | A |
| I-0094 | A |
| I-0095 | A |
| I-0096 | A |
| I-0097 | A |
| I-0098 | A |
| I-0099 | A |
| I-0100 | A |
| I-0102 | B |
| I-0103 | A |
| I-0105 | A |
| I-0106 | C |
| I-0111 | A |
| I-0112 | A |
| I-0114 | A |
| I-0116 | A |
| I-0129 | A |
| I-0132 | C |
| I-0133 | C |
| I-0134 | C |
| I-0135 | B |
| I-0136 | A |
| I-0143 | A |
| I-0144 | A |
| I-0149 | C |
| I-0151 | B |
| I-0152 | A |
| I-0154 | C |
| I-0165 | A |
| I-0166 | A |
| I-0194 | A |
| I-0196 | A |
| I-0204 | B |
| I-0207 | C |
| I-0208 | B |
| I-0213 | A |
| I-0453 | A |
| I-0454 | A |
| I-0455 | A |
| I-0456 | A |
| I-0458 | A |

TABLE 209-continued

| Compound No. | IC50 |
|---|---|
| I-0459 | A |
| I-0460 | A |
| I-0461 | A |
| I-0462 | A |
| I-0463 | A |
| I-0464 | A |
| I-0465 | A |
| I-0466 | A |
| I-0467 | A |
| I-0468 | A |
| I-0469 | A |
| I-0470 | A |
| I-0471 | A |
| I-0472 | A |
| I-0477 | A |
| I-0478 | A |
| I-0479 | C |
| II-0002 | A |
| II-0004 | A |
| II-0005 | A |
| II-0006 | A |
| II-0007 | A |
| II-0008 | A |
| II-0009 | A |
| II-0011 | A |
| II-0012 | A |
| II-0013 | A |
| II-0017 | A |
| II-0018 | A |
| II-0019 | A |
| II-0020 | A |
| II-0022 | A |
| II-0023 | A |
| II-0191 | A |
| II-0193 | A |
| II-0194 | A |
| II-0195 | A |
| II-0196 | A |
| II-0197 | A |
| II-0198 | A |
| II-0199 | A |
| II-0200 | A |
| II-0201 | A |
| II-0202 | A |
| II-0203 | A |
| II-0204 | A |
| II-0205 | A |
| II-0206 | A |
| II-0207 | A |
| II-0208 | A |
| II-0209 | A |
| II-0210 | A |
| II-0211 | A |
| II-0212 | A |
| II-0213 | A |
| II-0214 | A |
| II-0215 | A |
| II-0216 | A |
| II-0217 | A |
| II-0218 | A |
| II-0219 | A |
| II-0220 | A |
| II-0221 | A |
| II-0222 | A |
| II-0234 | A |
| II-0235 | A |
| II-0236 | A |
| II-0237 | A |
| II-0238 | A |
| II-0239 | A |
| II-0240 | A |
| II-0431 | A |
| II-0432 | A |
| II-0433 | A |
| II-0434 | A |
| II-0435 | A |
| II-0436 | A |
| II-0437 | A |
| II-0438 | A |
| II-0439 | A |
| II-0440 | A |
| II-0441 | A |
| II-0442 | A |
| II-0443 | A |
| II-0444 | A |
| II-0445 | A |
| II-0446 | A |
| II-0447 | A |
| II-0448 | A |
| II-0449 | A |
| II-0450 | A |
| II-0451 | A |
| II-0452 | A |
| II-0453 | A |
| II-0454 | A |
| II-0456 | A |
| II-0457 | A |
| II-0458 | A |
| II-0459 | A |
| II-0461 | A |
| II-0462 | A |
| II-0463 | A |
| II-0464 | A |
| II-0465 | A |
| II-0466 | A |
| II-0467 | A |
| II-0468 | A |
| II-0469 | A |
| II-0470 | A |

TABLE 210

| Compound No. | IC50 |
|---|---|
| I-0214 | A |
| I-0223 | C |
| I-0226 | A |
| I-0227 | A |
| I-0231 | A |
| I-0234 | A |
| I-0236 | A |
| I-0242 | A |
| I-0244 | A |
| I-0245 | A |
| I-0246 | A |
| I-0248 | A |
| I-0249 | A |
| I-0250 | A |
| I-0251 | A |
| I-0252 | A |
| I-0253 | A |
| I-0254 | A |
| I-0255 | A |
| I-0256 | A |
| I-0258 | C |
| I-0259 | A |
| I-0260 | A |
| I-0264 | A |
| I-0265 | A |
| I-0266 | A |
| I-0267 | A |
| I-0268 | A |
| I-0269 | A |
| I-0270 | A |
| I-0271 | A |
| I-0272 | A |
| I-0279 | A |
| I-0284 | A |
| I-0285 | A |
| I-0286 | A |

TABLE 210-continued

| Compound No. | IC50 |
|---|---|
| I-0287 | A |
| I-0289 | A |
| II-0024 | A |
| II-0025 | A |
| II-0027 | A |
| II-0028 | A |
| II-0029 | A |
| II-0030 | A |
| II-0031 | A |
| II-0032 | A |
| II-0033 | A |
| II-0035 | A |
| II-0037 | A |
| II-0038 | A |
| II-0039 | A |
| II-0040 | A |
| II-0041 | A |
| II-0042 | A |
| II-0044 | A |
| II-0046 | A |
| II-0047 | A |
| II-0048 | A |
| II-0049 | A |
| II-0050 | A |
| II-0051 | A |
| II-0052 | A |
| II-0053 | A |
| II-0054 | A |
| II-0056 | A |
| II-0057 | A |
| II-0058 | A |
| II-0059 | A |
| II-0060 | A |
| II-0061 | A |
| II-0062 | A |
| II-0063 | A |
| II-0064 | A |
| II-0065 | A |
| II-0066 | A |
| II-0067 | A |
| II-0242 | A |
| II-0243 | A |
| II-0244 | A |
| II-0245 | A |
| II-0246 | A |
| II-0247 | A |
| II-0248 | A |
| II-0249 | A |
| II-0250 | A |
| II-0251 | A |
| II-0252 | A |
| II-0253 | A |
| II-0254 | A |
| II-0260 | A |
| II-0261 | A |
| II-0262 | A |
| II-0263 | A |
| II-0264 | A |
| II-0265 | A |
| II-0266 | A |
| II-0267 | A |
| II-0268 | A |
| II-0269 | A |
| II-0270 | A |
| II-0271 | A |
| II-0276 | A |
| II-0277 | A |
| II-0279 | A |
| II-0280 | A |
| II-0281 | A |
| II-0283 | A |
| II-0285 | A |
| II-0286 | A |
| II-0287 | A |
| II-0291 | A |
| II-0293 | A |
| II-0294 | A |
| II-0295 | A |
| II-0471 | A |
| II-0472 | A |
| II-0473 | A |
| II-0474 | A |
| II-0475 | A |
| II-0476 | A |
| II-0477 | A |
| II-0478 | A |
| II-0479 | A |
| II-0480 | A |
| II-0485 | A |
| II-0486 | A |
| II-0487 | A |
| II-0488 | A |
| II-0489 | A |
| II-0491 | A |
| II-0495 | A |
| II-0496 | A |
| II-0497 | A |
| II-0498 | A |
| II-0500 | A |
| II-0501 | A |
| II-0502 | A |
| II-0503 | A |
| II-0504 | A |
| II-0505 | A |
| II-0506 | A |
| II-0507 | A |
| II-0508 | A |
| II-0509 | A |
| II-0510 | A |
| II-0511 | A |
| II-0512 | A |
| II-0513 | A |
| II-0514 | A |
| II-0515 | A |
| II-0516 | A |
| II-0517 | A |

TABLE 211

| Compound No. | IC50 |
|---|---|
| I-0290 | A |
| I-0301 | C |
| I-0306 | A |
| I-0307 | B |
| I-0310 | A |
| I-0316 | A |
| I-0318 | B |
| I-0320 | A |
| I-0321 | C |
| I-0330 | A |
| I-0331 | A |
| I-0332 | A |
| I-0333 | A |
| I-0334 | B |
| I-0335 | B |
| I-0339 | B |
| I-0340 | B |
| I-0344 | A |
| I-0346 | A |
| I-0348 | A |
| I-0349 | A |
| I-0350 | A |
| I-0352 | A |
| I-0355 | A |
| I-0356 | A |
| I-0357 | A |
| I-0358 | B |
| I-0359 | A |
| I-0364 | A |

TABLE 211-continued

| Compound No. | IC50 |
|---|---|
| I-0365 | A |
| I-0366 | A |
| I-0367 | A |
| I-0368 | A |
| I-0369 | A |
| I-0370 | A |
| I-0371 | A |
| I-0372 | A |
| I-0374 | A |
| II-0068 | A |
| II-0069 | A |
| II-0070 | A |
| II-0071 | A |
| II-0072 | A |
| II-0073 | A |
| II-0075 | A |
| II-0076 | A |
| II-0077 | A |
| II-0078 | A |
| II-0079 | A |
| II-0080 | A |
| II-0081 | A |
| II-0082 | A |
| II-0083 | A |
| II-0084 | A |
| II-0088 | A |
| II-0091 | A |
| II-0092 | A |
| II-0094 | A |
| II-0095 | A |
| II-0096 | A |
| II-0097 | A |
| II-0098 | A |
| II-0099 | A |
| II-0100 | A |
| II-0101 | A |
| II-0102 | A |
| II-0103 | A |
| II-0104 | A |
| II-0105 | A |
| II-0106 | A |
| II-0107 | A |
| II-0108 | A |
| II-0110 | A |
| II-0112 | A |
| II-0113 | A |
| II-0114 | A |
| II-0296 | A |
| II-0297 | A |
| II-0298 | A |
| II-0300 | A |
| II-0301 | A |
| II-0302 | A |
| II-0303 | A |
| II-0305 | A |
| II-0307 | A |
| II-0308 | A |
| II-0309 | A |
| II-0310 | A |
| II-0311 | A |
| II-0312 | A |
| II-0313 | A |
| II-0314 | A |
| II-0315 | A |
| II-0316 | A |
| II-0317 | A |
| II-0318 | A |
| II-0319 | A |
| II-0320 | A |
| II-0321 | A |
| II-0322 | A |
| II-0323 | A |
| II-0324 | A |
| II-0325 | A |
| II-0326 | A |
| II-0328 | A |
| II-0331 | C |

TABLE 211-continued

| Compound No. | IC50 |
|---|---|
| II-0333 | A |
| II-0336 | A |
| II-0337 | A |
| II-0338 | A |
| II-0339 | A |
| II-0340 | A |
| II-0341 | A |
| II-0342 | A |
| II-0518 | A |
| II-0519 | A |
| II-0520 | A |
| II-0524 | A |
| II-0526 | A |
| II-0527 | A |
| II-0528 | A |
| II-0529 | A |
| II-0530 | A |
| II-0531 | A |
| II-0532 | A |
| II-0533 | A |
| II-0534 | A |
| II-0535 | A |
| II-0536 | A |
| II-0537 | A |
| II-0538 | A |
| II-0539 | A |
| II-0540 | A |
| II-0541 | A |
| II-0542 | A |
| II-0544 | A |
| II-0546 | A |
| II-0547 | A |
| II-0549 | A |
| II-0551 | A |
| II-0552 | A |
| II-0553 | A |
| II-0554 | A |
| II-0555 | A |
| II-0556 | A |
| II-0557 | A |
| II-0558 | A |
| II-0560 | A |
| II-0561 | A |
| II-0562 | A |
| II-0563 | A |
| II-0564 | A |

TABLE 212

| Compound No. | IC50 |
|---|---|
| I-0378 | A |
| I-0379 | A |
| I-0380 | A |
| I-0381 | A |
| I-0382 | A |
| I-0384 | A |
| I-0385 | A |
| I-0386 | A |
| I-0390 | A |
| I-0392 | A |
| I-0396 | C |
| I-0397 | B |
| I-0399 | A |
| I-0400 | A |
| I-0401 | A |
| I-0402 | A |
| I-0403 | B |
| I-0404 | A |
| I-0405 | A |
| I-0406 | A |
| I-0407 | A |
| I-0408 | A |

TABLE 212-continued

| Compound No. | IC50 |
|---|---|
| I-0412 | C |
| I-0414 | B |
| I-0415 | C |
| I-0416 | C |
| II-0115 | A |
| II-0116 | A |
| II-0117 | A |
| II-0121 | A |
| II-0122 | A |
| II-0123 | A |
| II-0126 | A |
| II-0127 | A |
| II-0128 | A |
| II-0129 | A |
| II-0131 | A |
| II-0134 | A |
| II-0135 | A |
| II-0136 | A |
| II-0137 | A |
| II-0138 | A |
| II-0139 | A |
| II-0140 | A |
| II-0141 | A |
| II-0142 | A |
| II-0143 | A |
| II-0144 | A |
| II-0145 | A |
| II-0146 | A |
| II-0147 | A |
| II-0148 | A |
| II-0344 | A |
| II-0345 | A |
| II-0346 | A |
| II-0348 | A |
| II-0349 | A |
| II-0350 | A |
| II-0351 | A |
| II-0352 | A |
| II-0353 | A |
| II-0354 | A |
| II-0355 | A |
| II-0356 | A |
| II-0357 | A |
| II-0358 | A |
| II-0359 | A |
| II-0360 | A |
| II-0361 | A |
| II-0362 | A |
| II-0363 | A |
| II-0364 | A |
| II-0365 | A |
| II-0366 | A |
| II-0367 | A |
| II-0368 | A |
| II-0378 | A |
| II-0379 | A |
| II-0565 | A |
| II-0575 | A |
| II-0578 | A |
| II-0580 | A |
| II-0581 | A |
| II-0582 | A |
| II-0583 | A |
| II-0585 | A |
| II-0586 | A |
| II-0587 | A |
| II-0588 | A |
| II-0589 | A |
| II-0590 | A |
| II-0591 | A |
| II-0592 | A |
| II-0593 | A |
| II-0597 | A |
| II-0598 | A |
| II-0599 | A |
| II-0600 | A |
| II-0601 | A |

TABLE 212-continued

| Compound No. | IC50 |
|---|---|
| II-0602 | A |
| II-0603 | A |
| II-0605 | C |
| II-0606 | B |
| II-0607 | B |

TABLE 213

| Compound No. | IC50 |
|---|---|
| II-0610 | A |
| II-0611 | A |
| II-0612 | A |
| II-0613 | A |
| II-0614 | A |
| II-0615 | A |
| II-0616 | A |
| II-0617 | A |
| II-0618 | A |
| II-0619 | A |
| II-0620 | A |
| II-0621 | A |
| II-0622 | A |
| II-0623 | A |
| II-0624 | A |
| II-0625 | A |
| II-0626 | A |
| II-0627 | A |
| II-0628 | A |
| II-0629 | A |
| II-0630 | A |
| II-0631 | A |
| II-0632 | A |
| II-0633 | A |
| II-0634 | A |
| II-0635 | A |
| II-0636 | A |
| II-0637 | A |
| II-0638 | A |
| II-0639 | A |
| II-0640 | A |
| II-0641 | A |
| II-0642 | A |

The preparation examples shown below are only for illustrative purposes and are by no means intended to limit the scope of the invention.

The compound of the present invention can be administered as a pharmaceutical composition by any conventional route, particularly enterally, for example, orally, for example, in the form of a tablet or a capsule; parenterally, for example, in the form of an injectable preparation or a suspension; and topically, for example, in the form of a lotion, a gel, an ointment or a cream, or as a pharmaceutical composition in a transnasal form or a suppository form. A pharmaceutical composition comprising the compound of the present invention in a free form or in the form of a pharmaceutically acceptable salt together with at least one pharmaceutically acceptable carrier or diluent can be produced by a mixing, granulating, or coating method in a conventional manner. For example, the oral composition can be a tablet, a granular preparation, or a capsule, each containing an excipient, a disintegrating agent, a binder, a lubricating agent, and the like, as well as an active ingredient and the like. Furthermore, the composition for injection can be prepared as a solution or a suspension, may be sterilized, and may contain a preservative, a stabilizer, a buffering agent, and the like.

INDUSTRIAL APPLICABILITY

The compound according to the present invention has coronavirus 3CL protease inhibitory activity, and it is considered that the compound is useful as a therapeutic agent and/or a prophylactic agent for a disease or a condition associated with coronavirus 3CL proteases.

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

—X— is —$NR^6$—, —$CR^6R^{6'}$—, —O—, —S—, or a single bond;

The invention claimed is:

1. A compound represented by Formula (I):

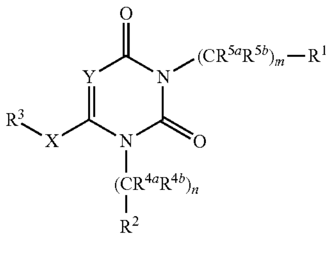

(I)

wherein

Y is N, or $CR^7$;

$R^7$ is a hydrogen atom, or substituted or unsubstituted alkyl;

$R^1$ is substituted or unsubstituted aromatic heterocyclyl, substituted or unsubstituted non-aromatic heterocyclyl, or substituted or unsubstituted carbamoyl;

$R^2$ is 6 membered aromatic carbocyclyl substituted with one halogen or one cyano, and further substituted with 1, 2, 3 or 4 substituent(s) selected from substituent group G, or 6 membered aromatic heterocyclyl substituted with one halogen or one cyano, and further substituted with 1 or 2 substituent(s) selected from substituent group G;

substituent group G is selected from the group consisting of halogen, cyano, alkyl, alkenyl, alkynyl, haloalkyl, alkyloxy, alkenyloxy, alkynyloxy and haloalkyloxy;

$R^6$ and $R^{6'}$ are each independently a hydrogen atom, or substituted or unsubstituted alkyl;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

n is 1;

$R^{4a}$ is each independently a hydrogen atom, or substituted or unsubstituted alkyl; and $R^{4b}$ is each independently a hydrogen atom, or substituted or unsubstituted alkyl, or a pharmaceutically acceptable salt thereof.

2. The compound according to claim 1, wherein

Y is N, or a pharmaceutically acceptable salt thereof.

3. The compound according to claim 1, wherein

—X— is —NH—, or a pharmaceutically acceptable salt thereof.

4. The compound according to claim 1, wherein m is 0 or 1, or a pharmaceutically acceptable salt thereof.

5. The compound according to claim 1, wherein $R^{4a}$ is each independently a hydrogen atom or unsubstituted alkyl, and $R^{4b}$ is each independently a hydrogen atom, or a pharmaceutically acceptable salt thereof.

6. The compound according to claim 1, wherein $R^{5a}$ is each independently a hydrogen atom, and $R^{5b}$ is each independently a hydrogen atom, or a pharmaceutically acceptable salt thereof.

7. The compound according to claim 1, wherein $R^1$ is substituted or unsubstituted aromatic heterocyclyl, or a pharmaceutically acceptable salt thereof.

8. The compound according to claim 1, wherein $R^1$ is substituted or unsubstituted aromatic heterocyclyl, m is 1, $R^{5a}$ is a hydrogen atom, and $R^{5b}$ is a hydrogen atom, or pharmaceutically acceptable salt thereof.

9. The compound according to claim 1, wherein $R^1$ is substituted or unsubstituted aromatic heterocyclyl, and m is 0, or a pharmaceutically acceptable salt thereof.

10. The compound according to claim 1, wherein $R^3$ is substituted or unsubstituted 6 membered aromatic carbocyclyl, substituted or unsubstituted 3 to 10 membered non-aromatic carbocyclyl, substituted or unsubstituted 5 to 6 membered aromatic heterocyclyl, substituted or unsubstituted 9 to 10 membered aromatic heterocyclyl, substituted or unsubstituted 13 to 15 membered aromatic heterocyclyl, or substituted or unsubstituted 3 to 20 membered non-aromatic heterocyclyl, or a pharmaceutically acceptable salt thereof.

11. The compound according to claim 1, wherein $R^3$ is substituted or unsubstituted 6 membered aromatic carbocyclyl, substituted or unsubstituted 9 to 10 membered aromatic heterocyclyl, or substituted or unsubstituted 9 to 13 membered non-aromatic heterocyclyl, or a pharmaceutically acceptable salt thereof.

12. The compound according to claim 1, wherein Formula (I) is Formula (I'):

(I')

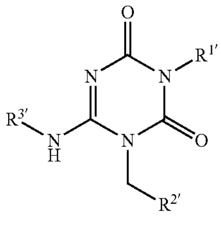

wherein $R^{1'}$ is a group represented by Formula:

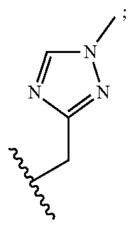 [SMILES: *Cc1ncn(C)n1]

$R^{2'}$ is a group represented by Formula:

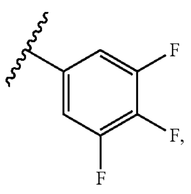

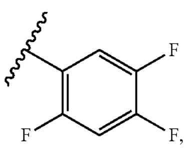

-continued

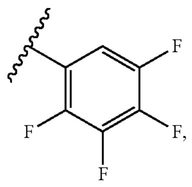

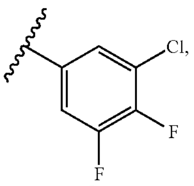

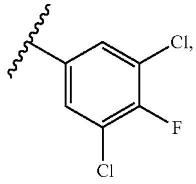

or

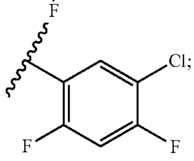

and $R^{3'}$ is a group represented by Formula:

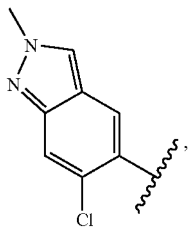

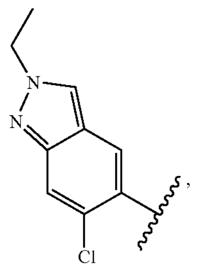

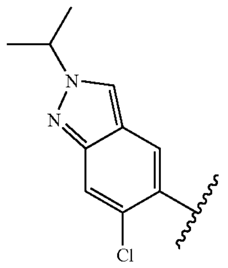

or

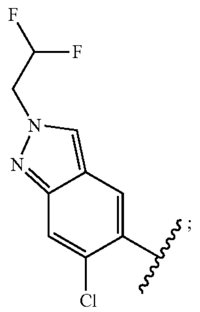

or a pharmaceutically acceptable salt thereof.

13. The compound according to claim 1, wherein Formula (I) is Formula (I'):

(I')

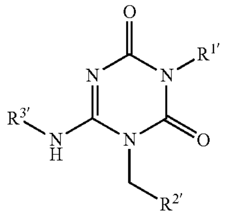

wherein
$R^{1'}$ is a group represented by Formula:
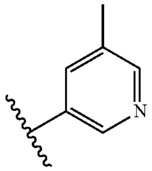 or 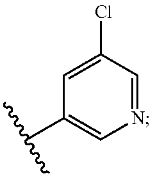
$R^{2'}$ is a group represented by Formula:
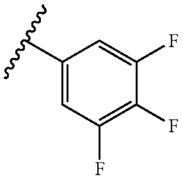, 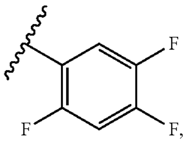
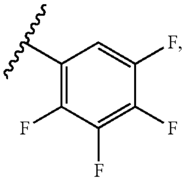 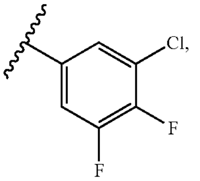
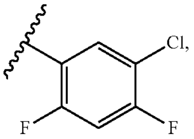 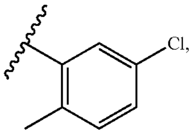
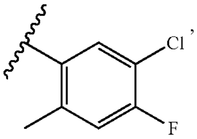 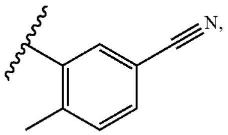
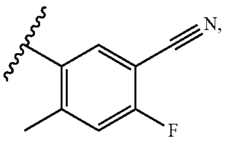 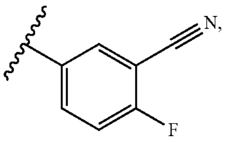
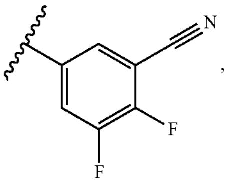, 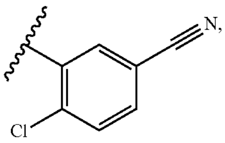 or
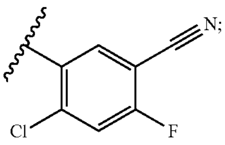
and
$R^{3'}$ is a group represented by Formula:
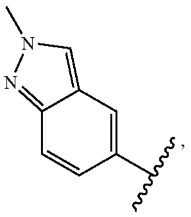, 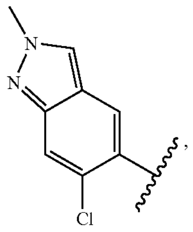,
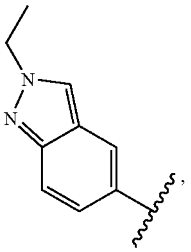, 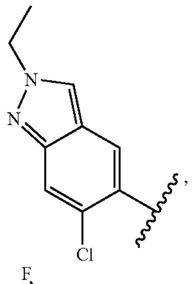,
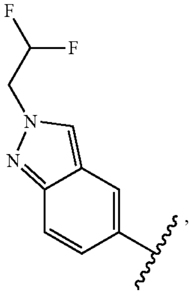, 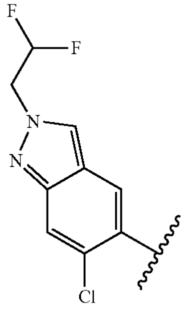 or
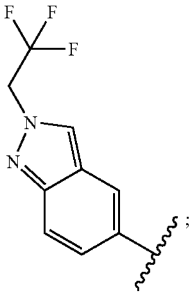;
or a pharmaceutically acceptable salt thereof.
14. The compound according to claim 1, wherein the compound is selected from the group consisting of:
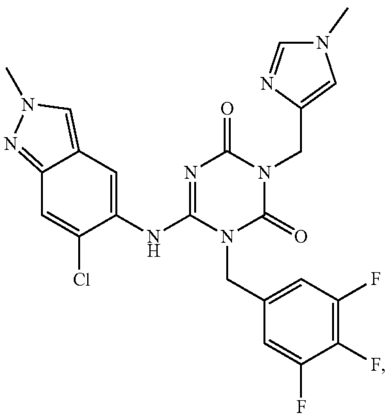

-continued
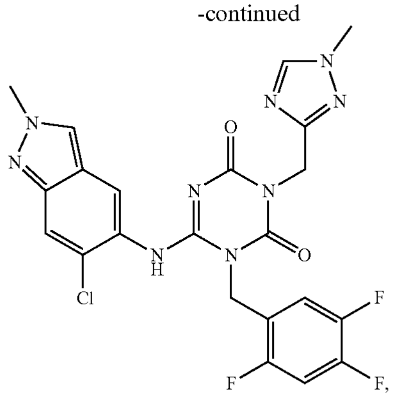
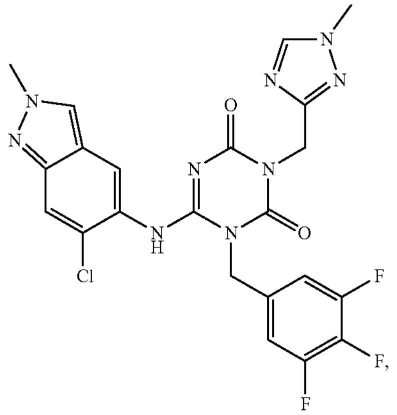
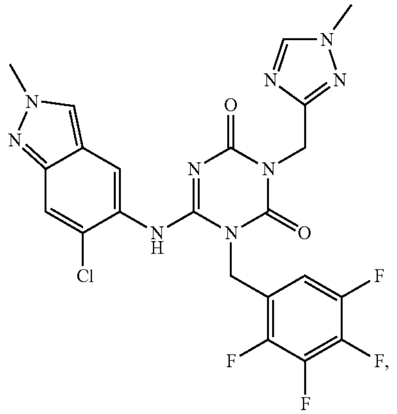
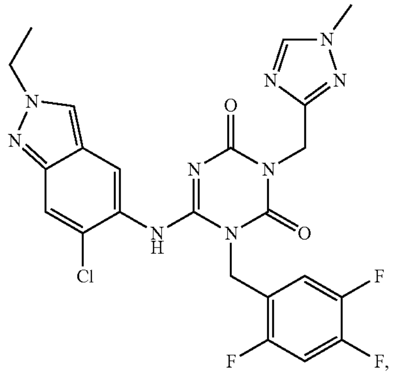
-continued
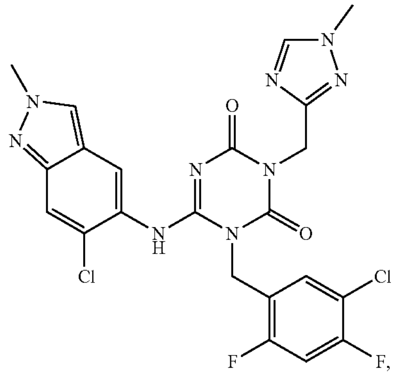
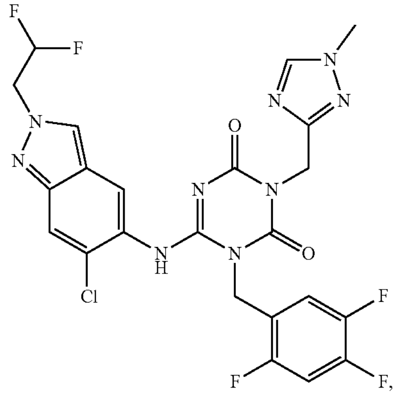
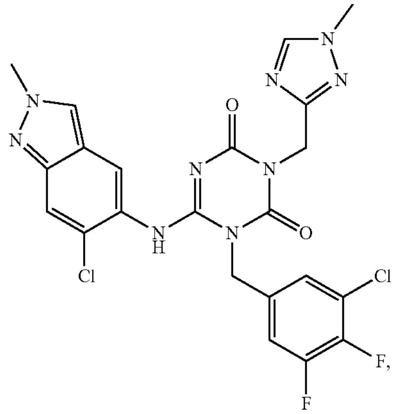
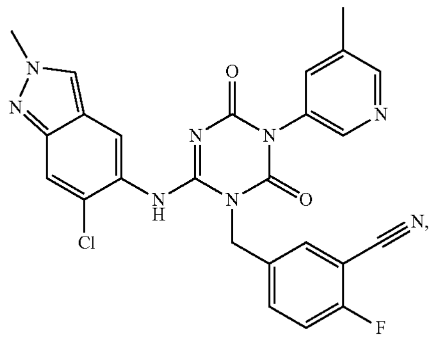

-continued

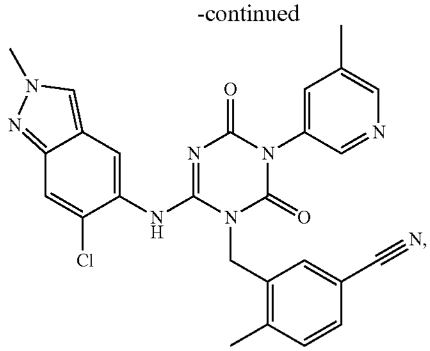

,

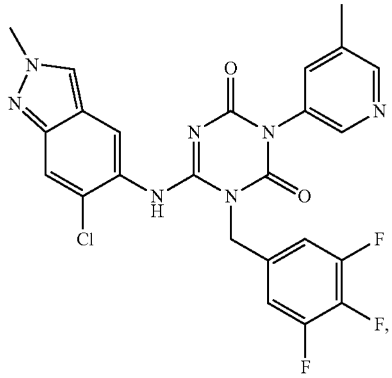

,

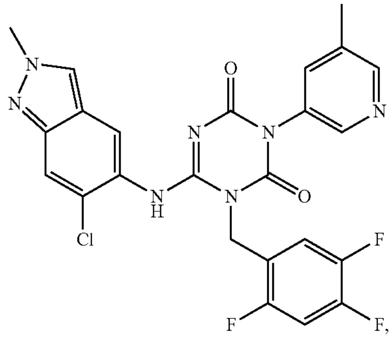

,

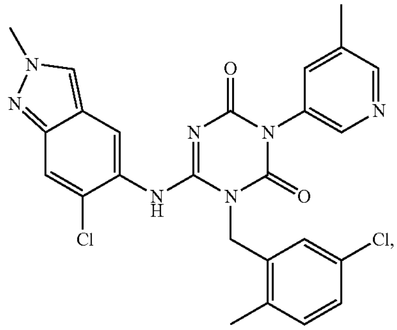

,

-continued

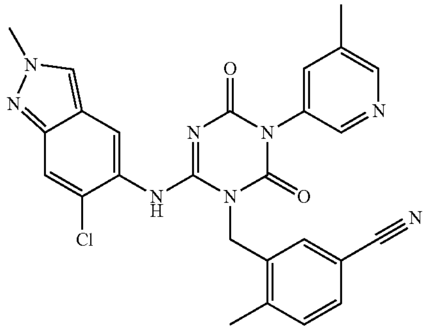

and

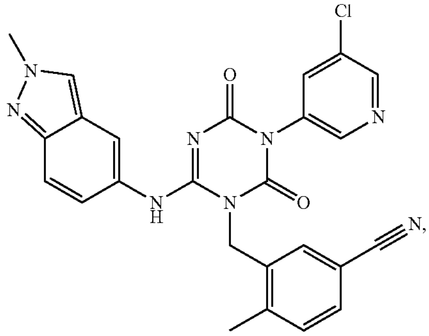

, or a pharmaceutically acceptable salt thereof.

15. A pharmaceutical composition comprising the compound according to claim 1, or a pharmaceutically acceptable salt thereof, and a pharmaceutically acceptable additive, carrier or diluent.

16. A method for inhibiting SARS-COV-2, comprising administering the compound according to claim 1, or a pharmaceutically acceptable salt thereof, to a subject.

17. A method for treating an infection caused by SARS-COV-2, comprising administering the compound according to claim 1, or a pharmaceutically acceptable salt thereof, to a subject.

* * * * *